United States Patent
Fu et al.

(10) Patent No.: US 9,566,312 B2
(45) Date of Patent: *Feb. 14, 2017

(54) CYCLIC PEPTIDES AND USE AS MEDICINES

(71) Applicant: Novartis AG, Basel (CH)

(72) Inventors: Jiping Fu, Danville, CA (US); Subramanian Karur, Dublin, CA (US); Xiaolin Li, Alameda, CA (US); Peichao Lu, Pleasant Hill, CA (US); Wosenu Mergo, Oakland, CA (US); Alexey Rivkin, Emeryville, CA (US); Zachary Kevin Sweeney, Redwood City, CA (US); Meiliana Tjandra, Dublin, CA (US); Andrew Weiss, San Francisco, CA (US); Aregahegn Yifru, Pleasant Hill, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/717,872

(22) Filed: May 20, 2015

(65) Prior Publication Data

US 2015/0306172 A1    Oct. 29, 2015

Related U.S. Application Data

(63) Continuation of application No. 14/037,644, filed on Sep. 26, 2012, now Pat. No. 9,072,696.

(60) Provisional application No. 61/707,902, filed on Sep. 29, 2012.

(51) Int. Cl.
  *A61K 38/12* (2006.01)
  *A61K 38/13* (2006.01)
  *C07K 7/64* (2006.01)
  *A61K 45/06* (2006.01)

(52) U.S. Cl.
  CPC ............. *A61K 38/13* (2013.01); *A61K 38/12* (2013.01); *A61K 45/06* (2013.01); *C07K 7/64* (2013.01); *C07K 7/645* (2013.01)

(58) Field of Classification Search
  None
  See application file for complete search history.

(56) References Cited

U.S. PATENT DOCUMENTS

| | | |
|---|---|---|
| 2006/0069015 A1 | 3/2006 | Molino et al. |
| 2010/0209390 A1 | 8/2010 | Or et al. |
| 2011/0008284 A1 | 1/2011 | Gao et al. |
| 2011/0008285 A1 | 1/2011 | Long et al. |
| 2011/0008286 A1 | 1/2011 | Wang et al. |

FOREIGN PATENT DOCUMENTS

| | | |
|---|---|---|
| EP | 296122 | 12/1988 |
| EP | 487289 | 5/1992 |
| WO | WO 96/06857 | 3/1996 |
| WO | WO 98/49193 | 11/1998 |
| WO | WO 99/62540 | 12/1999 |
| WO | WO 99/67280 | 12/1999 |
| WO | WO 00/51558 | 9/2000 |
| WO | WO 01/62775 | 8/2001 |
| WO | WO 2006/005580 | 1/2006 |
| WO | WO 2007/049803 | 5/2007 |
| WO | WO 2007/112345 | 10/2007 |
| WO | WO 2008/139986 | 11/2008 |
| WO | WO 2010/088573 | 8/2010 |
| WO | WO 2011/082289 | 7/2011 |
| WO | WO 2011/109037 | 9/2011 |
| WO | WO 2012/009715 | 1/2012 |
| WO | WO 2012/021796 | 2/2012 |
| WO | WO 2012/075494 | 6/2012 |
| WO | WO 2013/028615 | 2/2013 |

OTHER PUBLICATIONS

Eberle et al. "Preparation and in Vitro Activities of Ethers of [D-Serine]8-cyclosporin" *Journal of Medicinal Chemistry* 38(11):1853-64, 1995.

Michel Evers et al., "Synthesis of Non-Immunosuppressive Cyclophilin-Binding Cyclosporin A Derivatives as Potential Anti-HIV-1 Drugs" *Bioorganic and Medicinal Chemistry Letters* 13:4415-4419, 2003.

Ling Wei et al., "Synthesis and Neurotrophic Activity of Nonimmunosuppressant Cyclosporin A Derivatives" *Bioorganic and Medicinal Chemistry Letters* 14:4549-4551, 2004.

(Continued)

*Primary Examiner* — Thomas S Heard
(74) *Attorney, Agent, or Firm* — Michael G. Smith

(57) ABSTRACT

The present invention provides a compound of formula I;

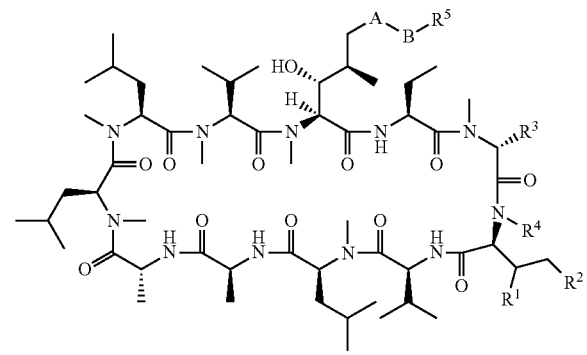

or a pharmaceutically acceptable salt thereof, wherein $R^1$, $R^2$, $R^3$, $R^4$, $R^5$, and A-B are as defined herein, which are non-immunosuppressive, cyclophilin-binding, mPTP blockers and are therefore useful for the prevention or treatment of diseases or disorders such as HCV infection, stroke, multiple sclerosis, HBV infection, HPV infection, asthma, cancer, muscular dystrophy, sepsis, ischemia/reperfusion injury, and heart failure.

22 Claims, No Drawings

(56) References Cited

OTHER PUBLICATIONS

Hengli Tang et al., "Cyclophilin Inhibitors as a Novel HCV Therapy" *Viruses* 21621-1634, 2010.
Bobardt et al., "HCV NSC5A and IRF9 Compete for CypA Binding" *Journal of Hepatology* 58:16-23, 2013.
Jiping Fu et al., "Potent Nonimmunosuppressive Cyclophilin Inhibitors With Improved Pharmaceutical Properties and Decreased Transporter Inhibition" *Journal of Medicinal Chemistry* 57:8503-8516, 2014.

CYCLIC PEPTIDES AND USE AS MEDICINES

CROSS-REFERENCE TO RELATED APPLICATION

This application is a continuation of U.S. patent application Ser. No. 14/037,644, filed 25 Sep. 2013, now allowed, which claims priority to U.S. provisional application Ser. No. 61/707,902, filed 29 Sep. 2012; the contents of each of these applications are incorporated herein by reference in their entirety.

FIELD OF THE INVENTION

The invention provides novel cyclic peptides, pharmaceutical compositions comprising such compounds and methods of using such compounds to treat or prevent diseases or disorders such as HCV infection, stroke, multiple sclerosis, HBV infection, HPV infection, asthma, cancer, muscular dystrophy, sepsis, ischemia/reperfusion injury, and heart failure.

BACKGROUND

The peptidyl prolyl cis-trans isomerase activity of cellular cyclophilins is essential for efficient hepatitis C virus (HCV) replication in hepatocytes. A large body of data, including clinical evidence, supports the idea that compounds that inhibit cyclophilin activity will be useful medicines for the treatment of HCV. These medicines may function by interacting with the NS5A and NS5B viral proteins and inhibiting proper assembly and function of the viral replication complex. Recently, published data has also suggested that some cyclophilin inhibitors may exert an antiviral effect by inhibiting cellular lipid trafficking or increasing the production of endogenous interferons.

The most studied class of cyclophilin inhibitors are structurally related to the immunosuppressant cyclosporine A (CsA). Since the discovery of CsA, several analogs have been identified that potently bind and inhibit cyclophilins but lack the ability of CsA to cause immunosuppression by binding calcineurin. In particular, CsA derivatives such as Debio025 and Scy-635 are non-immunosuppressive analogs of CsA that have been shown to reduce viral replication when administered HCV-infected patients.

Despite the efficacy of these agents, there is still a need for the identification and development of new cyclophilin inhibitors for the treatment of HCV and other diseases. Deb025, for example, has been reported to cause hyperbilirubinemia as a consequence of its ability to inhibit a variety of hepatic transporters. Inhibition of hepatic transporters is also a possible cause of undesirable drug-drug interactions.

SUMMARY

The present invention aims to provide non-immunosuppressive cyclophilin inhibitors with a reduced potential for causing adverse events, including hyperbilirubinemia or drug-drug interactions due to the inhibition of hepatic transporters or metabolizing enzymes. In addition to their application as effective medicines for the treatment of HCV infection, it is anticipated that such compounds will be used for the treatment of stroke, multiple sclerosis, HBV infection, HPV infection, asthma, cancer, muscular dystrophy, sepsis, ischemia/reperfusion injury, and heart failure.

In one aspect a compound of the formula (I) is provided

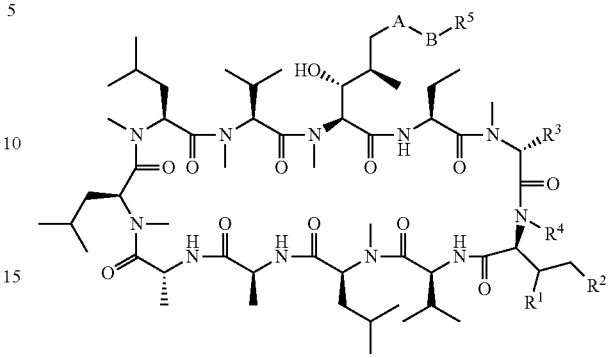

I or a pharmaceutically acceptable salt thereof, for use in therapy, wherein
A-B is —CH=CH, CH$_2$CH$_2$ or a cyclopropyl

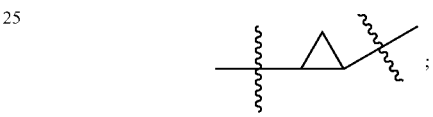

$R^1$ is C$_1$-C$_4$alkoxy or C$_1$-C$_4$ alkyl optionally substituted with C$_1$-C$_4$ alkoxy;

$R^2$ is
(i) —OH, —CN, —C(O)NRR', —NRC(O)R$^{15}$, —OC(O)NRR', —NR$^9$R$^{10}$, —SO$_2$R$^{1a}$, —SO$_2$NRR', —OR$^{1a}$, 4 to 8 membered heterocycle containing 1 to 3 heteroatom selected from N, S, and O, (C$_1$-C$_4$)alkyl-OH, (C$_1$-C$_4$)alkyl-CN, (C$_1$-C$_4$)alkyl-C(O)NRR', (C$_1$-C$_4$)alkyl-NRC(O)R$^{15}$, (C$_1$-C$_4$)alkyl-OC(O)NRR', (C$_1$-C$_4$)alkyl-NR$^9$R$^{10}$, (C$_1$-C$_4$)alkyl-SO$_2$R$^{1a}$, (C$_1$-C$_4$)alkyl-SO$_2$NRR', (C$_1$-C$_4$)alkyl-OR$^{1a}$, or (C$_1$-C$_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O(C$_1$-C$_4$)alkyl, oxo (=O), —S(O)$_2$(C$_1$-C$_4$)alkyl, —C(O)(C$_1$-C$_4$)alkyl, —C(O)$_2$(C$_1$-C$_4$)alkyl, C$_1$-C$_4$haloalkyl, C$_3$-C$_7$cycloalkyl, C$_1$-C$_4$ alkyl optionally substituted with C$_1$-C$_4$alkoxy and a 4 to 7 membered heterocycle containing 1 to 3 heteroatom selected from N, S, and O, wherein said heterocycle is optionally substituted with one or more halogen or C$_1$-C$_4$ alkyl;

(ii) a 4 to 8 membered heterocycle containing 1 to 3 heteroatom selected from N, S, and O or (C$_1$-C$_4$)alkyl-4 to 8 membered heterocycle containing 1 to 3 heteroatom selected from N, S, and O, wherein said heterocycles are substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or C$_1$-C$_4$ alkyl; or (iii) a 4 to 8 membered heterocycle containing 1 to 3 heteroatom selected from N, S, and O, or a (C$_1$-C$_4$)alkyl-4 to 8 membered heterocycle containing 1 to 3 heteroatom selected from N, S, and O, wherein said heterocycles are fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$alkoxy, oxo (=O), or $C_1$-$C_4$haloalkyl; wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^{1a}$ is (a) $C_1$-$C_4$alkyl, ($C_1$-$C_4$)alkyl-OH, ($C_1$-$C_4$)alkyl-$C_1$-$C_4$alkoxy, ($C_2$-$C_4$)alkyl-$NR^9R^{10}$, —CONRR', ($C_1$-$C_4$)alkyl-CONRR', a 4 to 8 membered heterocycle containing 1 to 3 heteroatom selected from N, S, and O, or a ($C_1$-$C_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with one or more halogen or $C_1$-$C_4$ alkyl;

(b) a 4 to 8 membered heterocycle containing 1 to 3 heteroatom selected from N, S, and O or ($C_1$-$C_4$)alkyl-4 to 8 membered heterocycle containing 1 to 3 heteroatom selected from N, S, and O wherein said heterocycles are optionally substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl; or (c) a 4 to 8 membered heterocycle containing 1 to 3 heteroatom selected from N, S, and O, or a ($C_1$-$C_4$)alkyl-4 to 8 membered heterocycle containing 1 to 3 heteroatom selected from N, S, and O, wherein said heterocycles are optionally fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$alkoxy oxo (=O), or $C_1$-$C_4$haloalkyl; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

R is H, $C_1$-$C_6$alkyl optionally substituted with at least one halogen, hydroxyl, or alkoxy R' is a $C_1$-$C_6$alkyl optional substituted with halogen, a $C_1$-$C_4$ alkoxy or a 4 to 7 membered heterocycle containing 1 to 3 heteroatom selected from N, S, and O, wherein said heterocycle is optionally substituted with at least one substituent selected from the group consisting of halogen and $C_1$-$C_4$ alkyl; or R and R' taken together with the nitrogen to which they are attached form a 4 to 8 membered heterocycle containing 1 to 3 heteroatom selected from N, S, and O, wherein said heterocycle is optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with at least one halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is substituted with a spiro group, wherein said spiro group is a 3 to 6 membered cycloalkyl or 4 to 6 membered heterocycloalkyl containing 1 to 3 heteroatoms selected from N, S or O, wherein said spiro group can optionally be substituted by halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$alkoxy, oxo (=O), or $C_1$-$C_4$haloalkyl; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^3$ is $C_1$-$C_6$alkyl optionally substituted with at least one substituent selected from the group consisting of OH, O($C_1$-$C_4$alkyl), —$NR^7R^8$, and S($C_1$-$C_6$ alkyl);

$R^4$ is $C_1$-$C_4$ alkyl;

$R^5$ is H, ($C_1$-$C_6$)alkyl optionally substituted with one or more halogen, —P(O)(OR$^a$)(OR$^b$), hydroxy, $C_{1-4}$ alkoxy, —C(O)OR$^a$, —NR$^a$R$^b$, —NHC(O)OR$^a$, or CN;

R$^a$ and R$^b$ are independently H or $C_1$-$C_4$alkyl, or R$^a$ and R$^b$ can form together a 4 to 7 membered heterocycle containing 1 to 3 heteroatom selected from N, S, P and O, wherein said heterocycle is optionally substituted with one or more halogen or $C_1$-$C_4$ alkyl;

$R^7$ is H or $C_1$-$C_4$ alkyl;

$R^8$ is H or $C_1$-$C_4$ alkyl; or $R^7$ and $R^8$ taken together from the nitrogen they are attached form a 4 to 8 membered heterocycle containing 1 to 3 heteroatoms selected from N, S, and O, wherein said heterocycle is optionally substituted with at least one substituent selected from the group consisting of halogen and $C_1$-$C_4$ alkyl;

$R^9$ is H, $C_1$-$C_4$alkyl optionally substituted with one or more halogen, one or more hydroxy, $C_1$-$C_4$alkoxy, 5 to 6 membered heteroaryl or 5 to 6 membered heterocycle;

$R^{10}$ is H, $C_1$-$C_4$alkyl optionally substituted with one or more halogen, $C_1$-$C_4$alkoxy or one or more hydroxy;

$R^{15}$ is a $C_1$-$C_6$ alkyl optional substituted with halogen, a $C_1$-$C_4$ alkoxy or a 4 to 7 membered heterocycle containing 1 to 3 heteroatom selected from N, S, and O, wherein said heterocycle is optionally substituted with one or more halogen or $C_1$-$C_4$ alkyl.

In another aspect, a method of treating a disorder or a disease selected from HCV infection, stroke, multiple sclerosis, HBV infection, HPV infection, asthma, cancer, muscular dystrophy, sepsis, ischemia/reperfusion injury, and heart failure is provided.

In yet another aspect, a pharmaceutical compositions is provided which comprises an effective amount of a compound of Formula I and a pharmaceutical carrier, wherein said effective amount is effective to treat disorder or diseases selected from HCV infection, stroke, multiple sclerosis, HBV infection, HPV infection, asthma, cancer, muscular dystrophy, sepsis, ischemia/reperfusion injury, and heart failure.

The invention pertains to compounds, pharmaceutical compositions containing the compounds and methods of use thereof. The present invention also relates to compounds which may be used, as cyclophilin binders and mitochondrial permeability transition pore (mPTP) blockers. Suitable diseases and disorders include HCV infection, stroke, multiple sclerosis, HBV infection, HPV infection, asthma, cancer, muscular dystrophy, sepsis, ischemia/reperfusion injury, and heart failure.

For purposes of interpreting this specification, the following definitions will apply unless specified otherwise and whenever appropriate, terms used in the singular will also include the plural and vice versa.

Definitions

Terms used in the specification have the following meanings:

"Optionally substituted" means the group referred to can be substituted at one or more positions by any one or any combination of the radicals listed thereafter.

"Halo" or "halogen", as used herein, may be fluorine, chlorine, bromine or iodine.

"$C_1$-$C_6$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.

"$C_1$-$C_6$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2-$, $(CF_3)_2CH-$, $CH_3-CF_2-$, $CF_3CF_2-$, $CF_3$, $CF_2H-$, $CF_3CF_2CHCF_3$ or $CF_3CF_2CF_2CF_2-$.

"$C_3$-$C_8$-cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing 1 to 7, 1 to 5 or 1 to 3 heteroatoms selected from the group consisting of nitrogen, oxygen and sulphur, which may be saturated, or partially saturated. The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, pyrrolidine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo [3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane, azetidine, ethylenedioxo, oxtane or thiazole.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include furan, isotriazole, thiadiazole, oxadiazole, indazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2,3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "hydroxy" or "hydroxyl" includes groups with an —OH.

The term "a," "an," "the" and similar terms used in the context of the present invention (especially in the context of the claims) are to be construed to cover both the singular and plural unless otherwise indicated herein or clearly contradicted by the context.

The term "spiro" as used herein includes 3- to 6-cycloalkyl or 4- to 6-heterocycle which can optionally be substituted as defined. Q is a suitable substituent that will be defined as different variable in the claims herein. Non limitative examples of sipro groups are:

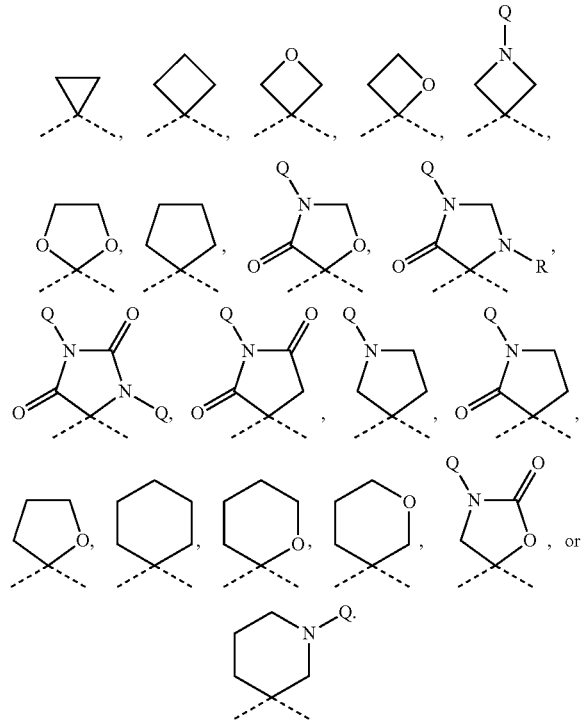

Various embodiments of the invention are described herein. It will be recognized that features specified in each embodiment may be combined with other specified features to provide further embodiments.

In another embodiment, a compound having Formula (II) is provided where $R^1$, $R^2$, $R^3$, and $R^4$, is defined above.

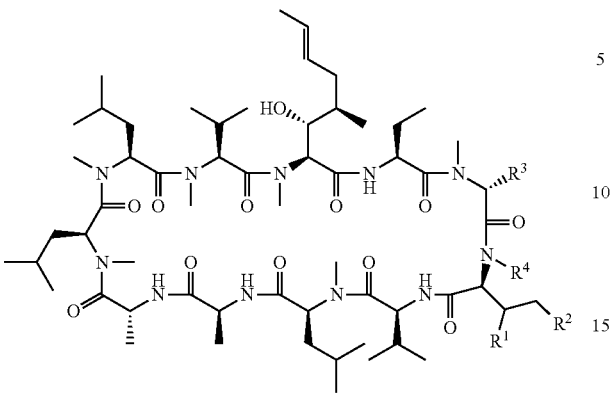

or a pharmaceutically acceptable salt thereof.

In another embodiment, a compound having Formula (I) or (II) above as described, wherein $R^1$ is —OCH$_3$;

$R^3$ is methyl, ethyl, isopropyl,

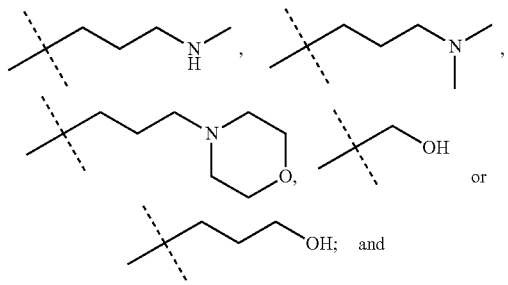

$R^4$ is —CH$_3$ or CH$_2$CH$_3$.

In yet another embodiment, a compound of Formula (I) or (II) above is described, wherein $R^2$ is (i) —OH, —CN, —C(O)NRR', —NRC(O)R$^{15}$, —OC(O)NRR', —NR$^9$R$^{10}$, —SO$_2$R$^{1a}$, —SO$_2$NRR', —OR$^{1a}$, 4 to 8 membered heterocycle containing 1 to 3 heteroatom selected from N, S, and O, (C$_1$-C$_4$)alkyl-OH, (C$_1$-C$_4$)alkyl-CN, (C$_1$-C$_4$)alkyl-C(O)NRR', (C$_1$-C$_4$) alkyl-NRC(O)R$^{15}$, (C$_1$-C$_4$)alkyl-OC(O)NRR', (C$_1$-C$_4$) alkyl-NR$^9$R$^{10}$, (C$_1$-C$_4$)alkyl-SO$_2$R$^{1a}$, (C$_1$-C$_4$)alkyl-SO$_2$NRR', (C$_1$-C$_4$)alkyl-OR$^{1a}$, or (C$_1$-C$_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O(C$_1$-C$_4$)alkyl, oxo (=O), —S(O)$_2$(C$_1$-C$_4$) alkyl, —C(O)(C$_1$-C$_4$)alkyl, —C(O)$_2$(C$_1$-C$_4$)alkyl, C$_1$-C$_4$haloalkyl, C$_3$-C$_7$cycloalkyl, C$_1$-C$_4$ alkyl optionally substituted with C$_1$-C$_4$alkoxy and a 4 to 7 membered heterocycle containing 1 to 3 heteroatom selected from N, S, and O, wherein said heterocycle is optionally substituted with one or more halogen or C$_1$-C$_4$ alkyl;

(ii) a 4 to 8 membered heterocycle containing 1 to 3 heteroatom selected from N, S, and O or (C$_1$-C$_4$)alkyl-4 to 8 membered heterocycle containing 1 to 3 heteroatom selected from N, S, and O, wherein said heterocycles are substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or C$_1$-C$_4$ alkyl; or (iii) a 4 to 8 membered heterocycle containing 1 to 3 heteroatom selected from N, S, and O, or a (C$_1$-C$_4$) alkyl-4 to 8 membered heterocycle containing 1 to 3 heteroatom selected from N, S, and O, wherein said heterocycles are fused to a 5 to 6 membered heterocycle containing 1 to 3 heteroatom selected from N, S, or O, wherein said fused heterocycle is optionally substituted with halogen, C$_1$-C$_4$alkyl, C$_1$-C$_4$alkoxy, oxo (=O), or C$_1$-C$_4$haloalkyl; or wherein said heterocycles are fused to a 5 to 6 membered heteroaryl containing 1 to 3 heteroatom selected from N, S, or O, wherein said fused heteroaryl is optionally substituted with halogen, C$_1$-C$_4$alkyl, C$_1$-C$_4$haloalkyl, C$_1$-C$_4$alkoxy, or oxo (=O);

$R^{1a}$ is (a) C$_1$-C$_4$alkyl, (C$_1$-C$_4$)alkyl-OH, (C$_1$-C$_4$)alkyl-C$_1$-C$_4$alkoxy, (C$_2$-C$_4$)alkyl-NR$^9$R$^{10}$, —CONRR', (C$_1$-C$_4$) alkyl-CONRR', a 4 to 8 membered heterocycle containing 1 to 3 heteroatom selected from N, S, and O, or a (C$_1$-C$_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O(C$_1$-C$_4$)alkyl, oxo (=O), —S(O)$_2$(C$_1$-C$_4$)alkyl, —C(O)(C$_1$-C$_4$)alkyl, —C(O)$_2$ (C$_1$-C$_4$)alkyl, C$_1$-C$_4$haloalkyl, C$_3$-C$_7$cycloalkyl, C$_1$-C$_4$ alkyl optionally substituted with C$_1$-C$_4$alkoxy and a 4 to 7 membered heterocycle containing 1 to 3 heteroatom selected from N, S, and O, wherein said heterocycle is optionally substituted with one or more halogen or C$_1$-C$_4$ alkyl;

(b) a 4 to 8 membered heterocycle containing 1 to 3 heteroatom selected from N, S, and O or (C$_1$-C$_4$)alkyl-4 to 8 membered heterocycle containing 1 to 3 heteroatom selected from N, S, and O, wherein said heterocycles are optionally substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or C$_1$-C$_4$ alkyl; or (c) a 4 to 8 membered heterocycle containing 1 to 3 heteroatom selected from N, S, and O, or a (C$_1$-C$_4$) alkyl-4 to 8 membered heterocycle containing 1 to 3 heteroatom selected from N, S, and O, wherein said heterocycles are optionally fused to a 5 to 6 membered heterocycle containing 1 to 3 heteroatom selected from N, S, or O, wherein said fused heterocycle is optionally substituted with halogen, C$_1$-C$_4$alkyl, C$_1$-C$_4$haloalkyl or C$_1$-C$_4$alkoxy; or wherein said heterocycles are fused to a 5 to 6 membered heteroaryl containing 1 to 3 heteroatom selected from N, S, or O, wherein said fused heteroaryl is optionally substituted with halogen, C$_1$-C$_4$alkyl, C$_1$-C$_4$alkoxy, oxo (=O), or C$_1$-C$_4$haloalkyl;

R is H, C$_1$-C$_6$alkyl optionally substituted with at least one halogen, hydroxyl, or alkoxy R' is a C$_1$-C$_6$alkyl optional substituted with halogen, a C$_1$-C$_4$ alkoxy or a 4 to 7 membered heterocycle containing 1 to 3 heteroatom selected from N, S, and O, wherein said heterocycle is optionally substituted with at least one substituent selected from the group consisting of halogen and C$_1$-C$_4$ alkyl; or R and R' taken together with the nitrogen to which they are attached form a 4 to 8 membered heterocycle containing 1 to 3 heteroatom selected from N, S, and O, wherein said heterocycle is optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with at least one halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is substituted with a spiro group, wherein said spiro group is a 3 to 6 membered cycloalkyl or 4 to 6 membered heterocycloalkyl containing 1 to 3 heteroatoms selected from N, S or O, wherein said spiro group can optionally be substituted by halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^3$ is $C_1$-$C_6$alkyl optionally substituted with at least one substituent selected from the group consisting of OH, O($C_1$-$C_4$alkyl), —NR$^7$R$^8$, and S($C_1$-$C_6$ alkyl);

$R^4$ is $C_1$-$C_4$ alkyl;

$R^7$ is H or $C_1$-$C_4$ alkyl;

$R^8$ is H or $C_1$-$C_4$ alkyl; or $R^7$ and $R^8$ taken together from the nitrogen they are attached form a 4 to 8 membered heterocycle containing 1 to 3 heteroatoms selected from N, S, and O, wherein said heterocycle is optionally substituted with one or more halogen or $C_1$-$C_4$ alkyl;

$R^9$ is H, $C_1$-$C_4$ alkyl optionally substituted with one or more halogen, one or more hydroxy, $C_1$-$C_4$alkoxy or 5 to 6 membered heterocycle;

$R^{10}$ is H, $C_1$-$C_4$ alkyl optionally substituted with one or more halogen, $C_1$-$C_4$alkoxy or one or more hydroxy; and $R^{15}$ is a $C_1$-$C_6$ alkyl optional substituted with halogen, a $C_1$-$C_4$ alkoxy or a 4 to 7 membered heterocycle containing 1 to 3 heteroatom selected from N, S, and O, wherein said heterocycle is optionally substituted with one or more halogen or $C_1$-$C_4$ alkyl.

In yet another embodiment, a compound of Formula (I) or (II) above is described, wherein $R^2$ is (i) —OH, —CN, —C(O)NRR', —NRC(O)R$^{15}$, —OC(O)NRR', —NR$^9$R$^{10}$, —SO$_2$R$^{1a}$, —SO$_2$NRR', —OR$^{1a}$, 4 to 8 membered heterocycle containing 1 to 3 heteroatom selected from N, S, and O, ($C_1$-$C_4$)alkyl-OH, ($C_1$-$C_4$)alkyl-CN, ($C_1$-$C_4$)alkyl-C(O)NRR', ($C_1$-$C_4$)alkyl-NRC(O)R$^{15}$, ($C_1$-$C_4$)alkyl-OC(O)NRR', ($C_1$-$C_4$)alkyl-NR$^9$R$^{10}$, ($C_1$-$C_4$)alkyl-SO$_2$R$^{1a}$, ($C_1$-$C_4$)alkyl-SO$_2$NRR', ($C_1$-$C_4$)alkyl-OR$^{1a}$, or ($C_1$-$C_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O($C_1$-$C_4$)alkyl, oxo (=O), —S(O)$_2$($C_1$-$C_4$) alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with one or more halogen or $C_1$-$C_4$ alkyl;

(ii) a 4 to 8 membered heterocycle containing 1 to 3 heteroatom selected from N, S, and O or ($C_1$-$C_4$)alkyl-4 to 8 membered heterocycle containing 1 to 3 heteroatom selected from N, S, and O, wherein said heterocycles are substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl; or (iii) a 4 to 8 membered heterocycle containing 1 to 3 heteroatom selected from N, S, and O, or a ($C_1$-$C_4$) alkyl-4 to 8 membered heterocycle containing 1 to 3 heteroatom selected from N, S, and O, wherein said heterocycles are fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$alkoxy, oxo (=O), or $C_1$-$C_4$haloalkyl; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^{1a}$ is (a) $C_1$-$C_4$alkyl, ($C_1$-$C_4$)alkyl-OH, ($C_1$-$C_4$)alkyl-$C_1$-$C_4$alkoxy, ($C_2$-$C_4$)alkyl-NR$^9$R$^{10}$, —CONRR', ($C_1$-$C_4$) alkyl-CONRR', a 4 to 8 membered heterocycle containing 1 to 3 heteroatom selected from N, S, and O, or a ($C_1$-$C_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$ ($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with one or more halogen or $C_1$-$C_4$ alkyl;

(b) a 4 to 8 membered heterocycle containing 1 to 3 heteroatom selected from N, S, and O or ($C_1$-$C_4$)alkyl-4 to 8 membered heterocycle containing 1 to 3 heteroatom selected from N, S, and O, wherein said heterocycles are optionally substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl; or (c) a 4 to 8 membered heterocycle containing 1 to 3 heteroatom selected from N, S, and O, or a ($C_1$-$C_4$) alkyl-4 to 8 membered heterocycle containing 1 to 3 heteroatom selected from N, S, and O, wherein said heterocycles are optionally fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

R is H, $C_1$-$C_6$alkyl optionally substituted with at least one halogen, hydroxyl, or alkoxy R' is a $C_1$-$C_6$alkyl optional substituted with halogen, a $C_1$-$C_4$ alkoxy or a 4 to 7 membered heterocycle containing 1 to 3 heteroatom selected from N, S, and O, wherein said heterocycle is optionally substituted with at least one substituent selected from the group consisting of halogen and $C_1$-$C_4$ alkyl; or R and R' taken together with the nitrogen to which they are attached form a 4 to 8 membered heterocycle containing 1 to 3 heteroatom selected from N, S, and O, wherein said heterocycle is optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with at least one halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is substituted with a spiro group, wherein said spiro group is a 3 to 6 membered cycloalkyl or 4 to 6 membered heterocycloalkyl containing 1 to 3 heteroatoms selected from N, S or O, wherein said spiro group can optionally be substituted by halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^3$ is $C_1$-$C_6$alkyl optionally substituted with at least one substituent selected from the group consisting of OH, O($C_1$-$C_4$alkyl), —NR$^7$R$^8$, and S($C_1$-$C_6$ alkyl);

$R^4$ is methyl;

$R^7$ is H or $C_1$-$C_4$ alkyl;

$R^8$ is H or $C_1$-$C_4$ alkyl; or $R^7$ and $R^8$ taken together from the nitrogen they are attached form a 4 to 8 membered heterocycle containing 1 to 3 heteroatoms selected from N, S, and O, wherein said heterocycle is optionally substituted with one or more halogen or $C_1$-$C_4$ alkyl;

$R^9$ is H, $C_1$-$C_4$ alkyl optionally substituted with one or more halogen, one or more hydroxy, $C_1$-$C_4$alkoxy or 5 to 6 membered heterocycle;

$R^{10}$ is H, $C_1$-$C_4$ alkyl optionally substituted with one or more halogen, $C_1$-$C_4$alkoxy or one or more hydroxy; and $R^{15}$ is a $C_1$-$C_4$ alkyl optional substituted with halogen, a $C_1$-$C_4$ alkoxy or a 4 to 7 membered heterocycle containing 1 to 3 heteroatom selected from N, S, and O, wherein said heterocycle is optionally substituted with one or more halogen or $C_1$-$C_4$ alkyl.

In yet another embodiment, a compound of Formula (I) or (II) above is described, wherein $R^2$ is (i) —OH, —CN, —C(O)NRR', —NRC(O)R$^{15}$, —OC(O)NRR', —NR$^9$R$^{10}$, —SO$_2$R$^{1a}$, —SO$_2$NRR', —OR$^{1a}$, 4 to 8 membered heterocycle containing 1 to 3 heteroatom selected from N, S, and O, ($C_1$-$C_4$)alkyl-OH, ($C_1$-$C_4$)alkyl-CN, ($C_1$-$C_4$)alkyl-C(O)NRR', ($C_1$-$C_4$)alkyl-NRC(O)R$^{15}$, ($C_1$-$C_4$)alkyl-OC(O)NRR', ($C_1$-$C_4$)alkyl-NR$^9$R$^{10}$, ($C_1$-$C_4$)alkyl-SO$_2$R$^{1a}$, ($C_1$-$C_4$)alkyl-SO$_2$NRR', ($C_1$-$C_4$)alkyl-OR$^{1a}$, or ($C_1$-$C_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with one or more halogen or $C_1$-$C_4$ alkyl;

(ii) a 4 to 8 membered heterocycle containing 1 to 3 heteroatom selected from N, S, and O or ($C_1$-$C_4$)alkyl-4 to 8 membered heterocycle containing 1 to 3 heteroatom selected from N, S, and O, wherein said heterocycles are substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl; or (iii) a 4 to 8 membered heterocycle containing 1 to 3 heteroatom selected from N, S, and O, or a ($C_1$-$C_4$)alkyl-4 to 8 membered heterocycle containing 1 to 3 heteroatom selected from N, S, and O, wherein said heterocycles are fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$alkoxy, oxo (=O), or $C_1$-$C_4$haloalkyl; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^{1a}$ is (a) $C_1$-$C_4$alkyl, ($C_1$-$C_4$)alkyl-OH, ($C_1$-$C_4$)alkyl-$C_1$-$C_4$alkoxy, ($C_2$-$C_4$)alkyl-NR$^9$R$^{10}$, —CONRR', ($C_1$-$C_4$)alkyl-CONRR', a 4 to 8 membered heterocycle containing 1 to 3 heteroatom selected from N, S, and O, or a ($C_1$-$C_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with one or more halogen or $C_1$-$C_4$ alkyl;

(b) a 4 to 8 membered heterocycle containing 1 to 3 heteroatom selected from N, S, and O or ($C_1$-$C_4$)alkyl-4 to 8 membered heterocycle containing 1 to 3 heteroatom selected from N, S, and O, wherein said heterocycles are optionally substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl; or (c) a 4 to 8 membered heterocycle containing 1 to 3 heteroatom selected from N, S, and O, or a ($C_1$-$C_4$) alkyl-4 to 8 membered heterocycle containing 1 to 3 heteroatom selected from N, S, and O, wherein said heterocycles are optionally fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (=O), or $C_1$-$C_4$haloalkyl;

$R^3$ is $C_1$-$C_6$alkyl optionally substituted with at least one substituent selected from the group consisting of OH, O($C_1$-$C_4$alkyl), —$NR^7R^8$, and S($C_1$-$C_6$ alkyl);

$R^7$ is H or $C_1$-$C_4$ alkyl;
$R^8$ is H or $C_1$-$C_4$ alkyl; or $R^7$ and $R^8$ taken together form a 4 to 8 membered heterocycle containing 1 to 3 heteroatoms selected from N, S, and O, wherein said heterocycle is optionally substituted with one or more halogen or $C_1$-$C_4$ alkyl;

$R^4$ is methyl.

In yet another embodiment, a compound of Formula (I) or (II) above is described, wherein
$R^1$ is $C_1$-$C_4$ alkyl optionally substituted with $C_1$-$C_4$ alkoxy.

In yet another embodiment, a compound of Formula (I) or (II) above is described, wherein
$R^1$ is methyl.

In yet another embodiment, a compound of Formula (I) or (II) above is described, wherein the compound is represented by formula IIIa or IIIb:

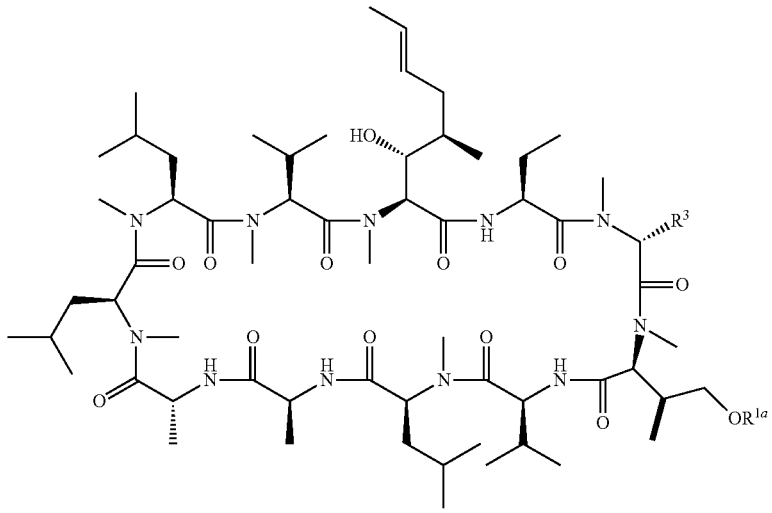

IIIa

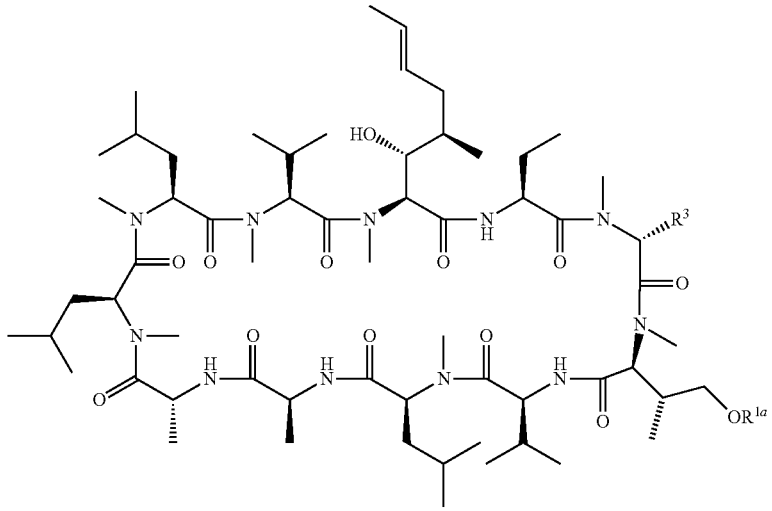

IIIb or a pharmaceutically acceptable salt thereof, for use in therapy, wherein
wherein,
$R^{1a}$ is
(a) $C_1$-$C_4$alkyl, ($C_1$-$C_4$)alkyl-OH, ($C_1$-$C_4$)alkyl-$C_1$-$C_4$alkoxy, ($C_2$-$C_4$)alkyl-$NR^9R^{10}$, —CONRR', ($C_1$-$C_4$) alkyl-CONRR', a 4 to 8 membered heterocycle containing 1 to 3 heteroatom selected from N, S, and O, or a (C$_1$-C$_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O(C$_1$-C$_4$)alkyl, oxo (=O), —S(O)$_2$(C$_1$-C$_4$)alkyl, —C(O)(C$_1$-C$_4$)alkyl, —C(O)$_2$(C$_1$-C$_4$)alkyl, C$_1$-C$_4$haloalkyl, C$_3$-C$_7$cycloalkyl, C$_1$-C$_4$ alkyl optionally substituted with C$_1$-C$_4$alkoxy and a 4 to 7 membered heterocycle containing 1 to 3 heteroatom selected from N, S, and O, wherein said heterocycle is optionally substituted with one or more halogen or C$_1$-C$_4$ alkyl;

(b) a 4 to 8 membered heterocycle containing 1 to 3 heteroatom selected from N, S, and O or (C$_1$-C$_4$)alkyl-4 to 8 membered heterocycle containing 1 to 3 heteroatom selected from N, S, and O, wherein said heterocycles are optionally substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or C$_1$-C$_4$ alkyl; or (c) a 4 to 8 membered heterocycle containing 1 to 3 heteroatom selected from N, S, and O, or a (C$_1$-C$_4$)alkyl-4 to 8 membered heterocycle containing 1 to 3 heteroatom selected from N, S, and O, wherein said heterocycles are optionally fused to a 5 to 6 membered heterocycle containing 1 to 3 heteroatom selected from N, S, or O, wherein said fused heterocycle is optionally substituted with halogen, C$_1$-C$_4$alkyl, C$_1$-C$_4$haloalkyl or C$_1$-C$_4$alkoxy; or wherein said heterocycles are fused to a 5 to 6 membered heteroaryl containing 1 to 3 heteroatom selected from N, S, or O, wherein said fused heteroaryl is optionally substituted with halogen, C$_1$-C$_4$alkyl, C$_1$-C$_4$alkoxy, oxo (=O), or C$_1$-C$_4$haloalkyl;

R$^3$ is C$_1$-C$_6$alkyl optionally substituted with at least one substituent selected from the group consisting of OH, O(C$_1$-C$_4$alkyl), —NR$^7$R$^8$, and S(C$_1$-C$_6$ alkyl);

R$^7$ is H or C$_1$-C$_4$ alkyl;

R$^8$ is H or C$_1$-C$_4$ alkyl; or

R$^7$ and R$^8$ taken together from the nitrogen they are attached form a 4 to 7 membered heterocycle containing 1 to 3 heteroatom selected from N, S, and O, wherein said heterocycle is optionally substituted with one or more halogen or C$_1$-C$_4$ alkyl;

R$^9$ is H, C$_1$-C$_4$ alkyl optionally substituted with one or more halogen or one or more hydroxy;

R$^{10}$ is H, C$_1$-C$_4$ alkyl optionally substituted with one or more halogen or one or more hydroxy; and R$^{15}$ is a C$_1$-C$_4$ alkyl optional substituted with halogen, a C$_1$-C$_4$ alkoxy or a 4 to 7 membered heterocycle containing 1 to 3 heteroatom selected from N, S, and O, wherein said heterocycle is optionally substituted with one or more halogen or C$_1$-C$_4$ alkyl.

In yet another embodiment, a compound of Formula (IIIa) or (IIIb) above is described, wherein R$^{1a}$ is (a) C$_1$-C$_4$alkyl, (C$_1$-C$_4$)alkyl-OH, (C$_1$-C$_4$)alkyl-C$_1$-C$_4$alkoxy, (C$_2$-C$_4$)alkyl-NR$^9$R$^{10}$, —CONRR', (C$_1$-C$_4$)alkyl-CONRR', a 4 to 8 membered heterocycle containing 1 to 3 heteroatom selected from N, S, and O, or a (C$_1$-C$_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O(C$_1$-C$_4$)alkyl, oxo (=O), —S(O)$_2$(C$_1$-C$_4$)alkyl, —C(O)(C$_1$-C$_4$)alkyl, —C(O)$_2$(C$_1$-C$_4$)alkyl, C$_1$-C$_4$haloalkyl, C$_3$-C$_7$cycloalkyl, C$_1$-C$_4$ alkyl optionally substituted with C$_1$-C$_4$alkoxy and a 4 to 7 membered heterocycle containing 1 to 3 heteroatom selected from N, S, and O, wherein said heterocycle is optionally substituted with one or more halogen or C$_1$-C$_4$ alkyl;

R$^3$ is C$_1$-C$_6$alkyl optionally substituted with at least one substituent selected from the group consisting of OH, O(C$_1$-C$_4$alkyl), —NR$^7$R$^8$, and S(C$_1$-C$_6$ alkyl);

R$^7$ is H or C$_1$-C$_4$ alkyl;

R$^8$ is H or C$_1$-C$_4$ alkyl; or

R$^7$ and R$^8$ taken together from the nitrogen they are attached form a 4 to 7 membered heterocycle containing 1 to 3 heteroatom selected from N, S, and O, wherein said heterocycle is optionally substituted with one or more halogen or C$_1$-C$_4$ alkyl.

In yet another embodiment, a compound of Formula (IIIa) or (IIIb) above is described, wherein R$^{1a}$ is (a) a 4 to 8 membered heterocycle containing 1 to 3 heteroatom selected from N, S, and O, or a (C$_1$-C$_4$)alkyl-4 to 8 membered heterocycle containing 1 to 3 heteroatom selected from N, S, and O, wherein said heterocycles are optionally substituted with at least one substituent selected from the group consisting of halogen, —OH, CN, —O(C$_1$-C$_4$)alkyl, oxo (=O), —S(O)$_2$(C$_1$-C$_4$)alkyl, —C(O)(C$_1$-C$_4$)alkyl, —C(O)$_2$(C$_1$-C$_4$)alkyl, C$_1$-C$_4$haloalkyl, C$_3$-C$_7$cycloalkyl, C$_1$-C$_4$ alkyl optionally substituted with C$_1$-C$_4$alkoxy and a 4 to 7 membered heterocycle containing 1 to 3 heteroatom selected from N, S, and O, wherein said heterocycle is optionally substituted with one or more halogen or C$_1$-C$_4$ alkyl;

R$^3$ is C$_1$-C$_6$alkyl optionally substituted with at least one substituent selected from the group consisting of OH, O(C$_1$-C$_4$alkyl), —NR$^7$R$^8$, and S(C$_1$-C$_6$ alkyl);

R$^7$ is H or C$_1$-C$_4$ alkyl;

R$^8$ is H or C$_1$-C$_4$ alkyl; or

R$^7$ and R$^8$ taken together from the nitrogen they are attached form a 4 to 7 membered heterocycle containing 1 to 3 heteroatom selected from N, S, and O, wherein said heterocycle is optionally substituted with one or more halogen or C$_1$-C$_4$ alkyl.

In yet another embodiment, a compound of Formula (IIIa) or (IIIb) above is described, wherein R$^{1a}$ is a 4 to 8 membered heterocycle containing 1 to 3 heteroatom selected from N, S, and O or (C$_1$-C$_4$)alkyl-4 to 8 membered heterocycle containing 1 to 3 heteroatom selected from N, S, and O, wherein said heterocycles are optionally substituted with a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or C$_1$-C$_4$ alkyl; or R$^3$ is C$_1$-C$_6$alkyl optionally substituted with at least one substituent selected from the group consisting of OH, O(C$_1$-C$_4$alkyl), —NR$^7$R$^8$, and S(C$_1$-C$_6$ alkyl);

R$^7$ is H or C$_1$-C$_4$ alkyl;

R$^8$ is H or C$_1$-C$_4$ alkyl; or

R$^7$ and R$^8$ taken together from the nitrogen they are attached form a 4 to 7 membered heterocycle containing 1 to 3 heteroatom selected from N, S, and O, wherein said heterocycle is optionally substituted with one or more halogen or C$_1$-C$_4$ alkyl.

In yet another embodiment, a compound of Formula (IIIa) or (IIIb) above is described, wherein R$^{1a}$ is (C$_1$-C$_4$)alkyl-OH, (C$_1$-C$_4$)alkyl-C$_1$-C$_4$ alkoxy, (C$_1$-C$_4$)alkyl-NR$^9$R$^{10}$, (C$_1$-C$_4$)alkyl-CONRR';

R$^3$ is C$_1$-C$_6$alkyl optionally substituted with at least one substituent selected from the group consisting of OH, O(C$_1$-C$_4$alkyl), —NR$^7$R$^8$, and S(C$_1$-C$_6$ alkyl);

R is H, C$_1$-C$_6$alkyl optionally substituted with at least one halogen, hydroxyl, or alkoxy R' is a $C_1$-$C_6$alkyl optional substituted with halogen, a $C_1$-$C_4$ alkoxy or a 4 to 7 membered heterocycle containing 1 to 3 heteroatom selected from N, S, and O, wherein said heterocycle is optionally substituted with at least one substituent selected from the group consisting of halogen and $C_1$-$C_4$ alkyl; or R and R' taken together with the nitrogen to which they are attached form a 4 to 8 membered heterocycle containing 1 to 3 heteroatom selected from N, S, and O, wherein said heterocycle is optionally substituted with at least one substituent selected from the group consisting of halogen, —OH, CN, —O($C_1$-$C_4$)alkyl, oxo (═O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$-$C_4$ alkyl optionally substituted with $C_1$-$C_4$alkoxy and a 4 to 7 membered heterocycle containing 1 to 3 heteroatom selected from N, S, and O, wherein said heterocycle is optionally substituted with at least one halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is substituted with a spiro group, wherein said spiro group is a 3 to 6 membered cycloalkyl or 4 to 6 membered heterocycloalkyl containing 1 to 3 heteroatoms selected from N, S or O, wherein said spiro group can optionally be substituted by halogen or $C_1$-$C_4$ alkyl; or R and R' taken together with the nitrogen to which they are attached form a 4 to 8 membered heterocycle containing 1 to 3 heteroatom selected from N, S, and O, wherein said heterocycle is fused to a 5 to 6 membered heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or wherein said heterocycles are fused to a 5 to 6 membered heteroaryl containing 1 to 3 heteroatom selected from N, S, or O, wherein said fused heteroaryl is optionally substituted with halogen, $C_1$-$C_4$alkyl, $C_1$-$C_4$alkoxy, oxo (═O), or $C_1$-$C_4$haloalkyl;

$R^7$ is H or $C_1$-$C_4$ alkyl;

$R^8$ is H or $C_1$-$C_4$ alkyl; or $R^7$ and $R^8$ taken together from the nitrogen they are attached form a 4 to 7 membered heterocycle containing 1 to 3 heteroatom selected from N, S, and O, wherein said heterocycle is optionally substituted with one or more halogen or $C_1$-$C_4$ alkyl;

$R^9$ is H, $C_1$-$C_4$ alkyl optionally substituted with one or more halogen or one or more hydroxy;

$R^{10}$ is H, $C_1$-$C_4$ alkyl optionally substituted with one or more halogen or one or more hydroxy.

In yet another embodiment, a compound of Formula (IIIa) or (IIIb) above is described, wherein $R^{1a}$ is ($C_1$-$C_4$)alkyl-$NR^9R^{10}$;

$R^3$ is $C_1$-$C_6$alkyl optionally substituted with at least one substituent selected from the group consisting of OH, O($C_1$-$C_4$alkyl), —$NR^7R^8$, and S($C_1$-$C_6$ alkyl);

$R^7$ is H or $C_1$-$C_4$ alkyl;

$R^8$ is H or $C_1$-$C_4$ alkyl; or $R^7$ and $R^8$ taken together from the nitrogen they are attached form a 4 to 7 membered heterocycle containing 1 to 3 heteroatom selected from N, S, and O, wherein said heterocycle is optionally substituted with one or more halogen or $C_1$-$C_4$ alkyl.

In yet another embodiment, a compound of Formula (IIIa) or (IIIb) above is described, $R^{1a}$ is H, —$CH_3$, —$CH_2CH_3$,

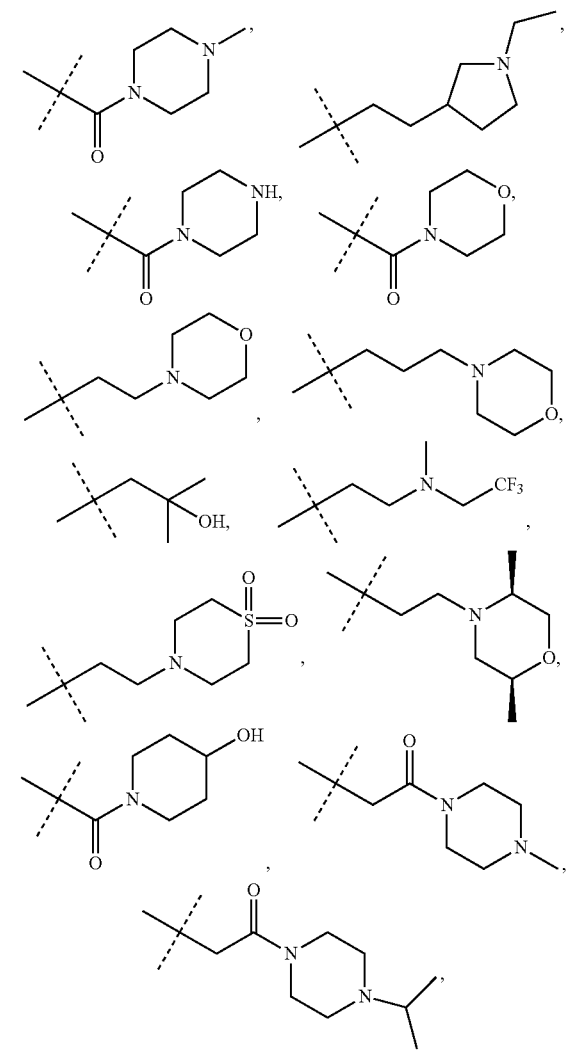

-continued

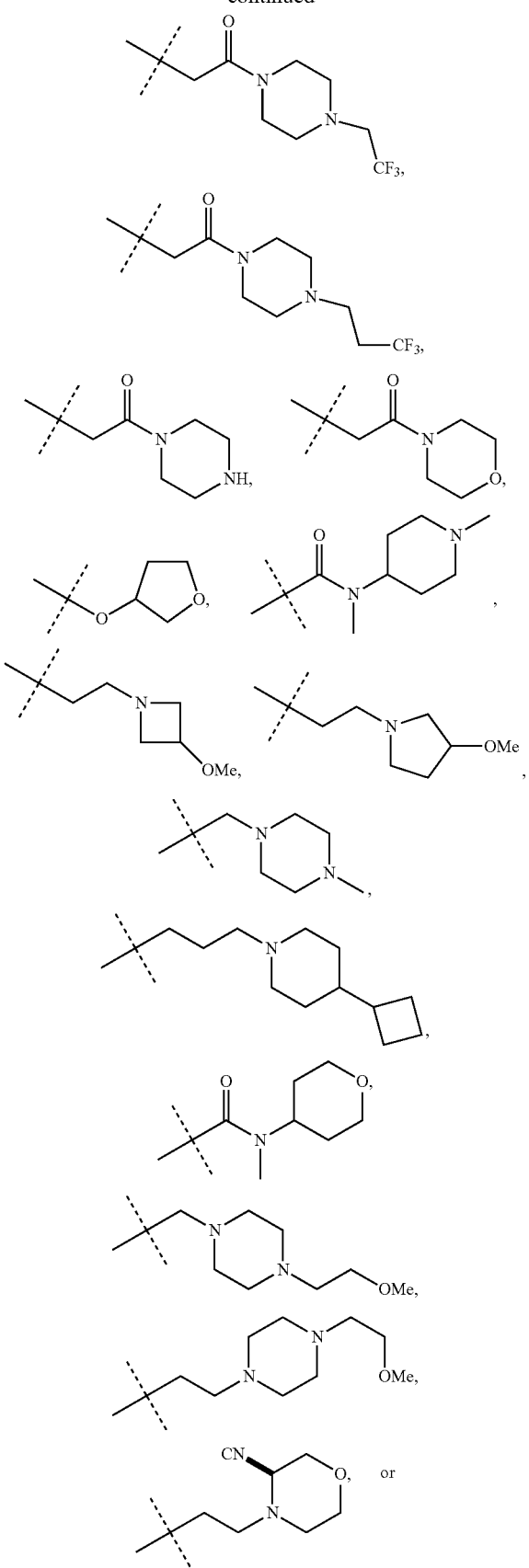

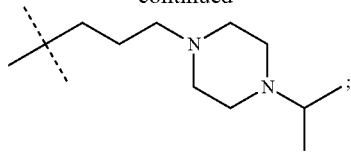

R[3] is $C_1$-$C_6$ alkyl optionally substituted with at least one substituent selected from the group consisting of OH, O($C_1$-$C_4$ alkyl), —NR[7]R[8], and S($C_1$-$C_6$ alkyl);

R[7] is H or $C_1$-$C_4$ alkyl;

R[8] is H or $C_1$-$C_4$ alkyl; or

R[7] and R[8] taken together from the nitrogen they are attached form a 4 to 7 membered heterocycle containing 1 to 3 heteroatom selected from N, S, and O, wherein said heterocycle is optionally substituted with one or more halogen or $C_1$-$C_4$ alkyl.

In yet another embodiment, a compound of Formula (IIIa) or (IIIb) above is described, R[1a] is H, —CH$_3$, —CH$_2$CH$_3$,

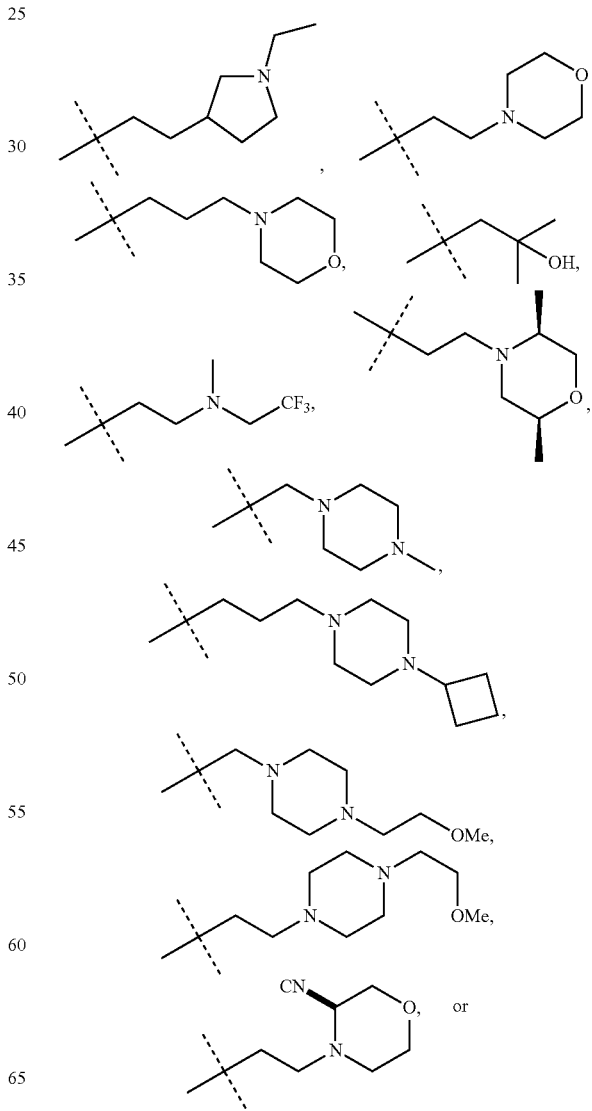

-continued

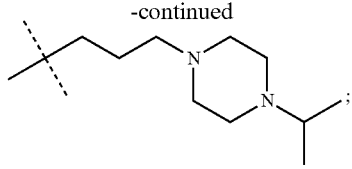

R³ is C₁-C₆alkyl optionally substituted with at least one substituent selected from the group consisting of OH, O(C₁-C₄alkyl), —NR⁷R⁸, and S(C₁-C₆ alkyl);
R⁷ is H or C₁-C₄ alkyl;
R⁸ is H or C₁-C₄ alkyl; or
R⁷ and R⁸ taken together from the nitrogen they are attached form a 4 to 7 membered heterocycle containing 1 to 3 heteroatom selected from N, S, and O, wherein said heterocycle is optionally substituted with one or more halogen or C₁-C₄ alkyl.

In yet another embodiment, a compound of Formula (IIIa) or (IIIb) above is described,
R¹ᵃ is H, —CH₃, —CH₂CH₃,

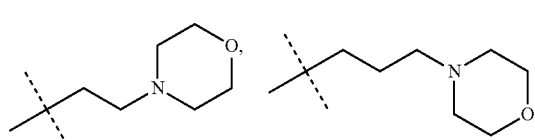

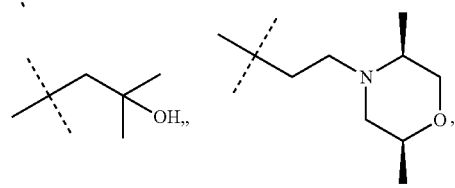

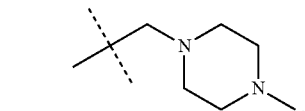

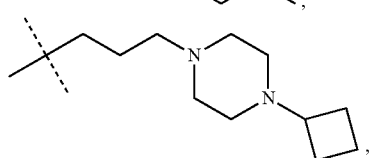

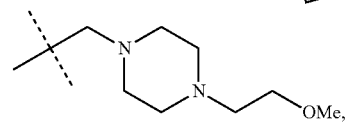

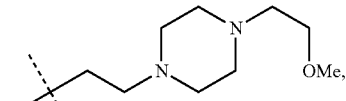

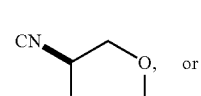

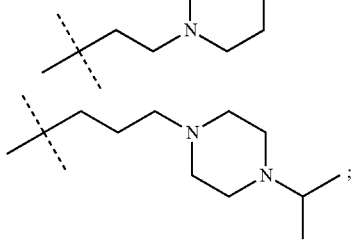

R³ is methyl, ethyl, isopropyl,

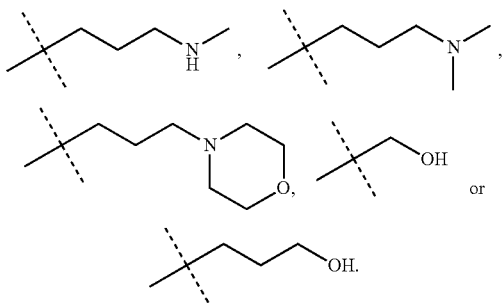

In yet another embodiment, a compound of Formula (IIIa) or (IIIb) above is described,
R¹ᵃ is

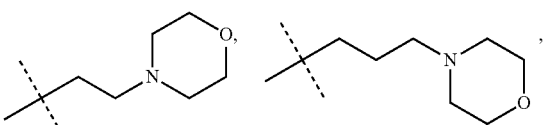

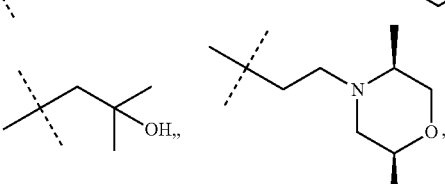

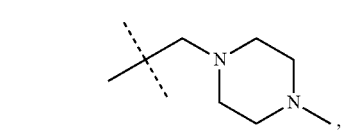

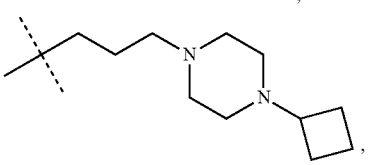

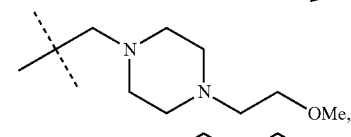

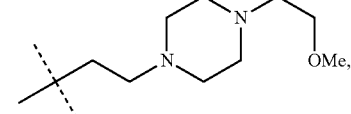

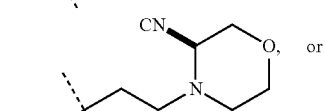

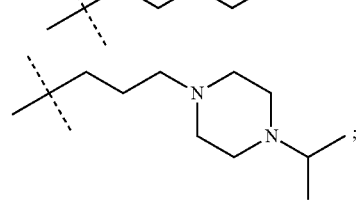

$R^3$ is methyl, ethyl, isopropyl,

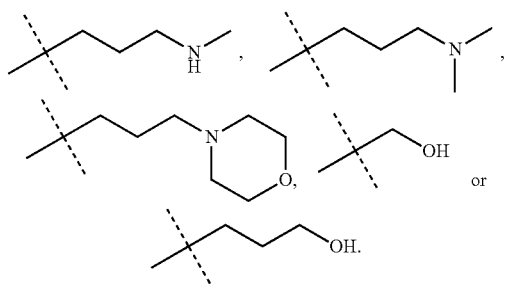

In yet another embodiment, a compound of Formula (I) or (II) above is described, wherein the compound is represented by formula IVa or IVb:

X is $NR^{101}$ or $CR^{102}R^{103}$;
p is 0, 1 or 2;
q is 0, 1 or 2;
u is 1, 2 or 3;
$R^{101}$ is —S(O)$_2$(C$_1$-C$_4$)alkyl, —C(O)(C$_1$-C$_4$)alkyl, —C(O)$_2$(C$_1$-C$_4$)alkyl, C$_1$-C$_4$haloalkyl C$_3$-C$_7$cycloalkyl, C$_1$-C$_4$ alkyl, a 4 to 7 membered heterocycle containing 1 to 3 heteroatom selected from N, S, and O, wherein said heterocycle is optionally substituted with one or more halogen or C$_1$-C$_4$ alkyl, or C$_0$-C$_4$alkyl optionally substituted by C$_1$-C$_4$alkoxy.
$R^{102}$ is H, —OH, CN, —O(C$_1$-C$_4$)alkyl, —S(O)$_2$(C$_1$-C$_4$) alkyl, —C(O)(C$_1$-C$_4$)alkyl, —C(O)$_2$(C$_1$-C$_4$)alkyl, C$_1$-C$_4$haloalkyl, C$_3$-C$_7$cycloalkyl, C$_1$-C$_4$ alkyl or a 4 to 7 membered heterocycle containing 1 to 3 heteroatom selected from N, S, and O, wherein said heterocycle is optionally substituted with one or more halogen or C$_1$-C$_4$ alkyl;

IVa

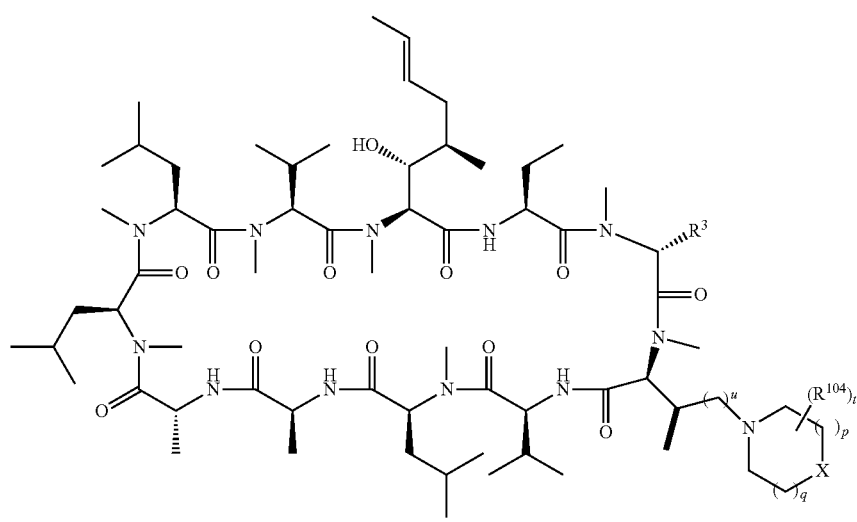

IVb

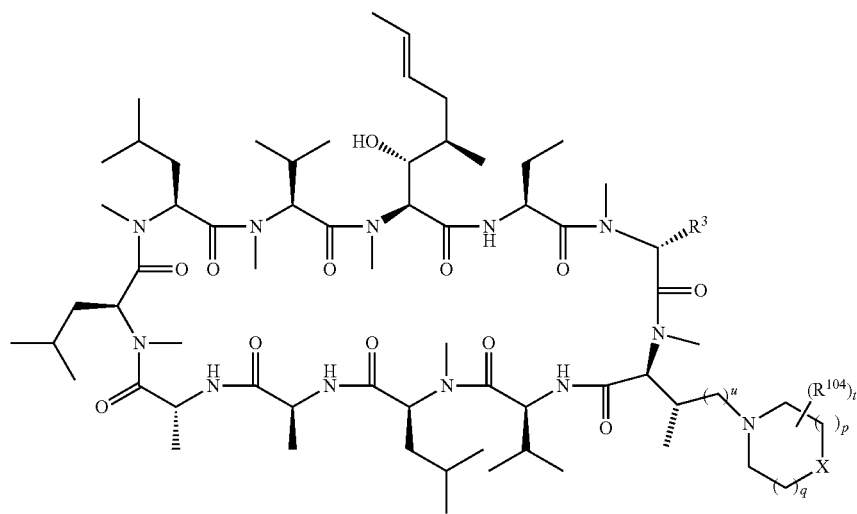

or a pharmaceutically acceptable salt thereof,
for use in therapy, wherein
$R^3$ is C$_1$-C$_6$alkyl optionally substituted with at least one substituent selected from the group consisting of OH, O(C$_1$-C$_4$alkyl), —NR$^7$R$^8$, and S(C$_1$-C$_6$ alkyl);

$R^{103}$ is H, halogen, —OH, CN, —C$_1$-C$_4$haloalkyl or C$_1$-C$_4$ alkyl; or
$R^{102}$ and $R^{103}$ taken together form an oxo group; or
$R^{102}$ and $R^{103}$ taken together may form a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl;

$R^{104}$ is halogen, —OH, —CN, —O($C_1$-$C_4$)alkyl, $C_1$-$C_4$haloalkyl, or $C_1$-$C_4$ alkyl optionally substituted by $C_1$-$C_4$ alkoxy;

t is 0, 1 or 2;

$R^{101}$ and $R^{104}$ taken together form 5 to 6 membered fused heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or $R^{101}$ and $R^{104}$ taken together form 5 to 6 membered fused heteroaryl containing 1 to 3 heteroatom selected from N, S, or O, wherein said fused heteroaryl is optionally substituted with halogen, $C_1$-$C_4$alkyl, $C_1$-$C_4$haloalkyl or $C_1$-$C_4$alkoxy;

$R^{104}$ and another $R^{104}$ may be taken together to form a bridge.

In yet another embodiment, wherein the compound is represented by formula IVa or IVb:

for use in therapy, wherein $R^3$ is $C_1$-$C_6$alkyl optionally substituted with at least one substituent selected from the group consisting of OH, O($C_1$-$C_4$alkyl), —$NR^7R^8$, and S($C_1$-$C_6$ alkyl);

X is O, $NR^{101}$ or $CR^{102}R^{103}$;

p is 0, 1 or 2;

q is 0, 1 or 2;

u is 1, 2 or 3;

$R^{101}$ is —$S(O)_2(C_1$-$C_4)$alkyl,
—$C(O)(C_1$-$C_4)$alkyl,
—$C(O)_2(C_1$-$C_4)$alkyl,
—$C_1$-$C_4$haloalkyl,
—$C_3$-$C_7$cycloalkyl,
—$C_1$-$C_4$ alkyl optionally substituted with $C_1$-$C_4$alkoxy, or
a 4 to 7 membered heterocycle containing 1 to 3 heteroatom selected from N, S, and O, wherein said heterocycle is optionally substituted with one or more halogen or $C_1$-$C_4$ alkyl;

$R^{102}$ is H, —OH, CN, —O($C_1$-$C_4$)alkyl, —$S(O)_2(C_1$-$C_4)$ alkyl, —$C(O)(C_1$-$C_4)$alkyl, —$C(O)_2(C_1$-$C_4)$alkyl, $C_1$-$C_4$haloalkyl, $C_3$-$C_7$cycloalkyl, $C_1$-$C_4$ alkyl or a 4 to

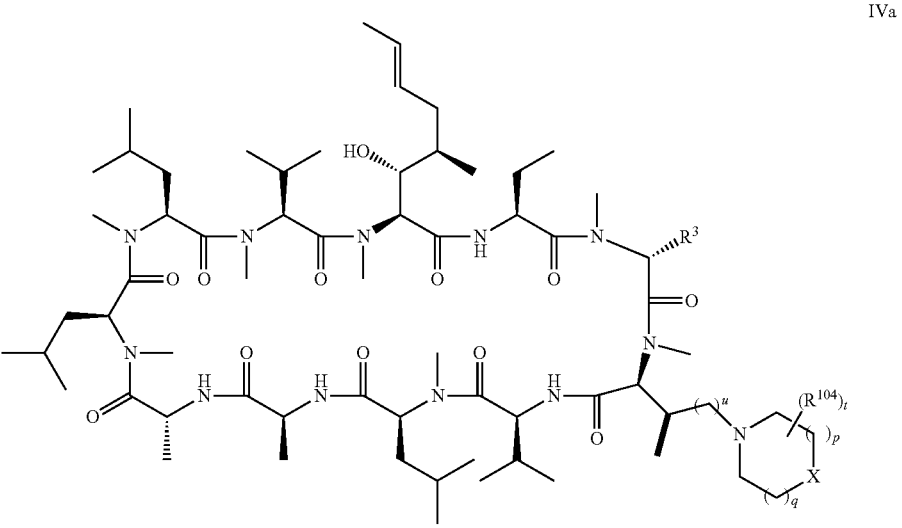

IVa

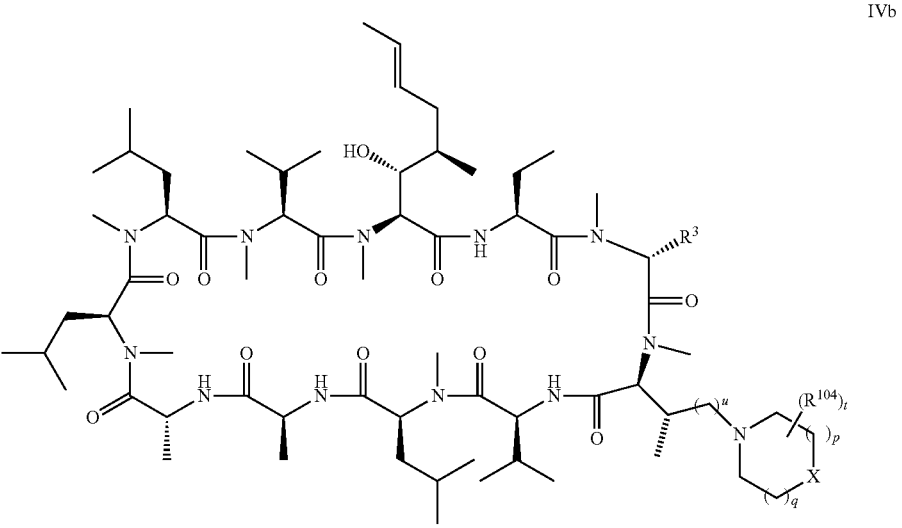

IVb or a pharmaceutically acceptable salt thereof, 7 membered heterocycle containing 1 to 3 heteroatom selected from N, S, and O, wherein said heterocycle is optionally substituted with one or more halogen or $C_1$-$C_4$ alkyl;

$R^{103}$ is H, halogen, —OH, CN, $C_1$-$C_4$haloalkyl or $C_1$-$C_4$ alkyl; or $R^{102}$ and $R^{103}$ taken together form an oxo group; or $R^{102}$ and $R^{103}$ taken together may form a Spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl;

$R^{104}$ is halogen, —OH, —CN, —O($C_1$-$C_4$)alkyl, $C_1$-$C_4$haloalkyl, or $C_1$-$C_4$ alkyl optionally substituted by $C_1$-$C_4$ alkoxy;

t is 0, 1 or 2;

$R^{101}$ and $R^{104}$ taken together form 5 to 6 membered fused heterocycle containing 1 to 3 heteroatom selected from N, S, or O, wherein said fused heterocycle is optionally substituted with halogen, $C_1$-$C_4$alkyl, $C_1$-$C_4$haloalkyl or $C_1$-$C_4$alkoxy; or $R^{101}$ and $R^{104}$ taken together form 5 to 6 membered fused heteroaryl containing 1 to 3 heteroatom selected from N, S, or O, wherein said fused heteroaryl is optionally substituted with halogen, $C_1$-$C_4$alkyl, $C_1$-$C_4$haloalkyl or $C_1$-$C_4$alkoxy;

$R^{104}$ and another $R^{104}$ may be taken together to form a bridge.

In yet another embodiment, a compound of Formula (IVa) or (IVb) above is described, wherein $R^3$ is $C_1$-$C_6$alkyl optionally substituted with at least one substituent selected from the group consisting of OH, O($C_1$-$C_4$alkyl), —NR$^7$R$^8$, and S($C_1$-$C_6$ alkyl);

X is NR$^{101}$ p is 1;

q is 1;

u is 1;

$R^{101}$ is —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_1$-$C_4$ alkyl, or $C_1$-$C_4$alkyl substituted by $C_1$-$C_4$alkoxy;

$R^{104}$ is halogen, —OH, CN, —O($C_1$-$C_4$)alkyl, $C_1$-$C_4$haloalkyl, or $C_1$-$C_4$ alkyl optionally substituted by $C_1$-$C_4$alkoxy;

t is 0, 1 or 2;

$R^{101}$ and $R^{104}$ taken together form 5 to 6 membered fused heteroaryl containing 1 to 3 heteroatom selected from N, S, or O, wherein said fused heteroaryl is optionally substituted with halogen, $C_1$-$C_4$alkyl, $C_1$-$C_4$haloalkyl or $C_1$-$C_4$alkoxy;

$R^{104}$ and another $R^{104}$ may be taken together to form a bridge.

In yet another embodiment, a compound of Formula (IVa) or (IVb) above is described, wherein $R^3$ is $C_1$-$C_6$ alkyl optionally substituted with at least one substituent selected from the group consisting of OH, O($C_1$-$C_4$alkyl), —NR$^7$R$^8$, and S($C_1$-$C_6$ alkyl);

X is NR$^{101}$ p is 1;

q is 1;

u is 1;

$R^{101}$ is —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl or $C_1$-$C_4$ alkyl, or $C_1$-$C_4$ substituted with $C_1$-$C_4$alkoxy $R^{104}$ is halogen, —OH, CN, —O($C_1$-$C_4$)alkyl, $C_1$-$C_4$haloalkyl, or $C_1$-$C_4$ alkyl;

t is 1 or 2;

$R^{101}$ and $R^{104}$ taken together form 5 to 6 membered fused heteroaryl containing 1 to 3 heteroatom selected from N, S, or O, wherein said fused heteroaryl is optionally substituted with halogen, $C_1$-$C_4$alkyl, $C_1$-$C_4$haloalkyl or $C_1$-$C_4$alkoxy.

In yet another embodiment, a compound of Formula (IVa) or (IVb) above is described, wherein $R^3$ is $C_1$-$C_6$ alkyl optionally substituted with at least one substituent selected from the group consisting of OH, O($C_1$-$C_4$alkyl), —NR$^7$R$^8$, and S($C_1$-$C_6$ alkyl);

X is NR$^{101}$ p is 1;

q is 1;

u is 1;

$R^{101}$ is $C_1$-$C_4$haloalkyl or $C_1$-$C_4$ alkyl substituted with $C_1$-$C_4$alkoxy t is 0.

In yet another embodiment, a compound of Formula (IVa) or (IVb) above is described, wherein X is O p is 1;

q is 1;

u is 1;

$R^{104}$ is halogen, —OH, CN, —O($C_1$-$C_4$)alkyl, $C_1$-$C_4$haloalkyl, or $C_1$-$C_4$ alkyl optionally substituted with $C_1$-$C_4$alkoxy;

t is 1 or 2.

In yet another embodiment, a compound of Formula (IVa) or (IVb) above is described, wherein X is CR$^{102}$R$^{103}$;

p is 0 or 1;

q is 0 or 1;

u is 1, 2 or 3;

$R^{102}$ is H, —OH, CN, —O($C_1$-$C_4$)alkyl, —S(O)$_2$($C_1$-$C_4$) alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, $C_1$—C alkyl or a 4 to 7 membered heterocycle containing 1 to 3 heteroatom selected from N, S, and O, wherein said heterocycle is optionally substituted with one or more halogen or $C_1$-$C_4$ alkyl;

$R^{103}$ is H, halogen, —OH, CN, —$C_1$-$C_4$haloalkyl or $C_1$-$C_4$ alkyl; or $R^{102}$ and $R^{103}$ taken together form an oxo group; or $R^{102}$ and $R^{103}$ taken together may form a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl;

$R^{104}$ is halogen, —OH, CN, —O($C_1$-$C_4$)alkyl, $C_1$-$C_4$haloalkyl, or $C_1$-$C_4$ alkyl;

t is 0, 1 or 2;

$R^{104}$ and another $R^{104}$ may be taken together to form a bridge.

In yet another embodiment, a compound of Formula (IVa) or (IVb) above is described, wherein X is CR$^{102}$R$^{103}$;

p is 0;

q is 0;

u is 1;

$R^{102}$ and $R^{103}$ taken together may form a spiro group, wherein said spiro group is a 3 to 6 membered cycloalkyl or 4 to 6 membered heterocycle containing 1 to 3 heteroatoms selected from N, S or O, wherein said spiro group can optionally be substituted by halogen or $C_1$-$C_4$ alkyl;

$R^{104}$ is halogen, —OH, CN, —O($C_1$-$C_4$)alkyl, $C_1$-$C_4$haloalkyl, or $C_1$-$C_4$ alkyl;
t is 0.
In yet another embodiment, a compound of Formula (I) or (II) above is described, wherein
$R^2$ is —OH,
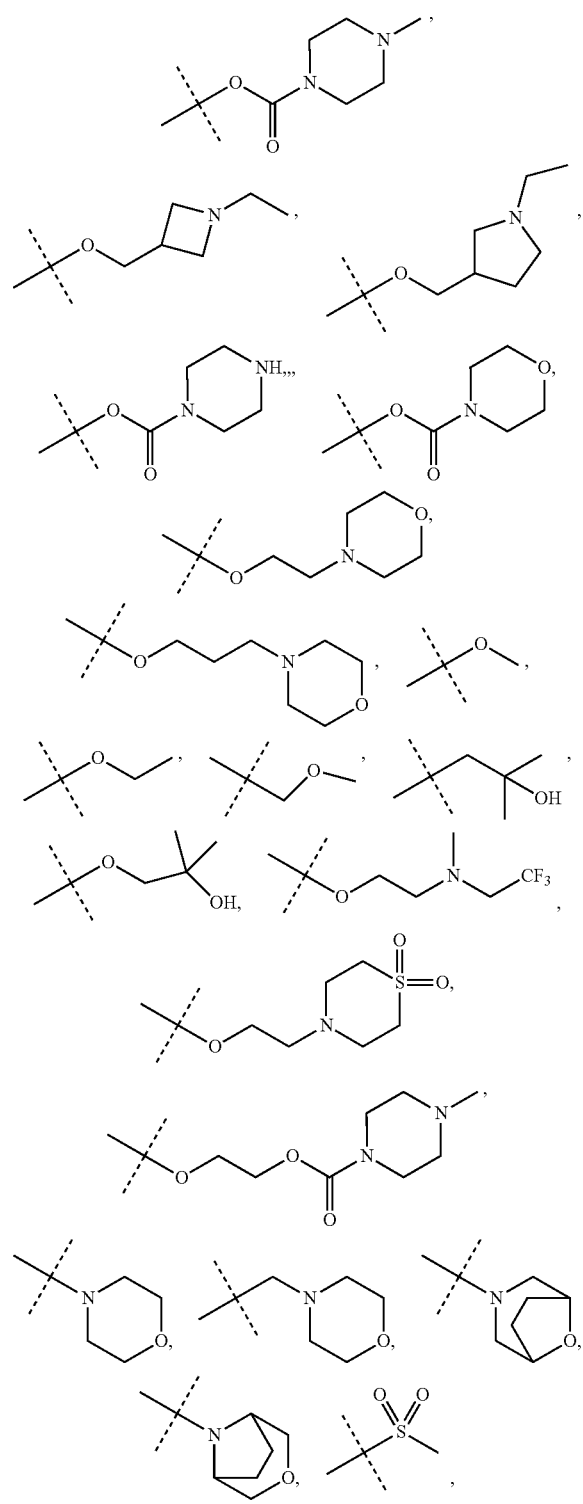
-continued
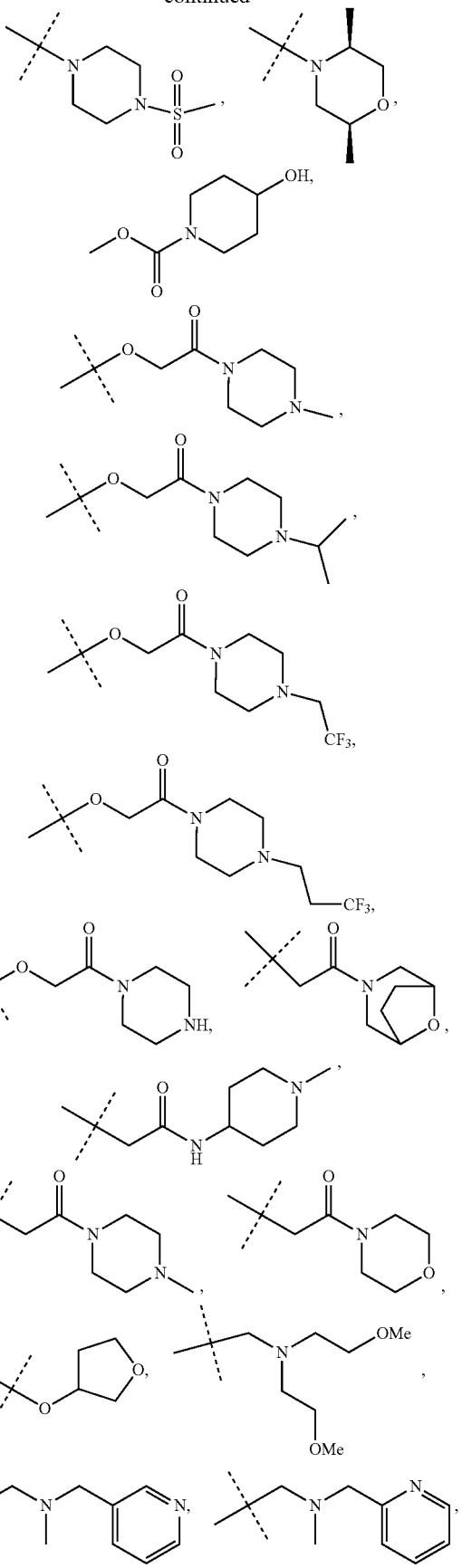

31
-continued
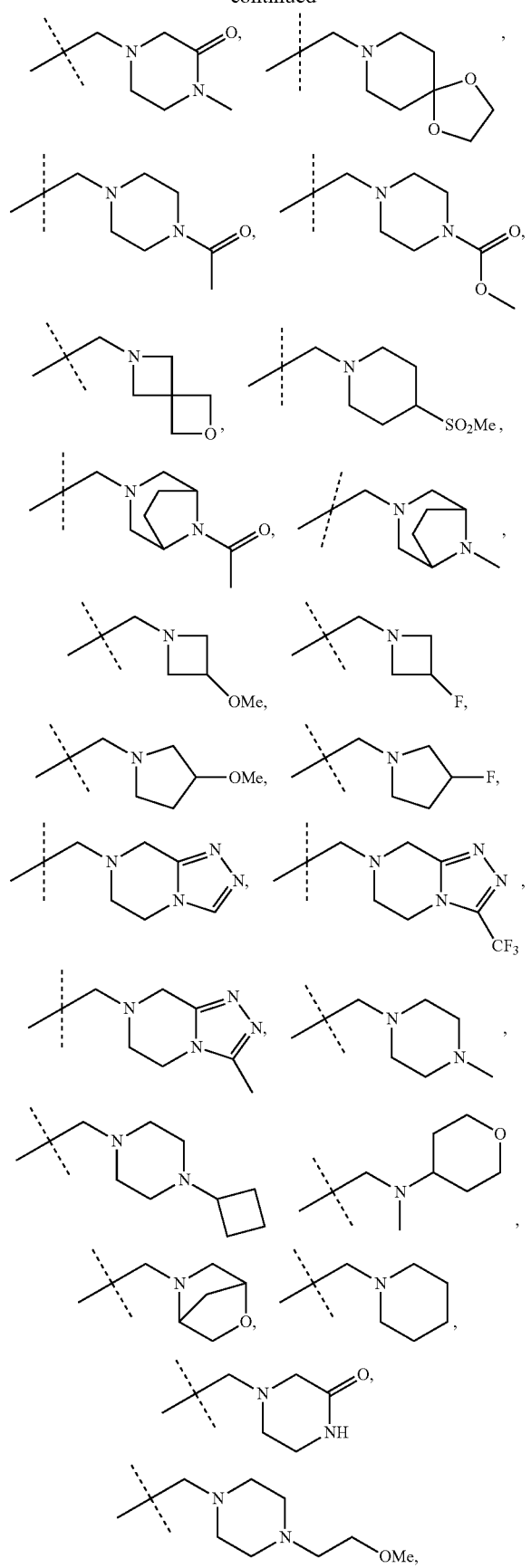
32
-continued
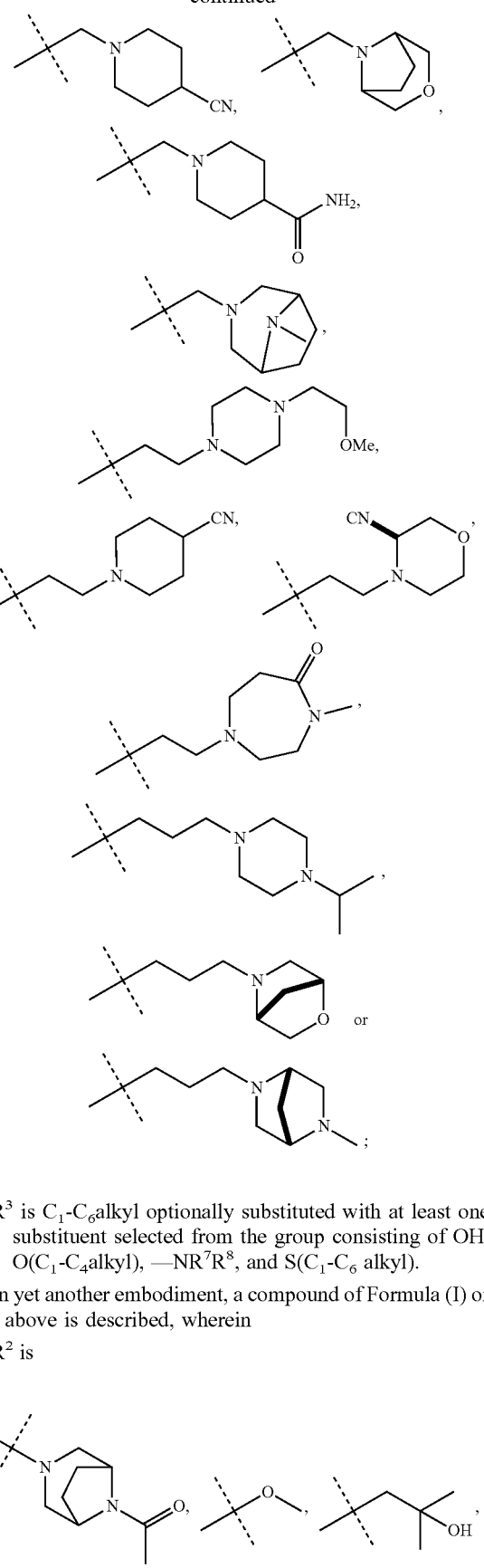
R³ is $C_1$-$C_6$alkyl optionally substituted with at least one substituent selected from the group consisting of OH, O($C_1$-$C_4$alkyl), —NR⁷R⁸, and S($C_1$-$C_6$ alkyl).
In yet another embodiment, a compound of Formula (I) or (II) above is described, wherein
R² is
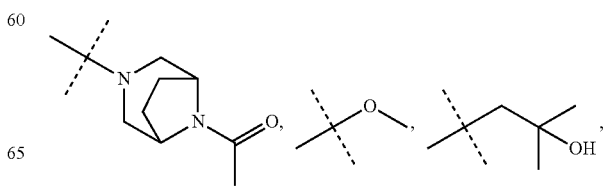

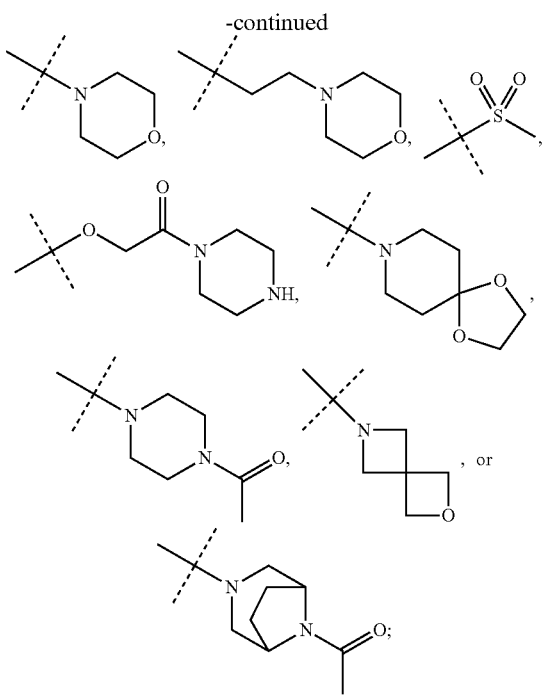

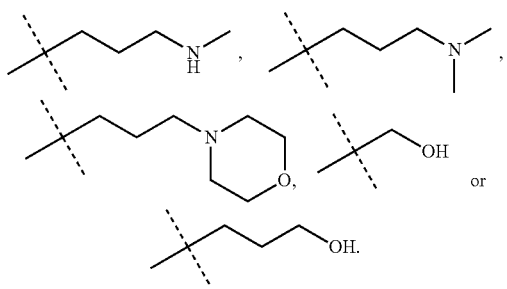

$R^3$ is $C_1$-$C_6$alkyl optionally substituted with at least one substituent selected from the group consisting of OH, O($C_1$-$C_4$alkyl), —$NR^7R^8$, and S($C_1$-$C_6$ alkyl).

In yet another embodiment, a compound of Formula (I), (II) above is described, wherein
$R^2$ is

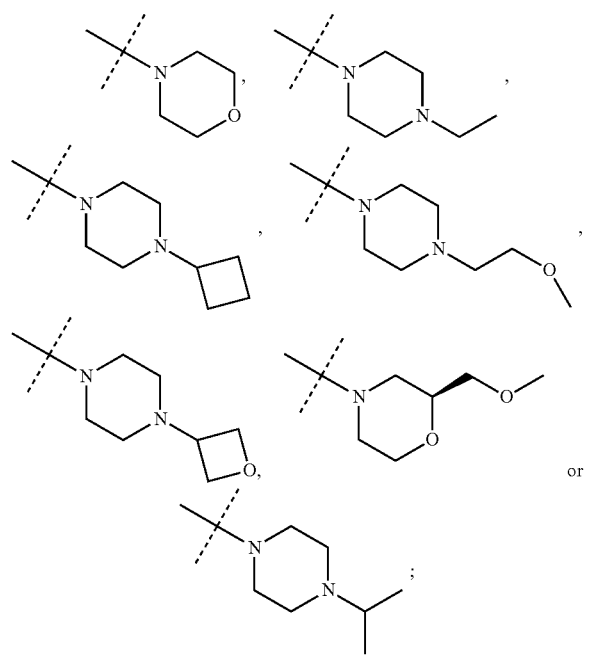

$R^3$ is $C_1$-$C_6$alkyl optionally substituted with at least one substituent selected from the group consisting of OH, O($C_1$-$C_4$alkyl), —$NR^7R^8$, and S($C_1$-$C_6$ alkyl).

In yet another embodiment, a compound of Formula (I), (II), (IIIa), (IIIb), (IVa) or (IVb) above is described, wherein $R^3$ is methyl, ethyl, isopropyl, In another embodiment, a pharmaceutical composition, comprising:
the compound according to any one of above embodiments of Formulae (I) to (IVb) or a pharmaceutically acceptable salt thereof, and
a pharmaceutically acceptable carrier.

In another embodiment, a pharmaceutical combination composition, comprising:
a therapeutically effective amount of the compound according to any one of above embodiments of Formulae (I) to (IVb) or a pharmaceutically acceptable salt thereof, and
one or more therapeutically active agents are selected from Interferons, ribavirin and ribavirin analogs, HCV NS3 protease inhibitors, HCV NS5a inhibitors, nucleoside and non-nucleoside NS5b inhibitors, HCV NS4a antagonists, TLR-7 agonists, HCV IRES inhibitors, pharmacokinetic enhancers, anti-fibrotic agents, or mixtures thereof.

In another embodiment, a pharmaceutical combination composition, wherein the one or more therapeutically active agents are selected from Interferons, ribavirin and ribavirin analogs, HCV NS3 protease inhibitors, HCV NS5a inhibitors, nucleoside and non-nucleoside NS5b inhibitors, or mixtures thereof.

In another embodiment, a pharmaceutical combination composition, wherein the one or more therapeutically active agents are selected from ribavirin and ribavirin analogs, HCV NS3 protease inhibitors, HCV NS5a inhibitors, nucleoside and non-nucleoside NS5b inhibitors, or mixtures thereof.

In another embodiment, a pharmaceutical combination composition, wherein the one or more therapeutically active agents are selected from ribavirin and ribavirin analogs, HCV NS3 protease inhibitors, HCV NS5a inhibitors, or mixtures thereof.

In another embodiment, a pharmaceutical combination composition, wherein the one or more therapeutically active agents are selected from ribavirin and ribavirin analogs, HCV NS3 protease inhibitors, or mixtures thereof.

In another embodiment, a pharmaceutical combination composition, wherein the one or more therapeutically active agents are selected from ribavirin and ribavirin analogs, HCV NS5a inhibitors, or mixtures thereof.

In another embodiment, a pharmaceutical combination composition, wherein the one or more therapeutically active agents are selected from HCV NS3 protease inhibitors, HCV NS5a inhibitors, or mixtures thereof.

In another embodiment, a method of modulating cyclophilins activity in a subject, comprising:
administering to the subject a therapeutically effective amount of the compound according to any one of Formulae (I) to (IVb) or a pharmaceutically acceptable salt thereof.

In another embodiment, a method of treating a disorder or a disease in a subject mediated by cyclophilins activity, comprising:
administering to the subject a therapeutically effective amount of the compound according to any one of above embodiments of Formulae (I) to (IVb) or a pharmaceutically acceptable salt thereof.

In another embodiment, the method above, wherein the disorder or the disease is selected from HCV infection, stroke, multiple sclerosis, HBV infection, HPV infection, asthma, cancer, muscular dystrophy, sepsis, ischemia/reperfusion injury, and heart failure.

In another embodiment, the method above, wherein the disorder or the disease is selected from HCV infection, HBV infection, or HPV infection.

In another embodiment, the method above, wherein the disorder or the disease is HCV infection.

In another embodiment, the method above, wherein the disorder or the disease is HBV infection.

In another embodiment, the method above, wherein the disorder or the disease is HPV infection.

In another embodiment, the method above, wherein the disorder or the disease is selected from stroke, ischemia/reperfusion injury and heart failure.

In another embodiment, the method above, wherein the disorder or the disease is selected from ischemia/reperfusion injury and heart failure.

In another embodiment, the method above, wherein the disorder or the disease is heart failure.

In another embodiment, a use of a compound according to any one of above embodiments of Formulae (I) to (IVb), or a pharmaceutically acceptable salt thereof, in the manufacture of a medicament for the treatment of a disorder or disease in a subject mediated by cyclophilins activity.

In another embodiment, a use of a compound according to any one of above embodiments of Formulae (I) to (IVb), or a pharmaceutically acceptable salt thereof, for the treatment of a disorder or disease in a subject mediated by cyclophilins activity.

In another embodiment, the use above, wherein the disorder or disease is selected from HCV infection, stroke, multiple sclerosis, HBV infection, HPV infection, asthma, cancer, muscular dystrophy, sepsis, ischemia/reperfusion injury, and heart failure.

In another embodiment, the use above, wherein the disorder or the disease is selected from HCV infection, HBV infection, or HPV infection.

In another embodiment, the use above, wherein the disorder or the disease is HCV infection.

In another embodiment, the use above, wherein the disorder or the disease is HBV infection.

In another embodiment, the use above, wherein the disorder or the disease is HPV infection.

In another embodiment, the use above, wherein the disorder or the disease is selected from stroke, ischemia/reperfusion injury and heart failure.

In another embodiment, the use above, wherein the disorder or the disease is selected from ischemia/reperfusion injury and heart failure.

In another embodiment, the use above, wherein the disorder or the disease is heart failure.

In another embodiment individual compounds according to the invention are those listed in the Examples section below.

In another embodiment the invention provides a compound according to anyone of the formulae I or II, which is selected from the group consisting of 2.1
3-[D-Ala]-4-[(2S,3S)-4-methoxy-3-methyl-2-(methylamino)butanoyl]-cyclosporin
2.2
3-[D-Ala]-4-[(2S,3R)-4-methoxy-3-methyl-2-(methylamino)butanoyl]-cyclosporin
2.3
3-[D-Ala]-4-[(2S,3R)-4-ethoxy-2-(ethylamino)-3-methylbutanoyl]-cyclosporin
2.4
3-[D-Ala]-4-[(2S,3S)-3-methyl-2-(methylamino)-4-(methylsulfonyl)butanoyl]-cyclosporin
2.5.1
3-[D-Ala]-4-[(2S,3S)-4-hydroxy-3-methyl-2-(methylamino)butanoyl]-cyclosporin
2.5.2
3-[D-Ala]-4-[(2S,3R)-3-methyl-2-(methylamino)-4-morpholinobutanoyl]-cyclosporin
2.5.3
3-[D-Ala]-4-[(2S,3R)-4-(8-oxa-3-azabicyclo[3.2.1]octan-3-yl)-3-methyl-2-(methylamino)butanoyl]-cyclosporin
2.5.4
3-[D-Ala]-4-[(2S,3R)-4-(3-oxa-8-azabicyclo[3.2.1]octan-8-yl)-3-methyl-2-(methylamino)butanoyl]-cyclosporin
2.5.5
3-[D-Ala]-4-[(2S,3R)-3-methyl-2-(methylamino)-4-(4-(methylsulfonyl)piperazin-1-yl)butanoyl]-cyclosporin
2.5.6
3-[D-Ala]-4-[(2S,3R)-4-((2S,5S)-2,5-dimethylmorpholino)-3-methyl-2-(methylamino)butanoyl]-cyclosporin
2.5.7
3-[D-Ala]-4-[(2S,3S)-3-methyl-2-(methylamino)-4-((morpholine-4-carbonyl)oxy)butanoyl]-cyclosporin
2.5.8
3-[D-Ala]-4-[(2S,3S)-4-((4-hydroxypiperidine-1-carbonyl)oxy)-3-methyl-2-(methylamino)butanoyl]-cyclosporin
2.5.9
3-[D-Ala]-4-[(2S,3S)-3-methyl-2-(methylamino)-4-((4-methylpiperazine-1-carbonyl)oxy)butanoyl]-cyclosporin
2.5.10
3-[D-Ala]-4[(2S,3R)-2-Amino-4-[4-(2-methoxy-ethyl)-piperazin-1-yl]-3-methyl-butanoyl]-cyclosporin
2.5.11
3-[D-Ala]-4[(2S,3R)-2-Amino-3-methyl-4-(4-oxetan-3-yl-piperazin-1-yl)]-butanoyl]-cyclosporin
2.5.12
3-[D-Ala]-4[(2S,3R)-2-Amino-4-(4-isopropyl-piperazin-1-yl)-butanoyl]-cyclosporin
2.5.13
3-[D-Ala]-4[(2S,3R)-2-Amino-4-(4-ethyl-piperazin-1-yl)-butanoyl]-cyclosporin
2.5.14
3-[D-Ala]-4[(2S,3R)-2-Amino-4-(4-cyclobutyl-piperazin-1-yl)-butanoyl]-cyclosporin
2.5.15
1-dihydro-3-[D-Ala]-4[(2S,3R)-2-Amino-4-(4-cyclobutyl-piperazin-1-yl)-butanoyl]-cyclosporin
2.5.16
3-[D-Ala]-4-[(2S,3R)-3-methyl-2-(methylamino)-4-(2-oxa-6-azaspiro[3.3]heptan-6-yl)butanoyl]-cyclosporin
2.5.17
3-[D-Ala]-4-[(2S,3R)-4-(3-methoxyazetidin-1-yl)-3-methyl-2-(methylamino)butanoyl]-cyclosporin
2.5.18
3-[D-Ala]-4-[(2S,3R)-4-(3,3-difluoropyrrolidin-1-yl)-3-methyl-2-(methylamino)butanoyl]-cyclosporin 2.5.19
3-[D-Ala]-4-[(2S,3R)-3-methyl-2-(methylamino)-4-(3-(trifluoromethyl)-5,6-dihydro-[1,2,4]triazolo[4,3-a]pyrazin-7(8H)-yl)butanoyl]-cyclosporin
2.5.20
3-[D-Ala]-4-[(2S,3R)-3-methyl-2-(methylamino)-4-(4-(methylsulfonyl)piperidin-1-yl)butanoyl]-cyclosporin
2.5.21
3-[D-Ala]-4-[(2S,3R)-3-methyl-2-(methylamino)-4-(1,4-oxazepan-4-yl)butanoyl]-cyclosporin
2.5.22
3-[D-Ala]-4-[(2S,3R)-4-((2-methoxyethyl)(methyl)amino)-3-methyl-2-(methylamino)butanoyl]-cyclosporin
2.5.23
3-[D-Ala]-4-[(2S,3R)-4-(4-acetylpiperazin-1-yl)-3-methyl-2-(methylamino)butanoyl]-cyclosporin
2.5.24
3-[D-Ala]-4-[(2S,3S)-4-((4-ethylpiperazine-1-carbonyl)oxy)-3-methyl-2-(methylamino)butanoyl]-cyclosporin
2.5.25
3-[D-Ala]-4-[(2S,3R)-3-methyl-4-(methyl(pyridin-3-ylmethyl)amino)-2-(methylamino)butanoyl]-cyclosporin
2.5.26
3-[D-Ala]-4-[(2S,3R)-4-(4-cyanopiperidin-1-yl)-3-methyl-2-(methylamino)butanoyl]-cyclosporin
2.5.27
3-[D-Ala]-4-[(2S,3R)-4-((2-(dimethylamino)-2-oxoethyl)(methyl)amino)-3-methyl-2-(methylamino)butanoyl]-cyclosporin
2.5.28
3-[D-Ala]-4-[(2S,3R)-3-methyl-2-(methylamino)-4-(1,4-dioxa-8-azaspiro[4.5]decan-8-yl)butanoyl]-cyclosporin
2.5.29
3-[D-Ala]-4-[(2S,3R)-3-methyl-2-(methylamino)-4-(4-methylpiperazin-1-yl)butanoyl]-cyclosporin
2.5.30
3-[D-Ala]-4-[(2S,3R)-3-methyl-2-(methylamino)-4-(3-oxopiperazin-1-yl)butanoyl]-cyclosporin
2.5.31
3-[D-Ala]-4-[(2S,3R)-4-(4-(ethoxycarbonyl)piperazin-1-yl)-3-methyl-2-(methylamino)butanoyl]-cyclosporin
2.5.32
3-[D-Ala]-4-[(2S,3S)-3-methyl-4-((methyl(1-methylpiperidin-4-yl)carbamoyl)oxy)-2-(methylamino)butanoyl]-cyclosporin
2.5.33
3-[D-Ala]-4-[(2S,3R)-3-methyl-2-(methylamino)-4-(2-oxa-6-azaspiro[3.4]octan-6-yl)butanoyl]-cyclosporin
2.5.34
3-[D-Ala]-4-[(2S,3R)-4-((S)-2-(methoxymethyl)morpholino)-3-methyl-2-(methylamino)butanoyl]-cyclosporin
2.5.35
1-dihydro-3-[D-Ala]-4-[(2S,3R)-4-(4-(2-methoxyethyl)piperazin-1-yl)-3-methyl-2-(methylamino)butanoyl]-cyclosporin
2.6.1
3-[D-Ala]-4-[(2S,3S)-3-methyl-2-(methylamino)-4-(2-oxo-2-(piperazin-1-yl)ethoxy)butanoyl]-cyclosporin
2.6.2
3-[D-Ala]-4-[(2S,3S)-4-(2-(4-cyclohexylpiperazin-1-yl)-2-oxoethoxy)-3-methyl-2-(methylamino)butanoyl]-cyclosporin
2.6.3
3-[D-Ala]-4-[(2S,3S)-3-methyl-2-(methylamino)-4-(2-(4-methylpiperazin-1-yl)-2-oxoethoxy)butanoyl]-cyclosporin
2.6.4
3-[D-Ala]-4-[(2S,3S)-4-(2-(4-isopropylpiperazin-1-yl)-2-oxoethoxy)-3-methyl-2-(methylamino)butanoyl]-cyclosporin
2.6.5
3-[D-Ala]-4-[(2S,3S)-3-methyl-2-(methylamino)-4-(2-oxo-2-(4-(2,2,2-trifluoroethyl)piperazin-1-yl)ethoxy)butanoyl]-cyclosporin
2.6.6
3-[D-Ala]-4-[(2S,3S)-3-methyl-2-(methylamino)-4-(2-oxo-2-(4-(3,3,3-trifluoropropyl)piperazin-1-yl)ethoxy)butanoyl]-cyclosporin
2.7
3-[D-Ala]-4-[(2S,3S)-4-(2-hydroxy-2-methylpropoxy)-3-methyl-2-(methylamino)butanoyl]-cyclosporin
2.8.1
3-[D-Ala]-4-[(2S,3S)-3-methyl-2-(methylamino)-4-(2-morpholinoethoxy)butanoyl]-cyclosporin
2.8.2
3-[D-Ala]-4-[(2S,3S)-4-(2-(1,1-dioxidothiomorpholino)ethoxy)-3-methyl-2-(methylamino)butanoyl]-cyclosporin
2.8.3
3-[D-Ala]-4-[(2S,3S)-3-methyl-4-(2-(methyl(2,2,2-trifluoroethyl)amino)ethoxy)-2-(methylamino)butanoyl]-cyclosporin
2.8.4
3-[D-Ala]-4-[(2S,3S)-4-(2-((2R,5R)-2,5-dimethylmorpholino)ethoxy)-3-methyl-2-(methylamino)butanoyl]-cyclosporin
2.8.5
3-[D-Ala]-4-[(2S,3S)-4-(2-(4-isopropylpiperazin-1-yl)ethoxy)-3-methyl-2-(methylamino)butanoyl]-cyclosporin
2.8.6
3-[D-Ala]-4-[(2S,3S)-3-methyl-2-(methylamino)-4-(2-((S)-3-methylmorpholino)ethoxy)butanoyl]-cyclosporin
2.8.7
3-[D-Ala]-4-[(2S,3S)-4-(2-((S)-3-methoxypyrrolidin-1-yl)ethoxy)-3-methyl-2-(methylamino)butanoyl]-cyclosporin
2.8.8
3-[D-Ala]-4-[(2S,3S)-4-(2-(4-cyclobutylpiperazin-1-yl)ethoxy)-3-methyl-2-(methylamino)butanoyl]-cyclosporin
2.8.9
3-[D-Ala]-4-[(2S,3S)-4-(2-(3-methoxyazetidin-1-yl)ethoxy)-3-methyl-2-(methylamino)butanoyl]-cyclosporin
2.8.10
1-dihydro-3-[D-Ala]-4-[(2S,3S)-3-methyl-2-(methylamino)-4-(2-morpholinoethoxy)butanoyl]-cyclosporin
2.8.11
3-[D-Ala]-4-[(2S,3S)-3-methyl-2-(methylamino)-4-(2-((S)-3-oxotetrahydro-1H-oxazolo[3,4-a]pyrazin-7(3H)-yl)ethoxy)butanoyl]-cyclosporin
2.9.
3-[D-Ala]-4-[(2S,3S)-3-methyl-2-(methylamino)-4-(2-((4-methylpiperazine-1-carbonyl)oxy)ethoxy)butanoyl]-cyclosporin
2.10
3-[D-Ala]-4-[(2S,3R)-4-cyano-3-methyl-2-(methylamino)butanoyl]-cyclosporin
2.11
3-[D-Ala]-4-[(S)-4-methoxy-3-(methoxymethyl)-2-(methylamino)butanoyl]-cyclosporin
2.12
3-[D-Ala]-4-[(2S,3R)-6-hydroxy-3,6-dimethyl-2-(methylamino)heptanoyl]-cyclosporin 2.12.2
3-[D-Ala]-4-[(2S,3R)-3,6-dimethyl-2-(methylamino)-6-((4-methylpiperazine-1-carbonyl)oxy)heptanoyl]-cyclosporin
2.13
3-[D-Ala]-4-[(2S,3R)-5-methoxy-3-methyl-2-(methylamino)pentanoyl]-cyclosporin
2.14.2
3-[D-Ala]-4-[(2S,3R)-6-(8-oxa-3-azabicyclo[3.2.1]octan-3-yl)-3-methyl-2-(methylamino)-6-oxohexanoyl]-cyclosporin
2.14.3
3-[D-Ala]-4-[(2S,3R)-3-methyl-2-(methylamino)-6-(4-methylpiperazin-1-yl)-6-oxohexanoyl]-cyclosporin
2.14.4
3-[D-Ala]-4-[(2S,3R)-3-methyl-2-(methylamino)-6-morpholino-6-oxohexanoyl]-cyclosporin
2.16
3-[D-Ala]-4-[(2S,3S)-3-methyl-2-(methylamino)-4-MS)-tetrahydrofuran-3-yl)oxy)butanoyl]-cyclosporin
2.17.1
3-[D-Ala]-4[(2S,3S)-2-Amino-3-methyl-4-morpholin-4-yl-butanoyl]-cyclosporin
2.17.2
3-[D-Ala]-4[(2S,3S)-2-Amino-4-(4-ethyl-piperazin-1-yl)-3-methyl-butanoyl]-cyclosporin
2.17.3
3-[D-Ala]-4[(2S,3S)-2-Amino-4-(4-cyclobutyl-piperazin-1-yl)-3-methyl-butanoyl]-cyclosporin
2.17.4
3-[D-Ala]-4[(2S,3S)-2-Amino-4-[4-(2-methoxy-ethyl)-piperazin-1-yl]-3-methyl-butanoyl]-cyclosporin
2.17.5
3-[D-Ala]-4[(2S,3S)-2-Amino-3-methyl-4-(4-oxetan-3-yl-piperazin-1-yl)-butanoyl]-cyclosporin
2.17.6
1-dihydro-3-[D-Ala]-4[(2S,3S)-2-Amino-4-[4-(2-methoxyethyl)-piperazin-1-yl]-3-methyl-butanoyl]-cyclosporin
2.17.7
1-dihydro-3-[D-Ala]-4[(2S,3S)-2-Amino-3-methyl-4-morpholin-4-yl-butanoyl]-cyclosporin
2.17.8
3-[D-Ala]-4[(2S,3S)-2-Amino-4-((S)-2-methoxymethyl-morpholin-4-yl)-3-methyl-butanoyl]-cyclosporin
2.17.9
3-[D-Ala]-4-[(2S,3S)-3-methyl-2-(methylamino)-4-(4-(methylsulfonyl)piperazin-1-yl)butanoyl]-cyclosporin
2.17.10
3-[D-Ala]-4-[(2S,3S)-3-methyl-2-(methylamino)-4-((S)-3-oxotetrahydro-1H-oxazolo[3,4-a]pyrazin-7(3H)-yl)butanoyl]-cyclosporin
2.17.11
3-[D-Ala]-4-[(2S,3S)-4-((S)-2-(methoxymethyl)morpholino)-3-methyl-2-(methylamino)butanoyl]-cyclosporin
2.17.12
1-dihydro-3-[D-Ala]-4-[(2S,3S)-4-((S)-2-(methoxymethyl)morpholino)-3-methyl-2-(methylamino)butanoyl]-cyclosporin
2.17.13
3-[D-Ala]-4-[(2S,3R)-4-hydroxy-3-methyl-2-(methylamino)butanoyl]-cyclosporin
2.17.14
3-[D-Ala]-4-[(2S,3R)-4-((4-ethylpiperazine-1-carbonyl)oxy)-3-methyl-2-(methylamino)butanoyl]-cyclosporin
2.18.1
3-[D-Ala]-4-[(2S,3R)-3-methyl-2-(methylamino)-5-morpholinopentanoyl]-cyclosporin
2.18.2
3-[D-Ala]-4-[(2S,3R)-5-(4-cyanopiperidin-1-yl)-3-methyl-2-(methylamino)pentanoyl]-cyclosporin
2.18.3
3-[D-Ala]-4-[(2S,3R)-5-(4-(2-methoxyethyl)piperazin-1-yl)-3-methyl-2-(methylamino)pentanoyl]-cyclosporin
2.18.4
3-[D-Ala]-4-[(2S,3R)-3-methyl-2-(methylamino)-5-((S)-2-methylpiperidin-1-yl)pentanoyl]-cyclosporin
2.18.5
3-[D-Ala]-4-[(2S,3R)-5-(3-methoxyazetidin-1-yl)-3-methyl-2-(methylamino)pentanoyl]-cyclosporin
2.18.6
3-[D-Ala]-4-[(2S,3R)-5-(4-ethylpiperazin-1-yl)-3-methyl-2-(methylamino)pentanoyl]-cyclosporin
2.18.7
3-[D-Ala]-4-[(2S,3R)-5-((S)-3-methoxypyrrolidin-1-yl)-3-methyl-2-(methylamino)pentanoyl]-cyclosporin
2.18.8
3-[D-Ala]-4-[(2S,3R)-3-methyl-2-(methylamino)-5-(piperidin-1-yl)pentanoyl]-cyclosporin
2.18.9
3-[D-Ala]-4-[(2S,3R)-3-methyl-2-(methylamino)-5-((S)-3-oxotetrahydro-1H-oxazolo[3,4-a]pyrazin-7(3H)-yl)pentanoyl]-cyclosporin
2.18.10
3-[D-Ala]-4-[(2S,3R)-5-(4-cyclobutylpiperazin-1-yl)-3-methyl-2-(methylamino)pentanoyl]-cyclosporin
2.8.11
3-[D-Ala]-4-[(2S,3S)-3-methyl-2-(methylamino)-4-(2-((S)-3-oxotetrahydro-1H-oxazolo[3,4-a]pyrazin-7(3H)-yl)ethoxy)butanoyl]-cyclosporin
2.19.1
3-[D-Ala]-4-[(2S,3R)-3-methyl-2-(methylamino)-6-morpholinohexanoyl]-cyclosporin
2.19.2
3-[D-Ala]-4-[(2S,3R)-6-(4-carbamoylpiperidin-1-yl)-3-methyl-2-(methylamino)hexanoyl]-cyclosporin
2.19.3
3-[D-Ala]-4-(2S,3R)-3-methyl-6-(8-methyl-3,8-diazabicyclo[3.2.1]octan-3-yl)-2-(methylamino)hexanoyl]-cyclosporin
2.19.4
3-[D-Ala]-4-[(2S,3R)-6-(4-ethylpiperazin-1-yl)-3-methyl-2-(methylamino)hexanoyl]-cyclosporin
2.19.5
3-[D-Ala]-4-[(2S,3R)-6-(4-methoxypiperidin-1-yl)-3-methyl-2-(methylamino)hexanoyl]-cyclosporin
2.19.6
3-[D-Ala]-4-[(2S,3R)-6-(4-(2-methoxyethyl)piperazin-1-yl)-3-methyl-2-(methylamino)hexanoyl]-cyclosporin
2.19.7
3-[D-Ala]-4-[(2S,3R)-3-methyl-2-(methylamino)-6-((4-methylpiperazine-1-carbonyl)oxy)hexanoyl]-cyclosporin
2.19.8
3-[D-Ala]-4-[(2S,3R)-3-methyl-2-(methylamino)-6-(((1-methylpiperidin-4-yl)carbamoyl)oxy)hexanoyl]-cyclosporin
2.19.9
3-[D-Ala]-4-[(2S,3R)-3-methyl-6-((methyl(1-methylpiperidin-4-yl)carbamoyl)oxy)-2-(methylamino)hexanoyl]-cyclosporin 2.20.1
3-[D-Ala]-4-[(2S,3S)-4-(((S)-4-ethylmorpholin-2-yl)methoxy)-3-methyl-2-(methylamino)butanoyl]-cyclosporin
2.20.2
3-[D-Ala]-4-[(2S,3S)-4-(((S)-4-isopropylmorpholin-2-yl)methoxy)-3-methyl-2-(methylamino)butanoyl]-cyclosporin
2.21.1
3-[D-Ala]-4-[(2S,3R)-3-methoxy-2-(methylamino)-4-morpholinobutanoyl]-cyclosporin
2.21.2
3-[D-Ala]-4-[(2S,3S)-3-methoxy-2-(methylamino)-4-(pyrrolidin-1-yl)butanoyl]-cyclosporin
2.21.3
3-[D-Ala]-4-[(2S,3S)-3-methoxy-4-(4-(2-methoxyethyl)piperazin-1-yl)-2-(methylamino)butanoyl]-cyclosporin
3.1
3-[(R)-2-(methylamino)butanoic acid]-4-[(2S,3S)-4-methoxy-3-methyl-2-(methylamino)butanoyl]-cyclosporin
3.2.1
3-[(R)-2,5-bis(methylamino)pentanoyl]-4-[(2S,3S)-4-methoxy-3-methyl-2-(methylamino)butanoyl]-cyclosporin
3.2.2
3-[(R)-5-(dimethylamino)-2-(methylamino)pentanoyl]-4-[(2S,3S)-4-methoxy-3-methyl-2-(methylamino)butanoyl]-cyclosporin
3.2.3
3-[D-ser]-4-[(2S,3S)-4-methoxy-3-methyl-2-(methylamino)butanoyl]-cyclosporin
3.3
3-[(R)-3-methyl-2-(methylamino)butanoyl]-4-[(2S,3S)-4-methoxy-3-methyl-2-(methylamino)butanoyl]-cyclosporin
3.4.1
3-[(R)-5-hydroxy-2-(methylamino)pentanoyl]-4-[(2S,3S)-3-methyl-2-(methylamino)-4-(methylsulfonyl)butanoyl]-cyclosporin
3.4.2
3-[(R)-2-(methylamino)-5-morpholinopentanoyl]-4-[(2S,3S)-3-methyl-2-(methylamino)-4-(methylsulfonyl)butanoyl]-cyclosporin The term "compounds of the present invention" or "a compound of the present invention" refers to a compound as defined in any one of embodiments of Formulae (I) to (IVb).

DETAILED DESCRIPTION

The compounds as defined in embodiments may be synthesized by the general synthetic routes below, specific examples of which are described in more detail in the Examples.

Scheme A illustrated the general method for the synthesis of cyclosporine analog peptide skeleton. These cyclosporine analogs are derived from cyclosporine A and they differ from cyclosporine A mainly in P3-P4 moiety. Following literature procedures, the P1 hydroxyl in cyclosporine was acetylated and P3-P4 amino acid could be excised to provide key intermediate a-1. The addition of new P3 and P4 amino acids could be achieved by either stepwise coupling of P4 followed by P3 or directly coupling with P3-P4 dipeptide. The P2 acid and P3 amine on this linear peptide a-2 were then deprotected. The resulting amino acid was subjected to peptide coupling condition to provide macrocycle a-4. Scheme 2 and 4 described more details on these steps. The macrocycle a-4 could also serve as an advanced intermediate for further modification. Examples of amine-functionalized cyclosporin derivative synthesis were described in Scheme 5.

Scheme A

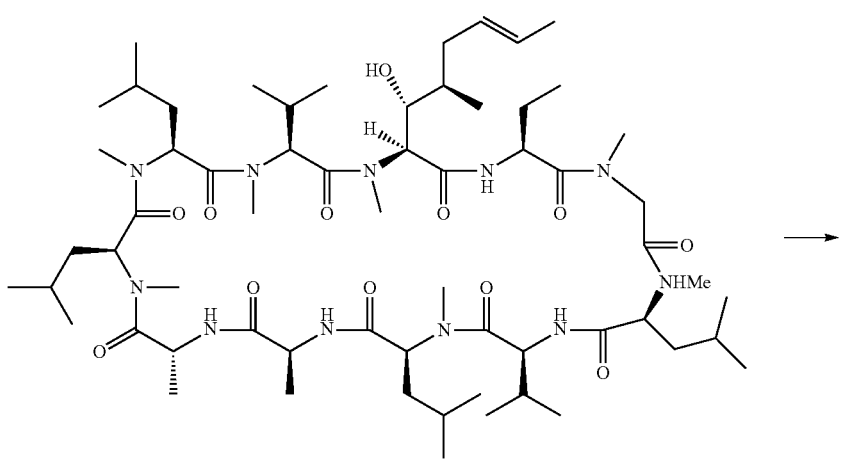

CsA

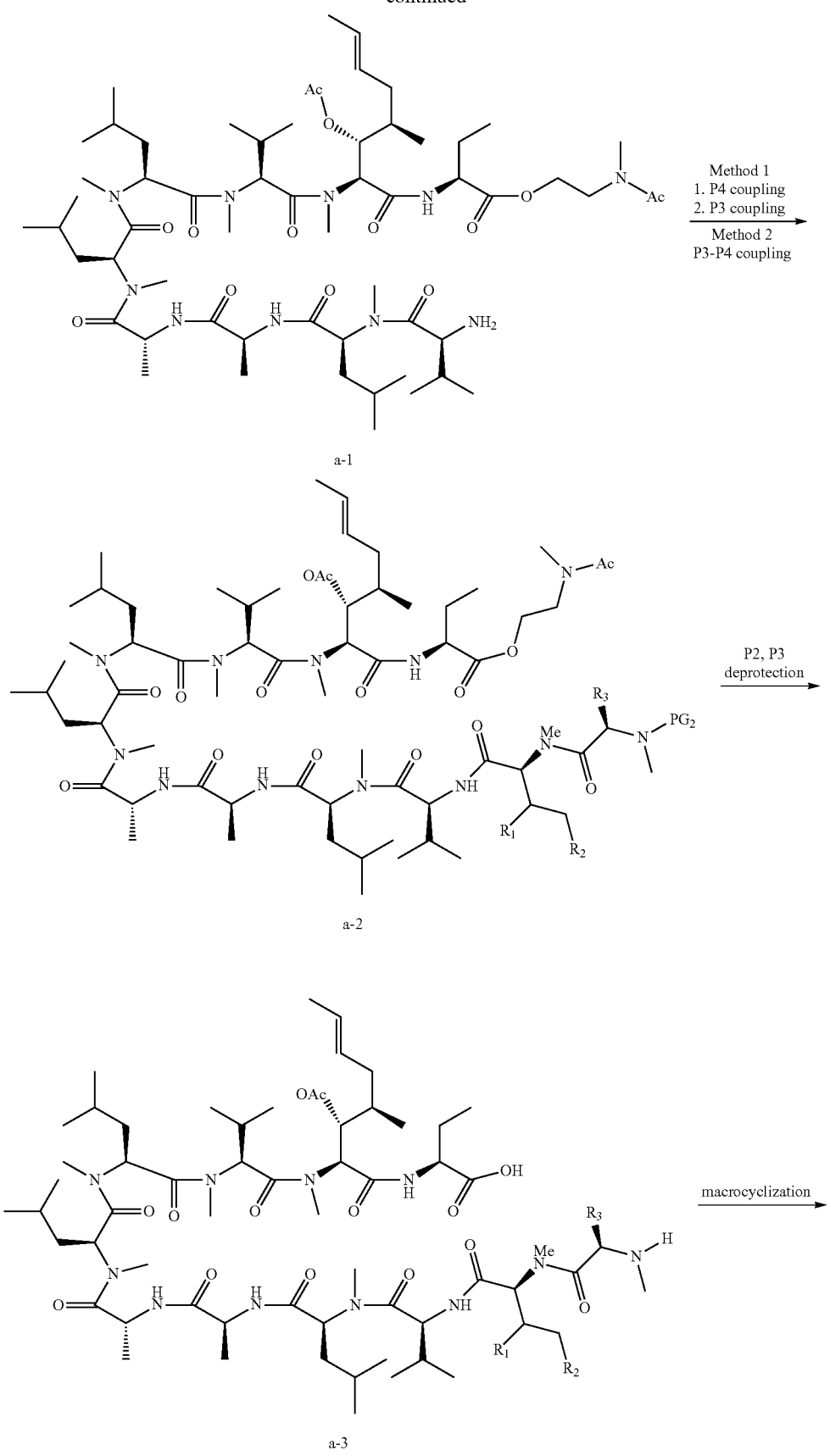

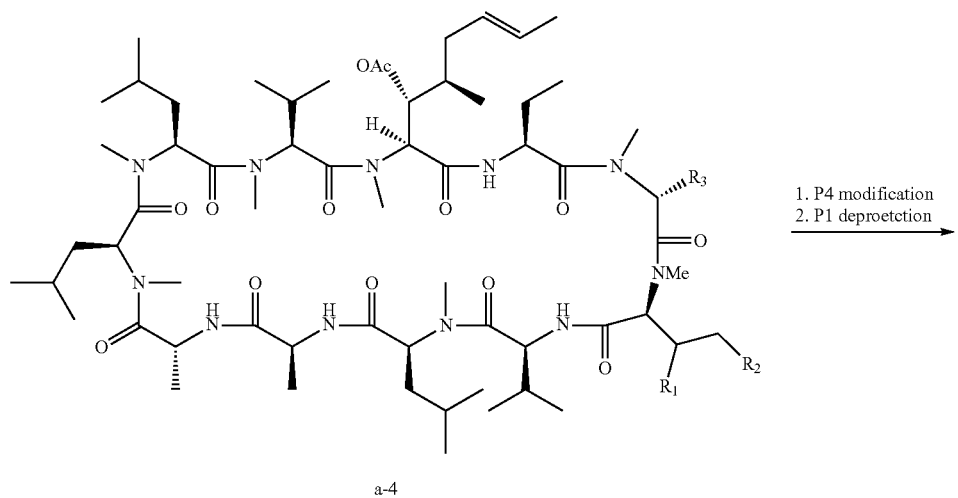

a-4

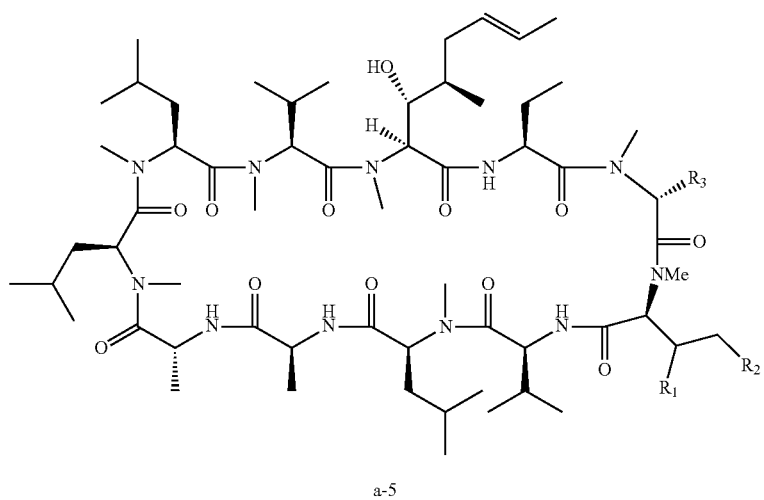

a-5

Scheme 1 illustrated the synthesis of P4 amino acids that are required for these novel cyclosporin inhibitors. The two chiral centers were constructed by Mannich reaction between furfural N-Boc imine and aldehyde catalyzed by appropriate proline catalyst. Furyl group was chosen as masked carboxylic acid, which can be revealed at suitable stage through oxidative cleavage of furan.

Scheme 1

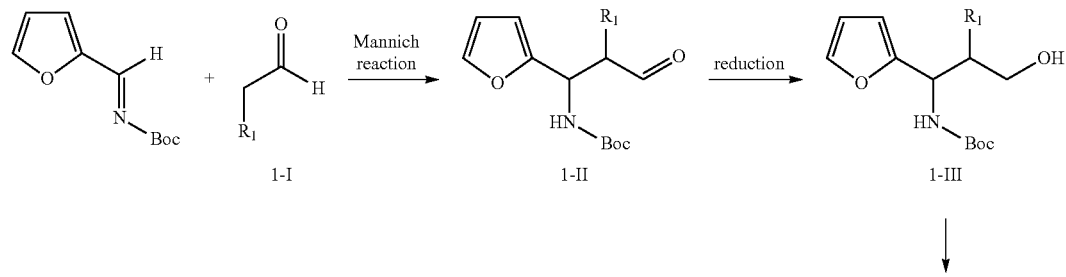

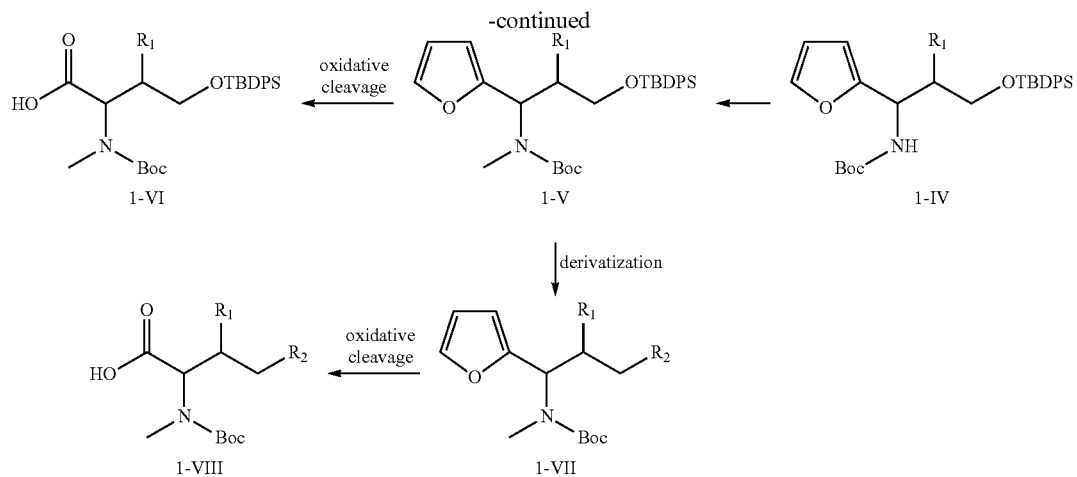

The synthesis started with Mannich reaction between imine and aldehyde 1-I using proline or proline derivative as catalysts to provide aldehyde 1-II. Both syn and anti diastereomers could be synthesized using appropriate catalysts. Compound 1-II was reduced to alcohol 1-III, which could be obtained in diastereomerically and enantiomerically pure form either by recrystallization or chiral chromatography separation. Compound 1-III was then protected as silyl ether and alkylated to give compound 1-V. Compound 1-VI was prepared from 1-V by oxidative conversion of the furan to the corresponding carboxylic acid.

The protected alcohol in 1-V could be further modified to generate additional series of P4 amino acids 1-VIII. Some examples of derivatization were illustrated in Scheme 6a, 6b, 7 and 8.

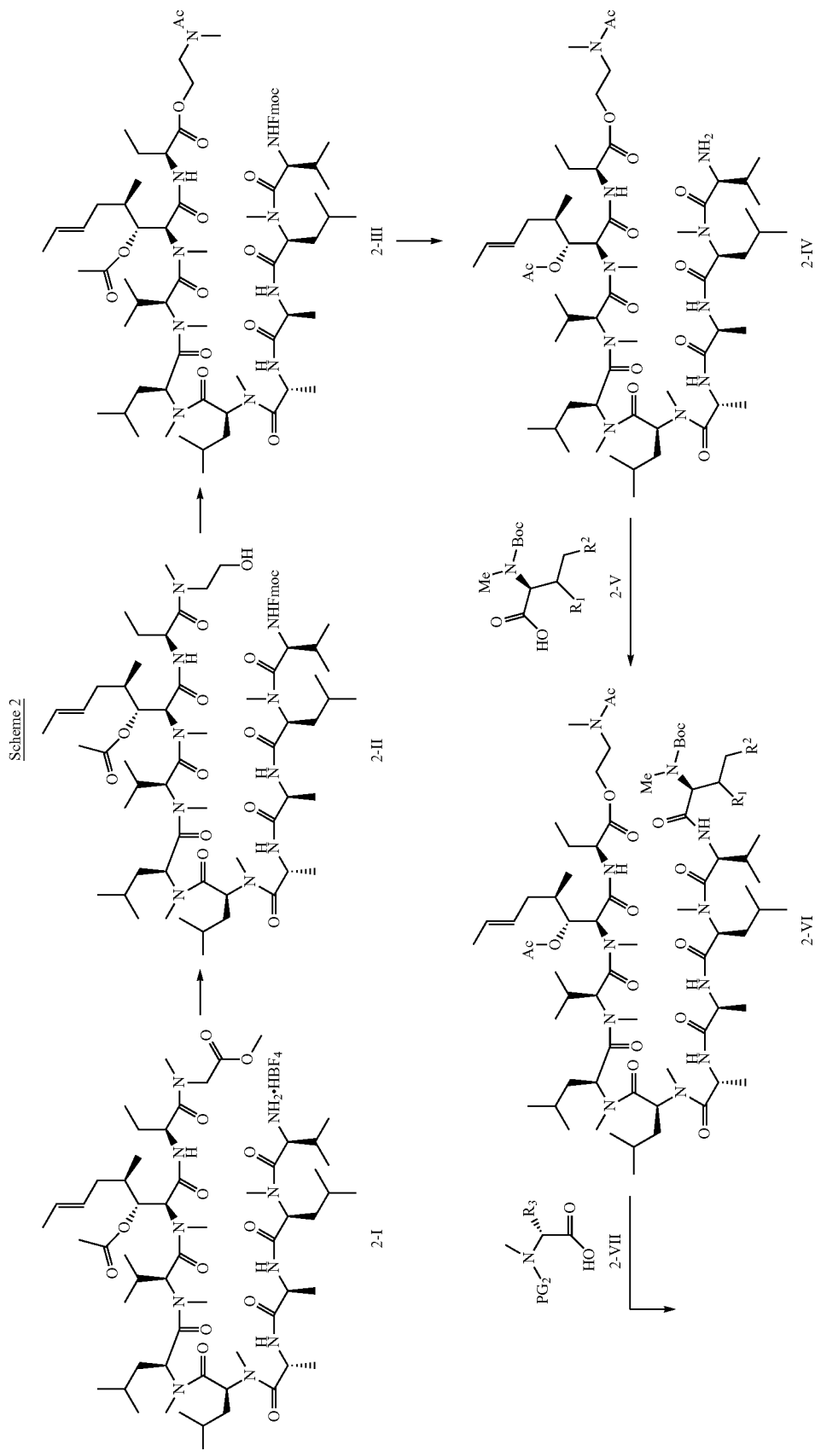

-continued
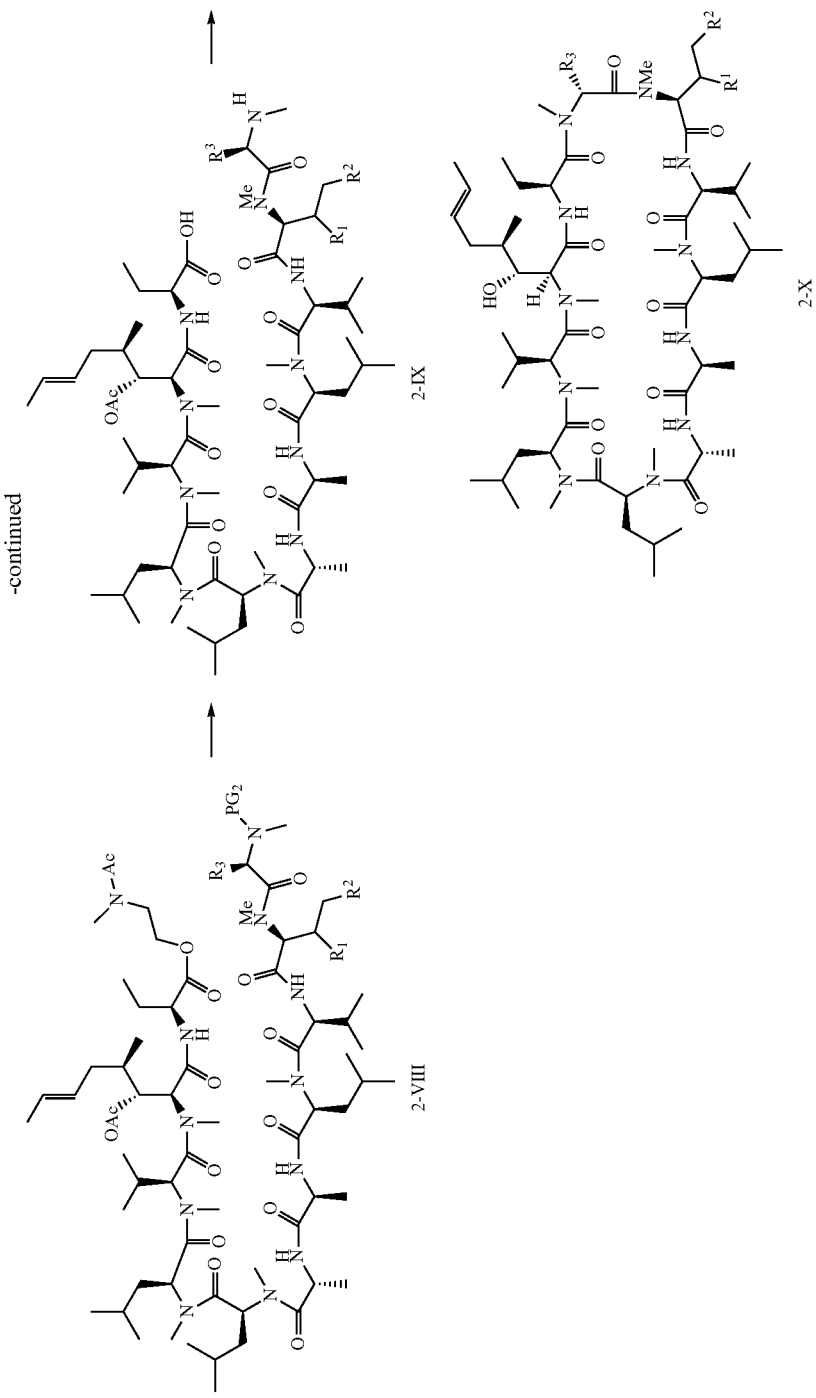

A general method for the synthesis of cyclosporine 2-X was described in Scheme 2. In this approach, the macrocyclization substrate 2-IX was prepared from 2-IV by stepwise installation of aminoacids 2-V and 2-VII.

Ester 2-I was reduced to the corresponding alcohol followed by N-Fmoc protection to provide compound 2-II. Rearrangement of 2-II under acidic conditions followed by N-acetylation gave compound 2-III. After removal of the Fmoc group, the amine 2-IV was coupled to carboxylic acid 2-V to provide intermediate 2-VI. The Boc protecting group was removed and amino acid 2-VII was coupled to the peptide to provide 2-VIII. Intermediate 2-VIII was converted to 2-IX by removal of the nitrogen protecting group and hydrolysis of the ester. Macrocycle 2-X was finally prepared from amino acid 2-IX via intramolecular amide formation and deacetylation.

Scheme 3

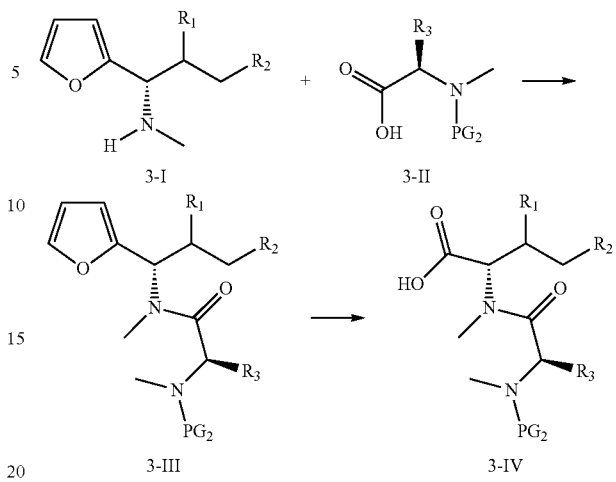

Scheme 4
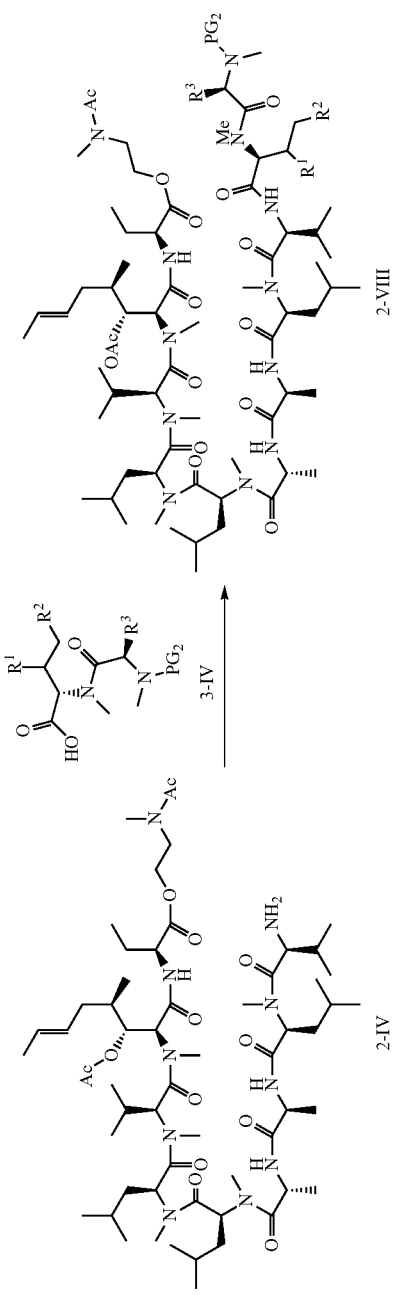
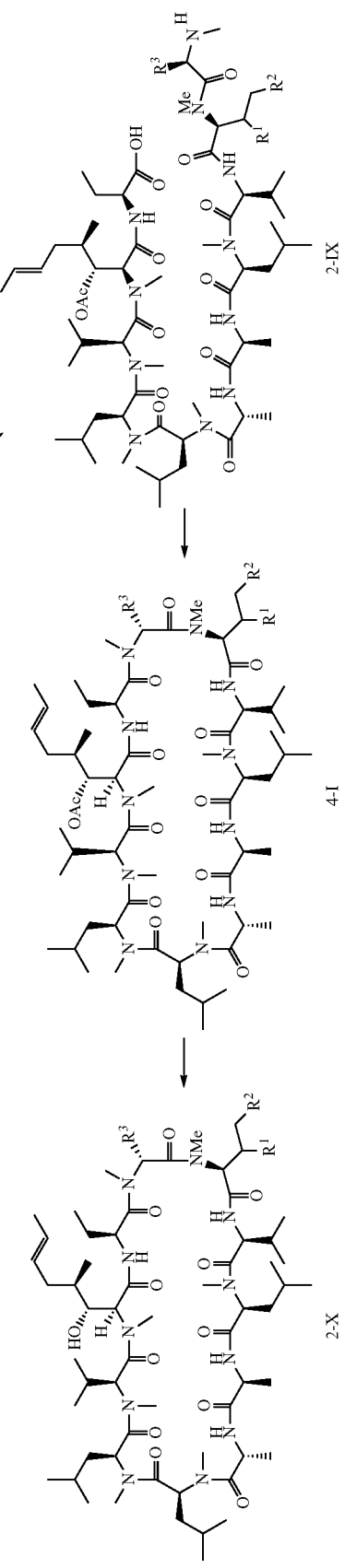

Scheme 3 and Scheme 4 described another approach toward the synthesis of macrocyclization substrate 2-IX from 2-IV. In this approach, instead of adding two amino acids in a stepwise fashion to the peptide chain, dipeptide 3-IV was synthesized and coupled to intermediate 2-IV.

Compound 3-II was prepared by amide coupling 3-I and 3-II. The furan was then converted to carboxylic acid 3-IV, which was then coupled with amine 2-IV to give 2-VIII. Compound 2-IX was prepared from 2-VIII by removing the amine protecting group followed by ester hydrolysis. Compound 2-IX was converted to macrocycle 4-I via intramolecular amide bond formation. The acetyl group in 4-I was removed under basic conditions to generate compound 2-X.

Scheme 5

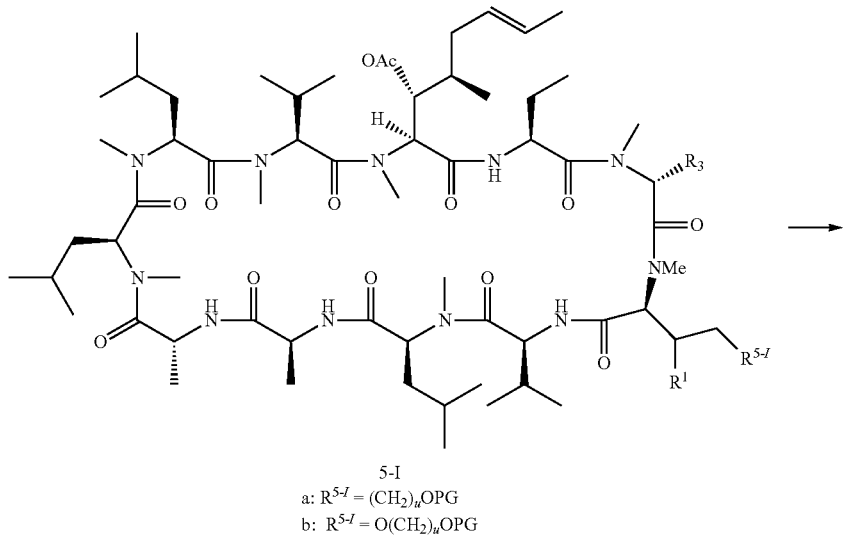

5-I
a: $R^{5-I} = (CH_2)_u OPG$
b: $R^{5-I} = O(CH_2)_u OPG$

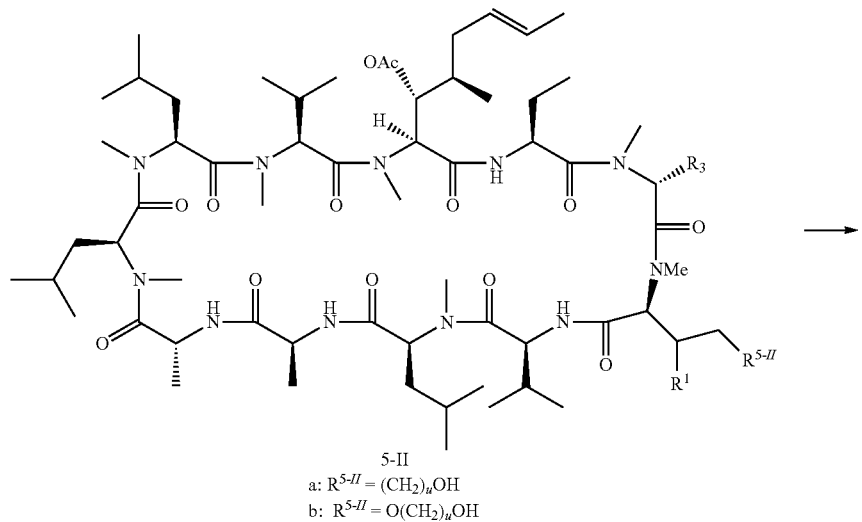

5-II
a: $R^{5-II} = (CH_2)_u OH$
b: $R^{5-II} = O(CH_2)_u OH$

-continued

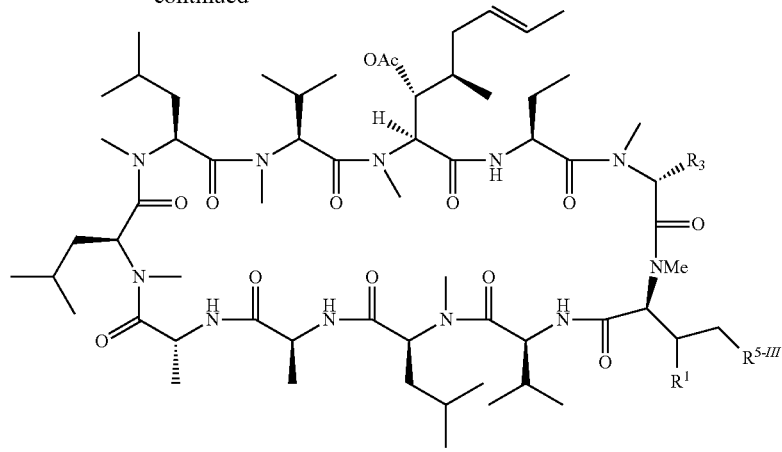

5-III
a: R[5-III] = CHO or (CH$_2$)$_{u-1}$CHO
b: R[5-III] = OCH$_2$CHO

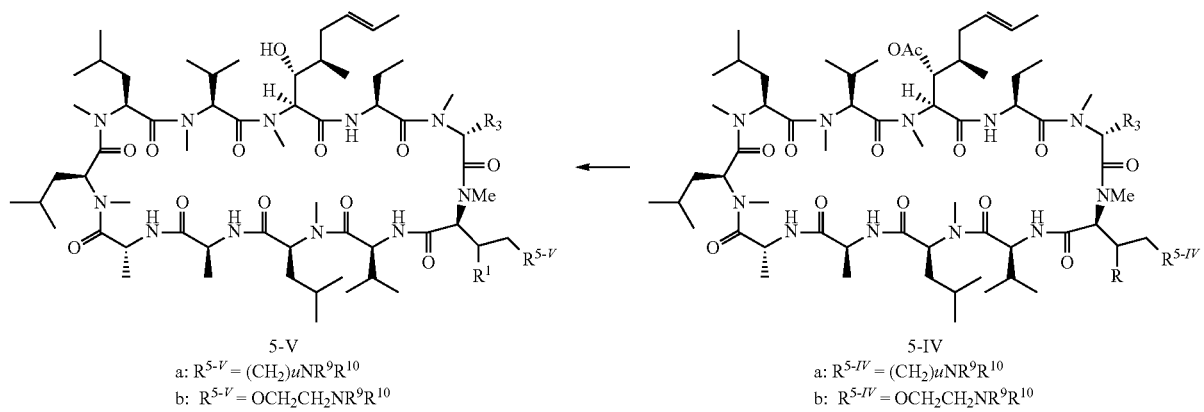

5-V
a: R[5-V] = (CH$_2$)$_u$NR$^9$R$^{10}$
b: R[5-V] = OCH$_2$CH$_2$NR$^9$R$^{10}$

5-IV
a: R[5-IV] = (CH$_2$)$_u$NR$^9$R$^{10}$
b: R[5-IV] = OCH$_2$CH$_2$NR$^9$R$^{10}$

Scheme 5 illustrated the synthesis of amine analogs 5-V from compound 5-I. The protecting group on the primary alcohol was removed, and the hydroxy group was oxidized to generate aldehyde 5-III. Compound 5-III was converted to amine 5-V by reductive amination followed by deacetylation.

Scheme 6a, 6b, 7, 8 illustrated examples of modifying protected alcohol in 1-V to generate a series of P4 amino acids. The furan intermediates could be converted to carboxylic acid by oxidative cleavage or further elaborated to provide P3-P4 dipeptide according to the general method described in Scheme 3.

Scheme 6a

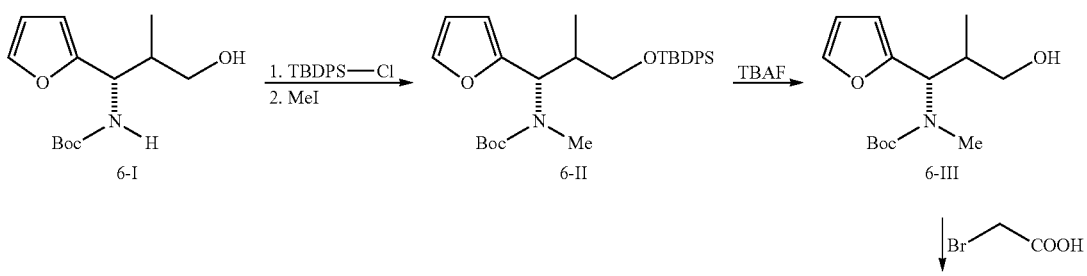

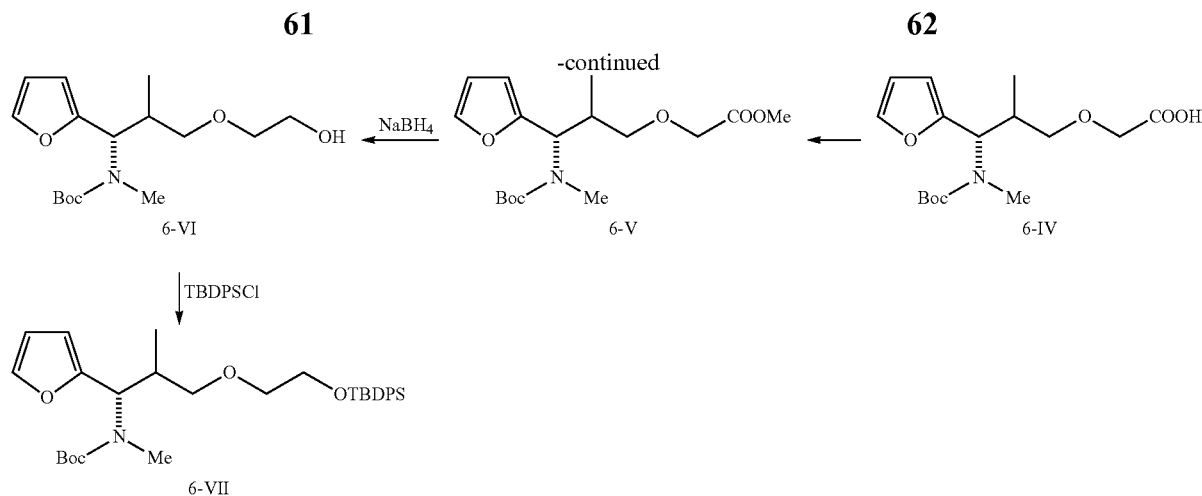

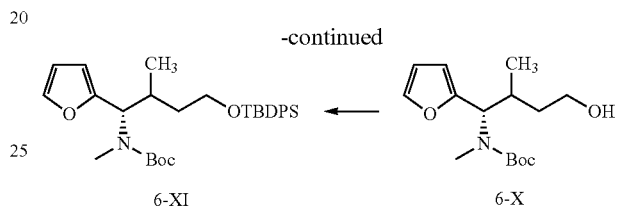

Synthesis of compound 6-VII from 6-I was illustrated in Scheme 6a. The hydroxy group in compound 6-I was protected as TBDPS ether and the nitrogen was methylated to provide 6-II. The TBDPS ether was then deprotected with TBAF and the resulting alcohol was alkylated with bromoacetic acid to give compound 6-IV. Formation of methyl ester 6-V, followed by reduction with NaBH$_4$ gave alcohol 6-VI, which was then protected as the TBDPS ether.

Synthesis of one carbon homologated derivative 6-XI was described in Scheme 6b. Aldehyde 6-VIII was prepared by oxidation of 6-III under Swern conditions. Treatment of 6-VIII with (methoxymethyl)triphenylphosphonium chloride and sodium hexamethyldiliazide produced vinyl ether 6-IX. Hydrolysis, reduction and protection yielded silyl ether 6-XI.

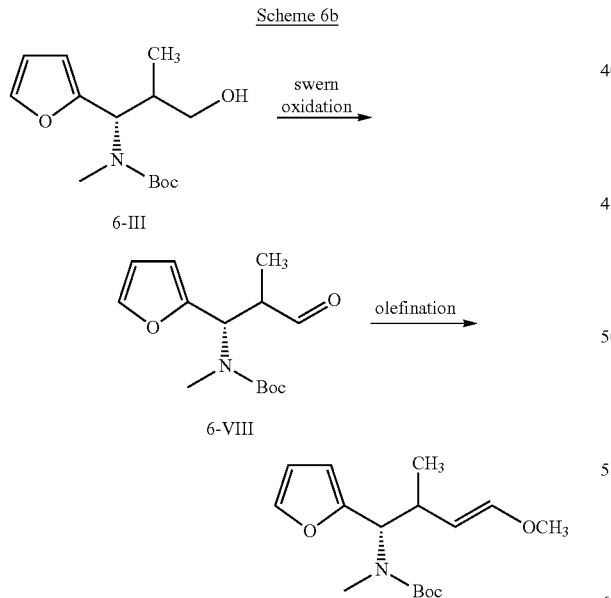

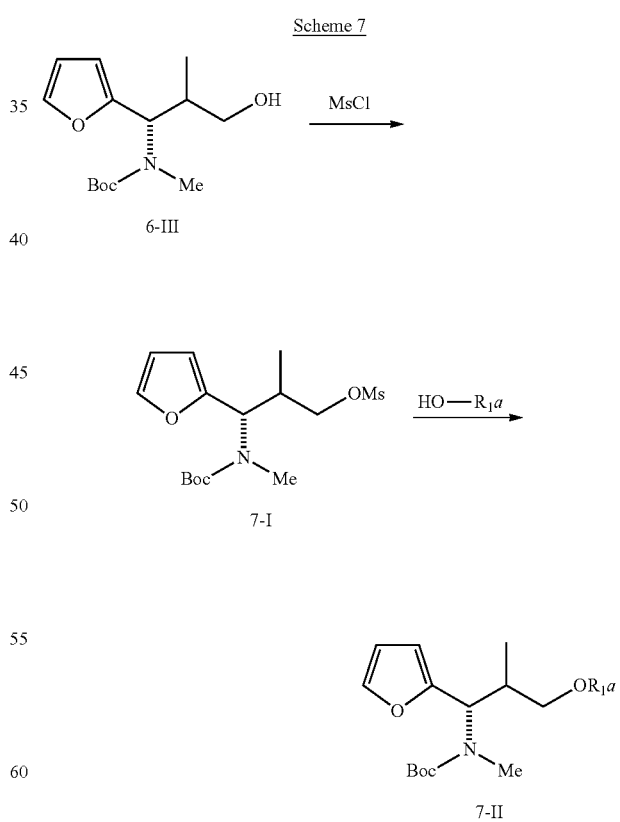

Compound 6-III could also be converted to the mesylate 7-I followed by displacement with various alcohols to give ether 7-II (Scheme 7).

Scheme 8
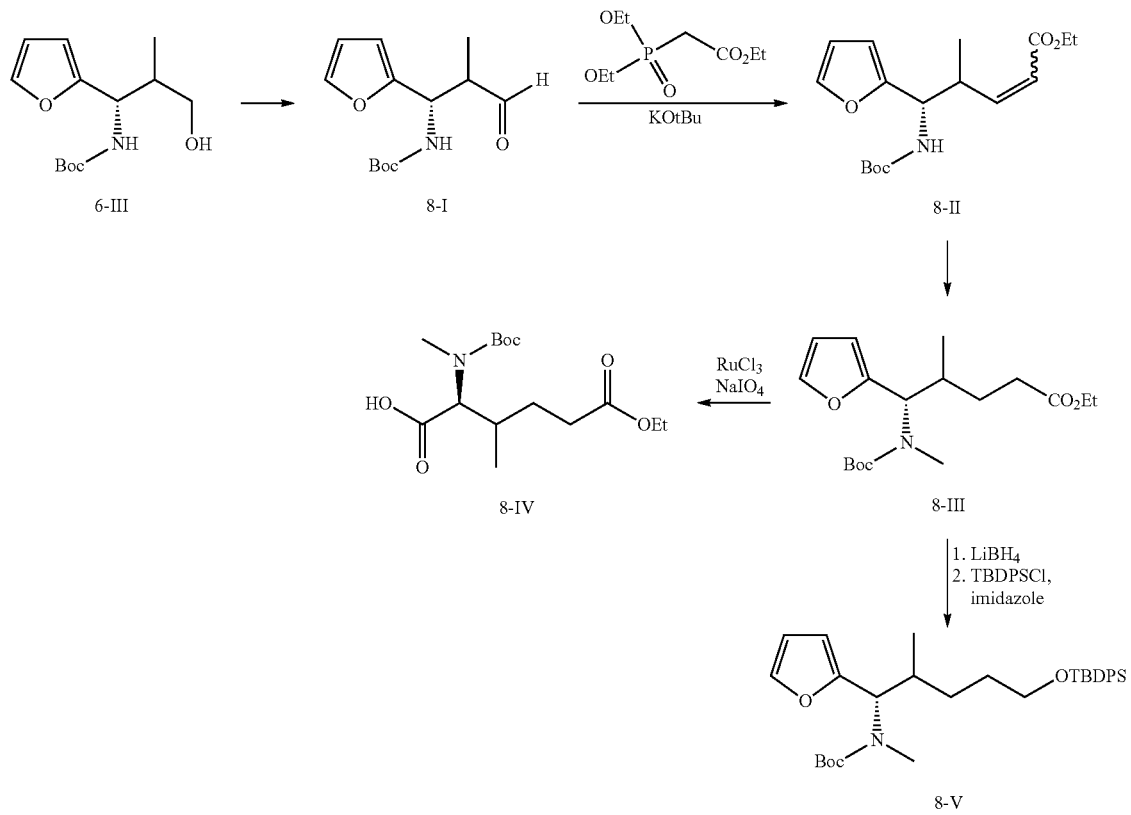
Synthesis of two carbon homologated silyl ether 8-V was described in Scheme 8. The hydroxy group in compound 6-III was oxidazed to give aldehyde 8-I. Olefination followed by reduction of the resulting olefin gave compound 8-III. Compound 8-III could be reduced and silylated to give silyl ether 8-V. The furan in 8-III could also be oxidized to afford P4 carboxylic acid 8-IV.

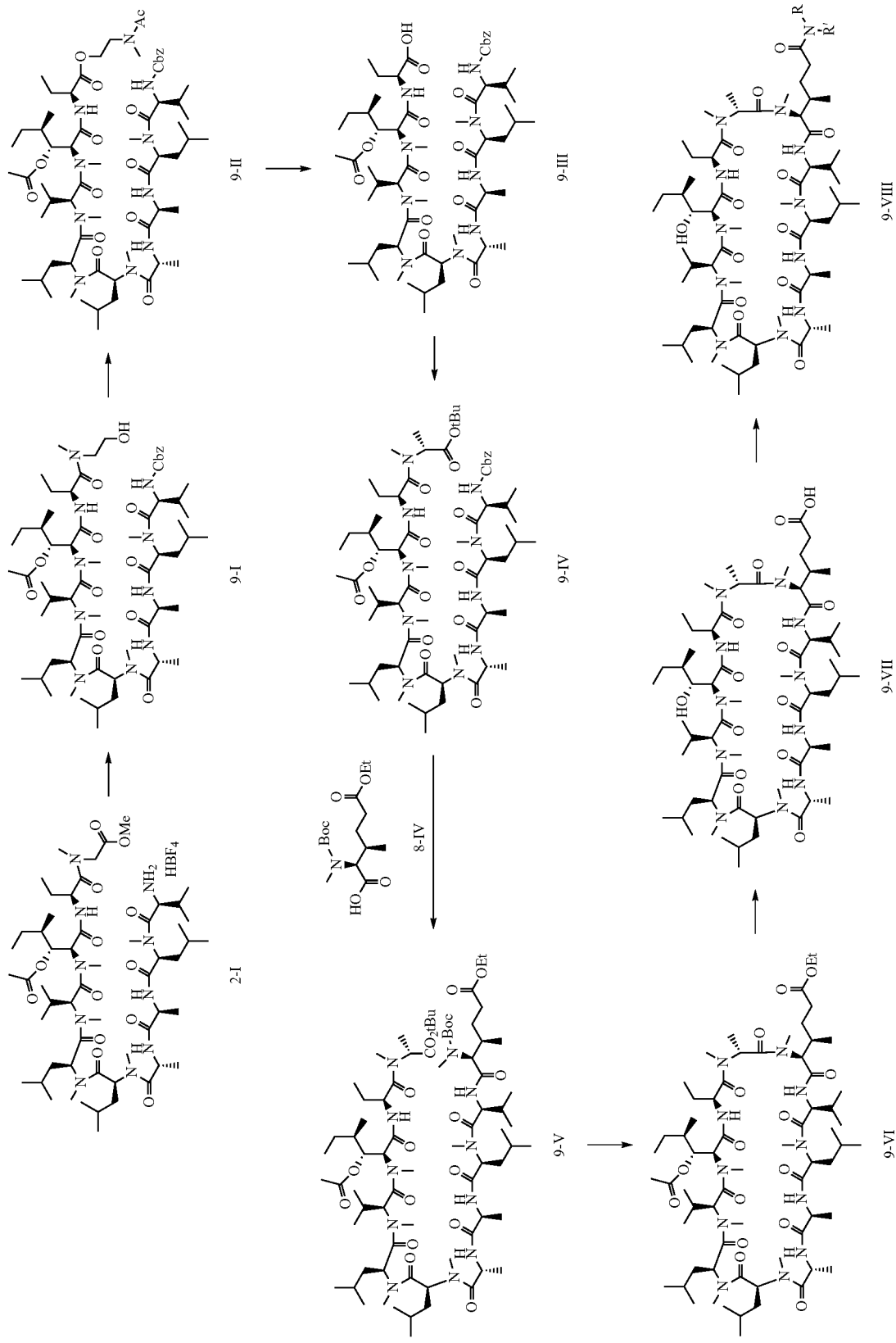

Compounds 9-VIII were prepared by the general method described in Scheme 9.

The amine in Compound 2-I was protected as the benzyl carbamate and the ester was reduced to the corresponding alcohol (9-I). Rearrangement under acidic conditions followed by N-acetylation gave compound 9-II. After hydrolysis of the ester, the resulting carboxylic acid (9-III) was coupled with (R)-2-Methylamino-propionic acid tert-butyl ester to provide 9-IV. The Cbz group in compound 9-IV was removed, and the amine 9-V was coupled to carboxylic acid 8-IV to provide compound 9-V. Removal of both Boc and t-Butyl ester protecting groups followed by intramolecular cyclization gave macrocycle 9-VI. The acetyl group at P1 and the ethyl ester at P4 were removed under basic conditions. Carboxylic acid 9-VII was then coupled with various amines to give compounds 9-VIII.

The synthesis of P4-amino acid 10-V and 10-VIII was illustrated in Scheme 10. Sharpless asymmetric aminohydroxylation reaction of 10-I gave Cbz protected aminoalcohol 10-II with excellent enantioselectivity and diastereoselectivity. The Ester was reduced and the resulting alcohol was protected as TBDPS ether 10-III. Dimethylation of 10-III gave product 10-IV, which was subjected to oxidative condition to provide Cbz protected P4 aminoacid 10-V. The hydroxyl group in 10-III could be inverted under Mitsunobu condition to give anti-aminoalcohol 10-VI. Dimethylation and oxidative cleavage of p-methoxyphenyl group provided carboxylic acid 10-VIII.

Scheme 10

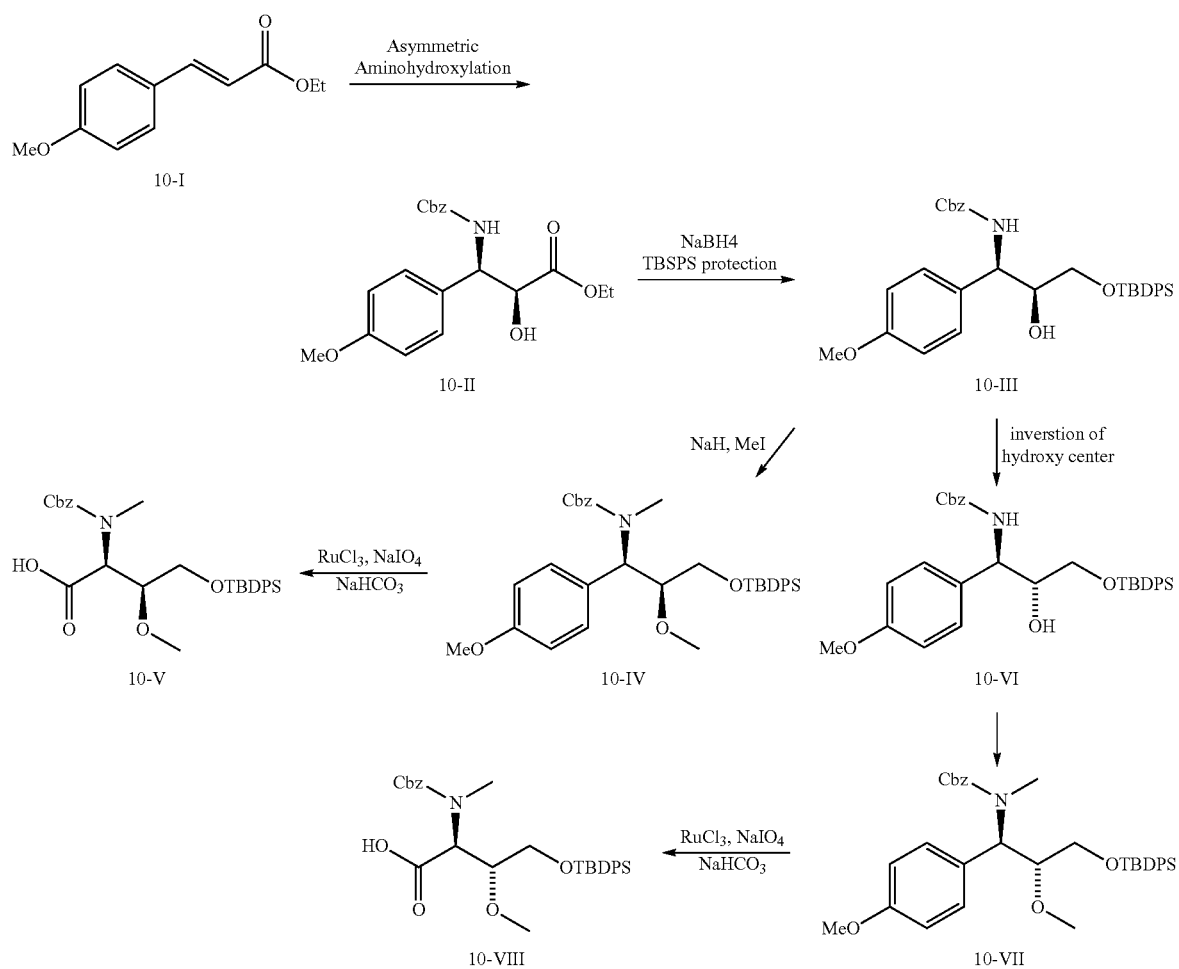

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methylcyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by cyclophilins activity, or (ii) associated with cyclophilins activity, or (iii) characterized by activity (normal or abnormal) of cyclophilins; or (2) reduce or inhibit the activity of cyclophilins; or (3) reduce or inhibit the interaction of cyclophilins with other proteins. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of cyclophilins; or at least partially reduce or inhibit the interaction of cyclophilins with other proteins.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment"

refers to preventing or delaying the onset or development or progression of the disease or disorder.

As used herein, a subject is "in need of" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound according to anyone of Formulae I to IVb, or a pharmaceutically acceptable salt thereof, and at least one other therapeutic agent as a combined preparation for simultaneous, separate or sequential use in therapy. In one embodiment, the therapy is the prevention or treatment of a disease or condition mediated by cyclophilins activity. Products provided as a combined preparation include a composition comprising the compound according to anyone of Formulae I to IVb, or a pharmaceutically acceptable salt thereof and the other therapeutic agent(s) together in the same pharmaceutical composition, or the compound according to anyone of Formulae I to IVb, or a pharmaceutically acceptable salt thereof and the other therapeutic agent(s) in separate form, e.g. in the form of a kit.

In one embodiment, the invention provides a pharmaceutical composition comprising a compound according to anyone of Formulae I to IVb, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of Formulae I to IVb or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formulae (I) to (IVb) for preventing and/or treating a disease or condition mediated by cyclophilins activity, wherein the medicament is prepared for administration with another therapeutic agent. The invention also provides the use of another therapeutic agent for preventing and/or treating a disease or condition mediated by cyclophilins activity, wherein the medicament is administered with a compound according to anyone of Formulae I to IVb, or a pharmaceutically acceptable salt thereof.

The invention also provides a compound of formulae (I-IVb) for use in a method of prevention and/or treating a disease or condition mediated by cyclophilins activity, wherein the compound according to anyone of Formulae I to IVb, or a pharmaceutically acceptable salt thereof, is prepared for administration with another therapeutic agent. The invention also provides another therapeutic agent for use in a method of preventing and/or treating a disease or condition mediated by cyclophilins activity wherein the other therapeutic agent is prepared for administration with a compound according to anyone of Formulae I to IVb, or a pharmaceutically acceptable salt thereof. The invention also provides a compound according to anyone of Formulae I to IVb, or a pharmaceutically acceptable salt thereof, for use in a method of preventing and/or treating a disease or condition mediated by cyclophilins activity wherein the compound according to anyone of Formulae I to IVb, or a pharmaceutically acceptable salt thereof, is administered with another therapeutic agent. The invention also provides another therapeutic agent for use in a method of preventing and/or treating a disease or condition mediated by cyclophilins activity wherein the other therapeutic agent is administered with a compound according to anyone of Formulae I to IVb, or a pharmaceutically acceptable salt thereof.

The invention also provides the use of a compound of formulae (I-IV) for preventing and/or treating a disease or condition mediated by cyclophilins activity wherein the patient has previously (e.g. within 24 hours) been treated with another therapeutic agent. The invention also provides the use of another therapeutic agent for preventing and/or treating a disease or condition mediated by cyclophilins activity wherein the patient has previously (e.g. within 24 hours) been treated with a compound according to anyone of Formulae I to IVb, or a pharmaceutically acceptable salt thereof.

In one embodiment, the other therapeutic agent is selected from therapies for disease caused by HCV infection that suppresses HCV viral replication bydirect or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01190121(A2), or U.S. Pat. No. 6,348,587B1 or WO 01160315 or WO 01132153 or non-nucleoside inhibitors such as, for example, benzimidazole polymerase inhibitors described in EP I162196AI or WO 02/04425.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Anti-HCV agents include those agents that are effective for diminishing or preventing the progression of hepatitis C related symptoms or disease. Anti-HCV agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase.

Inhibitors of another target in the HCV life cycle include agents (compounds or biologicals) that are effective to inhibit the formation and/or replication of HCV other than by inhibiting the function of the HCV NS3 protease. Agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

EXAMPLES

General Conditions

Mass spectra were run on LC-MS systems using electrospray ionization. These were WATERS Acquity Single Quard Detector. [M+1]$^+$ refers to mono-isotopic molecular weights.

NMR spectra were run on open access Varian 400 NMR spectrometers. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure. The structure of final products, intermediates and starting materials is confirmed by standard analytical methods, e.g., MS, and NMR. Abbreviations used are those conventional in the art. If not defined, the terms have their generally accepted meanings.

ABBREVIATIONS br broad
d doublet
DCM dichloromethane
DCE Dichloroethane
DMF N,N-dimethylformamide
DMAP 4-Dimethylaminopyridine
DMSO dimethylsulfoxide
EDCI 1-ethyl-3-(3'-dimethylaminopropyl) carbodiimide
EtOAc ethyl acetate
HPLC high pressure liquid chromatography
LC-MS liquid chromatography and mass spectrometry
MeOH methanol
MS mass spectrometry
m multiplet
min minutes
ml milliliter(s)
NMR nuclear magnetic resonance
ppm parts per million
Rt retention time
RT or rt room temperature
s singlet
t triplet
THF tetrahydrofuran
UPLC Ultra Performance Liquid Chromatography Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical UPLC conditions are as follows:

| Method A | |
|---|---|
| Column | Phenonemax Kinetix C18 Column; 2.1 mm × 50 mm; 2.6 u core size |
| Column Temperature | 50° C. |

| Method A | |
|---|---|
| Eluents | solvent A: water with 0.1% TFA; solvent B: CH$_3$CN with 0.1% TFA |
| Flow Rate | 1.2 mL/min |
| Gradient | 2-88% solvent B in 9.5 mins |

I. Synthesis of Intermediate 1

Step 1. Synthesis of I-b

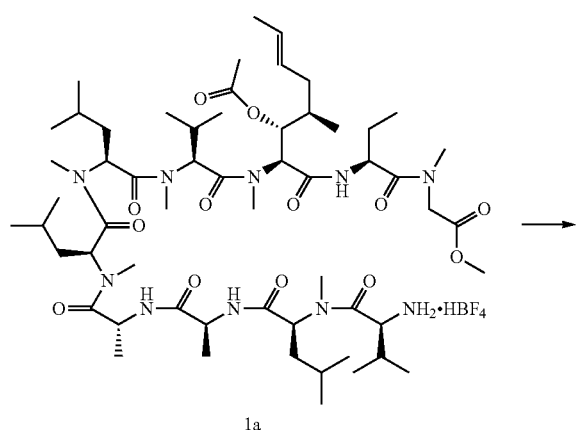

1a

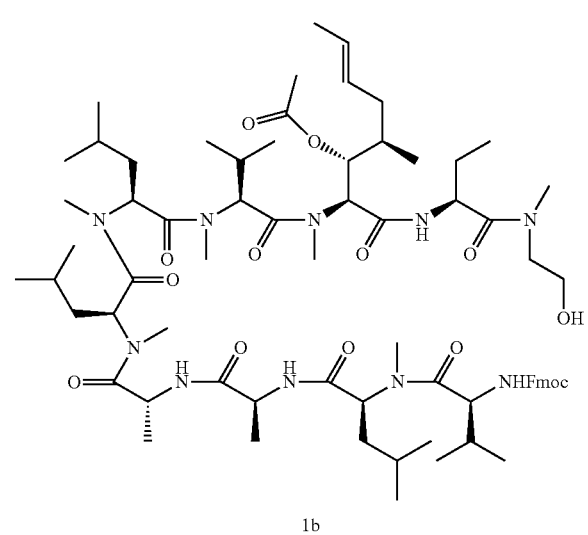

1b

To a solution of amino ester 1a (5.2 g, 4.2 mmol) in isopropanol (31.2 mL) and methanol (3.5 mL) at 0° C. was added NaBH$_4$ (0.80 g, 21.0 mmol, 5.0 equiv). After stirring at room temperature for 5 hours, the reaction mixture was diluted with ethyl acetate and quenched with 1.0 N HCl at 0° C. The pH of the reaction mixture was adjusted to pH 9 by adding saturated aqueous NaHCO$_3$ and Na$_2$CO$_3$. The aqueous layer was extracted with ethyl acetate. The combined organic layers were washed sequentially with saturated aqueous NaHCO$_3$ and brine, dried with Na$_2$SO$_4$, filtered and concentrated in vacuo to give the desired alcohol. MS m/z (M+1) 1122.1.

To a solution of the alcohol in methylene chloride (35 mL) at 0° C. was added DIPEA (1.40 mL, 7.94 mmol, 1.9 equiv) followed by Fmoc-chloride (0.924 g, 3.57 mmol, 0.85 equiv). After stirring at 0° C. for 3 hours, the reaction mixture was diluted with methylene chloride and washed with aqueous 10% citric acid. The organic layer was washed with saturated aqueous NaHCO$_3$, brine, dried with Na$_2$SO$_4$, filtered and concentrated in vacuo. Purification on silica gel chromatography (35% acetone/methylene chloride) afforded compound 1b (3.9 g, 71%). MS m/z (M+CH$_3$CN) 1384.4.

Step 2. Synthesis of 1c

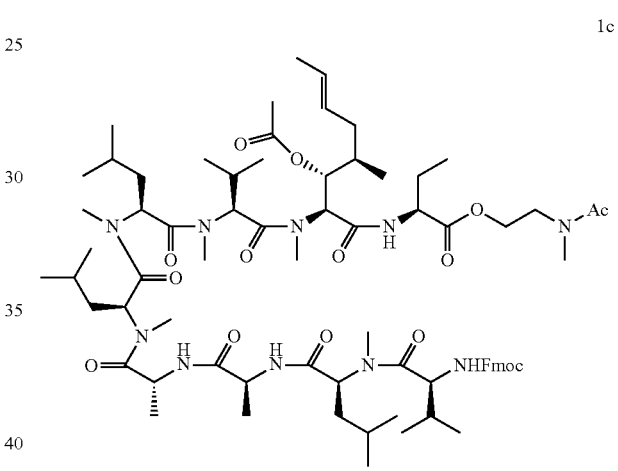

1c

To a solution of compound 1b (1.2 g, 0.92 mmol) in isopropanol (4.6 mL) at room temperature was added methanesulfonic acid (0.59 mL, 9.2 mmol, 10.0 equiv), and the resulting mixture was heated to 50° C. After heating for 15 hours, the reaction mixture was cooled to room temperature and concentrated in vacuo to ~1.0 mL, diluted with ethyl acetate and quenched with saturated aqueous NaHCO$_3$. The pH of the reaction mixture was adjusted to pH 9 by adding saturated aqueous Na$_2$CO$_3$. The organic layer was separated and washed with brine, Na$_2$SO$_4$, filtered and concentrated in vacuo. The residue was dissolved in methylene chloride (4.6 mL), and to this solution at 0° C. was added acetic anhydride (0.14 mL, 1.5 mmol, 1.7 equiv) followed by triethylamine (0.28 mL, 2.0 mmol, 2.2 equiv). After stirring at 0° C. for 12 hours, the reaction mixture was quenched with saturated aqueous NaHCO$_3$. The combined organic layers were washed with brine, dried with Na$_2$SO$_4$, filtered and concentrated in vacuo. Purification on silica gel chromatography (35% acetone/methylene chloride) afforded compound 1c (0.58 g, 46% yield). MS m/z (M+1) 1385.8

Step 3. Synthesis of Compound 1

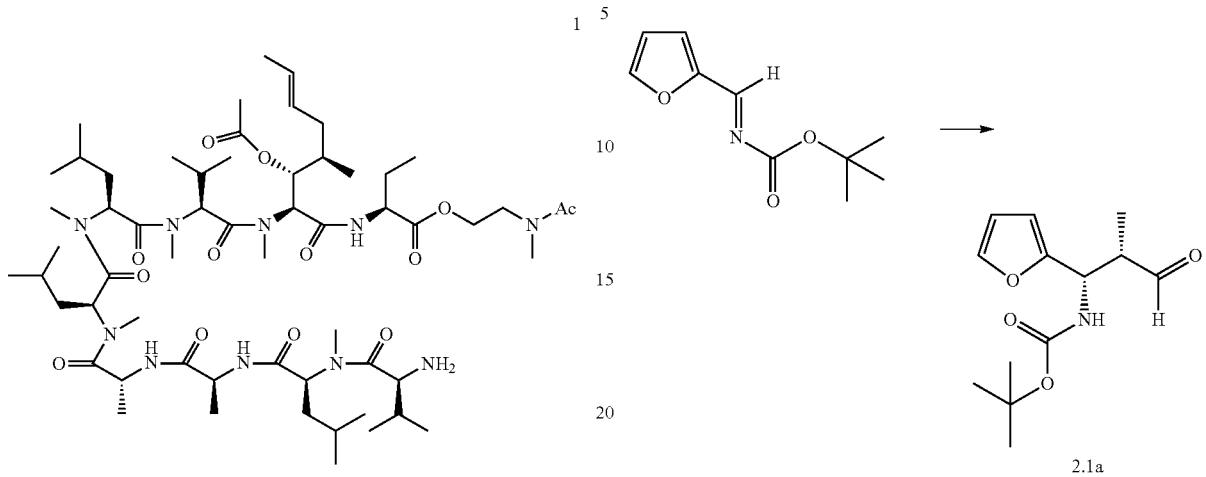

To a solution of compound 1c (10.0 g, 7.2 mmol) in methylene chloride (100 mL) was added tris-(2-aminoethyl)amine (1.30 mL, 8.7 mmol, 1.2 equiv) at room temperature. After stirring for 12 hours, the reaction mixture was quenched with saturated aqueous NH$_4$Cl (100 mL) followed by 0.5 M KHSO$_4$ to adjust the pH of the mixture to ~5. The aqueous layer was extracted with methylene chloride. The combined organic layers were washed with brine, dried with Na$_2$SO$_4$, filtered and concentrated in vacuo to afford compound 1 (7.4 g, 88%) which was used for the next step without further purification. MS m/z (M+1) 1163.6

II. Synthesis of Cyclophilin Inhibitors

II.1 Synthesis of Compound 2.1

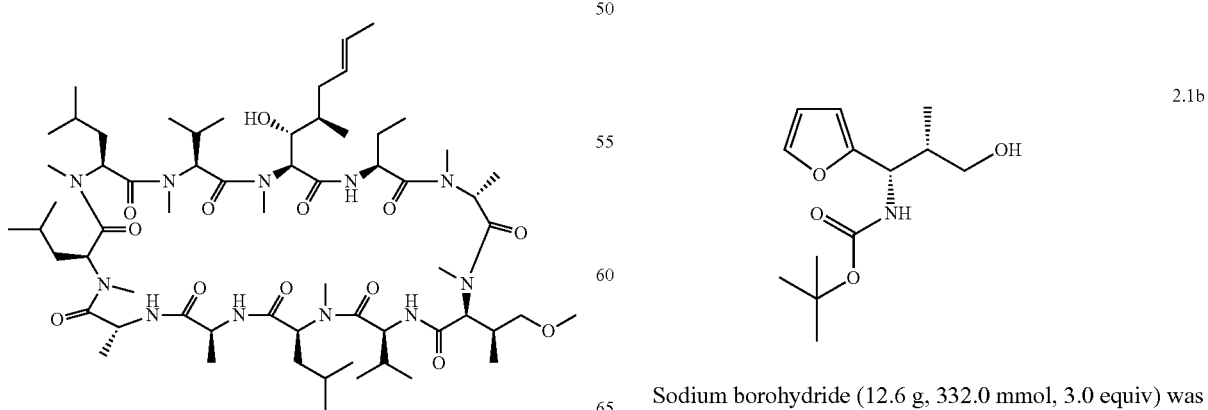

Step 1. Synthesis of (1S,2S)-1-Furan-2-yl-2-methyl-3-oxo-propyl)-carbamic acid tert-butyl ester [2.1a]

1-Furan-2-yl-meth-(E)-ylidene)-carbamic acid-tert-butyl ester (28.0 g, 143.0 mmol, 1.0 equiv) and propionaldehyde (16.7 g, 20.6 mL, 287.0 mmol, 2.0 equiv) were added to a 500 mL round bottom flask containing (2S,4R)-4-(tert-Butyl-diphenyl-silyloxy)-pyrrolidine-2-carboxylic acid (5.3 g. 14.3 mmol, 0.1 equiv) and acetonitrile (250 mL) at 4° C. After stirring at 4° C. for 18 hours, the reaction mixture was quenched with water and extracted with ethyl acetate. The organic layer was washed with 1.0 N hydrochloric acid and brine, dried over sodium sulfate and concentrated. The crude material was purified by silica gel column chromatography (heptanes/ethyl acetate) to give (1S,2S)-1-Furan-2-yl-2-methyl-3-oxo-propyl)-carbamic acid tert-butyl ester (29.0 g, 80% yield), which was >80% diastereomerically pure. $^1$H NMR (400 MHz, CDCl$_3$) 1.11 (dm, 3H); 1.44 (s, 9H); 2.92 (m, 1H); 5.10 (m, 2H); 6.20 (s, 1H); 6.34 (m, 1H); 7.35 (m, 1H,); 9.66 (m, 1H); 9.76 (s, 1H).

Step 2. Synthesis of (1S,2S)-1-Furan-2-yl-3-hydroxy-2-methyl-propyl)-carbamic acid tert-butyl) ester [2.1b]

Sodium borohydride (12.6 g, 332.0 mmol, 3.0 equiv) was slowly added to a solution of 2.1a (28 g, 111 mmol, 1.0 equiv) in MeOH (120 mL) at 0° C. After stirring at 0° C. for 2 hours, the reaction mixture was quenched with saturated ammonium chloride and extracted with ethyl acetate. The organic layer was washed with brine, dried over magnesium sulfate and concentrated. The crude material was recrystallized from hot heptane to provide 2.1b (12.2 g, 43% yield). ¹H NMR (400 MHz, CDCl₃) 0.74 (d, J=6.6, 3H); 1.46 (s, 9H); 2.25 (m, 1H); 3.32 (m, 1H); 3.52 (m, 2H); 5.11 (m, 2H); 6.15 (m, 1H); 6.36 (m, 1H); 7.36 (m, 1H).

Step 3. Synthesis of tert-butyl((1S,2S)-1-(furan-2-yl)-3-methoxy-2-methyl-propyl)-(methyl)carbamate [2.1c]

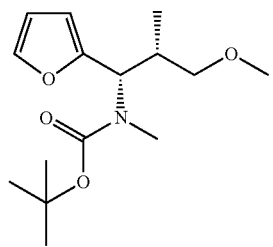

2.1c

60% sodium hydride (470 mg, 19.58 mmol, 10 equiv) was added to a solution of 2.1b (500 mg, 2.0 mmol, 1.0 equiv) in tetrahydrofuran (8 mL) at 0° C., followed by addition of DMF (1 mL) and MeI (1.78 g, 1.23 mL, 19.6 mmol, 10 equiv). The resulting mixture was stirred at room temperature for 18 hours. The mixture was then diluted with ethyl acetate, neutralized by addition of 1.0 N hydrochloric acid, washed with brine, dried over magnesium sulfate and concentrated to obtain 2.1c (555 mg, 100% yield). The crude material was used in the next step with no further purification. ¹H NMR (400 MHz, CDCl₃) 0.76 (m, 3H); 1.46 (br. s, 9H); 2.36 (m, 1H); 2.70 (br. s, 3H); 3.24 (s, 3H); 4.87-5.29 (m, 1H); 6.09-6.28 (m, 1H); 6.33 (s, 1H); 6.33 (m, 1H); 7.36 (s, 1H).

Step 4. Synthesis of (1S,2S)-1-Furan-2-yl-3-methoxy-2-methyl-propyl)-methyl-amine [2.1d]

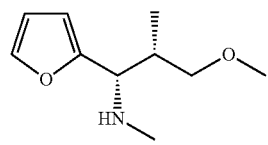

2.1d

Trifluoroacetic acid (2.72 mL, 35.3 mmol, 20.0 equiv) was added to a solution of ((1S,2S)-3-Methoxy-1-furan-2-yl-2-methyl-propyl)-methyl-carbamic acid tert-butyl ester (500 mg, 1.77 mmol, 1 equiv) in dichloromethane (10 mL) at 0° C. After stirring at 0° C. for 1 hour, the solution was concentrated. The remaining oil was diluted with ethyl acetate and then washed with saturated aqueous NaHCO₃ and brine. The organic layer was dried over magnesium sulfate and concentrated to give product 2.1d (323 mg, 100% yield). The crude material was used in the next step without further purification. ¹H NMR (400 MHz, CDCl₃) 0.85 (m, 3H); 1.46 (br. s, 9H); 2.36 (m, 1H); 2.70 (br. s, 3H); 3.24 (s, 3H); 4.87-5.29 (m, 1H); 6.09-6.28 (m, 1H); 6.33 (s, 1H); 6.33 (m, 1H); 7.36 (s, 1H)

Step 5. Synthesis of (R)-1-((1S,2S)-1-Furan-2-yl-3-methoxy-2-methyl-propyl)-methyl-carbamoyl-ethyl)-methyl carbamic acid tert-butyl ester [2.1e]

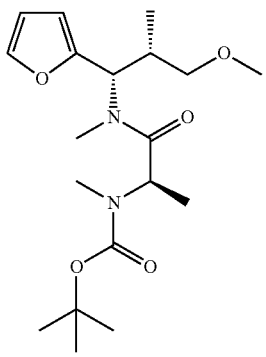

2.1e

A solution of (1S,2S)-1-Furan-2-yl-3-methoxy-2-methyl-propylmethyl-amine (600 mg, 3.27 mmol, 1.0 equiv) in dichloromethane (10 mL) was added to a mixture of (R)-2-(tert-Butoxycarbonyl-methyl-amino)-propanoic acid (799 mg, 3.93 mmol, 1.2 equiv), HATU (1.50 g, 3.93 mmol, 1.2 equiv) and DIPEA (2.86 mL, 16.37 mmol, 5.0 equiv) in DCM (10 mL). After stirring at room temperature for 16 hours, the mixture was diluted with ethyl acetate and washed sequentially with 1.0 N hydrochloric acid and brine. The organic layer was dried over magnesium sulfate and concentrated. The residue was purified by silica gel column chromatography, (heptanes/ethyl acetate) to give product 2.1e (543 mg, 45% yield). MS m/z (M+1) 369.3

Step 6. Synthesis of (2S,3S)-2-((R)-2-tert-Butoxycarbonyl-methyl-amino)-propionyl)-methyl-amino-4-methoxy-3-methyl-butric acid [2.1f]

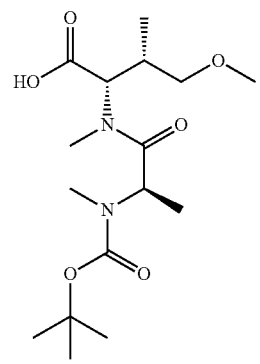

2.1f

Ruthenium(III) chloride (75 mg, 0.36 mmol, 0.3 equiv) was added to a well stirred mixture of sodium periodate (1.10 g, 4.72 mmol, 6.0 equiv) in acetonitrile/carbon tetrachloride/water (3 mL/2 mL/3 mL). After 15 minutes, (R)-1-((1S,2S)-1-furan-2-yl-3-methoxy-propyl)-methyl-carbamoyl-ethylmethyl carbamic acid tert-butyl ester (290 mg, 0.79 mmol, 1.0 equiv) was added. After stirring at room temperature for 5 minutes, the reaction mixture was diluted with water and extracted with ethyl acetate. The organic layer was washed with saturated aqueous. sodium bisulfite and brine, dried over magnesium sulfate, and concentrated to give product 2.1f (240 mg, 88% yield). MS m/z (M+1) 347.30

Step 7. Synthesis of 2.1g

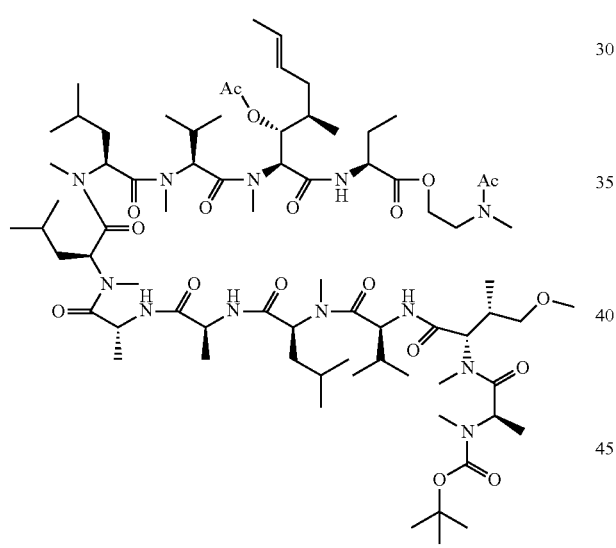

2.1g

To a mixture of 2.1f (120 mg, 0.35 mmol, 1.0 equiv), HATU (158 mg, 0.42 mmol, 1.2 equiv) and DIPEA (134 mg, 0.18 mL, 1.04 mmol, 3 equiv) in dichloromethane (2 mL) was added compound 1 (265 mg, 0.23 mmol, 0.66 equiv). After stirring at room temperature for 16 hours, the reaction mixture was diluted with ethyl acetate, washed with 1.0 N hydrochloric acid and brine. The organic layer was dried over magnesium sulfate and concentrated. The crude product was purified by silica gel column chromatography (heptanes/acetone) to give product 2.1g (517 mg, 100% yield). MS m/z (M+1) 1493.0

Step 8. Synthesis of 2.1h

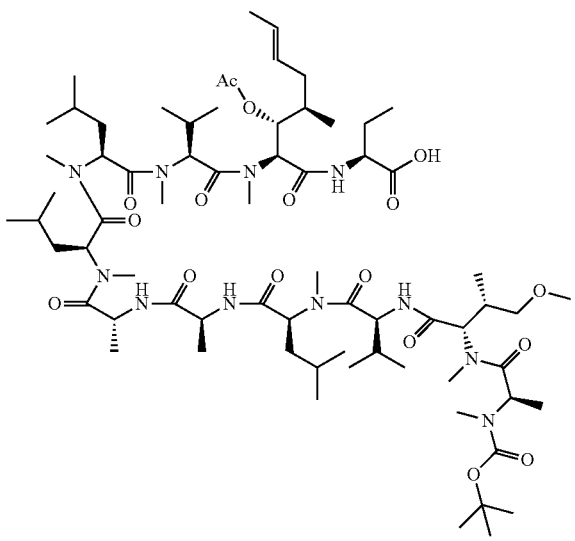

2.1h 0.5 M Sodium hydroxide (3.75 mL, 1.88 mmol, 8 equiv) was added to a solution of 2.1g (350 mg, 0.24 mmol, 1.0 equiv) in THF (6 mL) at 0° C. and the resulting solution was stirred at 0° C. for 1 hour. The solution was then diluted with ethyl acetate, washed with 1.0 N hydrochloric acid and brine, dried over magnesium sulfate and concentrated to give product 2.1 h (327 mg, 100% yield). MS m/z (M+1) 1393.80

Step 9. Synthesis of 2.1i

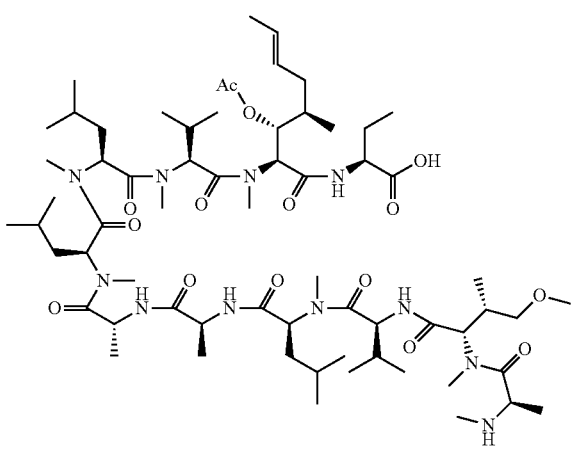

2.1i

Trifluoroacetic acid (1.0 mL, 13.0 mmol, 121 equiv) was added to a solution of 2.1h (150 mg, 0.11 mmol, 1 equiv) in dichloromethane (2 mL) at 0° C. After 1 hour, the solvent was evaporated. The remaining oil was dissolved in ethyl acetate, washed with saturated aqueous saturated aqueous sodium bicarbonate and brine, dried over magnesium sulfate and concentrated to give product 2.1i (139 mg, 100% yield). MS m/z (M+1) 1293.8

Step 10. Synthesis of 2.1j

To a solution of BOP (27.4 mg, 0.06 mmol, 2.0 equiv) in dichloromethane (20 mL) was added a solution of DMAP (7.56 mg, 0.06 mmol, 2 equiv) and 2.1i (40 mg, 0.03 mmol, 1.0 equiv) in dichloromethane (20 mL) over 15 min at room temperature. The resulting solution was stirred at room temperature for 20 hours. The solution was concentrated and the residue was dissolved in ethyl acetate, washed with brine, dried over magnesium sulfate and concentrated. The residue was purified by silica gel column chromatography (heptanes/acetone) to give product 2.1j (25 mg, 65% yield). MS m/z (M+1) 1275.80

Step 11. Synthesis of 2.1

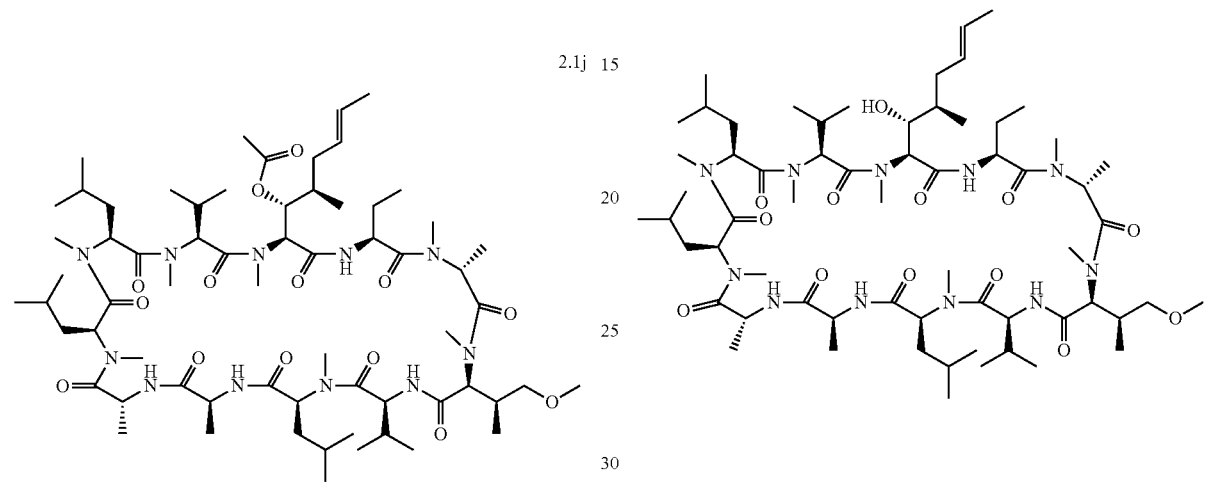

To a solution of 2.1j (25 mg, 0.02 mmol, 1.0 equiv) in THF (2 mL) was added 25% tetramethylammonium hydroxide (25% in MeOH, 71.5 mg, 0.196 mmol, 20 equiv) at 0° C. After stirring for 30 min at same temperature, the solution was extracted with EtOAc. The organic layer was washed with saturated aqueous saturated aqueous ammonium chloride and then with brine, dried with magnesium sulfate and concentrated. The residue was purified by HPLC to provide 2.1 (12 mg, 50% yield). MS m/z (M+1) 1234.3

II.2 Synthesis of 2.2

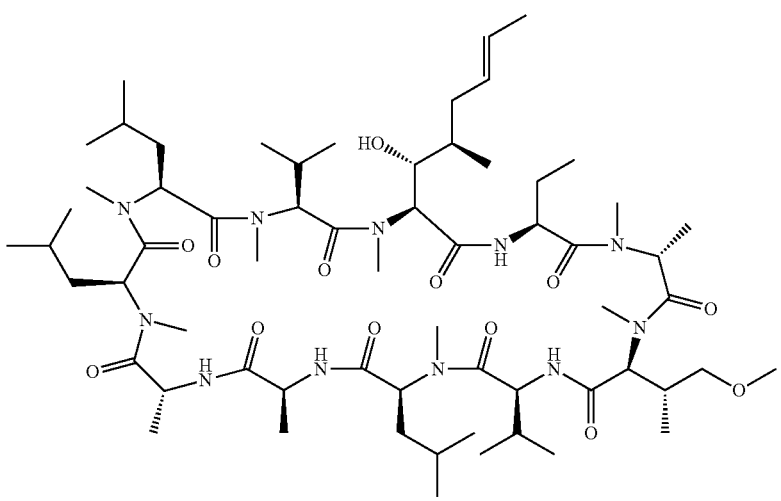

Step 1. Synthesis of ((1S,2R)-1-Furan-2-yl-2-methyl-3-oxo-propyl)-carbamic acid tert-butyl ester [2.2a]

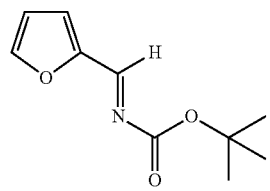

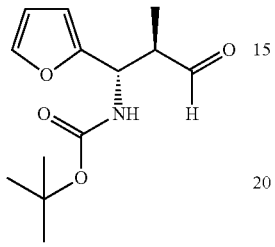

2.2a

To a solution of (S)-2-(diphenyl-trimethylsilanyloxymethyl)-pyrrolidine (417.0 mg, 1.3 mmol, 10 mol %) in acetonitrile (26 mL) at room temperature was added 1-propanal (2.6 mL, 38.4 mmol, 3.0 equiv) and 1-furan-2-yl-meth-(E)-ylidene]-carbamic acid tert-butyl ester (2.5 g, 12.8 mmol). After stirring at room temperature for 12 hours, the reaction mixture was quenched with water (20 mL) and extracted with EtOAc (3×30 mL). The organic layer was dried over $Na_2SO_4$, filtered and concentrated in vacuo. The crude residue was purified by column chromatography on silica gel (EtOAc/heptane) to give ((1S,2R)-1-furan-2-yl-2-methyl-3-oxo-propyl)-carbamic acid tert-butyl ester as a light yellow oil (2.4 g, 74% yield, dr=62:38) [dr=62:38 was determined by integration of one set of $^1$H NMR signal (major s, 9.68 ppm, minor s, 9.76 ppm)]. $^1$HNMR (400 MHz, $CDCl_3$) 9.76 (s, 1H), 9.68 (s, 1H), 7.34 (d, J=1.57 Hz, 1H), 6.38-6.17 (m, 2H), 5.08 (m, 2H), 2.94 (m, 1H), 1.44 (s, 9H), 1.09 (t, 3H).

Step 2. Synthesis of ((1S,2R)-1-Furan-2-yl-3-hydroxy-2-methyl-propyl)-carbamic acid tert-butyl ester [2.2b]

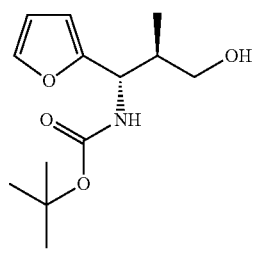

2.2b

To a solution of 2.2a (2.4 g, 9.48 mmol) in methanol (38 mL) at 0° C. was added $NaBH_4$ (1.8 g, 47.4 mmol, 5.0 equiv). After stirring for 1 hour, the reaction was diluted with EtOAc, washed with saturated aqueous $NH_4Cl$, brine, dried over $Na_2SO_4$, filtered and concentrated in vacuo. The residue was purified by HPLC purification using AD column: 90/10 heptane/EtOH to afford the desired diastereomer (503.0 mg, 20% yield). $^1$H NMR (400 MHz, $CDCl_3$) 7.36 (s, 1H), 6.34 (dd, J=3.13, 1.96 Hz, 1H), 6.18 (d, J=3.13 Hz, 1H), 5.13 (br-s, 2H), 3.51 (dd, J=11.74, 5.09 Hz, 2H), 3.33 (t, J=11.15 Hz, 1H), 2.24 (br-s, 2H), 1.47 (s, 9H), 0.73 (d, J=6.65 Hz, 3H).

Step 3. Synthesis of ((1S,2R)-1-Furan-2-yl-3-methoxy-2-methyl-propyl-methylcarbamic acid tert-butyl ester [2.2c]

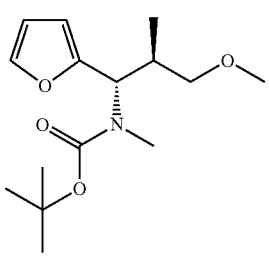

2.2c

To a suspension of NaH (379.0 mg, 9.5 mmol, 6.6 equiv) in THF (1 mL) at 0° C. was added ((1S,2R)-1-furan-2-yl-3-hydroxy-2-methyl-propyl)-carbamic acid tert-butyl ester (367.0 mg, 1.4 mmol) in THF (3 mL). The reaction mixture was stirred for 10 min at 0° C. followed by addition of MeI (0.539 mL, 8.6 mmol, 6.0 equiv) and DMF (0.4 mL). After stirring for 2 hours at room temperature, the reaction mixture was quenched with water (5 mL and extracted with EtOAc (30 mL). The combined organic layers were washed with brine, dried over $Na_2SO_4$ and concentrated in vacuo. The resulting residue was purified by column chromatography on silica gel (EtOAc/heptane) to give ((1S,2R)-1-furan-2-yl-3-methoxy-2-methyl-propyl methylcarbamic acid tert-butyl ester as a yellow oil (214.0 mg, 53% yield).

Step 4. Synthesis of (2S,3R)-2-(tertButoxycarbonyl-methyl-amino)-4-methoxy-3-methyl-butyric acid [2.2d]

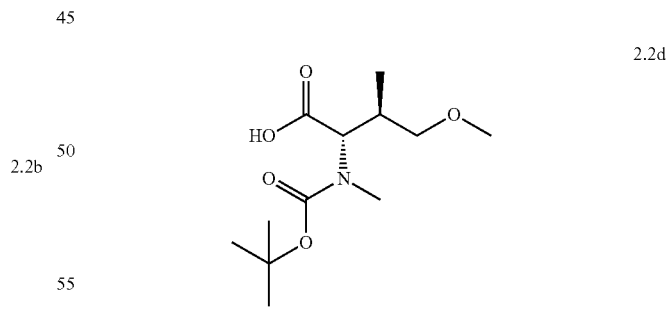

2.2d

To a stirred solution of $NaIO_4$ (969.0 mg, 4.5 mmol, 6.0 equiv) in $H_2O/CCl_4/CH_3CN$ (3/2/3, 21 mL) was added $RuCl_3$ (53.0 mg, 0.26 mmol, 0.34 equiv). After stirring for 15 minutes, a solution of ((1S,2R)-1-furan-2-yl-3-methoxy-2-methyl-propyl methylcarbamic acid tert-butyl ester (214.0 mg, 0.76 mmol) in $CH_3CN$ (4 mL) was added. After 15 minutes, the mixture was diluted with water (5 mL) and extracted with EtOAc (3×10 mL). The combined layers were washed successively with saturated aqueous $NaHSO_3$, brine, dried over $Na_2SO_4$, and concentrated in vacuo to give (2S,3R)-2-(tertbutoxycarbonyl-methyl-amino)-4-methoxy-3-methyl-butyric acid (180.0 mg).

Step 5. Synthesis of 2.2e

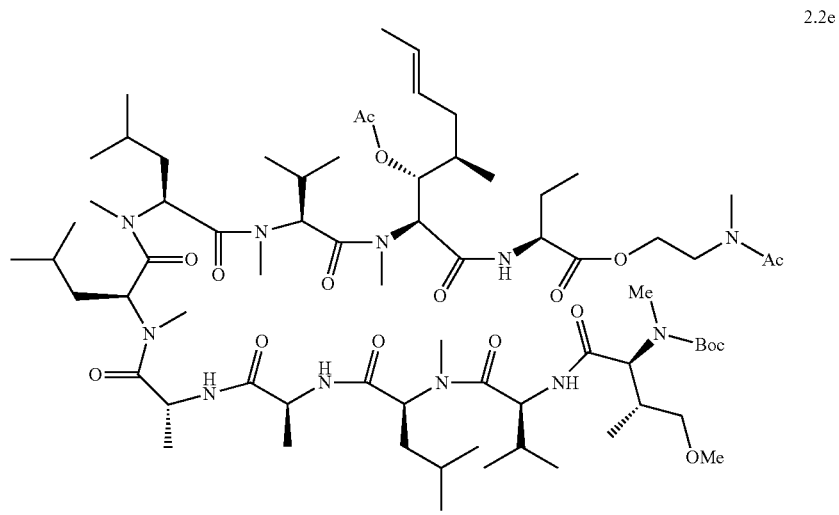 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@@H](C)COC)N(C)C(=O)OC(C)(C)C)C(C)C]

2.2e

To a solution of (2S,3R)-2-(tertbutoxycarbonyl-methyl-amino)-4-methoxy-3-methyl-butyric acid (34.0 mg, 0.13 mmol, 1.5 equiv) in DCM (1 mL) were added DIPEA (45.0 uL, 0.26 mmol, 3.0 equiv), HATU (33.0 mg, 90 umol, 1.2 equiv) and HOAt (14.0 mg, 0.1 mmol, 1.2 equiv). The mixture was stirred for 20 minutes and the amine 1 (100.0 mg, 90 umol) was added. After stirring for 3 hours at room temperature, the reaction mixture was diluted with EtOAc (30 mL) and washed with water and brine. The organic layer was dried over $Na_2SO_4$ and concentrated in vacuo. The resulting residue was purified by column chromatography on silica gel (MeOH/DCM) to give 2.2e (75.0 mg, 62% yield). MS m/z (M+1-Boc) 1307.7

Step 6. Synthesis of 2.2f

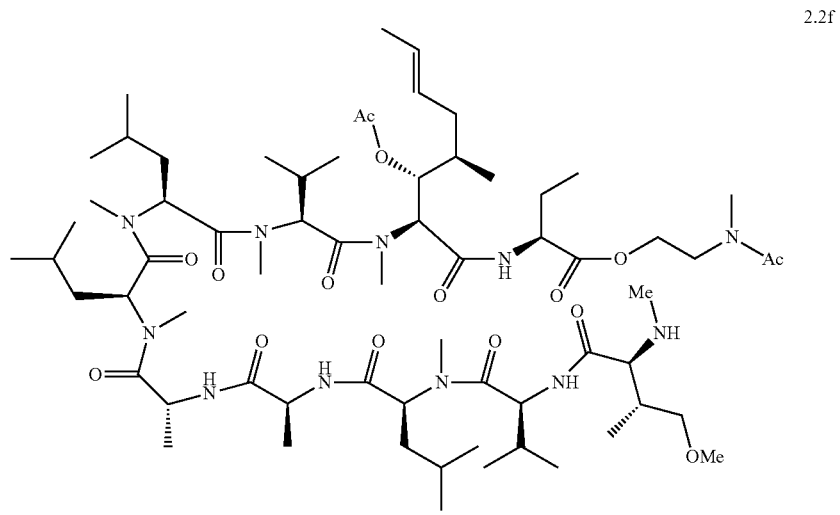 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@@H](NC)[C@@H](C)COC)C(C)C]

2.2f

To a solution of compound 2.2e (120.0 mg, 85.0 umol) in methylene chloride (0.57 mL) at 0° C. was added trifluoroacetic acid (0.28 mL). After stirring at room temperature for 1.5 hours, the reaction mixture was quenched with saturated aqueous sodium bicarbonate and diluted with methylene chloride. The aqueous layer was extracted with methylene chloride. The combined organic layers were washed with brine, dried with Na$_2$SO$_4$, filtered and concentrated in vacuo to afford compound 2.2f (110.0 mg). MS m/z (M+1) 1306.9

Step 7. Synthesis of 2.2g

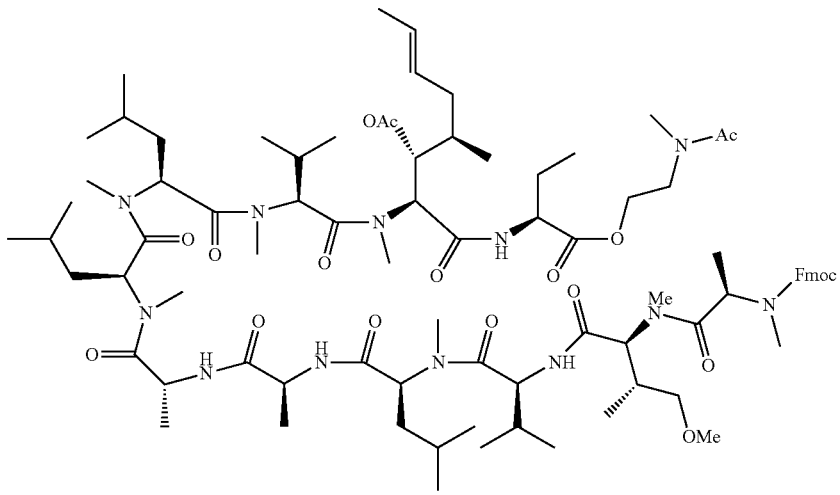

2.2g

To a solution of compound 2.2f (111 mg, 85.0 umol) in methylene chloride (0.85 mL) at 0° C. was added N-Fmoc-N-methyl-D-Alanine-OH (30 mg, 94.0 umol, 1.1 equiv) followed by HATU (48.5 mg, 0.128 mmol, 1.5 equiv) and DIPEA (44.5 uL, 0.255 mmol, 3.0 equiv). After stirring for 12 hours at room temperature, the reaction mixture was concentrated in vacuo and purified by silica gel chromatography (45% acetone/methylene chloride) to give compound 2.2g (73.5 mg, 54%). MS m/z (M+1) 1614.6

Step 8. Synthesis of 2.2h

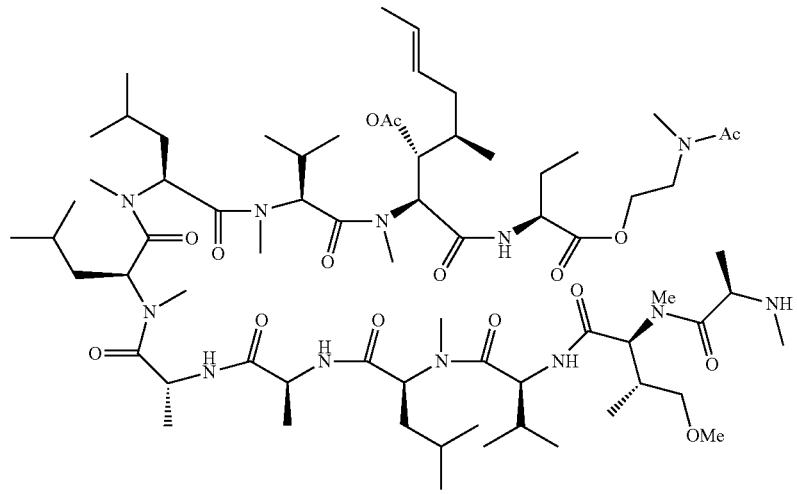

2.2h

To a solution of compound 2.2g (73.5 mg, 46.0 umol) in methanol:water (33:1, 0.515 mL) was added tetramethylammonium hydroxide (25% w/w in MeOH, 0.192 mL, 0.455 mmol, 10 equiv) at room temperature. After stirring for 1 hour, the reaction mixture was diluted with water and methylene chloride. The aqueous layer was extracted with methylene chloride. The combined organic layers were washed with brine, dried with $Na_2SO_4$, filtered and concentrated in vacuo to afford compound 2.2h (44.2 mg) which was used for the next step without further purification. MS m/z (M+1) 1250.7

Step 9. Synthesis of 2.2

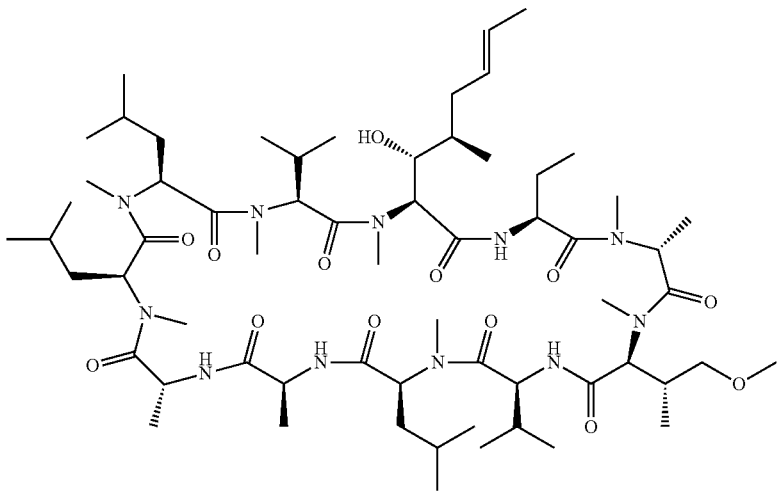

2.2

To a suspension of HATU (20.2 mg, 53.0 umol, 1.5 equiv) in methylene chloride (10 mL) at 0° C. was added dropwise a solution of compound 2.2f (44.2 mg, 35.0 umol) and DIPEA (19.0 uL, 0.106 mmol, 3.0 equiv) in methylene chloride (25 mL). After stirring at room temperature for 12 hours, the reaction mixture was quenched with saturated aqueous sodium bicarbonate and diluted with methylene chloride. The aqueous layer was extracted with methylene chloride. The combined organic layers were washed with brine, dried with $Na_2SO_4$, filtered and concentrated in vacuo. Purification by reverse phase HPLC afforded compound 2.2 (7 mg, 16% yield). MS m/z (M+1) 1232.8

II.3 Synthesis of Compound 2.3

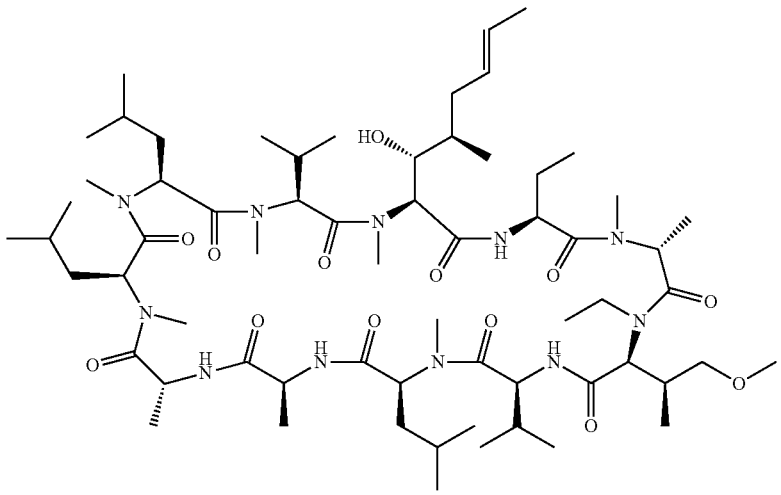

2.3

Step 1. Synthesis of ((1S,2S)-3-Ethoxy-1-furan-2-yl-2-methyl-propyl)-ethyl-carbamic acid tert-butyl ester [2.3a]

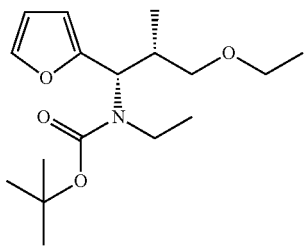

2.3a

A solution of 2.1b (1.0 g, 3.92 mmol, 1.0 equiv) in tetrahydrofuran (14 mL) was added to a suspension of 60% sodium hydride (1.03 g, 26.0 mmol, 6.6 equiv) in tetrahydrofuran (10 mL) at 0° C. To the reaction mixture was added EtI (3.7 g, 1.9 mL, 23.5 mmol, 6.0 equiv) and the resulting mixture was stirred at 0° C. for 10 minutes and room temperature for 16 hours. The reaction mixture was then diluted with ethyl acetate and neutralized with 1.0 N hydrochloric acid, washed with brine. The organic layer was dried over magnesium sulfate and concentrated. The residue was purified by silica gel column chromatography, (heptanes/ethyl acetate) to give product 2.3a (750 mg, 75% yield). $^1$H NMR (400 MHz, CDCl$_3$) ppm 0.74 (m 3H), 1.04 (br. S. 3H) 1.13 (s, 3H) 1.47 (a, 9H) 2.45 (m, 1H) 3.1 (m, 2H) 3.35 (m, 4H) 4.48-5.33 (m, 1H) 6.16-6.29 (m, 1H) 6.32 (m, 1H) 7.36 (d, J=0.78 Hz, 1H).

Step 2. Synthesis of Compound 2.3

Compound 2.3a was then converted to 2.3 according to the procedure described for the synthesis of 2.1. MS m/z (M+1) 1261.2

II.4. Synthesis of Compound 2.4

Step 1. Synthesis of 2.4a

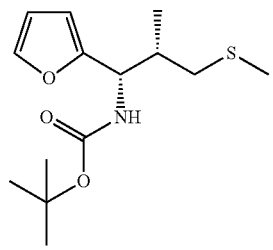

2.4a

To a solution of 2.1b (1.0 g, 3.9 mmol) in DCM (10.0 mL) at 0° C. was added TEA (1.1 mL, 7.8 mmol) and MsCl (0.37 mL, 4.7 mmol). After stirring at 0° C. for 1 hour, the reaction was quenched by addition of MeOH. The solution was then washed with saturated aqueous NH$_4$Cl solution, brine, dried over MgSO$_4$ and concentrated. The residue was dissolved in DMF (12 ml) and sodium methanethiolate (0.412 g, 5.88 mmol) was added in one portion. After stirring for 4 hours at room temperature, the reaction mixture was diluted with ethyl acetate, washed with water, brine, dried over sodium sulfate and concentrated. The resulting residue was purified by flash column chromatography on silica gel (0-80% ethyl acetate in heptane) to give 2.4a (1.1 g, 92% yield). MS m/z (M+1) 286.1

Step 2. Synthesis of 2.4b

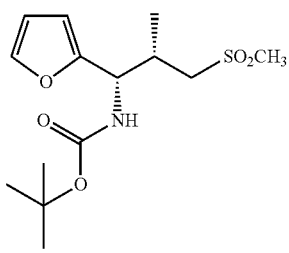

2.4b

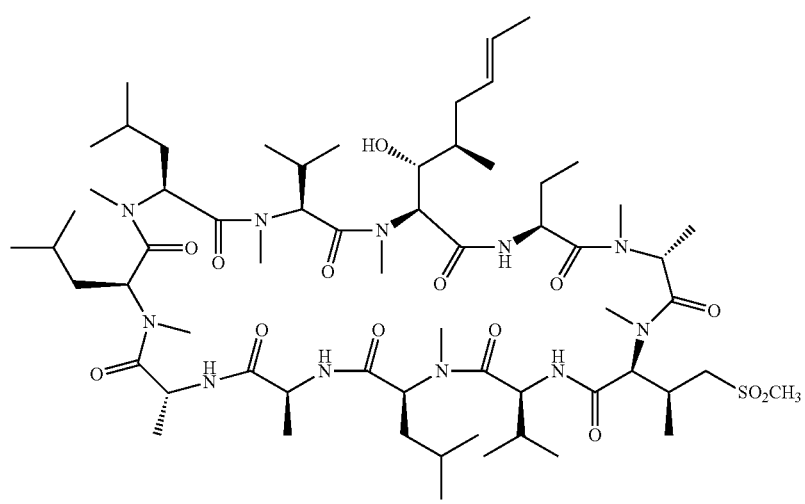

2.4

To a 0° C. solution of 2.4a (1.1 g, 3.85 mmol) in DCM (20 ml) was added m-CPBA (1.73 g, 7.71 mmol) in three portions. The reaction mixture was stirred for 3 h at room temperature. The reaction mixture was diluted with ethyl acetate, washed with water, saturated aqueous sodium bicarbonate solution, brine, dried over sodium sulfate and concentrated. The crude product was purified by flash column chromatography on silica gel (0-80% ethyl acetate in heptane) to give 2.4b (1.0 g, 82% yield) as a white solid. MS m/z (M+1) 318.0

Step 3. Synthesis of 2.4c

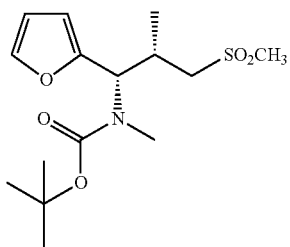

2.4c

To a 0° C. solution of 2.4b (1.0 g, 3.15 mmol) in THF (16 ml) was added sodium hydride (0.19 g, 4.73 mmol) in two portions. The mixture was stirred in an ice bath for 20 minutes, followed by the addition of DMF (1.60 ml) and iodomethane (0.39 ml, 6.30 mmol). The reaction mixture was stirred at room temperature for 1.5 hours. After this time, the reaction mixture was cooled to 0° C., and was quenched with water. The resulting solution was extracted with ethyl acetate. The organic phase was dried over sodium sulfate and concentrated to give crude 2.4c (1.0 g, 96% yield). The crude product was used in next reaction without further purification. MS m/z (M+1) 332.1

Step 4. Synthesis of 2.4d

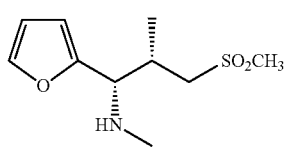

2.4d

To a 0° C. solution of 2.4c (400 mg, 1.21 mmol) in DCM (15 ml) was added 50% TFA in DCM (6 ml). The mixture was stirred in an ice bath for 1.5 hours. The solvent was removed under vacuum, and the residue was diluted with ethyl acetate and then basified with saturated aqueous sodium bicarbonate solution. The two phases were separated; the organic phase was washed with brine, dried over sodium sulfate and concentrated to give crude product 2.4d (250 mg, 90% yield). MS m/z (M+1) 232.1

Step 5. Synthesis of 2.4e

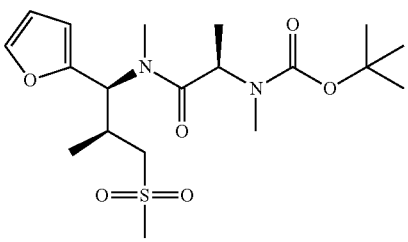

2.4e

To a solution of 2.4d (250 mg, 1.08 mmol) in DMF (3 ml) was added (R)-2-((tert-butoxycarbonyl)(methyl)amino)propanoic acid (220 mg, 1.08 mmol), followed by the addition of HATU (493 mg, 1.29 mmol) and DIEA (0.57 ml, 3.24 mmol). The resulting mixture was stirred at room temperature for 1 hour, after which, the reaction mixture was diluted with ethyl acetate and water. The two phases were separated; the organic phase was washed with saturated aqueous sodium bicarbonate solution, brine, dried over sodium sulfate and concentrated. The crude product was purified by flash column chromatography on silica gel eluting with 0-80% ethyl acetate in heptane to give 2.4e (290 mg, 64.4% yield). MS m/z (M+1) 417.1

Step 6. Synthesis of 2.4f

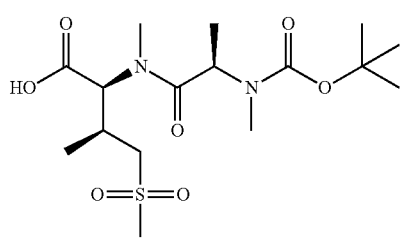

2.4f

To a well-stirred solution of sodium periodate (894 mg, 4.18 mmol) in acetonitrile (3 ml), CCl$_4$ (1.98 ml), water (3 ml) was added Ruthenium (III) Chloride (43.2 mg, 0.21 mmol). The mixture was stirred for at room temperature 15 minutes, followed by the addition of 2.4e (290 mg, 0.70 mmol) in 3 ml acetonitrile. The reaction mixture was stirred for 5 minutes at room temperature and was quenched with 10 mL water. The resulting mixture was extracted with ethyl acetate. The organic phase was washed with saturated aqueous NaHSO$_3$ solution, brine, dried over sodium sulfate and concentrated to give product 2.4f (150 mg, 54.6% yield). MS m/z (M+1) 395.1

Step 7. Synthesis of 2.4g
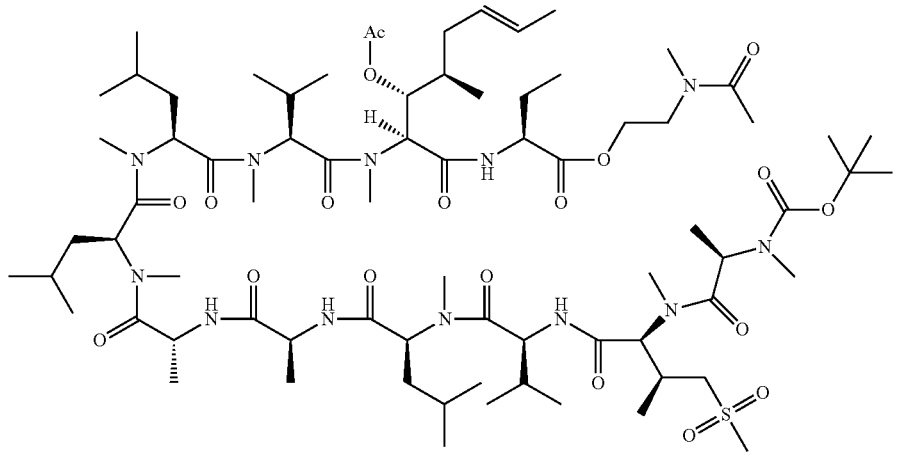
2.4g
To a solution of 2.4f (120 mg, 0.30 mmol) in DMF (3 ml) at 0° C. was added amino ester 1 (354 mg, 0.30 mmol), DIEA (0.159 ml, 0.91 mmol) and HATU (173 mg, 0.46 mmol). The resulting solution was stirred at room temperature for 2 hours. The reaction mixture was purified by flash column chromatography on silica gel eluting with 0-30% acetone in DCM to give 2.4g (150 mg, 32.0% yield). MS m/z (M+1) 1541
Step 8. Synthesis of 2.4h
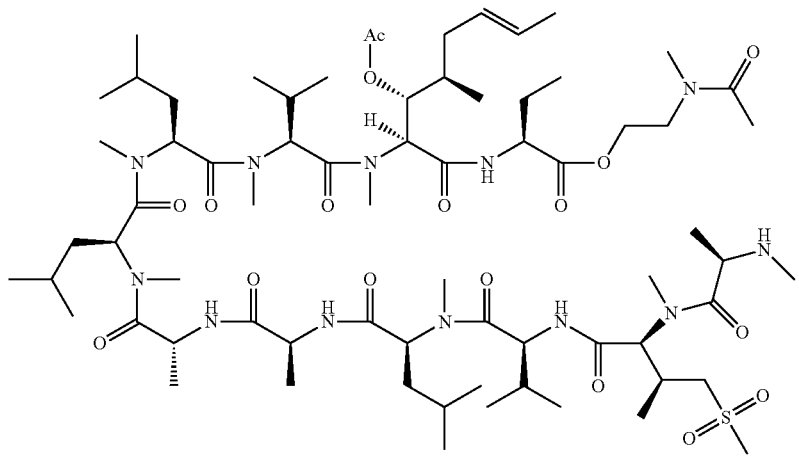
2.4h To an ice cold solution of 2.4g (150 mg, 0.097 mmol) in DCM (3 mL) was added 50% TFA in DCM (4 ml). The resulting solution was stirred at room temperature for 2 hours. After this time, the solvent was removed under vacuum. The resulting residue was diluted with ethyl acetate and was washed with saturated aqueous sodium bicarbonate solution, brine, dried over sodium sulfate, filtered and concentrated to give product 2.4h (140 mg, 90% yield). MS m/z (M+1) 1440

Step 9. Synthesis of 2.4i

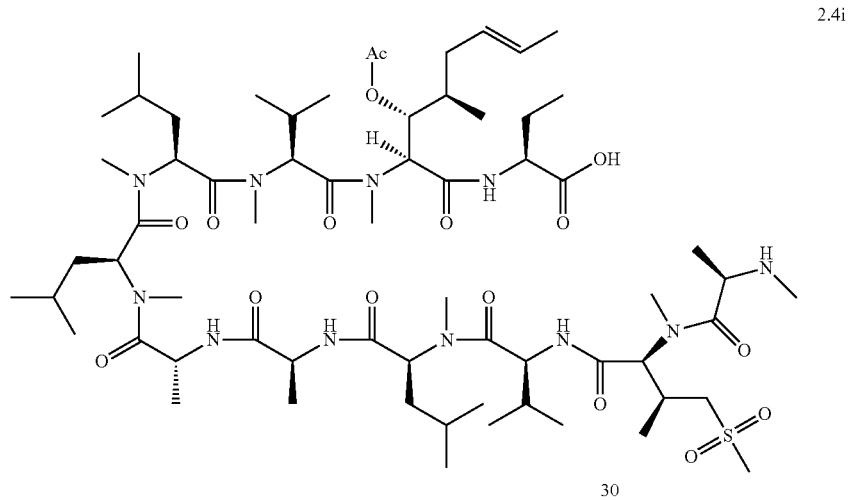

2.4i

To an ice cooled solution of 2.4h (140 mg, 0.097 mmol) in THF/MeOH/water (1 mL/1 mL/1 mL) was added lithium hydroxide (11.6 mg, 0.48 mmol). After stirring at 0° C. for 1 hour, the reaction mixture was diluted with ethyl acetate and water. To the mixture was then added 1.0 N HCl aq. solution (0.583 ml, 0.583 mmol) and the two phases were separated. The organic phase was washed with brine, dried and concentrated to give product 2.4i (110 mg, 55.7% yield). MS m/z (M+1) 1341

Step 10. Synthesis of 2.4j

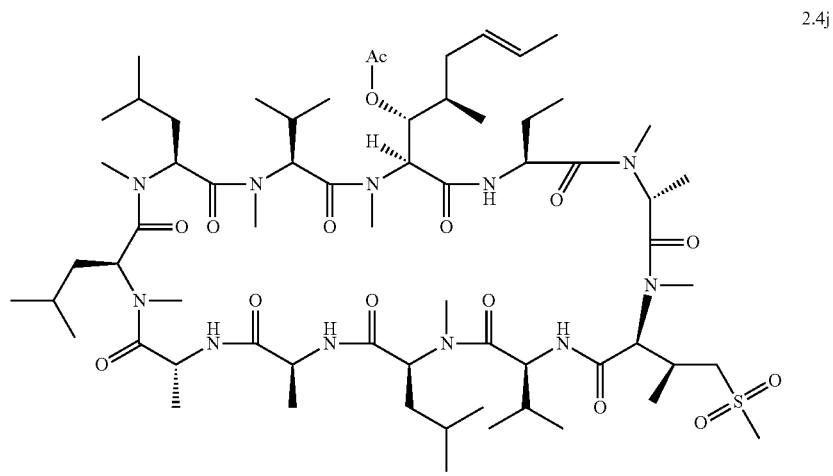 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)CS(C)(=O)=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.4j

To a solution of BOP (72.6 mg, 0.16 mmol) in DCM (200 ml), was added 2.4i (110 mg, 0.082 mmol), DMAP (20.05 mg, 0.16 mmol) in 50 ml DCM. The resulting solution was stirred at room temperature for 18 hours. The reaction mixture was washed with saturated aqueous sodium bicarbonate solution, brine, dried over sodium sulfate, and concentrated to give product 2.4j (140 mg, 90% yield). MS m/z (M+1) 1323

Step 12. Synthesis of 2.4

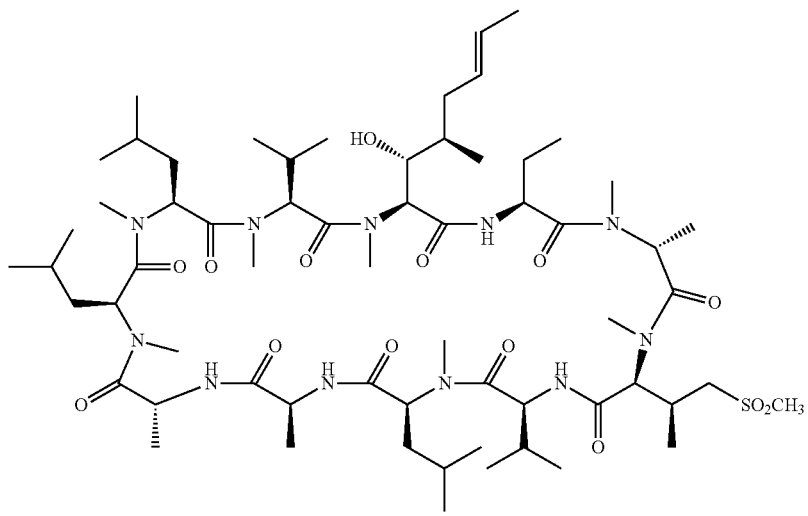

2.4

To an ice cooled solution of 2.4j (110 mg, 0.083 mmol) in MeOH (1.5 mL), was added tetramethylammonium hydroxide (25% weight in MeOH, 0.42 ml, 0.99 mmol). After stirring at room temperature for 2 hours, the reaction mixture was quenched with 1.0 M $NaHSO_4$ and the resulting solution was extracted with ethyl acetate. The organic phase was washed with brine, dried over sodium sulfate and concentrated. The crude product was purified by HPLC to give 2.4 (6.3 mg, 6% yield). MS m/z (M+1) 1281.

II.5.1 Synthesis of Compound 2.5.1

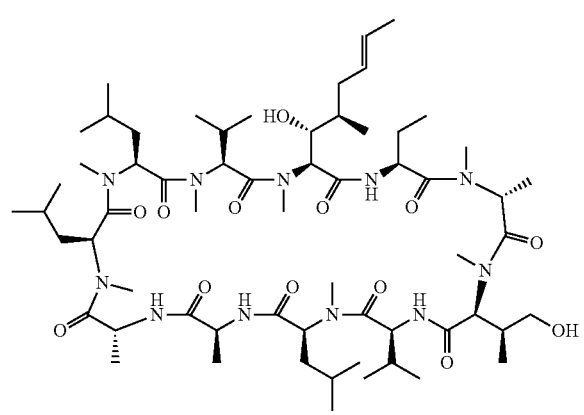

2.5.1

Step 1. Synthesis of (1S,2S)-3-(tert-butyl-diphenyl-silanyloxy)-1-furan-2-yl-2-methyl-propyl)-carbamic acid tert-butyl ester [2.5.1a]

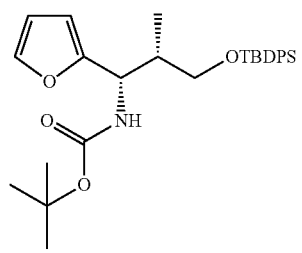

2.5.1a

To a solution of 2.1b (2.0 g, 7.8 mmol, 1.0 equiv) in DMF (30 mL) were added tert-Butyl-chloro-diphenyl-silane (2.4 g, 8.6 mmol, 1.1 equiv) and imidazole (1.2 g, 17.2 mmol, 2.2 equiv). After stirring at room temperature for 18 hours, the reaction was quenched by addition of 1.0 N hydrochloric acid solution and the mixture was extracted with EtOAc. The organic layer was washed with brine, dried over magnesium sulfate and concentrated to give product 2.5.1a (3.9 g, 100%) as a crude product. $^1$H NMR (400 MHz, $CDCl_3$) 0.85 (d, J=7.04 3H); 1.08 (s, 9H); 1.43 (s, 9H); 2.30 (m, 1H); 3.41 (m, 1H); 3.54 (m, 1H); 4.89 (m, 1H); 5.93 (s, 1H); 6.17 (m, 1H); 6.32 (m, 1H); 7.31 (s, 1H); 7.4 (m, 6H); 7.65 (m, 4H).

Step 2. Synthesis of ((1S,2S)-3-(tert-Butyl-diphenyl-silanyloxy)-1-furan-2-yl-2-methyl-propyl)-methyl-carbamic acid tert-butyl ester) [2.5.1 b]

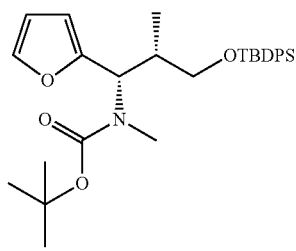

2.5.1b (1S,2S)-3-(tert-butyl-diphenyl-silanyloxy)-1-furan-2-yl-2-methyl-propyl)-carbamic acid tert-butyl ester 2.5.1a (3.9 g, 7.9 mmol, 1.0 equiv) was added to a suspension of 60% sodium hydride (0.94 g, 23.5 mmol, 3.0 equiv) in dry tetrahydrofuran (30 mL) at 0° C. under nitrogen. After stirring at 0° C. for 15 min, to this solution was added methyl iodide (3.7 g, 16.0 mL, 26.0 mmol, 3.3 equiv) and DMF (3 mL). The reaction mixture was then stirred at room temperature for 3 hours. The reaction was quenched with sat. ammonium chloride aq. solution and extracted with ethyl acetate. The organic layer was washed with brine, dried over sodium sulfate and concentrated to give obtain (1S,2S)-3-(tert-Butyl-diphenyl-silanyloxy)-1-furan-2-yl-2-methyl-propyl)-methyl-carbamic acid tert-butyl ester (4.0 g, 100%). $^1$H NMR (400 MHz, CDCl$_3$) 0.84 (m, 3H); 1.00 (s, 9H); 1.50 (s, 9H); 2.33 (m, 1H); 2.71 (m, 3H); 3.47 (m, 3H); 5.26 (m, 1H); 6.09 (m, 1H); 5.93 (s, 1H); 6.16 (m, 1H); 6.26 (m, 1H)

Step 3. Synthesis of (1S,2S)-3-((tert-butyldiphenyl-silyl)oxy)-1-(furan-2-yl)-N,2-dimethylpropan-1-amine [2.5.1c]

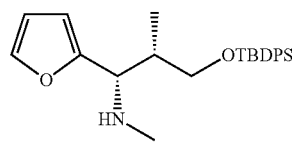

2.5.1c

To a solution of 2.5.1b (5.0 g, 9.85 mmol, 1.0 equiv) in dichloromethane (20 mL) at 0° C. was added trifluoroacetic acid (10.0 mL, 130.0 mmol, 13.2 equiv). After 1 hour of stirring at the same temperature, the solution was concentrated. The residue was diluted with ethyl acetate, washed with saturated aqueous NaHCO$_3$ and brine. The organic layer was dried over magnesium sulfate and concentrated to obtain 4.0 g (100% yield) of the titled compound ((1S,2S)-3-(tert-Butyl-diphenyl-silanyloxy)-1-furan-2-yl-2-methyl-propyl)-methyl-amine, which was used in the next step with no further purification.

Step 4. Synthesis of ((R)-1-((1S,2S)-3-(tert-Butyl-diphenyl-silanyloxy)-1-furan-2-yl-2-methyl-propyl)-methyl-carbamoyl)-ethyl)-methyl-carbamic acid-9H-fluoren-9-ylmethyl ester [2.5.1d]

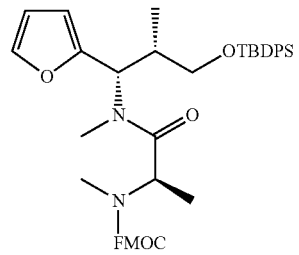

2.5.1d

To a mixture of (R)-2-(9H-Fluoren-9-yl-methoxycarbonyl)-methyl-amino)-propanoic acid (3.83 g, 11.8 mmol, 1.2 equiv), HATU (4.5 g, 11.8 mmol, 1.2 equiv) and DIPEA (3.8 g, 5.2 mL, 29.4 mmol, 3.0 equiv) in DCM (40 mL) was added a solution of ((1S,2S)-3-(tert-Butyl-diphenyl-silanyloxy)-1-furan-2-yl-2-methyl-propyl)-methyl-amine (4.0 g, 9.81 mmol, 1 equiv) in DCM (20 mL). After stirring at room temperature for 16 hours, the solution was diluted with ethyl acetate, washed with 1.0 N hydrochloric acid and brine. The organic layer was dried over magnesium sulfate and concentrated. The crude material was then purified by silica gel column chromatography (heptanes/ethyl acetate) to give product 2.5.1d (2.0 g, 29% yield). MS m/z (M+1) 715.2

Step 5. Synthesis of (2S,3S)-4-(tert-Butyl-diphenyl-silanyloxy-2-((R)-2-((9H-fluoren-9-ylmethoxycarbonyl)-methyl-amino)-propionyl)-methyl-amino)-3-methyl-butric acid [2.5.1e]

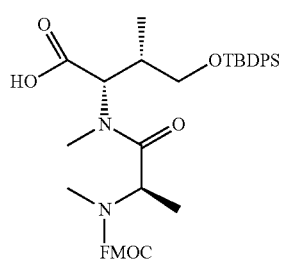

2.5.1e

Ruthenium(III) chloride (175 mg, 0.85 mmol, 0.3 equiv) was added to a well stirred suspension of sodium periodate (5.38 g, 25.2 mmol, 9.0 equiv) in acetonitrile/carbon tetrachloride/water (10 mL/6.67 mL/10 mL). After 15 minutes of stirring, ((R)-1-((1S,2S)-3-(tert-Butyl-diphenyl-silanyloxy)-1-furan-2-yl-2-methyl-propyl)-methyl-carbamoyl)-ethyl)-methyl-carbamic acid-9H-fluoren-9-ylmethyl ester (2.0 g, 2.80 mmol, 1.0 equiv) was added and stirring continued for 5 more minutes. The reaction mixture was then quenched with water (25 mL) and extracted with ethyl acetate. The organic layer was washed with saturated aqueous saturated aqueous sodium bisulfite then with brine, dried over magnesium sulfate and concentrated to give product 2.5.1e (1.94 g). The crude material was used in the next step with no further purification. MS m/z (M+1) 693.4

Step 6. Synthesis of 2.5.1f

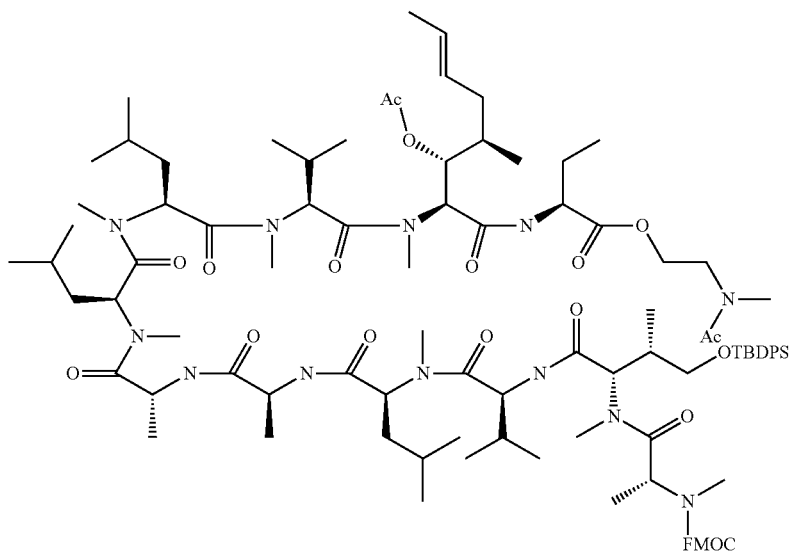

2.5.1f

To a suspension of 2.5.1e (1.43 g, 2.1 mmol, 1.0 equiv), HATU (784 mg, 2.1 mmol, 1.2 equiv) and DIPEA (666 mg, 0.90 mL, 5.16 mmol, 3 equiv) in dichloromethane (10 mL) was added compound 1 (2.0 g, 1.7 mmol, 1.0 equiv). The resulting suspension was stirred at room temperature for 16 hours, after which, it was diluted with ethyl acetate, washed with 1.0 N hydrochloric acid and then with brine. The organic layer was dried over magnesium sulfate and concentrated. The crude material was then purified by silica gel column chromatography (heptanes/acetone) to give product 2.5.1f (3.2 g, 100% yield). MS m/z (M+1) 1838.8

Step 7. Synthesis of 2.5.1g

Tris(2-aminoethyl) amine (573 mg, 0.59 mL, 3.92 mmol, 4.0 equiv) was added to a solution of 2.5.1f (1.8 g, 0.98 mmol, 1 equiv) in dichloromethane (12 mL) at room temperature and the resulting mixture was stirred at room temperature for 3 hours. The solution was then diluted with ethyl acetate; washed with 1.0 N hydrochloric acid, then with brine. The organic layer was dried over magnesium sulfate and concentrated to give product 2.5.1g (327 mg, 100% yield). MS m/z (M+1) 1617.0

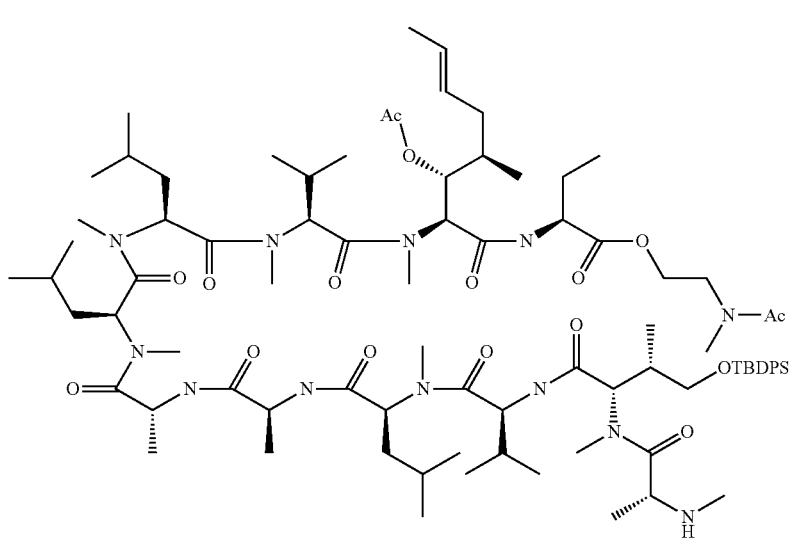

2.5.1g

Step 8. Synthesis of 2.5.1h

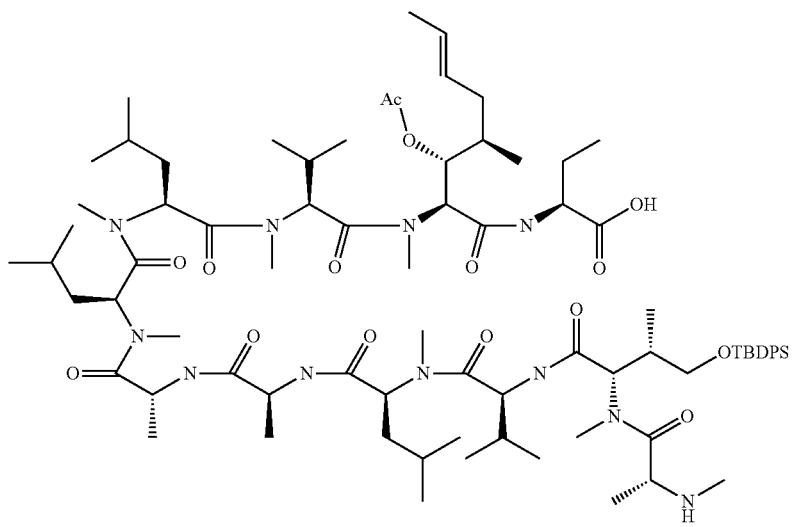

2.5.1h

To a solution of 2.5.1g (1.45 g, 0.88 mmol, 1 equiv) in THF (10 mL) was added 0.5 M sodium hydroxide (10.77 mL, 5.38 mmol, 6 equiv) at 0° C. and the resulting solution was stirred at 0° C. 1 hour. The solution was diluted with ethyl acetate, washed with 1.0 N hydrochloric acid and brine. The organic layer was dried over magnesium sulfate and concentrated to give product 2.5.1h (1.35 g, 100% yield). MS m/z (M+1) 1518.0

Step 9. Synthesis of 2.5.1i

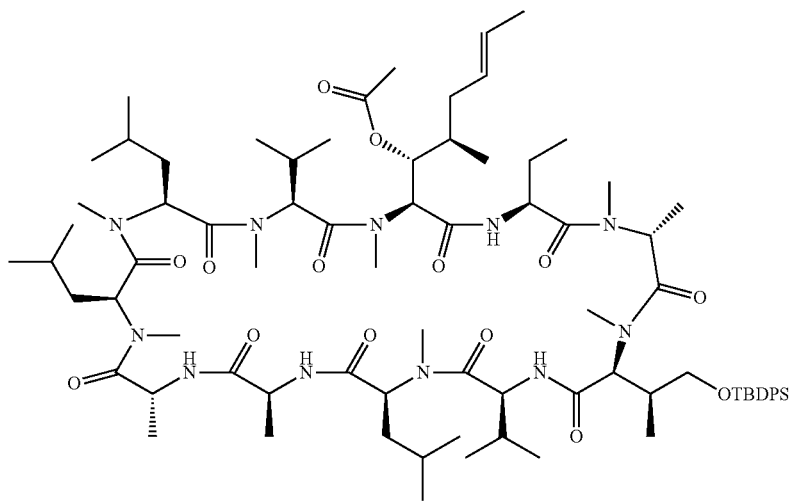

2.5.1i

To a solution of BOP (523 mg, 1.2 mmol, 2.0 equiv) in dichloromethane (50 mL) was added a solution of DMAP (240 mg, 2.0 mmol, 2.0 equiv) and 2.5.1h (1.45 g, 0.98 mmol, 1.0 equiv) in DCM (50 mL) over 15 minutes at room temperature. After stirring at room temperature for 20 hours, the solution was concentrated and the residue was dissolved in EtOAc. The solution was then washed with brine, dried over magnesium sulfate and concentrated. The residue was purified by silica gel column chromatography (heptanes/acetone) to give product 2.5.1i (590 mg, 40% yield). MS m/z (M+1) 1499.8

Step 10. Synthesis of 2.5.1j

Step 11. Synthesis of 2.5.1

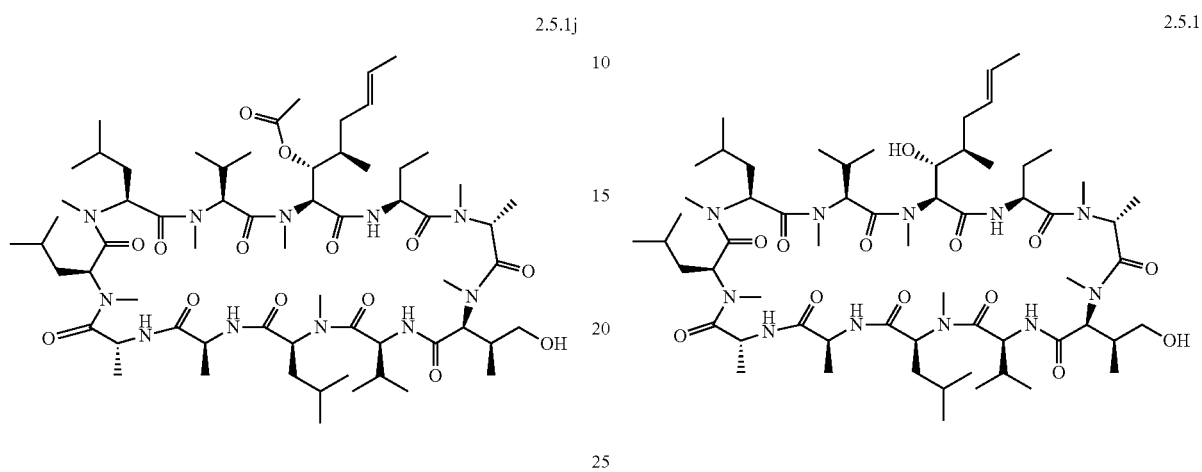

To a solution of 2.5.1i (550 mg, 0.37 mmol, 1.0 equiv) in THF (2.0 mL) was added TBAF (1.0 M in THF, 2.20 mL, 2.20 mmol, 6 equiv) and the resulting solution was stirred at room temperature for 1 hour. The reaction solution was then diluted with ethyl acetate, washed with brine, dried over magnesium sulfate and concentrated. The crude material was purified by silica gel column chromatography (heptanes/acetone) to give product 2.5.1j (347 mg, 75% yield). MS m/z (M+1) 1260.8

To a solution of 2.5.1j (15 mg, 0.012 mmol, 1.0 equiv) in THF (1.0 mL) was added tetrabutyl ammonium hydroxide and resulting solution was stirred at room temperature for 1 hour. The reaction mixture was then diluted with ethyl acetate, washed with saturated aqueous NH$_4$Cl and brine. The organic layer was dried with magnesium sulfate and concentrated. The residue was purified by reverse phase HPLC to give product 2.5.1 (2.5 mg, 17%). MS m/z (M+1) 1219.2

II.5.2 Synthesis of Compound 2.5.2

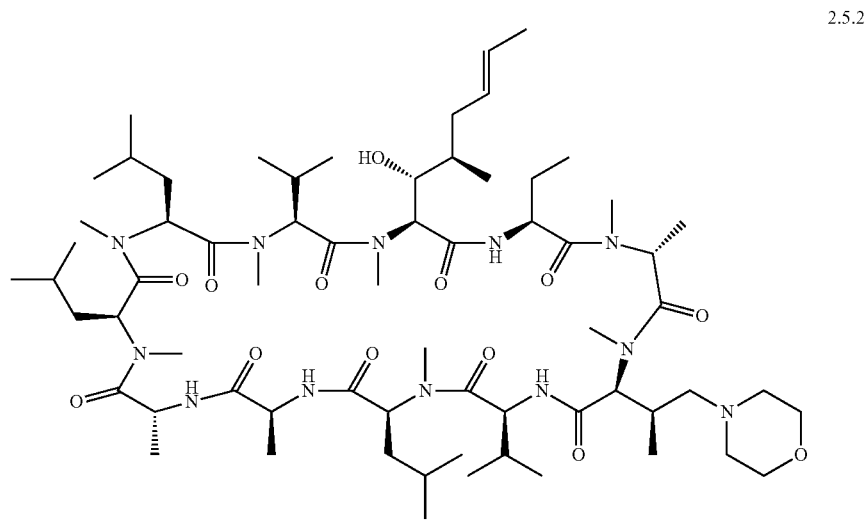 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of 2.5.2a

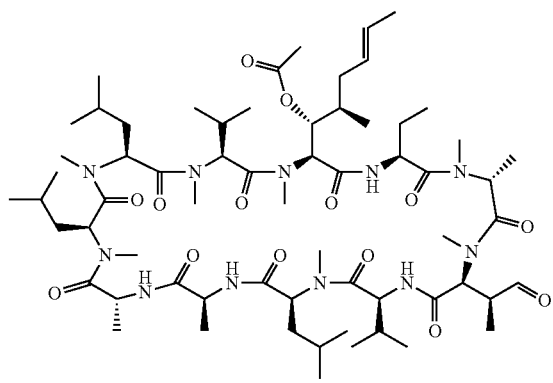

2.5.2a

To a solution of oxalyl chloride (161 mg, 0.111 mL, 1.27 mmol, 16 equiv) in DCM (2 mL) at −78° C. was added DMSO (198 mg, 0.18 mL, 2.54 mmol, 32 equiv) and the resulting solution was stirred at −78° C. for 10 minutes. To the reaction mixture was then added a solution of 2.5.1i (100 mg, 0.08 mmol, 1 equiv) in DCM (1.0 mL). After 10 minutes, TEA (281 mg, 0.387 mL, 2.78 mmol, 35 equiv) was added. The solution was stirred at −78° C. for 10 minutes and at room temperature for 30 minutes. The reaction was quenched by the addition of saturated aqueous saturated aqueous NH$_4$Cl solution. The mixture was extracted with ethyl acetate, washed with brine, dried with magnesium sulfate and concentrated. The crude material was used in the next step with no further purification. MS m/z (M+1) 1258.9

Step 2. Synthesis of 2.5.2b

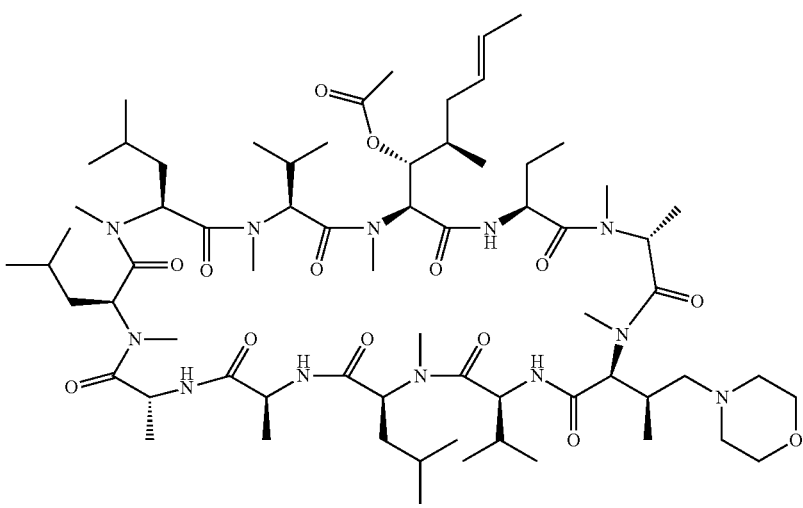

2.5.2b

To a solution of the 2.5.2a (50 mg, 0.04 mmol, 1.0 equiv) in CH$_3$CN (3 mL) was added morpholine (69 mg, 0.69 mmol, 20 equiv) and acetic acid (48 mg, 0.05 mL, 0.80 mmol, 20 equiv). After stirring at room temperature for 15 minutes, sodium triacetoxyborohydride (84 mg, 0.40 mmol, 10.0 equiv) was added and the resulting mixture was stirred at room temperature for 16 hours. To the reaction mixture was then added saturated aqueous saturated aqueous ammonium chloride solution and EtOAc. The phases were separated and the organic layer was washed with brine, dried over magnesium sulfate and concentrated to give product 2.5.2b. The crude material was used in the next step with no further purification. MS m/z (M+1) 1330.5

Step 3. Synthesis of 2.5.2

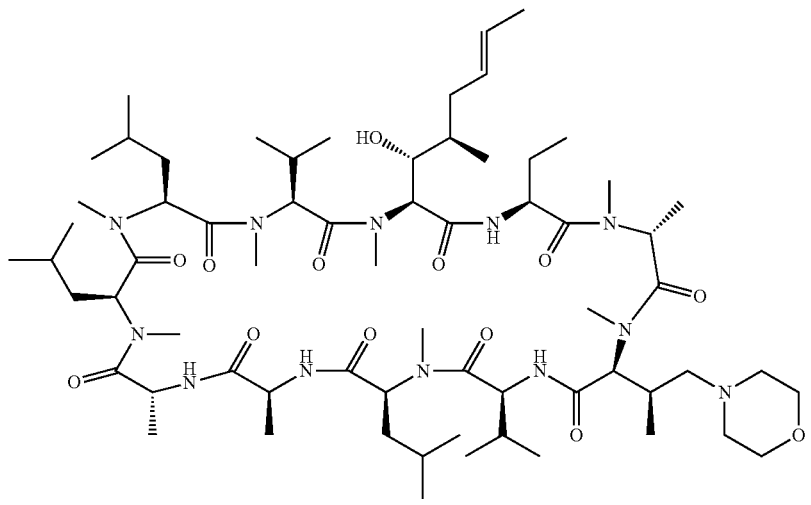

2.5.2

To a solution of 2.5.2b (50 mg, 0.04 mmol, 1.0 equiv) in THF (1 mL) was added tetramethylammonium hydroxide (25% weight in MeOH, 34 mg, 0.376 mmol, 20 equiv) at 0° C. After stirring for 30 minutes at 0° C., the reaction solution was diluted with ethyl acetate and washed with saturated aqueous $NH_4Cl$, brine, dried over magnesium sulfate and concentrated. The crude material was purified by reverse phase HPLC to give product 2.5.2 (21 mg, 43%). MS m/z (M+1) 1288.6

II.5.3 Synthesis of Compound 2.5.3

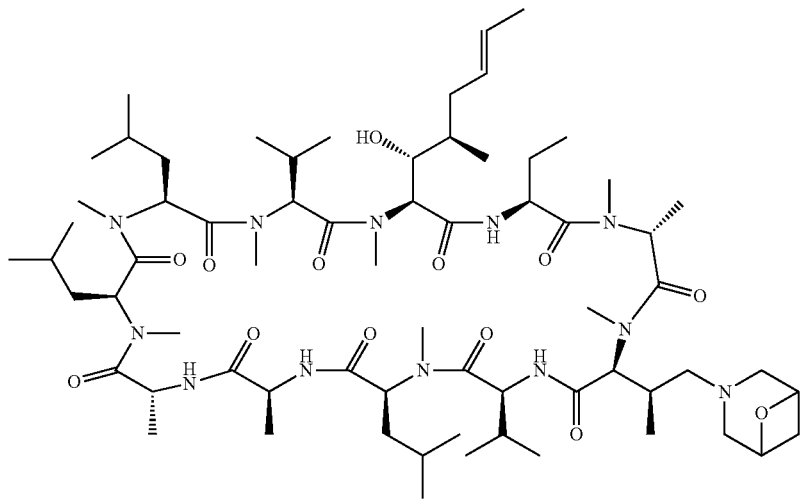

2.5.3

Compound 2.5.3 was prepared following the procedures described for the synthesis of 2.5.2 using 8-oxa-3-aza-bicyclo(3.2.1) octane in Step 2. MS m/z (M+1) 1314.0

II.5.4 Synthesis of Compound 2.5.4
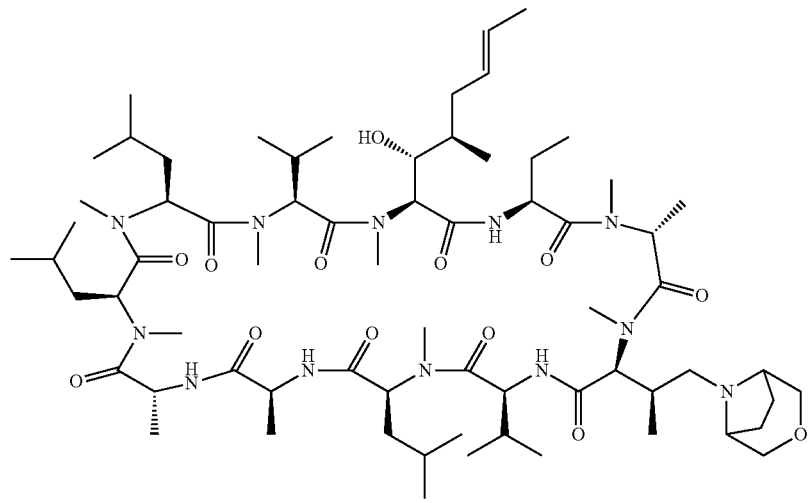
2.5.4
Compound 2.5.4 was prepared following the procedures described for the synthesis of 2.5.2 using 3-oxa-8-Azabicyclo(3.2.1)octane in Step 2. MS m/z (M+1) 1314.1
II.5.5 Synthesis of Compound 2.5.5
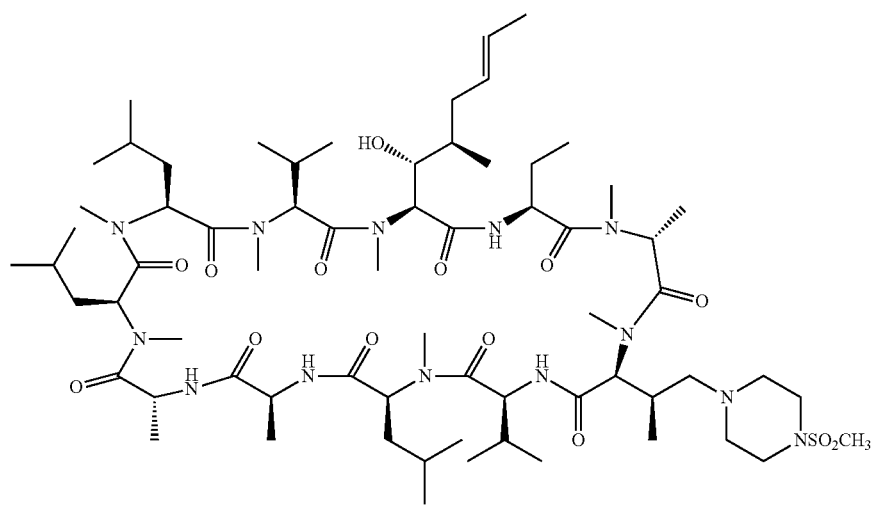
2.5.5
Compound 2.5.5 was prepared following the procedures described for the synthesis of 2.5.2 using 4-methanesulfonylpiperidine in Step 2. MS m/z (M+1) 1365.0

III.5.6 Synthesis of 2.5.6
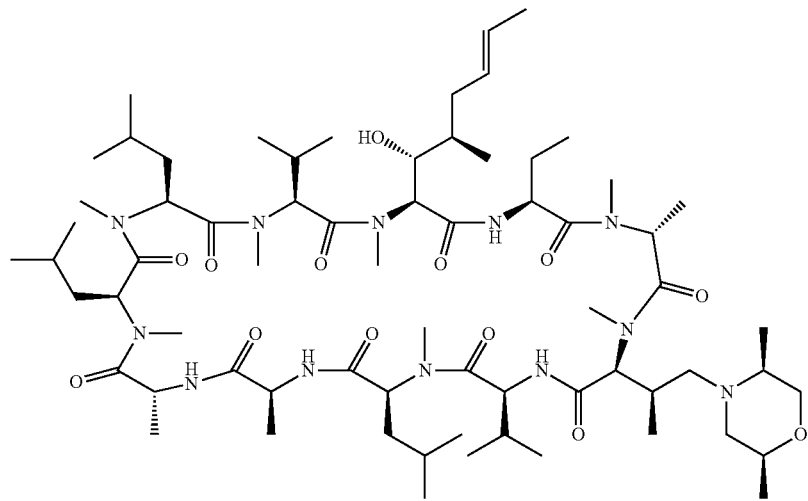
2.5.6
Compound 2.5.6 was prepared following the procedures described for the synthesis of 2.5.2 using (2S,5S)-2,5-dimethyl-morpholine in Step 2. MS m/z (M+1) 1316.9.
II.5.7 Synthesis of 2.5.7
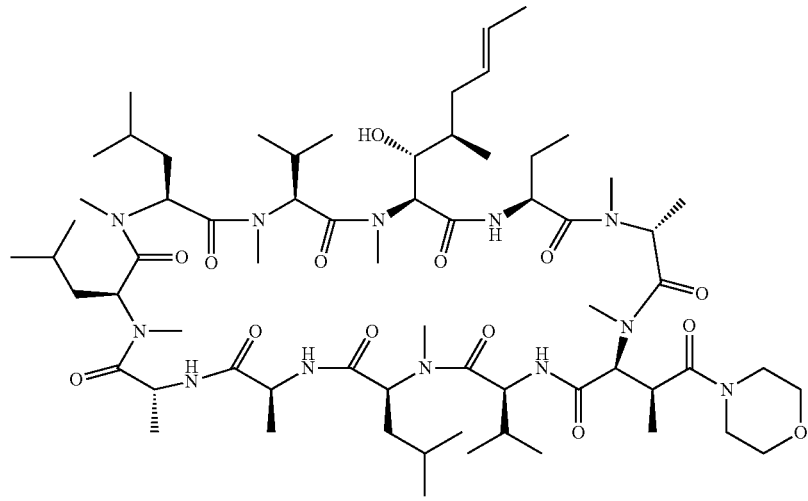
2.5.7

Step 1. Synthesis of 2.5.7a

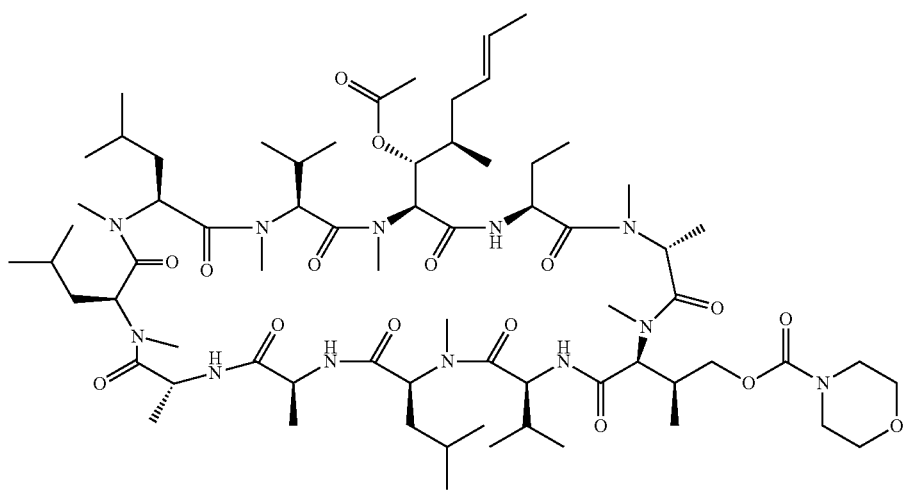

2.5.7a

To a solution of CDI (38.6 mg, 0.24 mmol, 10.0 equiv) in DCM (1.0 mL) at 0° C. was added 2.5.1i (30 mg, 0.024 mmol, 1.0 equiv) and the resulting solution was stirred at 0° C. for 30 minutes, then warmed to room temperature. To the solution was then added morpholine (21 mg, 0.021 mL, 0.24 mmol, 10 equiv) and triethylamine (24.1 mg, 0.033 mL, 0.024 mmol, 10.0 equiv). After stirring at room temperature for 1.5 hours, the solution was diluted with ethyl acetate, washed with brine, dried over magnesium sulfate and concentrated to give product 2.5.7a (33 mg, 100%). MS m/z (M+1) 1374.0

Step 2. Synthesis of 2.5.7

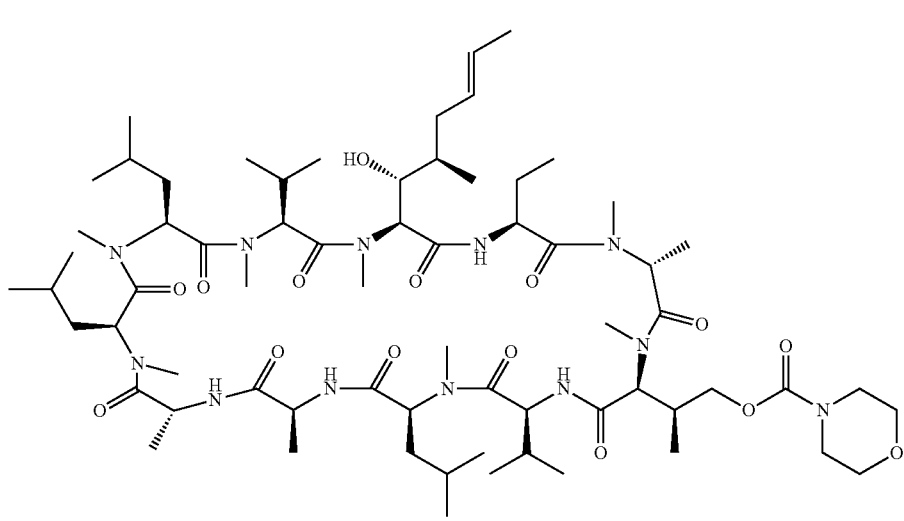

2.5.7

To a solution of 2.5.7a (33.0 mg, 0.024 mmol, 1.0 equiv) in tetrahydrofuran (1.0 ml) was added tetramethylammonium hydroxide (25% in MeOH, 44 mg, 0.48 mmol, 20 equiv) at 0° C. After stirring for 30 min at same temperature, the solution was diluted with ethyl acetate, washed with saturated aqueous saturated aqueous ammonium chloride solution and then with brine. The organic layer was dried over magnesium sulfate and concentrated. The residue was purified by reverse phase HPLC to give product 2.5.7 (8 mg, 34% yield). MS m/z (M+1) 1332.0

III.5.8 Synthesis of 2.5.8
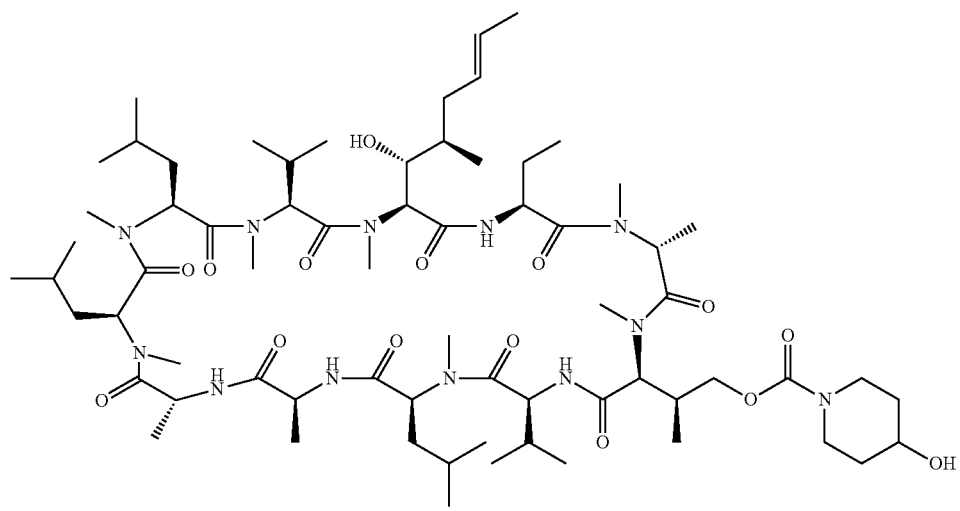
2.5.8
Compound 2.5.8 was prepared following the procedures described for the synthesis of 2.5.7 using piperidin-4-ol in Step 1. MS m/z (M+1) 1347.0.
II.5.9 Synthesis of 2.5.9
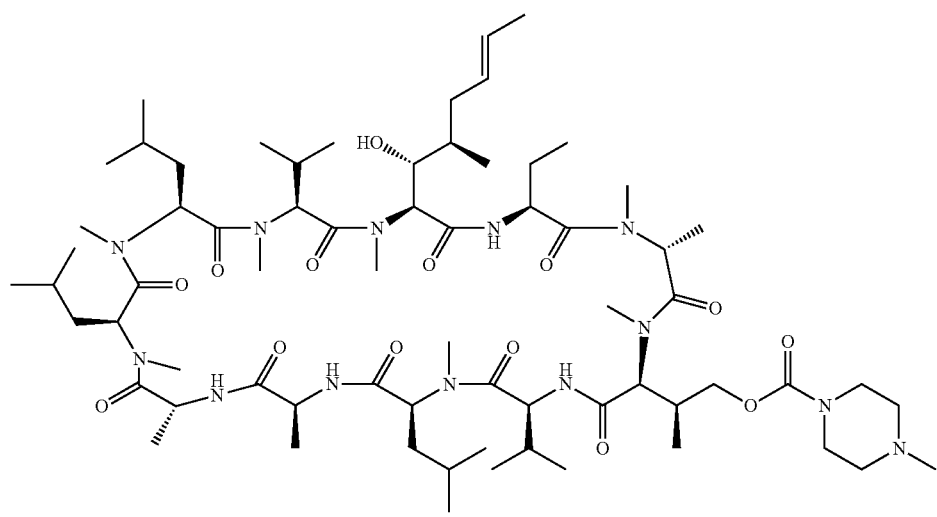
2.5.9
Compound 2.5.9 was prepared following the procedures described for the synthesis of 2.5.7 using of 1-methylpiperazine at Step 1. MS m/z (M+1) 1345.9

II.5.10 Synthesis of 2.5.10

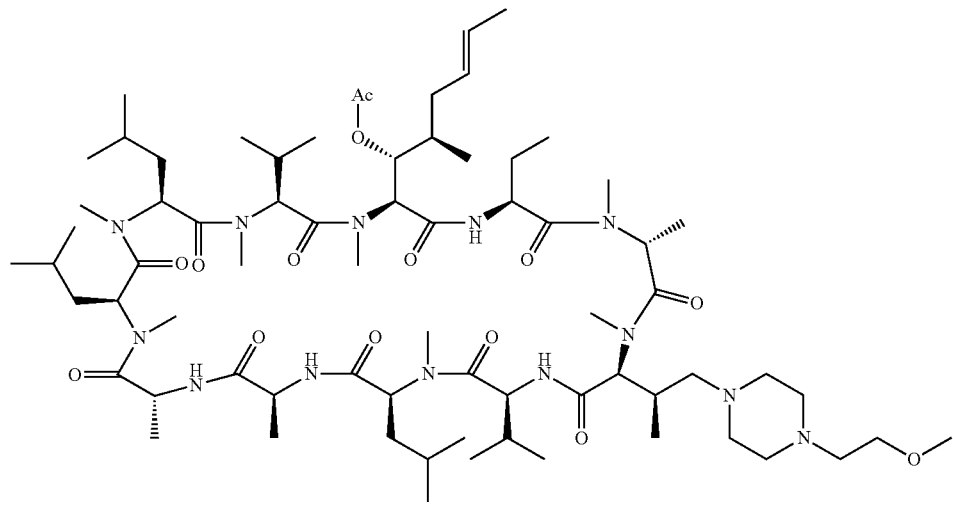

2.5.10

Step 1. Synthesis of 2.5.10a

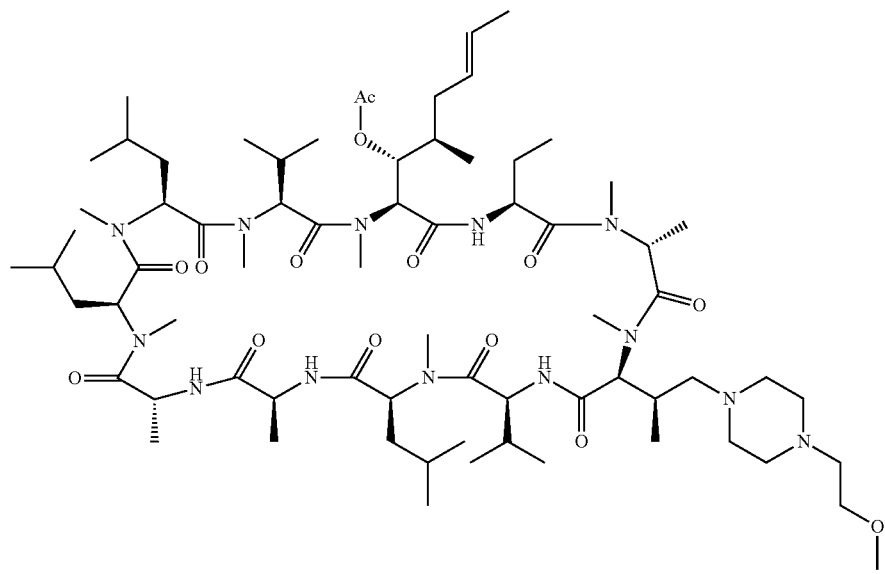

2.5.10a

To a solution of the 2.5.2a (1.2 g, 0.953 mmol, 1.0 equiv) in dichloroethane (25 mL) was added 1-(2-methoxyethyl)piperazine (1.375 g, 9.53 mmol, 10 equiv) and acetic acid (0.546 mL, 9.53 mmol, 10 equiv). After stirring at room temperature for 15 minutes, sodium triacetoxyborohydride (2.02 g, 9.53 mmol, 10.0 equiv) was added and the resulting mixture was stirred at room temperature for 3 hours. The mixture was diluted with EtOAc and washed with sat. aq. $NH_4Cl$ solution, brine, dried over $Na_2SO_4$ and concentrated. The crude material was used in the next step with no further purification.

Step 2. Synthesis of 2.5.10

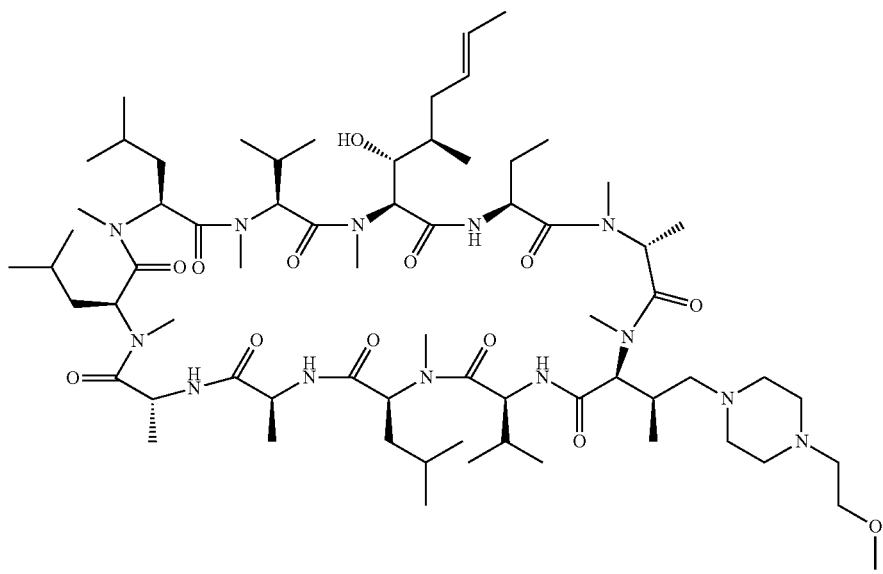

2.5.10

To a solution of 2.5.10a (1.25 g, 0.90 mmol, 1.0 equiv) in THF (15 mL) was added tetramethylammonium hydroxide (25% weight in MeOH, 2.74 g, 9.01 mmol, 10 equiv) at 0° C. After stirring for 2 hours at 0° C., the reaction solution was diluted with ethyl acetate and washed with saturated aqueous $NH_4Cl$, brine, dried over magnesium sulfate and concentrated. The crude material was purified by reverse phase HPLC. The collected fraction was dissolved in EtOAc and washed with sat. aq. $K_2CO_3$ solution to remove TFA. Obtained product 580 mg (yield 48%). MS m/z (M+1) 1345.9

II.5.11. Synthesis of 2.5.11

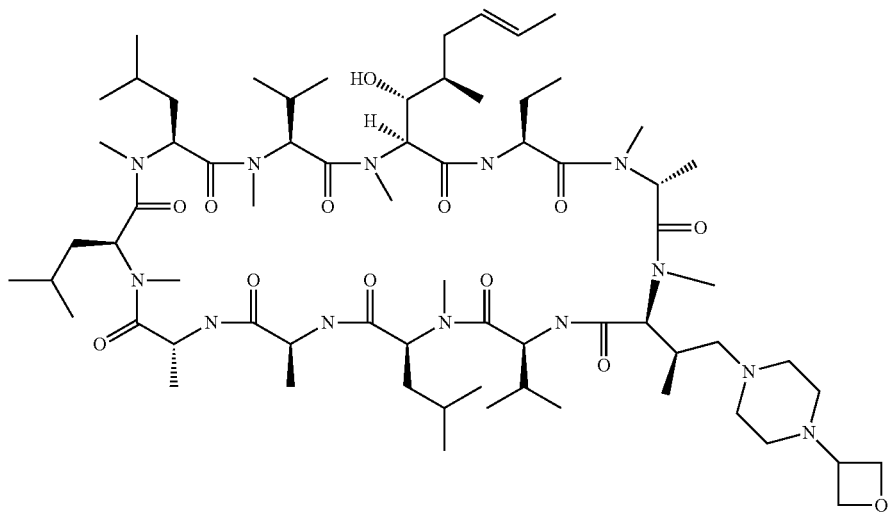

2.5.11

Compound 2.5.11 was prepared following the procedures described for the synthesis of 2.5.2 using 1-(oxetan-3-yl) piperazine. HRMS: 1342.9426 (calculated 1342.9442).

II.5.12. Synthesis of 2.5.12
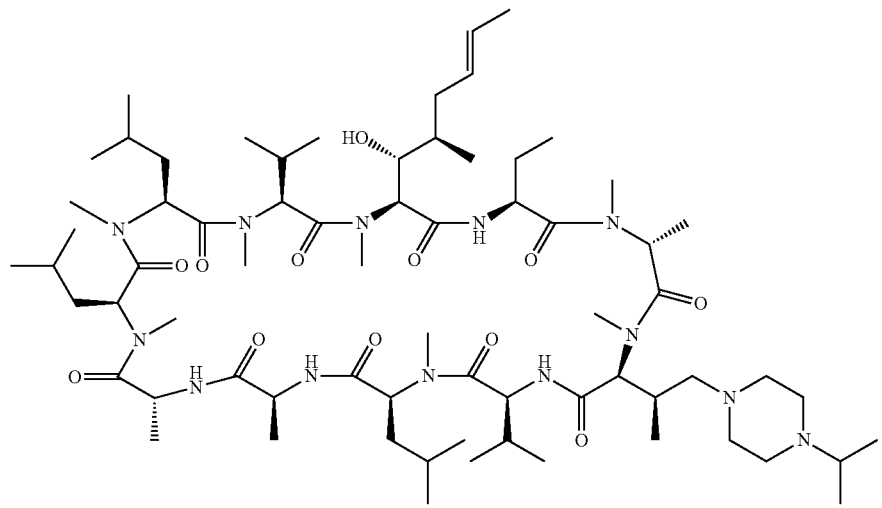
2.5.12
Compound 2.5.12 was prepared following the procedures described for the synthesis of 2.5.2 using 1-isopropylpiperazine in Step 2. MS m/z (M+1):1330.0
II.5.13 Synthesis of Compound 2.5.13
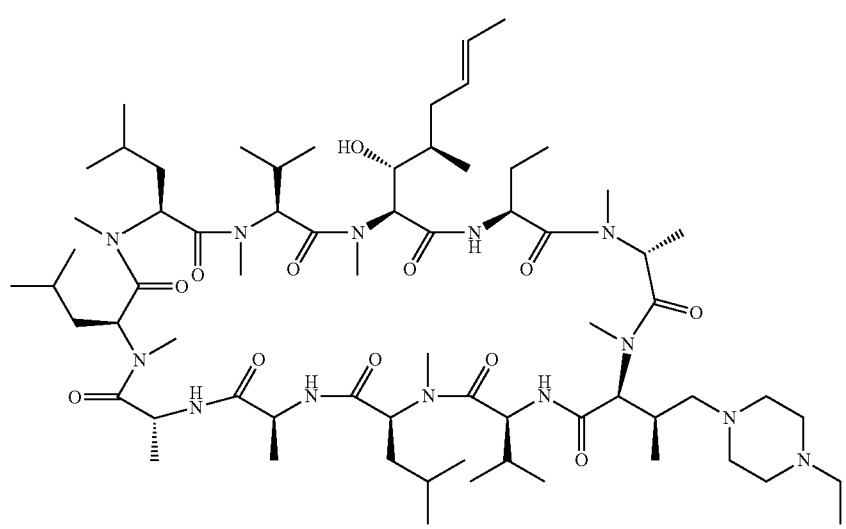
2.5.13
Compound 2.5.13 was prepared following the procedures described for the synthesis of 2.5.2 using 1-ethylpiperazine in Step 2. MS m/z (M+1):1315.9

II.5.14 Synthesis of Compound 2.5.14

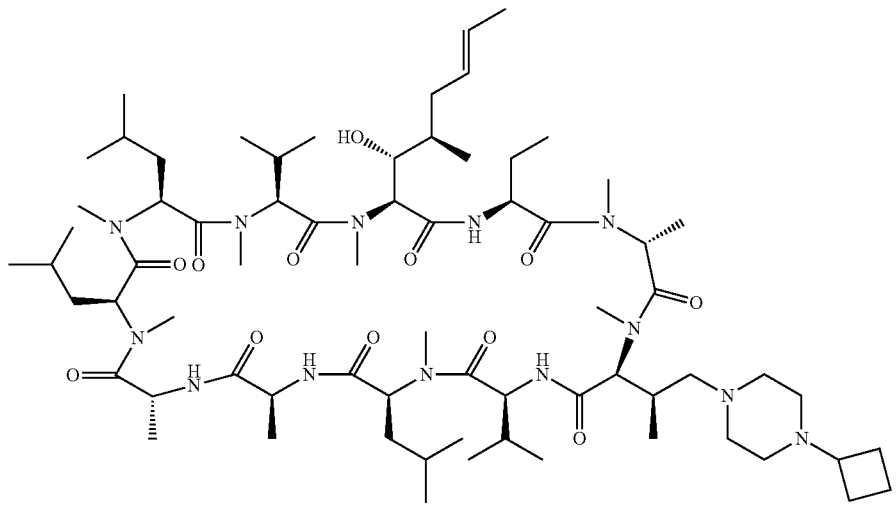

2.15.14

Compound 2.5.14 was prepared following the procedures described for the synthesis of 2.5.2 using 1-cyclobutylpiperazine in Step 2. MS m/z (M+1):1341.9

II.5.15. Synthesis of 2.5.15

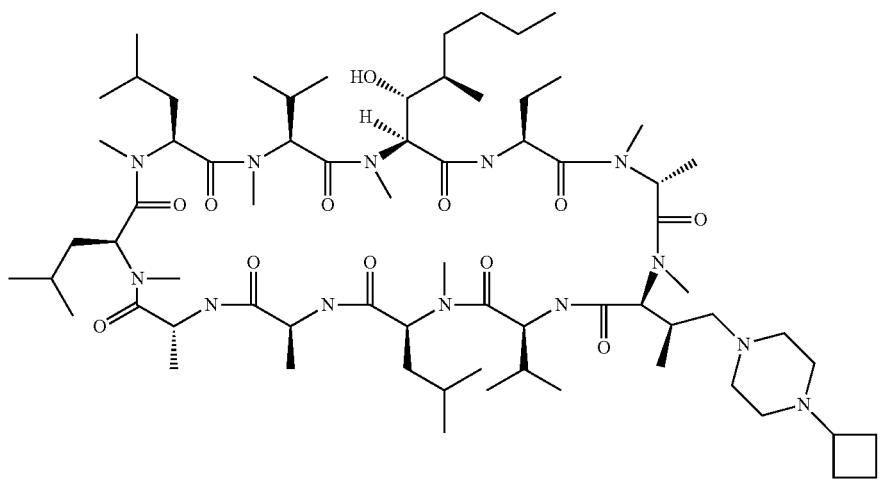

2.5.15

To a solution of 2.5.14 (65 mg, 0.048 mmol) in MeOH (3 mL) at room temperature was added Pd (10% on carbon, 50 mg) and the mixture was stirred under 1 atm of hydrogen for 30 minutes. The reaction mixture was then filtered and filtrate was concentrated to give product 2.5.15 (56 mg, 85% yield). HRMS: 1341.97104 (calculated 1341.97272)

II.5.16 Synthesis of Compound 2.5.16
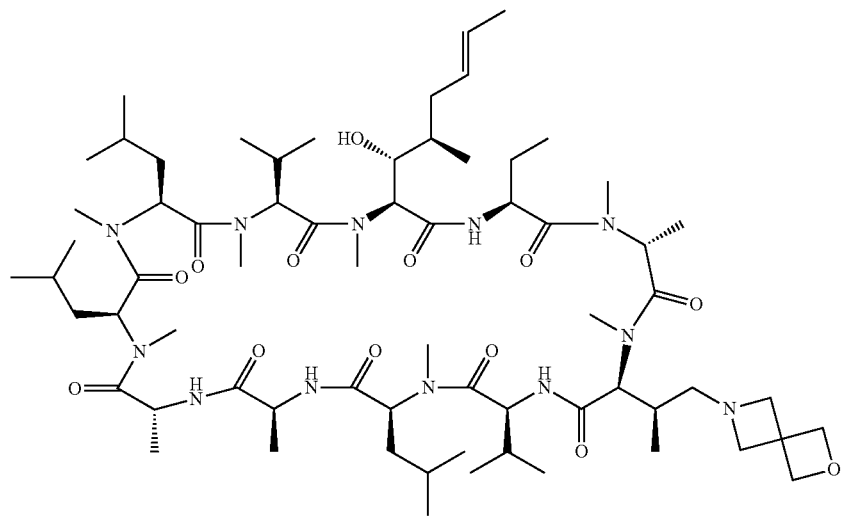
2.5.16
Compound 2.5.16 was prepared following the procedures described for the synthesis of 2.5.2 using 2-oxa-6-azaspiro[3.3]heptane in Step 2. HRMS m/z (M+1) 1299.9001
II.5.17 Synthesis of Compound 2.5.17
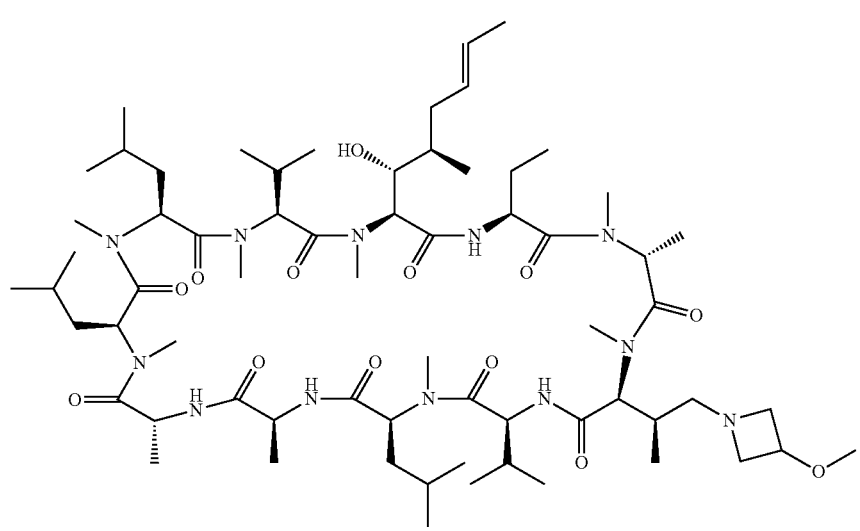
2.5.17
Compound 2.5.17 was prepared following the procedures described for the synthesis of 2.5.2 using 3-methoxyazetidine in Step 2. HRMS m/z (M+1) 1287.9019 (calculated 1287.9020)

II.5.18 Synthesis of Compound 2.5.18
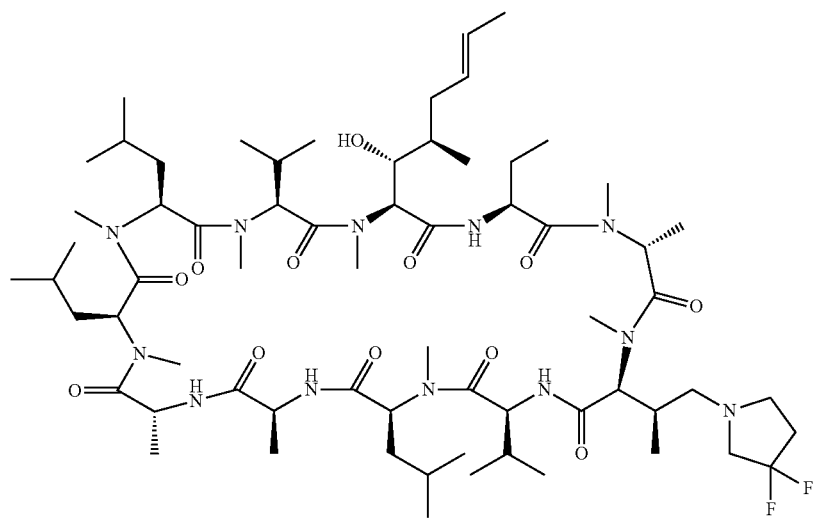
2.5.18
Compound 2.5.18 was prepared following the procedures described for the synthesis of 2.5.2 using 3,3-difluoropyrrolidine in Step 2. HRMS m/z (M+1) 1307.8875 (calculated 1307.8882)
II.5.19 Synthesis of Compound 2.5.19
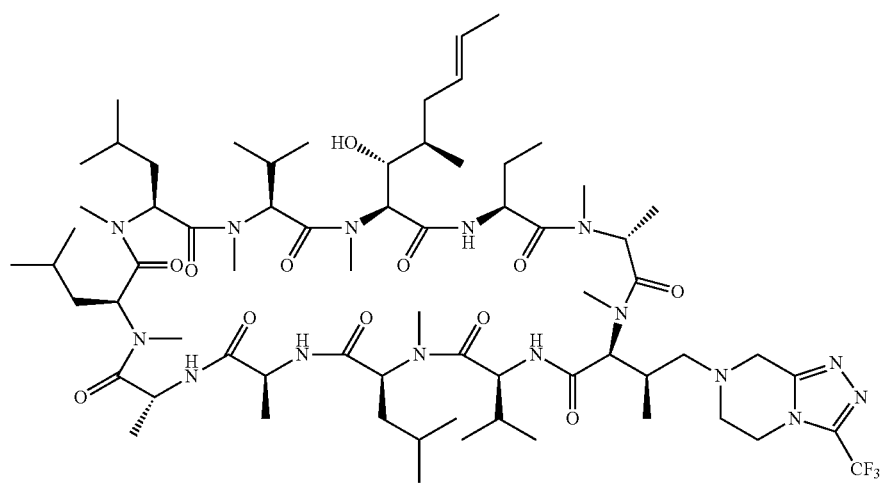
2.5.19
Compound 2.5.19 was prepared following the procedures described for the synthesis of 2.5.2 using 3-(trifluoromethyl)-5,6,7,8-tetrahydro-[1,2,4]triazolo[4,3-a]pyrazine in Step 2. HRMS m/z (M+1) 1392.8938 (calculated 1392.8958)

II.5.20 Synthesis of Compound 2.5.20
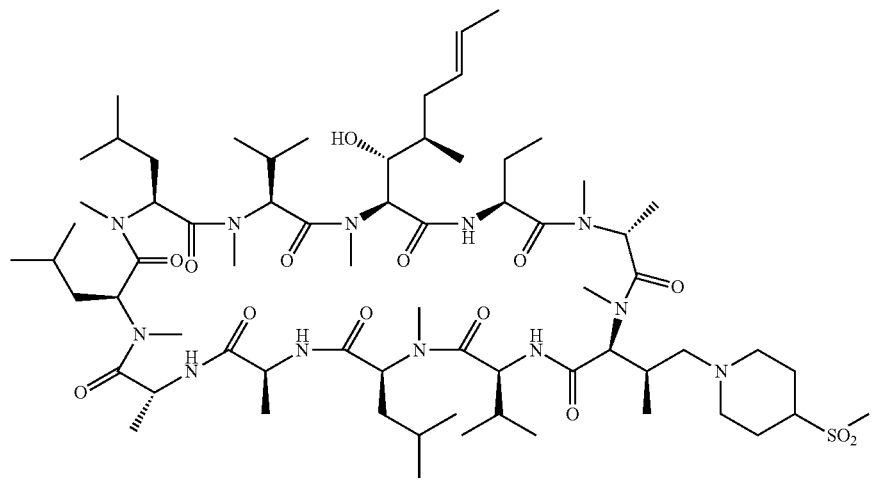
2.5.20
Compound 2.5.20 was prepared following the procedures described for the synthesis of 2.5.2 using 4-(methylsulfonyl) piperidine in Step 2. MS m/z (M+1) 1363.9008 (calculated 1363.9002)
II.5.21 Synthesis of Compound 2.5.21
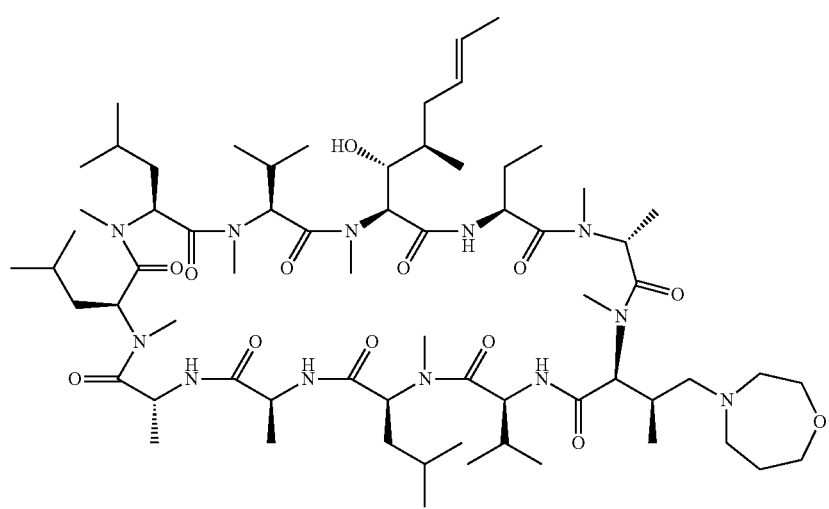
2.5.21
Compound 2.5.21 was prepared following the procedures described for the synthesis of 2.5.2 using homo piperazine in Step 2. MS m/z (M+1) 1302.8

II.5.22 Synthesis of Compound 2.5.22
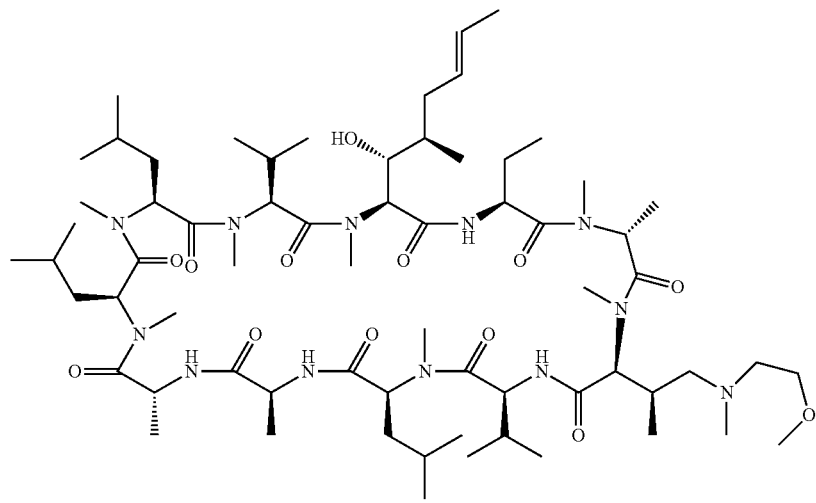
2.5.22
Compound 2.5.22 was prepared following the procedures described for the synthesis of 2.5.2 using 2-methoxy-N-methylethylamine in Step 2. MS m/z (M+1) 1290.1
II.5.23 Synthesis of Compound 2.5.23
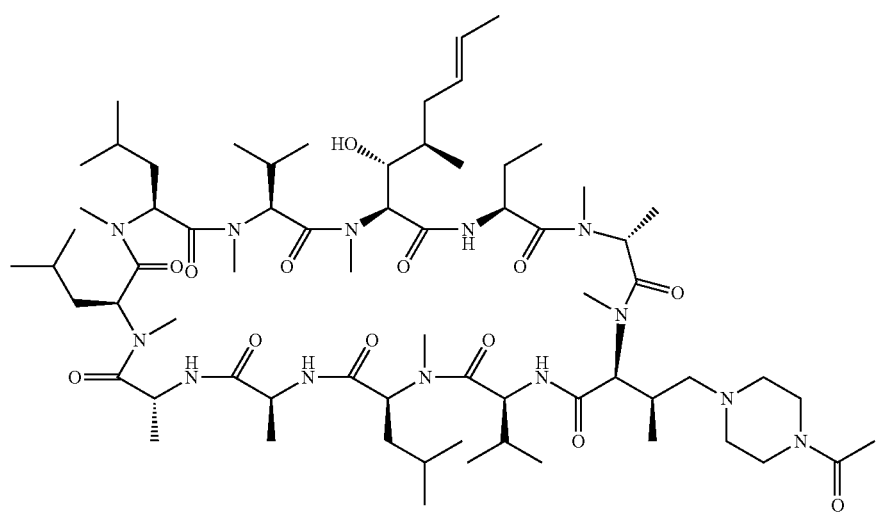
2.5.23
Compound 2.5.23 was prepared following the procedures described for the synthesis of 2.5.2 using 1-(piperazin-1-yl-)ethanone in Step 2. MS m/z (M+1) 1329.9

II.5.24 Synthesis of Compound 2.5.24
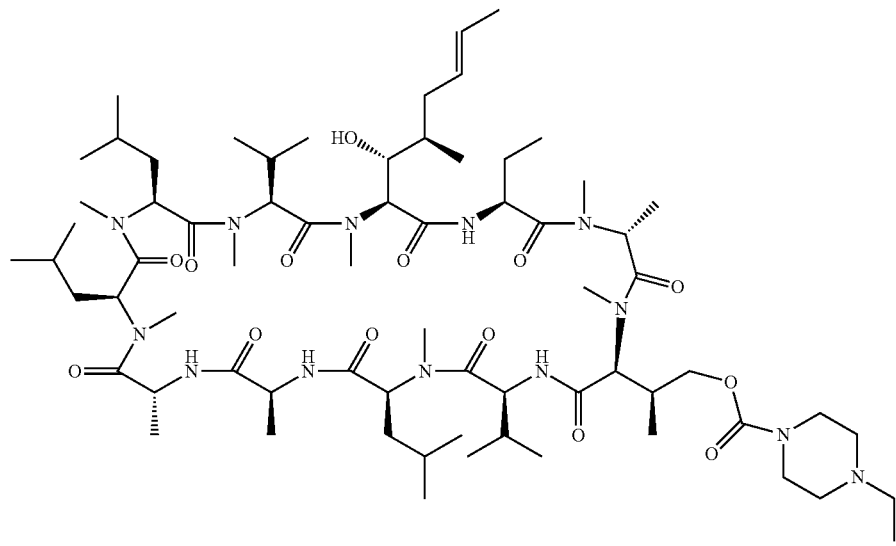
2.5.24
Compound 2.5.24 was prepared following the procedures described for the synthesis of 2.5.2 using 1-ethylpiperazine in Step 2. MS m/z (M+1) 1359.90
II.5.25 Synthesis of Compound 2.5.25
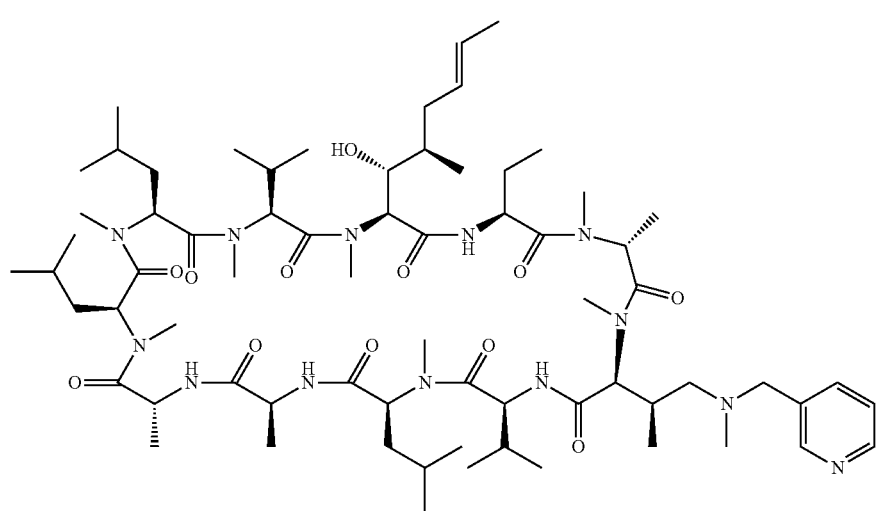
2.5.25
Compound 2.5.25 was prepared following the procedures described for the synthesis of 2.5.2 using N-methy-1-(pyridin-3-yl)methanamine in Step 2. MS m/z (M+1) 1323.9

II.5.26 Synthesis of Compound 2.5.26
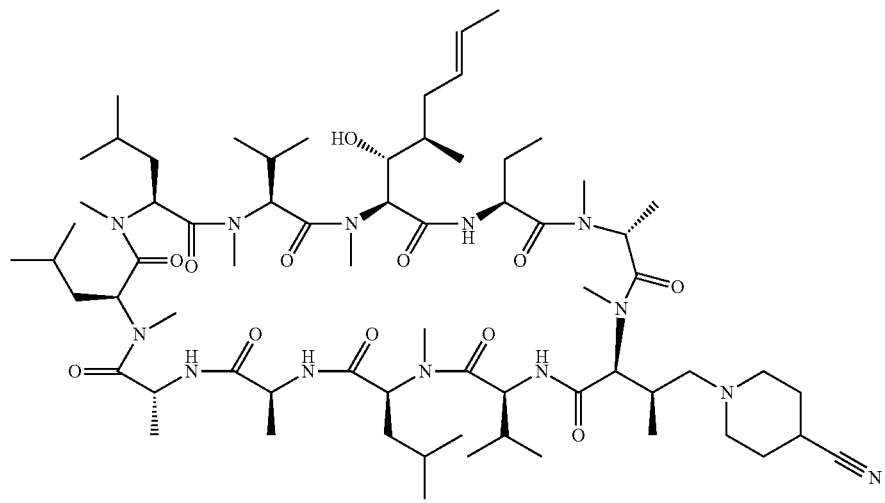
2.5.26
Compound 2.5.26 was prepared following the procedures described for the synthesis of 2.5.2 using piperidine-4-carbonitrile in Step 2. MS m/z (M+1) 1311.90
II.5.27 Synthesis of Compound 2.5.27
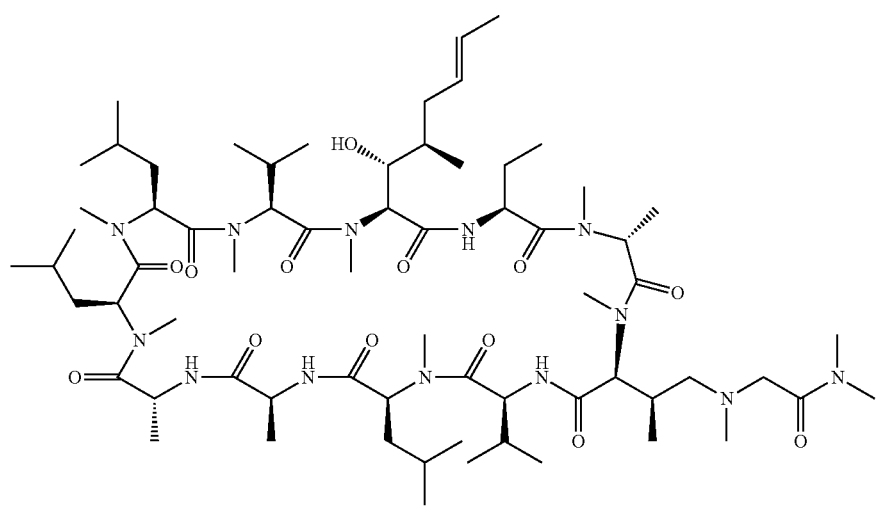
2.5.27
Compound 2.5.27 was prepared following the procedures described for the synthesis of 2.5.2 using N,N-dimethyl-2-(methylamino)acetamide in Step 2. MS m/z (M+1) 1317.9

II.5.28 Synthesis of Compound 2.5.28
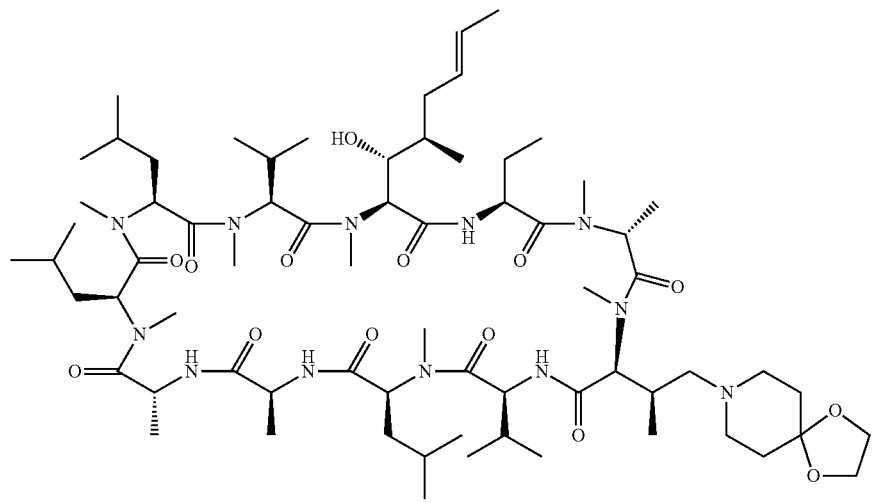
2.5.28
Compound 2.5.28 was prepared following the procedures described for the synthesis of 2.5.2 using 1,4-dioxa-8-azaspiro[4.5]decane in Step 2. MS m/z (M+1) 1345.0
II.5.29 Synthesis of Compound 2.5.29
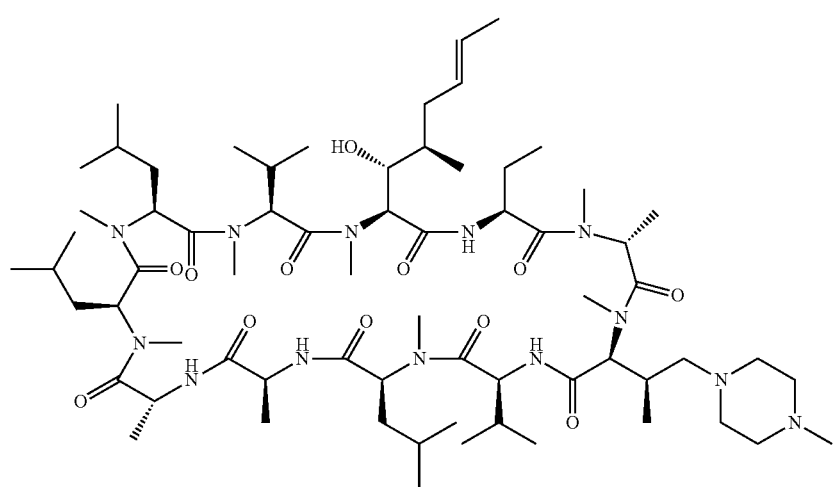
2.5.29
Compound 2.5.29 was prepared following the procedures described for the synthesis of 2.5.2 using 1-methylpiperazine in Step 2. MS m/z (M+1) 1300.9

II.5.30 Synthesis of Compound 2.5.30
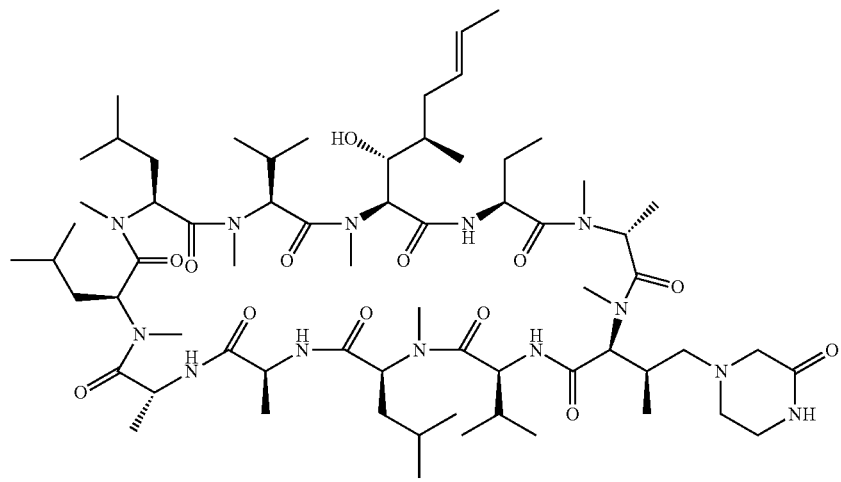
2.5.30
Compound 2.5.30 was prepared following the procedures described for the synthesis of 2.5.2 using piperazin-2-one in Step 2. HRMS m/z (M+1) 1300.8975 (calculated 1300.8972)
II.5.31 Synthesis of Compound 2.5.31
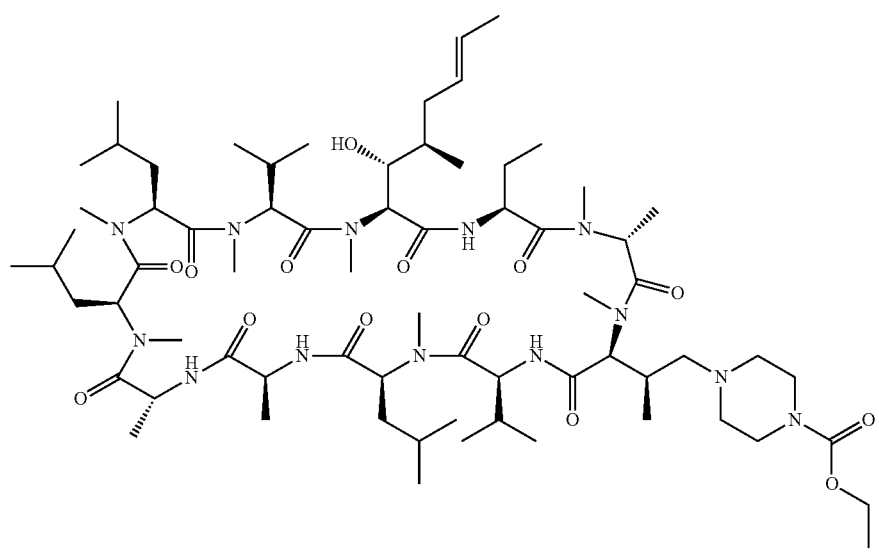
2.5.31
Compound 2.5.31 was prepared following the procedures described for the synthesis of 2.5.2 using ethyl piperazine-1-carboxylate in Step 2. HRMS m/z (M+1) 1358.9370 (calculated 1358.9391)

II.5.32 Synthesis of Compound 2.5.32
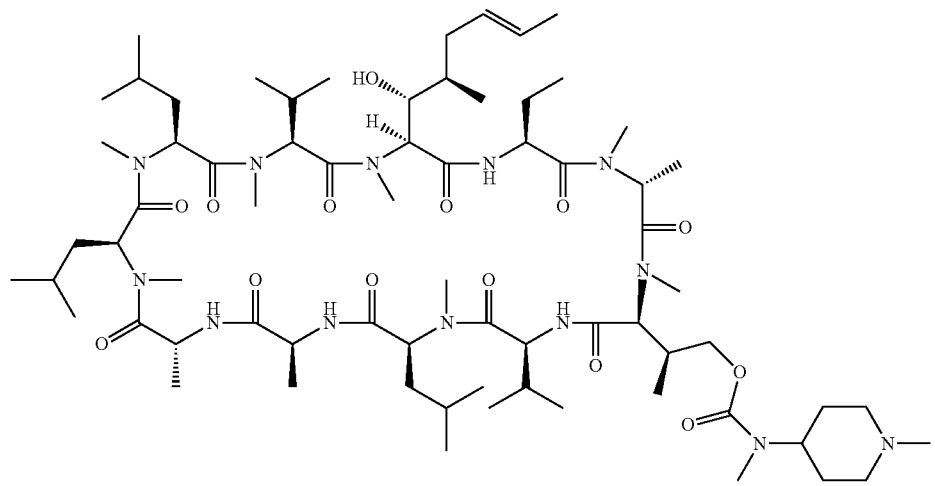
2.5.32
Compound 2.5.32 was prepared following the procedures described for the synthesis of 2.5.7 using N,1-dimethylpiperidin-4-amine in step 1. HRMS m/z (M+1) 1372.9535 (calculated: 1372.9547).
II.5.33 Synthesis of Compound 2.5.33
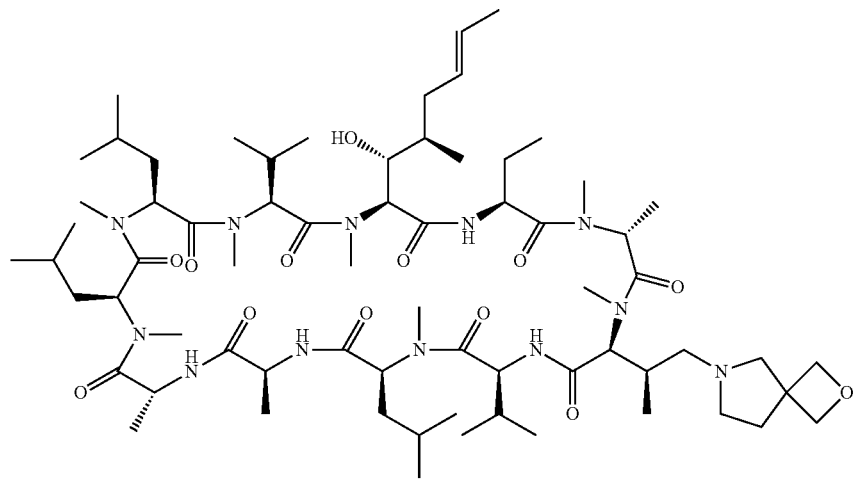
2.5.33
Compound 2.5.33 was prepared following the procedures described for the synthesis of 2.5.2 using 2-oxa-6-azaspiro[3.4]octane in Step 2. HRMS m/z (M+1) 1313.9169 (calculated 1313.9176)

II.5.34 Synthesis of Compound 2.5.34
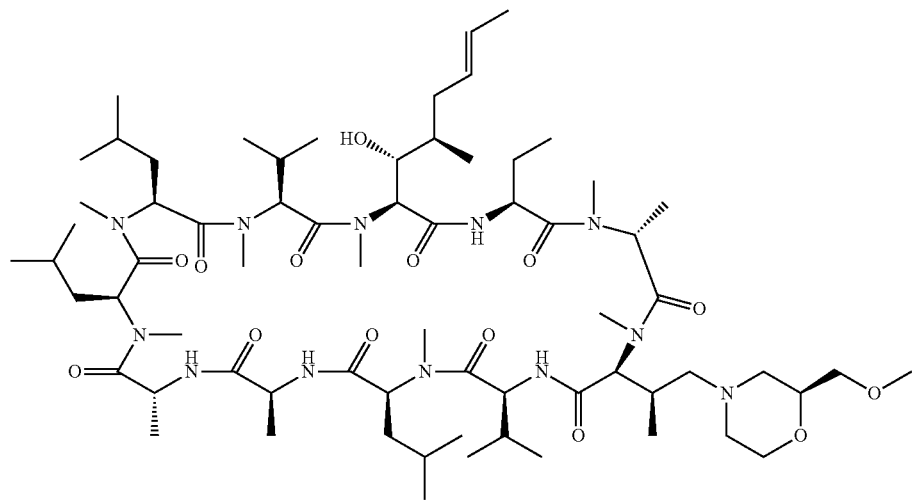
2.5.34
Compound 2.5.34 was prepared following the procedures described for the synthesis of 2.5.2 using (S)-2-(methoxymethyl)morpholine in Step 2. MS m/z (M+1) 1333.1
II.5.35. Synthesis of 2.5.35
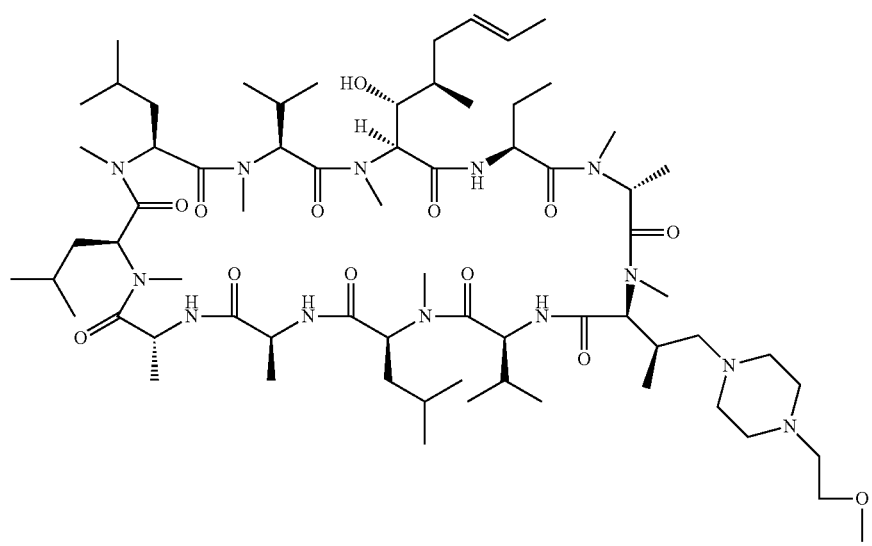
2.5.35
Compound was prepared following the procedures described for the synthesis of 2.5.15. HRMS m/z (M+1) 1346.9745 (calculated 1346.9755)

II.6.1 Synthesis of 2.6.1

2.6.1

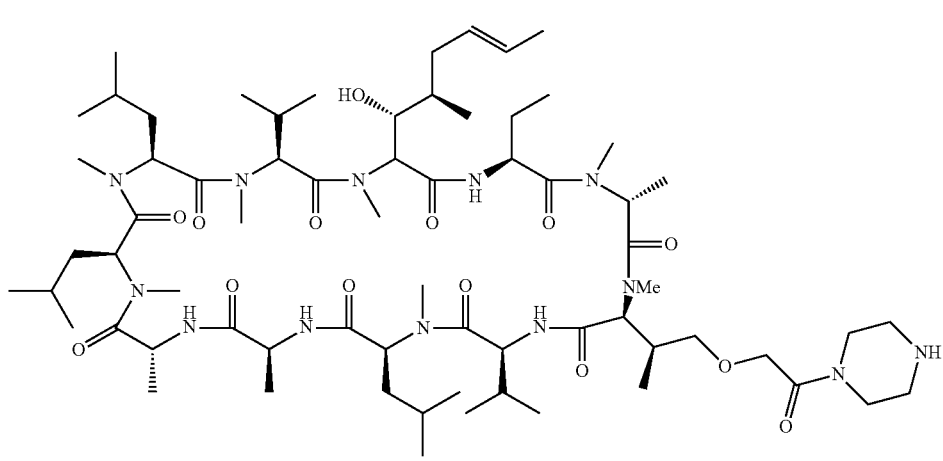

Step 1. Synthesis of tert-butyl((1S,2S)-1-(furan-2-yl)-3-hydroxy-2-methylpropyl)(methyl)carbamate [2.6.1a]

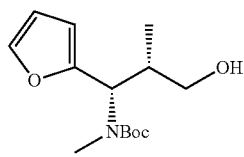

2.6.1a

To a solution of 2.5.1b (20 g, 39.4 mmol) in MeOH (197 mL) was added tetrabutyl ammonium flouride (1.0 M in THF, 47.3 mL, 47.3 mmol, 1.2 equiv) at room temperature. After stirring for overnight, the reaction mixture was added water and EtOAc. The phase were separated and the aqueous layer was extracted with EtOAc. The combined organic layer was washed with brine, dried over Na₂SO₄ and concentrated in vacuo. The residue was purified by silica gel column chromatography (EtOAc/heptane) to give ((1S,2S)-1-Furan-2-yl-3-hydroxy-2-methyl-propyl)-methyl-carbamic acid tert-butyl ester (10.51 g, 99%). $^1$H NMR (400 MHz, CDCl$_3$) 7.37 (s, 1H), 6.33 (s, 1H), 6.27 (br, s, 1H), 5.41 (br, s, 1H), 3.41 (br, s, 2H), 3.05 (s, 1H), 2.67 (s, 3H), 2.37 (m, 1H), 1.49 (s, 9H), 1.01 (m, 3H).

Step 2. Synthesis of [(2S,3S)-3-(tert-Butoxycarbonyl-methylamino)-3-furan-2-methylpropoxy]acetic acid [2.6.1 b]

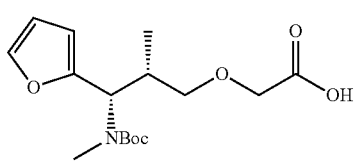

2.6.1b

To a suspension of NaH (60%, 134.0 mg, 3.4 mmol, 3.0 equiv) in THF (2.2 mL) at 0° C. was added 2.6.1a (300.0 mg, 1.1 mmol), bromoacetic acid (464.0 mg, 3.4 mmol, 3.0 equiv) and sodium iodide (167.0 mg, 1.1 mmol) successively. After stirring for 7 hours at room temperature, the reaction mixture was quenched with water at 0° C., diluted with EtOAc, and acidified with aqueous 1.0 N HCl aq. solution. The organic layer was separated, washed with brine, dried over Na₂SO₄, filtered and concentrated in vacuo to give [(2S,3S)-3-(tert-butoxycarbonyl methylamino)-3-furan-2-yl-2-methyl-propoxy]acetic acid (287.0 mg) which was used for the next step without further purification. MS m/z (M+Na) 350.0

Step 3. Synthesis of 4-{2-[(2S,3S)-3-(tert-Butoxycarbonyl-methylamino)-3-furan-2-yl-2-methyl-propoxy]-acetyl}-piperazine-1-carboxylic acid benzyl ester [2.6.1c]

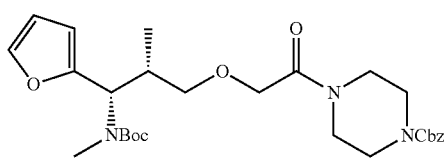

2.6.1c

To a solution of [(2S,3S)-3-(tert-butoxycarbonyl methylamino)-3-furan-methylpropoxy]acetic acid (473.0 mg, 1.5 mmol) in DCM (15 mL) were added DIPEA (757 uL, 4.3 mmol, 3 equiv) and HATU (714.0 mg, 1.9 mmol, 1.3 equiv) successively. After stirring for 10 min, the solution was added piperazine-1-carboxylic acid benzyl ester (637.0 mg, 2.9 mmol, 2.0 equiv) and the resulting solution was stirred for 3 hours. The reaction mixture was diluted with DCM (50 mL), washed with water and brine. The organic layer was dried over $Na_2SO_4$ and concentrated in vacuo. The resulting residue was purified by column chromatography on silica gel (EtOAc/heptane) to give 4-{2-[(2S,3S)-3-(tert-butoxy-carbonyl-methylamino)-3-furan-2-yl-2-methyl-propoxy]-acetyl}-piperazine-1-carboxylic acid benzyl ester (675.0 mg, 88% yield). $^1$H NMR (400 MHz, CDCl$_3$) 7.41-7.29 (m, 6H), 6.34-6.10 (2H), 5.29-4.94 (m, 3H), 4.04 (s, 2H), 3.74-3.49, (m, 10H), 2.68 (s, 3H), 2.40 (m, 1H), 1.46 (s, 9H). 1.26 (d, 3H). MS m/z (M+Na) 552.3

Step 4. Synthesis of 4-[2-(2S,3S)-3-Furan-2-yl-2-methyl-3-methylamino-propoxy)-acetyl]-piperazine-1-carboxylic acid benzyl ester [2.6.1d]

2.6.1d

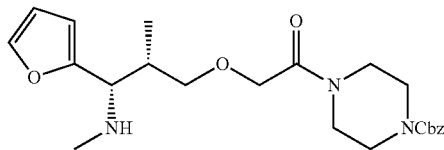

To a solution of 4-{2-[(2S,3S)-3-(tert-butoxycarbonyl-methylamino)-3-furan-2-yl-2-methyl-propoxy]-acetyl}-piperazine-1-carboxylic acid benzyl ester (250.0 mg, 0.47 mmol) in DCM (4 mL) at 0° C. was added TFA (4 mL). After stirring for 1 hour, the reaction mixture was diluted with DCM (30 mL) and washed with saturated aqueous NaHCO$_3$, brine, dried over Na$_2$SO$_4$, filtered, and concentrated in vacuo to give 4-[2-(2S,3S)-3-furan-2-yl-2-methyl-3-methyl-amino-propoxy)-acetyl]-piperazine-1-carboxylic acid benzyl ester as a solid (166.0 mg) which was used for the next step without further purification. MS m/z (M+1) 430.3

Step 5. Synthesis of 4-[2-(2S,3S)-3-{[(R)-2-(tert-Butoxycarbonyl-methylamino)-propionyl]-methyl-amino}-3-furan-2-yl-2-methylpropoxy)-acetyl]-piperazine-1-carboxylic acid benzyl ester [2.6.1e]

2.6.1e

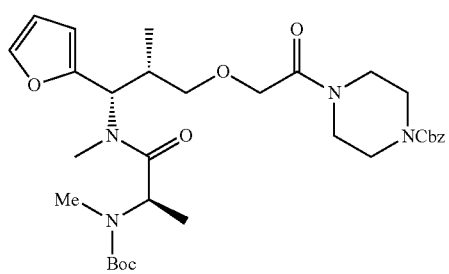

To a solution of Boc-N-methyl-D-alanine-OH (376.0 mg, 1.9 mmol, 2.0 equiv) in DCM (9 mL) were added DIPEA (484 uL, 2.8 mmol, 3.0 equiv) and HATU (703.0 mg, 1.9 mmol, 2.0 equiv) successively and stirred for 10 minutes after which 4-[2-(2S,3S)-3-furan-2-yl-2-methyl-3-methyl-amino-propoxy)-acetyl]piperazine-1-carboxylic acid benzyl ester (397.0 mg, 0.93 mmol) was added. After stirring at room temperature for 12 hours, the reaction mixture was diluted with DCM (50 mL), washed with water and brine. The organic layer was dried over Na$_2$SO$_4$ and concentrated in vacuo. The residue was purified by column chromatography on silica gel (acetone/heptane) to give 4-[2-(2S,3S)-3-{[R)-2-(tert-butoxycarbonyl-methylamino)-propionyl]-methylamino}-3-furan-2-yl-2-methylpropoxy)-acetyl]-piperazine-1-carboxylic acid benzyl ester (416.0 mg, 73% yield). MS m/z (M+1) 615.8

Step 6. Synthesis of 4-[2-((2S,3S)-3-{[(R)-2-(tert-Butoxycarbonyl-methyl-amino)propionyl]-methyl-amino}-3-carboxy-2-methyl-propoxy)acetyl]-piperazine-1-carboxylic acid benzyl ester [2.6.1f]

2.6.1f

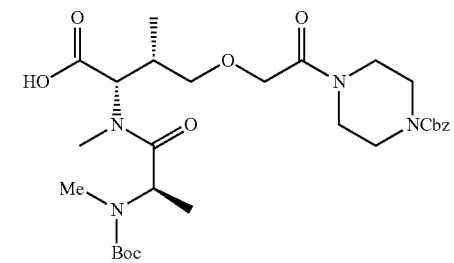

To a stirred mixture of NaIO$_4$ (868.0 mg, 4.0 mmol, 6.0 equiv) in H$_2$O/CCl$_4$/CH$_3$CN (3:2:3, 19 mL) was added RuCl$_3$ (48.0 mg, 0.23 mmol, 0.34 equiv). After stirring for 15 minutes, 4-[2-(2S,3S)-3-{[R)-2-(tert-butoxycarbonyl-methylamino)-propionyl]-methylamino}-3-furan-2-yl-2-methylpropoxy)-acetyl]-piperazine-1-carboxylic acid benzyl ester (416.0 mg, 0.68 mmol) in CH$_3$CN (3 mL) was added. After 15 minutes, the reaction mixture was diluted with water (10 mL) and extracted with EtOAc (3×20 mL). Combined organic layer was washed with saturated aqueous NaHSO$_3$, brine, dried over Na$_2$SO$_4$, and concentrated in vacuo to give 4-[2-((2S,3S)-3-{[(R)-2-(tert-butoxycarbonyl-methyl-amino)propionyl]-methylamino}-3-carboxy-2-methyl-propoxy)acetyl]-piperazine-1-carboxylic acid benzyl ester (480.0 mg) which was used for the next step without further purification. MS m/z (M+1) 593.3

Step 7. Synthesis of 2.6.1g

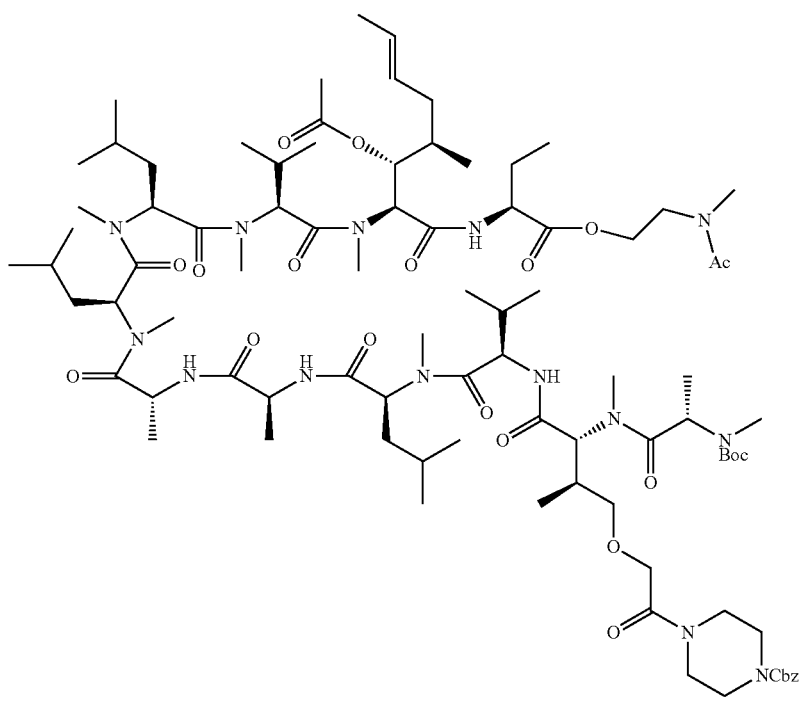

2.6.1g

To a solution of 2.6.1h (82.0 mg, 0.14 mmol, 1.1 equiv) in DCM (3 mL) at 0° C. were added DIPEA (65 uL, 0.37 mmol, 3.0 equiv), HATU (57.0 mg, 0.15 mmol, 1.2 equiv) and HOAt (20.0 mg, 0.15 mmol, 1.2 equiv) successively and stirred for 10 minutes after which the amine 1 (1.2 g, 1.1 mmol) was added. After stirring for 3 hours at room temperature, the reaction mixture was diluted with DCM (20 mL), washed with water and brine. The organic layer was dried over $Na_2SO_4$ and concentrated in vacuo. The resulting residue was purified by column chromatography on silica gel (acetone/heptane) to give 2.6.1g as a yellow solid (164.0 mg, 76% yield). MS m/z (M+Na) 1761.9

Step 8. Synthesis of 2.6.1h

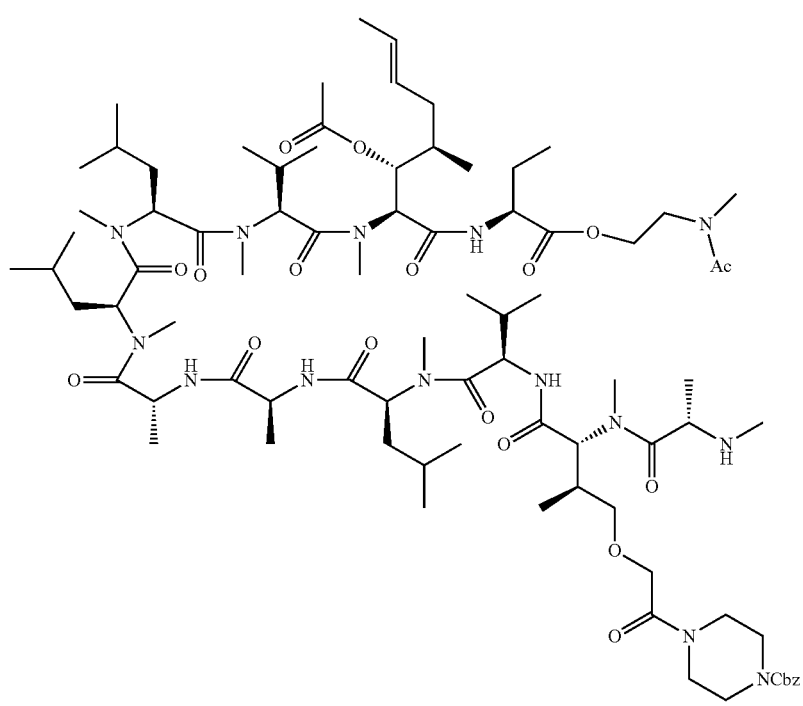

2.6.1h

To a solution of 2.6.1g (164.0 mg, 0.10 mmol) in DCM (708 uL) at 0° C. was added TFA (236 uL). After stirring for 1 hour, the reaction mixture was diluted with DCM (30 mL) and washed with saturated aqueous NaHCO$_3$, brine, dried over Na$_2$SO$_4$, filtered, and concentrated in vacuo to give 2.6.1h (155.0 mg). The crude material was used for the next step without further purification. MS m/z (M+Na) 1661.3

Step 9. Synthesis of 2.6.1i

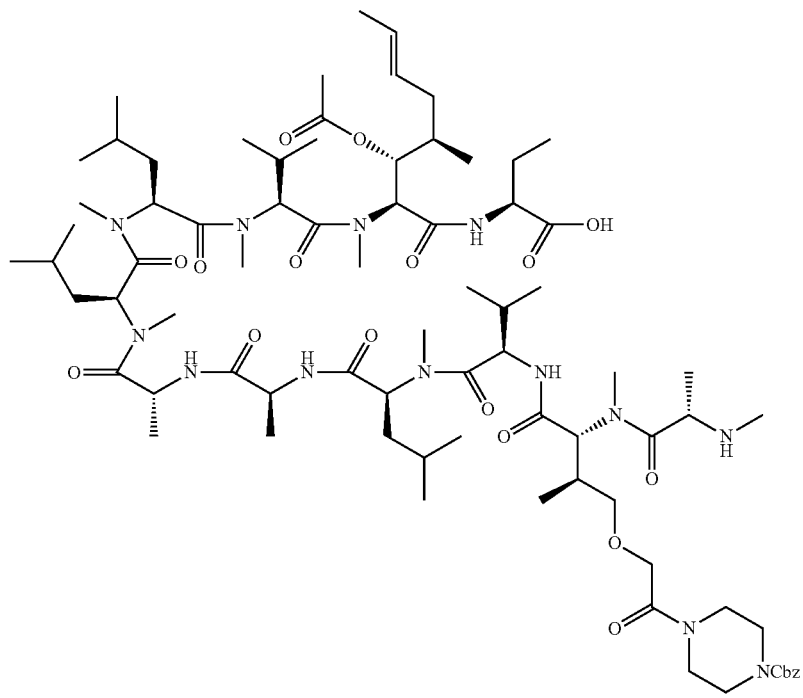

2.6.1i

To a solution of 2.6.1h (155.0 mg, 0.10 mmol) in THF/MeOH/water (1:1:1, 1 mL) at 0° C. was added lithium hydroxide monohydrate (20.0 mg, 0.5 mmol, 5.0 equiv). After stirring at 0° C. for 1 hour, the reaction mixture was diluted with DCM (20 mL), washed with aqueous 1.0 N HCl aq. solution, brine, dried over Na$_2$SO$_4$, filtered and concentrated in vacuo to afford 2.6.1i (65.0 mg, 45% yield). The crude material was used for the next step without further purification. MS m/z (M+H) 1539.6

Step 10. Synthesis of 2.6.1j

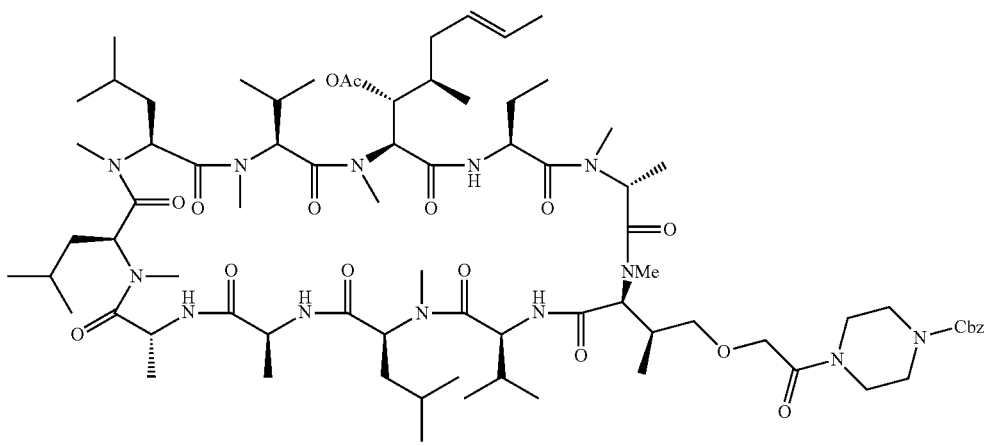

2.6.1j

To a solution of BOP (35.0 mg, 80.0 umol, 2.0 equiv) in DCM (12 mL) was slowly added a solution of DMAP (11.0 mg, 80.0 umol, 2.0 equiv) and compound 2.6.1i (65.0 mg, 40.0 umol) in DCM (30 mL) at 0° C. via additional funnel. After stirring at room temperature for 16 hours, the reaction mixture was concentrated in vacuo to half of the volume and washed with 10% citric acid, saturated aqueous NaHCO₃, and brine. The organic layer was dried over Na₂SO₄ and concentrated in vacuo. The residue was purified by column chromatography on silica gel (MeOH/DCM) to give product 2.6.1j (30.0 mg, 47%). MS m/z (M+Na) 1543.9

Step 11. Synthesis of 2.6.1k

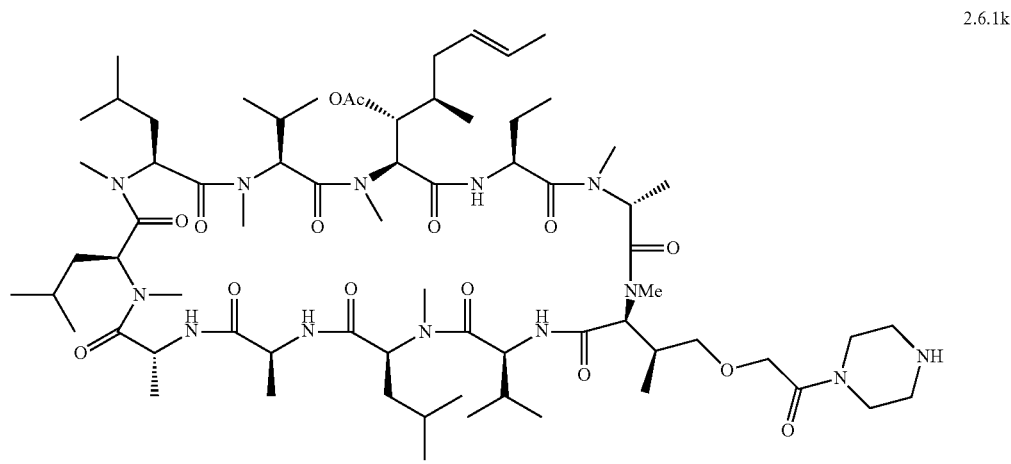 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)COCC(=O)N2CCNCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.6.1k

To a solution of 2.6.1j (40.0 mg, 30.0 umol) in DCM (263 uL) was added triethylamine (31 uL, 0.2 mmol, 8.5 equiv), triethylsilane (147 uL, 0.9 mmol, 35.0 equiv) and palladium acetate (6.0 mg, 30 umol, 1.0 equiv) successively. After stirring for 1 hour at room temperature, the reaction mixture was diluted with DCM and filtered through Celite. The filtrate was concentrated in vacuo to give 2.6.1k as a solid (40.0 mg) which was used for the next step without further purification. MS m/z (M+Na) 1409.4

Step 12. Synthesis of 2.6.1

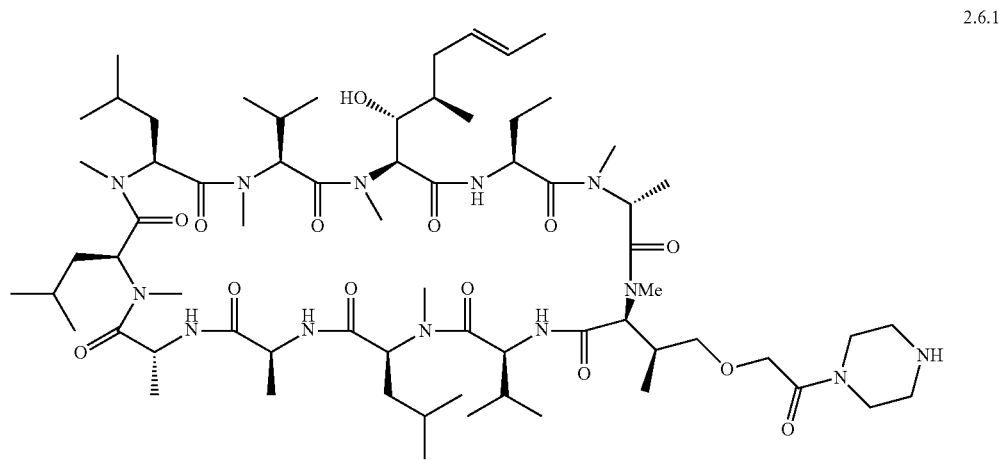 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCC(=O)N2CCNCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.6.1

To a solution of 2.6.1k (40.0 mg, 30.0 umol) in MeOH (1 mL) at 0° C. was added tetramethylammonium hydroxide (25% weight in MeOH, 121 uL, 0.3 mmol, 10.0 equiv). After stirring for 2 hours at room temperature, the reaction mixture was quenched with saturated aqueous $NaHSO_4$. The aqueous layer was extracted with DCM (2×10 mL). Combined organic layer was washed with brine, dried over $Na_2SO_4$, filtered and concentrated in vacuo. The crude residue was purified by reverse phase HPLC to give 2.6.1 as a white solid (5.0 mg, 13% yield). MS m/z (M+1) 1344.9

II.6.2 Synthesis of 2.6.2

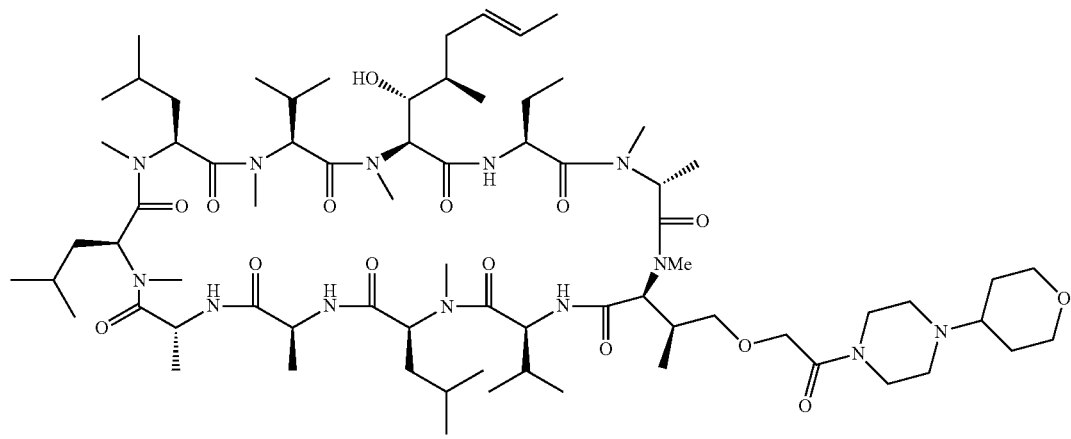

2.6.2

Step 1. Synthesis of 2.6.2a

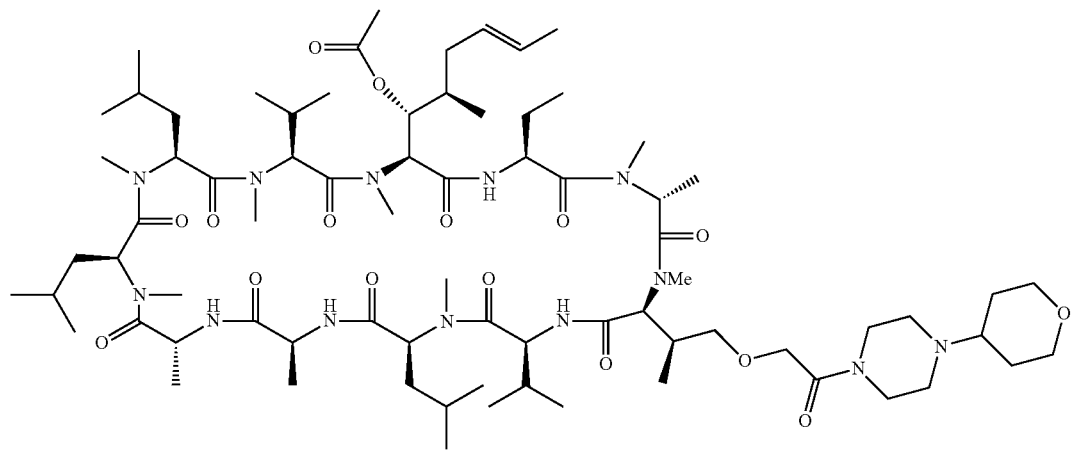

2.3.2a

To a suspension of compound 2.6.1k (80.0 mg, 60 umol) and tetrahydro-pyran-4-one (116.0 mg, 1.15 mmol, 20 equiv) in 1,2-dichloroethane (577 uL) at room temperature was added sodium triacetoxyborohydride (20.0 mg, 0.09 mmol, 1.6 equiv) and AcOH (4.0 uL, 0.12 mmol, 1.2 equiv). After stirring for 12 hours, the reaction mixture was quenched with saturated aqueous $NaHCO_3$, and the aqueous layer was extracted with DCM. Combined organic layer was washed with brine, dried over $Na_2SO_4$, and concentrated in vacuo to give compound 2.6.2a (100 mg). MS m/z (M+Na) 1493.9

Step 2. Synthesis of 2.6.2

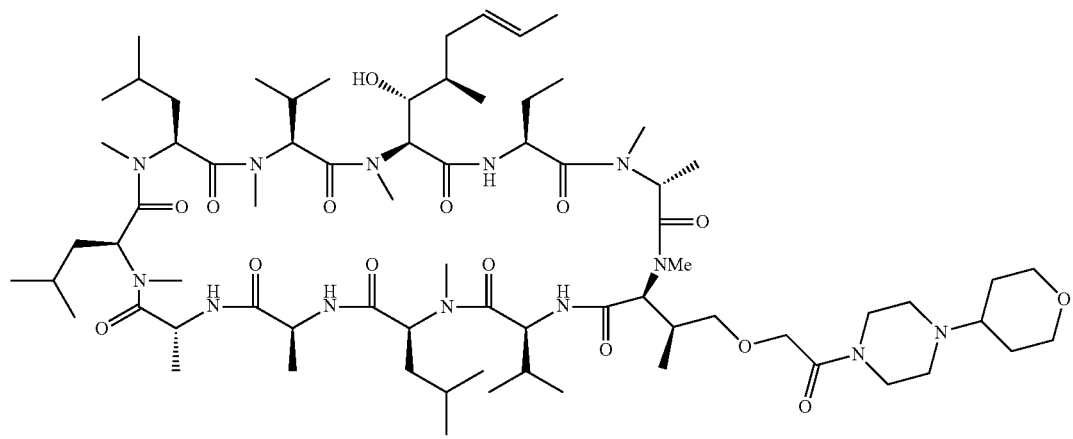

2.6.2

To a solution of 2.6.2a (100.0 mg, 70 umol) in MeOH (700 uL) at 0° C. was added tetramethylammonium hydroxide (25% in MeOH, 72.0 uL, 0.7 mmol, 10.0 equiv). After stirring for 2 hours at room temperature, the reaction mixture was neutralized by addition of saturated aqueous NaHSO$_4$ and the aqueous layer was extracted with DCM. The combined organic layer was washed with brine, dried over Na$_2$SO$_4$ and concentrated in vacuo. The residue was purified by reverse phase HPLC to give product (2.0 mg, 5.2 min). MS m/z (M+H) 1428.9.

II.6.3 Synthesis of 2.6.3

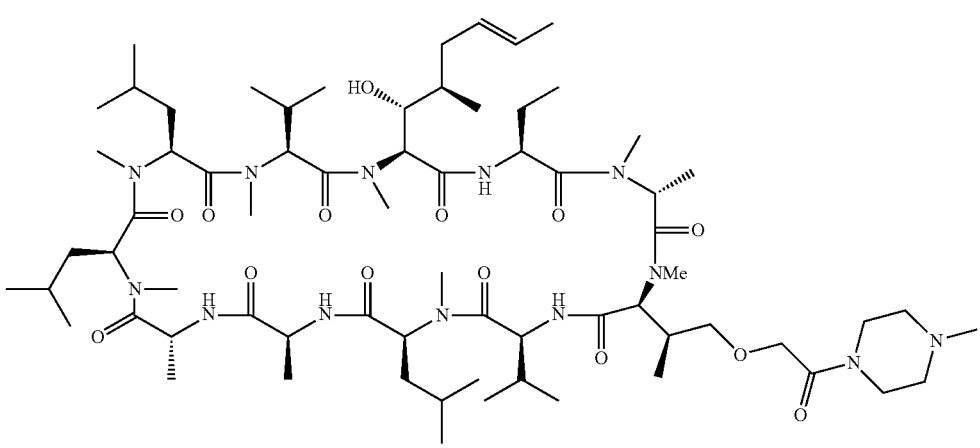

2.6.3

Step 1. Synthesis of 2.6.3a

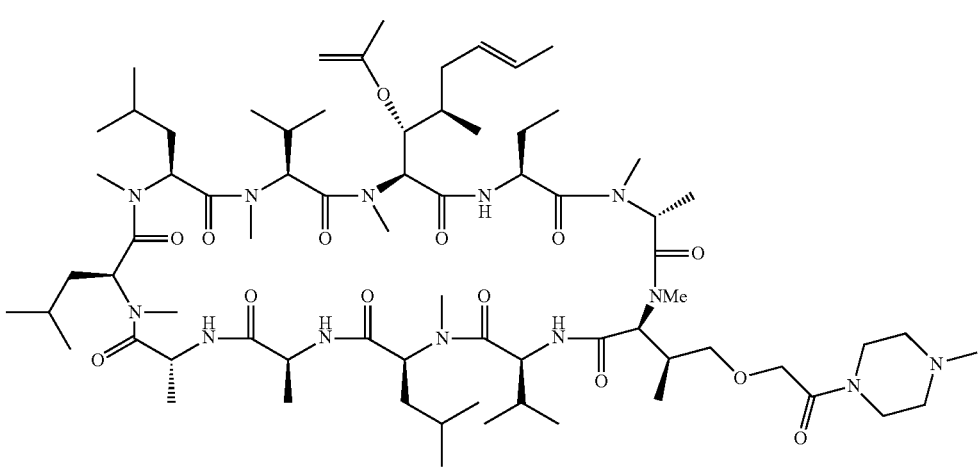

2.6.3a

To a suspension of compound 2.6.1k (133.0 mg, 0.1 mmol) and paraformaldehyde (23.0 mg, 1 mmol, 10 equiv) in 1,2-dichloroethane (1 mL) at room temperature was added sodium triacetoxyborohydride (33.0 mg, 0.15 mmol, 1.6 equiv) and AcOH (7.0 uL, 0.12 mmol, 1.2 equiv). After stirring for 12 hours, the reaction mixture was quenched with saturated aqueous NaHCO$_3$, and the aqueous layer was extracted with DCM. Combined organic layer was washed with brine, dried over Na$_2$SO$_4$, and concentrated in vacuo to give compound 2.6.3a (110.0 mg, 82% yield). MS m/z (M+Na) 1423.8.

Step 2. Synthesis of 2.6.3b

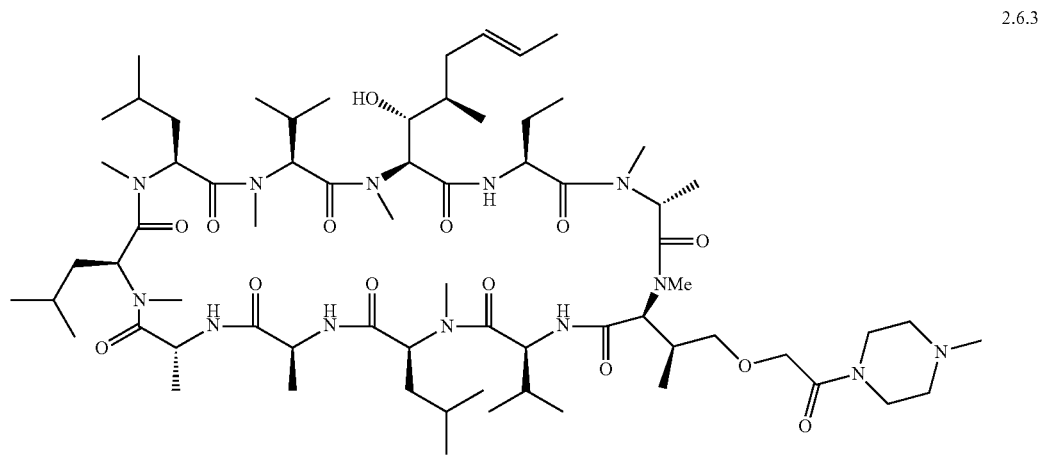 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCC(=O)N2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.6.3

To a solution of 2.6.3a (110.0 mg, 80.0 umol) in MeOH at 0° C. (2.5 mL) was added tetramethylammonium hydroxide (25% in MeOH, 83.0 uL, 0.8 mmol, 10.0 equiv). After stirring for 2 hours at room temperature, the reaction mixture was quenched with saturated aqueous NaHSO$_4$. The aqueous layer was extracted with DCM (2×10 mL). Combined organic layer was washed with brine, dried over Na$_2$SO$_4$ and concentrated in vacuo. The residue was purified by reverse phase HPLC to give 2.6.3b as a white solid (2.1 mg, 10% yield). MS m/z (M+H) 1358.9

II.6.4 Synthesis of 2.6.4

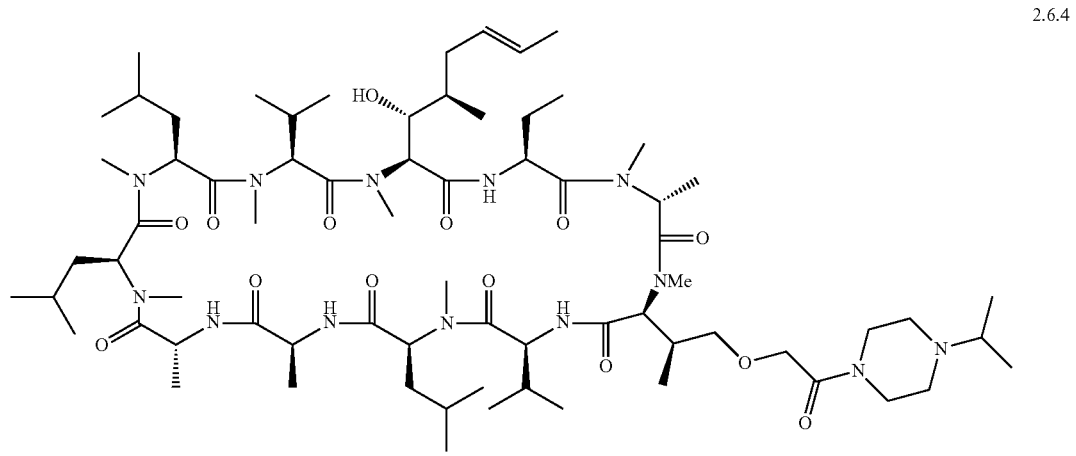 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCC(=O)N2CCN(C(C)C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.6.4

Step 1. Synthesis of 2.6.4a

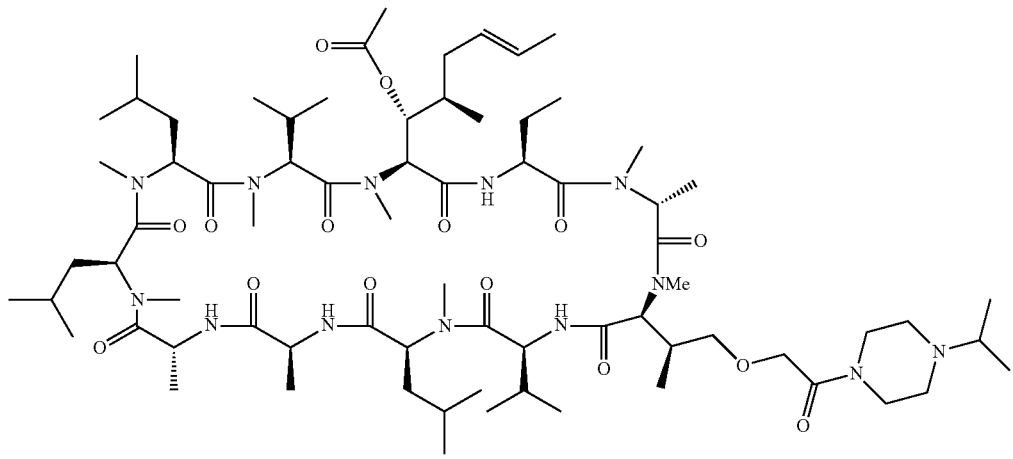

2.6.4a

To a suspension of compound 2.6.1k (250.0 mg, 0.18 mmol) and acetone (132 uL, 1.8 mmol, 10.0 equiv) in 1,2-dichloroethane (2 mL) at room temperature was added sodium triacetoxyborohydride (61.0 mg, 0.29 mmol, 1.6 equiv) and AcOH (13 uL, 0.12 mmol, 1.2 equiv). After stirring for 12 hours, the reaction mixture was quenched with saturated aqueous $NaHCO_3$. Aqueous layer was extracted with DCM. Combined organic layer was washed with brine and dried over $Na_2SO_4$, concentrated in vacuo to give 2.6.4a (164.0 mg, 65% yield). MS m/z (M+Na) 1451.8

Step 2 Synthesis of 2.6.4

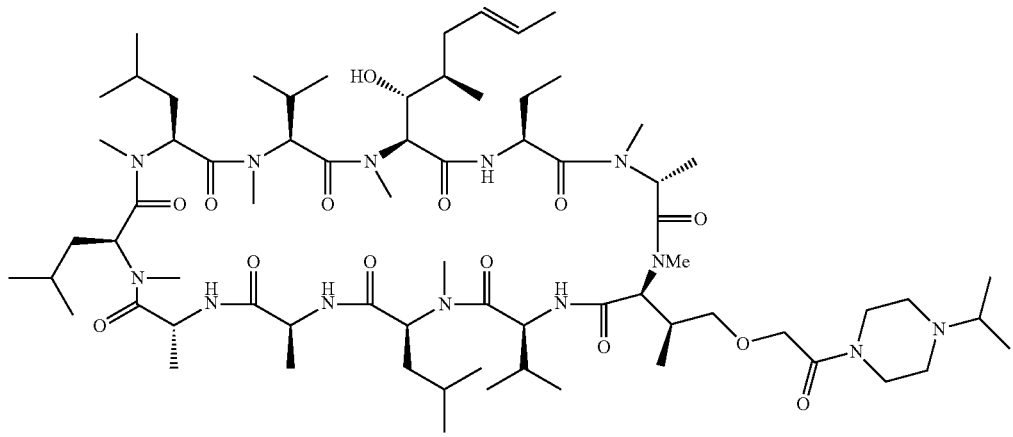

2.6.4

To a solution of 2.6.4a (164.0 mg, 0.12 mmol) in MeOH (4 mL) at 0° C. was added tetramethylammonium hydroxide (25% in MeOH, 121 uL, 1.1 mmol, 10.0 equiv). After stirring at room temperature for 2 hours, the reaction mixture was quenched with saturated aqueous $NaHSO_4$. The aqueous layer was extracted with DCM (2×10 mL). Combined organic layer was washed with brine, dried over $Na_2SO_4$ and concentrated. The residue was purified by reverse phase HPLC to give 2.6.4 as a white solid (2.0 mg, 10% yield). MS m/z (M+H) 1386.9.

II.6.5 Synthesis of 2.6.5

2.6.5

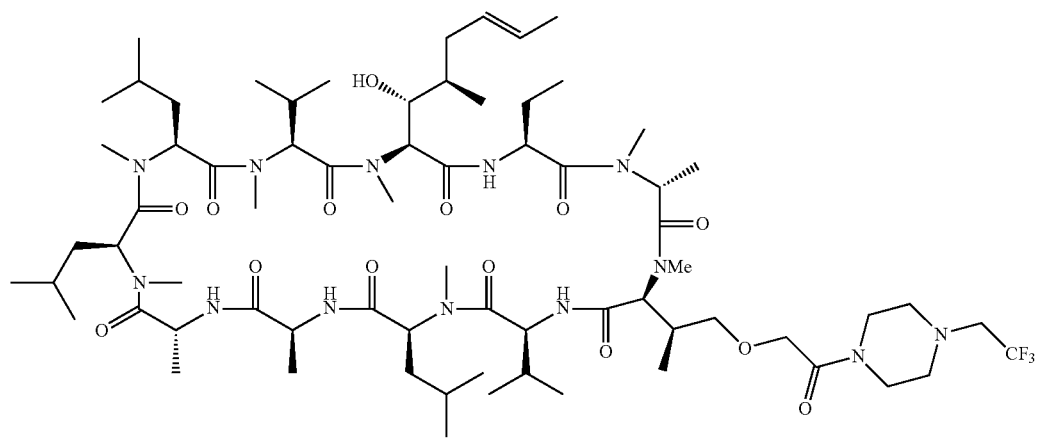

Step 1. Synthesis of 2.6.5a 2.6.5a

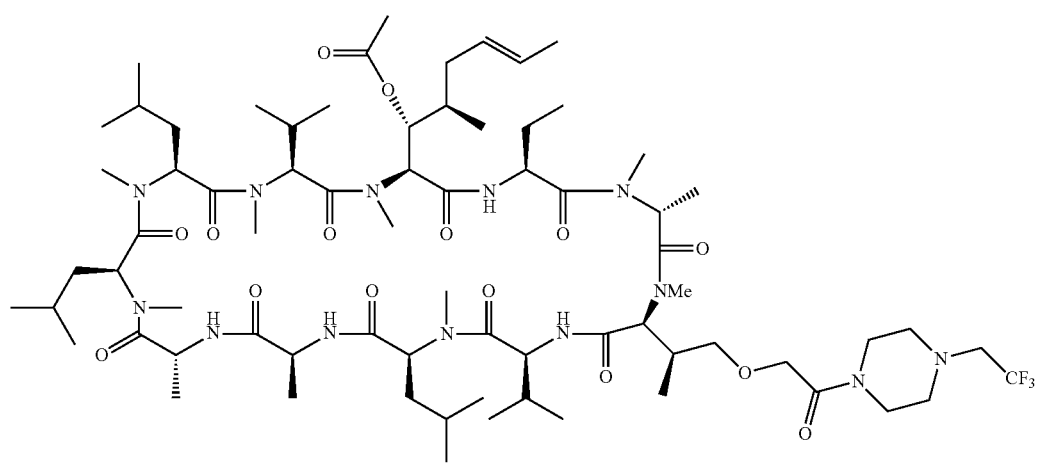

To a solution of compound 2.6.1k (50.0 mg, 40.0 umol) in THF (1 mL) was added DIPEA (44.0 uL, 0.25 mmol, 7.0 equiv) and 2,2,2-trifluoroethyl trifluoromethanesulfonate (26.0 uL, 0.18 mmol, 5.0 equiv) at room temperature. The reaction mixture was heated to 78° C. for 1 h under $N_2$. The reaction mixture was cooled to room temperature and diluted with EtOAc, washed with saturated aqueous $NaHCO_3$, brine and dried over $Na_2SO_4$. The organic layer was concentrated in vacuo to give 2.6.5a (80.0 mg) which was used for the next step without further purification.

Step 2. Synthesis of 2.6.5

2.6.5

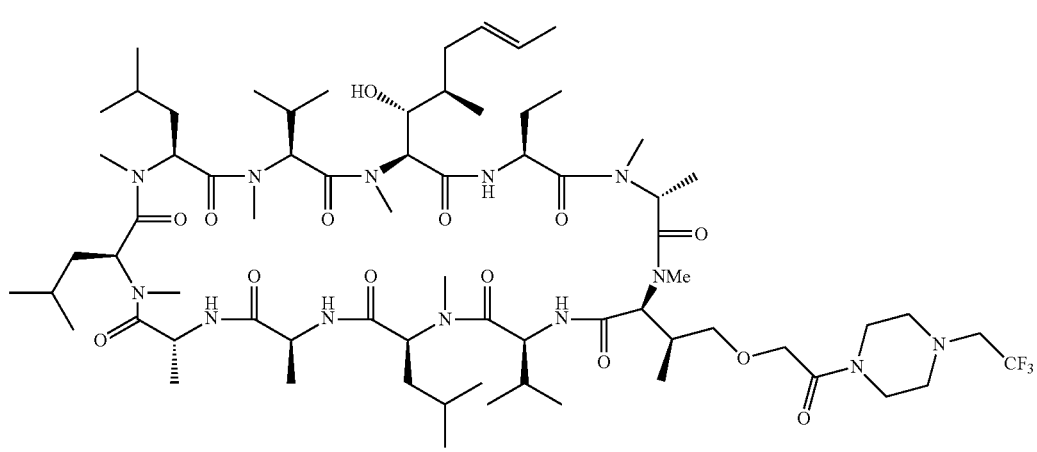

To a solution of 2.6.5a (80.0 mg, 60.0 umol) in MeOH (2 mL) at 0° C. was added tetramethylammonium hydroxide (25% in MeOH, 57 uL, 0.55 mmol, 10 equiv). After stirring at room temperature for 2 hours, the reaction mixture was quenched with saturated aqueous $NaHSO_4$. The aqueous layer was extracted with DCM (2×10 mL). Combined organic layer was washed with brine, dried over $Na_2SO_4$ and concentrated in vacuo. The residue was purified by reverse phase HPLC to give 2.6.5 as a white solid (1.1 mg, 10% yield). MS m/z (M+H) 1426.9

II.6.6 Synthesis of 2.6.6

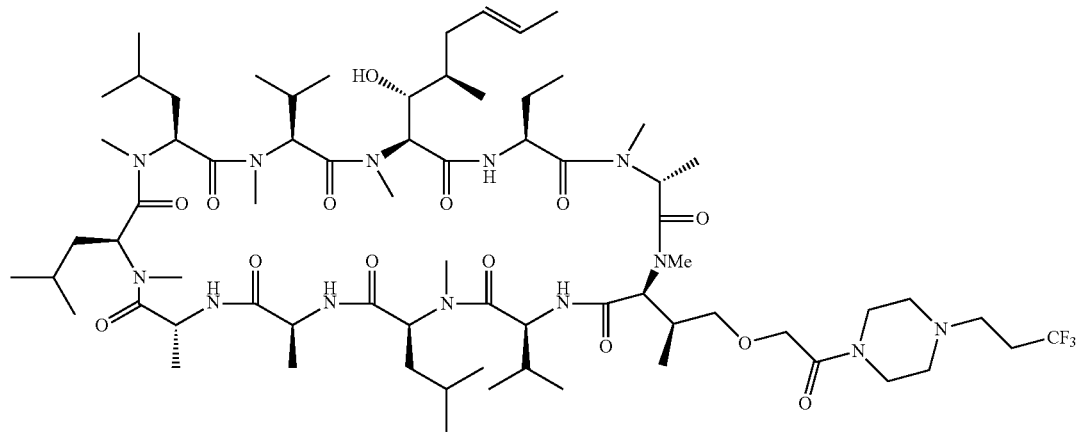

2.6.6

Step 1. Synthesis of 2.6.6a

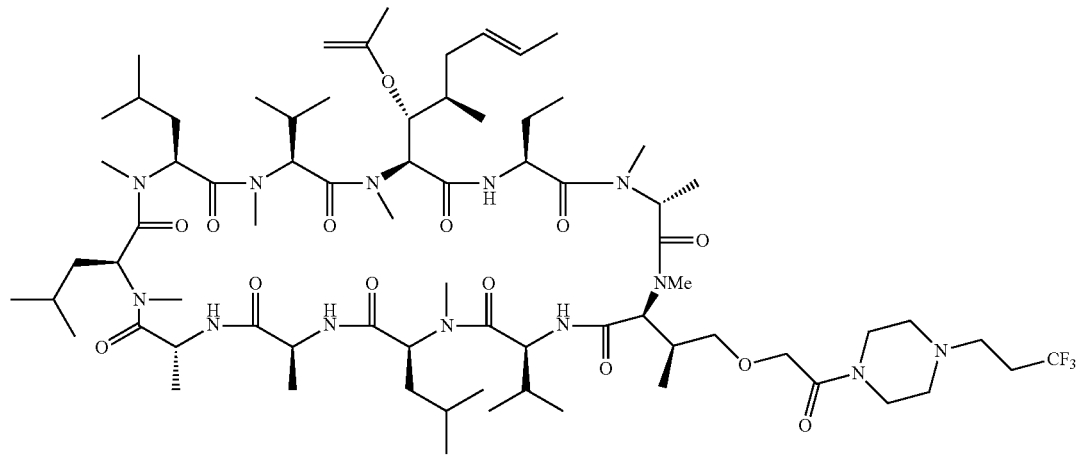

2.6.6a

To a solution of compound 2.6.1k (80.0 mg, 60.0 umol) and 3,3,3-trifluoropropanal (64 uL, 0.58 mmol, 10.0 equiv) in 1,2-dichloroethane (600 uL) at room temperature was added sodium triacetoxyborohydride (20.0 mg, 0.10 mmol, 1.6 equiv) and AcOH (4 uL, 70 umol, 1.2 equiv). After stirring for 12 hours, the reaction mixture was quenched with saturated aqueous $NaHCO_3$, and the aqueous layer was extracted with DCM. Combined organic layer was washed with brine, dried over $Na_2SO_4$, and concentrated in vacuo to give 2.6.6a (80.0 mg) which was used for the next step without further purification. MS m/z (M+H) 1484.0

Step 2. Synthesis of 2.6.6

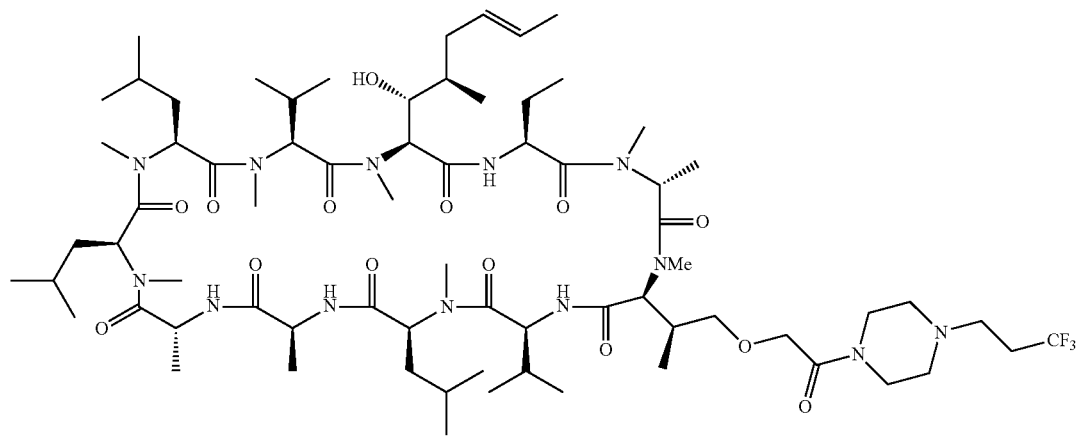

2.6.6

To a solution of 2.6.6a (80.0 mg, 60.0 umol) in MeOH (2 mL) at 0° C. was added tetramethylammonium hydroxide (25% in MeOH, 57 uL, 0.55 mmol, 10.0 equiv). After stirring at room temperature for 2 hours, the reaction mixture was quenched with saturated aqueous $NaHSO_4$. The aqueous layer was extracted with DCM (2×10 mL). Combined organic layer was washed with brine, dried over $Na_2SO_4$ and concentrated in vacuo. The residue was purified by reverse phase HPLC to give 2.6.6 (1.4 mg, 10% yield). MS m/z (M+H) 1440.9

II.7 Synthesis of Compound 2.7

After stirring for 30 minutes at room temperature, acetic acid (0.179 ml, 3.1 mmol, 1.0 equiv) was added dropwise to quench any unreacted TMS-diazomethane. The reaction mixture was concentrated in vacuo, and the residue was purified on silica gel chromatography (ethyl acetate:heptane) to give compound 2.7a (0.95 g, 89% yield). MS m/z (M+Na) 364.3. $^1$H NMR (400 MHz, $CDCl_3$) 7.30-7.40 (m, 1H), 6.32 (dd, J=1.86, 3.13 Hz, 1H), 6.27 (br-s) and 6.20 (br-s, 1H), 5.21 (d, J=11.15 Hz) and 5.03 (d, J=10.22 Hz, 1H), 3.96-4.02 (m, 2H), 3.71 (s, 3H), 3.39-3.46 (m, 1H), 3.20 (dd, J=6.92, 8.97 Hz, 1H), 2.69 (br-s, 3H), 2.39-2.52 (m, 1H), 1.47 (br-s., 9H), 1.08 (br-s., 3H).

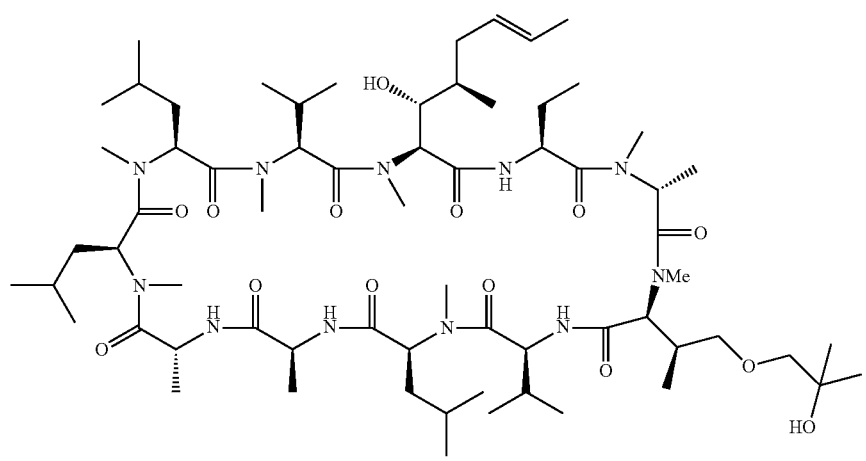

2.7

Step 1. Synthesis of Methyl 2-((2S,3S)-3-((tert-butoxycarbonyl)(methyl)amino)-3-(furan-2-yl)-2-methylpropoxy)acetate [2.7a]

Step 2. Synthesis of tert-Butyl((1S,2S)-1-(furan-2-yl)-3-(2-hydroxy-2-methylpropoxy)-2-methylpropyl)(methyl)carbamate [2.7b]

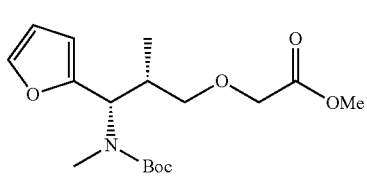

2.7a

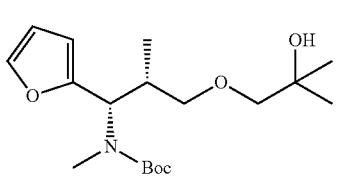

2.7b

To a solution of compound 2.6.1b (1.0 g, 3.1 mmol) in methanol (2 mL) at 0° C. was added TMS-diazomethane dropwise (1.0 M in hexanes, 6 mL, 6.0 mmol, 2.0 equiv).

To a solution of compound 2.7a (120.0 mg, 0.35 mmol) in ether (2 ml) at 0° C. was added methyl magnesium bromide (3 M in ether, 2 ml, 6.0 mmol, 17.0 equiv) dropwise. After stirring for 2 hours at 0° C., the reaction mixture was quenched with aqueous 1.0 M HCl aq. solution at 0° C. (pH ~5), extracted with DCM (3×3 mL), dried with Na₂SO₄, filtered and concentrated in vacuo to give compound 2.7b (120.0 mg) which was used for the next step without further purification. MS m/z (M+Na) 364.2

Step 3. Synthesis of (2S,3S)-2-((tert-butoxycarbonyl)(methyl)amino)-4-(2-hydroxy-2-methylpropoxy)-3-methylbutanoic acid [2.7c]

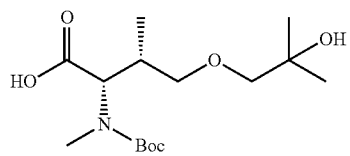

2.7c

To a solution of compound 2.7b (120.0 mg, 0.35 mmol) in water:CCl₄:MeCN (3:2:3, 9.6 ml) at room temperature was added sodium periodate (451.0 mg, 2.1 mmol, 6.0 equiv) followed by ruthenium chloride (25.0 mg, 0.12 mmol, 0.34 equiv). After stirring for 45 minutes, the aqueous layer was extracted with ethyl acetate (3×5 ml). Combined organic layer was washed with saturated aqueous NaHSO₃ (25 ml), brine, dried with anhydrous sodium sulfate, and concentrated in vacuo to give compound 2.7c (100.0 mg) which was used for the next step without further purification. MS m/z (M+Na) 342.2

Step 4. Synthesis of 2.7d

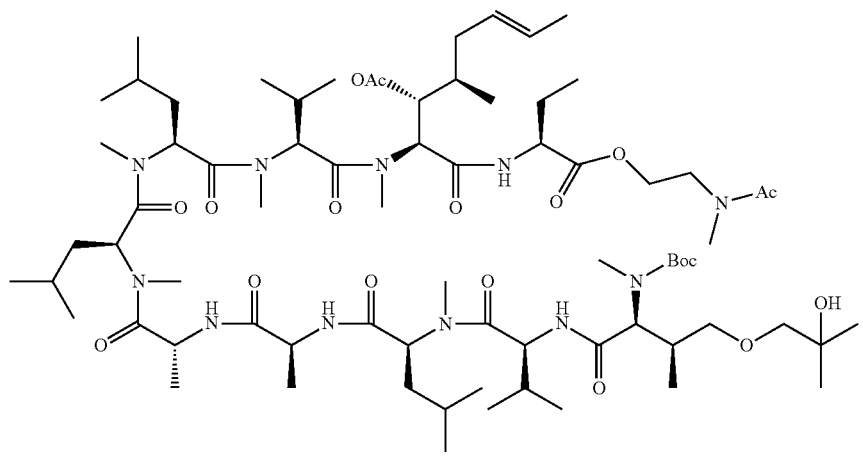

2.7d

To a solution of amine 1 (364.0 mg, 0.31 mmol) in DCM (4 mL) at 0° C. was added compound 2.7c (100.0 mg, 0.31 mmol, 1.0 equiv), DIPEA (0.273 ml, 1.57 mmol, 5.0 equiv), and HATU (155.0 mg, 0.41 mmol, 1.3 equiv). After stirring at room temperature for 12 hours, the reaction mixture was concentrated in vacuo and purified on silica gel chromatography (MeOH/DCM) to afford compound 2.7d (289 mg, 63% yield). MS m/z (M+Na) 1487.1

Step 5. Synthesis of 2.7e

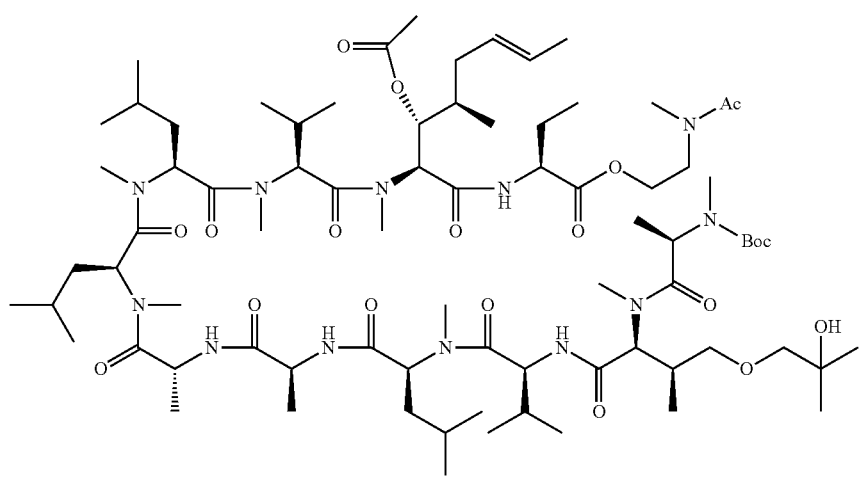

2.7e

To a solution of 2.7d (597.0 mg, 0.41 mmol) in DCM (1 ml) was added slowly at 0° C. a solution of TFA (1 mL) in DCM (3 mL). After stirring at 0° C. for 3 hours, the reaction mixture was quenched with saturated NaHCO$_3$ and extracted with DCM. Combined organic layer was dried with Na$_2$SO$_4$, filtered and concentrated in vacuo to give the de-Boc intermediate (557.0 mg) which was used for the next step without further purification. To a solution of the de-Boc intermediate (557.0 mg, 0.41 mmol) in DCM (5 mL) at 0° C. was added Boc-N-Me-D-Ala-OH (166.0 mg, 0.82 mmol, 2.0 equiv), DIPEA (0.37 ml, 2.0 mmol, 5.0 equiv) and HATU (310.0 mg, 0.82 mmol, 2.0 equiv). After stirring for 24 hours at room temperature, the reaction mixture was concentrated in vacuo and purified on silica gel chromatography (methanol/DCM) to give compound 2.7e (450.0 mg, 71%). MS m/z (M+Na) 1572.7

Step 6. Synthesis of 2.7f

To a solution of compound 2.7e (450.0 mg, 0.15 mmol) in DCM (1 mL) at 0° C. was added a solution of TFA (1 mL) in DCM (3 mL). After stirring at 0° C. for 30 minutes, the reaction was quenched by addition of saturated aqueous sodium bicarbonate and extracted with DCM (3×2 ml). Combined organic layer was dried with Na$_2$SO$_4$, filtered and concentrated in vacuo to afford de-Boc intermediate (210.0 mg) which was used for the next step without further purification.

To a solution of de-Boc intermediate in MeOH/THF/H$_2$O (1/1/1, 1.5 mL) at 0° C. was added LiOH.H$_2$O (20.0 mg, 0.48 mmol, 3.3 equiv). After stirring for 2 hours at 0° C., the reaction mixture was quenched with saturated KHSO$_4$ (10 ml) and extracted with DCM (3×10 ml). Combined organic layer was dried with anhydrous sodium sulfate and concentrated in vacuo to give compound 2.7f (196.0 mg) which was used for the next step without further purification. MS m/z (M+Na) 1372.7

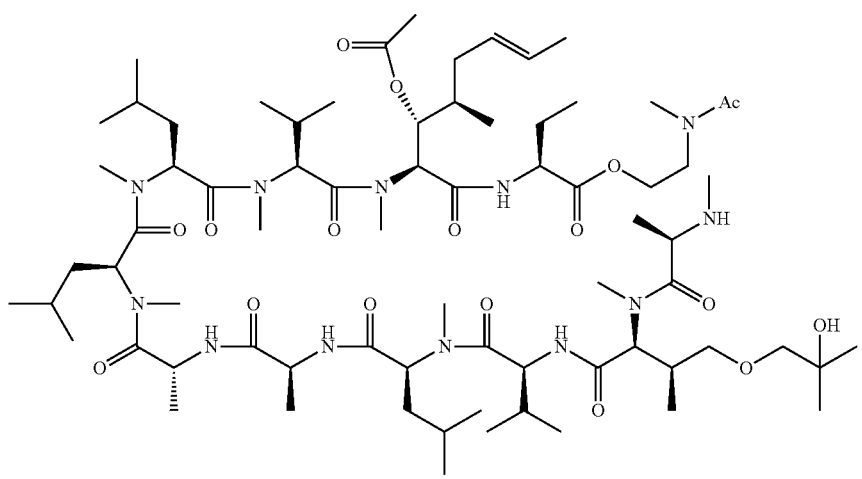

2.7f

Step 7. Synthesis of 2.7g

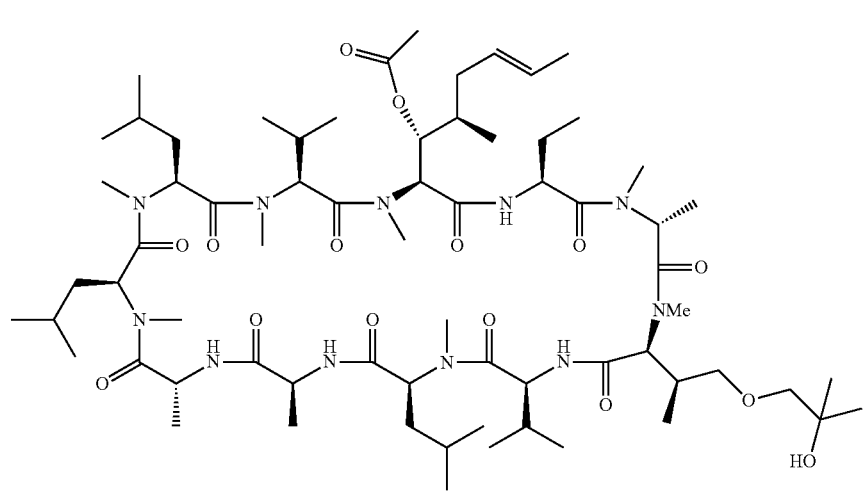

2.6.7g

To a solution of BOP (158.0 mg, 0.36 mmol, 2.0 equiv) in DCM (80 ml) at 0° C. was added a pre-mixed solution of DMAP (43.6 mg, 0.36 mmol, 2.0 equiv) and compound 2.7f (241.0 mg, 0.18 mmol) in DCM (100 mL) over 3 hours via additional funnel. After stirring at room temperature for 24 hours, the reaction mixture was concentrated in vacuo and purified on silica gel chromatography (methanol/DCM) to give compound 2.7g (103.0 mg, 43% yield). MS m/z (M+23) 1355.6

Step 8. Synthesis of 2.7

To a solution of 2.7g (103.0 mg, 77.0 umol) in methanol (2.4 ml) at 0° C. was added tetramethylammonium hydroxide (25% in MeOH, 0.35 ml, 0.85 mmol, 11.0 equiv). After stirring at room temperature for 2 hours, the reaction mixture was quenched with aqueous saturated $NaHSO_4$ (10 ml) and extracted with DCM. Combined organic layer was washed with saturated brine, dried with $Na_2SO_4$, filtered and concentrated in vacuo. The residue was purified on reverse phase HPLC to give compound 2.7 (87.0 mg, 87% yield). MS m/z (M+1) 1290.9

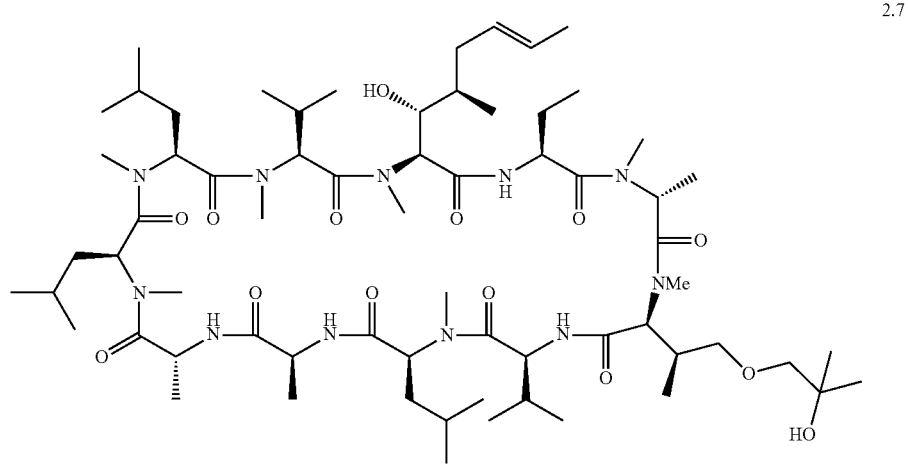 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.7

II.8.1 Synthesis of 2.8.1

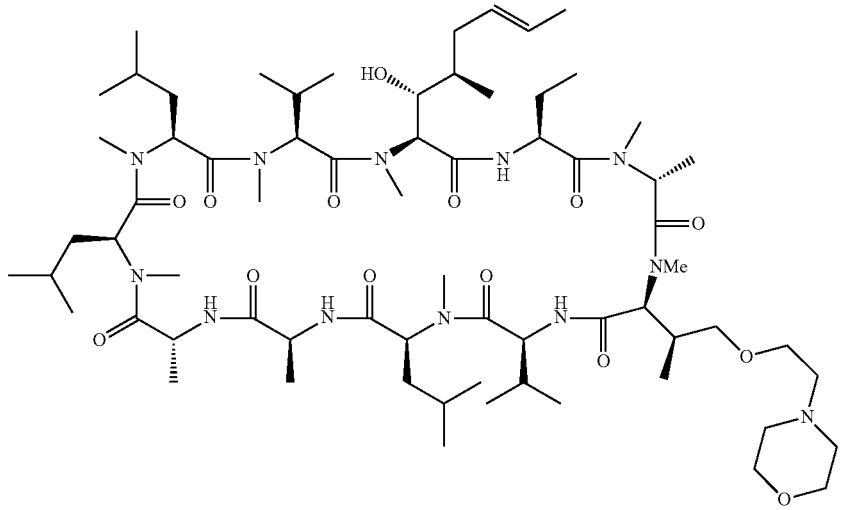

2.8.1

Step 1. Synthesis of tert-butyl((1S,2S)-1-(furan-2-yl)-3-(2-hydroxyethoxy)-2-methylpropyl)(methyl)carbamate [2.8.1a]

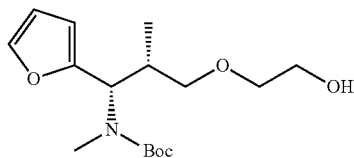

2.8.1a

To a solution of compound 2.7a (0.95 g, 2.78 mmol) in methanol (7 mL) was added sodium borohydride (1.05 g, 27.8 mmol, 10.0 equiv) at 0° C. After stirring for 1 hour, the reaction was quenched with 1.0 M sulfuric acid and extracted with DCM. Combined organic layer was dried with anhydrous sodium sulfate, filtered and concentrated in vacuo to give compound 2.8.1a (0.85 g) which was used for the next step without further purification. MS m/z (M+Na) 336.3

Step 2. Synthesis of tert-butyl((1S,2S)-3-(2-((tert-butyldiphenylsilyl)oxy)ethoxy-1-(furan-2-yl)-2-methylpropyl)(methyl)carbamate [2.8.1 b]

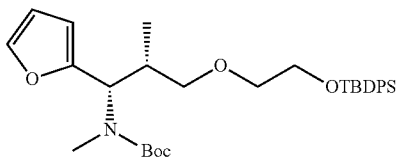

2.8.1b

To a solution of 2.8.1a (0.95 g, 3.03 mmol) in DCM (8 mL) at room temperature was added imidazole (0.31 g, 4.55 mol, 1.5 equiv) and TBDPS-Cl (0.9 ml, 3.5 mmol, 1.5 equiv). After stirring for 2 hours at room temperature, the reaction mixture was diluted with DCM (20 mL) and washed with aqueous 1.0 M Sulfuric Acid. Combined organic layers was dried with $Na_2SO_4$, filtered and concentrated in vacuo. The residue was purified on silica gel chromatography (ethyl acetate:heptane) to give compound 2.8.1b (1.6 g, 96%). MS m/z (M+Na) 574.4. $^1$H NMR (400 MHz, $CDCl_3$) 7.64-7.75 (m, 5H), 7.30-7.46 (m, 6H), 6.28 (d, J=1.86 Hz, 1H), 6.21 (br-s) and 6.15 (br-s, 1H), 5.15 (d, J=10.37 Hz) and 4.98 (d, J=10.56 Hz, 1H), 3.74 (t, J=5.31 Hz, 2H), 3.44 (qt, J=5.23, 10.91 Hz, 2H), 3.32 (br-s, 1H), 3.12 (dd, 1H), 2.70 (br-s, 3H), 2.43-2.36 (m, 1H), 1.46 (s, 9H), 1.03 (s, 3H), 1.07 (s, 9H).

Step 3. Synthesis of Benzyl((9S,10S,13R)-10-(furan-2-yl)-2,2,9,11-tetramethyl-12-oxo-3,3-diphenyl-4,7-dioxa-11-aza-3-silatetradecan-13-yl)(methyl)carbamate [2.8.1c]

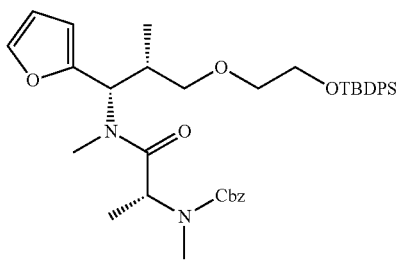

2.8.1c

To a solution of compound 2.8.1b (800.0 mg, 1.45 mmol) in DCM (1 ml) at 0° C. was added 4 M HCl in dioxane (5 mL). After stirring at 10° C. for 45 minutes, the reaction mixture was concentrated in vacuo to give the de-boc intermediate (655.0 mg) which was used for the next step without further purification. To a solution of de-boc intermediate (655.0 mg, 1.45 mmol) in DCM (10 ml) at 0° C. was added N-Me-Z-D-Ala-OH (688.0 mg, 2.90 mmol, 2.0 equiv) followed by HATU (827.0 mg, 2.18 mmol, 1.5 equiv) and DIPEA (1.26 ml, 7.25 mmol, 5.0 equiv). After stirring at room temperature for 12 hours, the reaction mixture was concentrated in vacuo and purified on silica gel chromatography (ethyl acetate:heptane) to give compound 2.8.1c (300.0 mg, 31%). MS m/z (M+1) 671.2

Step 4. Synthesis of (2S,3S)-2-((R)-2-((benzyloxy)carbonyl)(methyl)amino)-N-methylpropanamido)-4-(2-((tert-butyldiphenylsilyl)oxy)ethoxy)-3-methylbutanoic acid [2.8.1 d]

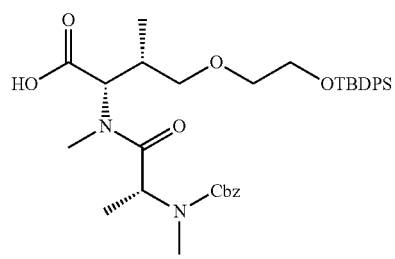

2.8.1d

To a solution of compound 2.8.1c (300.0 mg, 0.45 mmol) in heptane/ethyl acetate/water (3/1/4, 40 ml) at room temperature was added sodium periodate (669.0 mg, 3.13 mmol, 7.0 equiv) followed by $RuCl_3$ (75.0 mg, 0.29 mmol, 0.64 equiv). After stirring for 45 minutes, the reaction mixture was filtered through Celite. The filtrate was diluted with water and extracted with ethyl acetate. Combined organic layer was washed with saturated sodium bisulfite and brine. Combined organic layer was dried over sodium sulfate and concentrated in vacuo to give compound 2.8.1d (300.0 mg) which was subjected to the next step without further purification. MS m/z (M+1) 649.2

Step 5. Synthesis of 2.8.1e

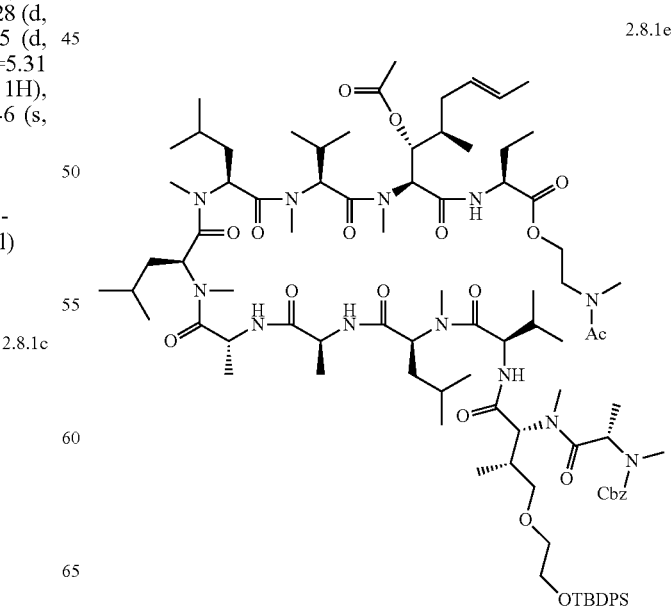

2.8.1e

To a solution of compound 2.8.1d (300.0 mg, 0.46 mmol) in DCM (5 mL) at 0° C. was added amine 1 (538.0 mg, 0.46 mmol) followed by DIPEA (0.40 ml, 2.31 mmol, 5.0 equiv) and HATU (246.0 mg, 0.65 mmol, 1.4 equiv). After stirring at room temperature for 12 hours, the reaction mixture was concentrated in vacuo and purified on a silica gel chromatography (acetone/DCM) to give compound 2.8.1e (520.0 mg, 63% yield). MS m/z (M+1) 1795.2

Step 6. Synthesis of 2.8.1f

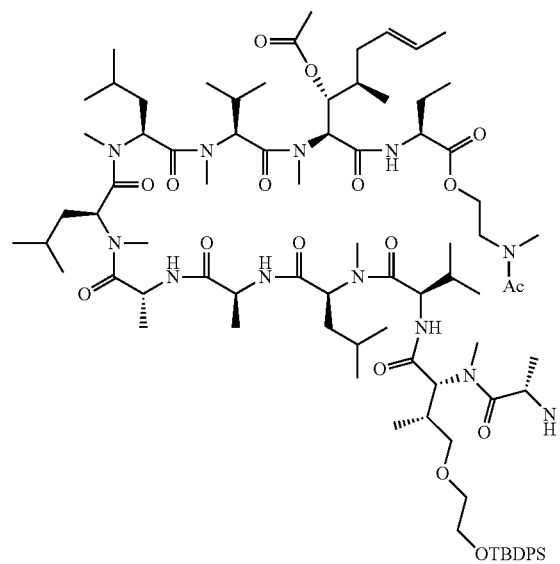

2.8.1f

To a solution of compound 2.8.1e (520.0 mg, 0.290 mmol in DCM (5 ml) was added triethylsilane (0.231 ml, 1.45 mmol, 5.0 equiv), triethylamine (0.202 ml, 1.45 mmol, 5.0 equiv) and palladium(II) acetate (32.5 mg, 0.14 mmol, 0.5 equiv). After stirring at room temperature for 4 hours, the reaction mixture was quenched with saturated aqueous ammonium chloride (20 mL) and filtered. The filtrate was diluted with DCM and washed with saturated sodium bicarbonate. Combined organic layer was dried with $Na_2SO_4$, filtered and concentrated to give 2.8.1f (481.0 mg) which was subjected to the next step without further purification. MS m/z (M+Na) 1693.2

Step 7. Synthesis of 2.8.1g

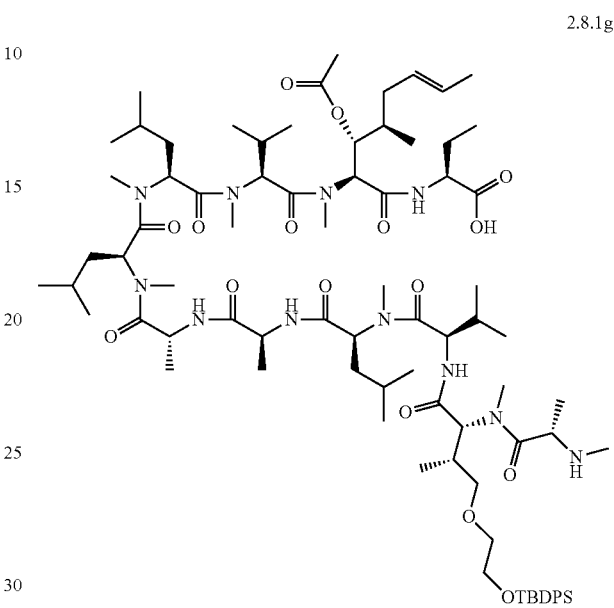

2.8.1g

To a solution of compound 2.8.1f (703.0 mg, 0.42 mmol) in THF/Water/Methanol (1/1/1. 4.2 mL) at 0° C. was added $LiOH.H_2O$ as a solid (55.0 mg, 1.31 mmol, 3.1 equiv). After stirring at 0° C. for 2 hours, the reaction mixture was quenched with aqueous saturated $KHSO_4$ (10 ml) and extracted with DCM (3×10 ml). Combined organic layer was dried with anhydrous sodium sulfate, filtered and concentrated in vacuo to give compound 2.8.1g (661.0 mg) which was subjected for the next step without further purification. MS m/z (M+1) 1562.3

Step 8. Synthesis of 2.8.1h

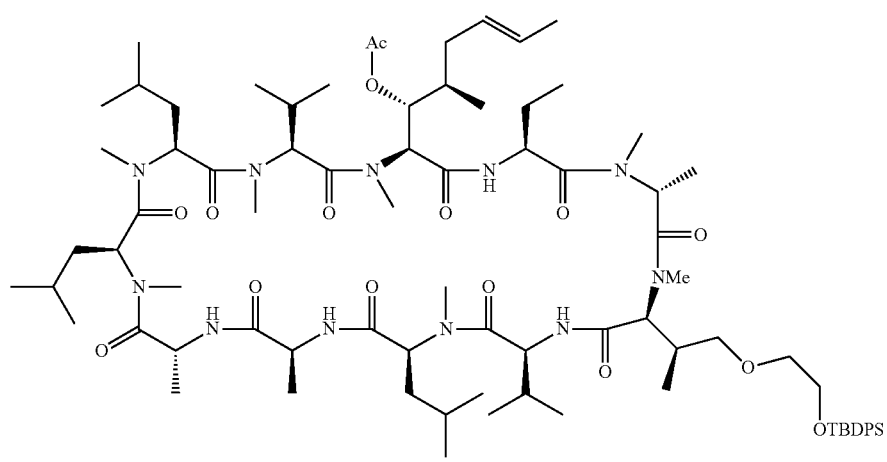

2.8.1h

To a solution of BOP (397.0 mg, 0.897 mmol, 2.0 equiv) in DCM (200 ml) at 0° C. was added a pre-mixed solution of compound 2.8.1g (700.0 mg, 0.448 mmol) and DMAP (110.0 mg, 0.897 mmol, 2.0 equiv) in DCM (250 mL) via additional funnel over a period of 3 hours. After stirring at room temperature for 24 hours, the reaction mixture was concentrated in vacuo and purified on silica gel chromatography (acetone/DCM) to give compound 2.8.1h (182 mg, 26% yield). MS m/z (M+23) 1566.1

Step 9. Synthesis of 2.8.1i

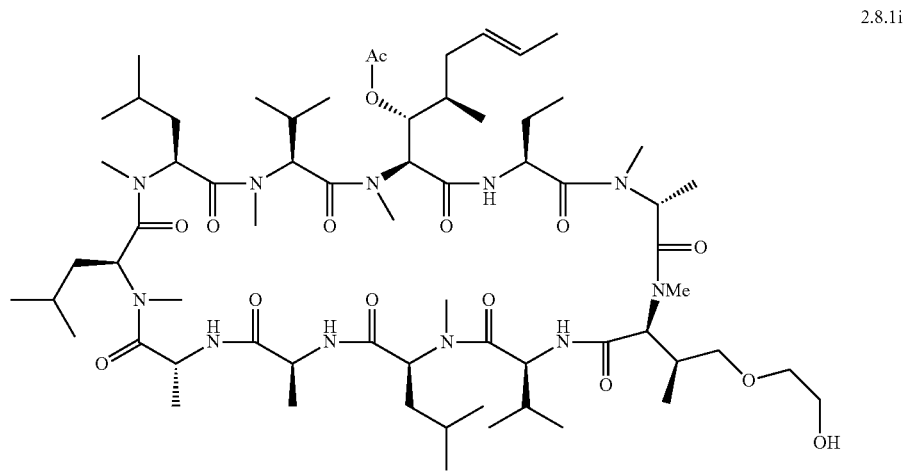 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)COCCO)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.8.1i

To a solution of compound 2.8.1h (140.0 mg, 91 umol) in THF (1.5 ml) at room temperature was added TBAF (1 M in THF, 1 ml, 1.0 mmol, 11.0 equiv). After stirring for 12 hours, the reaction mixture was diluted with DCM (5 ml), washed with aqueous saturated KHSO₄ (5 ml), saturated brine, dried with Na₂SO₄, filtered and concentrated in vacuo. The residue was purified on silica gel chromatography (MeOH/DCM) to give compound 2.8.1i (110.0 mg, 93% yield). MS m/z (M+Na) 1327.0

Step 10. Synthesis of 2.8.1j

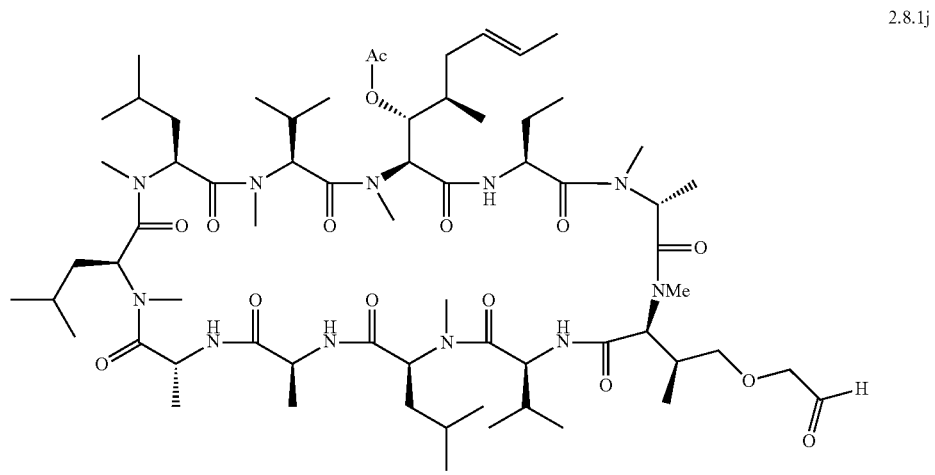 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)COCC=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.8.1j

To a cooled DCM (1 mL) at −78° C. was added oxalyl chloride (40 ul, 0.46 mmol, 19.9 equiv) followed by DMSO (0.1 ml, 1.41 mmol, 61.3 equiv), and the reaction mixture was stirred for 15 minutes at −78° C. A solution of compound 2.8.1i (30.0 mg, 23.0 umol) in DCM (0.5 mL) was added dropwise to the reaction mixture followed by triethylamine (0.112 ml, 0.81 mmol, 35.0 equiv). After stirring at −78° C. for 1 hour and room temperature for 1 hour, the reaction mixture was diluted with DCM (10 mL), washed with saturated brine, dried with $Na_2SO_4$, filtered and concentrated in vacuo to give compound 2.8.1j (31.6 mg) which was subjected to the next step without further purification. MS m/z (M+1) 1303.1

Step 11. Synthesis of 2.8.1k

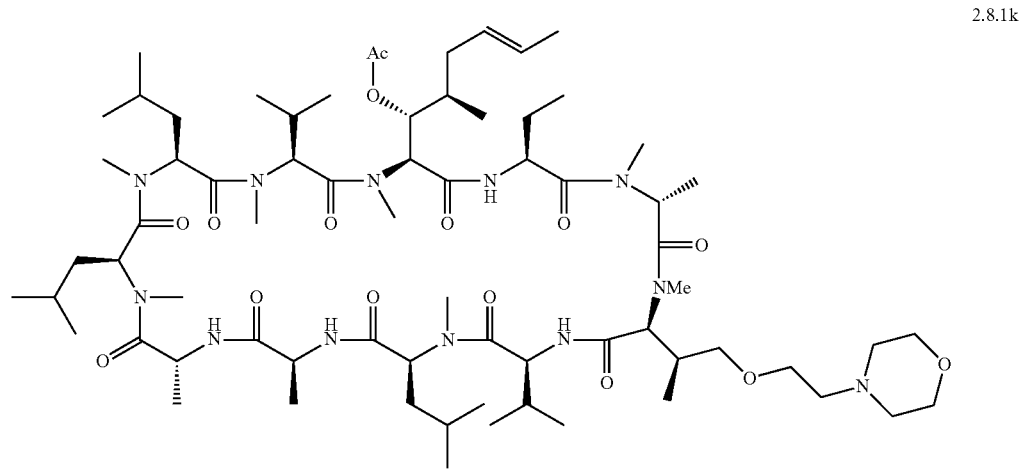 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)COCCN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.8.1k

To a solution of 2.8.1j in dichloroethane (1.5 ml) at room temperature was added morpholine (18 ul, 0.21 mmol, 9.0 equiv), acetic acid (12.0 ul, 0.21 mmol, 9.0 equiv) and sodium triacetoxyborohydride (43.9 mg, 0.21 mmol, 9.0 equiv). After stirring for 2 hours at room temperature, the reaction mixture was quenched with aqueous saturated sodium bicarbonate (5 ml). The aqueous layer was extracted with DCM. Combined organic layer was dried with $Na_2SO_4$, filtered and concentrated in vacuo to give compound 2.8.1k (31.6 mg) which was subjected to the next step without further purification. MS m/z (M+1) 1375

Step 12. Synthesis of 2.8.1

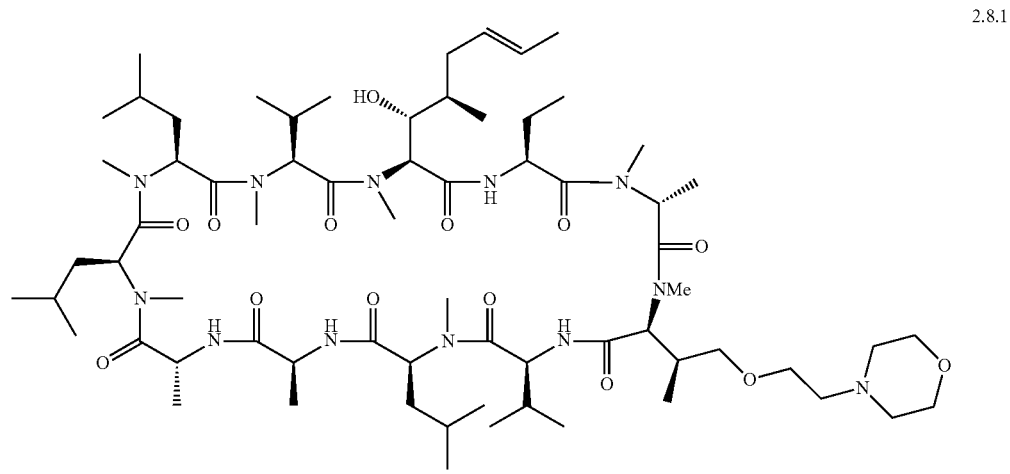 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.8.1

To a solution of 2.8.1k (31.6 mg, 23.0 umol) in methanol (2 mL) at 0° C. was added tetramethylammonium hydroxide (25% in methanol, 0.3 mL, 0.853 mmol, 37.0 equiv). After stirring at room temperature for 2 hours, the reaction mixture was quenched with aqueous saturated $KHSO_4$ (2 mL) and extracted with DCM. Combined organic layer was washed with brine, dried with $Na_2SO_4$, filtered and concentrated in vacuo. The residue was purified by reverse phase HPLC to give compound 2.8.1 (8.0 mg, 26% yield). MS m/z (M+1) 1331.9

II.8.2 Synthesis of Compound 2.8.2
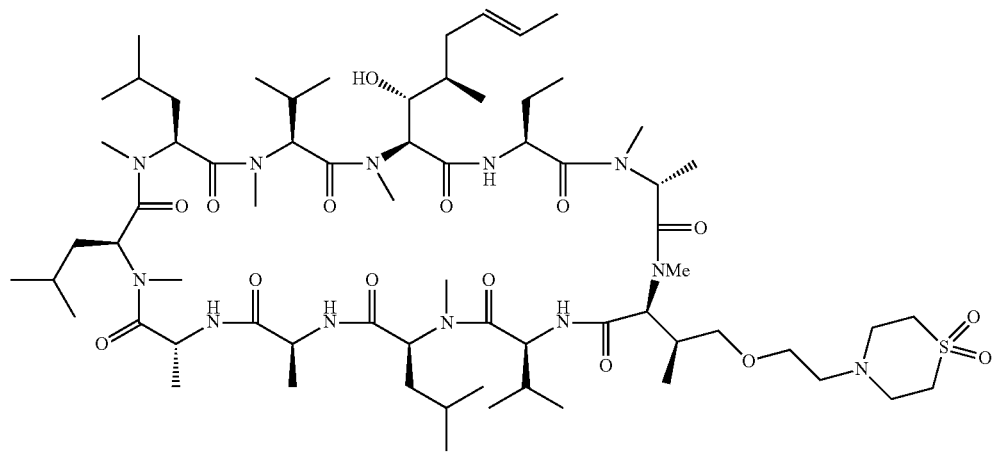
2.8.2
Compound 2.8.2 was prepared following the procedures described for the synthesis of 2.8.1 using thiomorpholine 1,1-dioxide in step 11. MS m/z (M+1) 1379.9
III.8.3 Synthesis of Compound 2.8.3
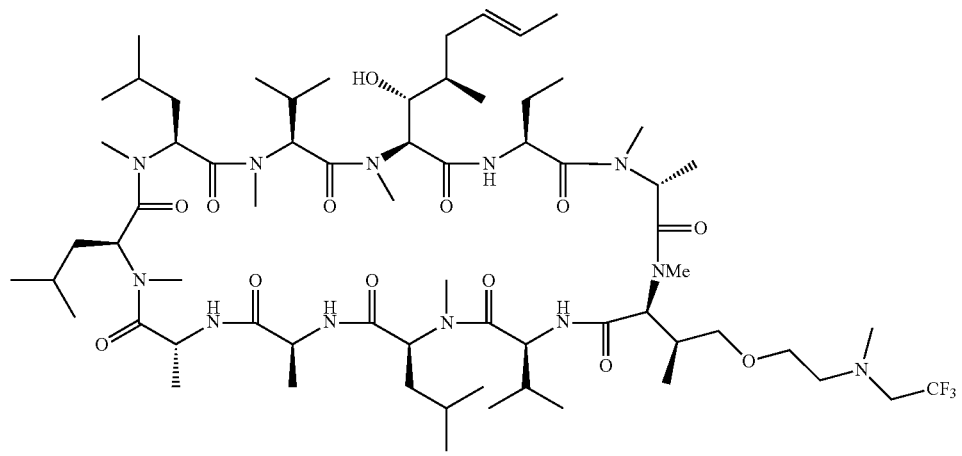
2.8.3
Compound 2.8.3 was prepared following the procedures described for the synthesis of 2.8.1 using trifluoroethyl methyl amine in step 11. MS m/z (M+1) 1357.9
II.8.4 Synthesis of Compound 2.8.4
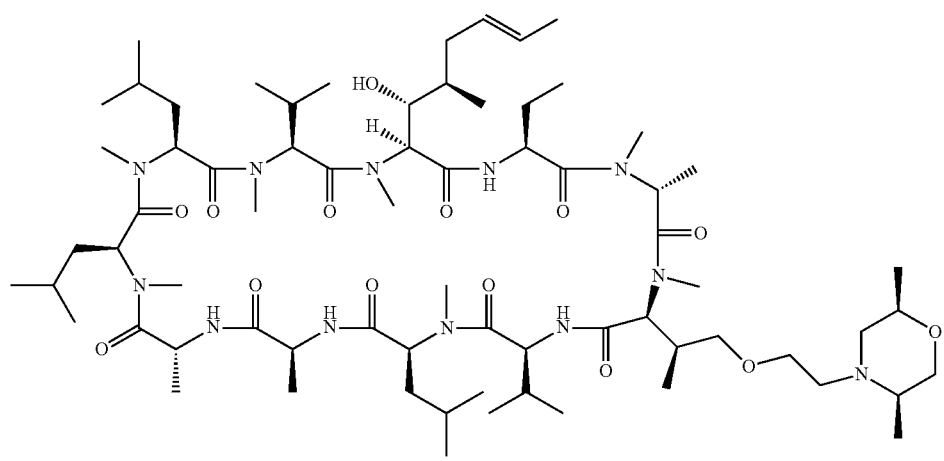
2.8.4

Compound 2.8.4 was prepared following the procedures described for the synthesis of 2.8.1 using (2R,5R)-2,5-Dimethylmorpholine in Step 11. MS m/z (M+1) 1359.9573

II.8.5 Synthesis of Compound 2.8.5

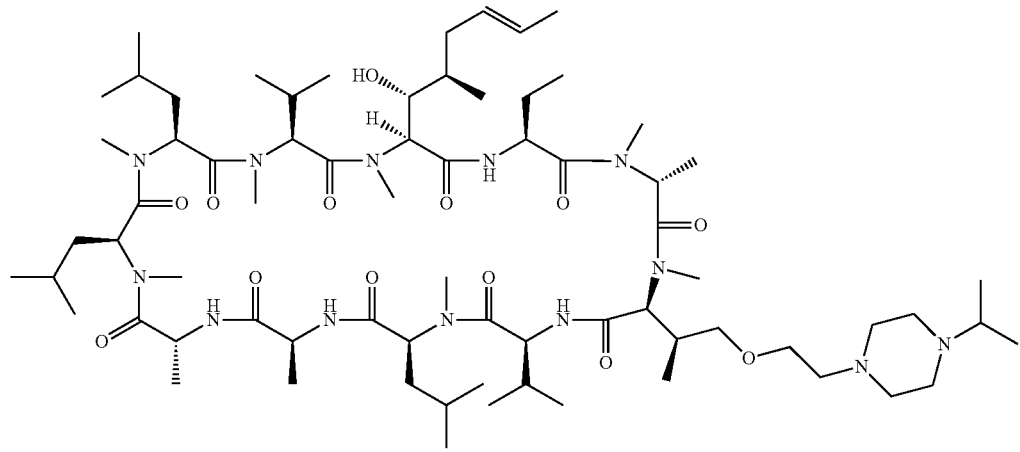

2.8.5

Compound 2.8.5 was prepared following the procedures described for the synthesis of 2.8.1 using 1-isopropylpiperazine in Step 11. HRMS m/z (M+1) 1372.9912

II.8.6 Synthesis of Compound 2.8.6

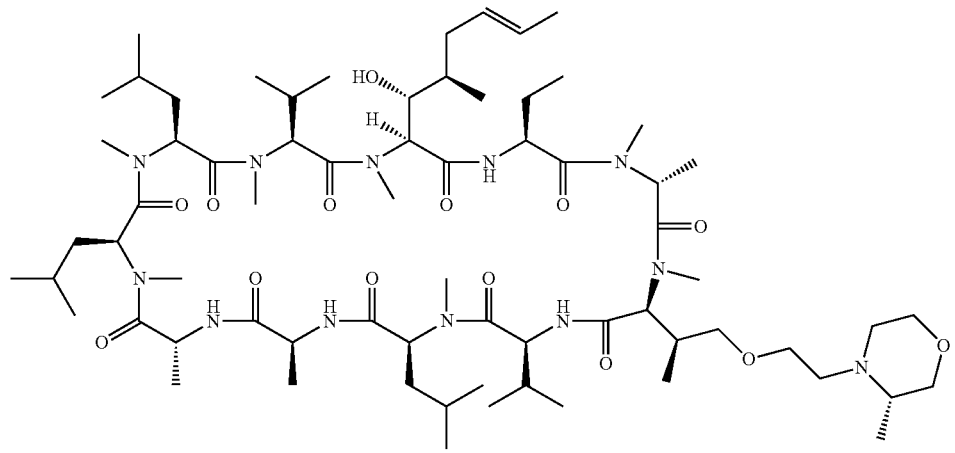

2.8.6

Compound 2.8.6 was prepared following the procedures described for the synthesis of 2.8.1 using (S)-3-Methylmorpholine in Step 11. HRMS m/z (M+1) 1345.9426

II.8.7 Synthesis of Compound 11.8.7
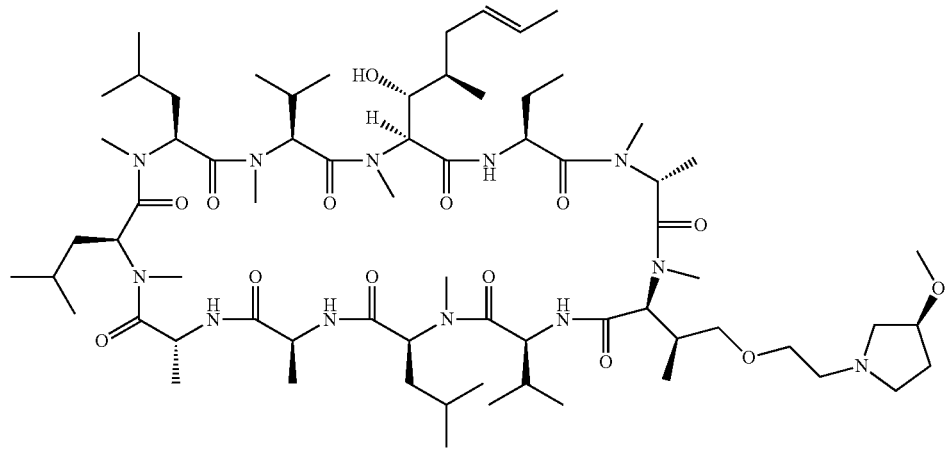
2.8.7
Compound 2.8.7 was prepared following the procedures described for the synthesis of 2.8.1 using (S)-3-Methoxypyrrolidine hydrochloride in Step 11. HRMS m/z (M+1) 1345.9408
II.8.8 Synthesis of Compound 2.8.8
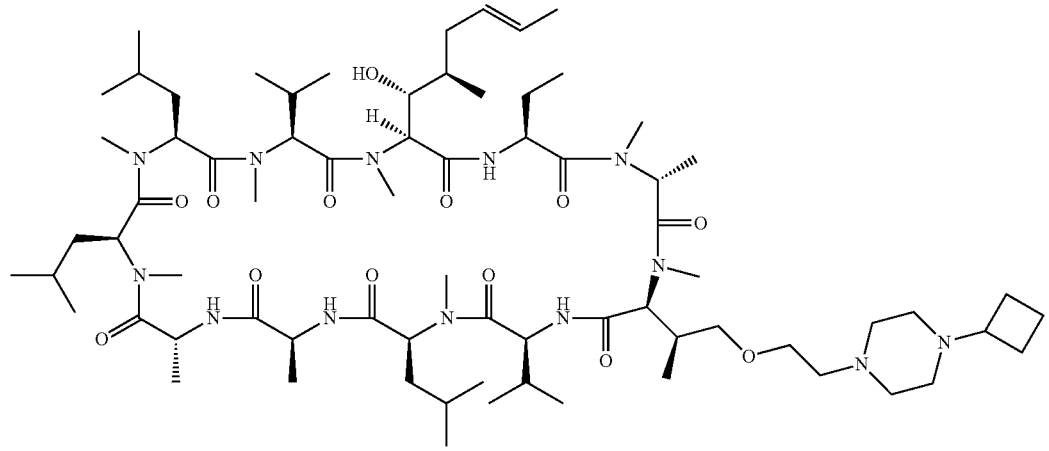
2.8.8
Compound 2.8.8 was prepared following the procedures described for the synthesis of 2.8.1 using 1-Cyclobutylpiperazine Dihydrochloride in Step 11. HRMS m/z (M+1) 1384.9869

II.8.9 Synthesis of Compound 2.8.9
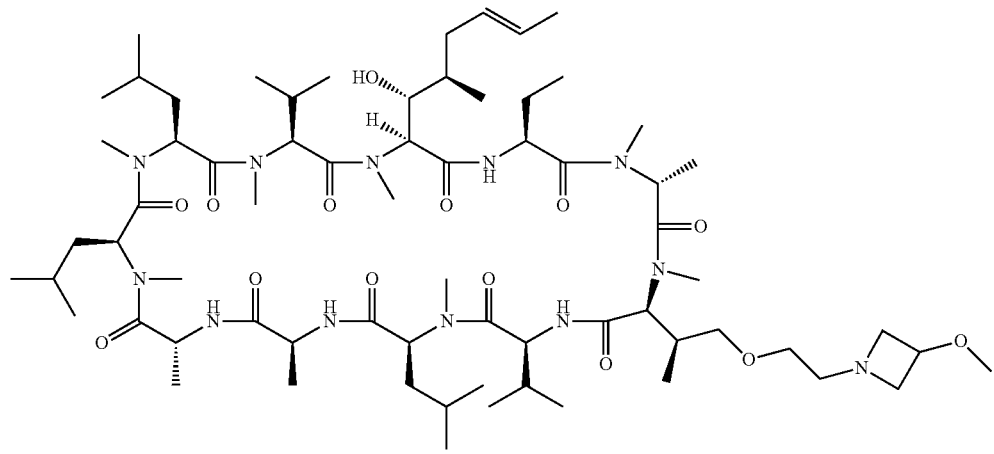
2.8.9
Compound 2.8.9 was prepared following the procedures described for the synthesis of 2.8.1 using 3-Methoxy-azetidine in Step 11. HRMS m/z (M+1) 1331.9259
II.8.10 Synthesis of Compound 2.8.10
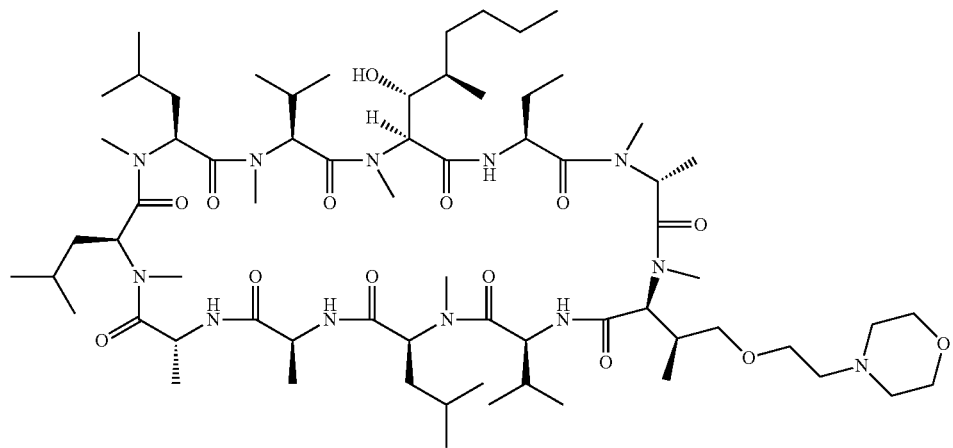
2.8.10
Compound 2.8.1 was converted to 2.8.10 following the procedures described for the synthesis of 2.5.15. HRMS m/z (M+1) 1333.9437

II.8.11 Synthesis of Compound 2.8.11
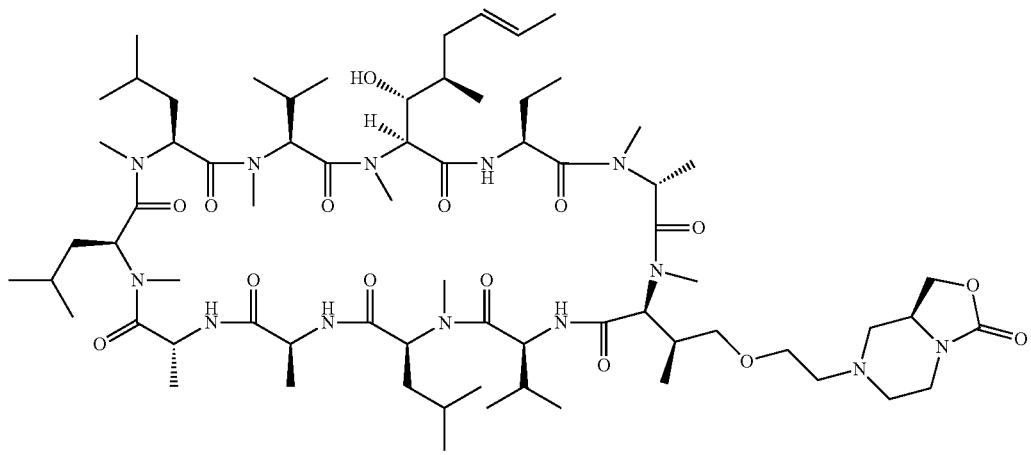
2.8.11
Compound 2.8.11 was prepared following the procedures described for the synthesis of 2.8.1 using (S)-hexahydro-oxazolo[3,4-a]pyrazin-3-one in Step 11. HRMS m/z (M+1) 1386.931
II.9. Synthesis of Compound 2.9
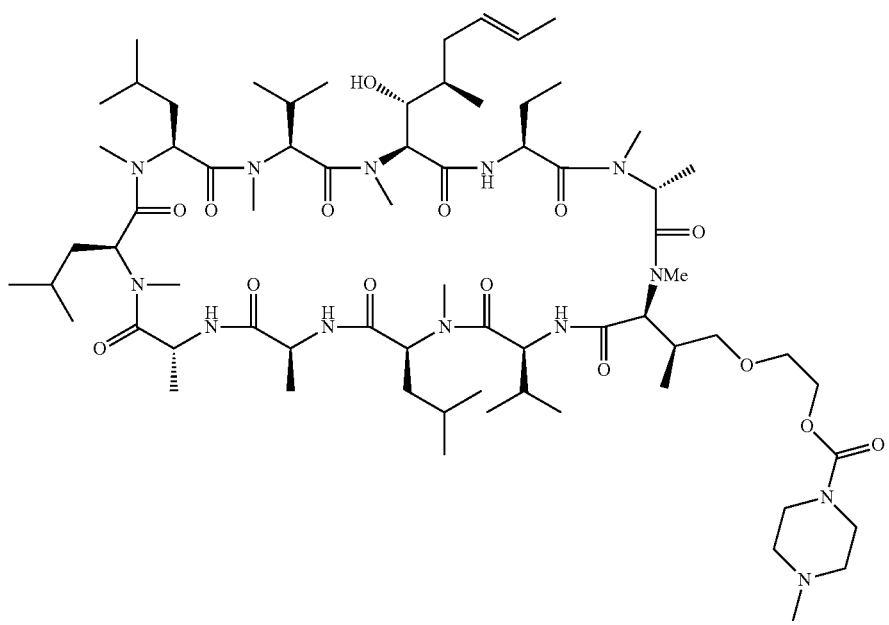
2.9

Step 1. Synthesis of 2.9a

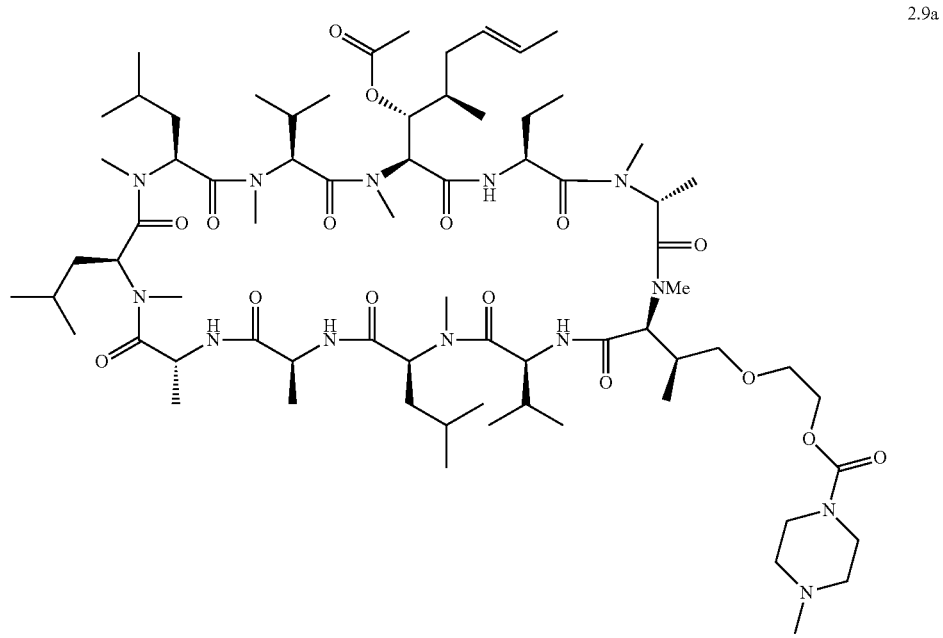 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)COCCOC(=O)N2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.9a

To a solution of 2.8.1i (33.0 mg, 31 umol) in DCM (1.5 mL) at 0° C. was added CDI (50.0 mg, 0.308 mmol, 12.2 equiv). The reaction mixture was stirred at room temperature for 2 hours after which N-methyl piperazine (28 ul, 0.253 mmol, 10.0 equiv) and triethylamine (35 ul, 0.253 mmol, 10.0 equiv) were added. After stirring at room temperature for 2 hours, the reaction mixture was concentrated in vacuo to give compound 2.9a (31.6 mg) which was subjected to the next step without further purification. MS m/z (M+Na) 1455.1

Step 2. Synthesis of 2.9

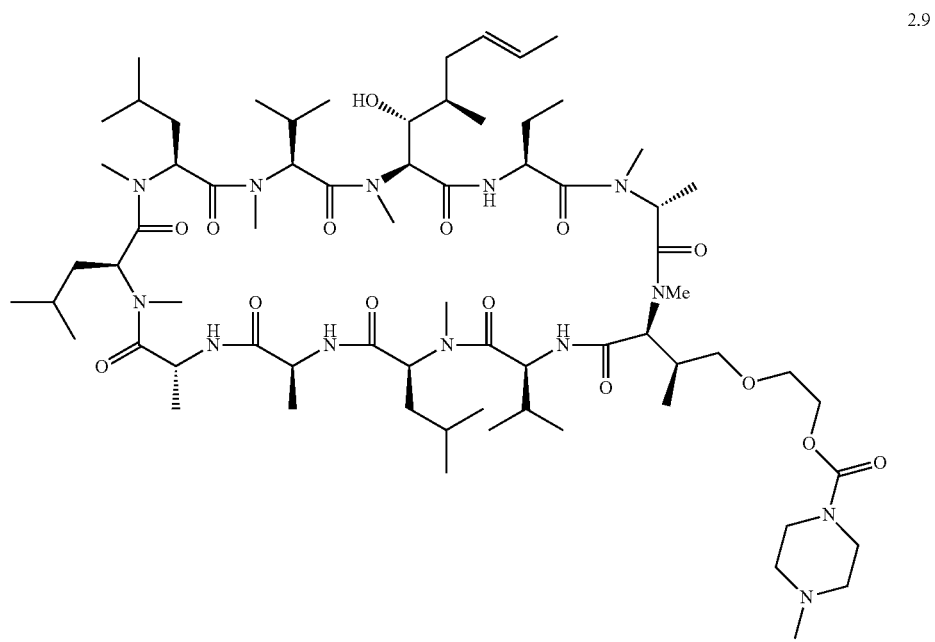 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCOC(=O)N2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.9

To a solution of 2.9a (31.6 mg, 23.0 umol) in methanol (2 mL) at 0° C. was added tetramethylammonium hydroxide (25% in methanol, 0.3 mL, 0.853 mmol, 37.0 equiv). After stirring at room temperature for 2 hours, the reaction mixture was quenched with aqueous saturated KHSO$_4$ (2 mL) and extracted with DCM. Combined organic layer was washed with saturated brine, dried with Na$_2$SO$_4$, filtered and concentrated in vacuo. The residue was purified by reverse phase HPLC to give compound 2.9 (9.0 mg, 29% yield). MS m/z (M+1) 1388.9

II.10. Synthesis of Compound 2.10

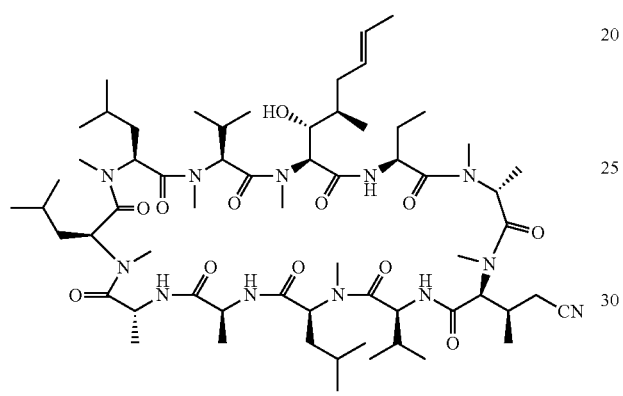

2.10

Step 1. Synthesis of 2.10a

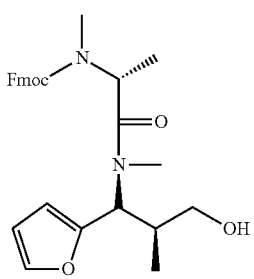

2.10a

A plastic tube was charged with 2.5.1d (500 mg) in THF (3.0 mL) and the resulting solution was stirred at room temperature for 24 hours. The solution was then diluted with EtOAc and basified by addition of sat. NaHCO$_3$ aq. solution. The phases were separated and the organic layer was washed with brine, dried over Na$_2$SO$_4$ and concentrated. The residue was purified by silica gel column chromatography (EtOAc/ heptane, 0 to 70%) to give product 199 mg (yield 60%). MS m/z (M+1) 477.3

Step 2. Synthesis of 2.10b

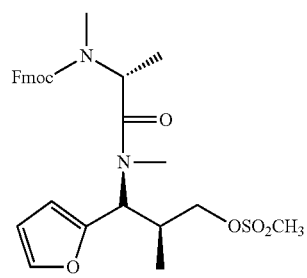

2.10b

To a solution of 2.10a (180 mg, 0.38 mmol, 1.0 equiv) in DCM (3.0 mL) at 0° C. was added TEA (0.10 mL, 0.75 mmol, 2.0 equiv) followed by MsCl (0.044 mL, 0.56 mmol, 1.5 equiv). After stirring at 0° C. for 1 hour, the reaction was quenched by addition of EtOH (0.5 mL) and EtOAc. The resulting solution was washed with saturated aqueous NH$_4$Cl solution, dried over Na$_2$SO$_4$ and concentrated. MS m/z (M+1) 555.2

Step 3. Synthesis of 2.10c

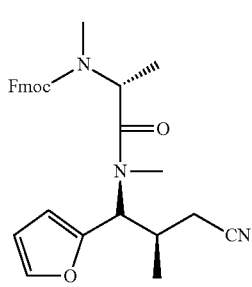

2.10c

To a solution of 2.10b (180 mg, 0.325 mmol, 1.0 equiv) in DMF (1.0 mL) was added NaCN (47 mg, 0.97 mmol, 3.0 equiv) and the mixture was stirred at 70° C. for 2 hours. The solution was filtered and the filtrate was diluted with EtOAc. The solution was washed with saturated aqueous NaHCO$_3$ solution and brine, dried over Na$_2$SO$_4$ and concentrated. The residue was dissolved in DCM (1.0 mL) and was added TEA (0.127 mL, 0.91 mmol, 3.0 equiv) and FmocCl (118 mg, 0.456 mmol, 1.5 equiv). After stirring at room temperature for 1 hour, the solution was concentrated and the residue was purified by silica gel column chromatography (EtOAc/heptane 0% to 70%) to give product 80 mg (54%). MS m/z (M+1) 486.3

Step 4. Synthesis of 2.10d

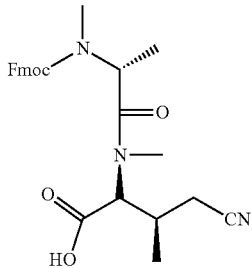

2.10d

To a solution of NaIO$_4$ (211 mg, 0.99 mmol, 6.0 equiv) in MeCN (0.6 mL), water (0.4 mL), CCl$_4$ (0.6 mL) was added RuCl$_3$ (10 mg, 0.049 mmol, 0.3 equiv). After stirred at room temperature for 10 minutes, it was added a solution of 2.10c (80 mg, 0.165 mmol, 1.0 equiv) in MeCN (0.3 mL and the resulting mixture was stirred at room temperature for 20 minutes. The mixture was diluted with EtOAc and quenched by addition of aq. NaHSO$_3$ solution. The phases were separated and the organic layer was washed with brine, dried over Na$_2$SO$_4$ and concentrated to provide the desired product (50 mg). MS m/z (M+1) 464.3

Step 5. Synthesis of 2.10e

To a solution of 2.10e (90 mg, 0.056 mmol, 1.0 equiv) in THF (1.0 mL)/water (0.5 mL) was added LiOH.H$_2$O (14 mg, 0.34 mmol, 6.0 equiv). After stirring at 0° C. for 3 hours, the reaction was acidified by addition of 1.0 N HCl aq. solution until pH=6. The solution was extracted with EtOAc, washed with brine, dried over Na$_2$SO$_4$ and concentrated. MS m/z (M+1) 1287.8

Step 7. Synthesis 2.10g

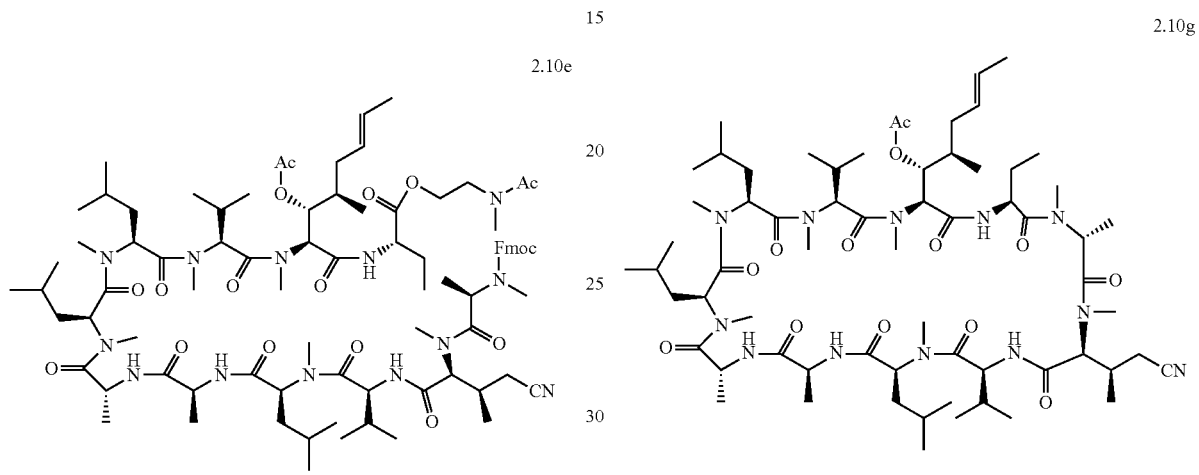

2.10e 2.10g

To a solution of 2.10d (56 mg, 0.11 mmol, 1.0 equiv) in DCM (0.5 mL) at 0° C. was added HATU (49 mg, 0.13 mmol, 1.2 equiv). After stirring at 0° C. for 5 minutes, compound 1 (113 mg, 0.097 mmol, 0.9 equiv) and NMM (33 mg, 0.32 mmol, 3.0 equiv) were added. The resulting solution was then stirred at 0° C. for 1 hour then at room temperature for 18 hours. The solution was diluted with EtOAc and washed with 1.0 N aq HCl solution, water, sat. NaHCO$_3$, brine, dried over Na$_2$SO$_4$ and concentrated. The residue was purified by silica gel column chromatography (acetone/heptane 0% to 90%) to give product 2.10e (90 mg). MS m/z (M+Na) 1632.0

Step 6. Synthesis 2.10f

To a solution of BOP (72 mg, 0.16 mmol, 3.0 equiv) in DCM (40 mL) was added a solution of 2.10f (70 mg, 0.054 mmol, 1.0 equiv) and DMAP (20 mg, 0.16 mmol, 3.0 equiv) over 1 hour. After stirring at room temperature for 3 days, the solution was washed with 1.0 N HCl aq. solution, sat. NaHCO$_3$ solution, brine, dried over Na$_2$SO$_4$ and concentrated. The residue was purified by silica gel column chromatography (acetone/heptane, 0% to 100%) to give product 2.10g (22 mg, 32%). MS m/z (M+1) 1269.9

Step 8. Synthesis of 2.10

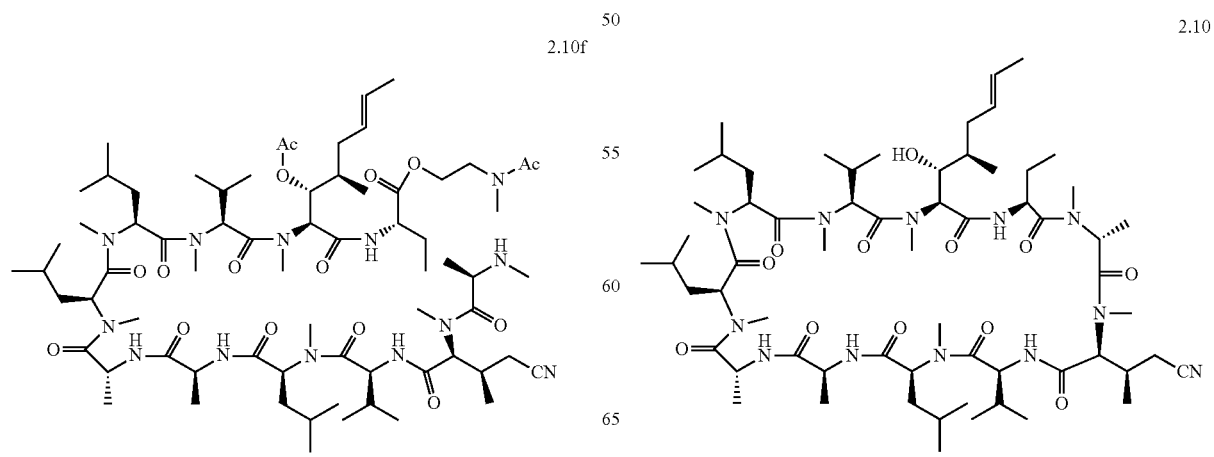

2.10f 2.10

To a solution of 2.10g (22 mg, 0.017 mmol, 1.0 equiv) in MeOH (1.0 mL) at 0° C. was added a solution of Me₄NOH (25% in MeOH, 63 mg, 0.17 mmol, 10 equiv). The solution was stirred at 0° C. for 1 hour and at room temperature for 2 hours. The solution was then diluted with EtOAc, acidified by addition of 10 N HCl solution until pH=6.0. The phases were separated and the organic layer was washed with brine, dried over Na₂SO₄ and concentrated. The residue was purified by reverse HPLC to give product 2.10 (7 mg, 31% yield). MS m/z (M+1) 1228.8

II.11 Synthesis of Compound 2.11

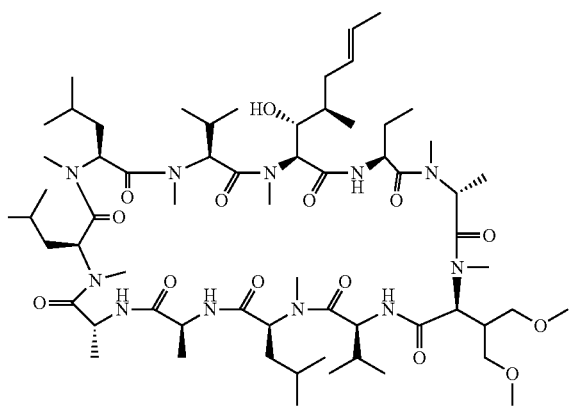

2.11

Step 1. Synthesis of ((S)-2-Benzyloxycarbonylamino-4-methoxy-3-methoxymethyl-butyric acid [2.11a]

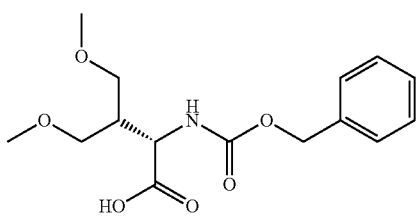

2.11a

To a solution of (S)-2-Benzyloxycarbonylamino-4-methoxy-3-methoxymethyl-butyric acid methyl ester (100 mg, 0.30 mmol, 1.0 equiv) in THF/MeOH/water (0.5 mL/0.5 mL/0.5 mL) was added LiOH.H₂O (38.7 mg, 0.92 mmol, 3.0 equiv). After stirring at 0° C. for 1 hour, the reaction was quenched by addition of 1.0 N aq. HCl solution until the pH of the solution was approximately 4. The mixture was extracted with EtOAc. The organic layer was washed with brine, dried over MgSO₄ and concentrated. MS m/z (M+1) 312.2

Step 2. Synthesis of (S)-2-(Benzyloxycarbonyl-methyl-amino)-4-methoxy-3-methoxymethyl-butyric acid [2.11 b]

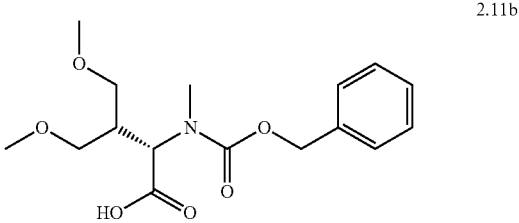 [SMILES: COCC(COC)[C@H](NC(=O)OCc1ccccc1)C(=O)O]

2.11b

NaH (42 mg, 1.0 mmol, 3.3 equiv) was added in 4 portions to a solution of (S)-2-Benzyloxycarbonylamino-4-methoxy-3-methoxymethyl-butyric acid (100 mg, 0.32 mmol, 1.0 equiv) in dry THF 1 mL at 0° C. After stirring at 0° C. for 10 minutes, it was added a solution of MeI (137 mg, 0.964 mmol, 3.0 equiv) in DMF/THF solution. The mixture was stirred at 0° C. for 1 hour then at room temperature for 16 hours. The reaction mixture was then added to saturated aqueous NH₄Cl solution at 0° C. The mixture was extracted with EtOAc. The organic layer was washed with brine, dried over Na₂SO₄ and concentrated to give product 2.11b (100 mg, 95% yield). The crude material was continued to the next step with no further purification. MS m/z (M+1) 326.3

Step 3. Synthesis of 2.11c

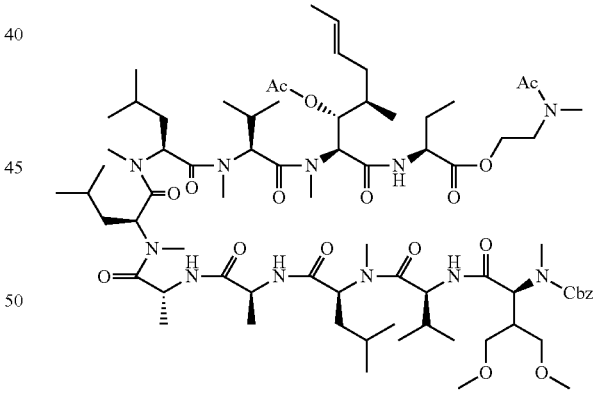

2.11c

To a solution of compound 1 (200 mg, 0.17 mmol, 1.0 equiv), (S)-2-(Benzyloxycarbonyl-methyl-amino)-4-methoxy-3-methoxymethyl-butyric acid (55.9 mg, 0.172 mmol, 1.0 equiv) at 0° C. was added HATU (92 mg, 0.24 mmol, 1.4 equiv) and NMM (52 mg, 0.52 mmol, 3.0 equiv). After stirring at room temperature for 24 hours, the solution was diluted with EtOAc, washed with 1.0 N HCl aq. solution, saturated aqueous NaHCO₃ solution, brine, dried over Na₂SO₄ and concentrated. The residue was purified by silica gel column chromatography (acetone/heptane 0% to 70%) to give product 130 mg (yield 51%). MS m/z (M+1) 1472.1

Step 4. Synthesis of 2.11d

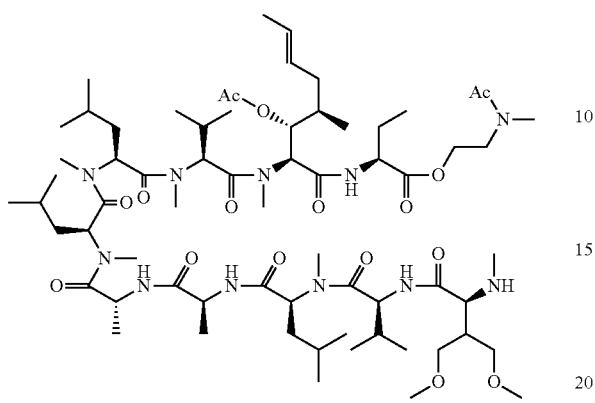

2.11d

To a solution of Pd(OAc)$_2$ (6.8 mg, 0.03 mmol, 0.3 equiv) in DCM (0.5 mL) was added 2.11c (150 mg, 0.10 mmol, 1.0 equiv), TEA (15 mg, 0.15 mmol, 1.5 equiv) and triethylsilane (35 mg, 0.30 mmol, 3.0 equiv). After stirring at room temperature for 3 hours, the mixture was filtered through Celite and the filtrate was concentrated. The residue was dissolved in EtOAc and the solution was washed with saturated aqueous NaHCO$_3$ solution, brine, dried over MgSO$_4$ and concentrated to give product 130 mg (yield 95%). The crude material was continued to the next step with no further purification. MS m/z (M+1) 1337.2

Step 5. Synthesis of 2.11e

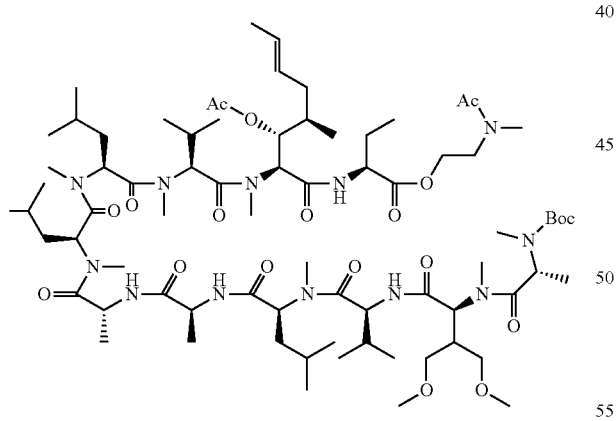

2.11e

To a solution of N-Me-N-Boc-D-Ala-OH (54.7 mg, 0.27 mmol, 3.0 equiv) in DCM (0.5 mL) and DMF (0.5 mL) at 0° C. was added HATU (102 mg, 0.27 mmol, 3.0 equiv). After stirring at 0° C. for 10 minutes, it was added a solution of 2.11d (120 mg, 0.09 mmol, 1.0 equiv) in DCM (0.5 mL) followed by NMM (54 mg, 0.54 mmol, 6.0 equiv). The resulting solution was stirred at 0° C. for 1 hour and room temperature for 18 hours. To the reaction solution was then added 1.0 N aq. HCl solution and EtOAc. The phases were separated and the aqueous layer was extracted with EtOAc. The combined organic layers were washed successively with water, saturated aqueous NaHCO$_3$ and brine. The organic phase was then dried over Na$_2$SO$_4$ and concentrated. The residue was purified by silica gel column chromatography (acetone/heptane 0% to 90%) to give product 56 mg. MS m/z (M+1) 1522.3

Step 6. Synthesis of 2.11f

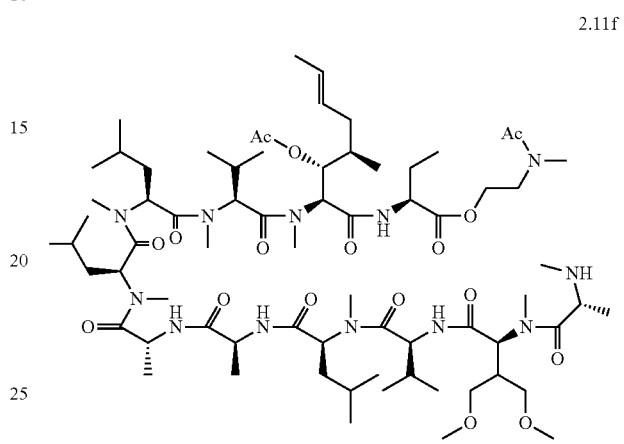

2.11f

To a solution of 2.11e (50 mg, 0.033 mmol) in DCM (1.0 mL) at 0° C. was added TFA (74 mg) and the solution was stirred at room temperature for 1 hour. After removal of the solvent in vacuo, the residue was dissolved in DCM and the solution was basified by addition of saturated aqueous NaHCO$_3$ solution. The phases were separated and the organic layer was washed with brine, dried over Na$_2$SO$_4$ and concentrated. The residue was dissolved in THF (1.0 mL)/water (0.5 mL) and to the solution at 0° C. was added LiOH.H$_2$O (6 mg). After stirring at 0° C. for 2 hours, the solution was diluted with EtOAc and acidified by addition of 1.0 N HCl aq. solution until pH=5. The phases were separated and the organic layer was washed with brine, dried over MgSO$_4$ and concentrated to give product 30 mg (yield 69%). The crude material was continued to the next step with no further purification. MS m/z (M+1) 1323.9

Step 7. Synthesis of 2.11

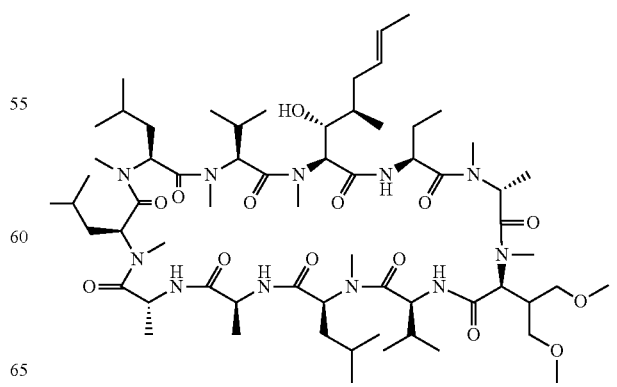

2.11

To a solution of BOP (32 mg, 0.073 mmol, 3.0 equiv) in DCM (20 mL) at room temperature was slowly added a solution of 2.11f (32 mg, 0.24 mmol, 1.0 equiv) and DMAP (0.073 mmol, 3.0 equiv) in DCM (10 mL) over 1 hour and the resulting solution was stirred at room temperature for 24 hours. The reaction solution was then washed successively with 1.0 N aq. HCl solution, saturated aqueous NaHCO₃ solution and brine. The organic layer was dried over Na₂SO₄ and concentrated. The residue was dissolved in MeOH and to this solution was added tetramethylammonium hydroxide 84 mg (25% in MeOH). After stirring at room temperature for 1 hour, the solution was diluted with EtOAc and acidified by addition of 1.0 N HCl aq. solution until pH=6. The phases were separated and the organic layer was washed with saturated aqueous NaHCO₃, brine, dried over Na₂SO₄ and concentrated. The residue was purified by HPLC to give product 12 mg (yield 41%). MS m/z (M+1) 1262.8

II.12. Synthesis of Compound 2.12

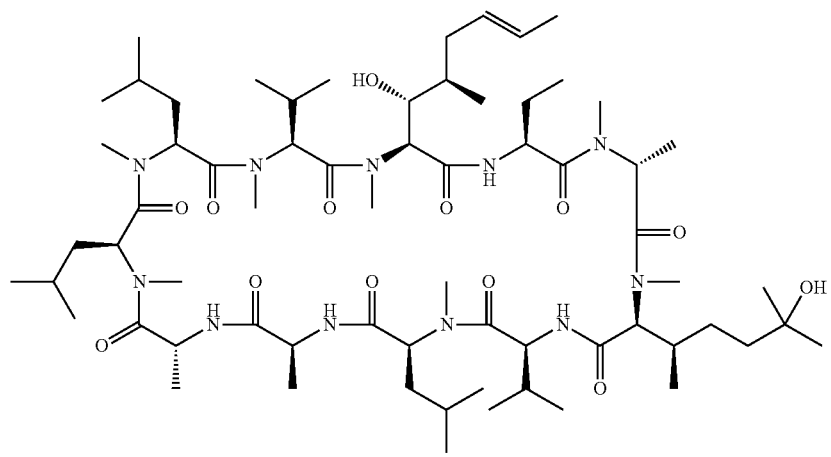

2.12

Step 1. Synthesis of ((1S,2S)-1-Furan-2-yl-2-methyl-3-oxo-propyl)-carbamic acid tert-butyl ester [2.12a]

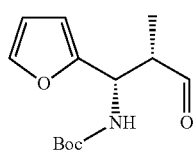

2.12a

To a solution of 2.1b (300 mg, 1.2 mmol) in CH₂Cl₂ (2.4 mL)/DMSO (1 mL, 14) at 0° C. was added DIEA (0.82 mL, 4.7 mmol) followed by pyridine sulfur trioxide (748 mg, 4.7 mmol). After stirring at 0° C. for 30 minutes, the reaction was quenched with water. The mixture was diluted with Et₂O and the phases were separated. The organic layer was washed with brine, dried over MgSO₄ and concentrated to give crude product 2.12a which was used in the next step with no further purification. MS m/z (M+23) 276.2. ¹H NMR (400 MHz, CDCl₃) δ ppm 1.10 (dt, J=7.09, 0.51 Hz, 3H) 1.34-1.46 (m, 10H) 2.88-2.97 (m, 1H) 6.20-6.24 (m, 1H) 6.30-6.35 (m, 1H) 7.25-7.31 (m, 1H) 7.35 (dt, J=1.90, 0.94 Hz, 1H) 9.73-9.79 (m, 1H).

Step 2. Synthesis of (4R,5S)-5-tert-Butoxycarbonylamino-5-furan-2-yl-4-methyl-pent-2-enoic acid ethyl ester [2.12b]

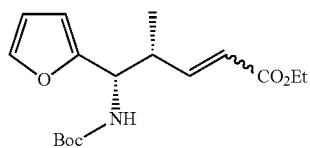

2.12b

To a solution of ethyl 2-triethylphosphono-acetate (2.2 mL, 11 mmol) in THF (30 mL) at 0° C. was added KOtBu (1.01 g, 9.02 mmol) and stirred for 1 hour at room temperature. The mixture was cooled to −78° C. To the mixture was added slowly a solution of 2.12a (0.993 g, 3.92 mmol) in THF (10 mL. The reaction mixture was poured onto a mixture of ice-cold water/Et₂O (10 mL/600 mL), washed with brine twice, dried over MgSO₄ and concentrated. Purification by silica gel column chromatography (0-50%, EtOAc/heptane) to give 2.12b (1.14 g, 90% yield). MS m/z (M+23) 346.2. ¹H NMR (E, major isomer) (400 MHz, CDCl₃) δ ppm 1.05 (d, J=6.90 Hz, 2H) 1.07-1.18 (m, 1H) 1.19-1.32 (m, 2H) 1.36-1.46 (m, 2H) 1.44 (s, 4H) 1.55-1.57 (m, 1H) 4.14-4.22 (m, 1H) 5.74-5.85 (m, 1H) 6.14-6.19 (m, 1H) 6.27-6.33 (m, 1H) 6.86 (dd, J=15.70, 8.17 Hz, 1H) 7.26 (s, 1H) 7.31-7.37 (m, 1H).

Step 3. Synthesis of (4R,5S)-5-(tert-Butoxycarbonyl-methyl-amino)-5-furan-2-yl-4-methyl-pent-2-enoic acid ethyl ester [2.12c]

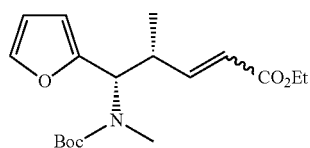

2.12c

To a solution of NaH (0.707 g, 17.7 mmol) in THF (10.7 mL) at 0° C. was added 2.12b (1.14 g, 3.53 mmol) in DMF (1 mL), followed by MeI (1.33 mL, 21.2 mmol). After stirring at 0° C. for 1 hour, the reaction mixture was poured onto a ice cold mixture of 1.0 M aq. NaHSO$_4$ solution and Et$_2$O. The separated organic layer was washed with brine, dried over MgSO$_4$, and concentrated. The residue was purified by silica gel column chromatography (0-50% EtOAc/heptane) to give 2.12c (1.08 g, 91% yield). MS m/z (M+23) 360.1

Step 4. Synthesis of (4R,5S)-5-(tert-Butoxycarbonyl-methyl-amino)-5-furan-2-yl-4-methyl-pentanoic acid ethyl ester [2.12d]

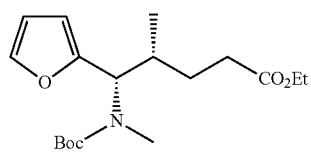

2.12d

To a solution of 2.12c (360 mg, 1.07 mmol) in ethyl acetate (5 mL) was added Pd/C (5% on charcoal, 114 mg, 0.107 mmol) and the resulting mixture was stirred under 1 atm of H$_2$ for 1 hour. The solid was then removed by filtration and the filtrate was concentrated in vacuo to afford 2.12d (360 mg) which was used in the next step without further purification. MS m/z (M+23) 362.3. $^1$H NMR (400 MHz, CDCl$_3$) δ ppm 0.91-0.97 (m, 3H) 1.24 (t, J=7.16 Hz, 3H) 1.36-1.47 (m, 7H) 1.47-1.52 (m, 5H) 1.52-1.57 (m, 4H) 2.66 (s, 3H) 4.10 (d, J=7.24 Hz, 2H) 6.31 (d, J=1.91 Hz, 2H) 6.32 (s, 1H) 7.26 (s, 3H) 7.35 (ddd, J=1.23, 0.78, 0.67 Hz, 1H).

Step 5. Synthesis of ((1S,2R)-1-Furan-2-yl-5-hydroxy-2,5-dimethyl-hexyl)-methyl-carbamic acid tert-butyl ester [2.12e]

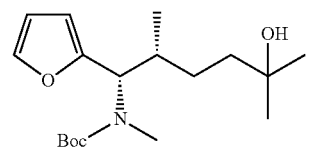

2.12e

To a solution of 2.12d (150 mg, 0.442 mmol) in diethyl ether (1 mL) at 0° C. was added MeMgBr (3.0 M in diethyl ether, 2.2 mL, 6.63 mmol) and the resulting solution was stirred at room temperature for 1.5 hours. The reaction was quenched by addition of 5 mL ice-cold 1.0 M NaHSO$_4$ aq. solution. The reaction mixture was diluted with diethyl ether, washed with brine twice, dried over MgSO$_4$ and concentrated to give product 2.12e (144 mg) which was used in the next step without purification. MS m/z (M+23) 348.2. $^1$H NMR (400 MHz, CDCl$_3$-d) δ ppm 0.95 (d, J=6.70 Hz, 3H) 1.03-1.12 (m, 3H) 1.13 (s, 5H) 1.26 (dd, J=1.03, 0.54 Hz, 2H) 1.26 (s, 1H) 1.43-1.53 (m, 11H) 1.53-1.57 (m, 2H) 1.58 (br. s., 2H) 2.04-2.16 (m, 2H) 2.68 (s, 3H) 5.28-5.35 (m, 1H) 6.31 (dd, J=3.23, 1.86 Hz, 1H) 7.26 (s, 2H) 7.33-7.39 (m, 1H)

Step 6. Synthesis of (2S,3R)-2-(tert-Butoxycarbonyl-methyl-amino)-6-hydroxy-3,6-dimethyl-heptanoic acid [2.12f]

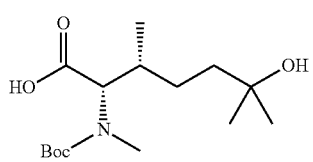

2.12f

Ruthenium(III) chloride (0.031 g, 0.15 mmol) was added to a well-stirred mixture of NaIO$_4$ (0.567 g, 2.65 mmol) in water/CCl$_4$/CH$_3$CN (4.5/3/4.5 mL). After 15 minutes of stirring, at 0° C., 2.12e (0.144 g, 0.442 mmol) in MeCN (0.3 mL) was added. After stirring at room temperature for 30 minutes, another 1 equivalent of NaIO$_4$ was added and the resulting mixture was stirred for another 20 minutes. The reaction was quenched with water and extracted with ethyl acetate three times. The combined ethyl acetate layer was washed with 20% NaHSO$_3$ aq. solution and brine, dried over MgSO$_4$ and concentrated to give 2.12f (134 mg) which was used in the next step with out purification. MS m/z (M+23) 326.2.

Step 7. Synthesis of 2.12g

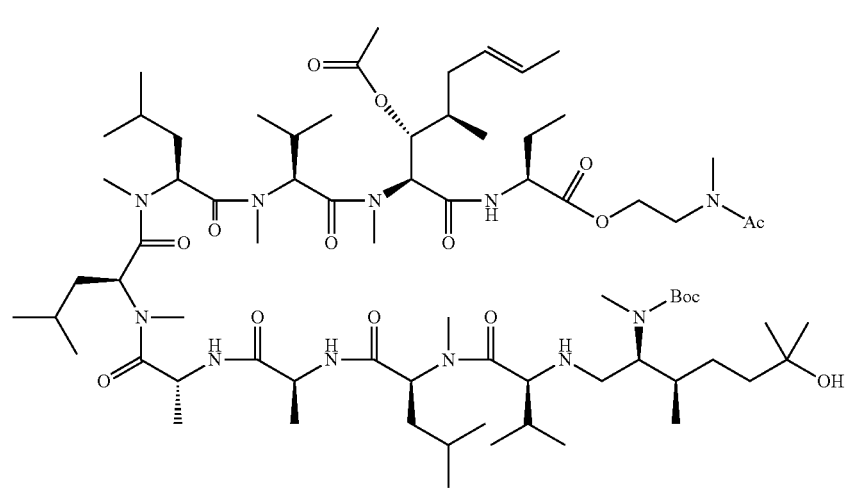

2.12g

To the solution of 2.12f (0.126 g, 0.415 mmol) and compound 1 (0.302 g, 0.26 mmol) in toluene (2.36 mL)/water (0.236 mL), was added HOBT (0.072 g, 0.467 mmol), NMM (0.143 mL, 1.3 mmol), followed by EDCI (0.09 g, 0.467 mmol) and the resulting mixture was stirred at 0° C. for 16 hours. The reaction mixture was then diluted with EtOAc, washed with saturated aqueous NaHCO₃, saturated aqueous NH₄Cl and brine. The organic layer was dried over MgSO₄ and concentrated. The crude material was purified by silica gel column chromatography (0-100% acetone/heptane) to give 2.12g (316 mg, 84% yield). MS m/z (M+23) 1471.8

Step 8. Synthesis of 2.12h

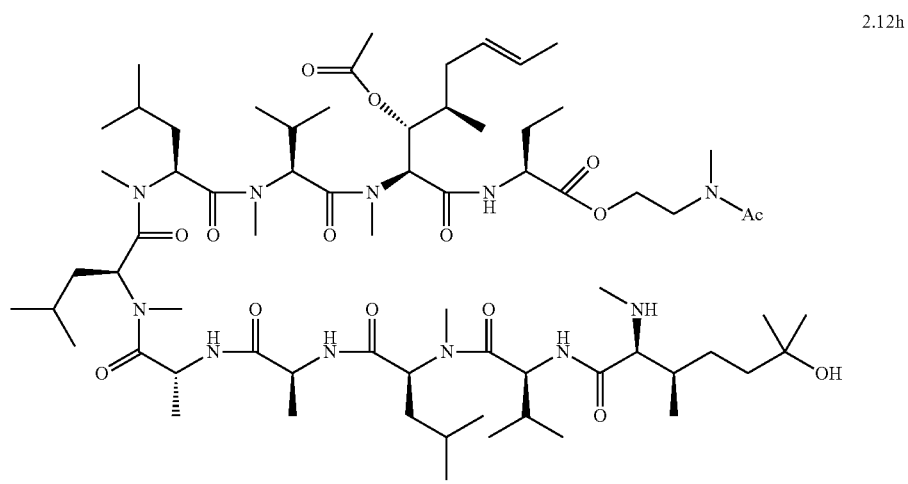 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@@H](NC)[C@H](C)CCC(C)(C)O)C(C)C]

2.12h

At 0° C., to the solution of 2.12g (316 mg, 0.218 mmol) in CH₂Cl₂ (1.45 mL) was added TFA (727 µL). The reaction was stirred at this temperature for 1 hour. After removal of most solvent in vacuo, the residue was dissolved in EtOAc, washed with saturated NaHCO₃ and brine. The organic layer was dried over MgSO₄ and concentrated to give product 2.12h (275 mg, 93%), which was used in the next step without further purification. MS m/z (M+23) 1371.5

Step 9. Synthesis of 2.12i

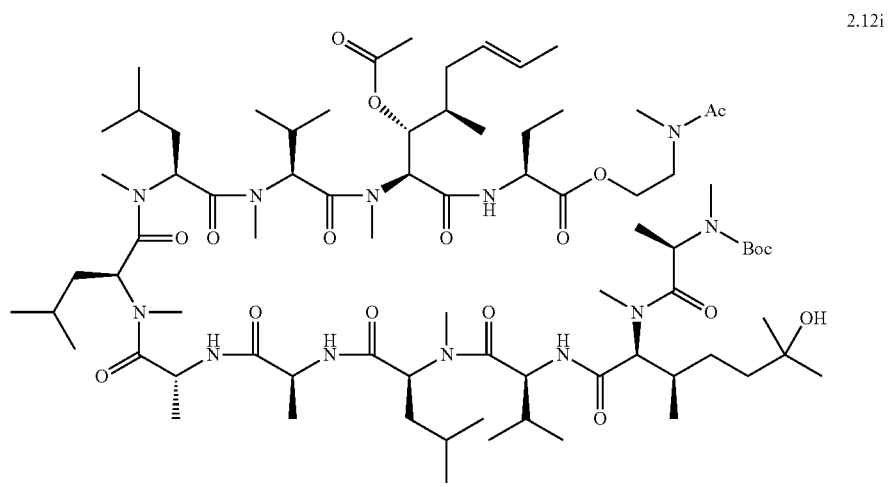 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)CCC(C)(C)O)N(C)C(=O)[C@@H](C)N(C)C(=O)OC(C)(C)C)C(C)C]

2.12i

To a solution of Boc-N-Me-D-alanine-OH (0.044 g, 0.215 mmol) and HATU (0.082 g, 0.215 mmol) in DCM (0.4 mL) at 0° C., was added DIEA (0.05 mL, 0.31 mmol) and stirred for 5 minutes at 0° C. The mixture was added to a solution of 2.12h (0.276 g, 0.205 mmol) and DIEA (0.05 mL, 0.31 mmol) in DCM (0.4 mL) at 0° C. After stirring at 0° C. for 3 hour, the reaction mixture was diluted with EtOAc, washed with saturated aqueous NaHCO$_3$ solution, saturated aqueous NH$_4$Cl solution and brine. The organic layer was dried over MgSO$_4$ and concentrated. The residue was purified by silica gel column chromatography, (0-100% Acetone/heptane), to give 2.12i (290 mg, 90% yield). MS m/z (M+23) 1556.6

Step 10. 2.12j

To a solution of 2.12i (290 mg, 0.189 mmol) in CH$_2$Cl$_2$ (2.52 mL) at 0° C. was added TFA (1.2 mL, 15.6 mmol). After stirring for 1 hour at 0° C., the reaction mixture was poured into an ice-cold aq. KHSO$_4$ solution (10 mL, 10 mmol). The mixture was extracted with EtOAc. The organic layer was washed with saturated aqueous NaHCO$_3$ solution, dried over MgSO$_4$ and concentrated. The residue was dissolved in THF (1.07 mL)/water (714 μL). The this solution at 0° C. was added LiOH.H$_2$O (30 mg, 0.714 mmol). After stirring for 1 hour, the reaction mixture was added to an ice-cold solution of aq. 1.0 N NaHSO$_4$ solution (1.2 mL, 1.25 mmol), diluted with EtOAc, washed with brine. The organic layer was dried over MgSO$_4$ and concentrated to give product 2.12j (230 mg, 97% yield), which was used in the next step without purification. MS m/z (M+1) 1335.6

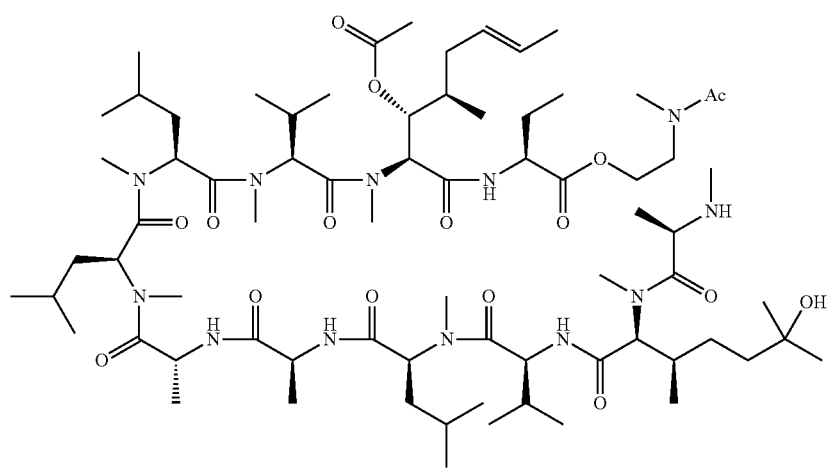

2.12j

Step 11. Synthesis of 2.12k

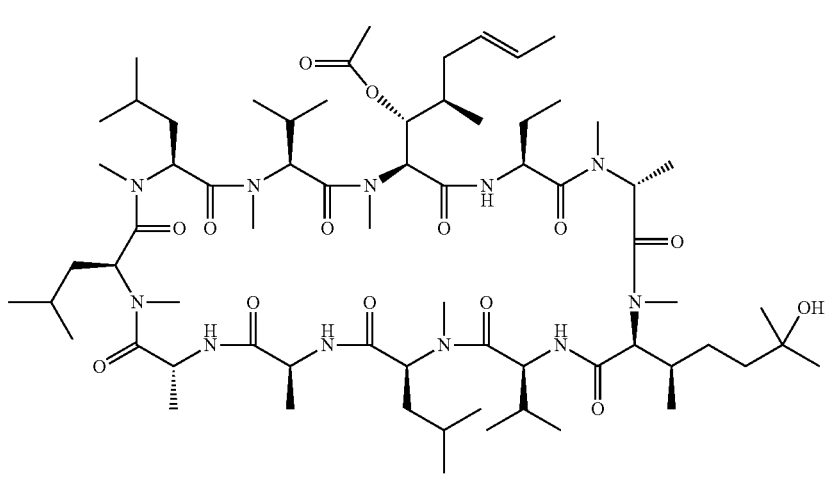

2.12k

A solution of 2.12j (31 mg, 0.023 mmol) and DMAP (5.67 mg, 0.046 mmol) in CH$_2$Cl$_2$ (12.5 mL) was added slowly to a solution of BOP (20.54 mg, 0.046 mmol) in CH$_2$Cl$_2$ (10 mL). After stirring room temperature overnight, the reaction solution was concentrated and the residue was dissolved in EtOAc. The solution was washed with 10% citric acid solution, sat. NaHCO$_3$ and brine. The organic layer was dried over Na$_2$SO$_4$ and concentrated. The residue was purified by reverse phase HPLC to give 2.12k (10 mg, 33% yield). MS m/z (M+1) 1317.7

Step 12. Synthesis of 2.12

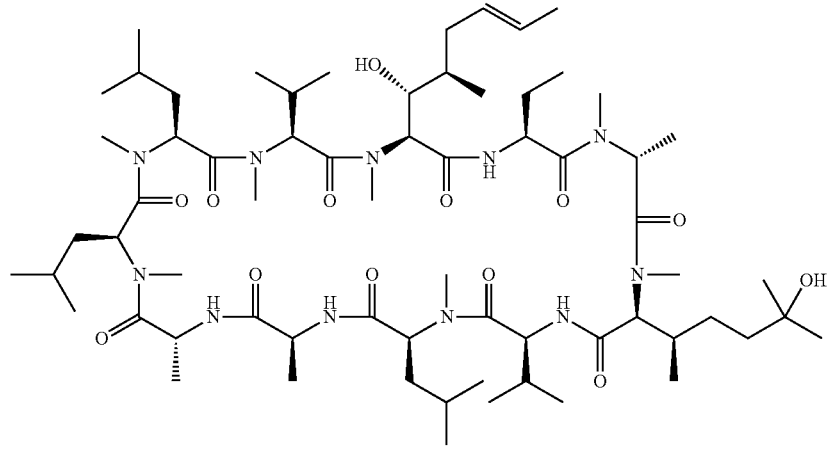

2.12

To a solution of 2.12k (18 mg, 0.014 mmol) in MeOH (0.45 mL) at 0° C. was added Me$_4$NOH (25% in MeOH, 49.8 mg, 0.137 mmol). After stirring at 0° C. for 1 hour, the reaction mixture was poured into an ice-cold 1.0 M aq. NaHSO$_4$ solution. The mixture was extracted with EtOAc. The organic phase was washed with brine, dried over MgSO$_4$ and concentrated. The residue was purified by reverse phase HPLC to afford 2.12 (6 mg, 34% yield). HRMS (m/z, M+1): 1274.9082

II.12.2 Synthesis of 2.12.2

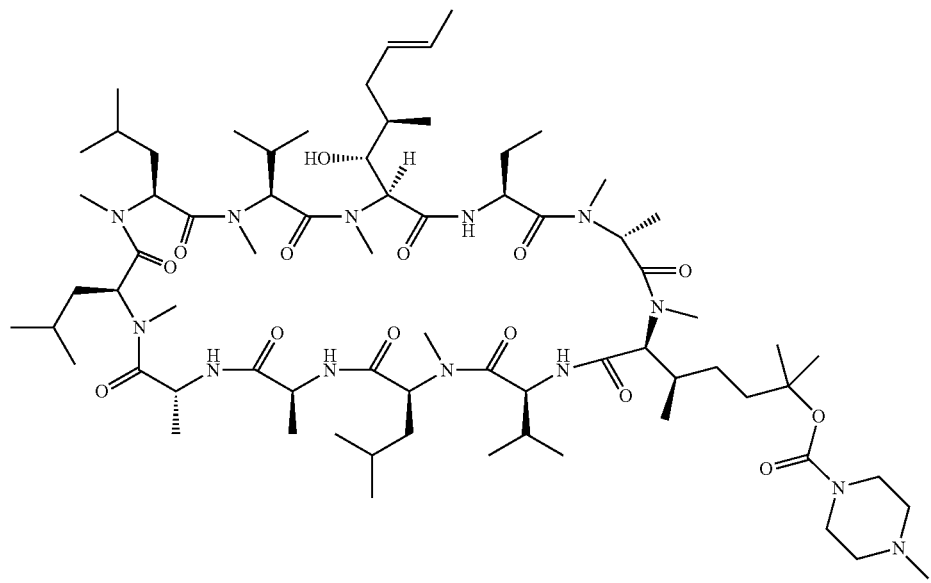

2.12.2

Compound 2.12.2 was prepared following the procedures described for the synthesis of 2.5.7 using 2.12k and N-methylpiperazine in step 1. HRMS m/z (M+1) 1400.9847 (calculated: 1400.9860)

II.13. Synthesis of Compound 2.13

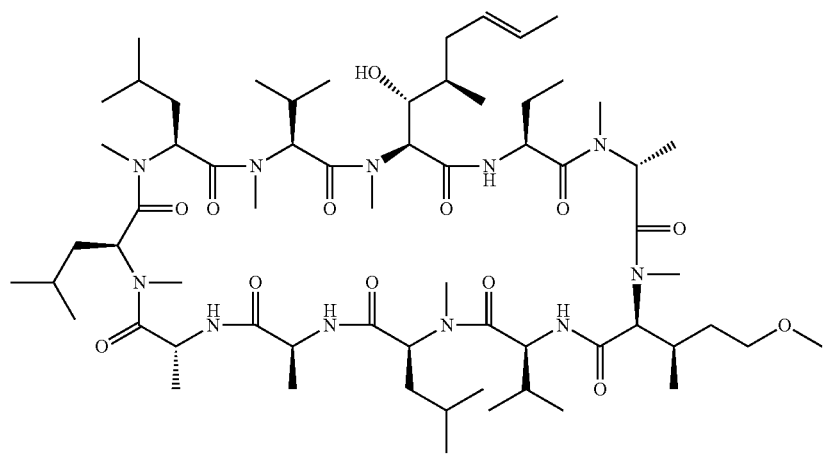

2.13

Step 1-2 Synthesis of ((1S,2S)-1-Furan-2-yl-2-methyl-3-oxo-propyl)-methyl-carbamic acid tert-butyl ester [2.13b] same as 2.12a

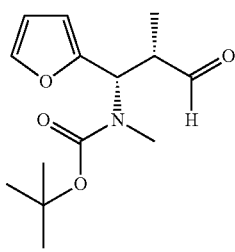

2.13b

Step 3. Synthesis of ((1S,2R)-1-Furan-2-yl-4-methoxy-2-methyl-but-3-enyl)-methyl-carbamic acid tert-butyl ester [2.13c]

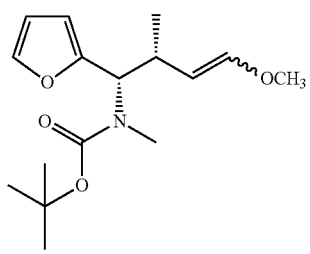

2.13c

To a solution of (methoxymethyl)triphenylphosphonium chloride (0.247 g, 0.720 mmol) in THF (0.5 mL) at 0° C. was added NaHMDS (1.0 M in hexanes, 0.72 mL). After stirring at 0° C. for 5 minutes, to the mixture was added a solution of 2.13b (0.048 g, 0.18 mmol) in THF (0.5 mL). The resulting solution was stirred at 0° C. for 30 minutes and then at room temperature for 18 hours. The reaction mixture was poured into a mixture of $Et_2O$ and saturated aqueous $NH_4Cl$ solution at 0° C. The phases were separated and the organic layer was washed with brine, dried over $MgSO_4$ and concentrated. The residue was purified by silica gel column chromatography (0-50% EtOAc/Heptane) to give 2.13c (48 mg, 90% yield). MS m/z (M+23) 308.2

Step 4. Synthesis of ((1S,2R)-1-Furan-2-yl-4-methoxy-2-methyl-butyl)-methyl-carbamic acid tert-butyl ester [2.13d]

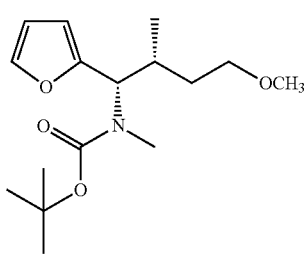

2.13d

To a solution of 2.13c (100 mg, 0.339 mmol) in ethyl acetate (2.3 mL) was added Pd/C (5% on carbon, 36.0 mg, 0.034 mmol) and the mixture was stirred under 1.0 at hydrogen for 1 hour. The solid was removed by filtration and the filtrate was concentrated. The residue was purified by silica gel column chromatography (0-30% EtOAc/Hep) to give product 2.13d (91 mg). MS m/z (M+23) 320.2. $^1$H NMR (300 MHz, $CDCl_3$-d) δ ppm 0.91-1.07 (m, 3H) 1.16-1.32 (m, 1H) 1.37-1.53 (m, 9H) 1.53-1.63 (m, 1H) 1.63-1.79 (m, 1H) 2.12-2.25 (m, 1H) 2.25-2.37 (m, 1H) 2.67 (s, 3H) 3.25-3.42 (m, 2H) 3.29 (s, 2H) 6.12-6.28 (m, 1H) 6.30 (dd, J=3.24, 1.81 Hz, 1H) 7.31-7.43 (m, 1H).

Step 5. Synthesis of (2S,3R)-2-(tert-Butoxycarbonyl-methyl-aminuteso)-5-methoxy-3-methyl-pentanoic acid [2.13e]

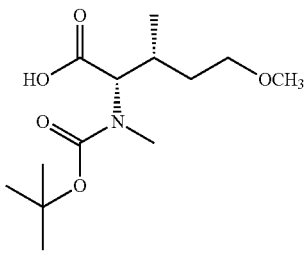

2.13e

Ruthenium(III) chloride (21.6 mg, 0.104 mmol) was added to a well-stirred mixture of $NaIO_4$ (393 mg, 1.836 mmol) in $H_2O/CCl_4/CH_3CN$ and the resulting mixture was stirred at 0° C. for 15 minutes. To the mixture was then added a solution of 2.13d (91 mg, 0.306 mmol) in MeCN (0.3 mL). After stirring at room temperature for 30 minutes, another 1 equivalent of $NaIO_4$ was added and the mixture was stirred for another 20 minutes. The reaction was quenched with water and extracted with EtOAc. The organic layer was washed with 20% $NaHSO_3$ aq. solution and brine, dried over $Na_2SO_4$ and concentrated to give product 2.13e (67.8 mg, 80% yield). The crude product was used in the next step without further purification. MS m/z (M+23) 298.2

Step 6. Synthesis of 2.13f

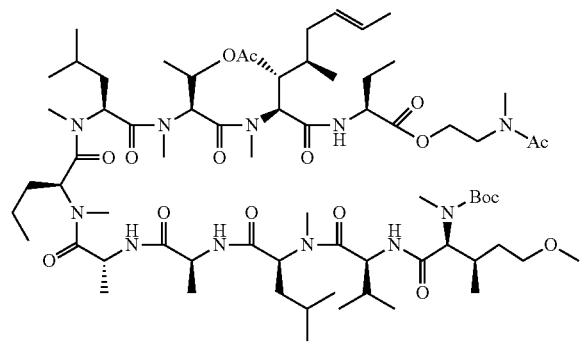

2.13f

To the solution of 2.13e (66.1 mg, 0.240 mmol), compound 1 (186 mg, 0.16 mmol) in toluene (1.4 mL)/water (145 μL) at 0° C., was added HOBT (44.1 mg, 0.288 mmol) and NMM (88 μL, 0.800 mmol). After stirring at 0° C. for 16 hours, the reaction mixture was diluted with EtOAc, washed with saturated aqueous $NaHCO_3$ solution, saturated aqueous $NH_4Cl$ solution and brine. The organic layer was dried over $MgSO_4$ and concentrated. The residue was purified by silica gel column chromatography (0-100% Acetone/DCM) to give 2.13f (178 mg, 78% yield). MS m/z (M+23) 1443.6

Step 7. Synthesis of 2.13g

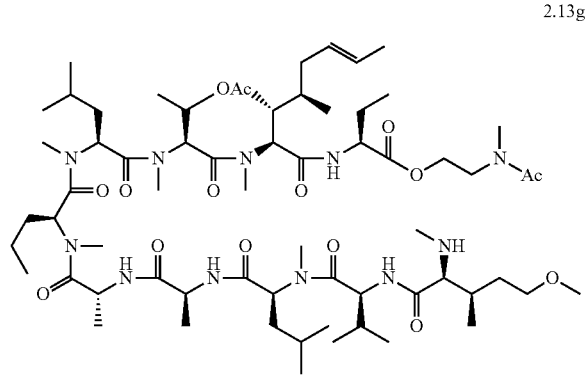 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CCC)N(C)C(=O)[C@@H](C)NC(=O)[C@H](C)NC(=O)[C@H](CC(C)C)N(C)C(=O)[C@@H](NC(=O)[C@@H](NC)[C@H](C)CCOC)C(C)C]

2.13g

To a solution of 2.13f (178 mg, 0.125 mmol) in $CH_2Cl_2$ (0.83 mL) at 0° C. was added TFA (0.42 mL) and the resulting solution was stirred at this temperature for 1 hour. After removal of most solvent under vacuum, the residue was dissolved in EtOAc, washed with saturated aqueous $NaHCO_3$ solution and brine. The organic layer was dried over $MgSO_4$ and concentrated to give product 2.13g (156 mg, 94%), which was used in the next step without further purification. MS m/z (M+23) 1343.3.

Step 8. Synthesis of 2.13i

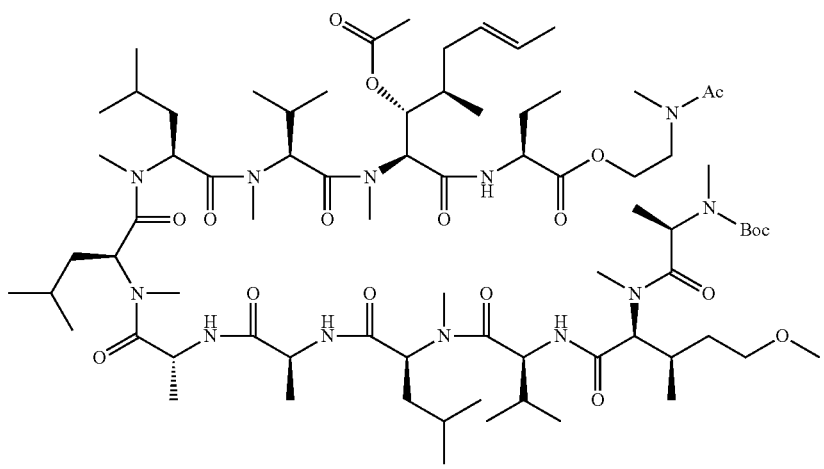

2.13h

To a solution of BOC—N-Me-D-alanine-OH (28.8 mg, 0.142 mmol) and HATU (53.9 mg, 0.142 mmol) in DCM (0.2 mL) at 0° C., was added DIEA (0.03 mL, 0.18 mmol). After stirring for 5 minutes, the mixture was added to a solution of 2.13g (156 mg, 0.118 mmol) and DIEA (0.03 mL, 0.18 mmol) in DCM (0.2 mL) at 0° C. and the resulting mixture was stirred at 0° C. The mixture was then diluted with EtOAc and washed with saturated aqueous NaHCO$_3$ solution, saturated aqueous NH$_4$Cl solution and brine. The organic phase was dried over MgSO$_4$ and concentrated. The residue was purified by silica gel column chromatography, (0-100% Acetone/DCM) to give 2.13h (131 mg, 73.6% yield). MS m/z (M+23) 1529.2

Step 9. Synthesis of 2.13i

To a solution of 2.13h (131 mg, 0.087 mmol) in CH$_2$Cl$_2$ (0.870 mL) at 0° C. was added TFA (0.5 mL, 6.49 mmol). After stirring at 0° C. for 1 hour, the reaction mixture was concentrated and then was diluted with EtOAc. The solution was then washed with saturated aqueous NaHCO$_3$ solution and brine, dried over MgSO$_4$ and concentrated. The residue was dissolved in THF/H$_2$O (3/2, 0.870 mL) and LiOH (18.2 mg, 0.43 mmol) was added. After stirring for 1 hour at 0° C., the solution was neutralized by addition of KHSO$_4$ solution (1.0 M in water, 0.87 mL, 0.87 mmol). The reaction mixture was diluted with EtOAc, washed with brine, followed by NaHCO$_3$ and brine. The organic phase was dried over MgSO$_4$ and concentrated to give product 2.13i (103 mg) was used in the next step with no further purification. MS m/z (M+1) 1306.9

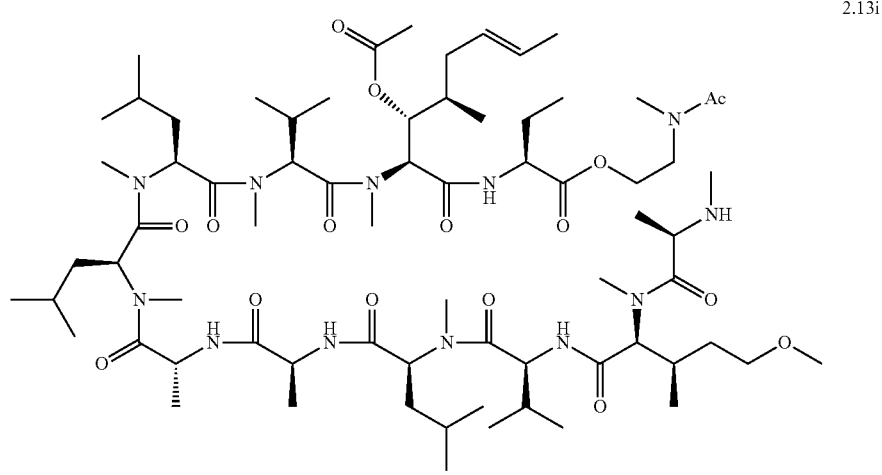 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)CCOC)N(C)C(=O)[C@@H](C)NC)C(C)C]

2.13i

Step 10. Synthesis of 2.13j

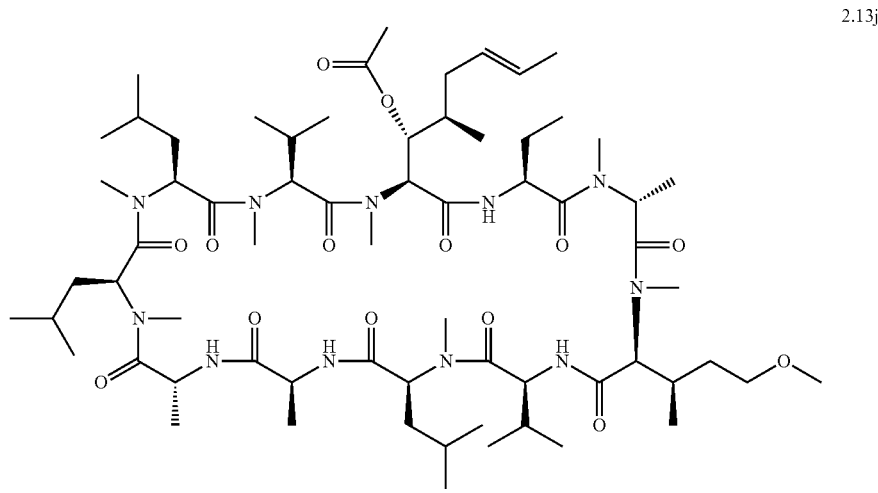 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)CCOC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.13j

A solution of 2.13i (100 mg, 0.077 mmol) and DMAP (18.7 mg, 0.153 mmol) in CH₂Cl₂ (54 mL) was added slowly to a solution of BOP (67.7 mg, 0.153 mmol) in CH₂Cl₂ (21 mL). After stirring at room temperature overnight, the solution was concentrated and the residue was dissolved in EtOAc. The resulting solution was washed with 10% citric acid, saturated aqueous NaHCO₃ solution and brine. After drying over Na₂SO₄, the solution was concentrated and the residue was purified by reverse phase HPLC to give 2.13j (60 mg, 0.047 mmol, 60.8% yield). MS m/z (M+1) 1311.8

Step 11. Synthesis of 2.13

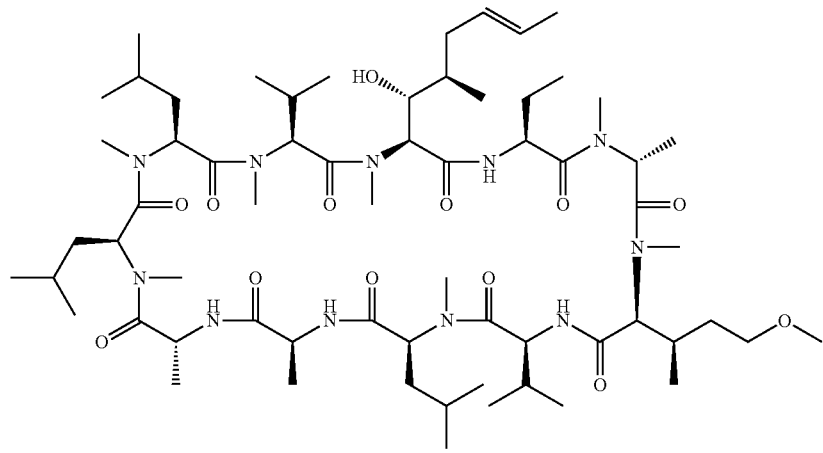

2.13

To a solution of 2.13j (55 mg, 0.043 mmol) in MeOH (456 μL) at 0° C. was added NMe₄OH (25% in MeOH, 156 mg, 0.427 mmol) and the resulting solution was stirred at 0° C. for 1 hour. The reaction mixture was then added to a mixture of 1.0 M NaHSO₄ aq. solution and EtOAc. The phases were separated and the organic phase was washed with brine, dried over MgSO₄ and concentrated. The residue was purified by reverse phase HPLC to provide product 2.13 (31 mg). HR LC/MS m/z (M+1) 1246.8750

II.14.1 Synthesis of Compound 2.14.1

Step 1. Synthesis of (2S,3R)-2-(tert-Butoxycarbonyl-methyl-aminuteso)-3-methyl-hexanedioic acid 6-ethyl ester [2.14.1d]

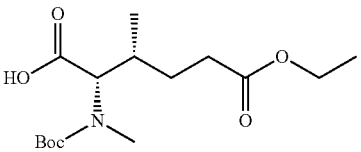

2.14.1d

Ruthenium(III) chloride (0.062 g, 0.301 mmol) was added to a well-stirred solution of NaIO₄ (1.134 g, 5.30 mmol) in water/CCl₄/CH₃CN and the resulting mixture was stirred at 0° C. for 15 minutes. To this mixture was then added 2.14.1c (0.3 g, 0.884 mmol) in acetonitrile (0.3 mL). After stirring at 0° C. for another 5 minutes, the reaction mixture was quenched with water, extracted with EtOAc. The organic layer was washed with 20% NaHSO₃ aq. solution and brine, dried over Na₂SO₄ and concentrated to give product 2.14.1d. The crude product was continued to the next step with no further purification. MS m/z (M+23) 340.2

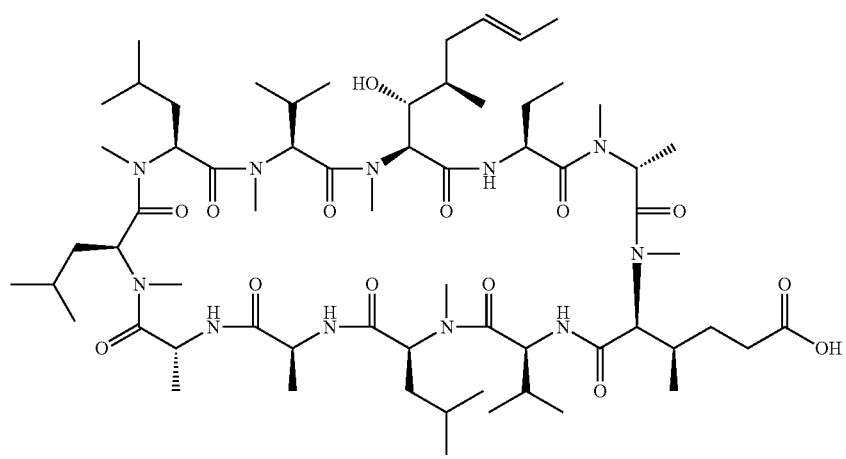

2.14.1

Step 2. Synthesis of 2.14.1e

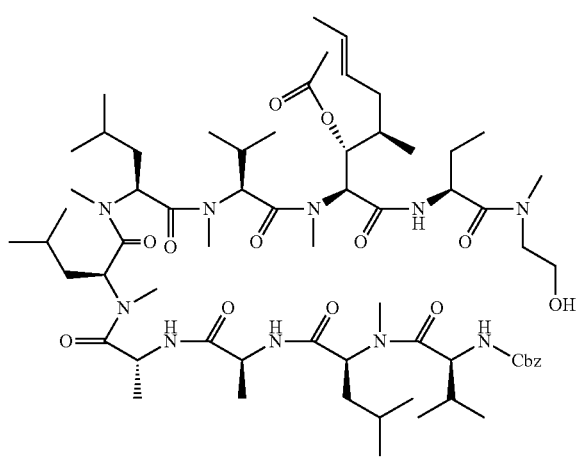

2.14.1e

To a mixture of compound 1a (9 g, 7.83 mmol) in DCM (20 mL) at room temperature was added DIEA (4.1 mL, 23.5 mmol) followed by slow addition of benzylchloroformate (1.34 mL, 9.4 mmol) over 10 minutes. After stirring at room temperature for 30 minutes, the reaction was quenched by addition of MeOH. The mixture was then acidified by addition of 6.0 N aq. HCl solution, diluted with water and extracted with DCM. The organic phase was dried over MgSO$_4$ and concentrated. The residue was dissolved in iPrOH/MeOH (50/5 mL) and NaBH$_4$ (1.78 g, 47 mmol) was added in batches. After stirring at room temperature for 2 hours, the reaction was quenched by addition of 6.0 N aq. HCl solution and extracted with DCM. The organic layer was dried over Na$_2$SO$_4$ and concentrated. The residue was purified by silica gel column chromatography (acetone/heptane 30-60%) to give product 2.14.1e (5 g). MS m/z (M+23) 1278.8

Step 3. Synthesis of 2.14.1f 2.14.1f

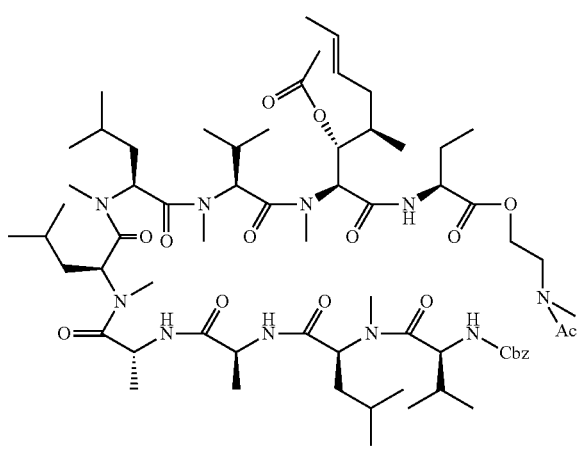

To a solution of 2.14.1e (3.32 g, 2.64 mmol) in i-PrOH (8 mL) was added MsOH (0.858 mL, 13.2 mmol). After stirring at 50° C. for 9 hours, the reaction mixture was diluted with EtOAc and neutralized by addition of 2.0 M Na$_2$CO$_3$ aq. solution. The separated organic layer was dried over Na$_2$SO$_4$ and concentrated. The residue was dissolved in DCM and to the resulting solution was added Ac$_2$O (0.25 mL, 2.64 mmol) followed by pyridine (0.21 mL, 0.264 mmol). After stirring at room temperature for 2 hours, the reaction mixture was diluted with EtOAc and washed with 0.1 N aq. HCl solution. The organic layer was dried over Na$_2$SO$_4$ and concentrated. The residue was purified by silica gel column chromatography (30-60% acetone/heptane) to give product 2.14.1f (1.4 g). MS m/z (M+23) 1320.8

Step 4. Synthesis of 2.14.1g-1 and 2.14.1g-2

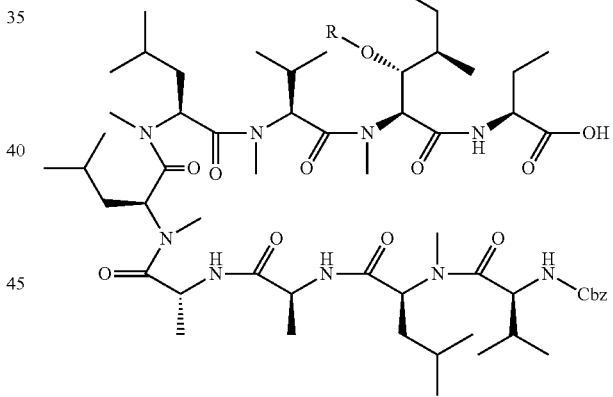

2.14.1g-1: R = H
2.14.1g-2: R = Ac

To a solution of 2.14.1f (1.3 g, 1 mmol) in THF/MeOH/water (3.0/2.0/1.0 mL) at 0° C. was added LiOH (2 mmol). The solution was then stirred at 0° C. for 2 hours and at room temperature for 6 hours. The mixture was acidified by addition of 1.0 N HCl aq. solution and extracted with DCM. The organic phase was dried over MgSO$_4$ and concentrated to give product (1.0 g) as a ½ mixture of 2.14.1g-1 [MS m/z (M+23) 1179.6] and 2.14.1g-2 [MS m/z (M+1) 1198.7]

Step 5. Synthesis of 2.14.1h

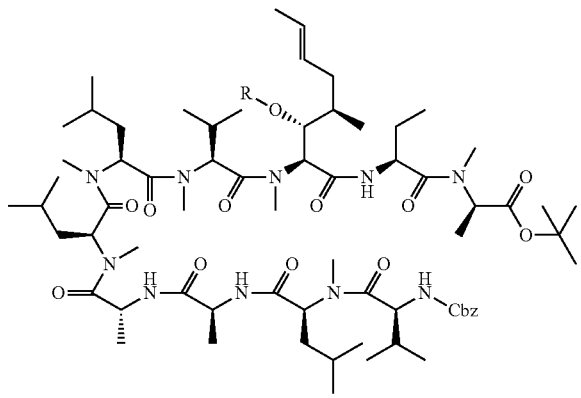

2.14.1h-1: R = H
2.14.1h-2: R = Ac

To the solution of 2.14.1g (480 mg, 0.40 mmol), N-Me-D-Ala-OtBu HCl (94 mg, 0.48 mmol) and 6-Cl-HOBt (98 mg, 0.52 mmol) in $CH_2Cl_2$ (801 µL) was added NMM (132 µL, 1.2 mmol). After stirring for 10 minutes, EDC (100 mg, 0.521 mmol) was added and the mixture was stirred at room temperature for 1 hour. The mixture was diluted with EtOAc, washed with saturated $NH_4Cl$ twice, brine and saturated aqueous $NaHCO_3$ solution. The organic phase was dried over $MgSO_4$ and concentrated to give product as mixtures of 2.14.1h-1 and 2.14.1h-2 (534 mg). To a solution of this product in DCM was added DMAP (50.3 mg, 0.411 mmol) and acetic anhydride (168 mg, 1.646 mmol). After stirring at room temperature for 30 minutes, MeOH (1 mL) was added and the reaction mixture was stirred for 10 minutes. The reaction was then diluted with EtOAc, washed with saturated aqueous $NaHCO_3$ solution, saturated aqueous $NH_4Cl$ solution and brine. The organic phase was dried over $MgSO_4$ and concentrated. The residue was purified by silica gel column chromatography (0-100% Acetone/DCM) to give product 2.14.1h-2 (570 mg, 84% yield). MS m/z (M+23) 1362.5.

Step 6. Synthesis of 2.14.1i

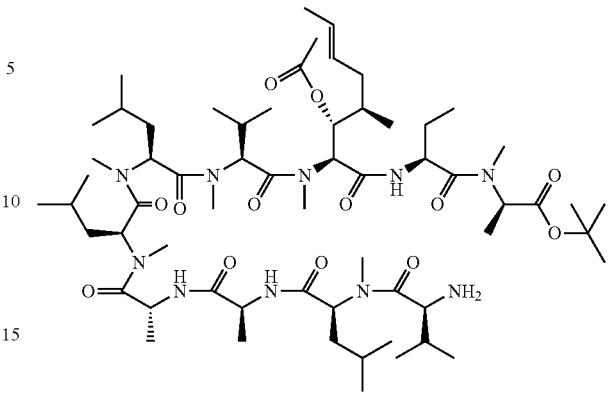

2.14.1i

To the solution of 2.14.1h (570 mg, 0.425 mmol) in $CH_2Cl_2$ (0.85 mL), was added TEA (59.3 µL, 0.425 mmol) and $Pd(OAc)_2$ (19.10 mg, 0.085 mmol). After stirring for 5 minutes, triethylsilane (204 µL, 1.28 mmol) was added. The resulted mixture was stirred for another 30 minutes. After removal of solid by filtration, the reaction mixture was diluted with EtOAc, washed with saturated aqueous $NaHCO_3$ solution, brine, and dried over $MgSO_4$. Solvent was removed under vacuum to give product 2.14.1i (512 mg, 100%). The crude product was used in the following step with no further purification. MS m/z (M+23) 1227.7

Step 7. Synthesis of 2.14.1j

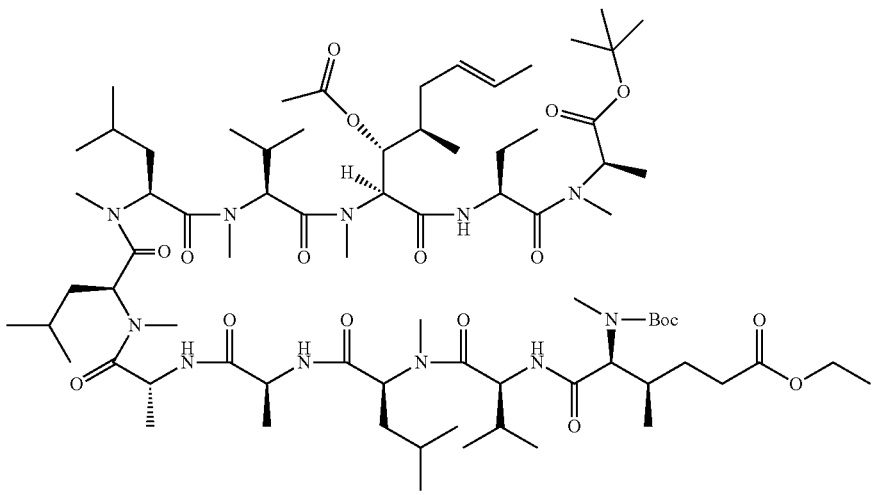

2.14.1j

To a mixture of 2.14.1d (270 mg, 0.850 mmol) and 2.14.1i (512 mg, 0.425 mmol) in toluene (3.8 mL)/water (0.38 mL) at 0° C. was added HOBT (130 mg, 0.850 mmol), EDC (163 mg, 0.850 mmol) and N-methylmorpholine (187 µL, 1.700 mmol), After stirring at this temperature for 16 hour, the reaction mixture was diluted with EtOAc, washed with saturated aqueous $NaHCO_3$ solution, saturated aqueous $NH_4Cl$ solution and brine. The organic phase was dried over $MgSO_4$ and concentrated. The residue was purified by silica gel column chromatography (0-100% Acetone/DCM) to give product 2.14.1j (510 mg, 80% yield). MS m/z (M+23) 1528.1

Step 8. Synthesis of 2.14.1k

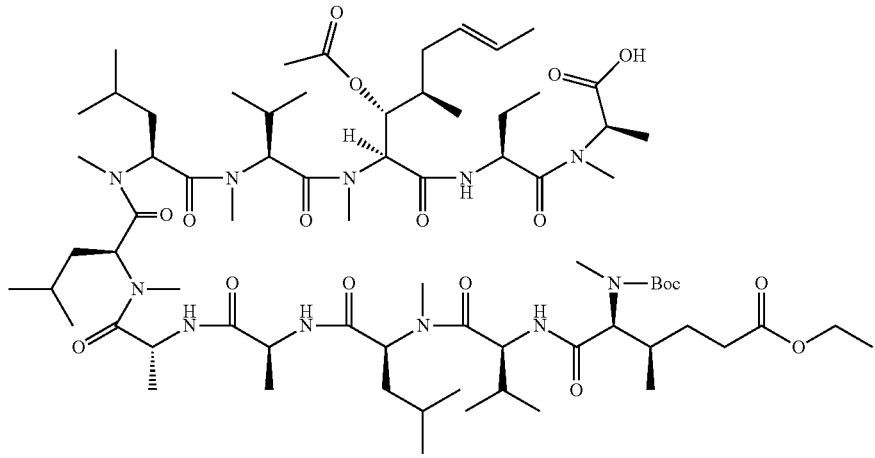

2.14.1k

To a solution of 2.14.1j (510 mg, 0.339 mmol) in $CH_2Cl_2$ (2.5 mL) was added TFA (0.84 mL) and the reaction was stirred for 3 hour at this temperature. After removing solvent under vacuum, the residue was poured onto ice-cold saturated $NaHCO_3$ and the mixture was extracted with EtOAc. The organic phase was washed with saturated aqueous $NaHCO_3$ solution and brine (50 mL), dried over $Na_2SO_4$, and concentrated to give product 2.14.1k (340 mg). MS m/z (M+23) 1371.0

Step 9 Synthesis of 2.14.1l

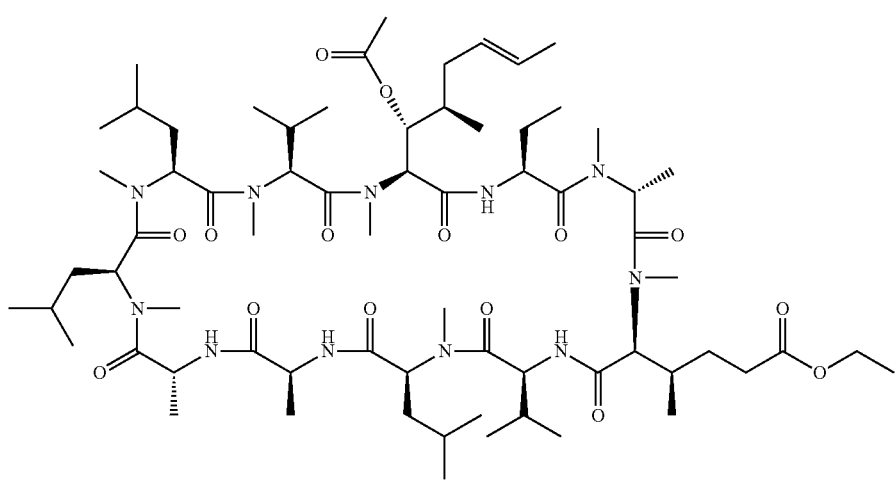

2.14.1l

To a solution of 2.14.1k (340 mg, 0.25 mmol) and 2,4,6-trimethylpyridine (101 μL, 0.75 mmol) in $CH_2Cl_2$ (250 mL) was added PyFFH(TFFH-Pyl) (104 mg, 0.32 mmol). After stirring at room temperature for 16 hours, the reaction mixture was concentrated and the residue was dissolved in EtOAc. The solution was washed with saturated aqueous $NaHCO_3$ solution, saturated aqueous $NH_4Cl$ solution and brine. The organic phase was dried over $MgSO_4$ and concentrated. The residue was purified by silica gel column chromatography (0-100% Acetone/DCM) followed by reverse phase HPLC to give product 2.14.1l (70 mg). MS m/z (M+23) 1353.7

Step 10. Synthesis of 2.14.1

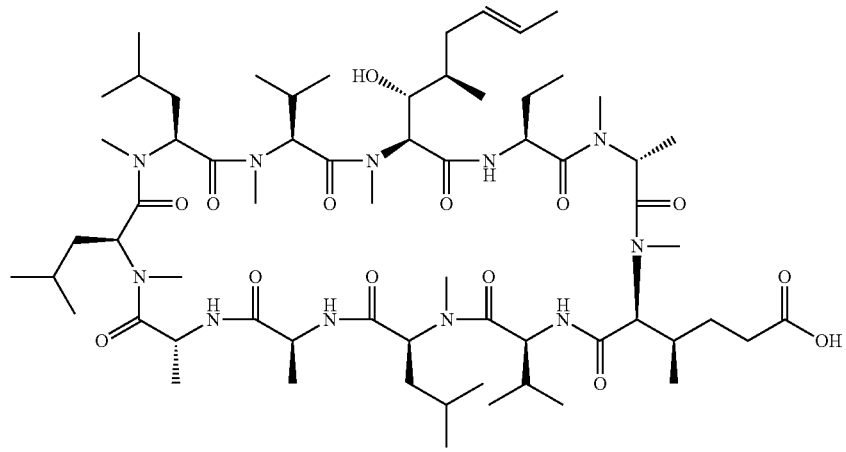

2.14.1

To the solution 2.14.1l (62 mg, 0.047 mmol) in MeOH (2 mL) and water (1 mL), was added tetramethylammonium hydroxide (704 mg, 1.16 mmol) at room temperature and the reaction was stirred at room temperature for 1 hour. The mixture was then dilute with EtOAc and wash with 1.0 M NaHSO$_4$ aq. solution. The organic layer was dried over Na$_2$SO$_4$ and concentrated to give product 2.14.1 (25 mg). HRMS m/z (M+1) 1260.8531, calculated 1260.8547

II.14.2. Synthesis of 2.14.2

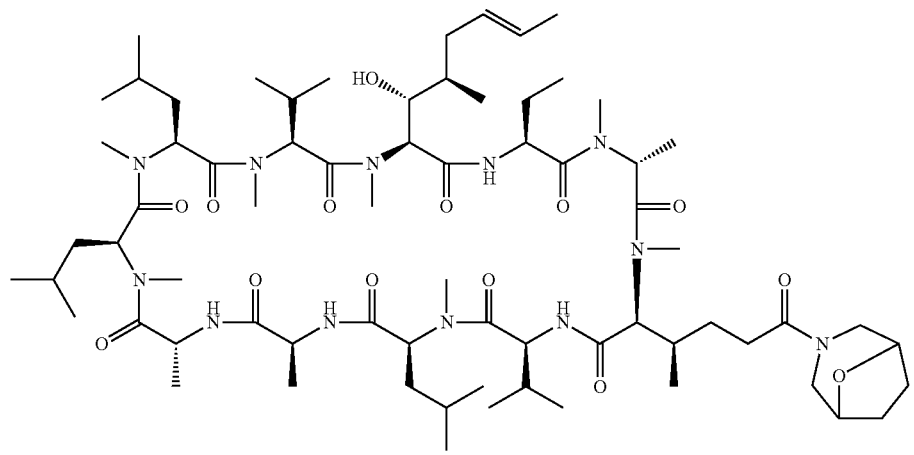

2.14.2

To the solution of 2.14.1 (12.6 mg, 0.01 mmol) in DCM (3 mL) at room temperature was added HATU (19 mg, 0.05 mmol) and DIEA (13 mg, 0.1 mmol). After stirring at room temperature for 10 minutes, 8-oxa-3-azabicyclo[3.2.1]octane (11.3 mg, 0.1 mmol) was added. The reaction was complete after 1 hour. The solvent was then removed under vacuum and the residue was purified by reverse phase HPLC to give product 2.14.2 (4.0 mg). HRMS m/z (M+1) 1355.9243, calculated 1355.9282

II.14.3. Synthesis of 2.14.3

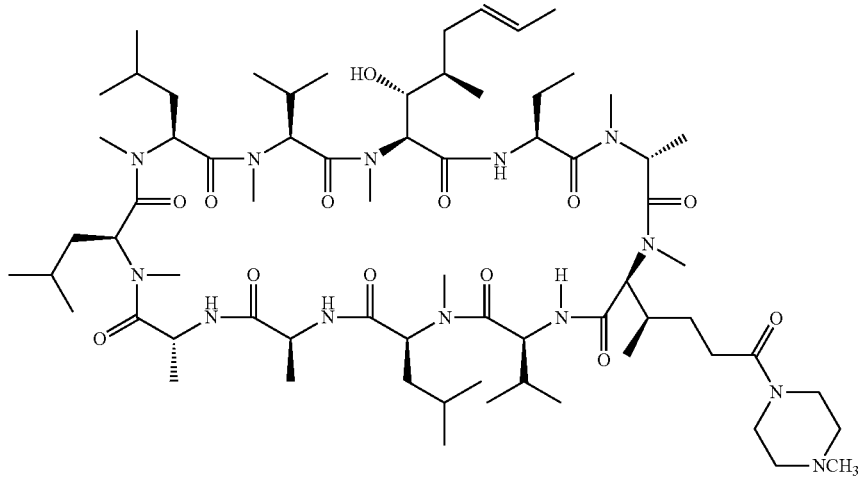

2.14.3

Compound 2.14.3 was synthesized followed the procedure described for the synthesis of 2.14.2. HRMS m/z (M+1) 1342.9415, calculated 1342.9442.

II.14.4. Synthesis of 2.14.4

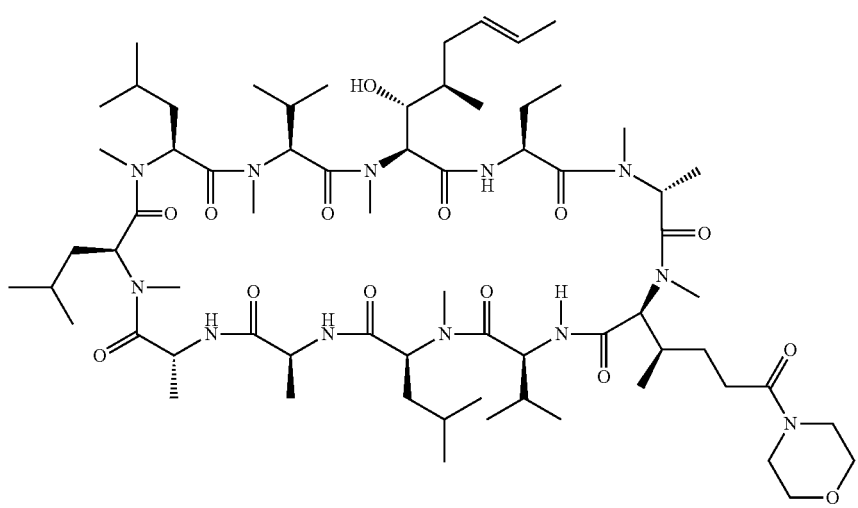

2.14.4

To the solution of 2.14.1 (25 mg, 0.02 mmol) in DCM (1 mL) at room temperature was added EDC (11.4 mg, 0.059 mmol) and Cl—HOBt (10 mg, 0.059 mmol). After stirring at room temperature for 10 minutes, the solution was added morpholine (8.6 mg, 0.1 mmol) and subsequently was stirred at room temperature for 2 hours. The mixture was then diluted with DCM and washed with aq. 1.0 M NaHSO$_4$ aq. solution. The organic layer was dried over Na$_2$SO$_4$ and concentrate. The residue was purified by reverse phase HPLC followed by silica gel column chromatography (acetone/heptane) to 100%) to give product 2.1 mg. HRMS m/z (M+1) 1325.9121, calculated 1329.9125.

II.16 Synthesis of Compound 2.16

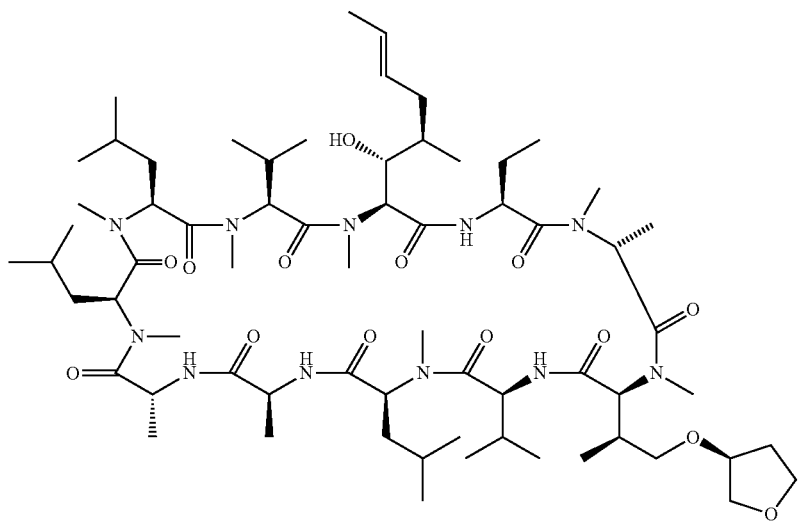

2.16

Step 1. Synthesis of (2S,3S)-3-((tert-butoxycarbonyl)(methyl)amino)-3-(furan-2-yl)-2-methylpropyl methanesulfonate [2.16a]

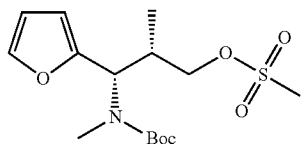

2.16a

To a solution of tert-butyl((1S,2S)-1-(furan-2-yl)-3-hydroxy-2-methylpropylmethyl)-carbamate (108 mg, 0.40 mmol) in DCM (2 mL) at 0° C. was added triethylamine (81 mg, 0.112 ml, 0.80 mmol, 2 equiv) followed by methanesulfonylchloride (55 mg, 0.037 ml, 0.48 mmol, 1.2 equiv) and the solution was stirred at 0° C. for 1 hour. The solution was diluted with 10 mL DCM and washed with sat. NH$_4$Cl solution, water and brine. After drying over MgSO$_4$ the solution was concentrated in vacuo to give crude product 2.16a (140 mg, 99% yield). $^1$H NMR (CDCl$_3$, 400 MHz) 7.38 (dd, J=1.76, 0.98 Hz, 1H) 6.35 (dd, J=3.13, 1.96 Hz, 1H) 6.31 (br. s., 1H) 5.29-5.32 (m, 1H) 4.16 (dd, J=9.98, 3.33 Hz, 1H) 3.90 (br. s., 1H) 2.89-2.96 (m, 3H) 2.68-2.75 (m, 3H) 2.55-2.67 (m, 1H) 1.48 (br. s., 9H) 1.11 (d, J=6.65 Hz, 3H)

Step 2. Synthesis of tert-butyl((1S,2S)-1-(furan-2-yl)-2-methyl-3-(((S)-tetrahydrofuran-3-yl)oxy)propyl)(methyl)carbamate [2.16b]

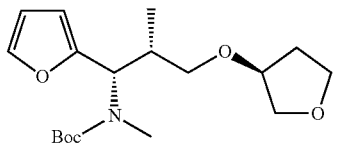

2.16b

To a solution of 2.16a in THF (6 mL) was added NaH (120 mg, 60% in mineral oil, 3 mmol, 8 equiv.) at 0° C. The mixture was stirred at room temperature for 30 minutes. After cooled down to 0° C. in an ice bath, to the solution was added (2S,3S)-3-((tert-butoxycarbonyl)(methyl)amino)-3-(furan-2-yl)-2-methylpropyl methanesulfonate in THF (2 mL) was added and the resulting mixture was heated to reflux for 16 hours. The reaction was quenched at room temperature by addition of saturated aqueous NH$_4$Cl solution. The mixture was neutralized to pH=7 by addition of 0.5 M KHSO$_4$ aq solution. The aqueous layer was extracted EtOAc. The combined organic layer was washed brine, dried over Na$_2$SO$_4$ and concentrated. The residue was purified by silica gel column chromatography (EtOAc/heptane, 15-50%) to give product 2.16b (50 mg, 39% yield). MS (m/z): 340 [M+1]. $^1$H NMR (CDCl$_3$, 400 MHz) 7.36 (dd, J=1.96, 0.78 Hz, 1H) 6.32 (dd, J=3.33, 1.76 Hz, 1H) 6.17-6.25 (br. d., 1H) 5.08-5.21 (br. dd, 1H) 3.92 (br. s., 1H) 3.76-3.86 (m, 2H) 3.66-3.76 (m, 2H) 3.27 (br. s., 1H) 3.08 (br. s., 1H) 2.71 (s, 3H) 2.32-2.45 (m, 1H) 1.74-1.91 (m, 2H) 1.58 (s, 1H) 1.41-1.53 (m, 9H) 1.03 (d, J=6.65 Hz, 3H)

Step 3. Synthesis of (2S,3S)-2-((tert-butoxycarbonyl)(methyl)amino)-3-methyl-4-(((S)-tetrahydrofuran-3-yl)oxy)butanoic acid [2.16c]

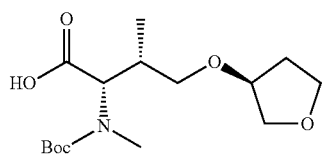

2.16c

A flask was charged with 2.16b (50 mg, 0.15 mmol), NaIO$_4$ (189 mg, 0.88 mmol, 6 equiv.) and EtOAc/heptane/water (1.5 mL/0.5 mL/2 mL). With vigorous stirring, RuCl$_3$ (6 mg, 0.03 mmol, 0.2 equiv) was added and the resulting mixture was stirred at room temperature for 1 hour. The reaction was quenched by addition of saturated aqueous NaHSO$_3$ solution and the mixture was extracted with EtOAc. The combined organic layers was washed with saturated aqueous NaHSO$_3$ solution, brine, dried over Na$_2$SO$_4$ and concentrated to give product 2.16c (34 mg, 73% yield). MS (m/z): 318 [M+1].

Step 4. Synthesis of Compound 2.16

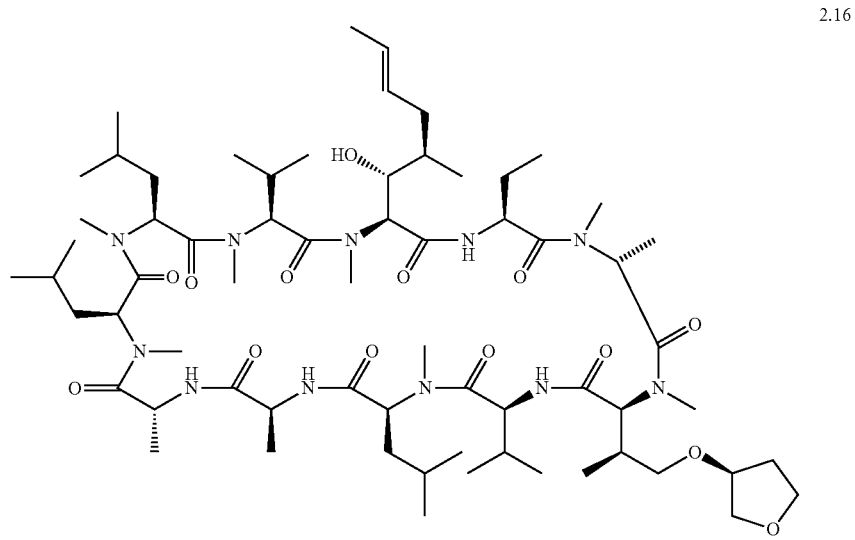 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CO[C@H]2CCOC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.16

Compound 2.16c was then converted to compound 2.16 according to the procedures described for the synthesis of compound 2.7 (step 4-step 8). HRMS: 1288.8828 [M+1].

II.17.1. Synthesis of 2.17.1

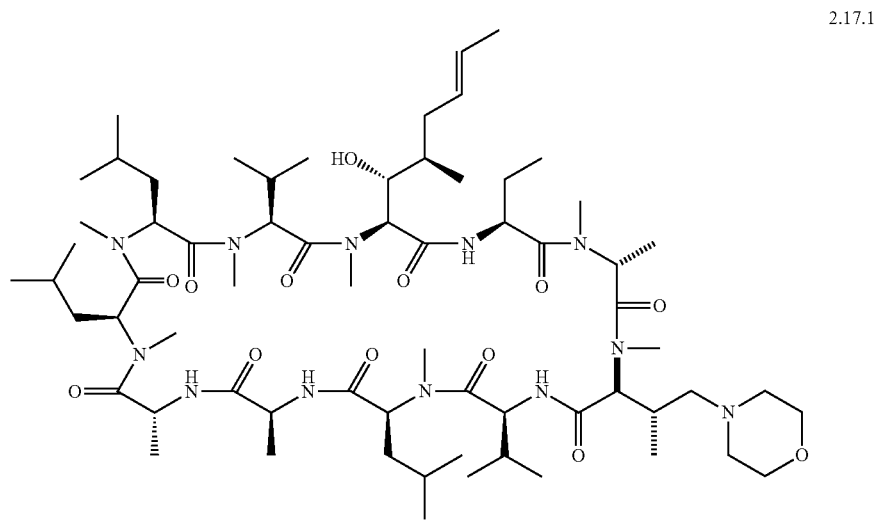 [SMILES: C/C=C/C[C@@H](C)[C@@H](O)[C@H]1C(=O)N[C@@H](CC)C(=O)N(C)[C@H](C)C(=O)N(C)[C@@H]([C@@H](C)CN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.17.1

Step 1. Synthesis of [(1S,2R)-3-(tert-Butyl-diphenyl-silanyloxy)-1-furna-2-yl-2-methyl-propyl]-carbamic acid tert-butyl ester [2.17.1a]

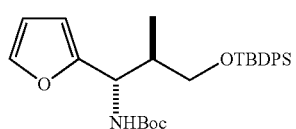

2.17.1a

To a solution of ((1S,2R)-1-furan-2-yl-3-hydroxy-2-methyl-propyl)-carbamic acid tert-butyl ester 2.2b (503.0 mg, 1.97 mmol) in DMF (3 mL) at 0° C. was added imidazole (295.0 mg, 4.33 mmol, 2.2 equiv) and TBDPSCl (596.0 mg, 2.2 mmol, 1.1 equiv). After stirring at room temperature for 12 hours, the reaction mixture was diluted with EtOAc (20 mL) and washed sequentially with water, aqueous 1.0 M HCl solution, saturated aqueous NaHCO$_3$ solution and brine. The organic layer was dried over anhydrous Na$_2$SO$_4$ and concentrated in vacuo. The residue was purified by silica gel column chromatography (EtOAc/heptane) to give 2.17.1a. MS (M+Na) 516.3

Step 2. Synthesis of [(1S,2R)-3-(tert-Butyl-diphenyl-silanyloxy)-1-furan-2-yl-2-methyl-propyl] methyl-carbamic acid tert-butyl ester [2.17.1b]

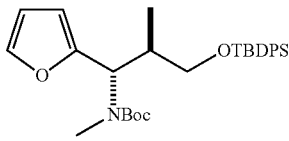

2.17.1b

To a suspension of NaH (294.0 mg, 7.4 mmol, 3.3 equiv, 60% in mineral oil)) in THF (3 mL) at 0° C. was added 2.17.1a (1.1 g, 2.2 mmol) in THF (4 mL). After stirring at 0° C. for 0 minutes, to this solution was added MeI (418 μL, 6.7 mmol, 3.0 equiv) and DMF (0.68 mL). After stirring for 2 hours at room temperature, the reaction mixture was quenched with water and extracted with EtOAc. The organic layer was washed with brine, dried over $Na_2SO_4$ and concentrated in vacuo. The resulting residue was purified by silica gel column chromatography to give 2.17.1b (884.0 mg, 78% yield). $^1$H NMR (400 MHz, $CDCl_3$) ppm 7.69 (m, 5H), 7.42 (m, 5H), 7.33 (s, 1H), 6.30 (d, J=1.96 Hz, 1H), 6.25-6.02 (m, 1H), 5.28-4.80 (m, 1H), 3.57 (m, 1H), 3.53 (s, 3H), 2.67-2.47 (m, 2H), 2.35 (m, 1H), 1.07 (s, 9H), 1.04 (s, 9H), 0.90 (d, 2H).

Step 3. Synthesis of (1S,2R)-3-((tert-butyldiphenyl-silyl)oxy)-1-(furan-2-yl)-N,2-dimethylpropan-1-amine [2.17.1c]

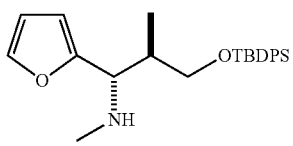

2.17.1c

A round bottom flask was charged with 2.17.1b (4.2 g, 8.3 mmol) and 1,4-dioxane (4.0 mL). To this solution at 0° C. was added a cold solution of HCl in dioxane (4.0 N, 21 mL, 84 mmol, 10 equiv). After stirring at 0° C. for 4 hours, the reaction solution was concentrated under vacuum with water bath temperature at 20° C. The residue was diluted with EtOAc and basified by addition of sat. aq. $NaHCO_3$ solution. The phases were separated and the organic layer was washed with brine, dried over $Na_2SO_4$ and concentrated to give product 3.4 g (100%). The crude material was continued to the next step with no further purification. MS (M+H) 408.3

Step 4. Synthesis of [2.17.1d]

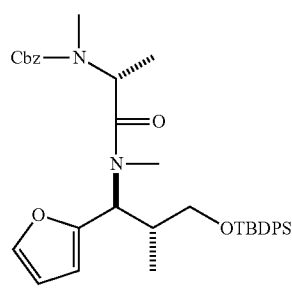

2.17.1d

To a solution of Cbz-N-Me-D-Ala (2.4 g, 10.2 mmol, 1.3 equiv) in DCM (20 mL) at 0° C. was added HATU (4.2 g, 11.0 mmol, 1.4 equiv) and DIPEA (4.1 mL, 23.5 mmol, 3.0 equiv). After stirring at 0° C. for 10 mins, a solution of 2.17.1c (3.2 g, 7.85 mmol, 1.0 equiv) in DCM (5 mL) was added and the mixture was stirred at 0° C. for 2 hours and at room temperature for 18 hours. The solution was then concentrated under vacuum and the residue was dissolved in EtOAc. The solution was washed with sat. aq. $NaHCO_3$ solution, water, 1.0 N HCl aq. solution, brine. After dried over $Na_2SO_4$, the solution was concentrated and the residue was purified by silica gel column chromatography, EtOAc/heptane (0 to 40%), to give product 4.4 g (yield 89%). MS (M+H) 627.4

Step 5. Synthesis of 2.17.1e

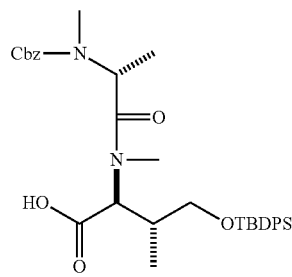

2.17.1e

To a mixture of $NaIO_4$ (9.01 g, 42.1 mmol, 6.0 equiv) and 2.17.1d (4.4 g, 7.0 mmol, 1.0 equiv) in $CH_3CN/CCl_4$/water (38 mL/25 mL/38 mL) was added $RuCl_3$ (0.87 g, 4.2 mmol, 0.6 equiv) and the resulting mixture was stirred at room temperature for 3 hours. The reaction mixture was diluted with EtOAc and quenched by addition of sat. aq. $NaHSO_3$ solution. The phases were separated and the aqueous layer was extracted with EtOAc. The combined organic layer was washed with brine, dried over $Na_2SO_4$ and concentrated.

The remaining oil was dissolved in MeOH (10 mL) and EtOAc (5 mL). To this solution was added sat. aq. $NaHCO_3$ solution (15 mL) followed by $H_2O_2$ (2.6 mL) and the resulting mixture was stirred at room temperature for 1 hour. To the reaction mixture was then added EtOAc and the phases were separated. The organic layer was washed with sat. aq. $Na_2S_2O_3$ solution, brine, dried over $Na_2SO_4$ and concentrated to give product 4.0 g (crude yield 95%). The crude material was continued to the next step with no further purification. MS (M+H) 605.4.

Step 6. Synthesis of 2.17.1f

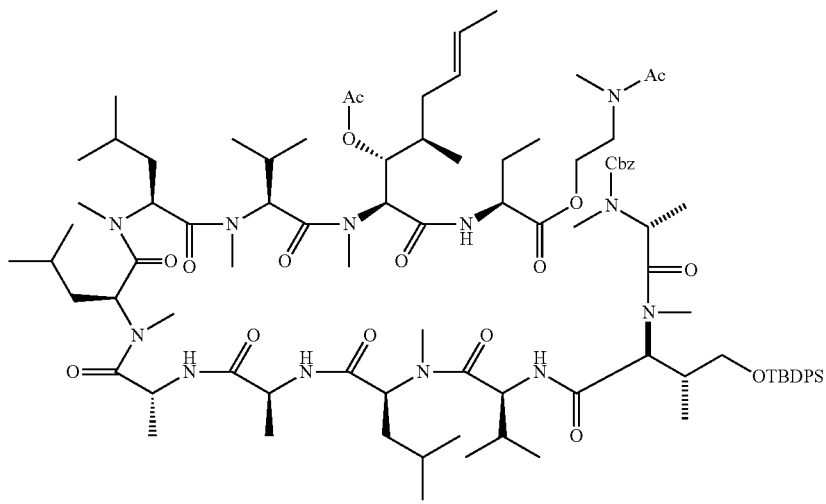

2.17.1f

To a solution of 2.17.1e (3.9 g, 5.2 mmol, 80% purity, 1.1 equiv) in DCM (25.0 mL) at 0° C. was added HATU (2.3 g, 6.2 mmol, 1.3 equiv) and DIPEA (2.5 mL, 14.2 mmol, 3.0 equiv). After 10 minutes, amine 1 (5.5 g, 4.7 mmol, 1.0 equiv) was added and the reaction mixture was stirred at 0° C. for 1 hour and room temperature for 18 hours. The reaction solution was then concentrated and the residue was dissolved in EtOAc. The solution was washed with sat. aq. NaHCO$_3$ solution, 1.0 N HCl aq. solution, brine, dried over Na$_2$SO$_4$ and concentrated. The residue was purified by silica gel column chromatography (acetone/heptane 0 to 60%) to give product 4.8 g (yield 58%). MS (M+H) 1751.2

Step 7. Synthesis of 2.17.1g

To a solution of 2.17.1f (4.8 g, 2.7 mmol, 1.0 equiv) in DCM (25 mL) was added Pd(OAc)$_2$ (0.31 g, 1.37 mmol, 0.5 equiv), TEA (3.0 mL, 21.9 mmol, 6.0 equiv) and triethyl silane (2.6 mL, 16.5 mmol, 6.0 equiv). After stirring at room temperature for 2 hours, the reaction mixture was concentrated under vacuum and the residue was dissolved in EtOAc, filtered through celite. The filtrate was washed with sat. aq. NaHCO$_3$ solution, brine, dried over Na$_2$SO$_4$ and concentrated to give product 4.3 g (yield 97%). The crude material was continued to the next step with no further purification. MS (M+H) 1617.3

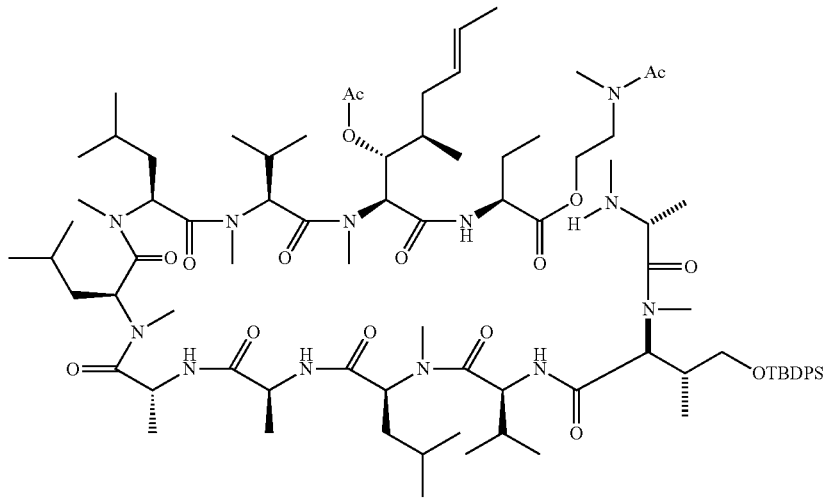

2.17.1g

Step 8. Synthesis of 2.17.1h

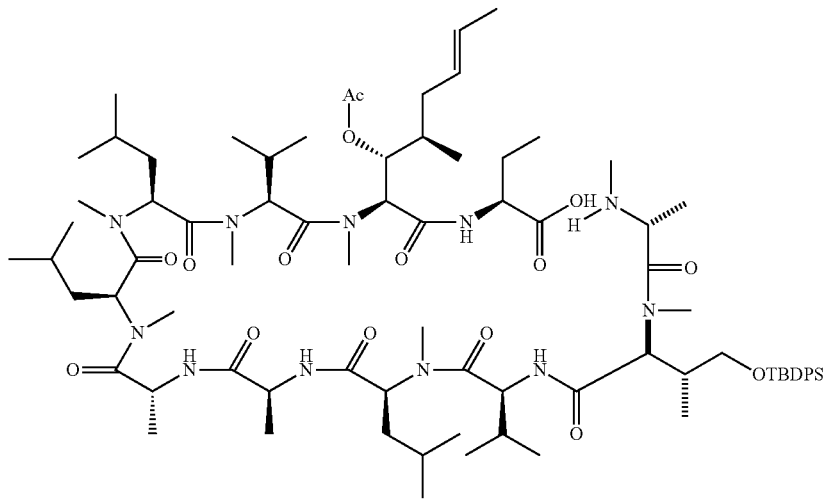

2.17.1h

To a solution of 2.17.1g (4.3 g, 2.7 mmol, 1.0 equiv) in THF (20.0 mL) at 0° C. was added NaOH aq. solution (21 mL, 0.5 M, 10.5 mmol, 4.0 equiv) and the resulting solution was stirred at 0° C. for 3 hours. The reaction solution was then acidified by addition of 1.0 N HCl aq. solution until pH=6 and then extracted with EtOAc. The combined organic layer was washed with brine, dried over $MgSO_4$ and concentrated to give product 4.1 g (yield 100%). The crude material was continued to the next step with no further purification. MS (M+H) 1517.9

Step 9. Synthesis of 2.17.1i

To a solution of BOP (2.3 g, 5.3 mmol, 2.0 equiv) in DCM (750 mL) was added a solution of 2.17.1h (4.0 g, 2.6 mmol, 1.0 equiv) and DMAP (5.3 mmol, 2.0 equiv) in DCM (250 mL) over 2 hours. After stirring at room temperature for 18 hours, the reaction solution was concentrated under vacuum. The residue was dissolved in EtOAc and washed with 1.0 N HCl aq. solution, water, brine, dried over $Na_2SO_4$ and concentrated. The residue was purified by silica gel column chromatography (EtOAc/heptane 0 to 100%) to give product 2.7 g (68%). MS (M+H) 1499.9

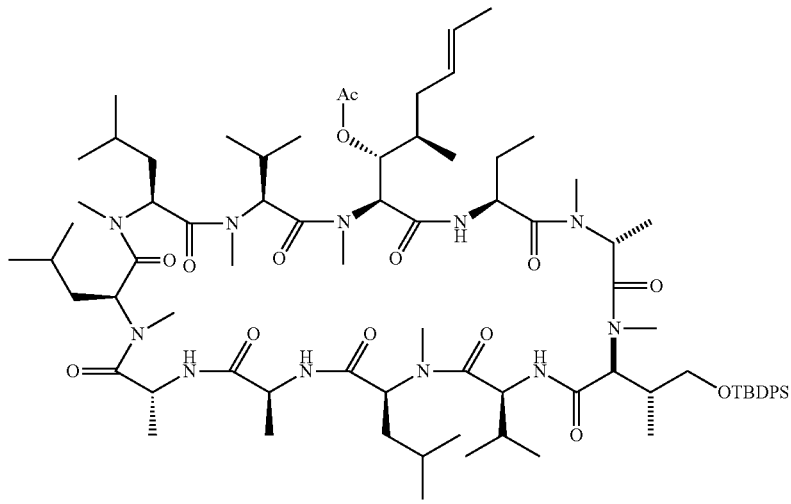

2.17.1i

Step 10. Synthesis of 2.17.1j

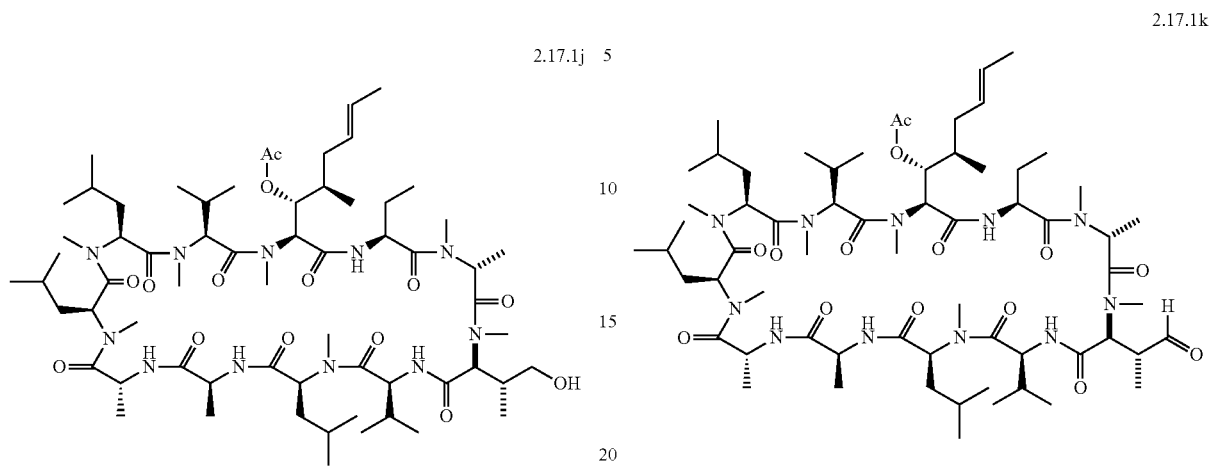

To a solution of TBAF in THF (18.0 mL, 1.0 M in THF, 18.0 mmol, 10.0 equiv) at room temperature was added 2.17.1i (2.7 g, 1.8 mmol, 1.0 equiv). After stirring at room temperature, the solution was diluted with EtOAc and washed with water, brine, dried over $Na_2SO_4$ and concentrated. The residue was purified by silica gel column chromatography, acetone/heptane (0% to 100%) to give product 1.7 g (yield 75%). MS (M+H) 1261.9

Step 11. Synthesis of 2.17.1k

To a solution of 2.17.1j (700 mg, 0.55 mmol) in DCM (1 mL) at 0° C. was added DIEPA (0.29 mL, 1.7 mmol, 3.0 equiv) and a solution of $Py.SO_3$ (442 mg, 2.8 mmol, 5.0 eqiv) in DMSO (0.5 mL) and the resulting solution was stirred at 0° C. for 30 minutes. The reaction was quenched by addition of sat. aq. $NH_4Cl$ solution and then extracted with EtOAc. The combined organic layer was washed with brine, dried with $MgSO_4$ and concentrated. The crude material was used in the next step with no further purification. MS m/z (M+23) 1281.9

Step 12. Synthesis of 2.17.1l

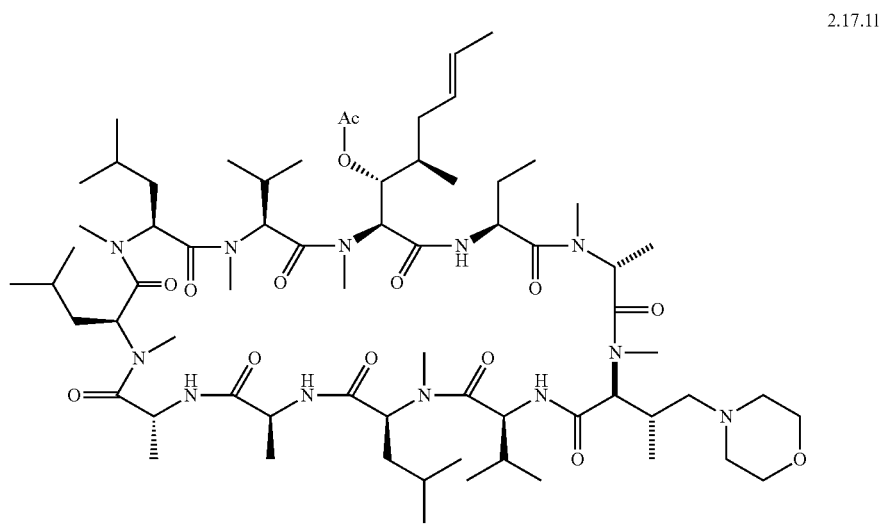 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@@H](C)CN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

To a solution of 2.17.1k (800 mg, 0.64 mmol, 1.0 equiv) in $CH_3CN$ (3.2 mL) was added morpholine (111 mg, 1.3 mmol, 2.0 equiv) acetic acid (38 mg, 0.64 mmol, 1.0 equiv) and $Na_2SO_4$ (50 mg). After stirring at room temperature for 5 minutes, sodium triacetoxyborohydride (269 mg, 1.3 mmol, 2.0 equiv) was added and the resulting mixture was stirred at room temperature for 1 hour. To the reaction mixture was then added sat. aq.$NH_4Cl$ solution and EtOAc. The phases were separated and the organic layer was washed with brine, dried over $MgSO_4$ and concentrated to give product (846 mg). The crude material was used in the next step with no further purification. MS m/z (M+1) 1331.0

Step 13. Synthesis of 2.17.1

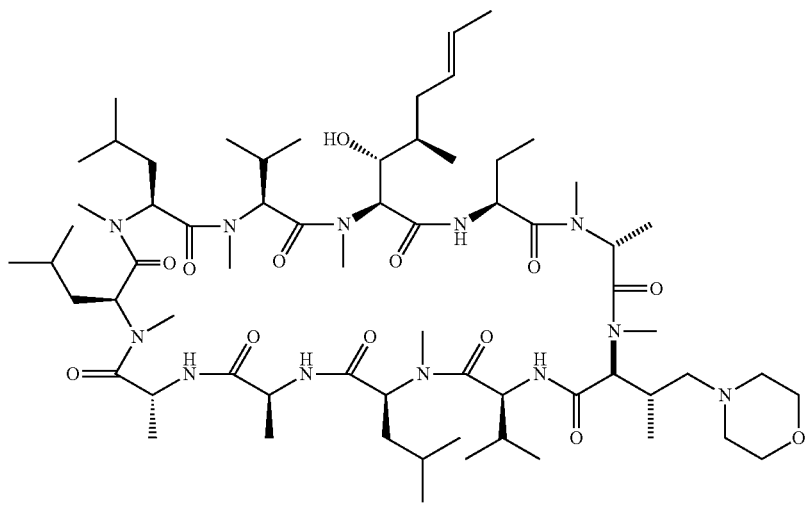

2.17.1

To a solution of 2.17.11 (846 mg, 0.64 mmol) in MeOH (3.2 mL) was added tetramethylammonium hydroxide (25% weight in MeOH, 2.3 g, 6.4 mmol, 10 equiv) at 0° C. After stirring for 30 minutes at 0° C., the reaction solution was diluted with EtOAc and washed with sat. aq. $NH_4Cl$ solution, brine, dried over $MgSO_4$ and concentrated. The crude material was purified by reverse phase HPLC to give product as TFA salt which was basified with saturated $NaHCO_3$ aqueous solution to obtain salt-free form 2.17.1 (430 mg, 53% yield). HRMS: 1287.9006 (calculated 1287.9020)

II.17.2 Synthesis of 2.17.2

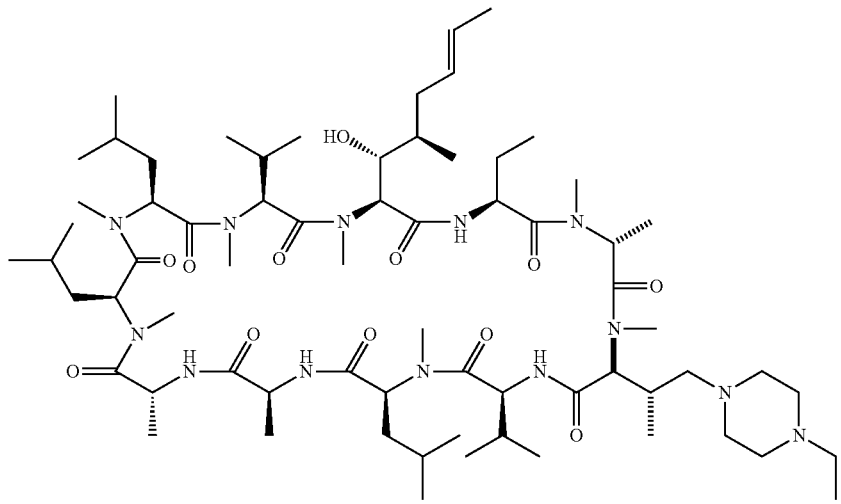

2.17.2

Compound 2.17.2 was prepared following the procedures described for the synthesis of 2.17.1 using 1-ethyl-piperazine at step 12. HRMS: 1314.9467 (calculated 1314.9492)

II.17.3 Synthesis of 2.17.3
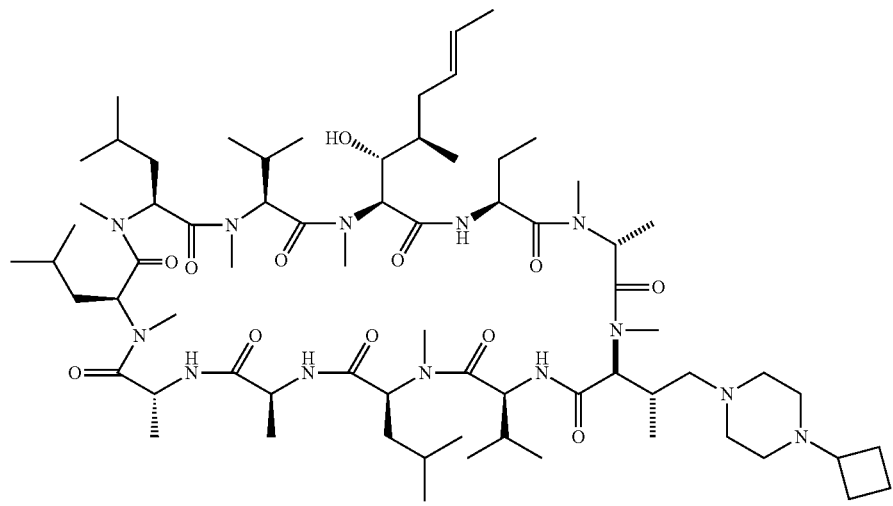
2.17.3
Compound 2.17.3 was prepared following the procedures described for the synthesis of 2.17.1 using 1-cyclobutyl-piperazine at step 12. HRMS: 1340.9640 (calculated 1340.9649)
II.17.4 Synthesis of 2.17.4
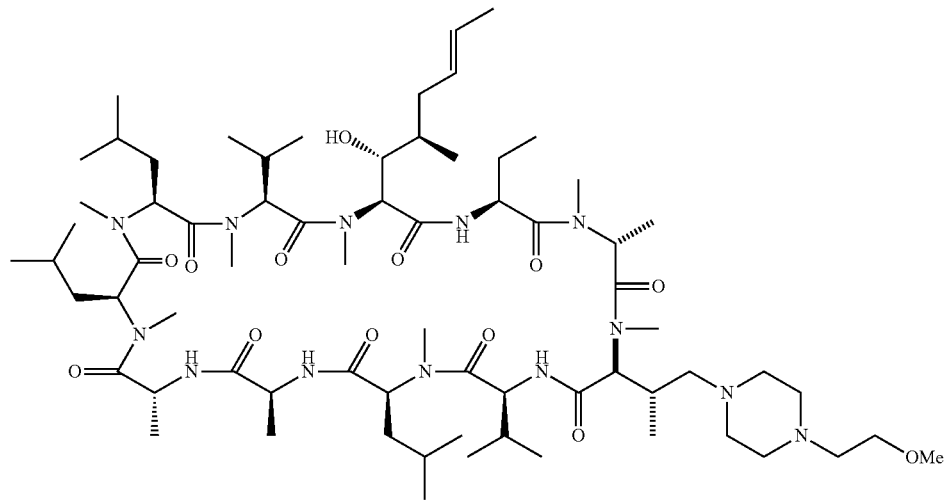
2.17.4
Compound 2.17.4 was prepared following the procedures described for the synthesis of 2.17.1 using 1-(2-methoxy-ethyl)-piperazine at step 12. HRMS: 1344.9588 (calculated 1344.9598)

II.17.5 Synthesis of 2.17.5

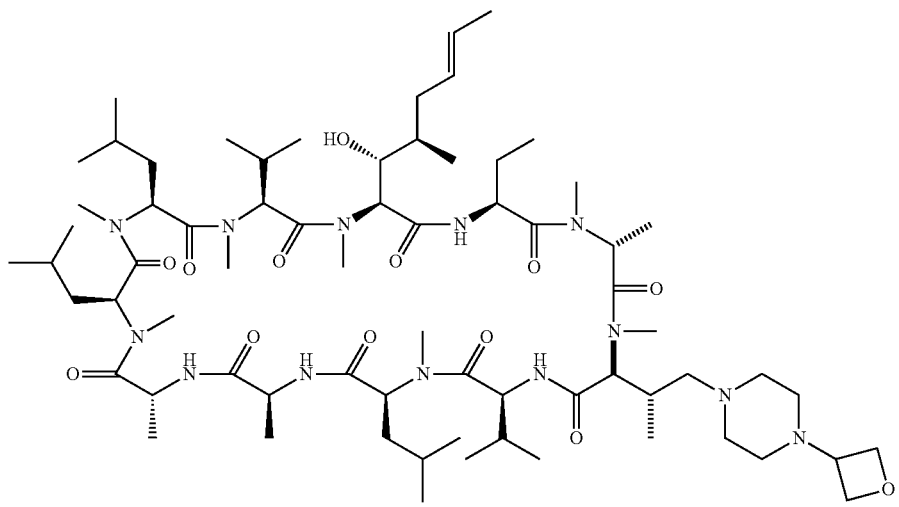

2.17.5

Compound 2.17.5 was prepared following the procedures described for the synthesis of 2.17.1 using 1-(oxetan-3-yl)piperazine at step 12. HRMS: 1342.9424 (calculated 1342.9442)

II.17.6 Synthesis of 2.17.6

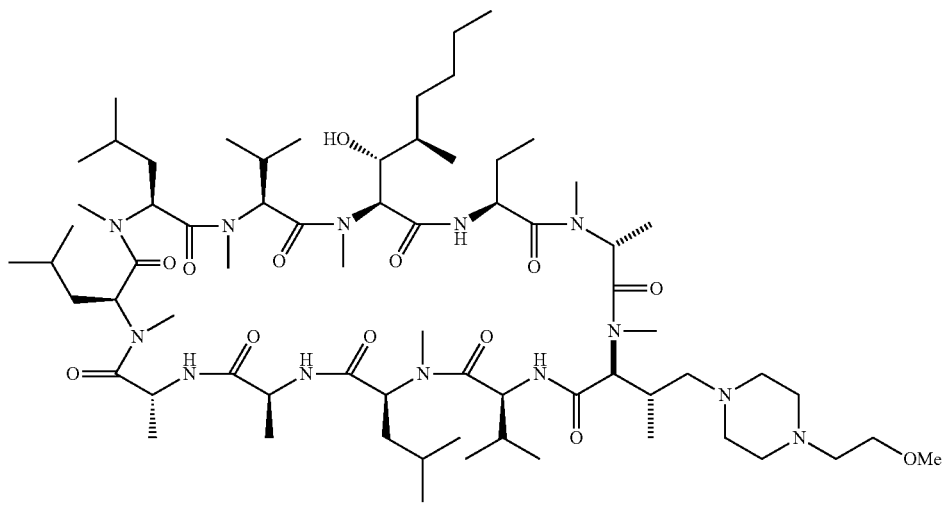

2.17.6

To a solution of 2.17.4 (14 mg, 0.01 mmol, 1.0 equiv) in ethanol (1 mL) was added palladium (10% on carbon, 4 mg, 0.003 mmol, 0.3 equiv) at room temperature and the mixture was stirred at room temperature for 1 hour. The reaction mixture was then filtered through celite and the filtrate was concentrated. The residue was purified by reverse phase HPLC to give product 2.17.6 (11 mg, 97% yield). HRMS: 1346.9746 (calculated 1346.9755)

II.17.7. Synthesis of 2.17.7

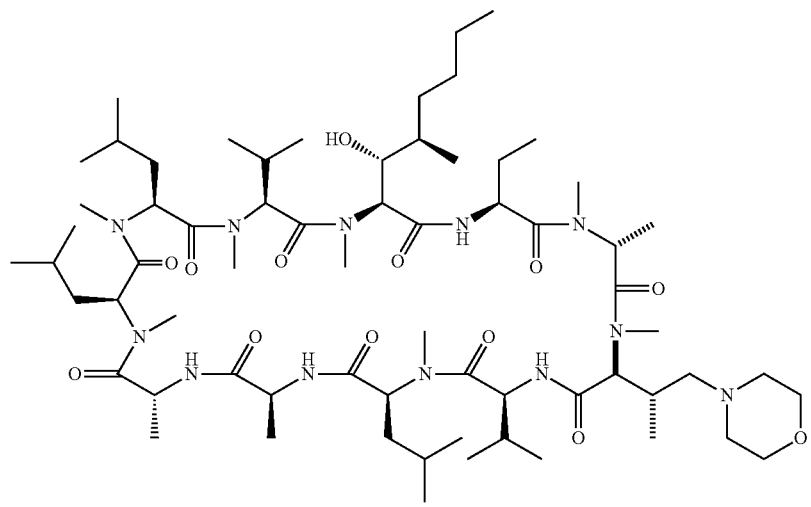

2.17.7

To a solution of 2.17.1 (255 mg, 0.198 mmol, 1.0 equiv) in ethanol (6 mL) was added palladium (10% on carbon, 211 mg, 0.198 mmol, 1.0 equiv) at room temperature and the reaction mixture was stirred under 1 atm of hydrogen for 4 hours. The mixture was then filtered through celite and the filtrate was concentrated under vacuum. The residue was purified by reverse phase HPLC to give product 2.17.7 (43.2 mg, 17% yield). MS m/z (M+1) 1289.9159

II.17.8. Synthesis of 2.17.8

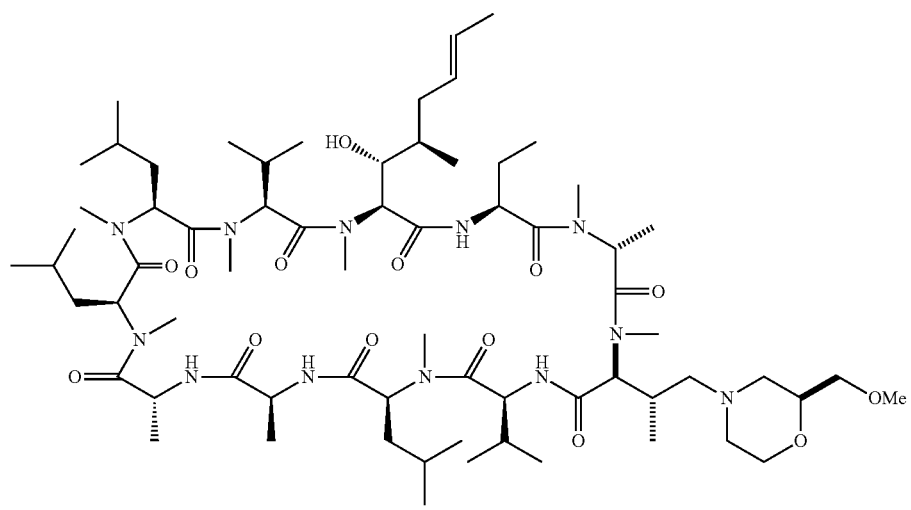

2.17.8

Compound 2.17.8 was prepared following the procedures described for the synthesis of 2.17.1 using (S)-2-(methoxymethyl)morpholine in Step 12. MS m/z (M+1) 1332.9

II.17.9. Synthesis of 2.17.9
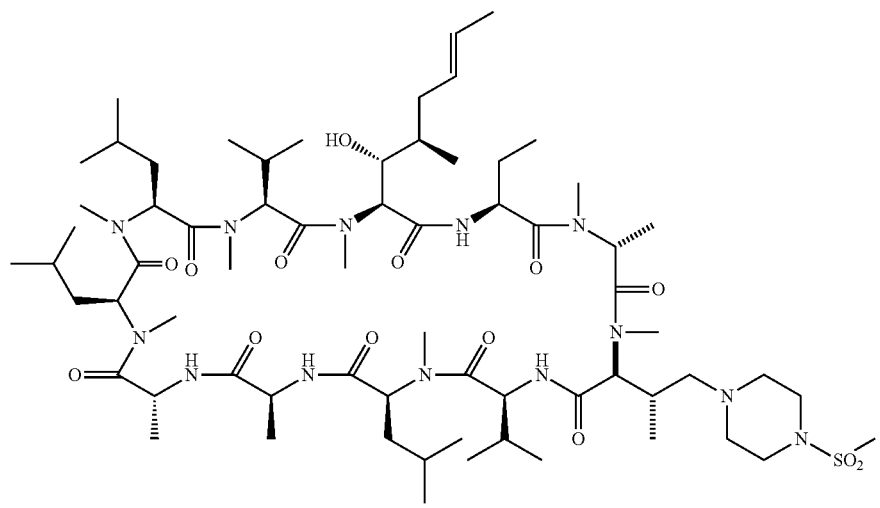
2.17.9
Compound 2.17.9 was prepared following the procedures described for the synthesis of 2.17.1 using 1-(methylsulfonyl)piperazine in Step 12. HRMS m/z (M+1) 1364.8933 (calculated 1364.8955)
II.17.10. Synthesis of 2.17.10
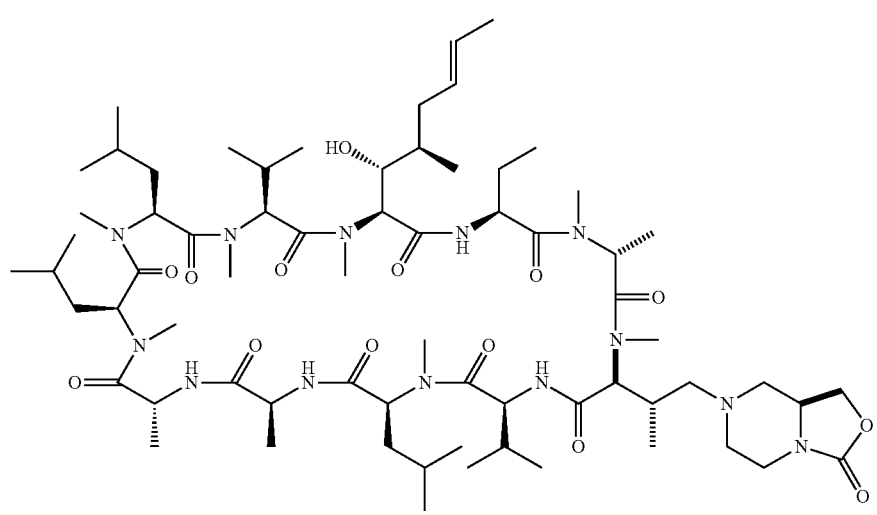
2.17.10
Compound 2.17.10 was prepared following the procedures described for the synthesis of 2.17.1 using (S)-tetrahydro-1H-oxazolo[3,4-a]pyrazin-3(5H)-one in Step 12. HRMS m/z (M+1) 1342.9055 (calculated 1342.9078)

II.17.11 Synthesis of 2.17.11
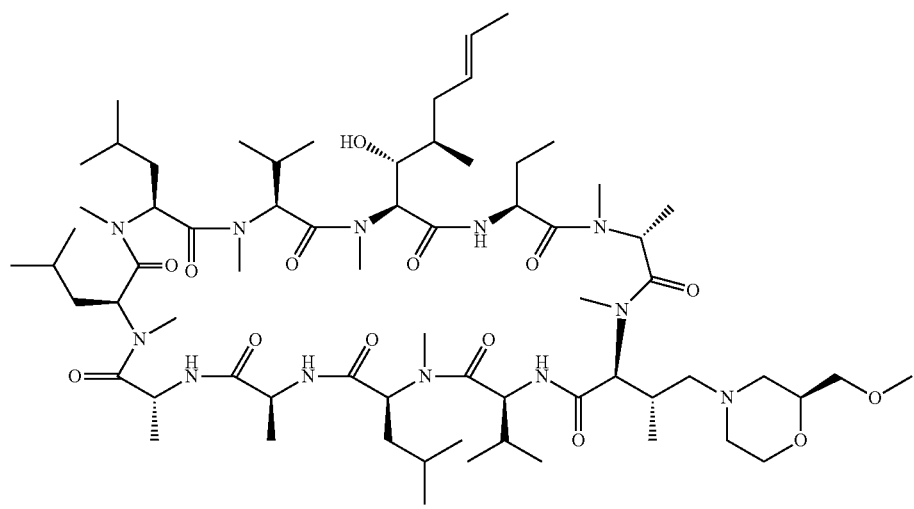 [SMILES: C/C=C/C[C@@H](C)[C@@H](O)[C@H]1C(=O)N[C@@H](CC)C(=O)N(C)[C@H](C)C(=O)N(C)[C@@H]([C@@H](C)CN2CCO[C@H](COC)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
Compound was prepared following the procedures described for the synthesis of 2.17.1. HRMS m/z (M+1) 1331.9257 (calculated 1331.9282)
II.17.12 Synthesis of 2.17.12
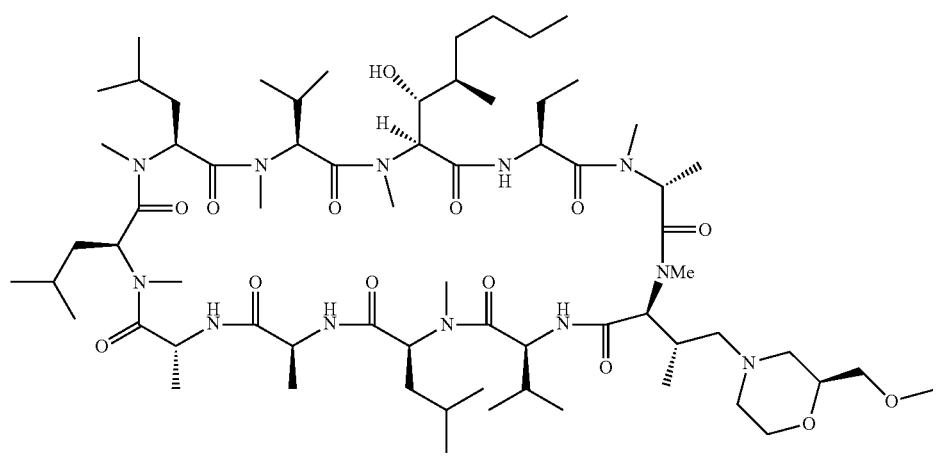 [SMILES: CCCC[C@@H](C)[C@@H](O)[C@H]1C(=O)N[C@@H](CC)C(=O)N(C)[C@H](C)C(=O)N(C)[C@@H]([C@@H](C)CN2CCO[C@H](COC)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
Compound 2.17.11 was converted to 2.17.12 following the procedures described for the synthesis of 2.5.15. HRMS m/s (M+1) 1333.9408

II.17.14 Synthesis of 2.17.14
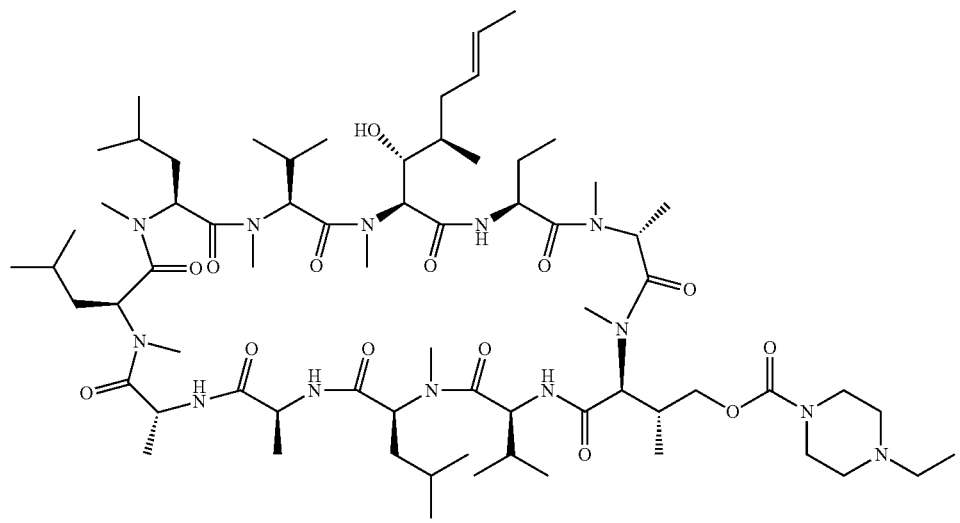
2.17.14
Compound 2.17.14 was prepared following the procedures described for the synthesis of 2.5.7 using 2.17.1j and 1-ethylpiperazine in Step 1. HRMS m/z (M+1) 1358.9368 (calculated 1358.9391)
II.18.1 Synthesis of 2.18.1
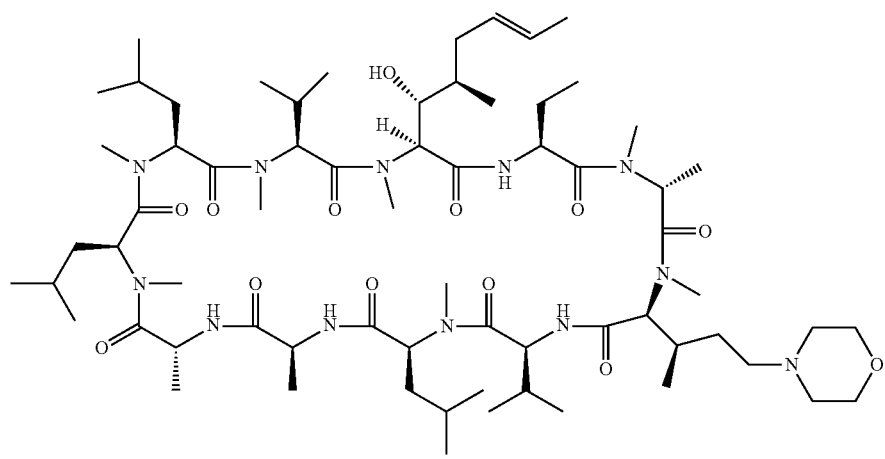
2.18.1
Step 1-2. Synthesis of tert-butyl((1S,2R,E)-1-(furan-2-yl)-4-methoxy-2-methylbut-3-en-1-yl)(methyl)carbamate [2.18.1b] same as 2.13c
Step 3. Synthesis of tert-butyl((1S,2R)-1-(furan-2-yl)-2-methyl-4-oxobutyl)(methyl)carbamate [2.18.1c]
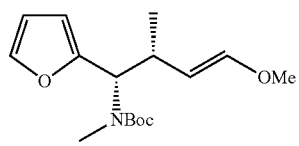
2.18.1b
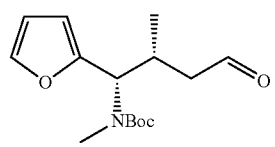
2.18.1c To a solution of 2.18.1b (3.55 g, 12.02 mmol) in acetone was added PPTS (4.53 g, 18.03 mmol, 1.5 equiv). After stirring for 24 hours, the reaction mixture was poured into saturated aqueous NaHCO₃ solution and extracted with EtOAc. The phases were separated and the organic layer was washed with brine, dried over Na₂SO₄, filtered and concentrated. The residue was purified by silica gel chromatography (EtOAc/heptane) to give product 2.18.1c (2.66 g, 79%). ¹H NMR (400 MHz, CDCl₃) δ ppm 9.65 (s, 1H), 7.35 (s, 1H), 6.66-5.96 (br-s, 2H), 5.25-4.78 (m, 1H), 2.80 (m, 1H), 2.72 (s, 3H), 2.72-2.59 (m, 2H), 1.47 (s, 9H), 0.74 (d, J=6.65 Hz, 3H).

Step 4. Synthesis of tert-butyl((1S,2R)-1-(furan-2-yl)-4-hydroxy-2-methylbutyl)(methyl)carbamate [2.18.1d]

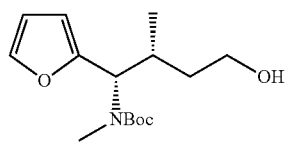

2.18.1d

NaBH₄ (1.8 g, 47.3 mmol, 5.0 equiv) was added to a solution of 2.18.1c (2.66 g, 9.46 mmol) in methanol (38 mL) at 0° C. After stirring for 1 hour, the reaction mixture was diluted with EtOAc, washed with saturated aqueous NH₄Cl, brine, dried over Na₂SO₄, filtered and concentrated. The residue was purified by silica gel chromatography (EtOAc/heptane) to give product 2.18.1d (2 g, 75% yield). ¹H NMR (400 MHz, CDCl₃) δ ppm 7.35 (s, 1H), 6.27 (br-s, 2H), 5.13-4.87 (d, J=9.78 Hz, 1H), 3.67 (m, 2H), 2.68 (s, 3H), 2.32 (m, 1H), 1.47 (s, 9H), 1.27 (m, 2H), 0.88 (d, J=6.65 Hz, 3H).

Step 5. Synthesis of tert-butyl((1S,2R)-4-((tert-butyldiphenylsilyl)oxy)-1-(furan-2-yl)-2-methylbutyl)(methyl)carbamate [2.18.1e]

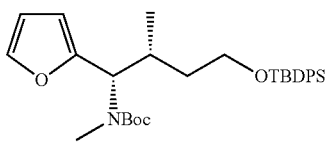

2.18.1e

To a solution of 2.18.1d (1.87 g, 6.60 mmol) in DMF (9.7 mL) at 0° C. was added imidazole (988 mg, 14.52 mmol, 2.2 equiv) and TBDPSCl (2.18 g, 7.92 mmol, 1.2 equiv). After stirring at room temperature for 12 hours, the reaction mixture was diluted with EtOAc (20 mL) and washed sequentially with water (5 mL), aqueous 1.0 M HCl solution, saturated aqueous NaHCO₃ solution and brine. The organic layer was dried over Na₂SO₄ and concentrated. The residue was purified by silica gel column chromatography (EtOAc/heptane) to give product 2.18.1e (3.55 g, yield 100%).

Step 6. Synthesis of (1S,2R)-4-((tert-butyldiphenylsilyl)oxy)-1-(furan-2-yl)-N,2-dimethylbutan-1-amine [2.18.1f]

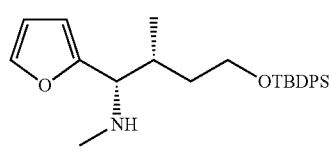

2.18.1f

To a solution of 2.18.1e in dioxane (4.8 mL) at 0° C. was added HCl in dioxane (4.0 M, 3.6 mL, 14.4 mmol, 15 equiv.). After stirring for 6 hours, the reaction mixture was diluted with DCM (30 mL) and washed with saturated aqueous NaHCO₃, brine, dried over Na₂SO₄ and concentrated to give product 2.18.1f (385 mg, 95%). The crude material was used in the next step with no further purification.

Step 7. Synthesis of Benzyl((S)-1-(((1S,2R)-4-((tert-butyldiphenylsilyl)oxy)-1-(furan-2-yl)-2-methylbutyl)(methyl)amino)-1-oxopropan-2-yl)(methyl)carbamate [2.18.1g]

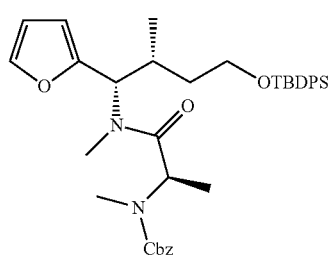

2.18.1g

To a solution of (R)-2-(((benzyloxy)carbonyl)(methyl)amino)propanoic acid (433 mg, 1.8 mmol, 2.0 equiv) in DCM (9 mL) was added DIPEA (2.3 mL, 4.57 mmol, 5.0 equiv) and HATU (694 mg, 1.8 mmol, 2.0 equiv). The mixture was stirred for 10 minutes after which 2.18.1g (385 mg, 0.92 mmol) was added. After stirring at room temperature for 4 hours, the reaction mixture was diluted with DCM (50 mL), washed with water and brine. The organic layer was dried over Na₂SO₄ and concentrated. The resulting residue was purified by silica gel column chromatography (heptane/acetone) to give product 2.18.1g (242.0 mg, 41% yield). MS m/z (M+1) 641.5.

Step 8. Synthesis of (2S,3R)-2-((S)-2-(((benzyloxy)carbonyl)(methyl)amino)-N-methylpropanamido)-5-((tert-butyldiphenylsilyl)oxy)-3-methylpentanoic acid [2.18.1 h]

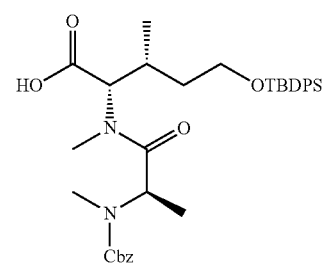

2.18.1h

To a stirred mixture of NaIO$_4$ (485.0 mg, 2.30 mmol, 6.0 equiv) in H$_2$O/CCl$_4$/CH$_3$CN (3/2/3, 10.4 mL) was added RuCl$_3$ (26.6 mg, 0.13 mmol, 0.34 equiv) and the mixture was stirred vigorously for 15 minutes. To the mixture was then added a solution of 2.18.1g (242.0 mg, 0.38 mmol) in CH$_3$CN (3 mL). After stirring for 15 minutes, the reaction mixture was diluted with water and extracted with EtOAc. The combined organic layer was washed with saturated aqueous NaHSO$_3$ solution, brine, dried over Na$_2$SO$_4$, and concentrated to give product 2.18.1h (242.0 mg) which was used for the next step without further purification. MS m/z (M+1) 619.4.

Step 9. Synthesis of [2.18.1i]

DIPEA (191 mg, 0.258 mL, 1.48 mmol, 4 equiv), HATU (183 mg, 0.48 mmol, 1.3 equiv) and HOAT (65.3 mg, 0.48 mmol, 1.3 equiv) were added to a solution of 2.18.1i (240 mg, 0.39 mmol, 1.05 equiv) in DCM (3.7 mL). The resulting mixture was stirred at 0° C. for 10 minutes, after which amine 1 (430 mg, 0.37 mmol) was added. After stirring for 3 hours at room temperature, the reaction mixture was diluted with DCM (20 mL), washed with water and brine. The organic layer was dried over Na$_2$SO$_4$ and concentrated. The residue was purified by silica gel column chromatography (acetone/heptane) to give product 2.8.1i (545 mg, 84% yield). MS m/z (M+Na) 1765.1.

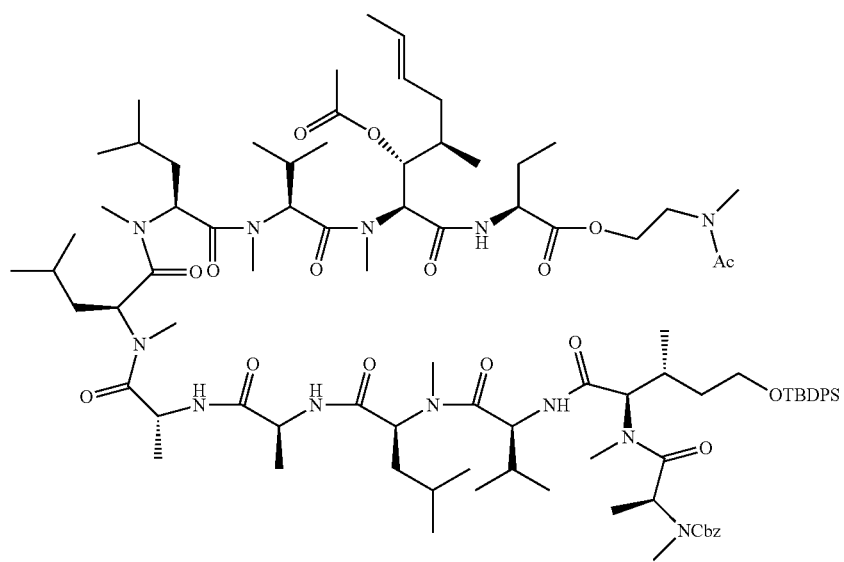

2.8.1i

Step 10. Synthesis of [2.18.1j]

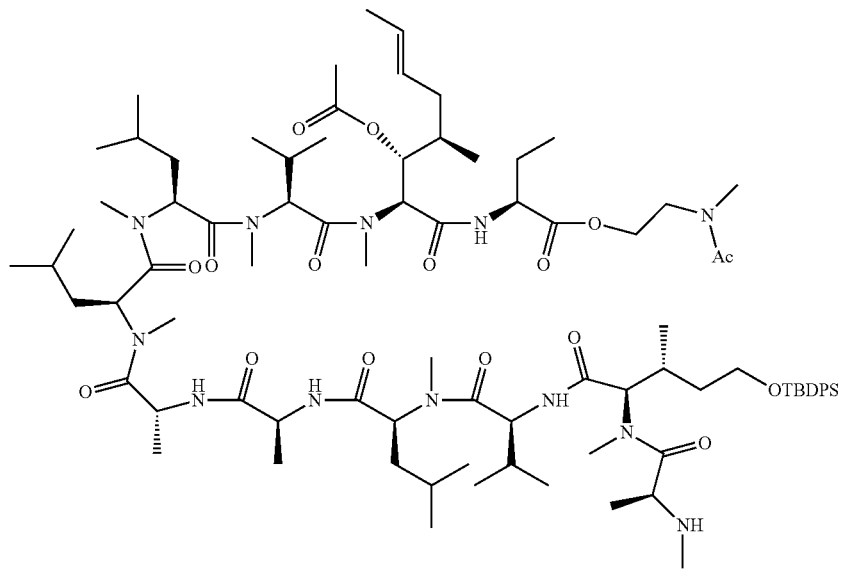

2.18.1j

To a solution of 2.18.1i (545 mg, 0.31 mmol) in DCM (3 mL) was added triethylsilane (1.7 mL, 10.8 mmol, 35.0 equiv), triethylamine (0.366 ml, 2.63 mmol, 8.5 equiv), and palladium(II) acetate (69.3 mg, 0.31 mmol, 1.0 equiv). After stirring at room temperature for 1 hour, the reaction mixture was quenched with saturated aqueous ammonium chloride solution and filtered through celite. The filtrate was diluted with DCM and washed with saturated aqueous NaHCO$_3$ solution. The combined organic layer was dried over Na$_2$SO$_4$, filtered and concentrated to give product 2.18.1j (504 mg). The crude material was used in the next step with no further purification. MS m/z (M+1) 1631.2.

Step 11. Synthesis of [2.18.1k]

To a solution of 2.18.1j (504.0 mg, 0.31 mmol) in THF/Water (1/1, 3.2 mL) at 0° C. was added LiOH.H$_2$O (64.9 mg, 1.6 mmol, 5.0 equiv). After stirring at 0° C. for 1.5 hours, the reaction mixture was diluted with DCM. The mixture was then washed with aqueous 1.0 N HCl solution and brine. The separated organic layer was dried with Na$_2$SO$_4$, filtered and concentrated to give product 2.18.1k (516.0 mg), which was used in the next step without further purification. MS m/z (M+1) 1531.9.

2.18.1k

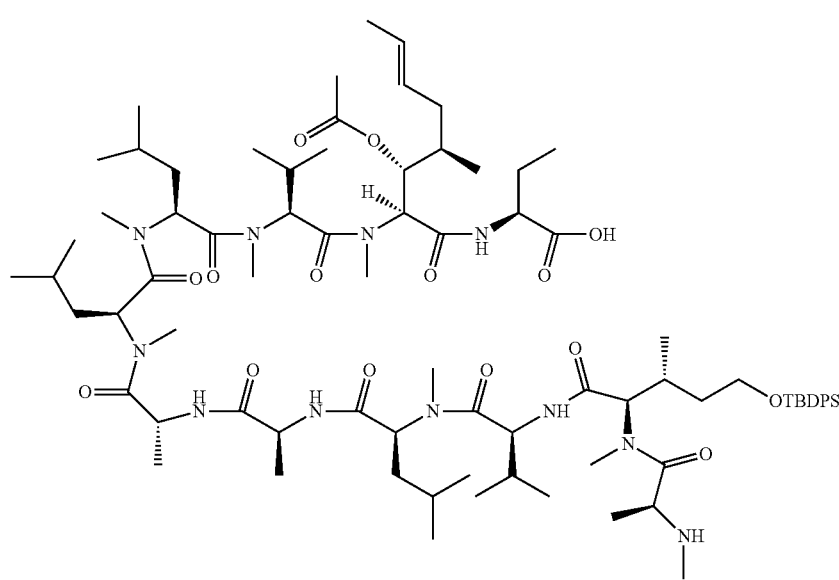

Step 12. Synthesis of 2.18.1l 2.18.1l

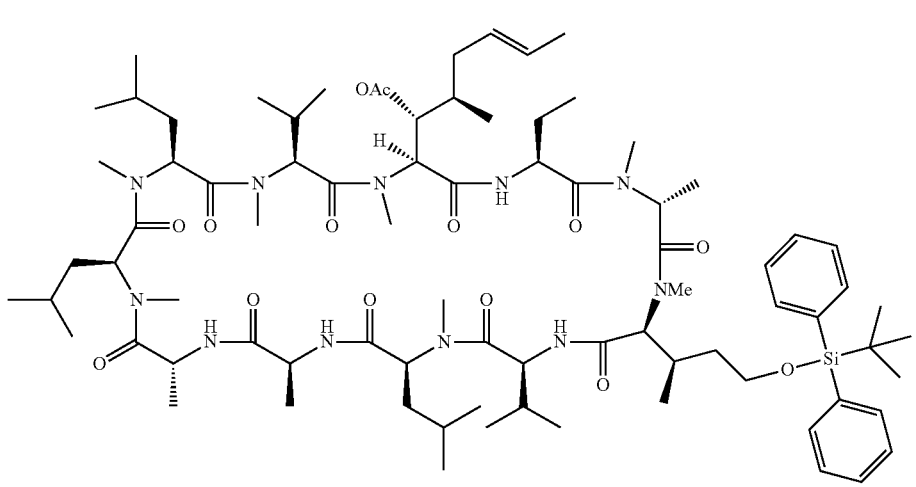

To a suspension of BOP (298 mg, 0.674 mmol, 2.0 equiv) in DCM (96 ml) at 0° C. was added a solution of 2.18.1k (516 mg, 0.337 mmol) and DMAP (82 mg, 0.67 mmol, 2.0 equiv) in DCM (241 mL) via additional funnel over a period of 3 hours. After stirring at room temperature for 24 hours, the reaction solution was concentrated and the residue was purified by silica gel chromatography (acetone/DCM) to give product 2.18.1l (478 mg, 94% yield). MS m/z (M+23) 1536.0.

Step 13. Synthesis of 2.18.1m

To a solution of oxalyl chloride (0.052 mL, 0.593 mmol, 20.0 equiv) in DCM was added DMSO (0.130 mL, 1.83 mmol, 61.0 equiv) at −78° C. After 15 minutes, a solution of 2.18.1m (38.0 mg, 0.030 mmol) in DCM (1.0 mL) was added and the resulting solution was stirred at −78° C. for 1 hour. To the solution was then added triethylamine (0.145 mL, 1.04 mmol, 35.0 equiv) and the solution was stirred at −78° C. to 0° C. for 1.5 hours before was quenched with

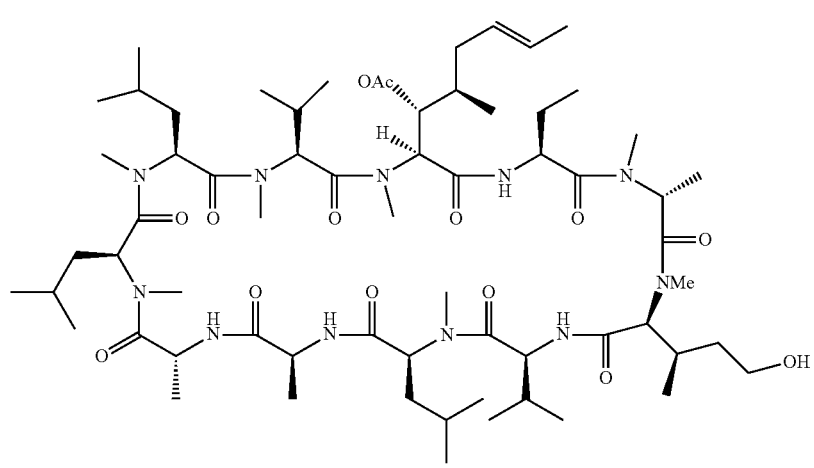

2.18.1m

To a solution of 2.18.1l (478.0 mg, 0.32 mmol) in THF (3.2 mL) was added TBAF (1.0 M in THF, 1.90 mL, 1.90 mmol, 6.0 equiv) at room temperature. After stirring at room temperature for 12 hours, the reaction solution was diluted with DCM and washed with brine, dried over Na$_2$SO$_4$ and concentrated. The residue was purified by silica gel chromatography to give product 2.18.1m (200 mg, 50% yield). MS m/z (M+1) 1275.9.

Step 14. Synthesis of 2.18.1n saturated aqueous NH$_4$Cl solution. The phases were separated and the aqueous layer was extracted with DCM. The combined organic layer was washed with brine, dried over Na$_2$SO$_4$, filtered and concentrated to give product 2.18.1n (38.0 mg) which was used in the next step without further purification. MS m/z (M+1) 1272.9.

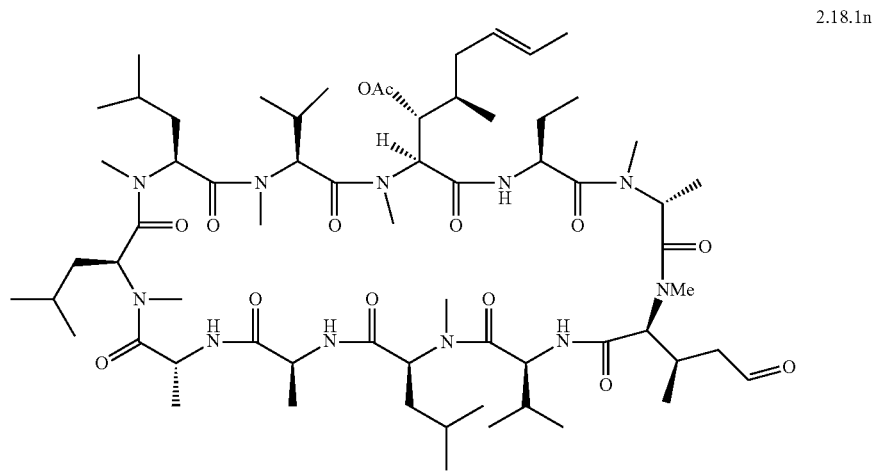 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)CC=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.18.1n

Step 15. Synthesis of 2.18.1o

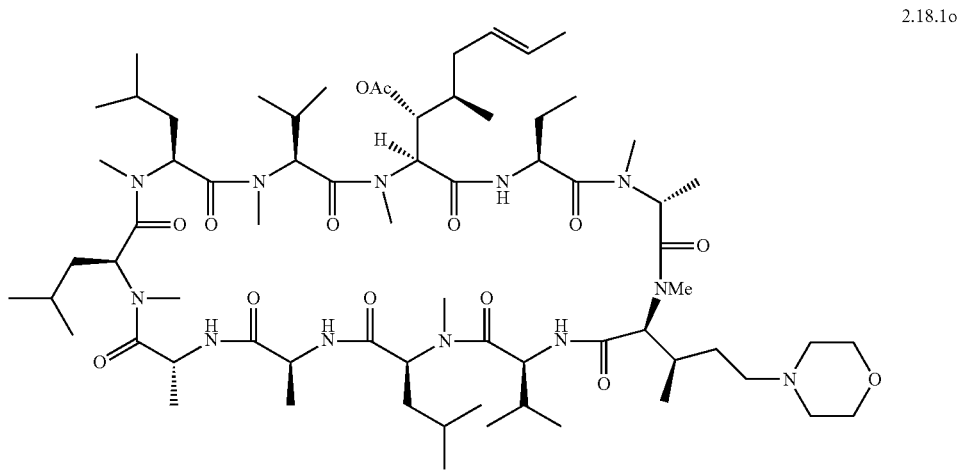 [SMILES: C/C=C/C[C@@H](C)[C@@H](OC(C)=O)[C@H]1C(=O)N[C@@H](CC)C(=O)N(C)[C@H](C)C(=O)N(C)[C@@H]([C@H](C)CCN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.18.1o

To a solution of 2.18.1n (38.0 mg, 0.030.0 mmol) in dichloroethane (1.5 mL) at room temperature was added morpholine (23.4 mg, 0.270 mmol, 9.0 equiv) and acetic acid (15 mL, 0.270 mmol, 9.0 equiv) followed by sodium triacetoxyborohydride (57.0 mg, 0.270 mmol, 9.0 equiv). After stirring the reaction mixture for 12 hours, the reaction was quenched at 0° C. with saturated aqueous $NH_4Cl$. The phases were separated and the aqueous layer was extracted with methylene chloride. The combined organic layer was washed with brine, dried with $Na_2SO_4$, filtered and concentrated to give product 2.18.1o (38 mg), which was used in the next step with no further purification. MS m/z (M+1) 1345.6.

Step 16. Synthesis of 2.18.1

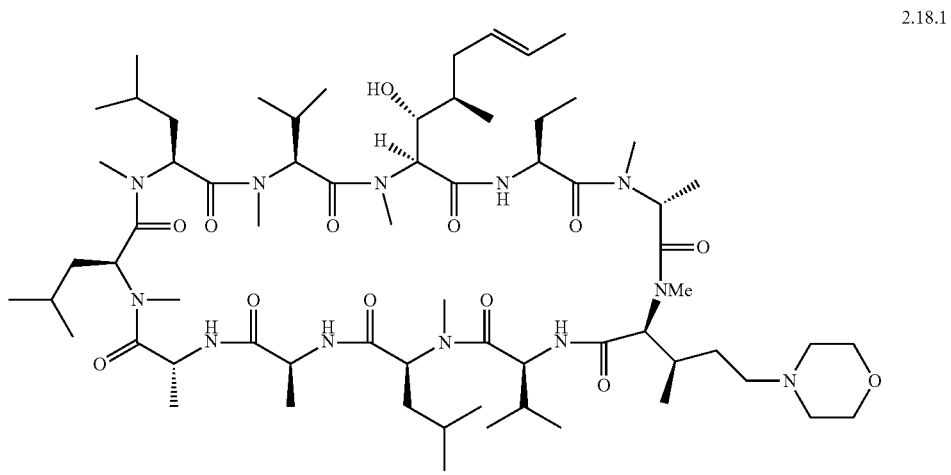 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2.18.1

To a solution of 2.18.1o (40.0 mg, 0.030 mmol) in MeOH (1 mL) at 0° C. was added tetramethylammonium hydroxide (25% in MeOH, 0.031 mL, 0.398 mmol, 10.0 equiv). After stirring for 2 hours at room temperature, the reaction mixture was quenched with saturated aqueous $NaHSO_4$ solution. The phases were separated and the aqueous layer was extracted with DCM. The combined organic layer was washed with brine, dried over $Na_2SO_4$ and concentrated. The residue was purified by reverse phase HPLC to give product 2.18.1 (2.2 mg). HRMS m/z 1301.9152.

II.18.2 Synthesis of 2.18.2
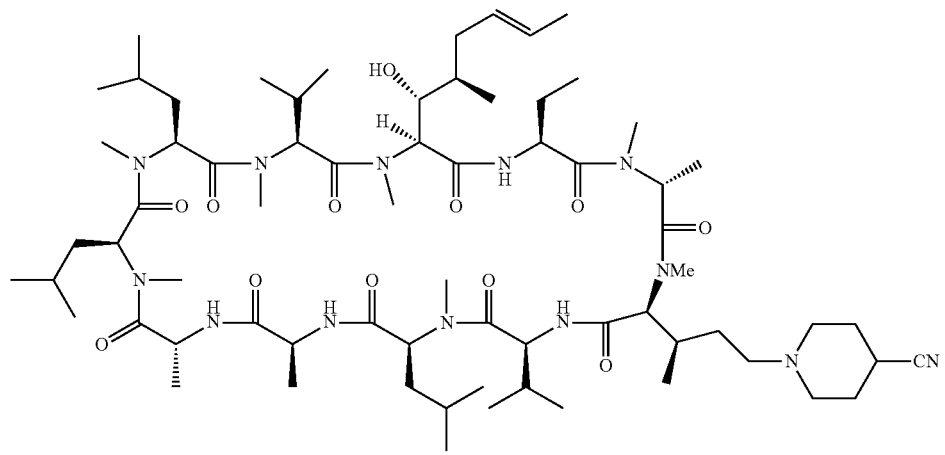
2.18.2
Compound 2.18.2 was prepared following the procedures described for the synthesis of 2.18.1 using piperidine-4-carbonitrile in Step 15. MS m/z (M+1) 1324.9
II.18.3 Synthesis of 2.18.3
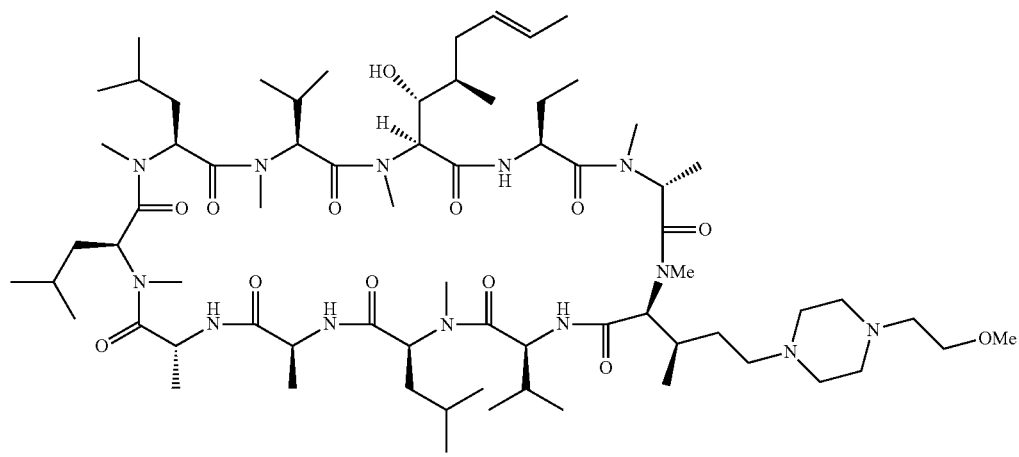
2.18.3
Compound 2.18.3 was prepared following the procedures described for the synthesis of 2.18.1 using 1-(2-methoxyethyl)piperazine in Step 15. HRMS m/z 1358.973.
II.18.4 Synthesis of 2.18.4
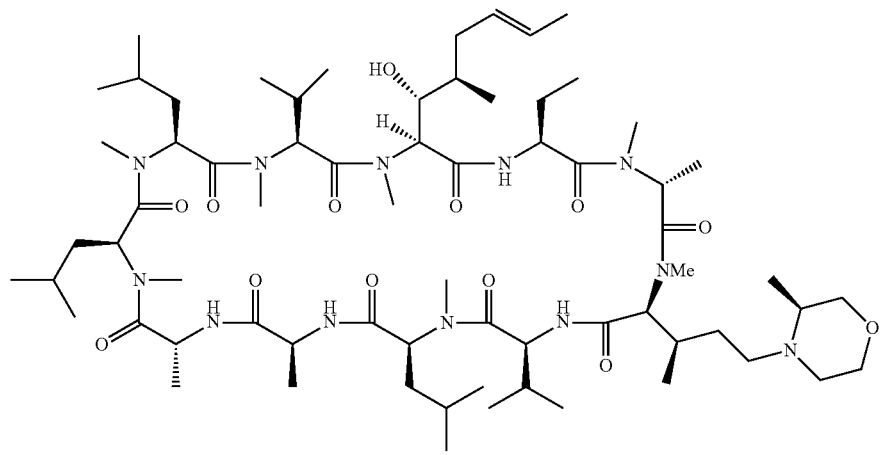
2.18.4

Compound 2.18.4 was prepared following the procedures described for the synthesis of 2.18.1 using (S)-3-methylmorpholine in Step 15. HRMS m/z 1315.9314.

II.18.5 Synthesis of 2.18.5

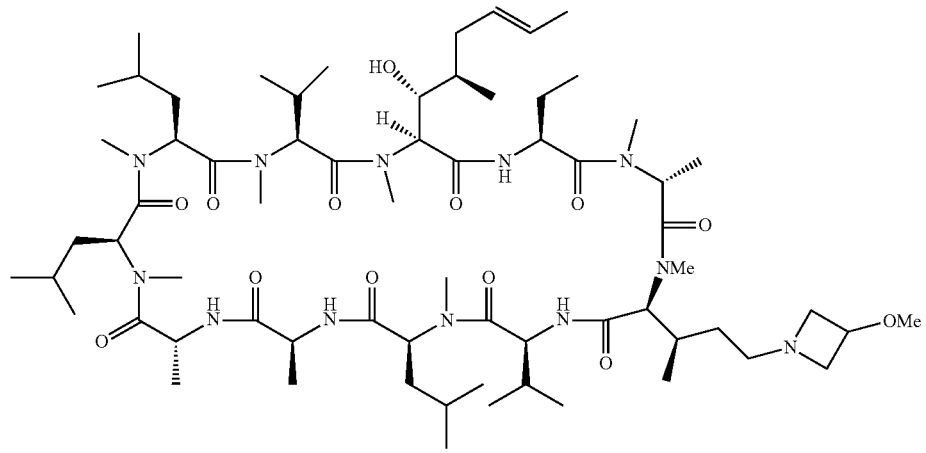

2.18.5

Compound 2.18.5 was prepared following the procedures described for the synthesis of 2.18.1 using 3-methoxyazetidine in Step 15. HRMS m/z 1301.9180.

II.18.6 Synthesis of 2.18.6

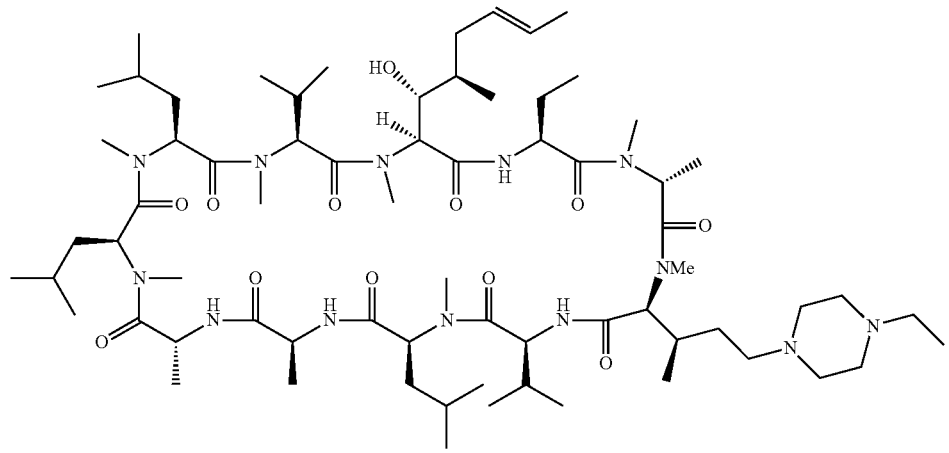

2.18.6

Compound 2.18.6 was prepared following the procedures described for the synthesis of 2.18.1 using 1-ethylpiperazine in Step 15. HRMS m/z 1328.9635.

II.18.7 Synthesis of 2.18.7
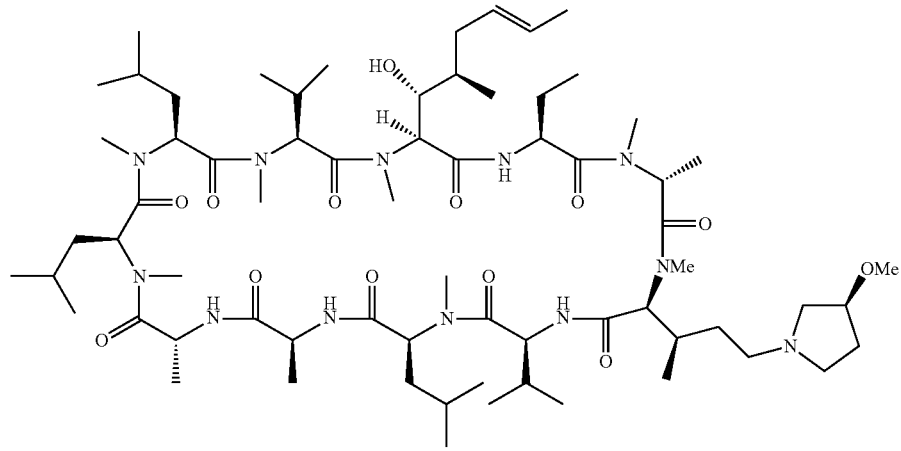
2.18.7
Compound 2.18.7 was prepared following the procedures described for the synthesis of 2.18.1 using (S)-3-methoxypyrrolidine in Step 15. HRMS m/z 1315.9327.
II.18.8 Synthesis of 2.18.8
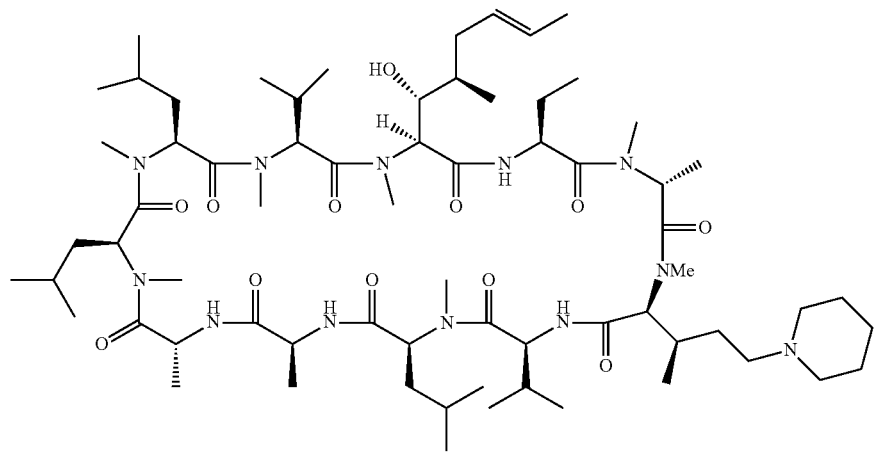
2.18.8
Compound 2.18.8 was prepared following the procedures described for the synthesis of 2.18.1 using piperidine in Step 15. HRMS m/z 1299.9364.

II.18.9 Synthesis of 2.18.9
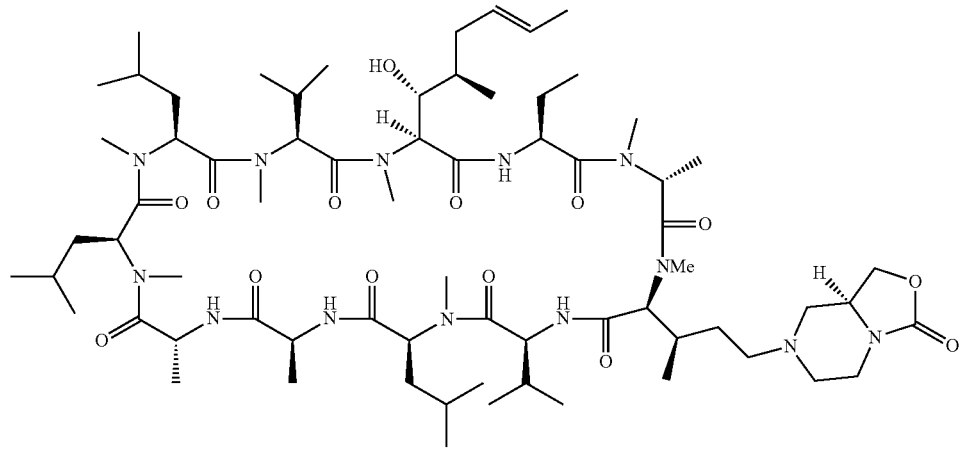
2.18.9
Compound 2.18.9 was prepared following the procedures described for the synthesis of 2.18.1 using (S)-tetrahydro-1H-oxazolo[3,4-a]pyrazin-3(5H)-one in Step 15. HRMS m/z 1356.9219.
II.18.10 Synthesis of 2.18.10
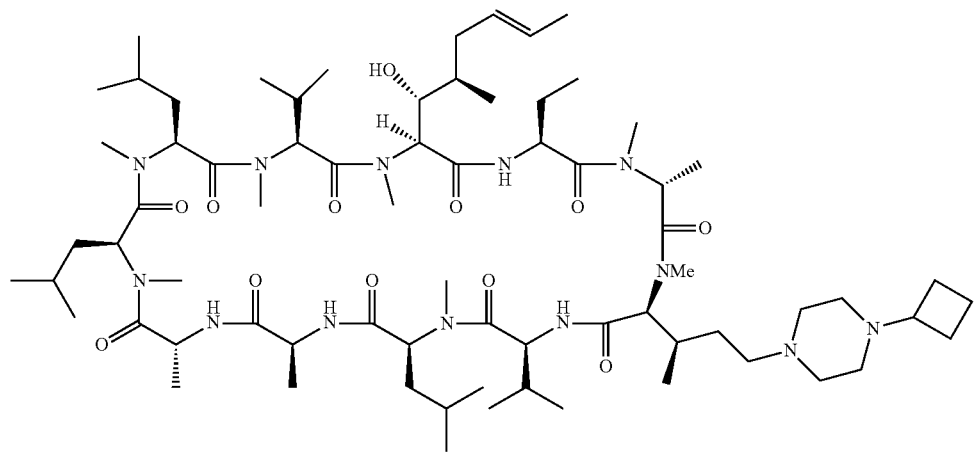
2.18.10
Compound 2.18.10 was prepared following the procedures described for the synthesis of 2.18.1 using 1-cyclobutylpiperazine in Step 15. HRMS m/z 1354.9783.

II.19.1 Synthesis of compound 2.19.1

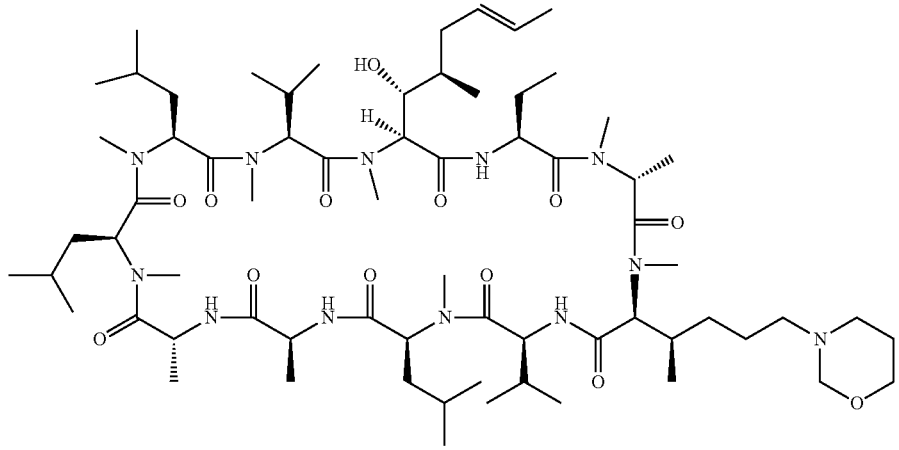

2.19.1

Step 1. Synthesis of tert-butyl((1S,2R)-1-(furan-2-yl)-5-hydroxy-2-methylpentyl)-(methyl)carbamate [2.19.1a]

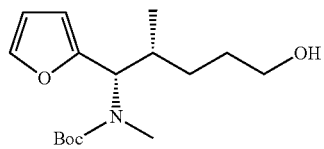

2.19.1a

To a solution of compound 2.12d (0.6 g, 1.77 mmol) in THF (3.5 mL) was added lithium borohydride (2.0 M in THF, 8.8 mL, 17.7 mmol, 10.0 equiv) and the resulting mixture was stirred at 50° C. for 1 hour. The reaction mixture was cooled at room temperature and EtOAc (2.0 mL) was added. After stirring for 10 minutes, the reaction mixture was quenched by addition of 1.0 N HCl aqueous solution. The phases were separated and the aqueous layer was extracted with DCM. The organic layer was dried over sodium sulfate, filtered and concentrated to give product 2.19.1a (0.54 g) which was used in the next step with no further purification. MS m/z (M+Na) 320.2

Step 2. Synthesis of tert-butyl((1S,2R)-5-((tert-butyldiphenylsilyl)oxy)-1-(furan-2-yl)-2-methylpentyl)(methyl)carbamate [2.19.1 b]

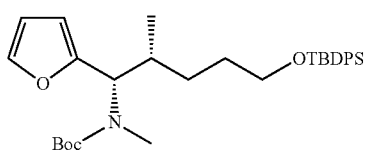

2.19.1b

To a solution of 2.19.1a (0.622 g, 2.09 mmol) in DCM (5.5 mL) at room temperature was added imidazole (0.21 g, 3.14 mol, 1.5 equiv) and TBDPS-Cl (0.62 ml, 2.4 mmol, 1.15 equiv). After stirring for 2 hours at room temperature, the reaction mixture was diluted with DCM and washed with 1.0 M sulfuric acid aqueous solution, dried over Na$_2$SO$_4$, filtered and concentrated. The residue was purified by silica gel chromatography (EtOAc/heptane) to give product 2.19.1b (1 g, 89%). MS m/z (M+Na) 558.4.

Step 3. Synthesis of (9H-fluoren-9-yl)methyl((R)-1-(((1S,2R)-5-((tert-butyldiphenylsilyl)-oxy)-1-(furan-2-yl)-2-methylpentyl)(methyl)amino)-1-oxopropan-2-yl)(methyl)carbamate [2.19.1c]

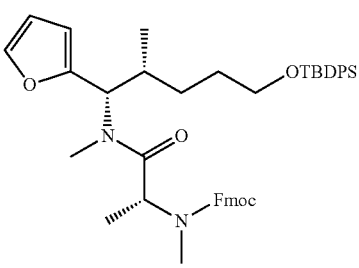

2.19.1c

To a solution of 2.19.1b (520 mg, 0.97 mmol) in DCM (1.0 mL) at 0° C. was added 4.0 M HCl in dioxane (2.4 mL). After stirring at 0° C. for 2 hours, the reaction mixture was concentrated to give the de-boc intermediate which was used in the next step without further purification. To a solution of de-boc intermediate in DCM (2.0 mL) at 0° C. was added Fmoc-N-Me-D-Ala-OH (411 mg, 1.26 mmol, 1.3 equiv) followed by HATU (498.0 mg, 1.31 mmol, 1.35 equiv) and DIPEA (0.51 ml, 2.91 mmol, 3.0 equiv). After stirring at room temperature for 12 hours, the reaction mixture was concentrated and the residue was purified on silica gel chromatography (EtOAc/heptane) to give product 2.19.1c (370 mg, 51%). MS m/z (M+Na) 765.5

Step 4. Synthesis of (2S,3R)-2-((R)-2-((((9H-fluoren-9-yl)methoxy)carbonyl)(methyl)amino-)N-methylpropanamido)-6-((tert-butyldiphenylsilyl)oxy)-3-methylhexanoic acid [2.19.1d]

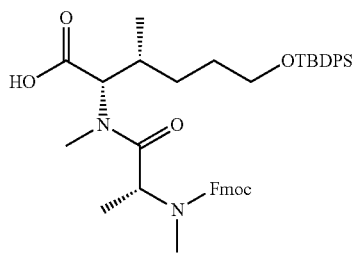

2.19.1d

To a mixture of 2.19.1c (370.0 mg, 0.498 mmol) in heptane/ethyl acetate/water (3/1/4, 40 mL) at room temperature was added sodium periodate (669.0 mg, 3.13 mmol, 7.0 equiv) followed by RuCl$_3$ (75.0 mg, 0.29 mmol, 0.64 equiv). After stirring at room temperature for 45 minutes, the reaction mixture was filtered through Celite. The filtrate was diluted with water and extracted with EtOAc. The combined organic layers were washed with saturated aqueous sodium bisulfite solution and brine. The organic layer was dried over sodium sulfate and concentrated to give product 2.19.1d (359.0 mg) which was used in the next step with no further purification. MS m/z (M+1) 721.5

Step 5. Synthesis of 2.19.1e

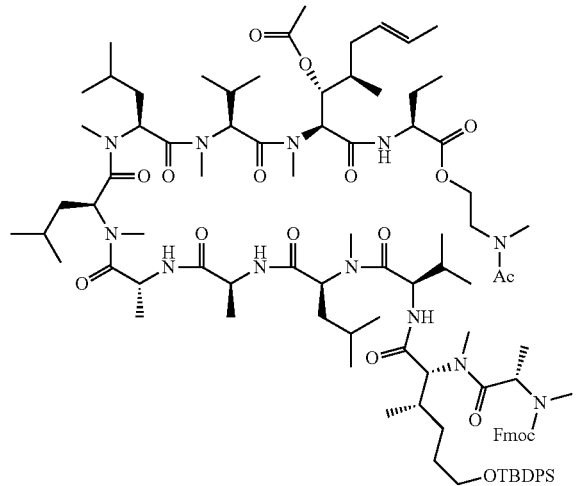

2.19.1e

To a solution of 2.19.1d (359.0 mg, 0.498 mmol) in DCM (5 mL) at 0° C. was added amine 1 (580.0 mg, 0.5 mmol) followed by NMM (0.27 ml, 2.49 mmol, 5.0 equiv), HOBt (114 mg. 0.747 mmol, 1.5 eq) and EDCI (143 mg, 0.747 mmol, 1.5 equiv). The reaction mixture was slowly warmed to room temperature and stirred at this temperature for 12 hours. The solvent was then removed under vacuum and the residue was purified by silica gel chromatography (acetone/DCM) to give product 2.19.1e (660.0 mg, 71% yield). MS m/z (M+Na) 1889.1

Step 6. Synthesis of 2.19.1f

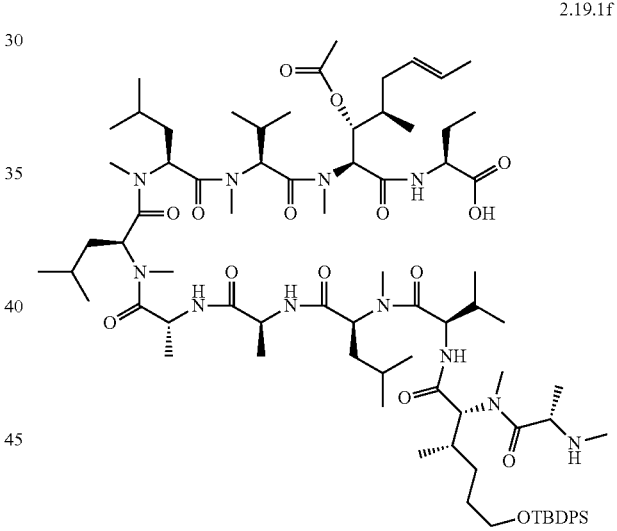

2.19.1f

To a solution of 2.19.1e (360 mg, 0.19 mmol) in THF/Water (3/2, 5.0 mL) at 0° C. was added LiOH.H$_2$O (139 mg, 5.79 mmol, 30 equiv). After stirring at 0° C. for 2 hours, the reaction mixture was quenched with saturated aqueous KHSO$_4$ solution (10 mL) and extracted with DCM. The combined organic layer was dried over Na$_2$SO$_4$, filtered and concentrated to give product 2.19.1f (320 mg) which was used in the next step with no further purification. MS m/z (M+1) 1545.8

Step 7. Synthesis of 2.19.1g

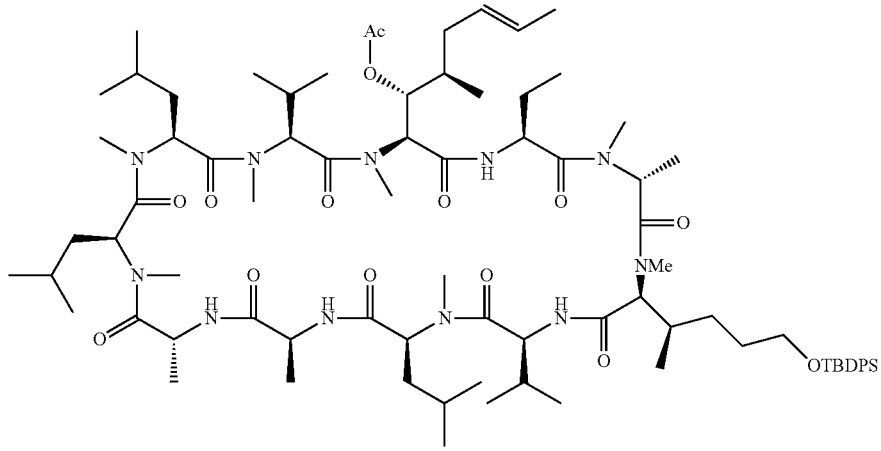

2.19.1g

To a solution of BOP (171.0 mg, 0.386 mmol, 2.0 equiv) in DCM (30 ml) at room temperature was added a solution of compound 2.19.1f (298.0 mg, 0.193 mmol) and DMAP (47.0 mg, 0.386 mmol, 2.0 equiv) in DCM (70 mL) via additional funnel over a period of 30 minutes. After stirring at room temperature for 24 hours, the reaction mixture was concentrated and the residue was purified by silica gel chromatography (acetone/DCM) to give product 2.19.1g (280 mg). MS m/z (M+23) 1550.0

Step 8. Synthesis of 2.19.1h

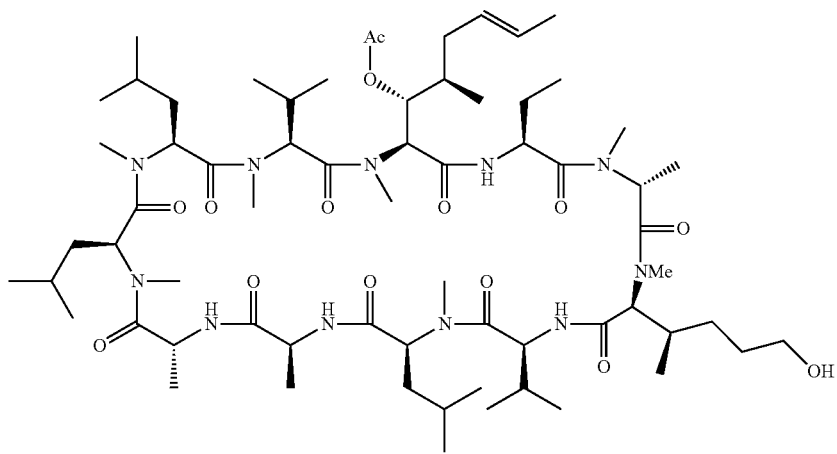

2.19.1h

To a solution of 2.19.1g (295.0 mg, 0.193 umol) in THF (1.5 mL) at room temperature was added TBAF (1.0 M in THF, 5.8 ml, 1.0 mmol, 30 equiv). After stirring at room temperature for 12 hours, the reaction mixture was diluted with DCM, washed with saturated aqueous $KHSO_4$ solution and brine, dried with $Na_2SO_4$, filtered and concentrated. The residue was purified by silica gel chromatography (MeOH/DCM) to give product 2.19.1h (138.0 mg, 56% yield). MS m/z (M+Na) 1311.9

Step 9. Synthesis of 2.19.1i

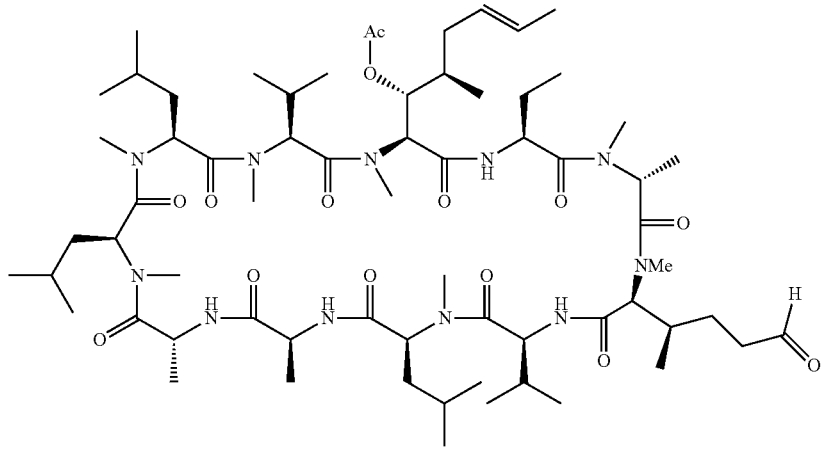

2.19.1i

To a solution of oxalyl chloride (0.087 ml, 0.99 mmol, 16 equiv) in DCM (4.0 mL) at −78° C. was added DMSO (0.14 ml, 1.99 mmol, 32 equiv) and the solution was stirred at −78° C. for 15 minutes. To this solution was then added a solution of 2.19.1h (80.0 mg, 0.062 mmol) in DCM (0.5 mL) followed by triethylamine (0.3 mL, 2.2 mmol, 35.0 equiv). After stirring at −78° C. for 15 minutes and room temperature for 15 minutes, the reaction mixture was diluted with DCM, washed with brine, dried over $Na_2SO_4$, filtered and concentrated to give product 2.19.1i (80 mg) which was used in the next step with no further purification. MS m/z (M+1) 1309.8

Step 10. Synthesis of 2.19.1j

To a solution of 2.19.1i in dichloroethane (1.5 mL) at room temperature was added morpholine (0.049 mL, 0.56 mmol, 9.0 equiv), acetic acid (0.032 mL, 0.56 mmol, 9.0 equiv) and sodium triacetoxyborohydride (118 mg, 0.56 mmol, 9.0 equiv). After stirring at room temperature for 1 hour, the reaction mixture was quenched with saturated aqueous $NaHCO_3$ (5 mL). The phases were separated and the aqueous layer was extracted with DCM. The combined organic layers were dried with $Na_2SO_4$, filtered and concentrated to give product 2.19.1j (84 mg) which was used in the next step with no further purification. MS m/z (M+1) 1358.8

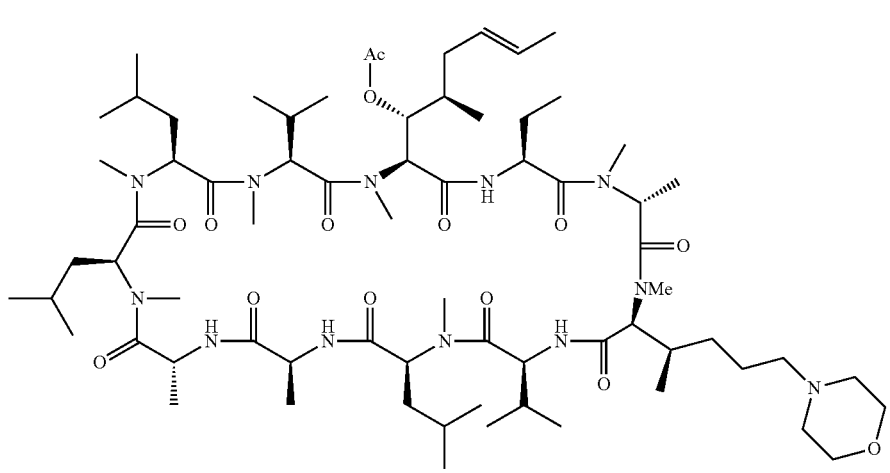

2.19.1j

Step 11. Synthesis of 2.19.1

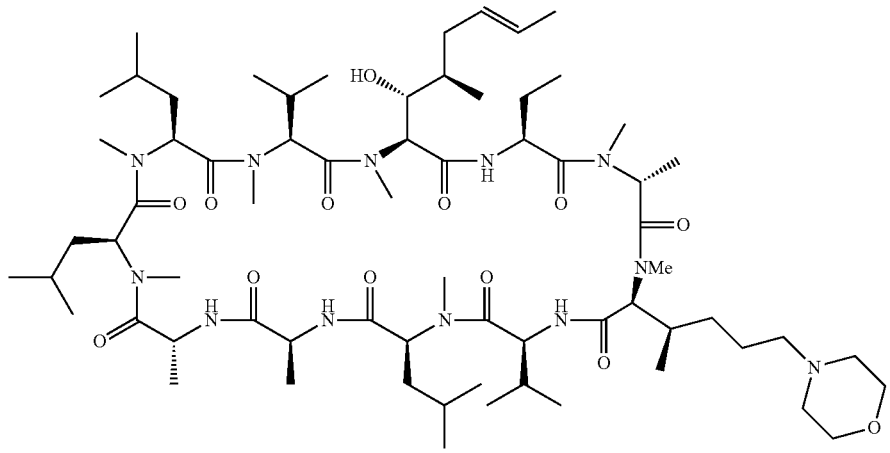

2.19.1

To a solution of 2.19.1j (84 mg, 0.062 mmol) in MeOH (1 mL) at 0° C. was added tetramethylammonium hydroxide (25% in methanol, 1.1 g, 3 mmol, 50.0 equiv). After stirring at 0° C. for 1 hours, the reaction mixture was quenched with saturated aqueous KHSO$_4$ solution (2 mL) and extracted with DCM. The combined organic layer was washed with brine, dried over Na$_2$SO$_4$, filtered and concentrated in vacuo. The residue was purified by reverse phase HPLC to give product 2.19.1 (14 mg, 17% yield). HRMS m/z (M+1) 1315.9336 (calculated 1315.9333)

II.19.2 Synthesis of 2.19.2

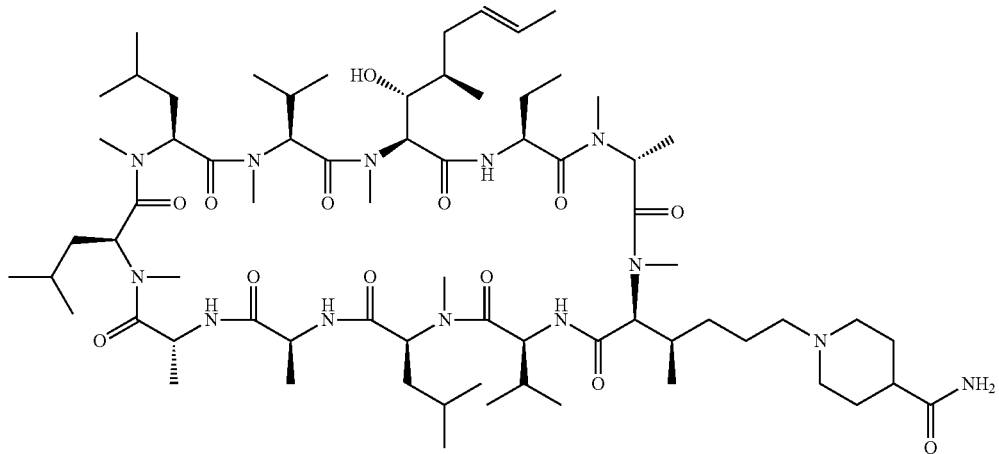

2.19.2

Compound 2.19.2 was prepared following the procedures described for the synthesis of 2.19.1 using piperidine-4-carboxamide in Step 10. HRMS m/z (M+1) 1356.9602 (calculated 1356.9598)

II.19.3 Synthesis of Compound 2.19.3
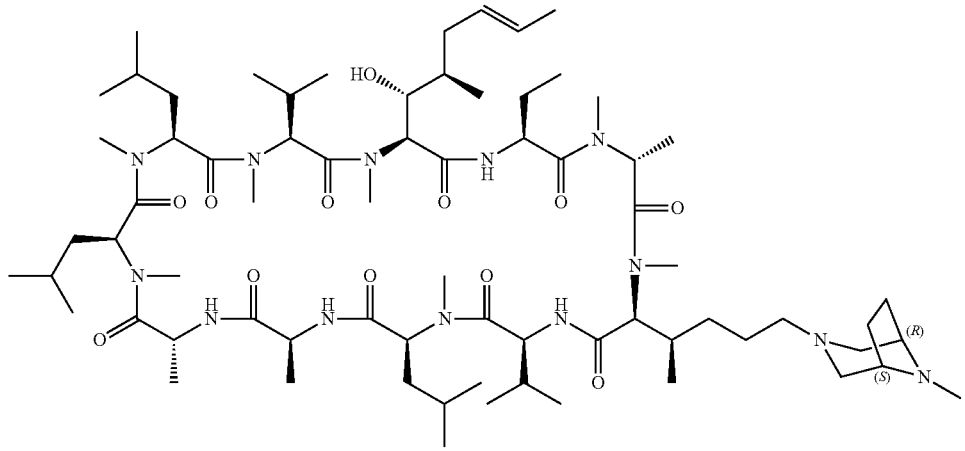
2.19.3
Compound 2.19.3 was prepared following the procedures described for the synthesis of 2.19.1 using 8-methyl-3,8-diazabicyclo[3.2.1]octane in Step 10. MS m/z (M+1) 1354.9801 (calculated 1354.9805).
II.19.4 Synthesis of Compound 2.19.4
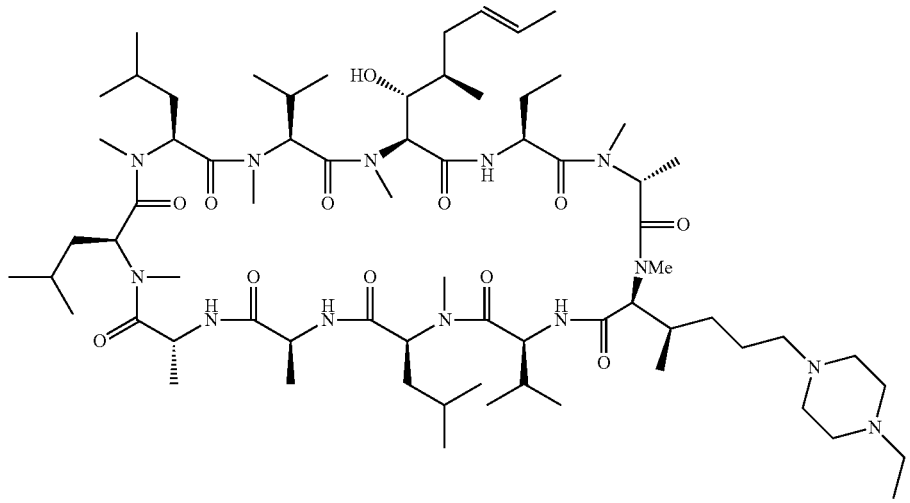
2.19.4
Compound 2.19.4 was prepared following the procedures described for the synthesis of 2.19.1 using 1-ethylpiperazine in Step 10. HRMS m/z (M+1) 1342.9816 (calculated 1346.9805)

II.19.5 Synthesis of Compound 2.19.5
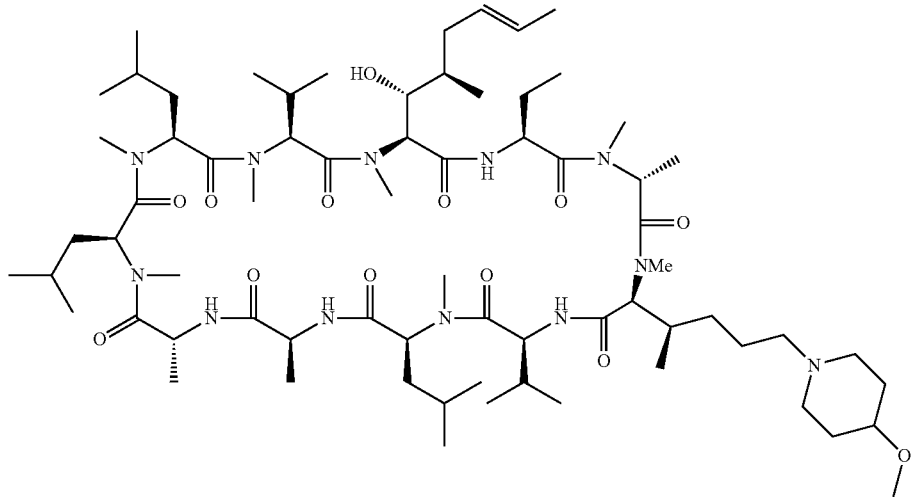
2.19.5
Compound 2.19.5 was prepared following the procedures described for the synthesis of 2.19.1 using 4-methoxypiperidine in Step 10. HRMS m/z (M+1) 1343.9635 (calculated 1343.9646)
II.19.6 Synthesis of 2.19.6
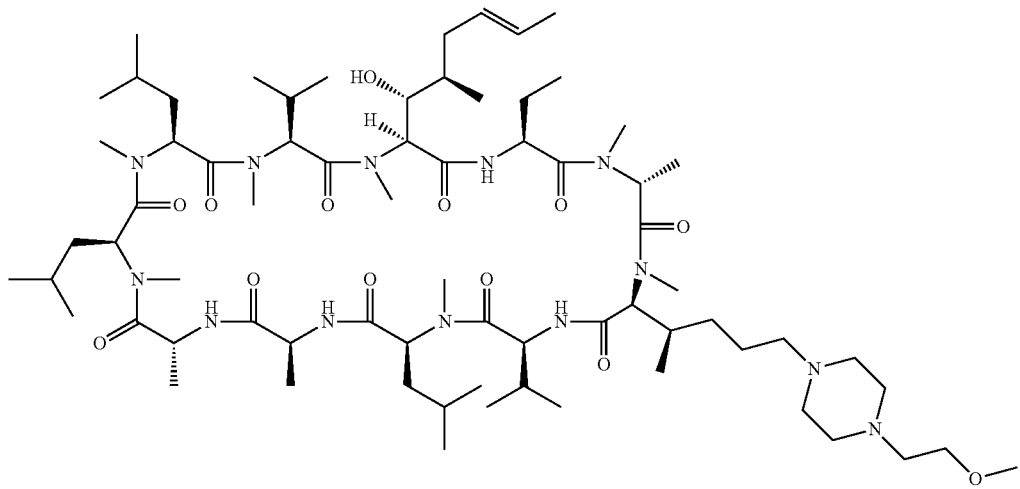
2.19.6
Compound 2.19.6 was prepared following the procedures described for the synthesis of 2.19.1. HRMS m/z (M+1) 1372.9893 (calculated 1372.9911)

II.19. Synthesis of 2.19.7
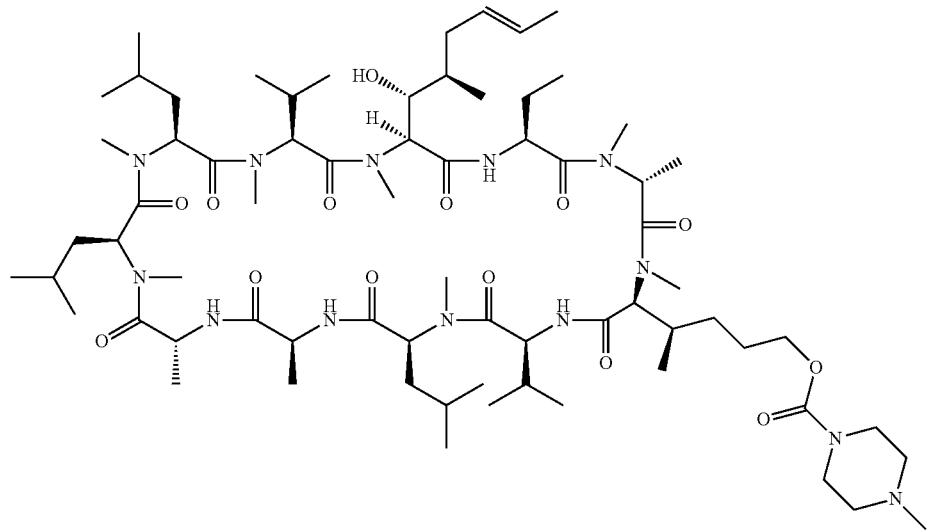
2.19.7
Compound 2.19.7 was prepared following the procedures described for the synthesis of 2.9 using 2.19.1h and 1-methylpiperazine in step 1. HRMS m/z (M+1) 1372.9532 (calculated: 1372.9547)
II.19.8 Synthesis of 2.19.8
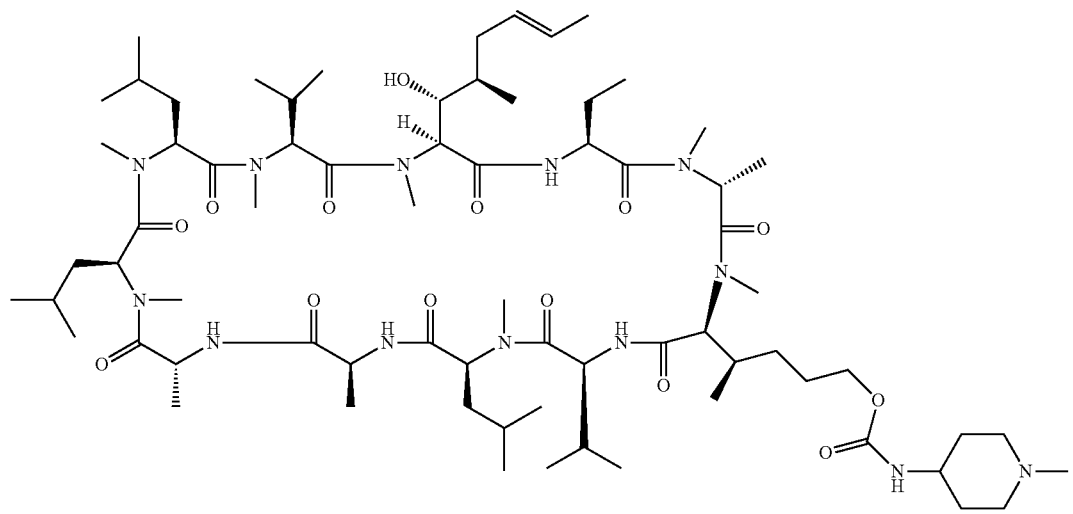
2.19.8
Compound 2.19.8 was prepared following the procedures described for the synthesis of 2.9 using 2.19.1h and 1-methylpiperidin-4-amine in step 1. HRMS m/z (M+1) 1386.9697 (calculated: 1386.9704).

II.19.9 Synthesis of Compound 2.19.9

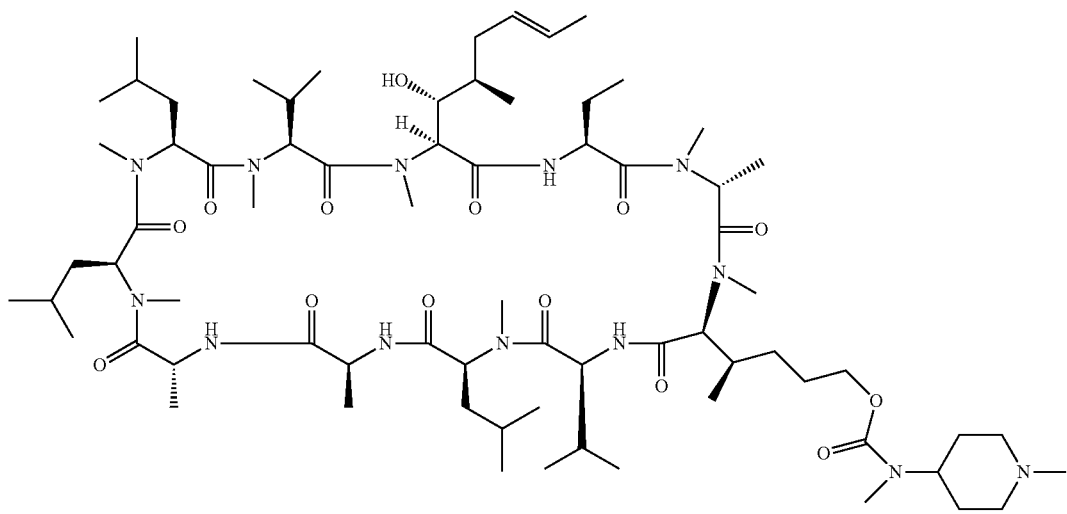

2.19.9

Compound 2.19.9 was prepared following the procedures described for the synthesis of 2.9 using 2.19.1h and N,1-dimethylpiperidin-4-amine in step 1. HRMS m/z (M+1) 1400.9834 (calculated: 1400.9860).

II.20.1 Synthesis of Compound 2.20.1

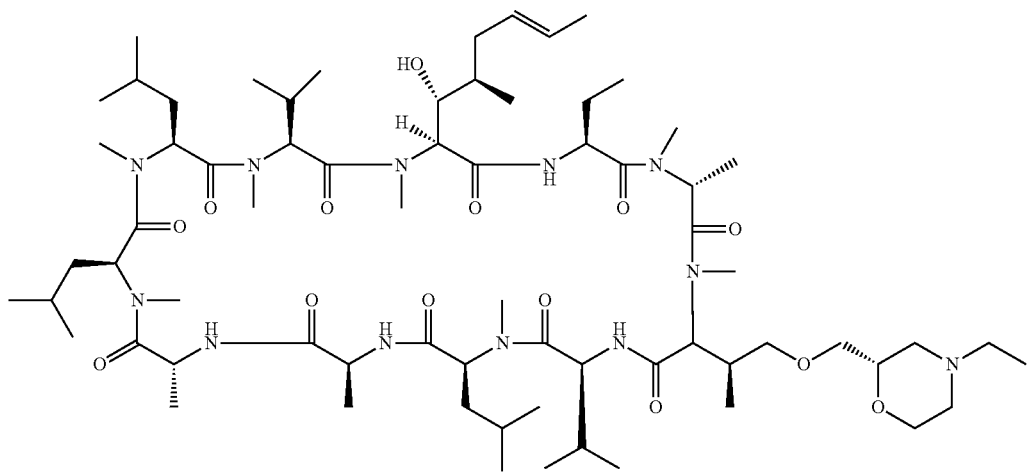

2.20.1

Step 1. Synthesis of (S)-morpholin-2-ylmethanol [2.20.1a]

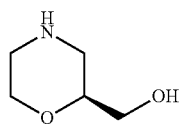

2.20.1a

TFA (1.064 mL, 13.81 mmol, 50 equiv) was added to a solution of (S)-tert-butyl 2-(hydroxymethyl)morpholine-4-carboxylate (60 mg, 0.276 mmol) in DCM (2 mL) and the resulting solution was stirred at room temperature 1 hour. The solvent was then removed under vacuum and the residue was continued to the next step with no further purification. MS m/z (M+1) 118.1

Step 2. Synthesis of (S)-benzyl 2-(hydroxymethyl)morpholine-4-carboxylate [2.20.1b]

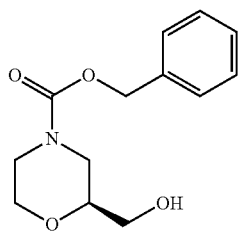

2.20.1b

Benzyl chloroformate (0.598 mL, 0.956 mmol, 3.5 equiv) was added slowly to a solution of DIPEA (0.477 mL, 2.73 mmol, 10 equiv) and 2.20.1a (64 mg, 0.547 mmol) in DCM (2 mL). The resulting mixture was stirred at room temperature for 4 hours. EtOAc and saturated aqueous NaHCO$_3$ solution were then added to the mixture. The phases were separated and the organic layer was extracted with EtOAc. The combined organic layers were washed with brine, dried over Na$_2$SO$_4$ and concentrated. The remaining oil was purified by silica gel column chromatography (EtOAc/heptane, 40-100%) to give product 74 mg (54% yield). MS m/z (M+1) 252.2.

Step 3. Synthesis of (2S,3S)-3-((tert-butoxycarbonyl)(methyl)amino)-3-(furan-2-yl)-2-methylpropyl methanesulfonate [2.20.1c]

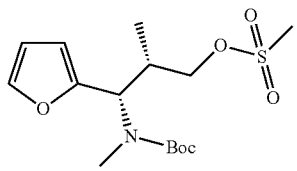 [SMILES: C[C@H](COS(C)(=O)=O)[C@@H](c1ccco1)N(C)C(=O)OC(C)(C)C]

Methanesulfonyl chloride (0.069 mL, 0.891 mmol, 1.2 equiv) was added to a solution of 2.1b (200 mg, 0.743 mmol) and triethylamine (0.207 mL, 1.485 mmol, 2.0 equiv) in DCM (4 mL) at 0° C. and the resulting solution was stirred at 0° C. for 1 hour. The reaction mixture was then diluted with DCM and was washed with saturated aqueous NH$_4$Cl solution, water and brine, dried over MgSO$_4$ and concentrated. The residue was continued to the next step with no further purification (258 mg, 100% yield). MS m/z (M+Na) 370.2.

Step 4. Synthesis of (S)-benzyl 2-(((2S,3S)-3-((tert-butoxycarbonyl)(methyl)amino)-3-(furan-2-yl)-2-methylpropoxy)methyl)morpholine-4-carboxylate [2.20.1d]

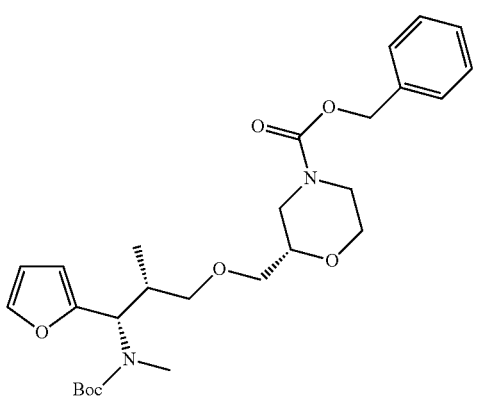

2.20.1d

NaH (59.9 mg 60% in mineral oil, 1.497 mmol, 2.0 equiv) was added to a solution of 2.20.1b (376 mg, 1.497 mmol, 2.0 equiv) in DMF (3 mL) at 0° C. After 30 minutes, 2.20.1c (260 mg, 0.75 mmol, 1.0 equiv) was added at 0° C. and the resulting mixture was stirred at room temperature for 4 hours. The reaction was quenched by addition of saturated aqueous NH$_4$Cl solution. The mixture was neutralized by addition of 1.0 M aqueous KHSO$_4$ solution and then extracted with EtOAc. The combined organic layers were washed with brine, dried over Na$_2$SO$_4$. The remaining oil was purified by silica gel column chromatography (EtOAc/heptane 15-50%) to afford product 170 mg (45% yield). MS m/z (M+Na) 525.4.

Step 5. Synthesis of (2S,3S)-4-(((S)-4-((benzyloxy)carbonyl)morpholin-2-yl)methoxy)-2-((tert-butoxycarbonyl)(methyl)amino)-3-methylbutanoic acid [2.20.1e]

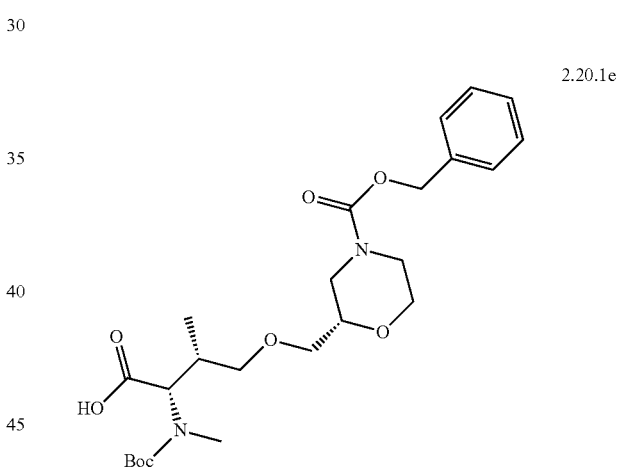

2.20.1e

To a mixture of 2.20.1d (115 mg, 0.229 mmol) and NaIO$_4$ (294 mg, 1.373 mmol, 6.0 equiv) EtOAc/heptane/water (3/14, 8 mL), RuCl$_3$ (14 mg, 0.069 mmol, 0.3 equiv) was added with vigorous stirring. After 1 hour, the reaction was quenched by adding saturated aqueous NaHSO$_3$ solution and the mixture was stirred for another 2 hours. The mixture was then extracted with EtOAc. The combined organic layers were washed with saturated aqueous NaHSO$_3$ solution and brine, dried over Na$_2$SO$_4$ and concentrated to afford product 2.20.1e (110 mg, 100% yield). The crude material was continued to the next step without further purification. MS m/z (M+Na) 503.3.

Step 6. Synthesis of 2.20.1f

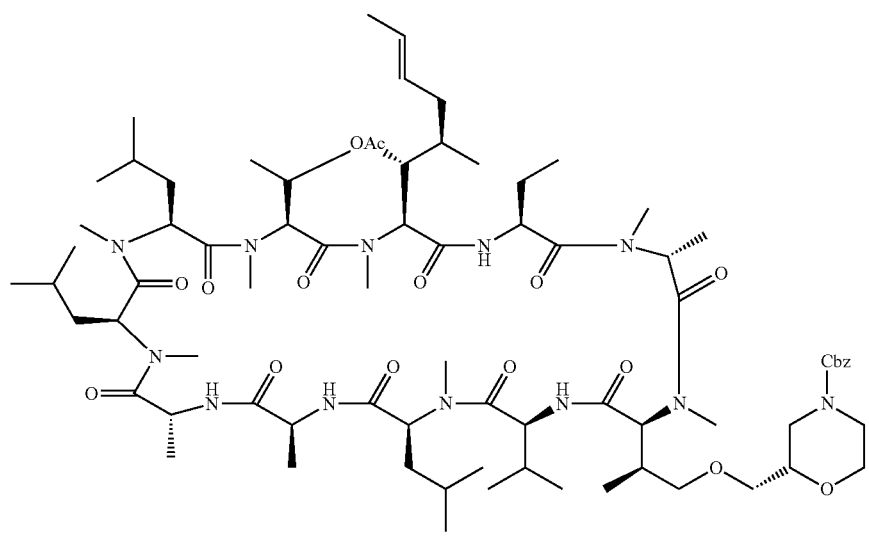

2.20.1f

Compound 2.20.1f was prepared from 2.20.1e following the procedures described from the synthesis of 2.7 (step 4-7). MS m/z (M+1) 1495.1

Step 7. Synthesis of 2.20.1g

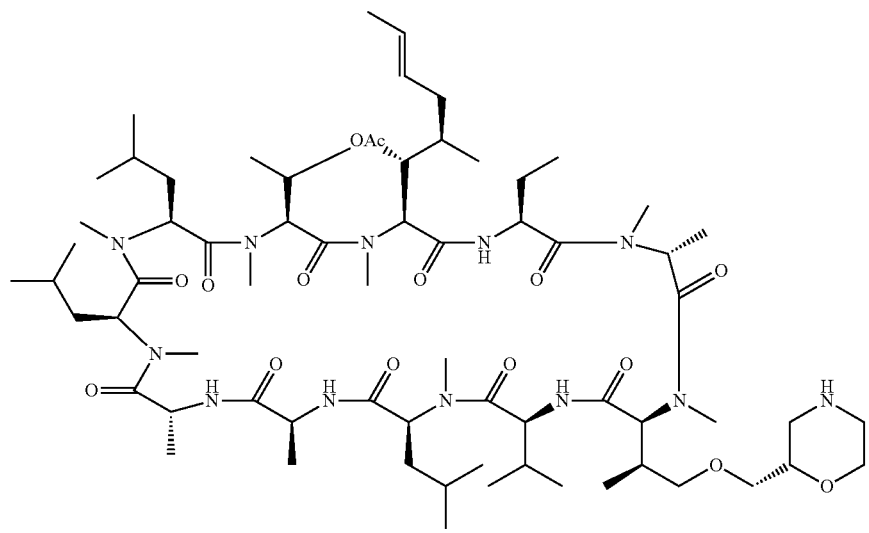

2.20.1g

A flask was charged with 2.20.1f (70 mg, 0.047 mmol, 1 equiv) and DCM (0.5 mL). To this solution, TEA (0.052 mL, 0.375 mmol, 8.0 equiv), triethylsilane (0.262 mL, 1.640 mmol, 35 equiv) and Pd(OAc)$_2$ (10.5 mg, 0.047 mmol, 1.0 equiv) was added. After stirring at room temperature for 1 hour, the reaction mixture was quenched by adding saturated aqueous NH$_4$Cl solution. The mixture was filtered through Celite and the filtrate was extracted with DCM. The combined organic layers were washed with saturated aqueous NaHCO$_3$ solution, dried over Na$_2$SO$_4$ and concentrated to give product 2.20.1g (50 mg, 78% yield). The crude material was used in the next step without further purification. MS m/z (M+1) 1360.8

Step 8. Synthesis of 2.20.1h

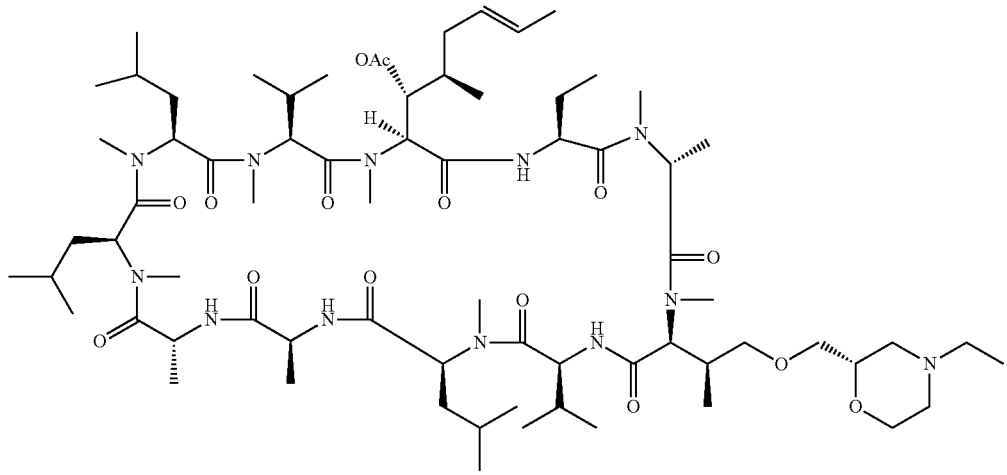

2.20.1h

Acetaldehyde (0.021 mL, 0.368 mmol, 10 equiv) was added to a solution of 2.20.1g (50 mg, 0.037 mmol, 1 equiv) in DCE (1 mL) at room temperature. After 5 minutes, sodium triacetoxyborohydride (12.5 mg, 0.059 mmol, 1.6 equiv) and acetic acid (0.003 mL, 0.44 mmol, 1.2 equiv) were added. The resulting mixture was stirred at room temperature for 20 hours. After cooled in an ice-water bath, the reaction mixture was quenched at 0° C. by adding saturated aqueous $NH_4Cl$ solution and then extracted with DCM. The combined org. layers were washed with saturated aqueous $NaHCO_3$ solution and brine, dried with $Na_2SO_4$ and concentrated to afford product 2.20.1 h 50 mg (98% yield) desired product was afforded. MS m/z (M+1) 1389.0

Step 9. Synthesis of 2.20.1

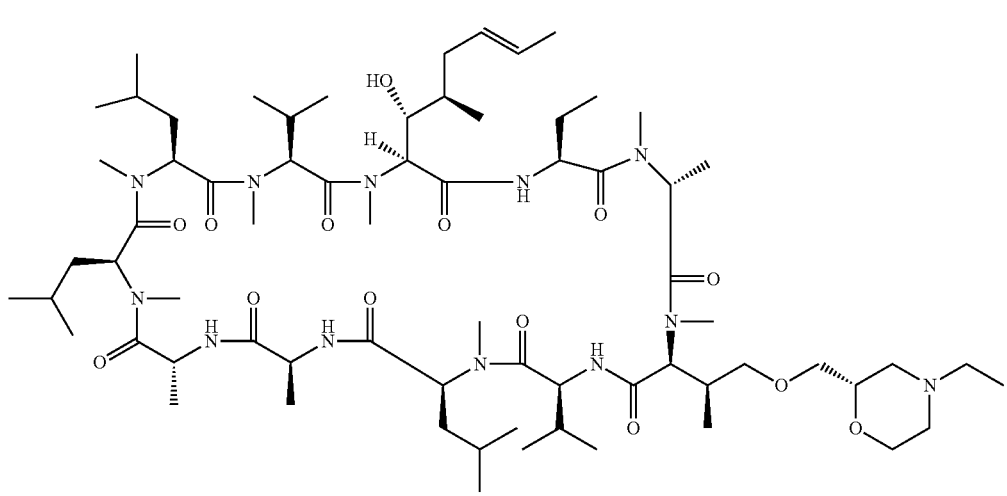

2.20.1

Tetramethylammonium hydroxide (25% in MeOH, 0.036 mL, 0.36 mmol, 10.0 equiv) was added to a solution of 2.20.1h (50 mg, 0.036 mmol) in MeOH (1 mL) at 0° C. After stirring for 2 hours at room temperature, the reaction mixture was neutralized by addition of saturated aqueous $NaHSO_4$. The mixture was then extracted with DCM. The combined organic layers were washed with brine, dried over $Na_2SO_4$ and concentrated in vacuo. The residue was purified by reverse phase HPLC to give product 2.20.1 (10.1 mg, 21% yield) MS m/z (M+1) 1346.9.

II.20.2 Synthesis of Compound 2.20.2

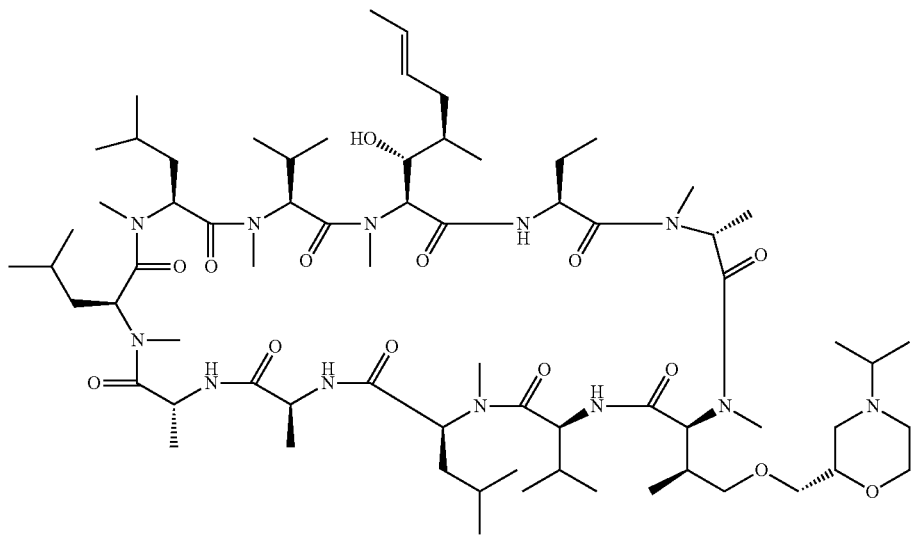

2.20.2

Compound 2.20.2 was prepared following the procedures described for the synthesis of 2.20.1 using acetone in step 8. MS m/z (M+1) 1361.0

II.21.1 Synthesis of 2.21.1

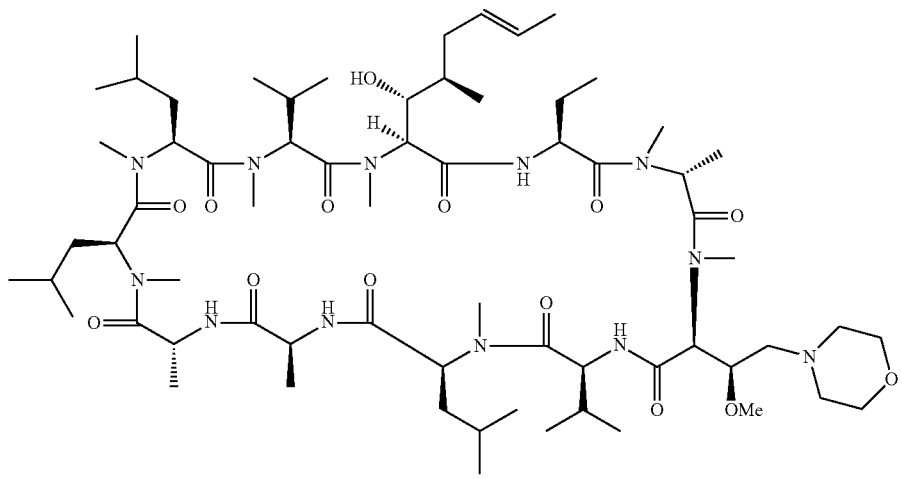

2.21.1

Step 1. Synthesis of (2S,3R)-ethyl 3-(((benzyloxy) carbonyl)amino)-2-hydroxy-3-(4-methoxyphenyl) propanoate [2.21.1a]

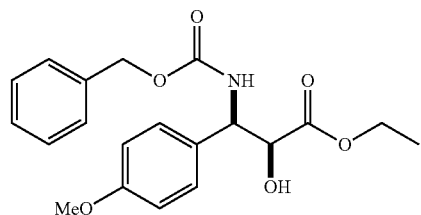

2.21.1a

Benzyl carbamate (4.89 g, 32 mmol, 2.3 equiv) was dissolved in 24 mL of n-PrOH. A solution of NaOH (1.3 g, 32 mmol, 2.3 equiv) in 36 mL of H$_2$O was added to this stirred solution and the mixture was cooled at 0° C. in an ice water bath. To the mixture was then added tort-butyl hypochlorite (3.5 g, 32 mmol, 2.3 mmol). After stirring at 0° C. for 10 minutes, (DHQD)$_2$PHAL (0.55 g, 0.7 mmol, 0.05 equiv) and 12 mL of n-PrOH was added. The reaction flask was immersed in a room-temperature water bath and stirred for 5 minutes. Methyl 4-methoxycinnamate (2.9 g, 14 mmol, 1.0 equiv) was added, followed by K$_2$OsO$_2$(OH)$_4$ (207 mg, 0.56 mmol, 0.04 equiv). The reaction mixture was stirred for 2 hour at 0° C. by which it transformed into a pale yellow slurry. The precipitate was isolated by filtration. One wash with ice-cold EtOH—H$_2$O (1:1, 5 mL) yielded product 2.21.1a as a white solid (3.5 g, 67%, >99% ee). MS m/z (M+Na$^+$) 396

Step 2. Synthesis of benzyl((1R,2S)-2,3-dihydroxy-1-(4-methoxyphenyl)propyl)carbamate [2.21.1 b]

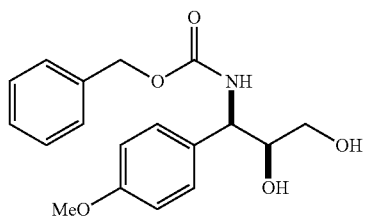

2.21.1b

NaBH$_4$ (1.06 g, 28 mmol, 3.0 equiv) was added to a solution of 2.21.1a (3.5 g, 9.4 mmol, 1.0 equiv) in THF (10.0 mL) and MeOH (30 mL) at 0° C. The resulting mixture was stirred at room temperature for 1 hour, after which, another 0.3 g of NaBH$_4$ (300 mg, 7.8 mmol, 0.8 equiv) was added. After stirring at room temperature for 30 minutes, the solvent was removed under vacuum. The residue was dissolved in EtOAc and saturated aqueous NaHCO$_3$ solution was added. The phases were separated and the organic layer was washed with brine, dried over Na$_2$SO$_4$ and concentrated. The crude material was used in the next step with no further purification. MS m/z (M+Na): 354

Step 3. Synthesis of benzyl((1R,2S)-3-((tert-butyldiphenylsilyl)oxy)-2-hydroxy-1-(4-methoxyphenyl)propyl)carbamate [2.21.1c]

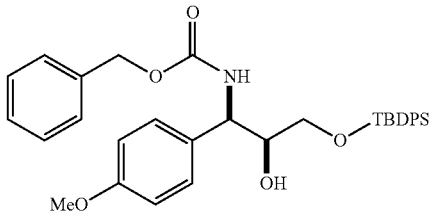

2.21.1c

TBDPSCl (3.5 g, 12.6 mmol, 1.1 equiv) and imidazole (1.95 g, 28.7 mmol, 2.5 equiv) were added to a solution of 2.21.1b (3.8 g, 11.4 mmol, 1.0 equiv) in DMF (11.5 mL) at room temperature and the mixture was stirred at room temperature for 1 hour. The mixture was diluted with EtOAc and washed with saturated aqueous NH$_4$Cl solution, brine, dried over Na$_2$SO$_4$ and concentrated. The residue was purified by silica gel column chromatography (EtOAc/heptane, 0 to 50%) to give product 5.4 g (83% yield). MS m/z (M+Na) 592

Step 4. Synthesis of benzyl((1R,2S)-3-((tert-butyldiphenylsilyl)oxy)-2-methoxy-1-(4-methoxyphenyl)propyl)(methyl)carbamate [2.21.1d]

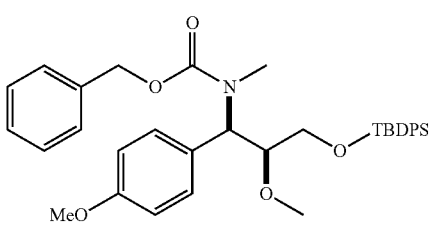

2.21.1d

NaH (1.73 g, 43.4 mmol, 6.0 equiv) was slowly added to a solution of MeI (1.7 g, 43.4 mmol, 6.0 equiv) and 2.21.1c (4.1 g, 7.3 mmol, 1.0 equiv) in DMF (40 mL) at 0° C. After stirring at 0° C. for 1 hour, the reaction mixture was diluted with EtOAc and quenched by addition of saturated aqueous NH$_4$Cl solution. The phases were separated and the organic layer was washed with brine, dried over Na$_2$SO$_4$ and concentrated. The residue was purified by silica gel column chromatography (EtOAc/heptane 0 to 50%) to give product 3.2 g (74% yield). MS m/z (M+Na$^+$) 620

Step 5. Synthesis of (2S,3S)-2-(((benzyloxy)carbonyl)(methyl)amino)-4-((tert-butyldiphenylsilyl)oxy)-3-methoxybutanoic acid [2.21.1.e]

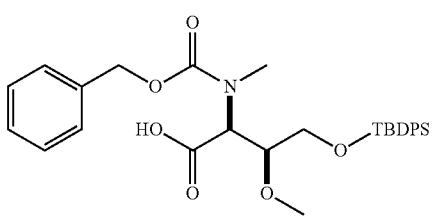

2.21.1e

NaIO$_4$ (4.3 g, 20.1 mmol, 8.0 equiv), RuCl$_3$ (0.31 g, 1.5 mmol, 0.6 equiv) and NaHCO$_3$ (0.2 g, 2.5 mmol, 1.0 equiv) were added to a mixture of 2.21.1d (1.5 g, 2.5 mmol, 1.0 equiv) in CH$_3$CN/EtOAc/water (9 mL/9 mL/48 mL) at room temperature. After stirring at room temperature for 24 hours, the reaction mixture was diluted with EtOAc, acidified by addition of 1.0 N HCl aqueous solution and filtered. The filtrate was washed with saturated aqueous NaHSO$_3$ solution, brine, dried over Na$_2$SO$_4$ and concentrated. The residue was purified by silica gel column chromatography (acetone/heptane) to give product 400 mg (yield 30%). MS m/z (M+H$^+$) 536

Step 6. Synthesis of Compound 2.21.1f

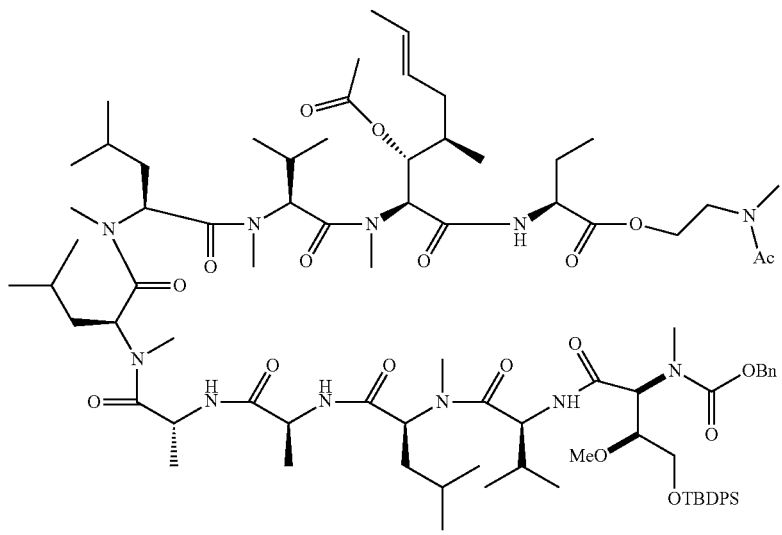

2.21.1f

HATU (273 mg, 0.72 mmol, 1.2 equiv) and DIPEA (232 mg, 1.8 mmol, 3.0 equiv) was added to a solution of 2.21.1e (400 mg, 0.60 mmol, 1.0 equiv) in DCM (3.0 mL) at 0° C. After 10 minutes, amine 1 (695 mg, 0.60 mmol, 1.0 equiv) was added and the resulting mixture was stirred at 0° C. for 1 hour and at room temperature for 18 hours. The solution was concentrated and the residue was dissolved in EtOAc. The solution was washed with 1.0 N HCl aqueous solution, water, saturated aqueous NaHCO$_3$ solution, brine, dried over Na$_2$SO$_4$ and concentrated. The residue was purified by silica gel column chromatography (acetone/heptane 0 to 70%) to give product 450 mg (yield 45%). MS m/z (M+H$^+$) 1682

Step 7. Synthesis of Compound 2.21.1g

TEA (135 mg, 1.3 mmol, 5.0 equiv), Et$_3$SiH (187 mg, 1.6 mmol, 6.0 equiv) and Pd(OAc)$_2$ (18 mg, 0.08 mmol, 0.3 equiv) were added to a solution of 2.21.1f (450 mg, 0.27 mmol, 1.0 equiv) in DCM (1.0 mL). After stirring at room temperature for 30 minutes, the mixture was diluted with EtOAc and filtered through Celite. The filtrate was washed with saturated aqueous NaHCO$_3$ solution, brine, dried over Na$_2$SO$_4$ and concentrated. The crude material was used in the next step with no further purification. MS m/z (M+Na$^+$) 1570

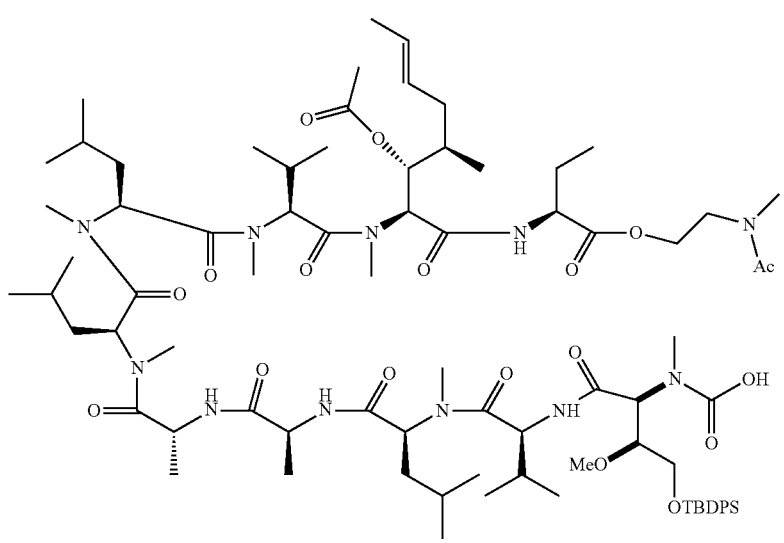

2.21.1g

Step 8. Synthesis of Compound 2.21.1h

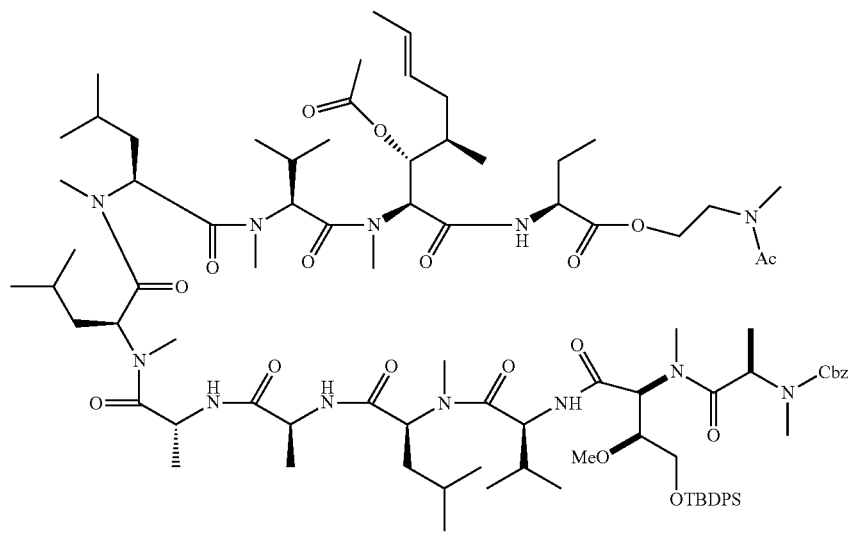

2.21.1h

HATU (275 mg, 0.72 mmol, 2.7 equiv) and DIPEA (104 mg, 0.8 mmol, 3.0 equiv) were added to a solution of (R)-2-(((benzyloxy)carbonyl)(methyl)amino)propanoic acid (190 mg, 0.8 mmol, 3.0 equiv) in DCM (2.0 mL) and DMF (1.0 mL) at 0° C. After 10 minutes, 2.21.1g (414 mg, 0.27 mmol, 1.0 equiv) was added to the solution and the resulting mixture was stirred at 0° C. for 1 hour and at room temperature for 18 hours. The solution was concentrated and the residue was dissolved in EtOAc. The solution was washed with 1.0 N HCl aqueous solution, saturated aqueous NaHCO$_3$ solution, brine, dried over Na$_2$SO$_4$ and concentrated. The residue was purified by silica gel column chromatography (acetone/heptane, 0 to 70%) to give product 350 mg (yield 74%). MS m/z (M+H$^+$) 1767

Step 9. Synthesis of 2.21.1

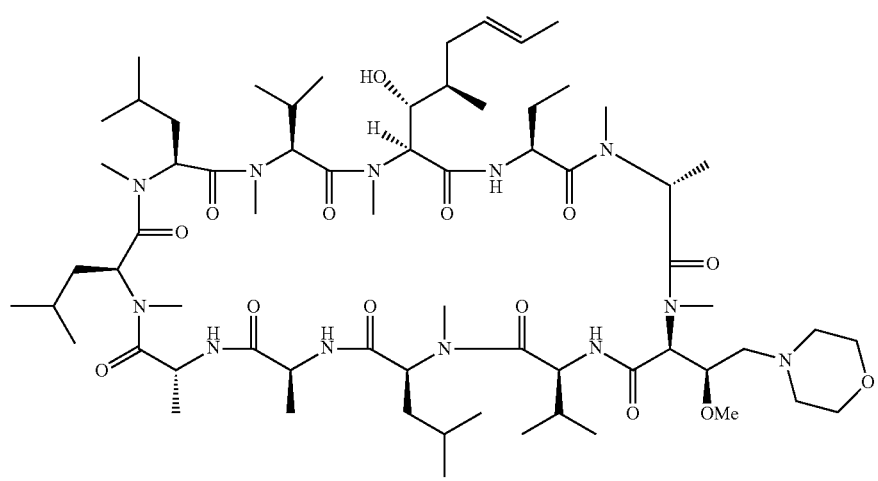

2.21.1

Compound 2.21.1.h was converted to 2.21.1 following the procedures (step 10-15) described for the synthesis of 2.18.1. MS m/z (M+H$^+$) 1304

II.21.2 Synthesis of Compound 2.21.2

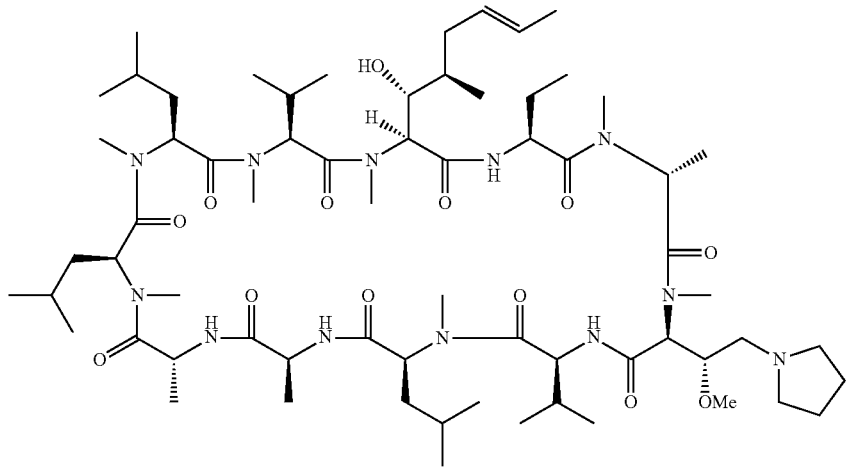

2.21.2

Step 1. Synthesis of (5R,6R)-5-(4-methoxyphenyl)-10,10-dimethyl-3-oxo-1,9,9-triphenyl-2,8-dioxa-4-aza-9-silaundecan-6-yl 4-nitrobenzoate [2.21.2a]

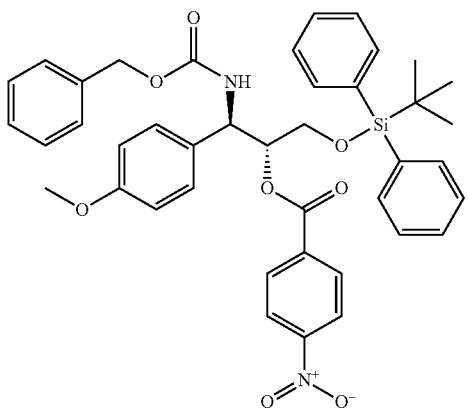

2.21.2a

DIAD (7.88 mL, 40.5 mmol, 3 equiv) was added dropwise to a solution of 2.21.1b (7.7 g, 13.5 mmol, 1 equiv), p-nitrobenzoic acid (6.78 g, 40.5 mmol, 3 equiv) and PPh$_3$ (10.63 g, 40.5 mmol, 3 quiv) in THF (175 mL) at 0° C. The mixture was then allowed to warm to room temperature and stirred at this temperature for 16 hours. The solvent was removed under vacuum and EtOAc was added to the residue. The mixture was washed with saturated aqueous NaHCO$_3$ solution, dried over Na$_2$SO$_4$ and concentrated. The crude material was purified by silica gel column chromatography (EtOAc/heptane, 5-50%) to afford product 2.21.2a (7.3 g, 75% yield). MS m/z (M+H) 719.3

Step 2. Synthesis of (5R,6R)-5-(4-methoxyphenyl)-10,10-dimethyl-3-oxo-1,9,9-triphenyl-2,8-dioxa-4-aza-9-silaundecan-6-yl 4-nitrobenzoate [2.21.2b]

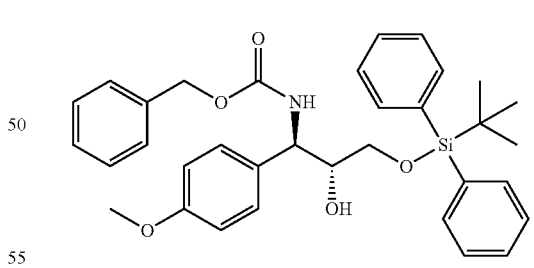

2.21.2b

Sodium azide (904 mg, 13.91 mmol, 5 equiv) was added to a solution of 2.21.2a (2.0 g, 2.78 mmol, 1 equiv) in MeOH (50 mL) and the mixture was heated at 45° C. for 16 hours. The solvent was removed under reduced pressure and the residue was purified by silica gel column chromatography (EtOAc/heptane, 25-50%) to give product 2.21.2b (900 mg, 57% yield). MS m/z (M+Na) 592.4

Step 3. Synthesis of 2.21.2

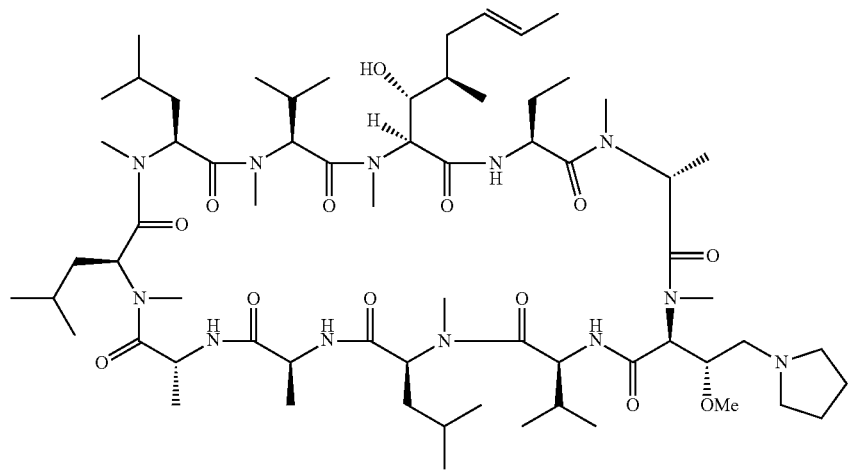

2.21.2

Compound 2.21.2b was converted to 2.21.2 following the procedures described for the synthesis of 2.21.1 (step 4-9). Pyrrolidine was used in the reductive amination step. MS m/z (M+1) 1288.9

II.21.3. Synthesis of Compound 2.21.3

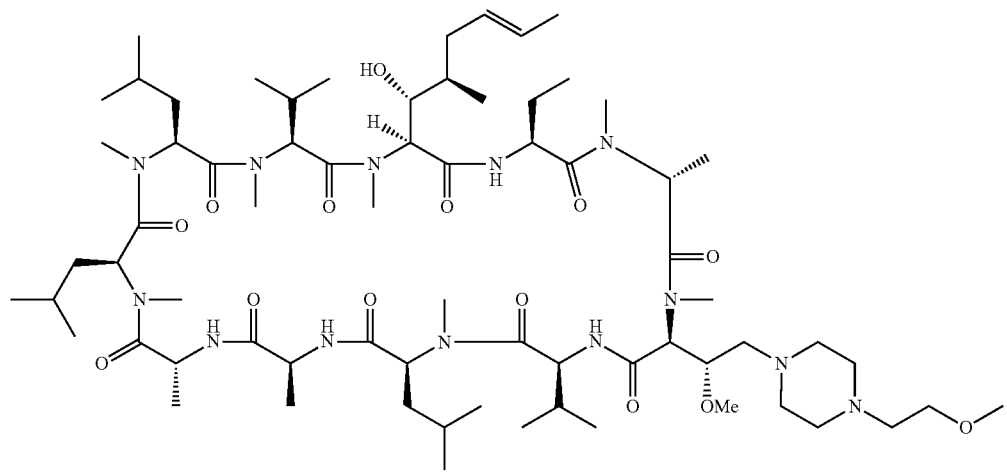

2.21.3

Compound 2.21.2b was converted to 2.21.3 following the procedures described for the synthesis of 2.21.1 (step 4-9). 1-(2-Methoxyethyl)piperazine was used in the reductive amination step MS m/z (M+1) 1362.0

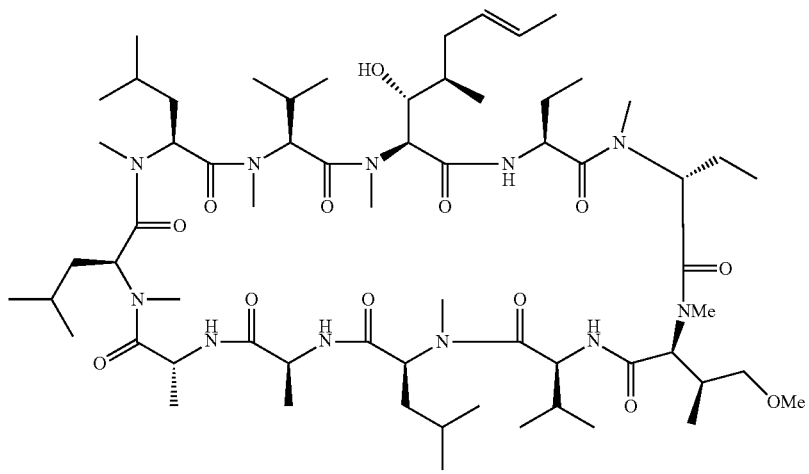

3.1

Step 1. Synthesis of (R)-2-((tert-butoxycarbonyl)(methyl)amino)butanoic acid [3.1a]

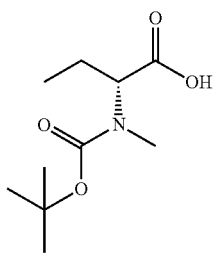

3.1a

To a solution of N-Boc-D-Val-OH (0.678 g, 3.34 mmol) in THF (11.1 mL) at 0° C. was added MeI (2.09 mL, 33.4 mmol, 10.0 equiv). NaH (60%, 1.33 g, 33.4 mmol, 10.0 equiv) was added as a solid to the suspension over a period of 2 hours. After stirring for 12 hours at room temperature, the reaction mixture was diluted with diethyl ether and quenched with water slowly. Aqueous layer was extracted with diethyl ether followed by acidified to pH 3 with 10% citric acid and extraction with ethyl acetate. Combined organic layer was washed with brine, dried with Na$_2$SO$_4$, filtered and concentrated in vacuo to afford compound 3.1a (0.73 g) which was used for the next step without further purification. MS m/z (M+Na) 240.2. $^1$H NMR (400 MHz, CDCl$_3$) 4.56 and 4.37 (br-s, 1H), 2.83 (br-s, 3H), 2.08-1.92 (m, 1H), 1.85-1.68 (m, 1H), 1.48 (br-s, 9H), 0.96 (t, J=7.38 Hz, 3H).

Step 2. (2S,3S)-2-((tert-butoxycarbonyl)(methyl)amino)-4-methoxy-3-methylbutanoic acid [3.1b]

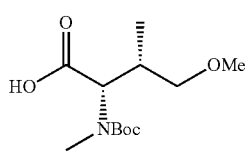

3.1b

To a suspension of NaIO$_4$ (0.83 g, 3.87 mmol, 6.0 equiv) in water/CCl$_4$/acetonitrile (3/2/3, 17.9 mL) was added RuCl$_3$ (45.0 mg, 0.22 mmol, 0.34 equiv) at room temperature. After stirring for 15 minutes, a solution of compound 2.1c (0.183 g, 0.65 mmol) in acetonitrile (2.0 mL) was added. After stirring for another 15 minutes, the reaction was quenched with water. The aqueous layer was extracted with ethyl acetate. Combined organic layer was washed with brine, dried with Na$_2$SO$_4$, filtered and concentrated in vacuo to afford compound 3.1b (0.17 g).

Step 3. Synthesis of 3.1c

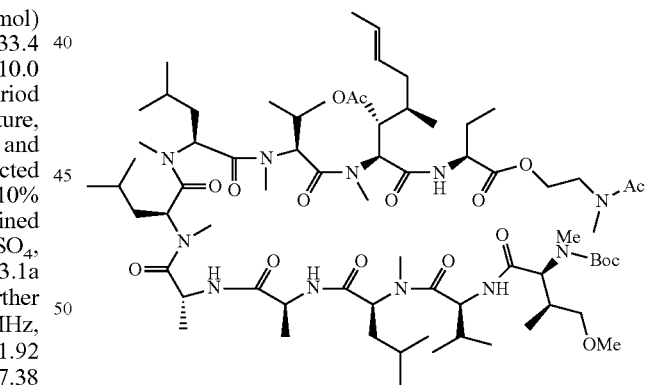

3.1c

To a solution of compound 3.1b (0.168 g, 0.65 mmol, 1.5 equiv) in methylene chloride (4.3 mL) at 0° C. was added HOAt (70.2 mg, 0.52 mmol, 1.2 equiv) followed by compound 1 (0.50 g, 0.430 mmol), HATU (0.180 g, 0.47 mmol, 1.1 equiv) and DIPEA (0.23 mL, 1.29 mmol, 3.0 equiv). After stirring at room temperature for 12 hours, the reaction mixture was partitioned between water and methylene chloride. Aqueous layer was extracted with methylene chloride. Combined organic layer was washed with brine, dried with Na$_2$SO$_4$, filtered and concentrated in vacuo. Purification by silica gel chromatography (45% acetone/methylene chloride) afforded compound 3.1c (0.42 g, 69% yield). MS m/z (M+Na) 1428.7

Step 4. Synthesis of 3.1d

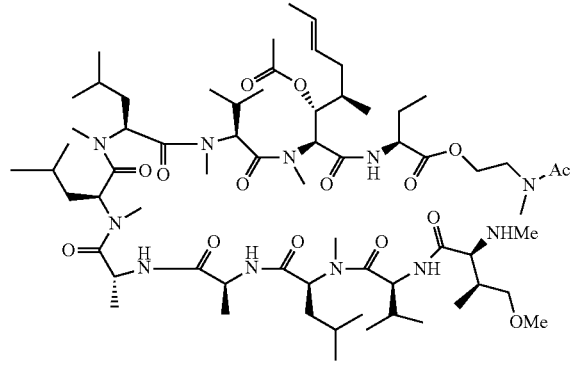

3.1d

To as solution of compound 3.1c (0.39 g, 0.28 mmol) in methylene chloride (1.9 mL) at 0° C. was added TFA (0.93 mL). After stirring at room temperature for 30 minutes, the reaction mixture was quenched with saturated aqueous NaHCO$_3$ and diluted with methylene chloride. The aqueous layer was extracted with methylene chloride. The combined organic layer was washed with brine, dried with Na$_2$SO$_4$, filtered and concentrated in vacuo to afford compound 3.1d (0.36 g) which was used for the next step without further purification. MS m/z (M+1) 1306.8

Step 5. Synthesis of 3.1e

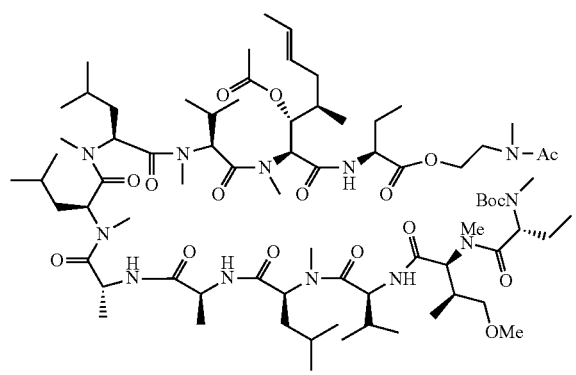

3.1e

To a solution of compound 3.1d (0.150 g, 0.114 mmol) in methylene chloride (0.57 mL) at 0° C. was added compound 3.1a (74.6 mg, 0.343 mmol, 3.0 equiv) followed by HATU (0.131 g, 0.343 mmol, 3.0 equiv) and DIPEA (0.12 mL, 0.686 mmol, 6.0 equiv). After stirring at room temperature for 12 hours, the reaction mixture was partitioned between water and methylene chloride. The aqueous layer was extracted with methylene chloride. The combined organic layer was washed with brine, dried with Na$_2$SO$_4$, filtered and concentrated in vacuo. Purification on silica gel chromatography (45% acetone/methylene chloride) afforded compound 3.1e (0.122 mg, 71% yield). MS m/z (M+H) 1506.3

Step 6. Synthesis of 3.1f

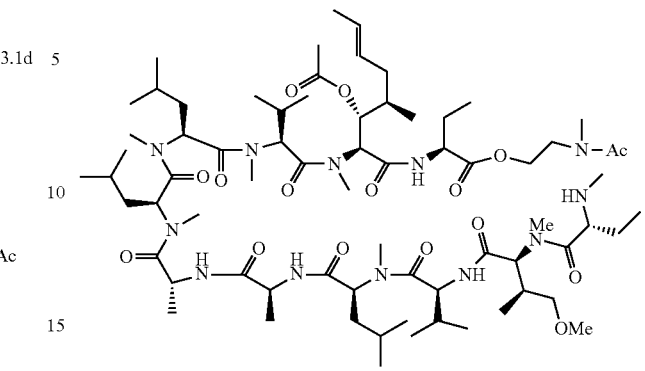

3.1f

To a solution of compound 3.1e (0.122 g, 81 umol) in methylene chloride (0.54 mL) at 0° C. was added TFA (0.27 mL). After stirring at 0° C. for 2 hours, the reaction mixture was quenched with saturated aqueous NaHCO$_3$ and diluted with methylene chloride. The aqueous layer was extracted with methylene chloride. The combined organic layers were washed with brine, dried with Na$_2$SO$_4$, filtered and concentrated in vacuo to afford compound 3.1f (0.114 g) which was used for the next step without further purification. MS m/z (M+1) 1406.1

Step 7. Synthesis of 3.1g

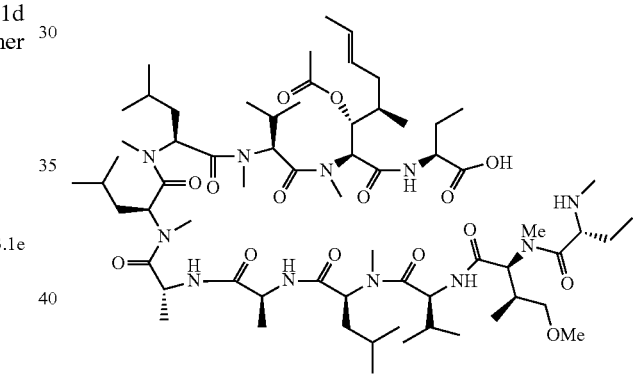

3.1g

To a solution of compound 3.1f (0.114 g, 81 umol) in THF/water (1/1, 1.72 mL) at 0° C. was added solid LiOH.H$_2$O (17.0 mg, 0.405 mmol, 5.0 equiv). After stirring at 0° C. for 3 hours, the reaction mixture was quenched with 1.0 M HCl aq. solution (0.49 mL, 0.486 mmol, 6.0 equiv) and diluted with methylene chloride. The aqueous layer was extracted with methylene chloride. The combined organic layer was washed with brine, dried with Na$_2$SO$_4$, filtered and concentrated in vacuo to afford compound 3.1g (0.10 g). MS m/z (M+1) 1307.0

Step 8. Synthesis of 3.1 h

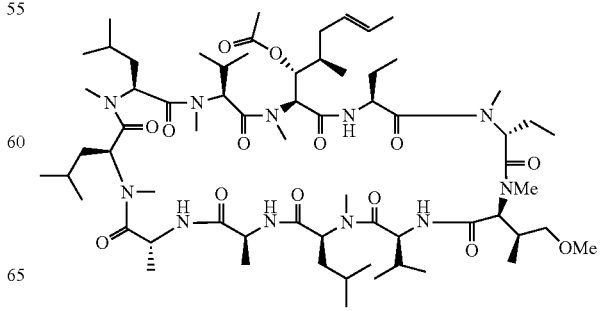

3.1h

To a suspension of BOP (71.6 mg, 0.162 mmol, 2.0 equiv) in methylene chloride (20.3 mL) 0° C. was added dropwise a solution of compound 3.1g (0.106 g, 81.0 umol) and DMAP (19.8 mg, 0.162 mmol, 2.0 equiv) in methylene chloride (60.8 mL) via additional funnel. After stirring at room temperature for 12 hours, the reaction mixture was washed with 10% citric acid followed by saturated aqueous NaHCO$_3$. The aqueous layer was extracted with methylene chloride. The combined organic layer was washed with brine, dried with Na$_2$SO$_4$, filtered and concentrated in vacuo. Purification on silica gel chromatography afforded compound 3.1 h (100.9 mg, 97%). MS m/z (M+1) 1289.8

Step 9. Synthesis of 3.1

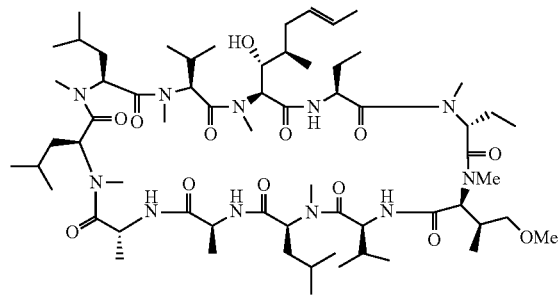

3.1

To a solution of compound 3.1 h (0.101 g, 78.0 umol) in methanol (2.6 mL) at 0° C. was added tetramethylammonium hydroxide (25% w/w in MeOH, 0.138 mL, 0.391 mmol, 10 equiv). After stirring for 2 hours at room temperature, the reaction mixture was quenched with saturated aqueous sodium bisulfate and diluted with methylene chloride. The aqueous layer was extracted with methylene chloride. The combined organic layer was washed with brine, dried with Na$_2$SO$_4$, filtered and concentrated in vacuo. Purification on reverse phase HPLC afforded compound 3.1 (25.0 mg, 26% yield). MS m/z (M+1) 1246.9

III.2.1. Synthesis of Compound 3.2.1

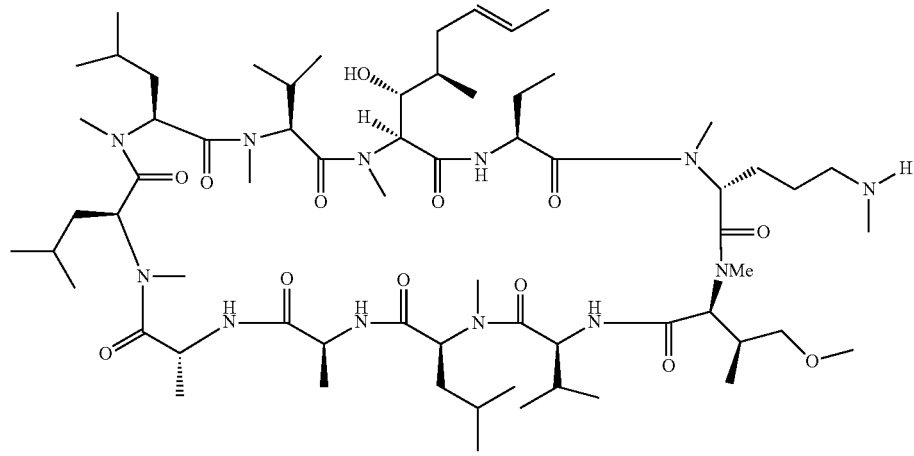 [SMILES: C/C=C/C[C@@H](C)[C@@H](O)[C@H]1C(=O)N[C@@H](CC)C(=O)N(C)[C@H](CCCNC)C(=O)N(C)[C@@H]([C@H](C)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of (R)-5-(((benzyloxy)carbonyl)amino)-2-((tert-butoxycarbonyl)amino)pentanoic acid [3.2.1a]

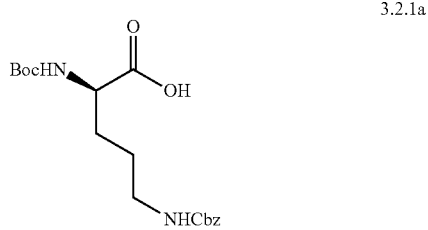 [SMILES: CC(C)(C)OC(=O)N[C@H](CCCNC(=O)OCc1ccccc1)C(=O)O]

3.2.1a

To a solution of Boc-D-Orn-OH (0.50 g, 2.2 mmol) in aqueous NaOH (1M, 5 mL) at 0° C. was added benzyl chloroformate (0.37 mL, 2.6 mmol, 1.2 equiv) followed by aqueous NaOH (1 M, 5 mL). After stirring for 2 hours at room temperature, the reaction mixture was poured to separatory funnel and extracted with ether. The aqueous layer was acidified to pH 3 with aqueous 10% citric acid and extracted with ethyl acetate. The combined organic layer was washed with brine, dried with Na$_2$SO$_4$, filtered and concentrated in vacuo to afford compound 3.2.1a (0.57 g, 72%) which was used for the next step without further purification. MS m/z (M+Na) 389.2. $^1$H NMR (400 MHz, DMSO-d$_6$) 12.37 (br-s, 1H), 7.35-7.25 (m, 5H), 7.20 (t, J=5.31 Hz, 1H), 7.01 (d, J=8.02 Hz, 1H), 4.97 (s, 2H), 3.83-3.77 (m, 1H), 2.94 (dd, 2H), 1.67-1.56 (m, 1H), 1.53-1.37 (m, 3H), 1.34 (s, 9H).

Step 2. Synthesis of (R)-5-(((benzyloxy)carbonyl)(methyl)amino)-2-((tert-butoxycarbonyl)(methyl)amino)pentanoic acid [3.2.1 b]

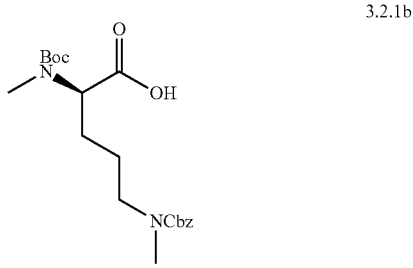 [SMILES: CN(CCC[C@H](C(=O)O)N(C)C(=O)OC(C)(C)C)C(=O)OCc1ccccc1]

3.2.1b

To a solution of compound 3.2.1a (0.57 g, 1.55 mmol) in THF (7.7 mL) at 0° C. was added methyl iodide (0.78 mL, 12.4 mmol, 8.0 equiv) followed by sodium hydride (60%, 0.55 g, 13.6 mmol, 8.8 equiv). After stirring for 12 hours at room temperature, the reaction mixture was slowly quenched with water at 0° C. The mixture was acidified with saturated aqueous NaHSO$_4$ and extracted with methylene chloride. The combined organic layer was washed with brine, dried with Na$_2$SO$_4$, filtered and concentrated in vacuo. Purification by silica gel chromatography (15% acetone/methylene chloride) afforded compound 3.2.1b (0.44 g, 71%).

MS m/z (M+Na) 417.2. $^1$H NMR (400 MHz, DMSO-d$_6$) 12.60 (br-s, 1H), 7.35-7.25 (m, 5H), 5.02 (s, 2H), 4.51-4.42 and 4.26-4.15 (m, 1H), 3.34-3.24 (m, 1H), 3.20-3.18 (m, 1H), 2.81 (d, J=8.71 Hz, 3H), 2.65 (br-s, 3H), 1.78-1.69 (m, 1H), 1.68-1.54 (m, 1H), 1.38-1.28 (m, 11H).

Step 3. Synthesis of [3.2.1c]

To a solution of compound 3.1d (0.400 g, 0.306 mmol) in methylene chloride (1.5 mL) at 0° C. was added compound 3.2.1b (0.345 g, 0.875 mmol, 2.8 equiv) followed by HATU (0.349 g, 0.918 mmol, 3.0 equiv) and DIPEA (0.32 mL, 1.84 mmol, 6.0 equiv). After stirring at room temperature for 12 hours, the reaction mixture was partitioned between water and methylene chloride. The aqueous layer was extracted with methylene chloride. The combined organic layer was washed with brine, dried with Na$_2$SO$_4$, filtered and concentrated in vacuo. Purification on silica gel chromatography (45% acetone/methylene chloride) afforded compound 3.2.1c (0.39 g, 76%). MS m/z (M+H) 1683.0

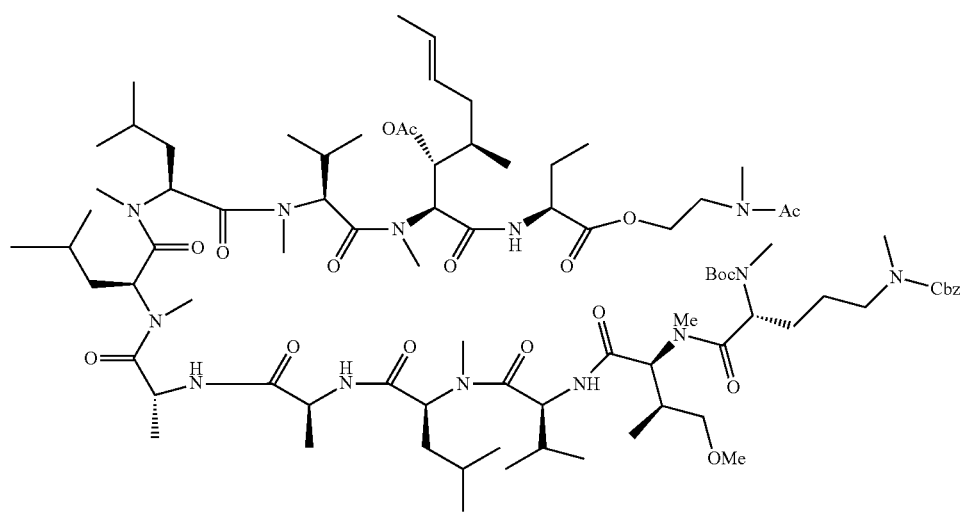

3.2.1c

Step 4. Synthesis of [3.2.1d]

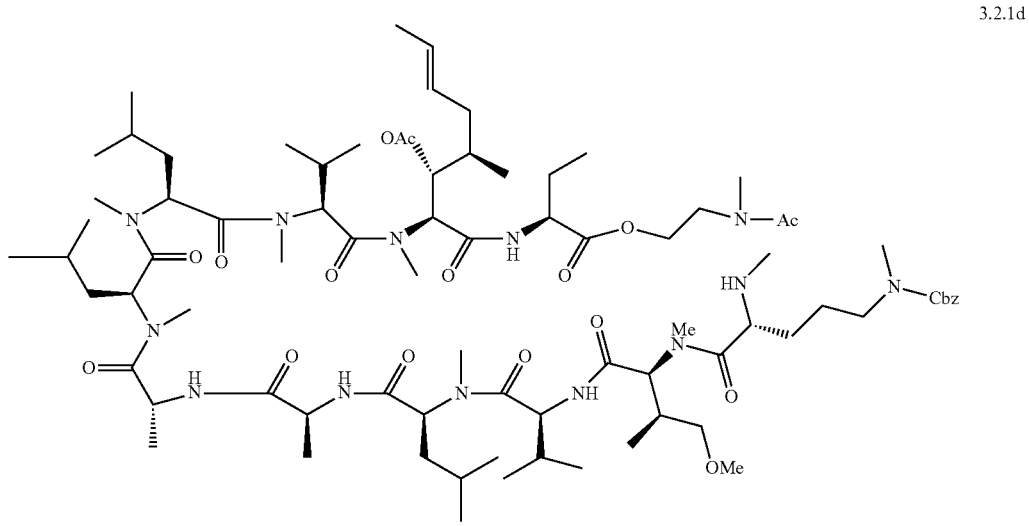 [SMILES: C/C=C/C[C@@H](C)[C@@H](OC(C)=O)[C@@H](C(=O)N[C@@H](CC)C(=O)OCCN(C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)COC)N(C)C(=O)[C@@H](CCCN(C)C(=O)OCc1ccccc1)NC)C(C)C]

3.2.1d

To a solution of compound 3.2.1c (0.115 g, 68 umol) in methylene chloride (0.46 mL) at 0° C. was added TFA (0.23 mL). After stirring at 0° C. for 2 hours, the reaction mixture was quenched with saturated aqueous NaHCO$_3$ and diluted with methylene chloride. The aqueous layer was extracted with methylene chloride. The combined organic layer was washed with brine, dried with Na$_2$SO$_4$, filtered and concentrated in vacuo to afford compound 3.2.1d (0.10 g). MS m/z (M+1) 1583.6

Step 5. Synthesis of [3.2.1e]

To a suspension of BOP (60.2 mg, 0.136 mmol, 2.0 equiv) in methylene chloride (20 mL) at 0° C. was added dropwise a solution of compound 3.2.1e (0.101 mg, 68.0 umol) and DMAP (16.6 mg, 0.136 mmol, 2.0 equiv) in methylene chloride (50 mL) via additional funnel. After stirring at room temperature for 12 hours, the reaction mixture was washed with 10% citric acid followed by saturated aqueous NaHCO$_3$. The aqueous layer was extracted with methylene

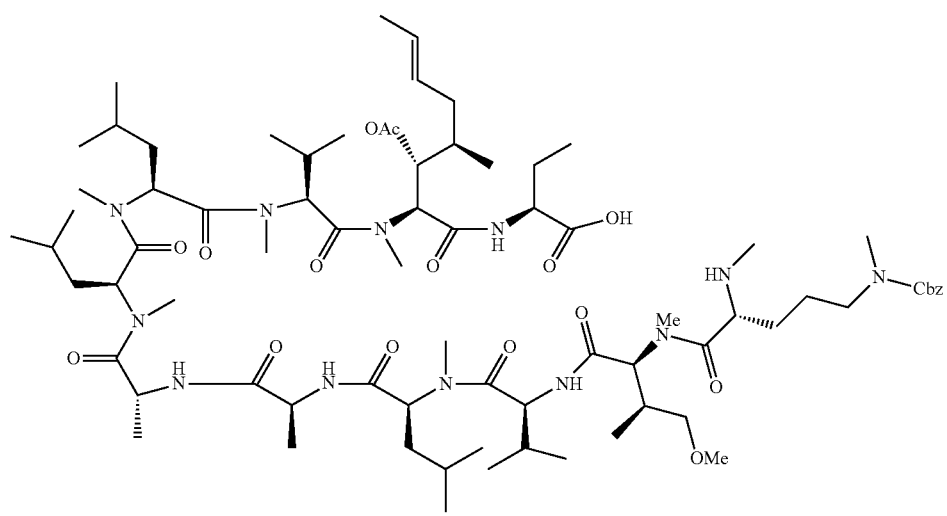

3.2.1e

To a solution of compound 3.2.1d (0.108 g, 68 umol) in THF:methanol:water (1:1:1, 1.45 mL) at 0° C. was added LiOH.H$_2$O as a solid (9.3 mg, 0.388 mmol, 5.7 equiv). After stirring at 0° C. for 3 hours, the reaction mixture was quenched with 1.0 M HCl aq. solution (0.48 mL, 0.476 mmol, 7.0 equiv) and diluted with methylene chloride. The aqueous layer was extracted with methylene chloride. The combined organic layer was washed with brine, dried with Na$_2$SO$_4$, filtered and concentrated in vacuo to afford compound 3.2.1e (0.10 g). MS m/z (M+1) 1483.8

Step 6. Synthesis of 3.2.1f chloride. The combined organic layer was washed with brine, dried with Na$_2$SO$_4$, filtered and concentrated in vacuo. Purification on silica gel chromatography afforded compound 3.2.1f (44.8 mg, 45% yield). MS m/z (M+1) 1465.8

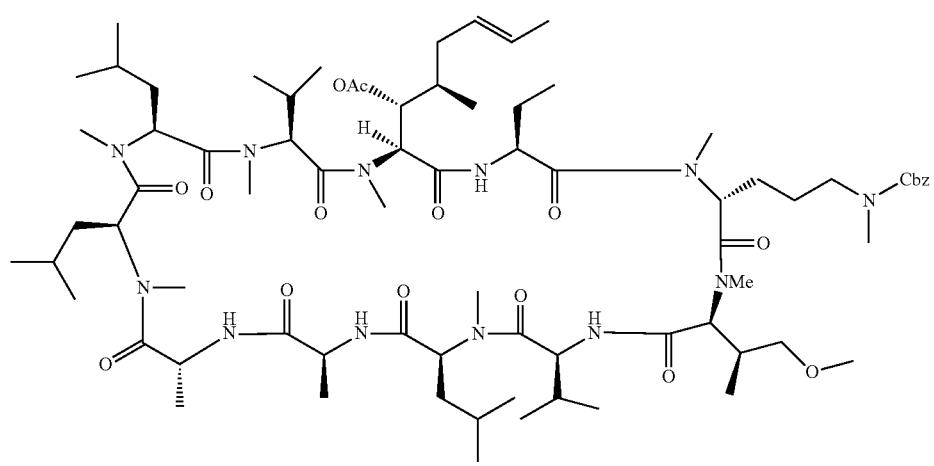

3.2.1f

Step 7. Synthesis of 3.2.1g

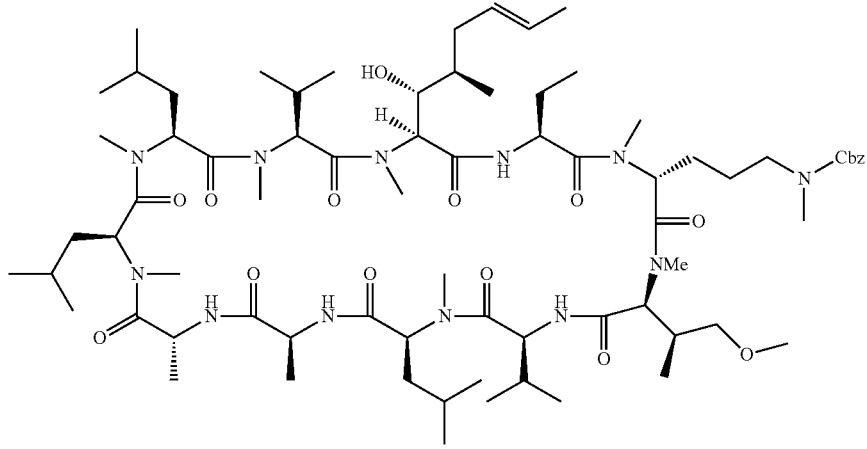

3.2.1g

To a solution of compound 3.2.1f (44.8 mg, 31.0 umol) in methanol (1.0 mL) at 0° C. was added tetramethylammonium hydroxide (25% w/w in MeOH, 0.129 mL, 0.306 mmol, 10 equiv). After stirring for 2 hours at room temperature, the reaction mixture was quenched with saturated aqueous sodium bisulfate and diluted with methylene chloride. The aqueous layer was extracted with methylene chloride. The combined organic layer was washed with brine, dried with $Na_2SO_4$, filtered and concentrated in vacuo. Purification on reverse phase HPLC afforded compound 3.2.1g (17.3 mg, 39% yield). MS m/z (M+1) 1423.9

Step 8. Synthesis of 3.2.1

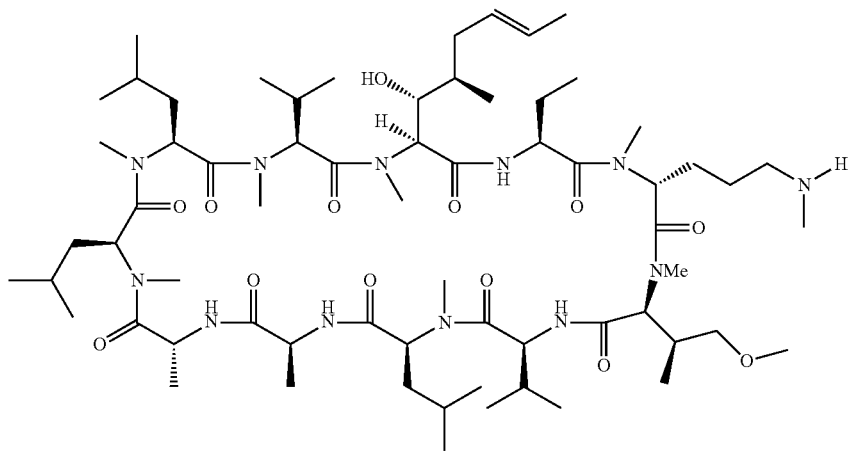

3.2.1

To a solution of compound 3.2.1g (12.0 mg, 8.43 umol) in methylene chloride (0.20 mL) at room temperature was added triethylamine (10.0 uL, 72.0 umol, 8.5 equiv) followed by triethylsilane (47.1 uL, 0.295 mmol, 35.0 equiv) and palladium (II) acetate (1.89 mg, 8.43 umol, 1.0 equiv). After stirring for 1 hour at room temperature, the reaction mixture was filtered through Celite with a methanol wash. The filtrate was concentrated in vacuo and purified by reverse phase HPLC to afford compound 3.2.1 (3.7 mg, 34%). MS m/z (M+1) 1289.9

III.2.2. Synthesis of Compound 3.2.2

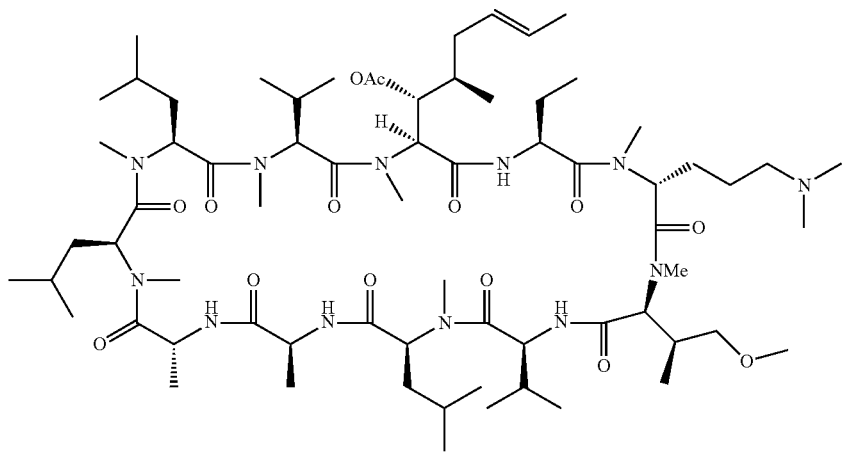 [SMILES: C/C=C/C[C@@H](C)[C@@H](OC(C)=O)[C@H]1C(=O)N[C@@H](CC)C(=O)N(C)[C@H](CCCN(C)C)C(=O)N(C)[C@@H]([C@H](C)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of [3.2.2a]

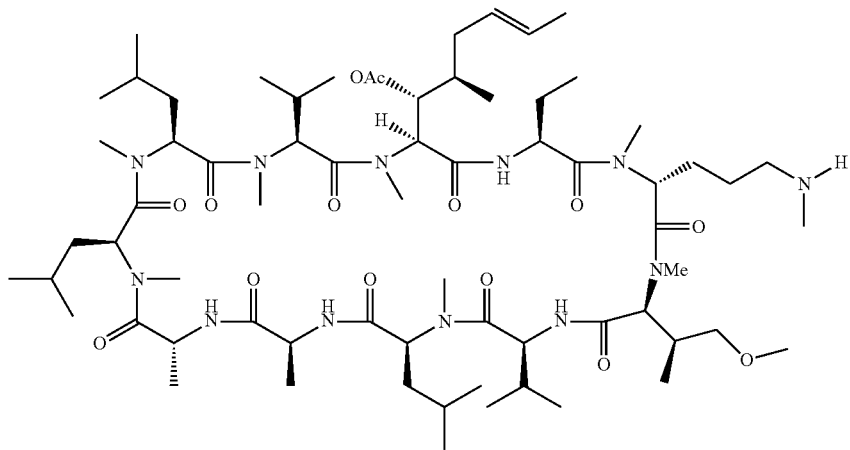

3.2.2a

To a solution of compound 3.2.1f (0.129 g, 88.0 umol) in methylene chloride (0.88 mL) at room temperature was added triethylamine (0.104 mL, 0.748 mmol, 8.5 equiv) followed by triethylsilane (0.492 mL, 3.08 mmol, 35.0 equiv) and palladium (II) acetate (19.7 mg, 88.0 umol, 1.0 equiv). After stirring for 1 hour at room temperature, the reaction mixture was filtered through Celite, washing with methanol. The filtrate was concentrated in vacuo to afford compound 3.2.2a (0.117 g). MS m/z (M+1) 1331.8

Step 2. Synthesis of [3.2.2b]

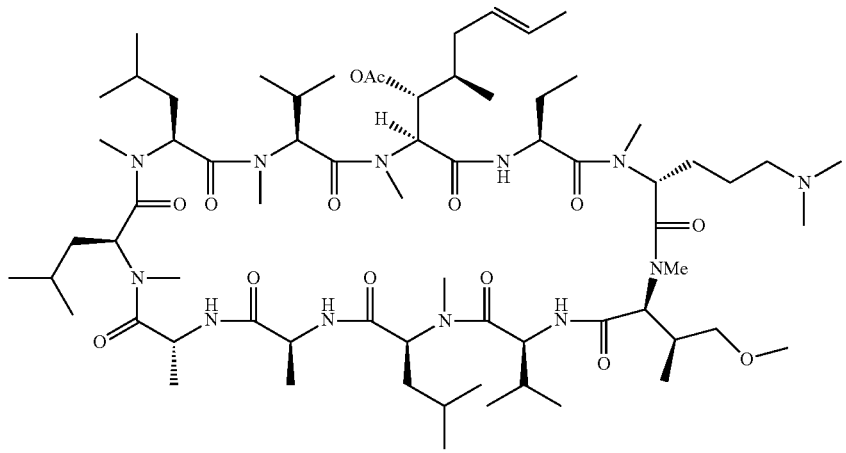

3.2.2b

To a solution of compound 3.2.2a (59.0 mg, 44.0 umol) in dichloroethane (0.44 mL) at room temperature was added formaldehyde (37% in water, 36.0 uL, 0.440 mmol, 10.0 equiv) followed by acetic acid (3.0 uL, 53.0 umol, 1.2 equiv). After stirring for 10 minutes, sodium triacetoxyborohydride (15.0 mg, 70.0 umol, 1.6 equiv) was added to the reaction mixture, and the resulting suspension was stirred at room temperature for 1 hour. The reaction was quenched with saturated aqueous $NaHCO_3$ and diluted with methylene chloride. The aqueous layer was extracted with methylene chloride. The combined organic layer was washed with brine, dried with $Na_2SO_4$, filtered and concentrated in vacuo to afford compound 3.2.2b (59.0 mg) which was used for the next step without further purification. MS m/z (M+1) 1345.6

Step 3. Synthesis of 3.2.2

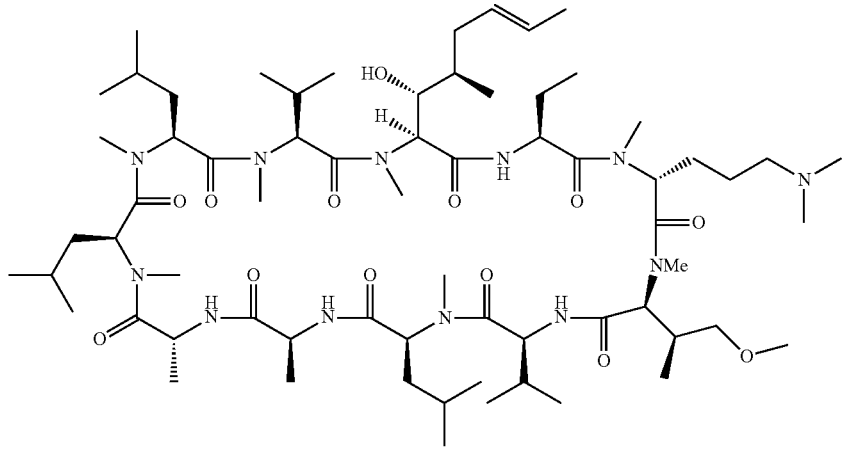

3.2.2

To a solution of compound 3.2.2b (59.2 mg, 44.0 umol) in methanol (1.4 mL) at 0° C. was added tetramethylammonium hydroxide (25% w/w in MeOH, 0.205 mL, 0.583 mmol, 13.0 equiv). After stirring for 2 hours at room temperature, the reaction mixture was quenched with saturated aqueous sodium bisulfate and diluted with methylene chloride. The aqueous layer was extracted with methylene chloride. The combined organic layer was washed with brine, dried with $Na_2SO_4$, filtered and concentrated in vacuo. Purification by reverse phase HPLC afforded compound 3.2.2 (18.5 mg, 32% yield). MS m/z (M+1) 1303.9

III.3.2.3 Synthesis of Compound 3.2.3

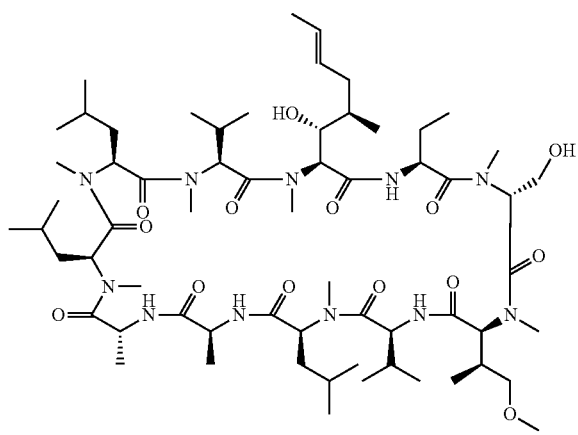 [SMILES: C/C=C/C[C@@H](C)[C@@H](O)[C@H]1C(=O)N[C@@H](CC)C(=O)N(C)[C@H](CO)C(=O)N(C)[C@@H]([C@H](C)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of (R)-2-(((benzyloxy)carbonyl)(methyl)amino)-3-(tert-butoxy)propanoic acid [3.2.3a]

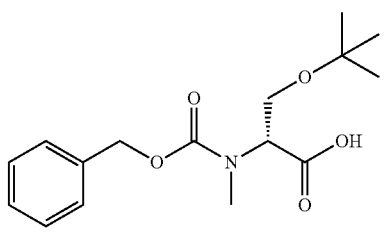

3.2.3a

To a solution of Z—N-Me-D-Ser(tBu)-OH.DCHA (1.0 g, 2.04 mmol) in ethyl acetate (80 mL) was added 0.1 N NaHSO$_4$ solution (21 mL, 2.1 mmol) and the resulting mixture was stirred at room temperature for 45 minutes. The phases were separated and the queous layer was extracted with ethyl acetate. Combined organic layer was washed with brine, dried with Na$_2$SO$_4$, filtered and concentrated in vacuo to afford compound 3.2.3a (0.678 g) which was used for the next step without further purification. MS m/z [M+1] 310.2

Step 2. Synthesis of 3.2.3b

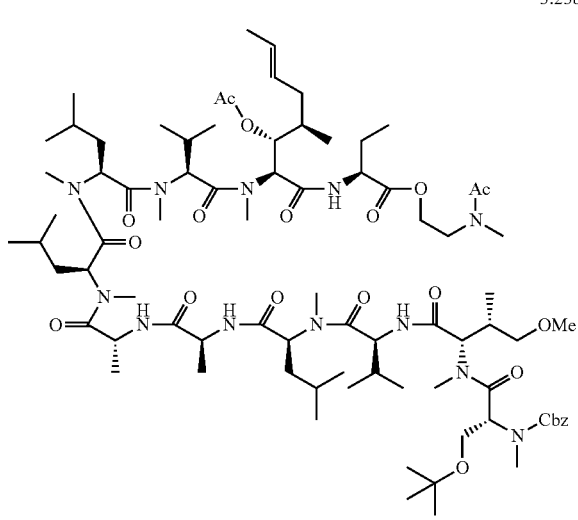

3.23b

To a solution of compound 3.2.3a (355 mg, 1.148 mmol, 3 equiv), HATU (436 mg, 1.148 mmol, 3 equiv), and DIEA (0.401 ml, 2.296 mmol, 6 equiv) in DCM (3 mL) and DMF (21 mL) was added compound 3.1d (0.50 g, 0.383 mmol, 1 equiv) in DCM (2.5 mL). The resulting solution was stirred at room temperature for 17 hours. The reaction solution was diluted with EtOAc and 0.5N NaHSO$_4$ solution and then separated into two layers. The organic phase was washed with water, saturated aqueous sodium bicarbonate solution and brine, dried with Na$_2$SO$_4$, filtered and concentrated in vacuo. Purification on silica gel chromatography (7% methanol/methylene chloride) afforded compound 3.2.3b (0.652 g, 71% pure, 76% yield). MS m/z [M+1] 1598.3

Step 3. Synthesis of 3.2.3c

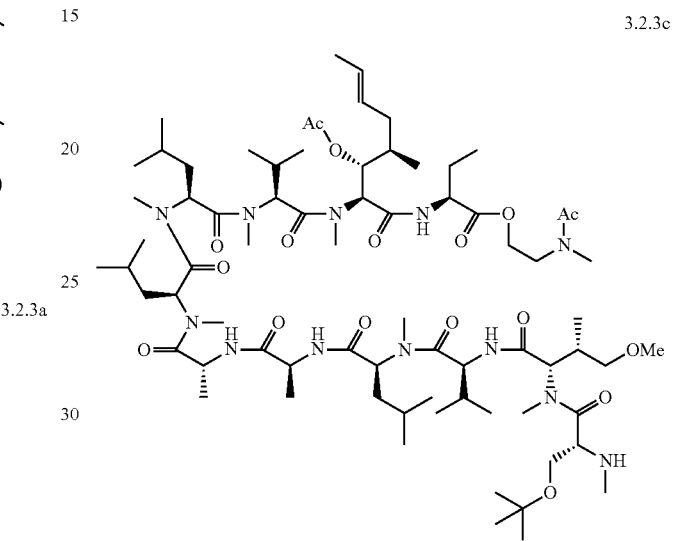

3.2.3c

To a solution of compound 3.2.3b (65.5 mg, 0.045 mmol) in DCM (1.2 mL) was added TEA (0.051 ml, 0.363 mmol), triethylsilane (0.250 ml, 1.567 mmol) and palladium (II) acetate (10.05 mg, 0.045 mmol). After stirring at 32° C. for 2 hours, the reaction mixture was diluted with ethyl acetate and methanol, filtered and concentrated in vacuo to afford crude compound 3.2.3c (0.12 g) which was purified by reverse phase column chromatography [C-18] to provide compound 3.2.3c (47 mg) as TFA salt powder. MS m/z [M+1]$^+$ 1464.1

Step 4. Synthesis of 3.2.3d

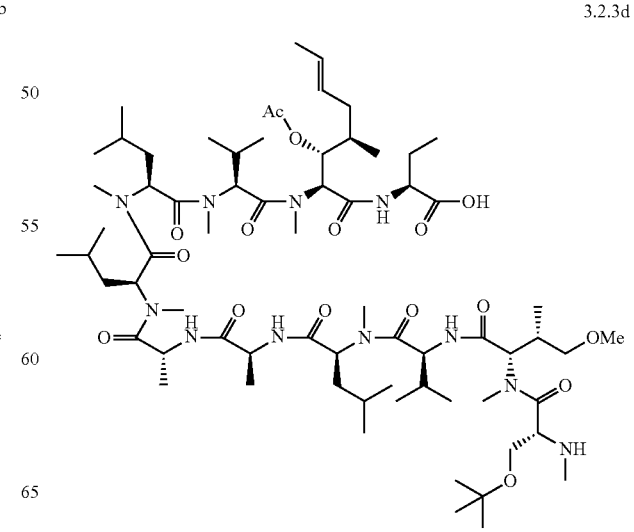

3.2.3d

To a solution of compound 3.2.3c (47 mg, 32 umol) in THF/water (2/1, 1.2 mL) at 0° C. was added LiOH.H₂O as a solid (9.43 mg, 0.225 mmol, 7.0 equiv). After stirring at 0° C. for 1 hour, the reaction mixture was quenched with 1.0 M HCl aq. solution (0.4 mL, 0.4 mmol, 12.5 equiv) and diluted with ethyl acetate. The aqueous layer was extracted with ethyl acetate. Combined organic layer was washed with brine, dried with Na₂SO₄, filtered and concentrated in vacuo to afford compound 3.2.3d (51 mg) which was used for the next step without further purification. MS m/z [M+1] 1365.1

Step 5. Synthesis of 3.2.3e

To a solution of BOP (33 mg, 74 umol, 2.2 equiv) in DCM (10 mL) at 0° C. was added slowly a solution of compound 3.2.3d (51 mg, 32 umol) and DMAP (10.3 mg, 84 umol, 2.5 equiv) in DCM (15 mL) via additional funnel. After stirring at room temperature for 22 hours, the reaction solution was washed with 10% citric acid followed by saturated aqueous NaHCO₃. The aqueous layer was extracted with methylene chloride. Combined organic layer was washed with brine, dried with Na₂SO₄, filtered and concentrated in vacuo to provide compound 3.2.3e (53 mg) which was used for the next step without further purification. MS m/z [M+1] 1348.1

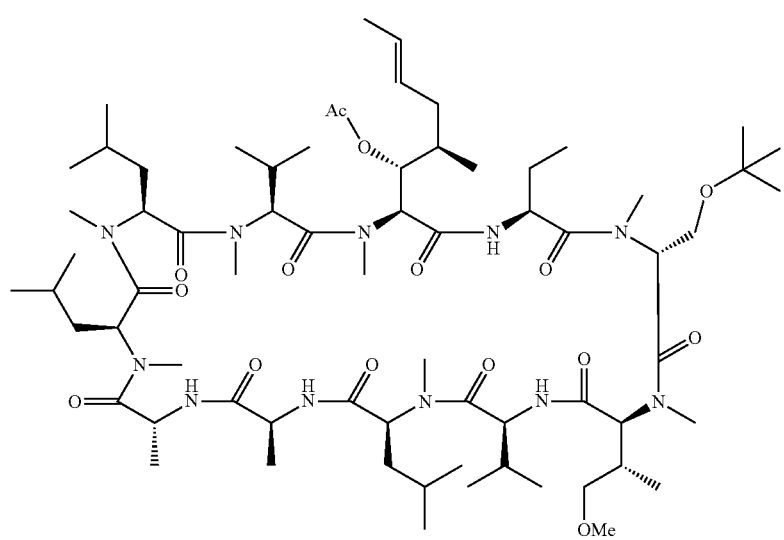

3.2.3e

Step 6. Synthesis of 3.2.3f

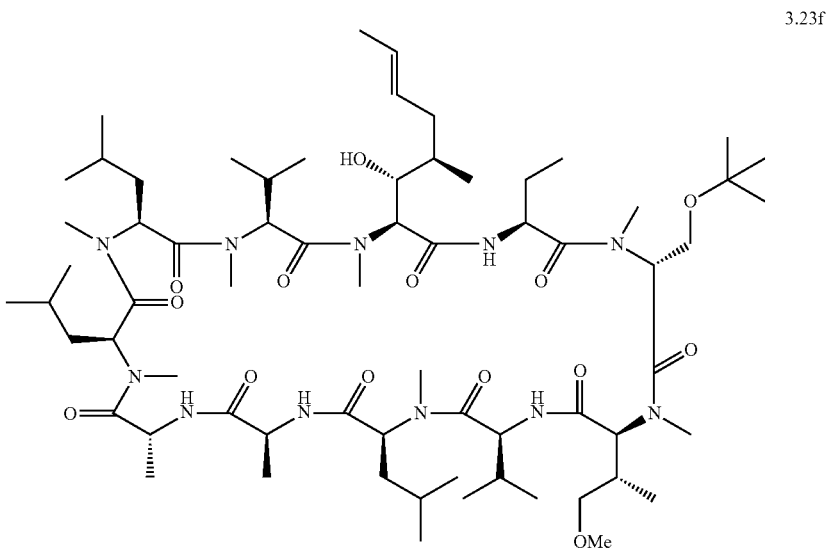 [SMILES: C/C=C/C[C@@H](C)[C@@H](O)[C@H]1C(=O)N[C@@H](CC)C(=O)N(C)[C@H](COC(C)(C)C)C(=O)N(C)[C@@H]([C@H](C)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

3.23f

To a solution of compound 3.2.3e (53 mg, 39 umol) in methanol (1.6 mL) at 0° C. was added tetramethylammonium hydroxide (25% w/w in MeOH, 0.25 mL, 0.59 mmol, 15 equiv). After stirring for 17 hours at room temperature, the reaction mixture was quenched with saturated aqueous sodium bisulfate and diluted with methylene chloride. The aqueous layer was extracted with methylene chloride. Combined organic layer was washed with brine, dried with Na₂SO₄, filtered and concentrated in vacuo to provide compound 3.2.3f (43 mg) which was used for the next step without further purification. MS m/z [M+1] 1305.1

Step 7. Synthesis of 3.2.3

3.2.3

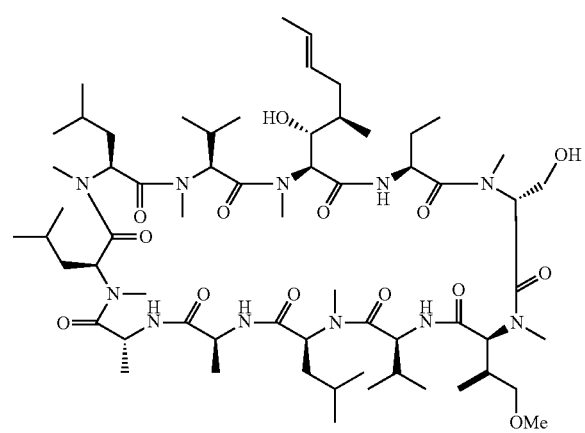

To a solution of compound 3.2.3f (43 mg, 26 umol) in DCM (1.5 ml) was added trifluoroacetic acid (1.0 ml, 13 mmol) and water (20 ul). After stirring at room temperature for 1 hour, the reaction mixture was concentrated in vacuo to afford crude compound 3.2.3 (63 mg) which was purified by reverse phase column chromatography [C-18] to provide pure compound 3.2.3 (5.9 mg, 16% yield). MS m/z (M+1) 1249.1

III.3. Synthesis of 3.3

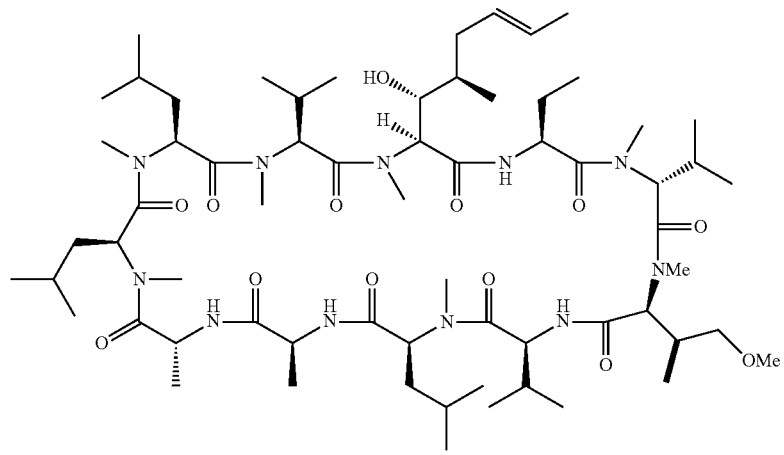 [SMILES: C/C=C/C[C@@H](C)[C@@H](O)[C@H]1C(=O)N[C@@H](CC)C(=O)N(C)[C@H](C(C)C)C(=O)N(C)[C@@H]([C@H](C)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of (R)-2-((tert-butoxycarbonyl)(methyl)amino)-3-methylbutanoic acid [3.3a]

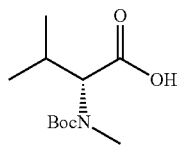

3.3a

To a solution of N-Boc-D-Val-OH (1.0 g, 4.60 mmol) in THF (15.3 mL) at 0° C. was added MeI (2.88 mL, 46.0 mmol, 10.0 equiv). NaH (60%, 1.84 g, 46.0 mmol, 10.0 equiv) was added as a solid to the suspension over a period of 2 hours. After stirring for 12 hours at room temperature, the reaction mixture was diluted with diethyl ether and quenched with water slowly. Aqueous layer was extracted with diethyl ether followed by acidified to pH 3 with 10% citric acid and extraction with ethyl acetate. Combined organic layer was washed with brine, dried with Na₂SO₄, filtered and concentrated in vacuo to afford compound 3.3a (1.07 g) which was used for the next step without further purification. MS m/z (M+Na) 254.2. ¹H NMR (400 MHz, CDCl₃) 4.02-4.17 (m, 1H), 2.88 (s, 3H), 2.40-2.14 (m, 1H), 1.54-1.39 (m, 9H), 1.03 (d, J=6.60 Hz, 3H), 0.92 (d, J=6.70 Hz, 3H).

Step 2. Synthesis of 3.3b

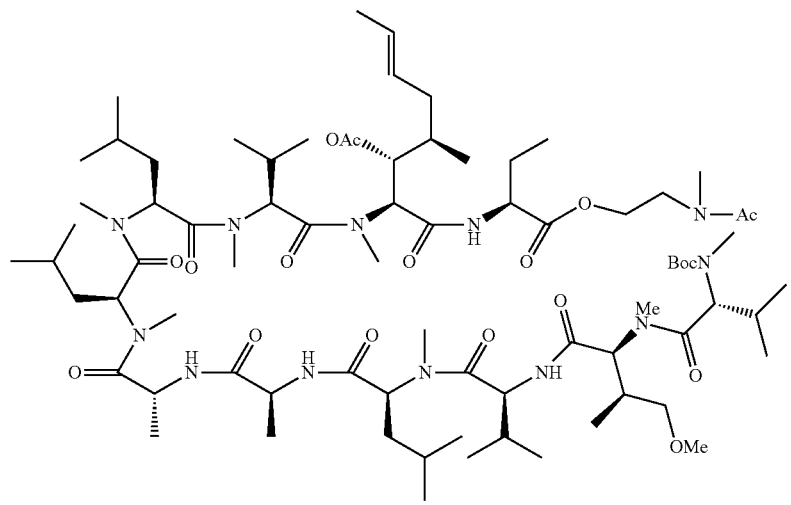

3.3b

To a solution of compound 3.1d (0.165 g, 0.126 mmol) in methylene chloride (0.63 mL) at 0° C. was added compound 3.3a (87.0 mg, 0.378 mmol, 3.0 equiv) followed by HATU (0.144 g, 0.378 mmol, 3.0 equiv) and DIPEA (0.13 mL, 0.755 mmol, 6.0 equiv). After stirring at room temperature for 12 hours, the reaction mixture was partitioned between water and methylene chloride. Aqueous layer was extracted with methylene chloride. Combined organic layer was washed with brine, dried with $Na_2SO_4$, filtered and concentrated in vacuo. Purification on silica gel chromatography (45% acetone/methylene chloride) afforded compound 3.3b (93.8 mg, 49%). MS m/z (M+Na) 1542.3

Step 3. Synthesis of 3.3c

To a solution of compound 3.3b (93.8 mg, 62 umol) in methylene chloride (0.41 mL) at 0° C. was added TFA (0.21 mL). After stirring at 0° C. for 2 hours, the reaction mixture was quenched with saturated aqueous $NaHCO_3$ and diluted with methylene chloride. Aqueous layer was extracted with methylene chloride. Combined organic layer was washed with brine, dried with $Na_2SO_4$, filtered and concentrated in vacuo to afford compound 3.3c (88.0 mg) which was used for the next step without further purification. MS m/z (M+1) 1420.1

3.3c

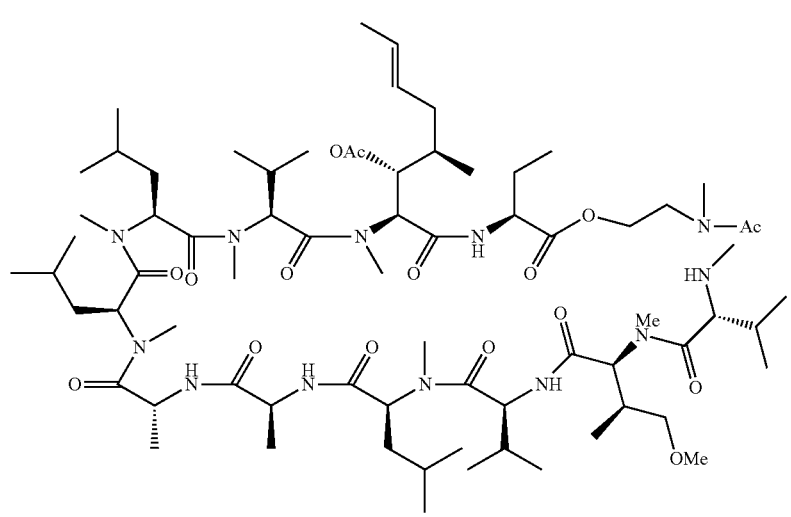

Step 4. Synthesis of 3.3d

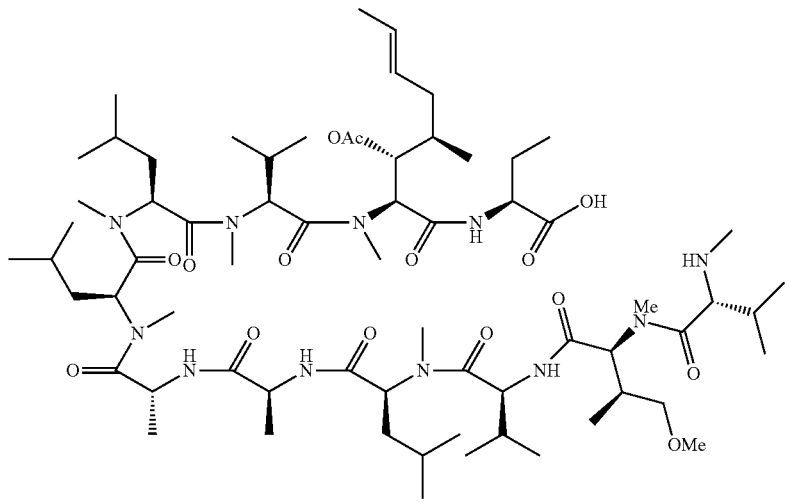

3.3d

To a solution of compound 3.3c (88.0 mg, 62 umol) in THF/water (1/1, 1.32 mL) at 0° C. was added LiOH.H₂O as a solid (13.0 mg, 0.310 mmol, 5.0 equiv). After stirring at 0° C. for 3 hours, the reaction mixture was quenched with 1.0 M HCl aq. solution (0.37 mL, 0.372 mmol, 6.0 equiv) and diluted with methylene chloride. Aqueous layer was extracted with methylene chloride. Combined organic layer was washed with brine, dried with Na₂SO₄, filtered and concentrated in vacuo to afford compound 3.3d (82 mg) which was used for the next step without further purification. MS m/z (M+1) 1321.0

Step 5. Synthesis of 3.3e

To a suspension of BOP (54.8 mg, 0.124 mmol, 2.0 equiv) in methylene chloride (15.5 mL) 0° C. was added dropwise a solution of compound 3.3d (82.0 mg, 62.0 umol) and DMAP (15.2 mg, 0.124 mmol, 2.0 equiv) in methylene chloride (46.5 mL) via additional funnel. After stirring at room temperature for 12 hours, the reaction mixture was washed with 10% citric acid followed by saturated aqueous NaHCO₃. The aqueous layer was extracted with methylene chloride. Combined organic layer was washed with brine, dried with Na₂SO₄, filtered and concentrated in vacuo. Purification on silica gel chromatography afforded compound 3.3e (65.5 mg, 81%). MS m/z (M+1) 1302.9

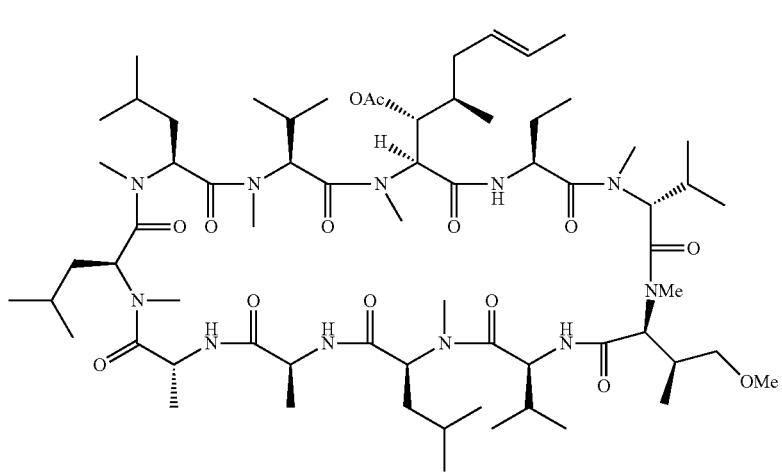

3.3e

Step 6. Synthesis of 3.3

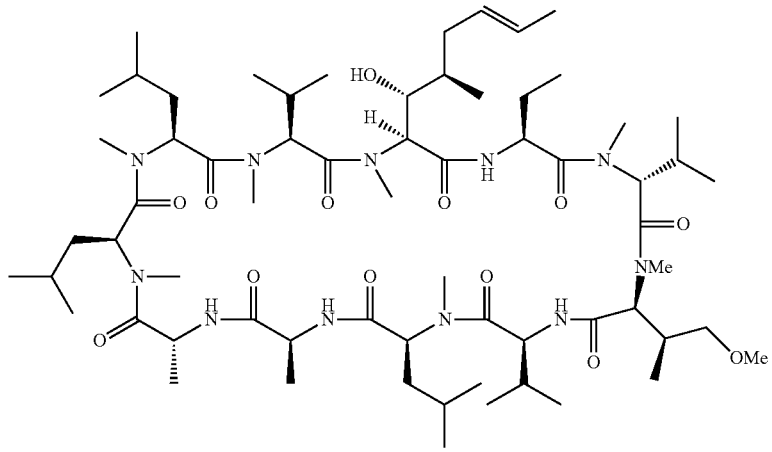

3.3

To a solution of compound 3.3e (65.5 mg, 50.3 umol) in methanol (1.7 mL) at 0° C. was added tetramethylammonium hydroxide (25% w/w in MeOH, 0.177 mL, 0.503 mmol, 10 equiv). After stirring for 2 hours at room temperature, the reaction mixture was quenched with saturated aqueous sodium bisulfate and diluted with methylene chloride. The aqueous layer was extracted with methylene chloride. Combined organic layer was washed with brine, dried with $Na_2SO_4$, filtered and concentrated in vacuo. Purification on reverse phase HPLC afforded compound 3.3 (14.0 mg, 22% yield). MS m/z (M+1) 1260.8

III.4.1 Synthesis of Compound 3.4.1

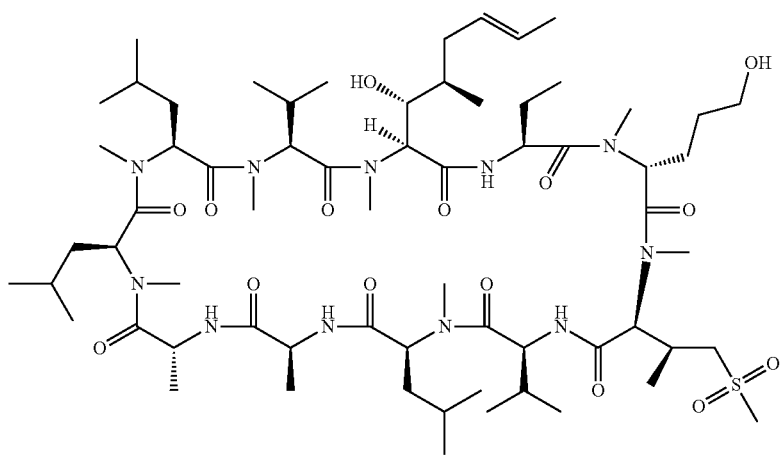 [SMILES: C/C=C/C[C@@H](C)[C@@H](O)[C@H]1C(=O)N[C@@H](CC)C(=O)N(C)[C@H](CCCO)C(=O)N(C)[C@@H]([C@H](C)CS(C)(=O)=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of 3.4.1a

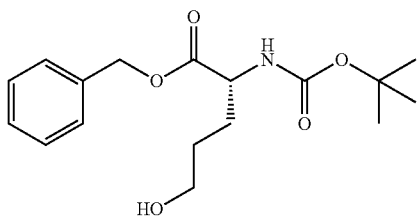

3.4.1a

To a solution of (R)-5-(benzyloxy)-4-(tert-butoxycarbonylamino)-5-oxopentanoic acid (8 g, 23.71 mmol) in THF (80 ml) at −18° C. was added N-methylmorpholine (2.87 ml, 26.1 mmol) and ethyl chloroformate (2.50 ml, 26.1 mmol). The reaction mixture was stirred for 3 hours in an ice bath. The white color precipitated N-methylmorpholine hydrochloride was removed by filtration. The filter cake was rinsed with 30 ml THF. The combined filtrate was cooled to 0° C. in an ice bath and was slowly added sodium borohydride (1.35 g, 35.6 mmol), followed by the addition of water (16 mL). After stirring at 0° C. for 40 minutes, the reaction mixture was quenched with sat. $NH_4Cl$ aq. solution (20 ml) at 0° C. and was stirred for 20 minutes. The mixture was then extracted with ethyl acetate. The combined organic phase was washed with brine, dried over sodium sulfate and concentrated. The residue was purified by silica gel column chromatography (ethyl acetate/heptanes 0-80%) to give product 3.4.1a (7.2 g, 94% yield). MS m/z (M+1) 324.1

Step 2. Synthesis of 3.4.1 b

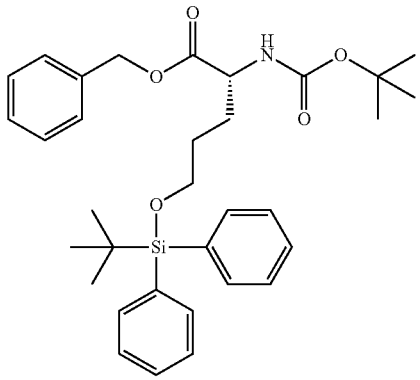

3.4.1b

To an ice-cooled solution of 3.4.1a (4.4 g, 13.61 mmol) in DMF (40 mL) was added imidazole (1.66 g, 24.49 mmol), followed by the addition of tert-butylchloro diphenylsilane (4.60 ml, 17.69 mmol) and the resulting mixture was stirred at ambient temperature for 48 hours. The reaction solution was diluted with ethyl acetate, washed with water (2×150 ml), brine, dried over sodium sulfate and concentrated. The residue was purified by silica gel column chromatography (ethyl acetate/heptane, 0-100%) to give product 3.4.1b (8.2 g, 66.5% yield). MS m/z (M+1) 562.1

Step 3. Synthesis of 3.4.1c

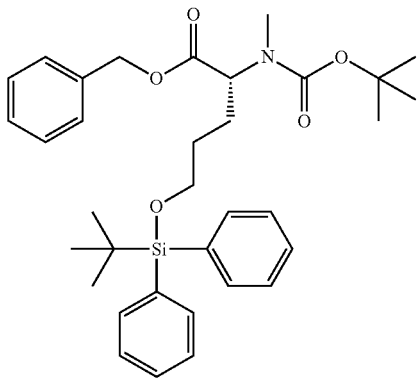

3.4.1c

To a solution of 3.4.1b (1.5 g, 2.0 mmol) in THF (18 mL) at −78° C. under nitrogen was added KHMDS (1.0 M in THF, 2.2 ml, 2.2 mmol) and the resulting solution was stirred at same temperature for 40 minutes. To this solution was then added iodomethane (1.25 ml, 20 mmol). The reaction temperature was gradually warmed to room temperature and was stirred for 18 hours. The reaction was quenched with saturated $NH_4Cl$ aqueous solution and extracted with ethyl acetate. The organic phase was washed with brine, dried over sodium sulfate and concentrated. The crude product was purified by silica gel column chromatography (EtOAc/heptane, 0-100%) to give 3.4.1c (600 mg, 52% yield). MS m/z (M+1) 576.1

Step 4. Synthesis of 3.4.1d

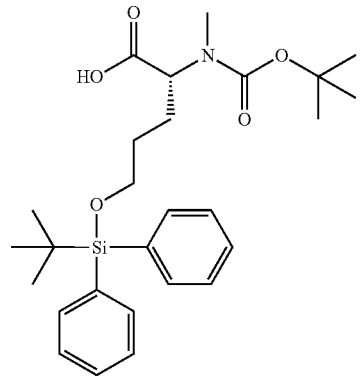

3.4.1d

To a solution of 3.4.1c (600 mg, 1.04 mmol) in MeOH (20 mL) at room temperature was added Pd (10% on carbon, 222 mg, 0.21 mmol). The suspension was purged with nitrogen for 5 minutes and then was stirred under 1 atm of hydrogen for 2 hours. The reaction mixture was diluted with DCM and filtered through Celite. The filtrate was concentrated to give product 3.4.1d (520 mg, 98% yield). MS m/z (M+1) 486.1

Step 5. Synthesis of 3.4.1e

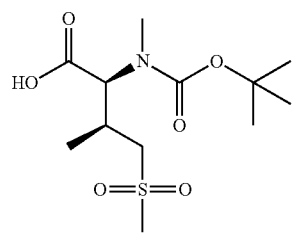

3.4.1e

To a well-stirred solution of sodium periodate (3.1 g, 14.48 mmol) in acetonitrile (11 ml), $CCl_4$ (7.26 ml), water (11 ml) was added Ruthenium (Ill) Chloride (150 mg, 0.72 mmol). The mixture was stirred for 15 minutes at room temperature followed by the addition of 2.4c (0.8 g, 2.41 mmol) in acetonitrile (20 ml). After stirring at room temperature for 5 minutes, the reaction mixture was quenched with water (30 mL). The aqueous phase was extracted with ethyl acetate. The organic phase was washed with saturated aqueous $NaHSO_3$ solution, brine, dried over sodium sulfate and concentrated to give product 3.4.1e (400 mg, 53.6% yield). MS m/z (M+Na) 332.1

Step 6. Synthesis of 3.4.1f

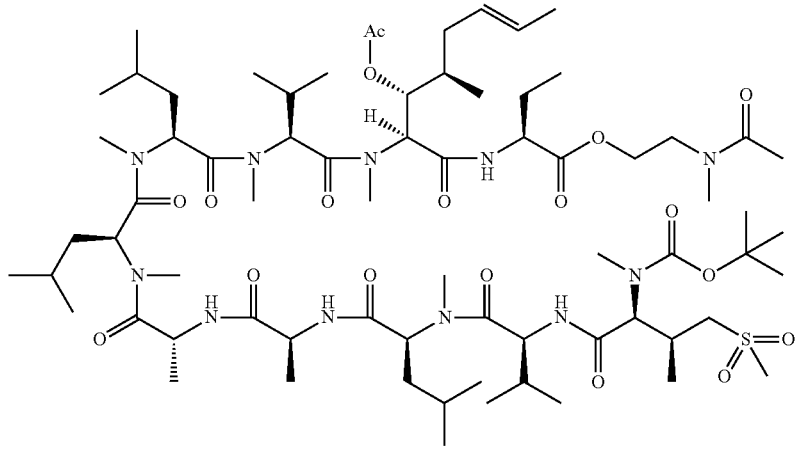

3.4.1f

To an ice cooled solution of 3.4.1e (399 mg, 1.29 mmol), HATU (490 mg, 1.29 mmol), HOAT (175 mg, 1.29 mmol) and DIEA (0.45 ml, 2.58 mmol) in DCM (6 ml) was added amine 1 (500 mg, 0.43 mmol) in DCM (5 ml). The resulting solution was stirred at room temperature for 2 hours. The reaction mixture was diluted with ethyl acetate, and washed with water, brine, dried over sodium sulfate and concentrated. The crude product was purified by silica gel column chromatography (EtOAc/heptane, 0 to 100%) to give 3.4.1f (250 mg, 0.17 mmol, 40% yield). MS m/z (M+1) 1455.8

Step 7. Synthesis of 3.4.1g

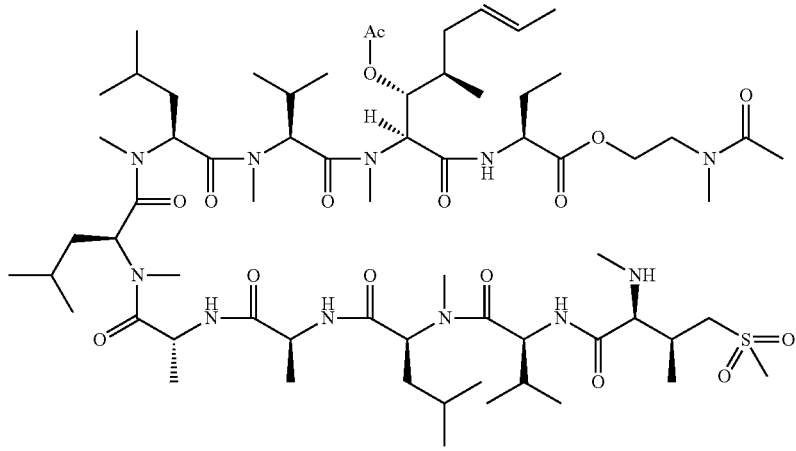

3.4.1g

To an ice cooled solution of 3.4.1f (250 mg, 0.17 mmol) in DCM (6 ml) was added 50% TFA in DCM (6 ml). The resulting solution was stirred at ambient temperature for 1 hour. The reaction solution was concentrated and the residue was diluted with ethyl acetate, washed with saturated aqueous sodium bicarbonate solution, brine, dried over sodium sulfate and concentrated to give product 3.4.1g (150 mg, 64.4% yield). MS m/z (M+H) 1354.8

Step 8. Synthesis of 3.4.1h

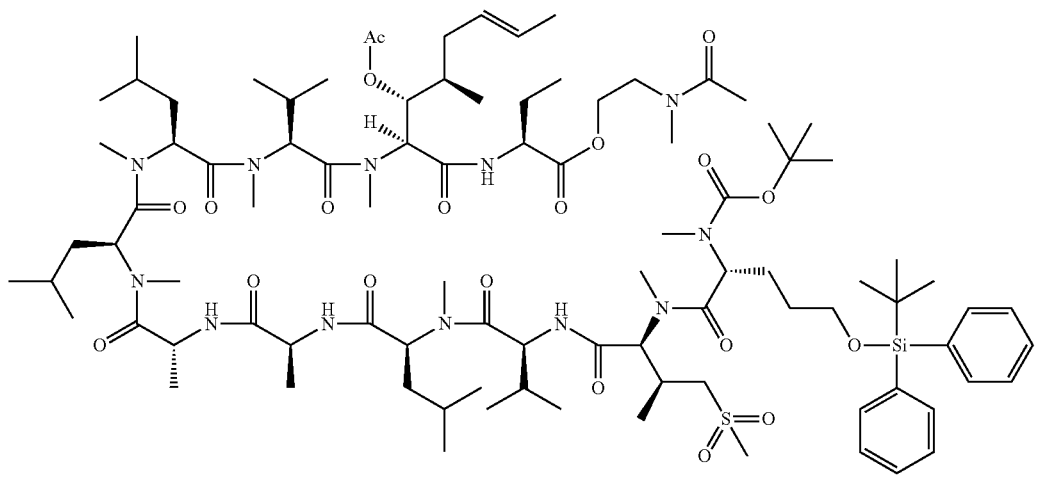

3.4.1h

To an ice cooled solution of 3.4.1g (150 mg, 0.11 mmol) in DMF (2 mL) was added 3.4.1d (161 mg, 0.33 mmol), DIEA (0.12 ml, 0.66 mmol) and HATU (126 mg, 0.33 mmol). After stirring at room temperature for 18 hours, the reaction mixture was diluted with ethyl acetate, washed with saturated aqueous sodium bicarbonate solution, brine, dried over sodium sulfate and concentrated. The crude product was purified by silica gel flash column chromatography eluting with 0-80% acetone in DCM to give 3.4.1h (100 mg, 49.6% yield). MS m/z (M+H) 1823.1

Step 9. Synthesis of 3.4.1i

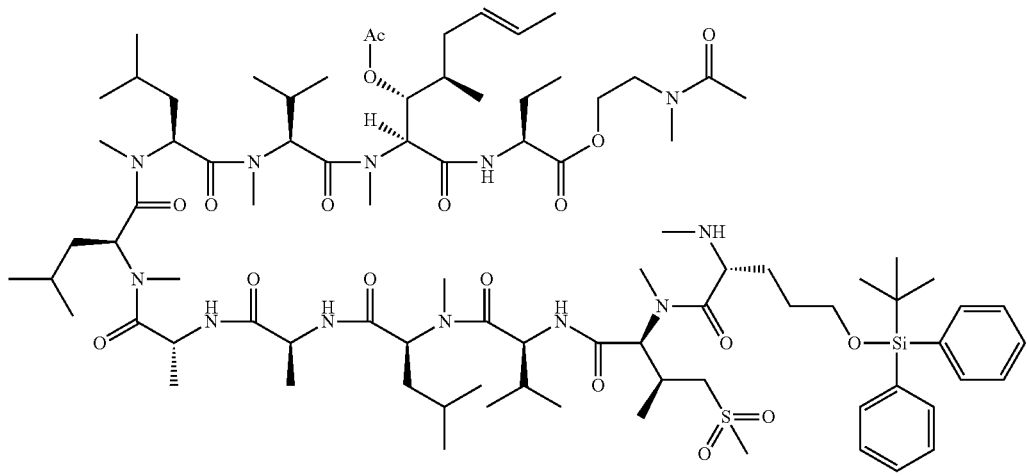

3.4.1i

To an ice cooled solution of 3.4.1 h (100 mg, 0.055 mmol) in DCM (5 ml) was added 50% TFA in DCM (6 mL). The resulting solution was stirred at 0° C. 30 minutes and at room temperature for 1.5 hours. The reaction mixture was concentrated and the residue was diluted with ethyl acetate, washed with saturated aqueous sodium bicarbonate solution, brine, dried over sodium sulfate and concentrated to give 3.4.1i (95 mg, 99% yield). MS m/z (M+H) 1723.1

Step 10. Synthesis of 3.4.1j

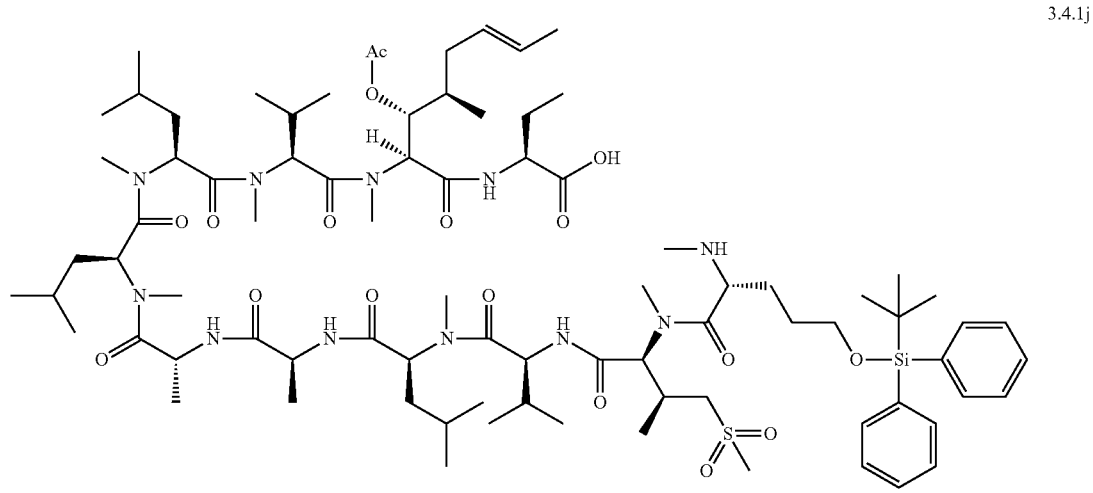 [SMILES: C/C=C/C[C@@H](C)[C@@H](OC(C)=O)[C@@H](C(=O)N[C@@H](CC)C(=O)O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H]([C@H](C)CS(C)(=O)=O)N(C)C(=O)[C@@H](CCCO[Si](c1ccccc1)(c1ccccc1)C(C)(C)C)NC)C(C)C]

3.4.1j

To an ice cooled solution of 3.4.1i (95 mg, 0.055 mmol) in mixture solvent THF (1 mL), MeOH (1 mL), water (1 mL) was added LiOH (6.60 mg, 0.27 mmol) and the resulting solution was stirred at 0° C. for 1 hour. The reaction mixture was concentrated and the residue was dissolved in EtOAc, neutralized with 1.0 N HCl aq. solution (6 equiv, 0.33 mL). The organic phase was washed with brine, dried over sodium sulfate and concentrated to give crude 3.4.1j (80 mg, 88% yield). MS m/z (M+H) 1623.9

Step 11. Synthesis of 3.4.1k

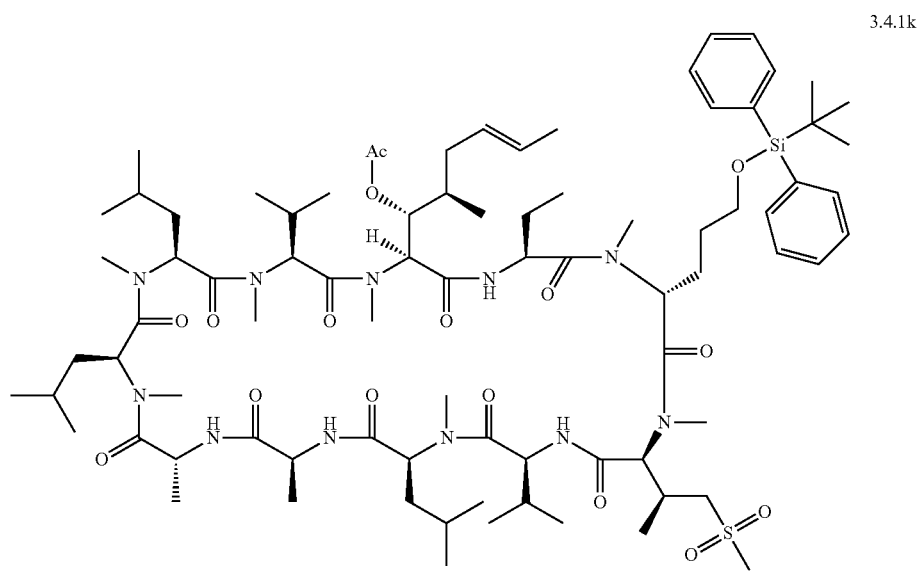 [SMILES: C/C=C/C[C@@H](C)[C@@H](OC(C)=O)[C@H]1C(=O)N[C@@H](CC)C(=O)N(C)[C@H](CCCO[Si](c2ccccc2)(c2ccccc2)C(C)(C)C)C(=O)N(C)[C@@H]([C@H](C)CS(C)(=O)=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

3.4.1k

To a solution of BOP (43.6 mg, 0.099 mmol) in DCM (150 mL), was added a solution of 3.4.1j (80 mg, 0.049 mmol) and DMAP (12 mg, 0.099 mmol) in DCM (50 mL). The resulting solution was stirred at ambient temperature for 16 hours. The reaction mixture was then washed with saturated aqueous sodium bicarbonate solution, brine, dried over sodium sulfate and concentrated to give crude 3.4.1k (75 mg, 94% yield), MS m/z (M+H) 1605.9

Step 12. Synthesis of 3.4.1l

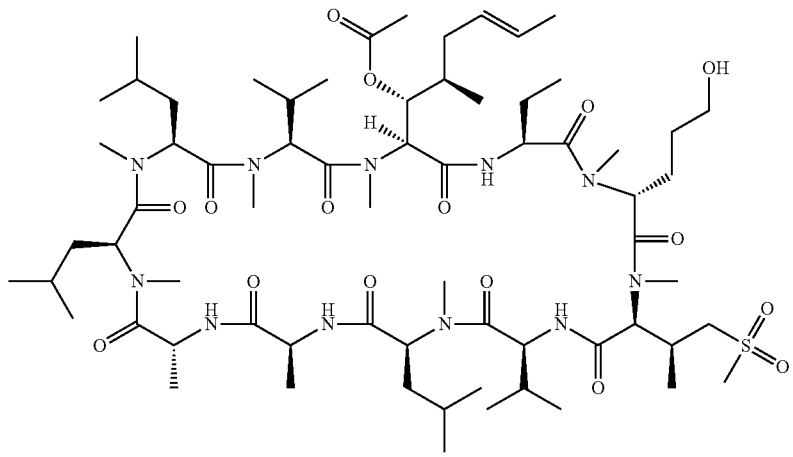

3.4.1l

To an ice cooled solution of 3.4.1k (120 mg, 0.075 mmol) in THF (1 mL) was added 1 TBAF (1.0 M in THF, 0.11 mL, 0.11 mmol). After stirring at room temperature for 18 hours, the reaction solution was diluted with ethyl acetate, washed with water, brine, dried over sodium sulfate and concentrated to give crude 3.4.1l (100 mg, 98% yield). MS m/z (M+H) 1367.6

Step 13. Synthesis of 3.4.1

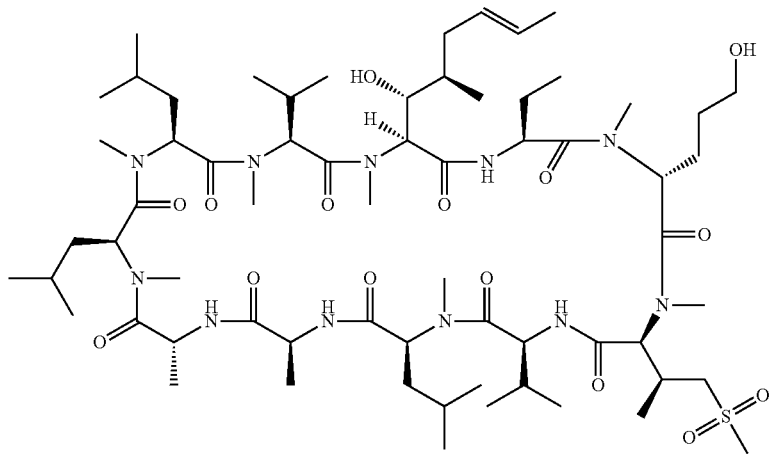

3.4.1

To an ice cooled solution of 3.4.1l (50 mg, 0.037 mmol) in MeOH (2 mL), was added MeNOH (25% w/w in MeOH, 0.18 mL, 0.44 mmol) and the resulting solution was stirred at room temperature for 4 hours. The reaction mixture was quenched with 1.0 M $KHSO_4$ aq. solution and extracted with ethyl acetate. The organic phase was washed with brine, dried over sodium sulfate, and concentrated. The crude product was purified by HPLC to give 3.4.1 (7.1 mg, 14.6% yield). MS m/z (M+H) 1324.8

III.4.2 Synthesis of compound 3.4.2

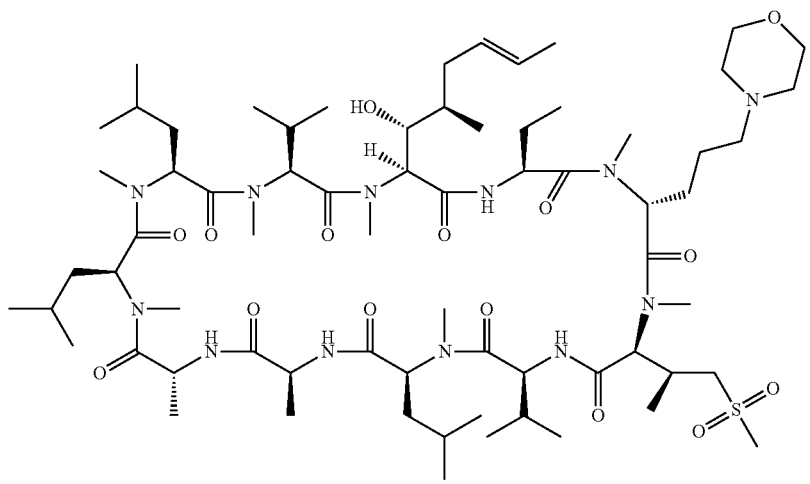 [SMILES: C/C=C/C[C@@H](C)[C@@H](O)[C@H]1C(=O)N[C@@H](CC)C(=O)N(C)[C@H](CCCN2CCOCC2)C(=O)N(C)[C@@H]([C@H](C)CS(C)(=O)=O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Step 1. Synthesis of 3.4.2a

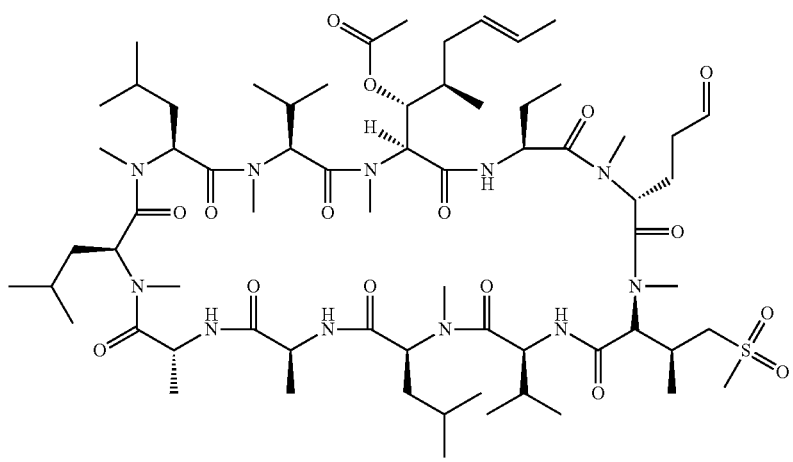

3.4.2a

To a solution of oxalyl dichloride (0.051 ml, 0.58 mmol) in DCM (1 mL) at −78° C. was added DMSO (0.083 ml, 1.17 mmol). After 20 minutes, 3.4.1o (50 mg, 0.037 mmol) in 0.5 mL DCM was added. After stirring at −78° C. for another 30 minutes, TEA (0.17 ml, 1.28 mmol) was added. The solution was then slowly warmed to room temperature and stirred for 30 minutes. The reaction was quenched with 5.0 mL saturated aqueous NH$_4$Cl solution and extracted with ethyl acetate. The organic phase was washed with brine, dried over sodium sulfate, and concentrated to give crude 3.4.2a (60 mg, 96% yield). The crude product was used in the next step with no further purification. MS m/z (M+1) 1364.9

Step 2. Synthesis of 3.4.2b

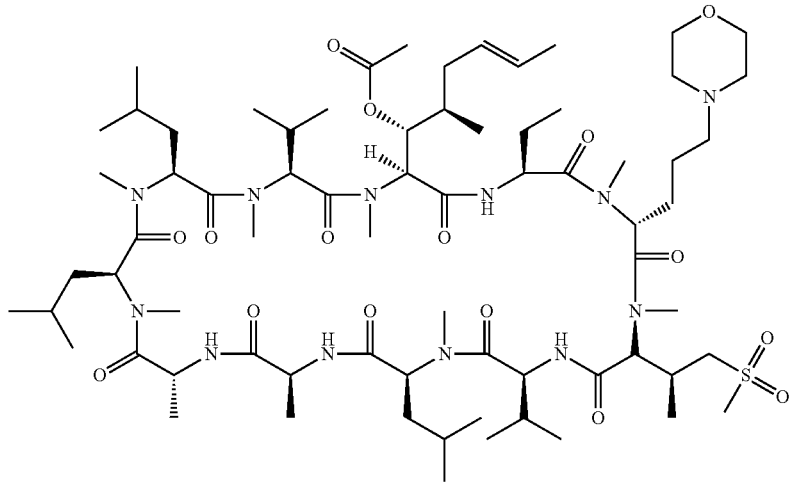

3.4.2b

To a solution of 3.4.2a (50 mg, 0.037 mmol) in acetonitrile (3 mL) at ambient temperature was added morpholine (0.13 ml, 1.46 mmol), sodium triacetoxyborohydride (78 mg, 0.37 mmol) and acetic acid (0.021 ml, 0.37 mmol). After stirring at room temperature for 16 hours, the reaction was quenched with 5.0 mL saturated aqueous $NH_4Cl$ solution at 0° C. and extracted with ethyl acetate. The organic phase was washed with brine, dried over sodium sulfate and concentrated to give crude 3.42b, which was used in the following step with no further purification. MS m/z (M+1) 1436.8

Step 3. Synthesis of 3.4.2

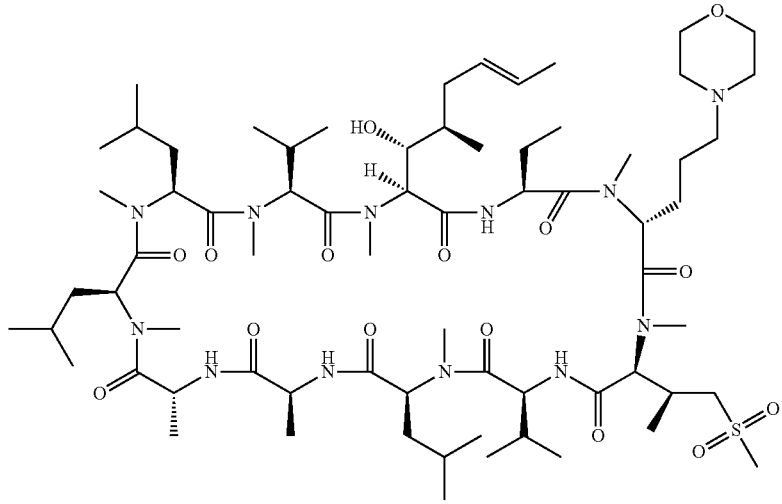

3.4.2

To an ice cooled solution of 3.4.2b (30 mg, 0.021 mmol) in MeOH (1 mL) was added $Me_4NOH$ (25% w/w in MeOH, 0.11 ml, 0.25 mmol) and the resulting solution was stirred at room temperature for 2 hours. The reaction mixture was quenched with 1.0 M $KHSO_4$ aq. solution (1 mL) and extracted with ethyl acetate. The organic phase was washed with brine, dried over sodium sulfate, and concentrated. The crude product was purified by HPLC to give 3.4.2 (3 mg, 9.8% yield). MS m/z (M+1) 1394.8

TABLE 1
UPLC retention time and HRMS
| | Structure | Retention time (mins) | HRMS |
|---|---|---|---|
| 2.1 | 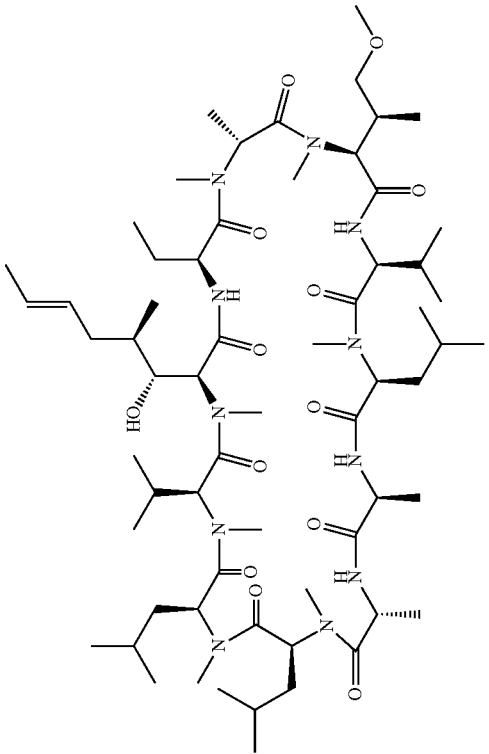 | 6.295 | 1232.8596 |
| 2.2 | 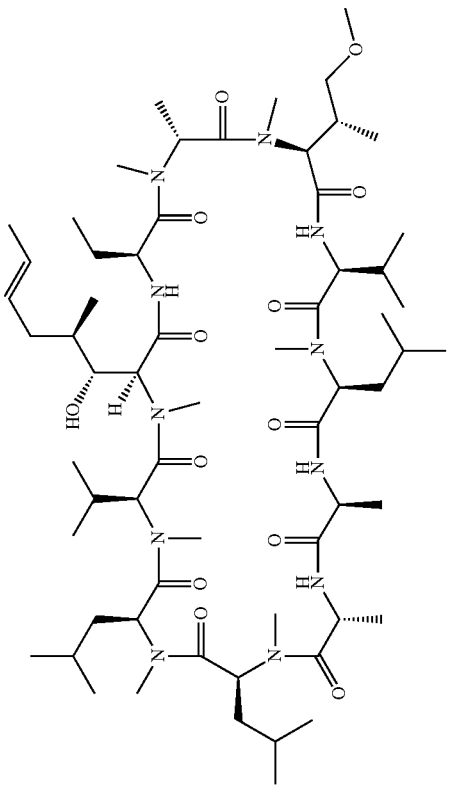 | 6.29 | 1232.8580 |

TABLE 1-continued
UPLC retention time and HRMS
| | Structure | Retention time (mins) | HRMS |
|---|---|---|---|
| 2.3 | 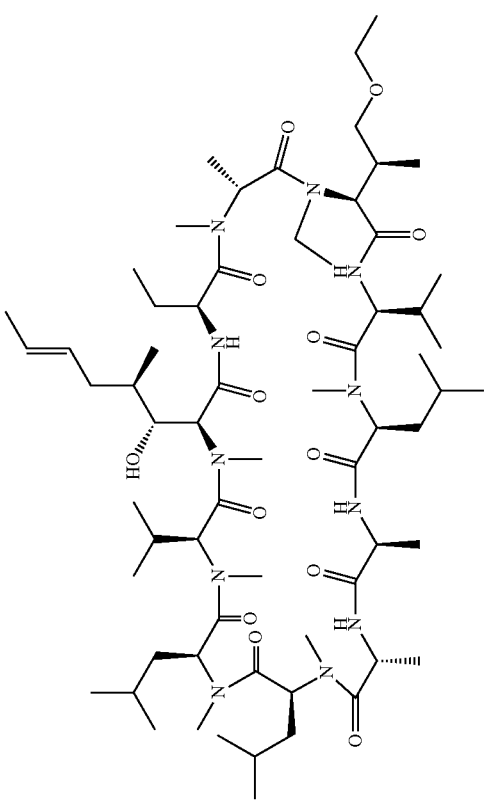 | 5.893 | |
| 2.4 | 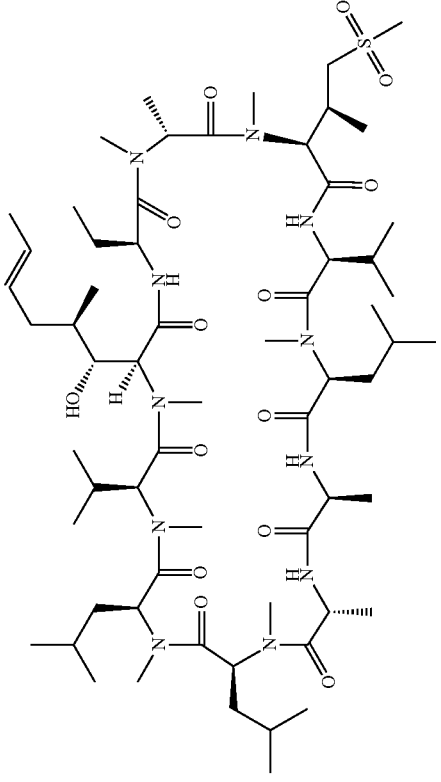 | 5.972 | 1280.8250 |

TABLE 1-continued
UPLC retention time and HRMS
| | Structure | Retention time (mins) | HRMS |
|---|---|---|---|
| 2.5.1 | 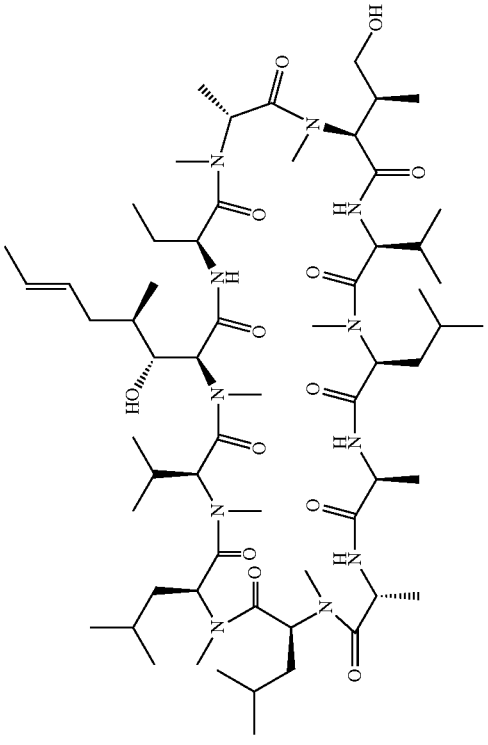 | 5.945 | 1218.8439 |
| 2.5.2 | 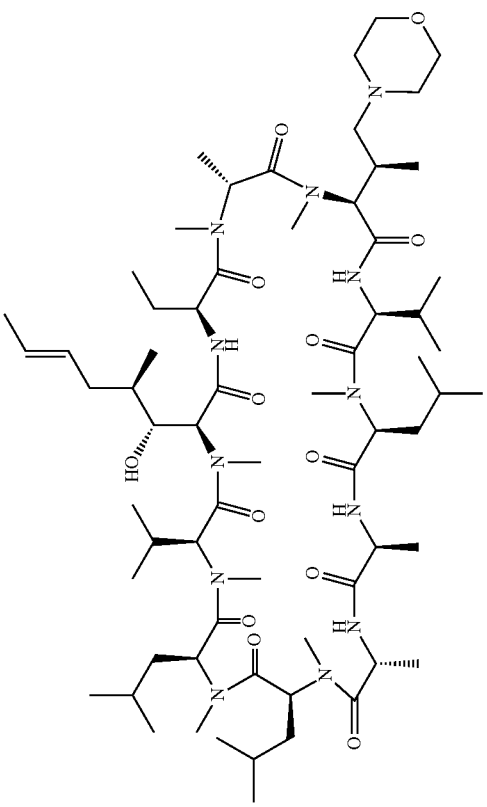 | 5.371 | 1287.903 |

TABLE 1-continued

UPLC retention time and HRMS

| | Structure | Retention time (mins) | HRMS |
|---|---|---|---|
| 2.5.3 | 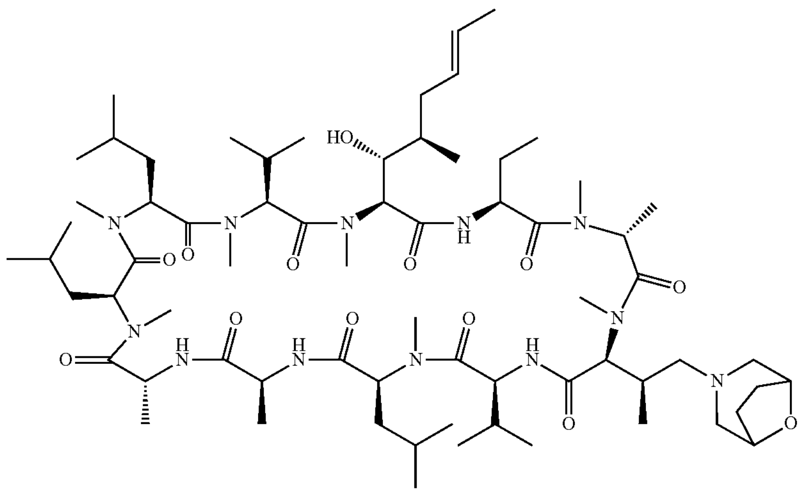 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CC3CCC(C2)O3)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.834 | 1313.917 |
| 2.5.5 | 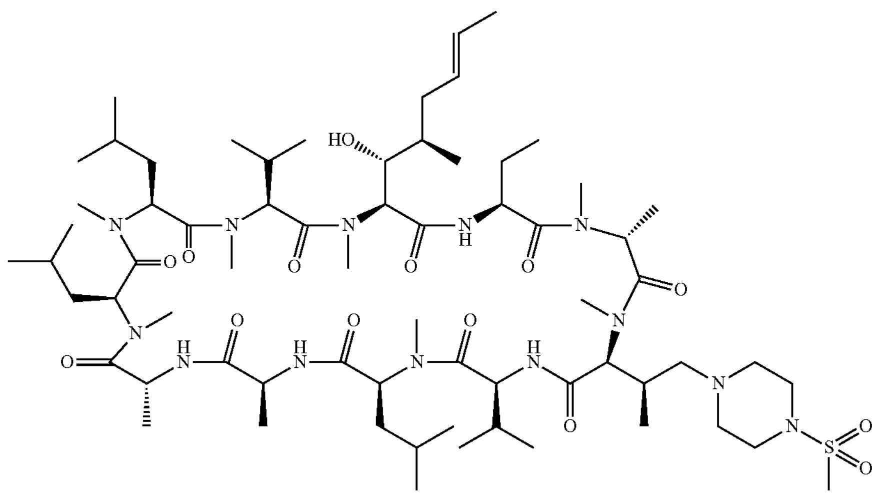 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCN(S(C)(=O)=O)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.444 | 1364.8948 |

TABLE 1-continued
UPLC retention time and HRMS
| | Structure | Retention time (mins) | HRMS |
|---|---|---|---|
| 2.5.6 | 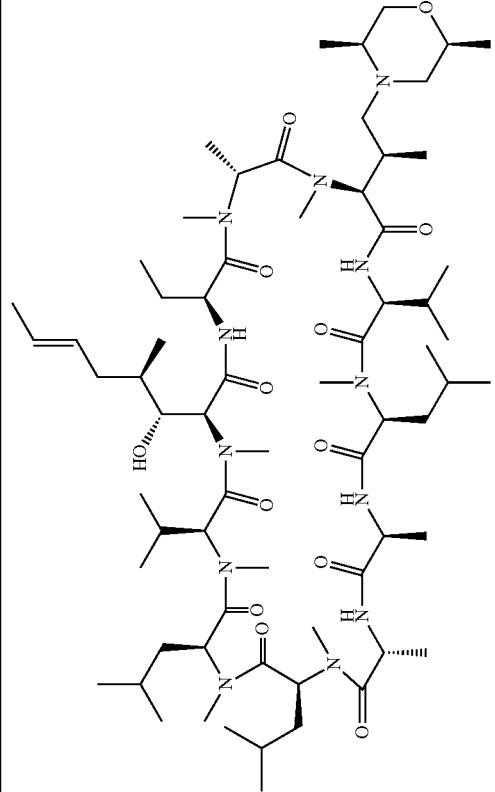 | 5.847 | 1315.9299 |
| 2.5.7 | 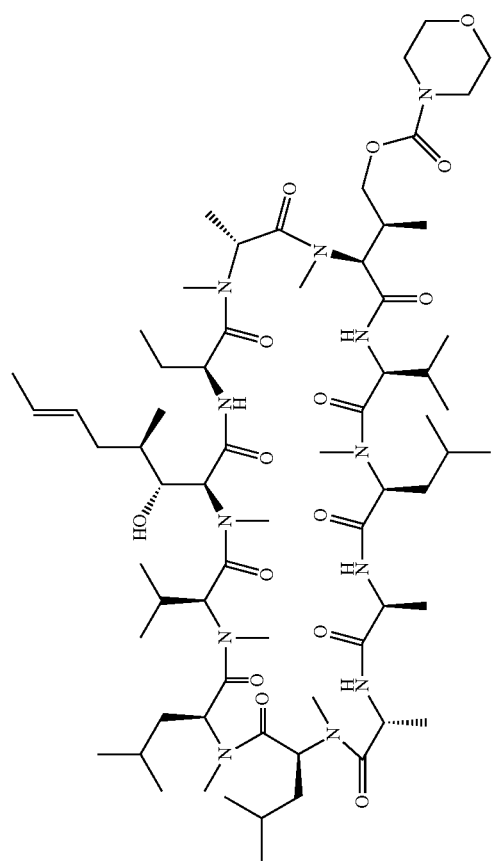 | 6.085 | 1331.8883 |

TABLE 1-continued

UPLC retention time and HRMS

| | Structure | Retention time (mins) | HRMS |
|---|---|---|---|
| 2.5.8 | 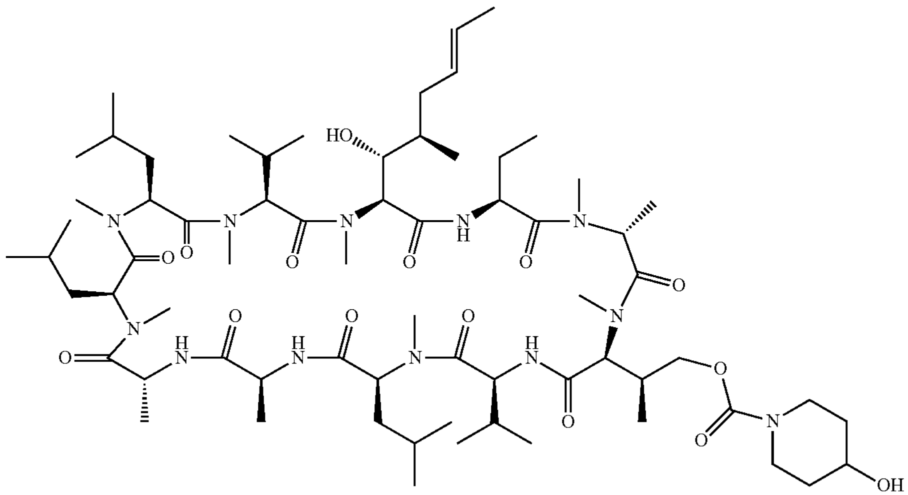 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COC(=O)N2CCC(O)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.71 | 1345.9047 |
| 2.5.9 | 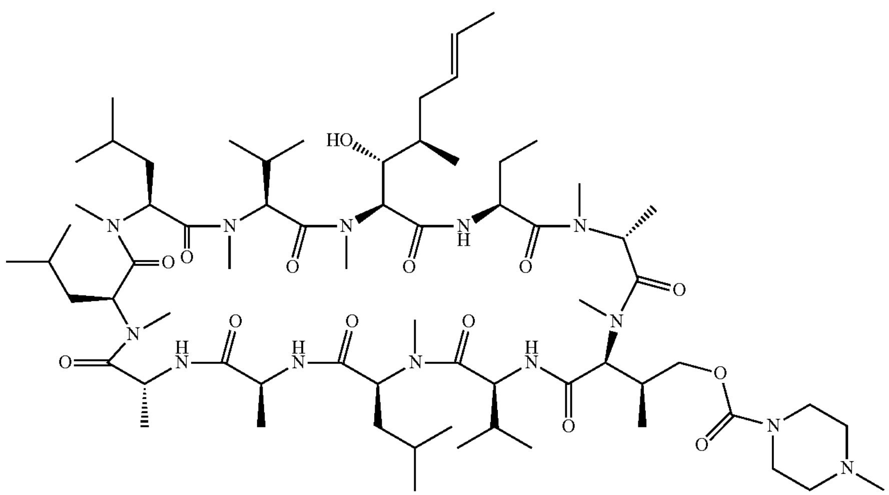 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COC(=O)N2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | | |

TABLE 1-continued
UPLC retention time and HRMS
| | Structure | Retention time (mins) | HRMS |
|---|---|---|---|
| 2.5.10 | 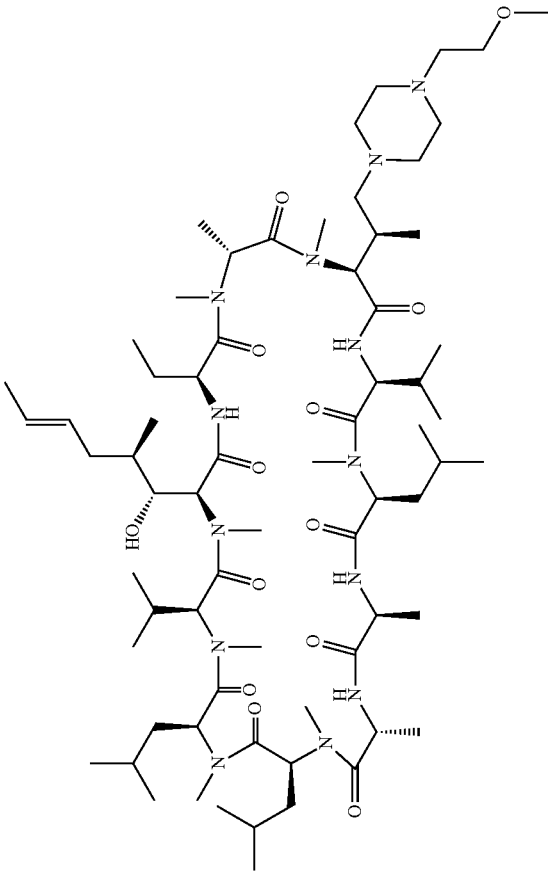 | 5.14 | 1344.9593 |
| 2.5.11 | 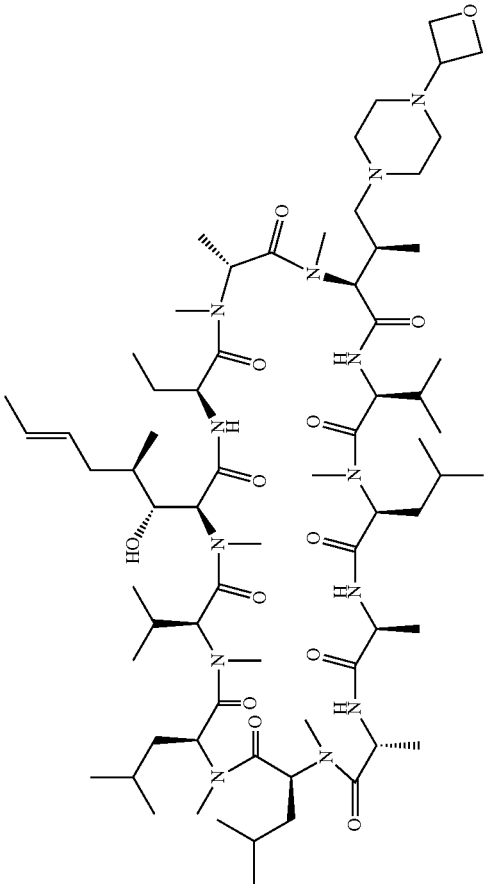 | 5.34 | 1342.9442 |

TABLE 1-continued
UPLC retention time and HRMS
| | Structure | Retention time (mins) | HRMS |
|---|---|---|---|
| 2.5.12 | 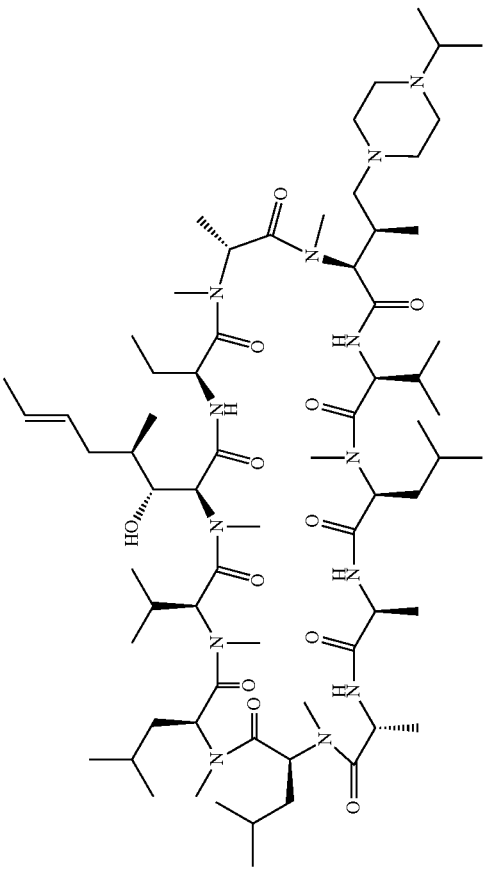 | 5.11 | 1328.9604 |
| 2.5.13 | 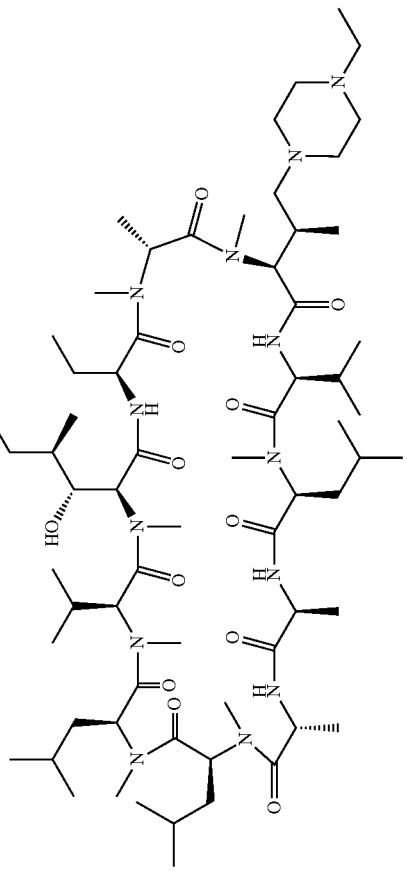 | 5.10 | 1314.9487 |

TABLE 1-continued

UPLC retention time and HRMS

| | Structure | Retention time (mins) | HRMS |
|---|---|---|---|
| 2.5.14 | 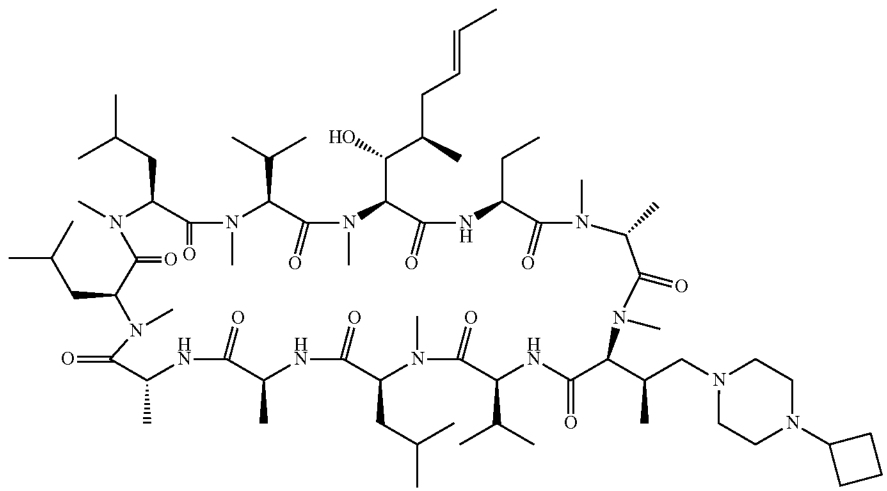 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCN(C3CCC3)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.19 | 1340.9643 |
| 2.5.15 | 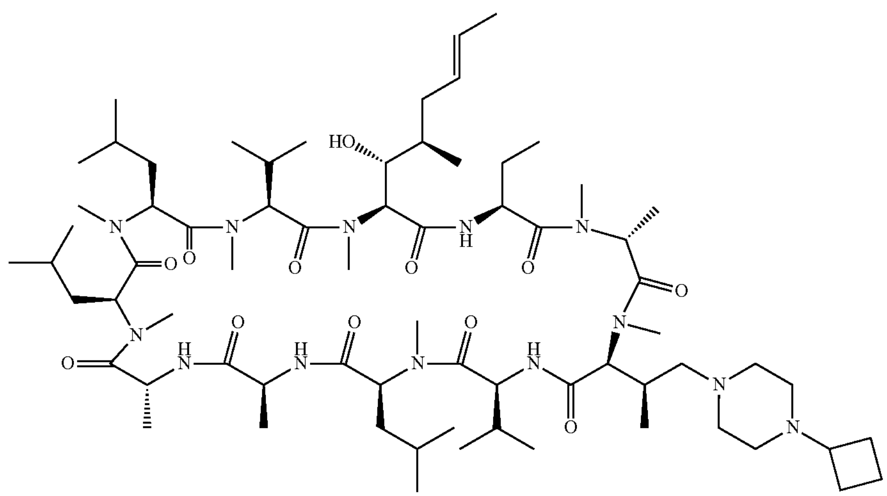 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCN(C3CCC3)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.30 | 1341.9710 |

TABLE 1-continued

UPLC retention time and HRMS

| | Structure | Retention time (mins) | HRMS |
|---|---|---|---|
| 2.5.16 | 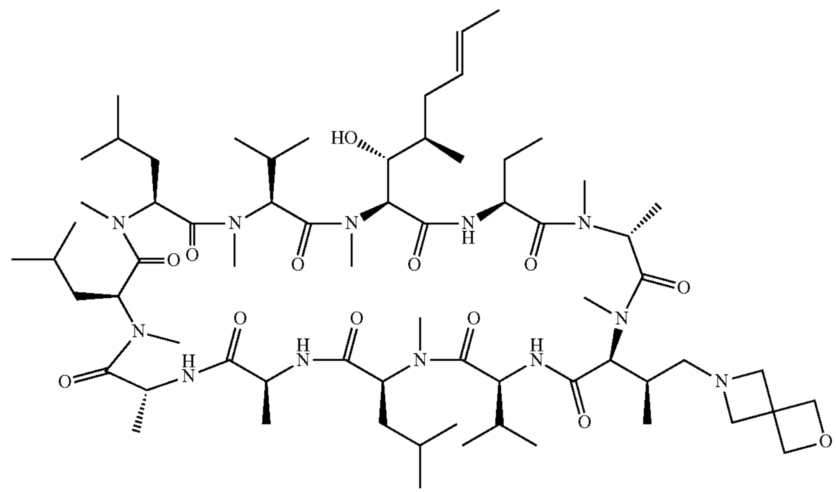 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CC3(COC3)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.30 | 1299.9001 |
| 2.5.17 | 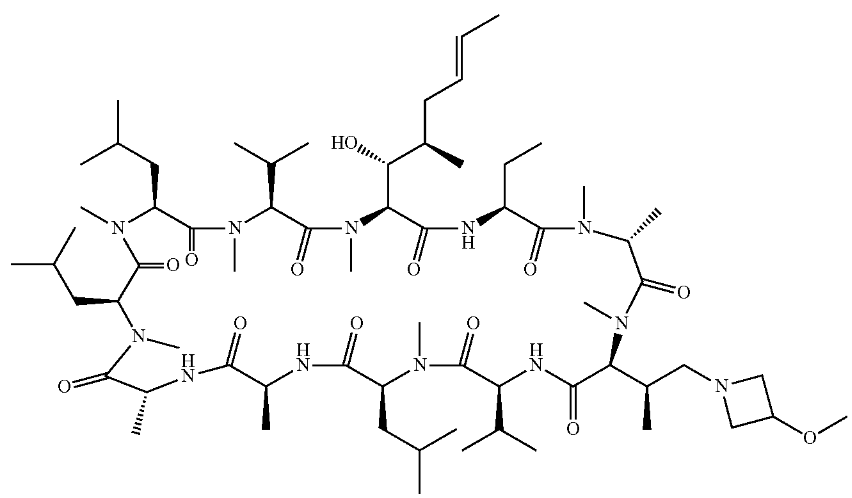 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CC(OC)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.46 | 1287.09019 |

TABLE 1-continued

UPLC retention time and HRMS

| | Structure | Retention time (mins) | HRMS |
|---|---|---|---|
| 2.5.18 | 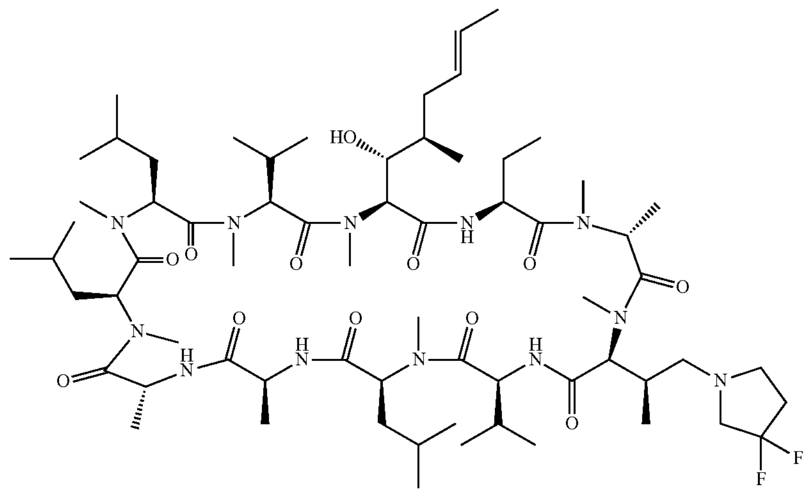 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCC(F)(F)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.56 | 1307.8875 |
| 2.5.19 | 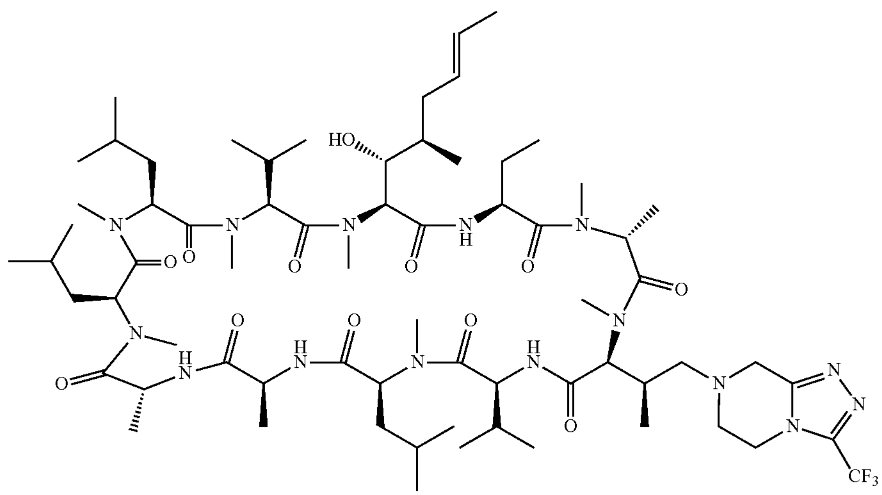 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCn3c(nnc3C(F)(F)F)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 6.17 | 1392.8938 |

TABLE 1-continued

UPLC retention time and HRMS

| | Structure | Retention time (mins) | HRMS |
|---|---|---|---|
| 2.5.20 | 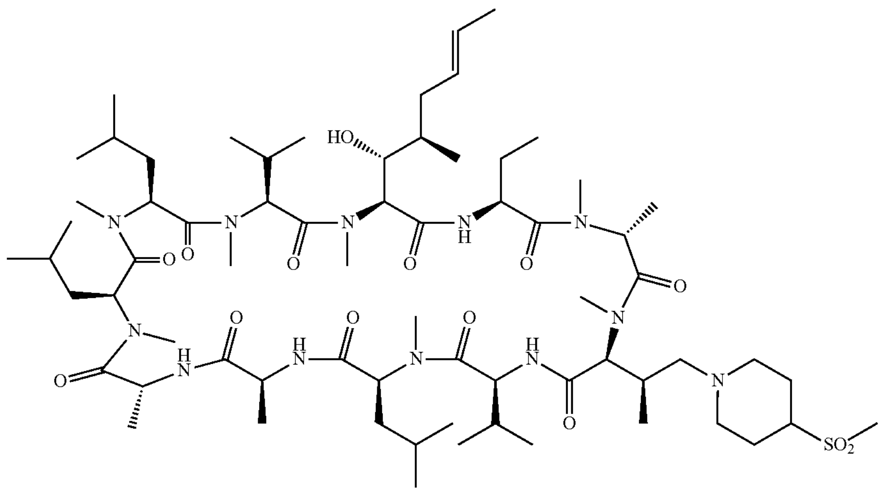 | 5.38 | 1363.9008 |
| 2.5.21 | 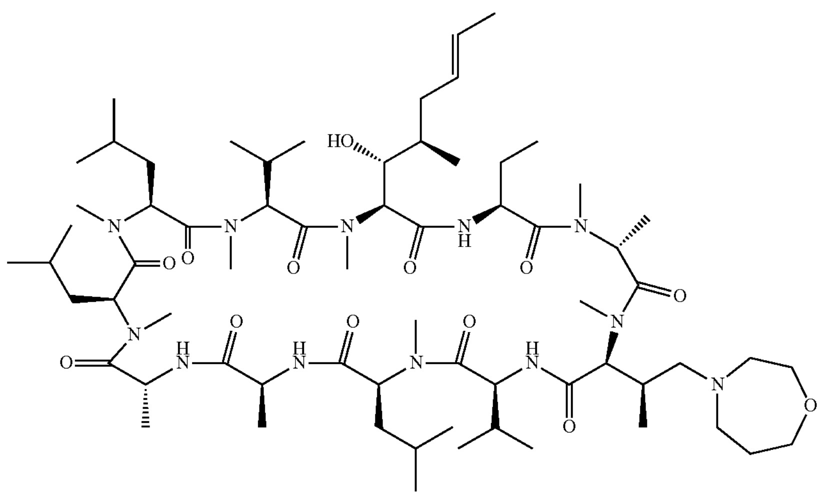 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.56 | 1301.9144 |

TABLE 1-continued
UPLC retention time and HRMS
| | Structure | Retention time (mins) | HRMS |
|---|---|---|---|
| 2.5.22 | 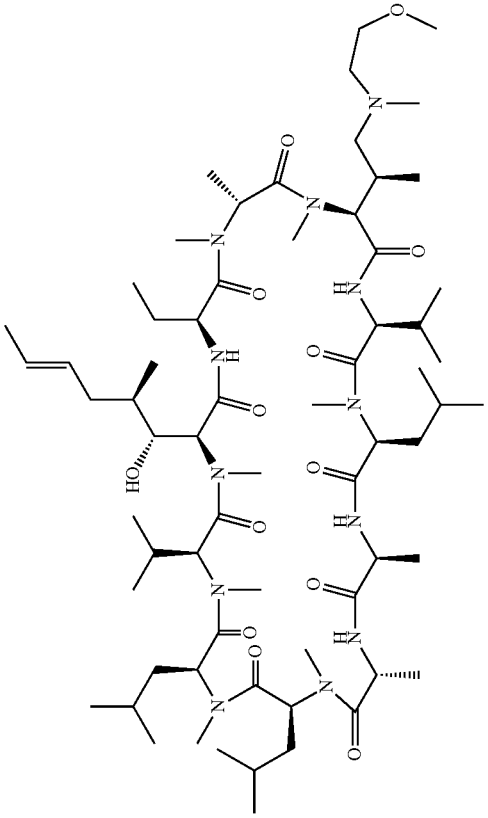 | 5.65 | |
| 2.5.23 | 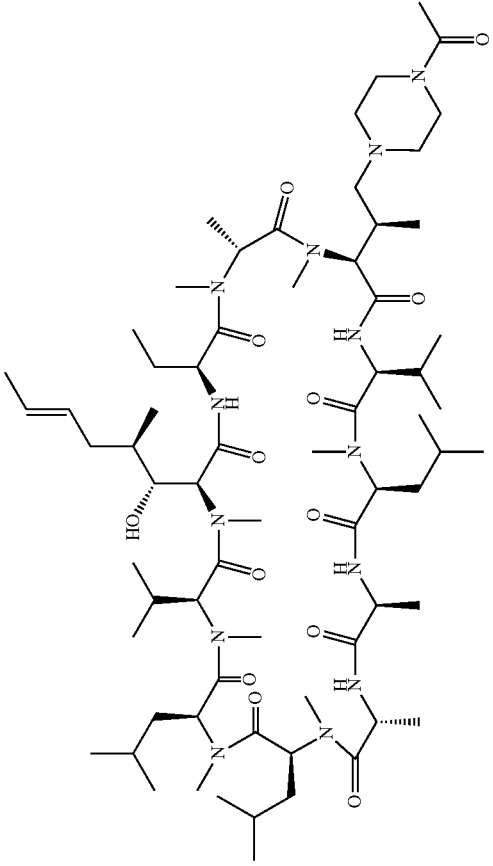 | 5.27 | 1328.9294 |

TABLE 1-continued
UPLC retention time and HRMS
| | Structure | Retention time (mins) | HRMS |
|---|---|---|---|
| 2.5.24 | 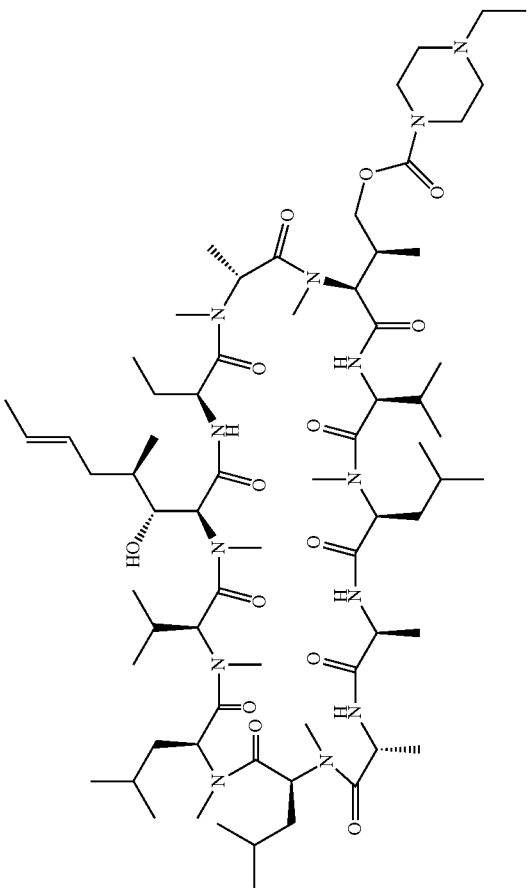 | 5.56 | 1358.9424 |
| 2.5.25 | 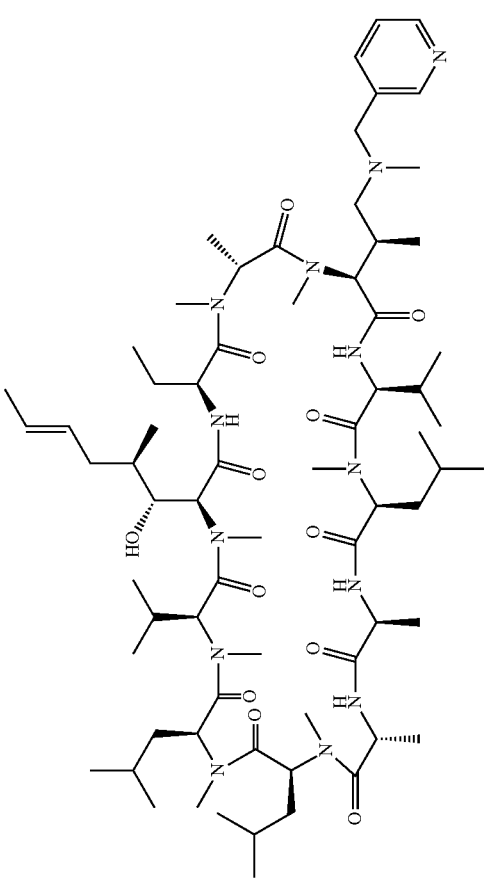 | 5.17 | 1322.9194 |

TABLE 1-continued
UPLC retention time and HRMS
| | Structure | Retention time (mins) | HRMS |
|---|---|---|---|
| 2.5.26 | 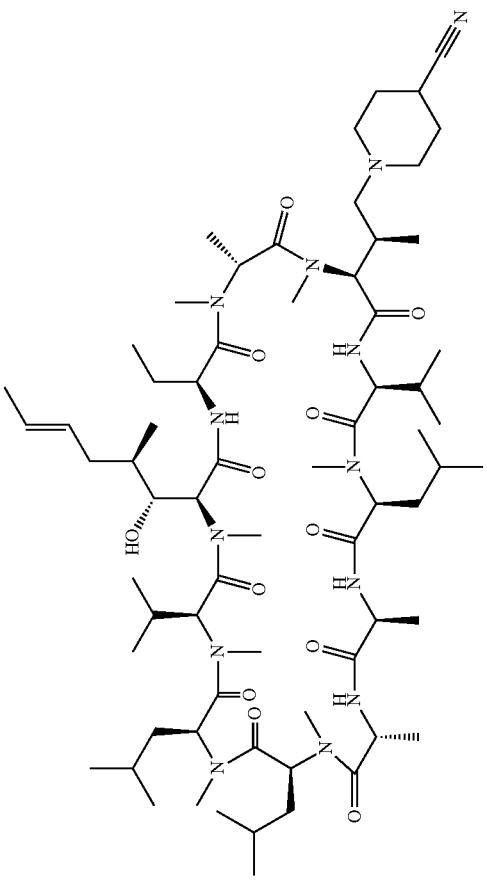 | 5.54 | 1310.0189 |
| 2.5.27 | 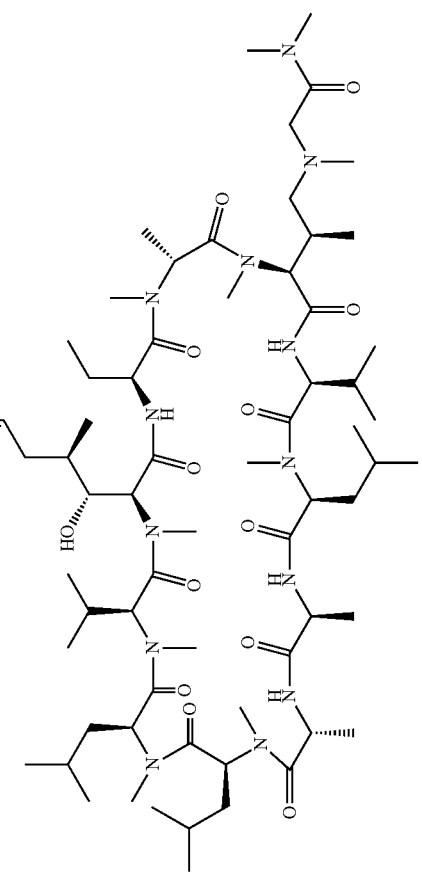 | 5.49 | 1316.9294 |

TABLE 1-continued

UPLC retention time and HRMS

| | Structure | Retention time (mins) | HRMS |
|---|---|---|---|
| 2.5.28 | 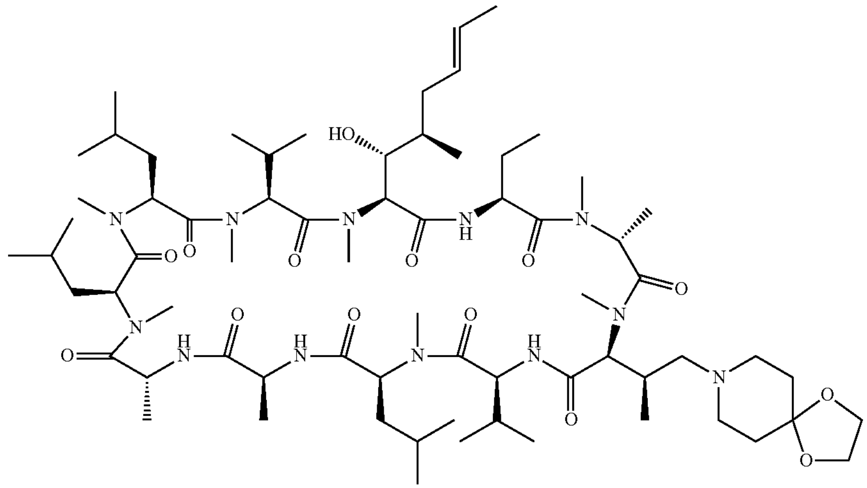 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCC3(CC2)OCCO3)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.61 | 1343.9292 |
| 2.5.29 | 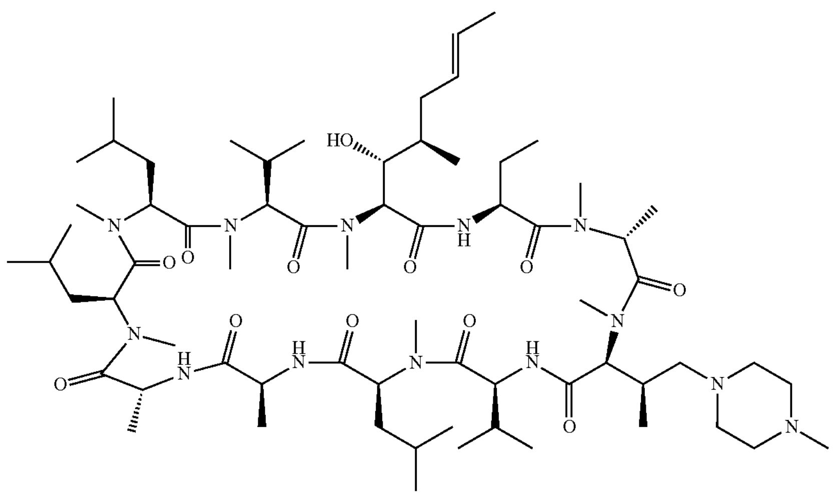 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 4.92 | 1300.9332 |

TABLE 1-continued

UPLC retention time and HRMS

| | Structure | Retention time (mins) | HRMS |
|---|---|---|---|
| 2.5.30 | 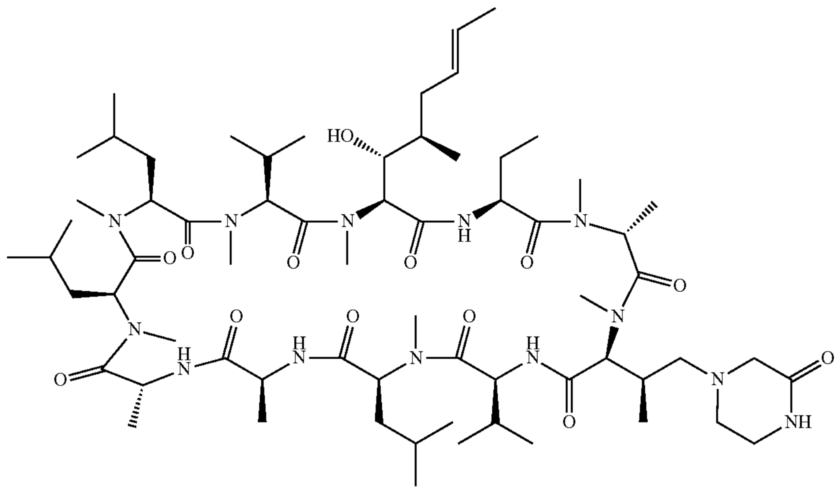 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCNC(=O)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.09 | 1300.8975 |
| 2.5.31 | 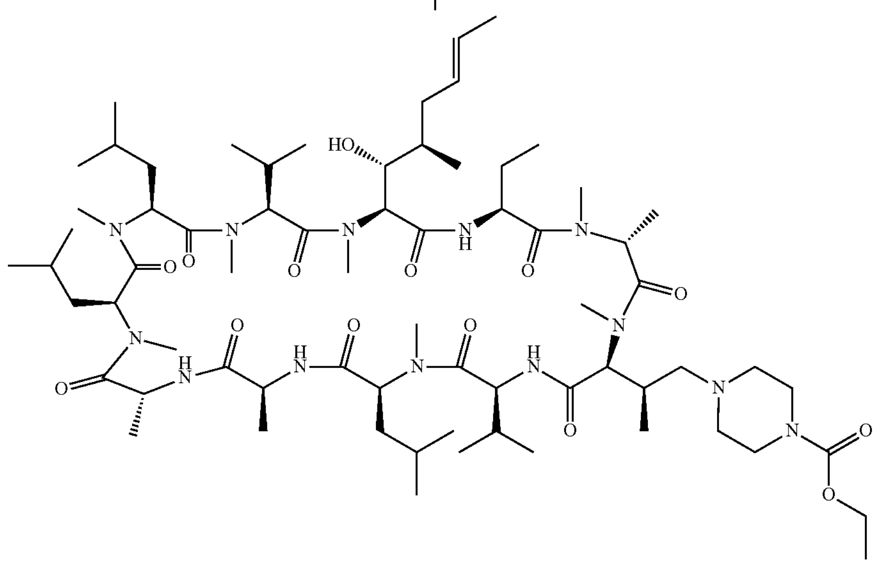 | 5.53 | 1358.9370 |

TABLE 1-continued

UPLC retention time and HRMS

| | Structure | Retention time (mins) | HRMS |
|---|---|---|---|
| 2.5.32 | 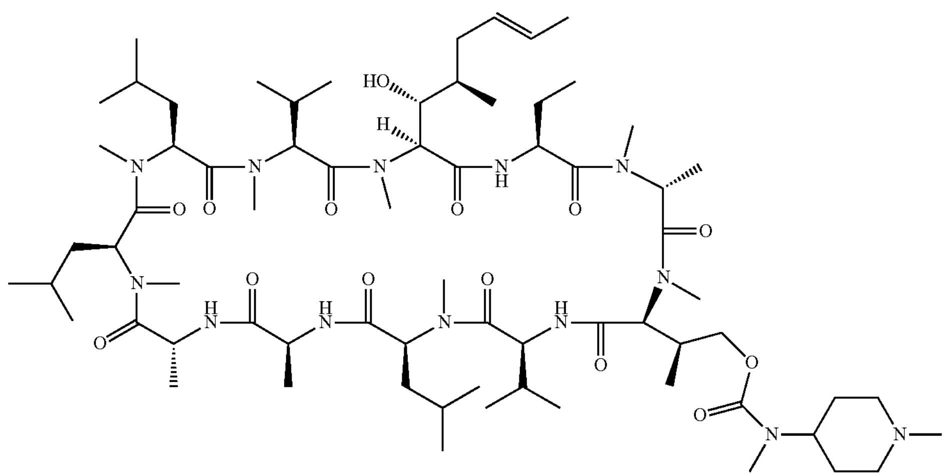 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COC(=O)N(C)C2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.27 | 1372.9535 |
| 2.5.33 | 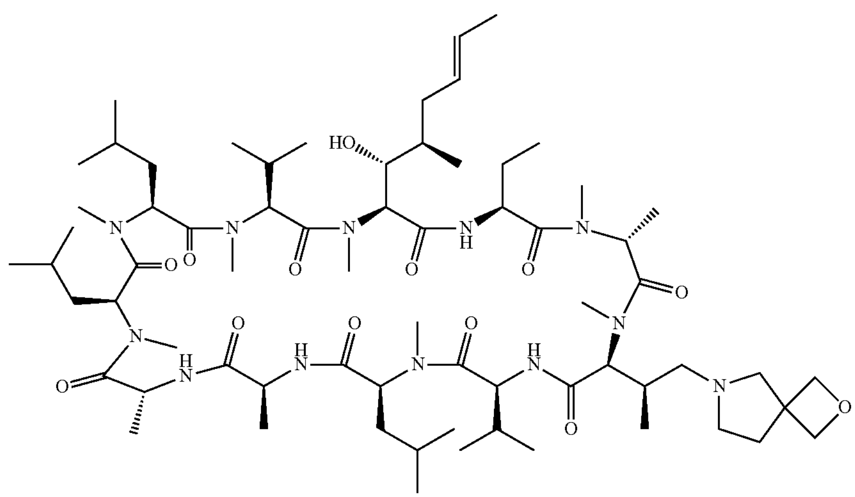 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CN2CCC3(COC3)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | | 1313.9169 |

TABLE 1-continued
UPLC retention time and HRMS
| | Structure | Retention time (mins) | HRMS |
|---|---|---|---|
| 2.5.34 | 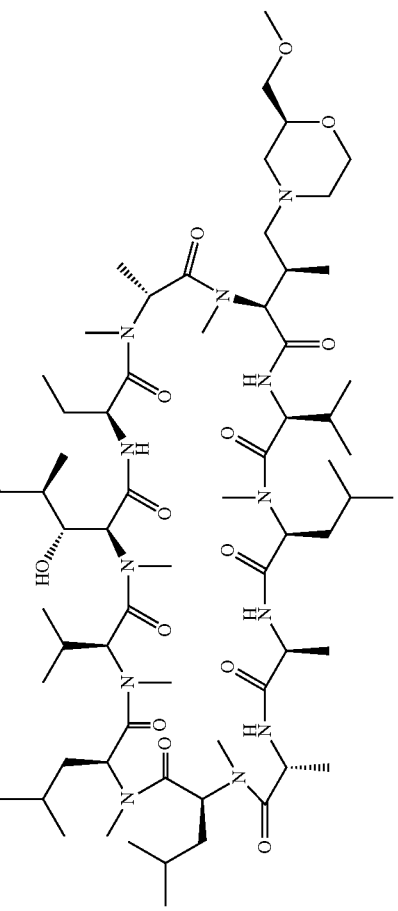 | 5.51 | 1331.9280 |
| 2.5.35 | 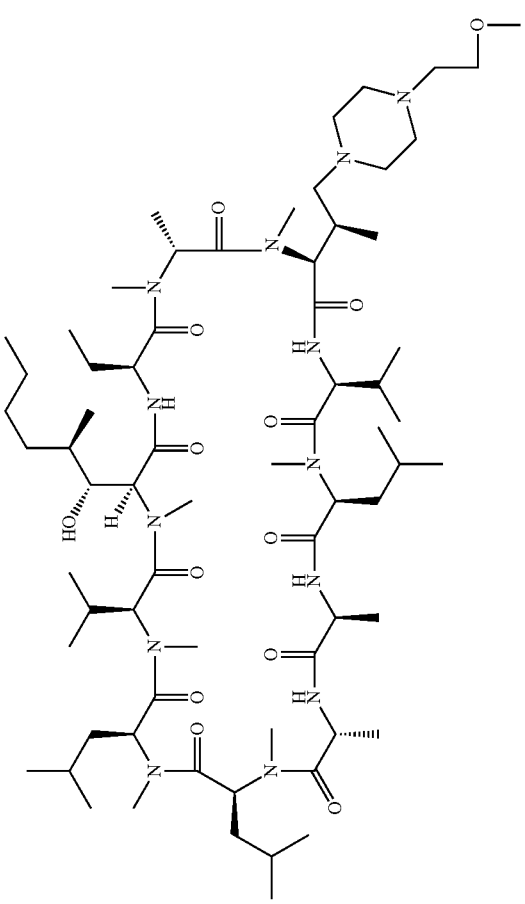 | 5.25 | 1346.9745 |

TABLE 1-continued

UPLC retention time and HRMS

| | Structure | Retention time (mins) | HRMS |
|---|---|---|---|
| 2.6.1 | 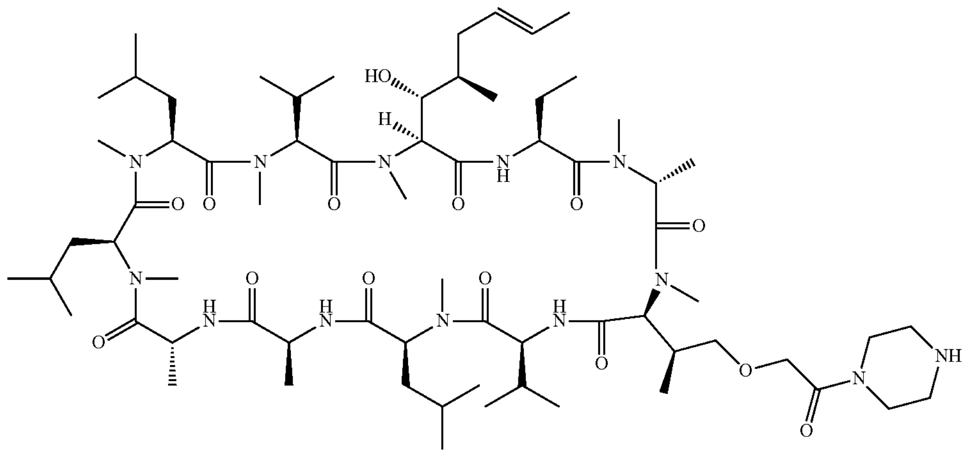 [SMILES: C/C=C/C[C@@H](C)[C@@H](O)[C@@H](C(=O)N[C@@H](CC)C(=O)N(C)[C@H](C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@@H](NC)[C@H](C)COCC(=O)N1CCNCC1)C(C)C] | 5.10 | 1344.9222 |
| 2.6.2 | 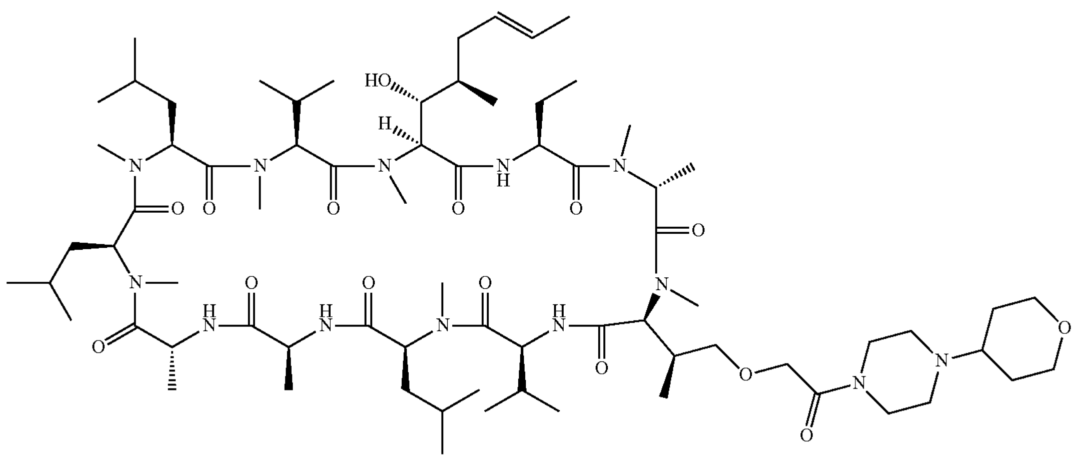 [SMILES: C/C=C/C[C@@H](C)[C@@H](O)[C@@H](C(=O)N[C@@H](CC)C(=O)N(C)[C@H](C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@@H](NC)[C@H](C)COCC(=O)N1CCN(C2CCOCC2)CC1)C(C)C] | 5.19 | 1428.9777 |

TABLE 1-continued

UPLC retention time and HRMS

| | Structure | Retention time (mins) | HRMS |
|---|---|---|---|
| 2.6.3 | 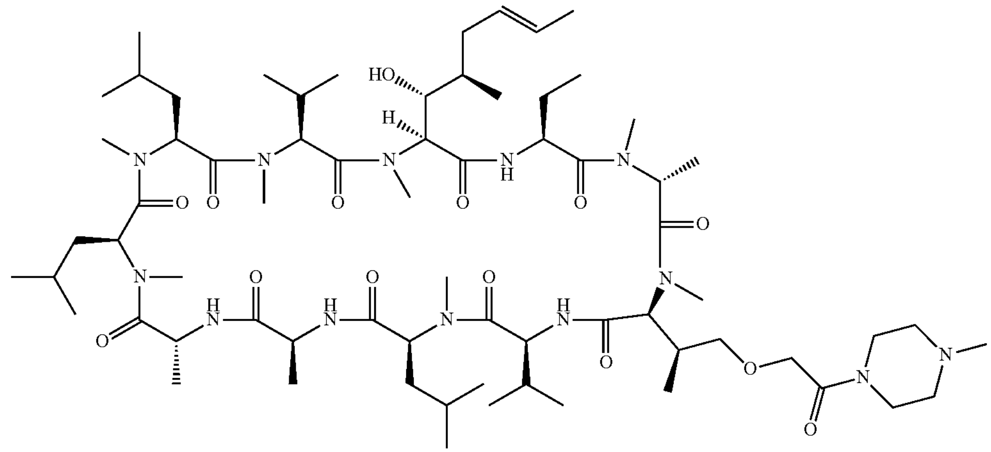 [SMILES: C/C=C/C[C@@H](C)[C@@H](O)[C@@H](C(=O)N[C@@H](CC)C(=O)N(C)[C@H](C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@@H](NC)[C@H](C)COCC(=O)N1CCN(C)CC1)C(C)C] | 5.10 | 1358.9358 |
| 2.6.4 | 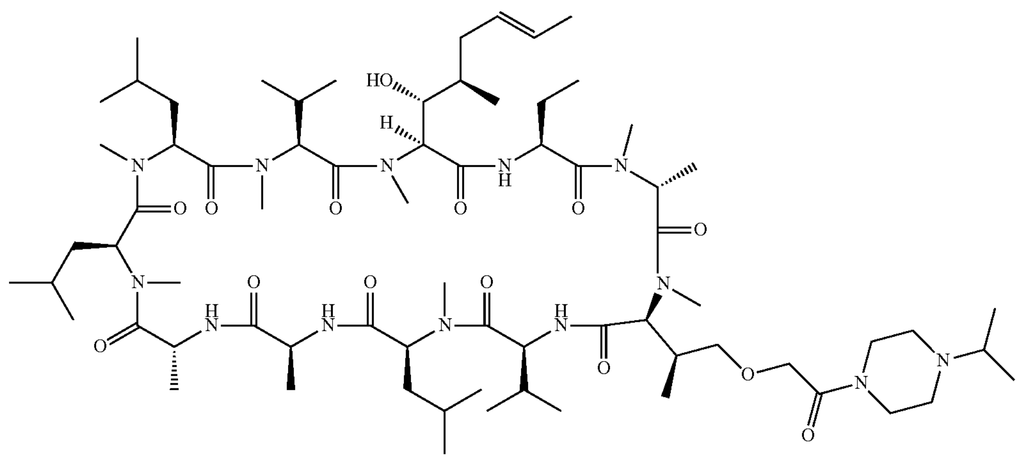 [SMILES: C/C=C/C[C@@H](C)[C@@H](O)[C@@H](C(=O)N[C@@H](CC)C(=O)N(C)[C@H](C)C(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@@H](NC)[C@H](C)COCC(=O)N1CCN(C(C)C)CC1)C(C)C] | 5.10 | 1386.9655 |

TABLE 1-continued
UPLC retention time and HRMS
| | Structure | Retention time (mins) | HRMS |
|---|---|---|---|
| 2.6.5 | 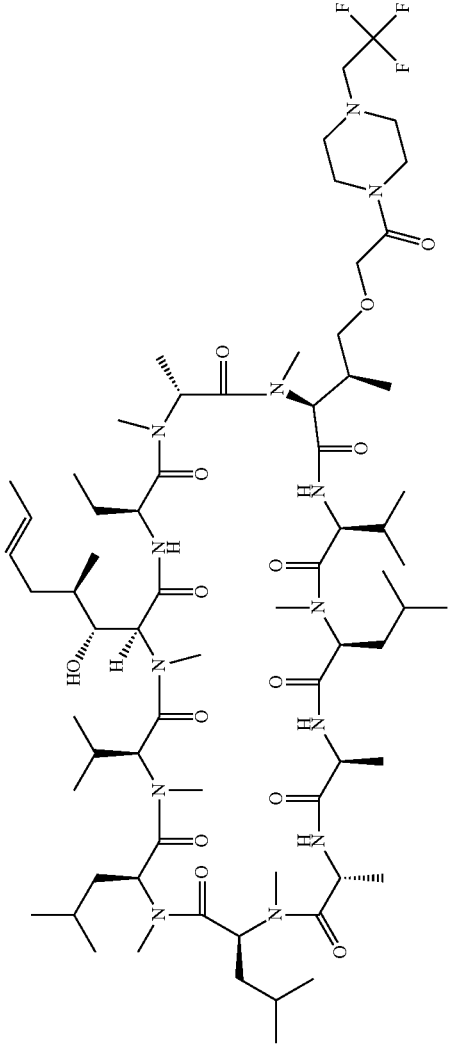 | 6.40 | 1426.9238 |
| 2.6.6 | 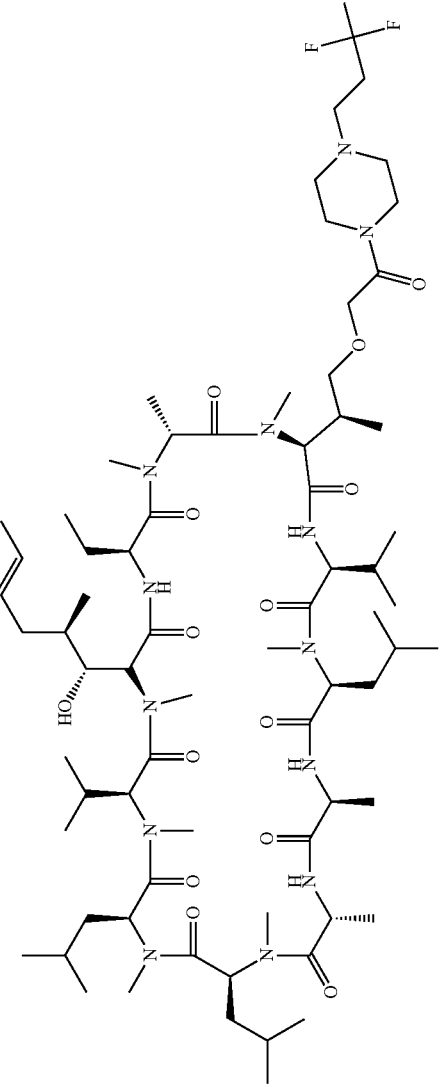 | 5.40 | 1440.9366 |

TABLE 1-continued
UPLC retention time and HRMS
| | Structure | Retention time (mins) | HRMS |
|---|---|---|---|
| 2.7 | 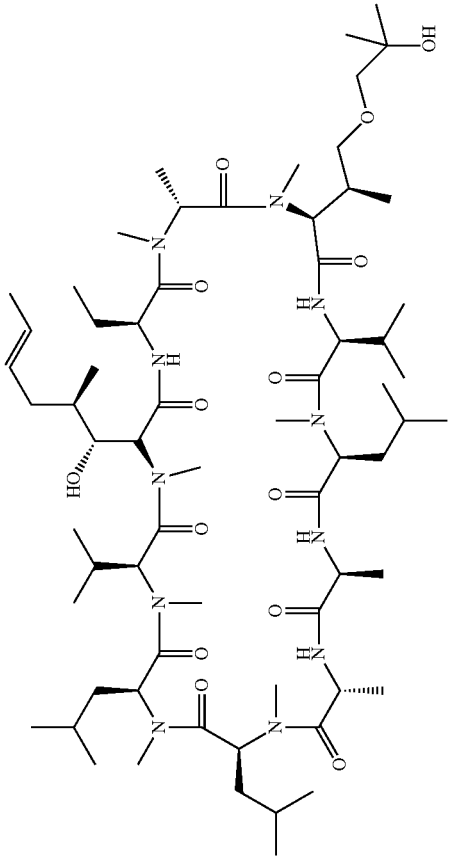 | 6.30 | 1290.8995 |
| 2.8.1 | 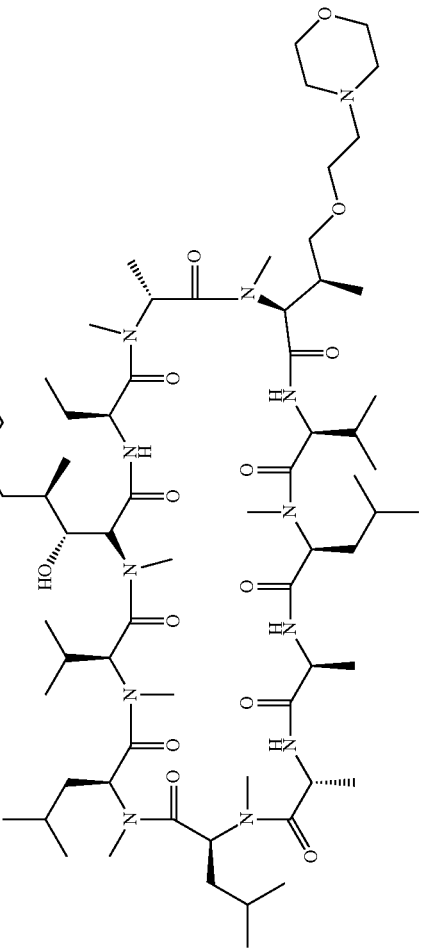 | 5.37 | 1331.9238 |

TABLE 1-continued
UPLC retention time and HRMS
| | Structure | Retention time (mins) | HRMS |
|---|---|---|---|
| 2.8.2 | 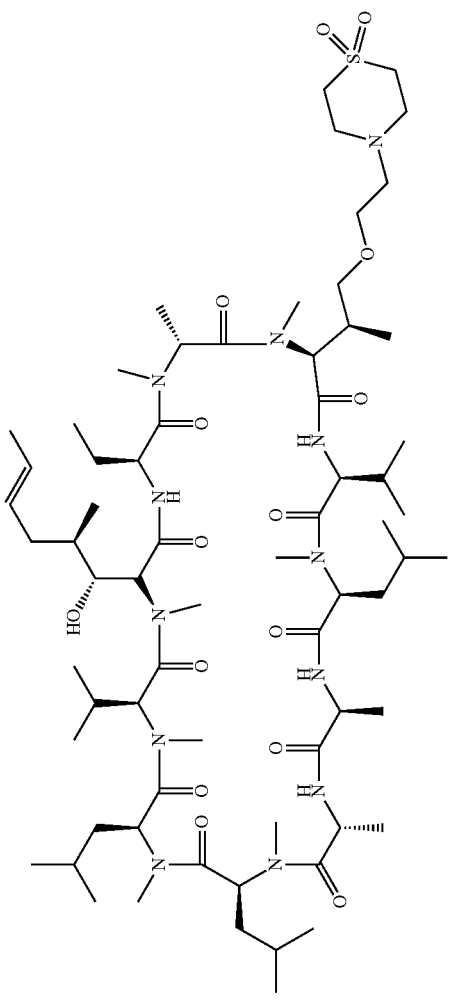 | 5.33 | 1379.8951 |
| 2.8.3 | 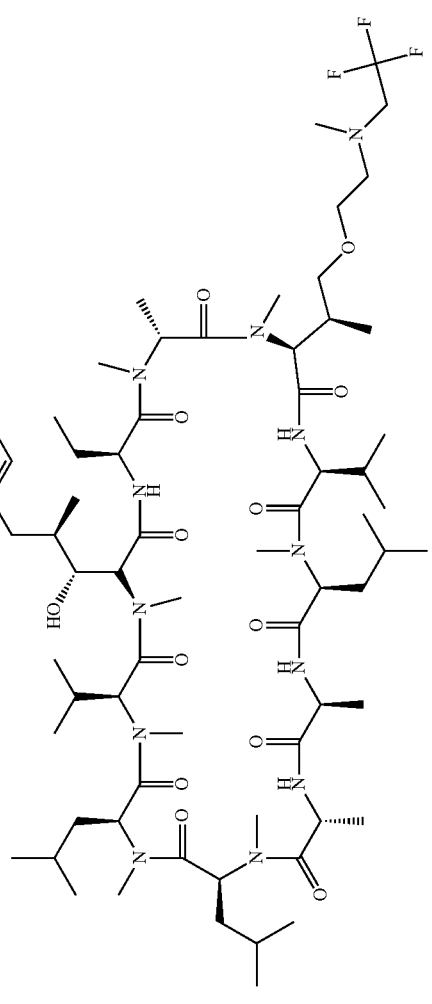 | 5.76 | 1357.905 |

TABLE 1-continued

UPLC retention time and HRMS

| | Structure | Retention time (mins) | HRMS |
|---|---|---|---|
| 2.8.4 | 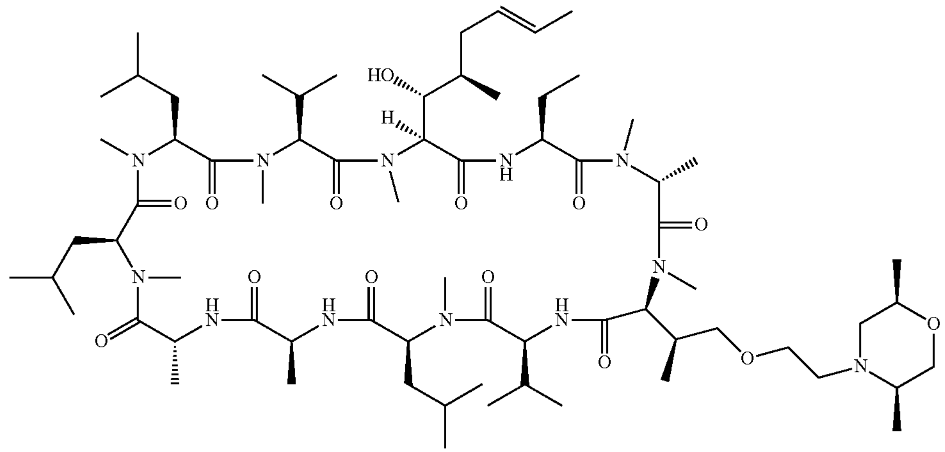 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2C[C@@H](C)OC[C@H]2C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.55 | 1359.9573 |
| 2.8.5 | 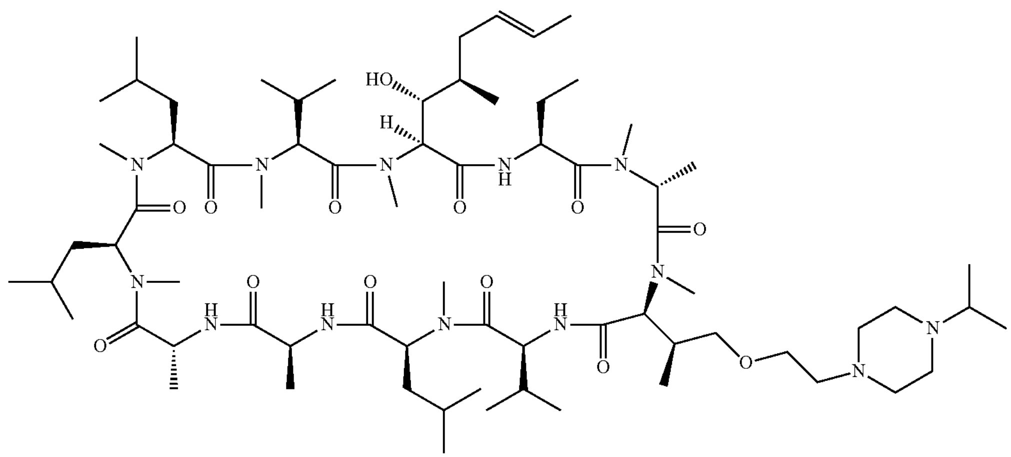 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2CCN(C(C)C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 4.93 | 1372.9912 |

TABLE 1-continued

UPLC retention time and HRMS

| | Structure | Retention time (mins) | HRMS |
|---|---|---|---|
| 2.8.6 | 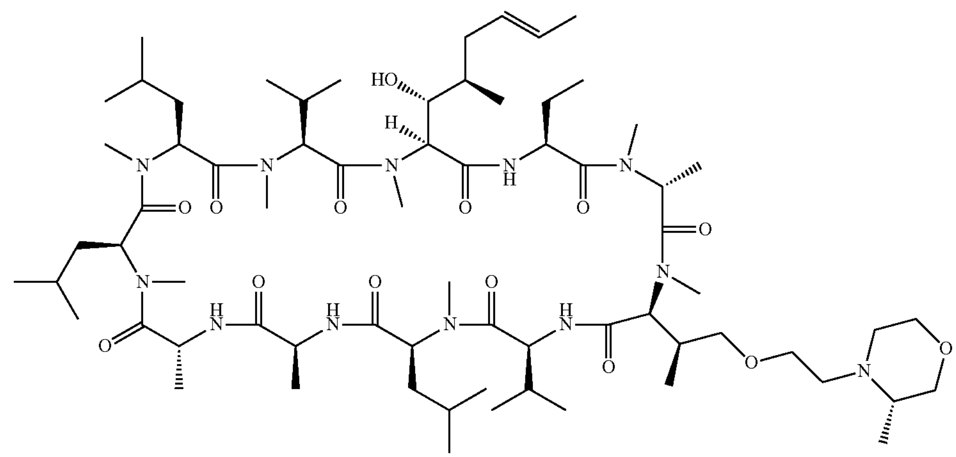 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2CCOC[C@@H]2C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.36 | 1345.9426 |
| 2.8.7 | 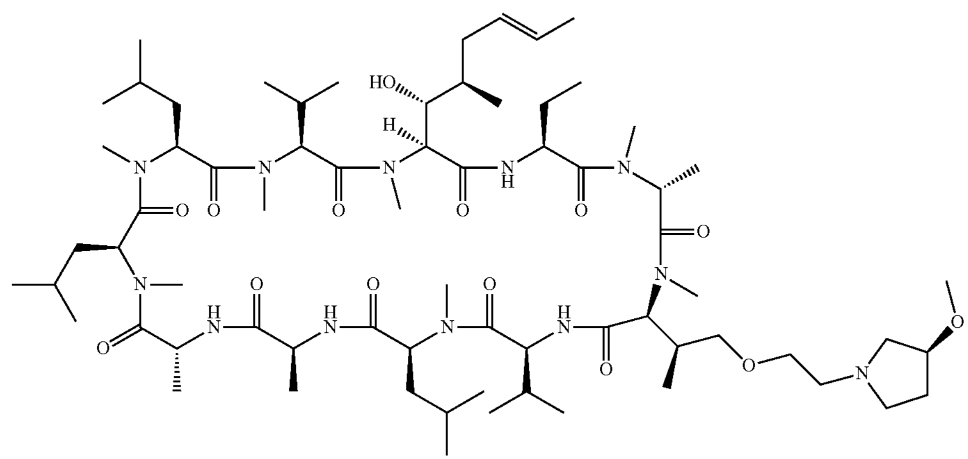 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2CC[C@H](OC)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.43 | 1345.9408 |

TABLE 1-continued

UPLC retention time and HRMS

| | Structure | Retention time (mins) | HRMS |
|---|---|---|---|
| 2.8.8 | 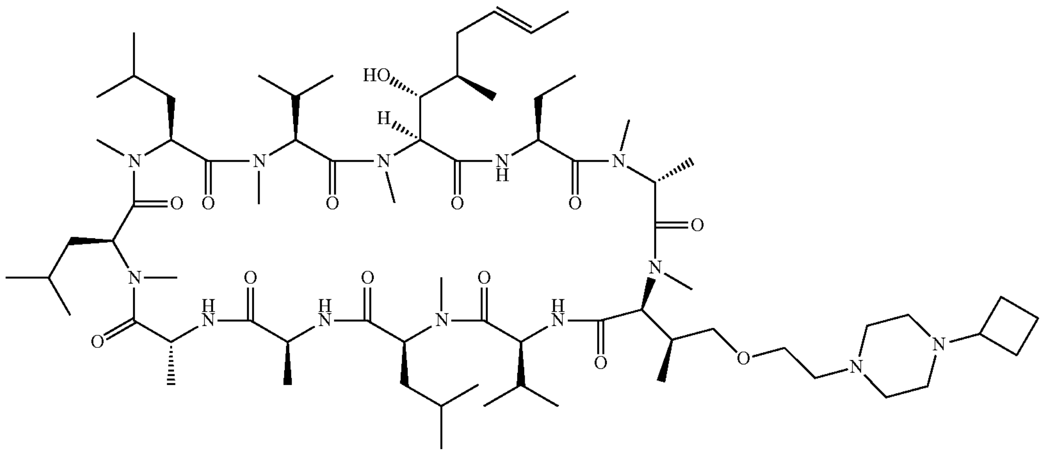 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2CCN(C3CCC3)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.04 | 1384.9869 |
| 2.8.9 | 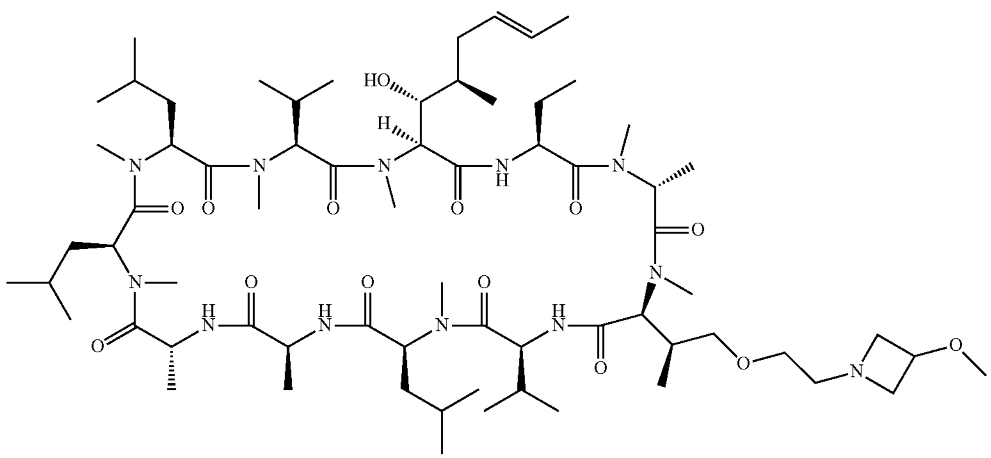 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COCCN2CC(OC)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.37 | 1331.9259 |

TABLE 1-continued
UPLC retention time and HRMS
| | Structure | Retention time (mins) | HRMS |
|---|---|---|---|
| 2.8.10 | 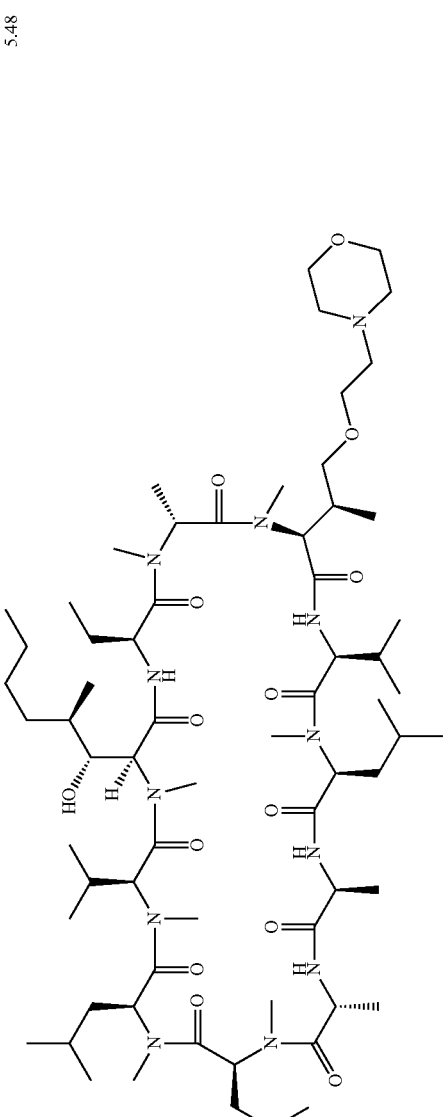 | 5.48 | 1333.9437 |
| 2.8.11 | 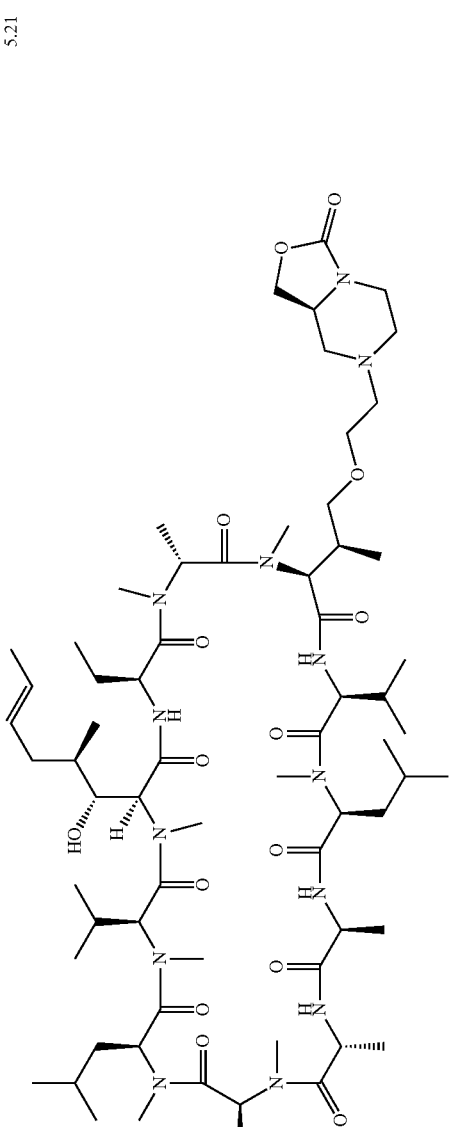 | 5.21 | 1386.9310 |

TABLE 1-continued

UPLC retention time and HRMS

| | Structure | Retention time (mins) | HRMS |
|---|---|---|---|
| 2.9 | 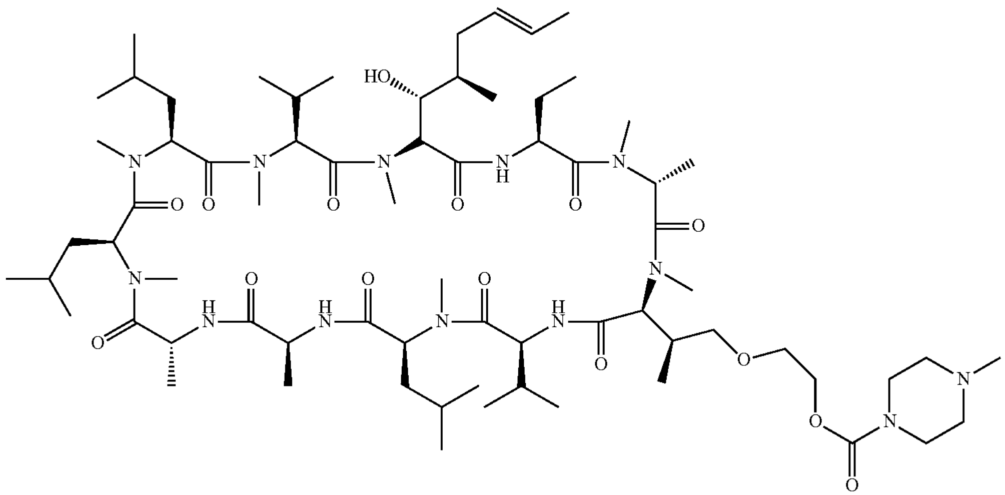 | 5.23 | 1388.9496 |
| 2.10 | 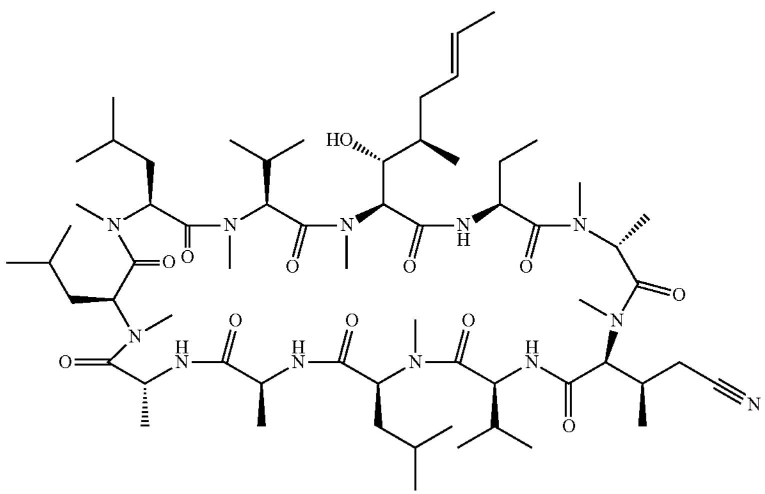 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CC#N)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 6.12 | 1227.8428 |

TABLE 1-continued

UPLC retention time and HRMS

| | Structure | Retention time (mins) | HRMS |
|---|---|---|---|
| 2.11 | 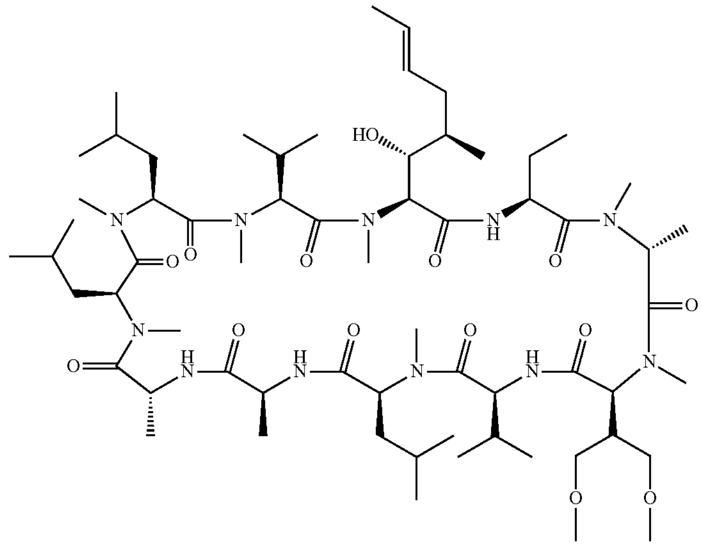 [SMILES: C/C=C/C[C@@H](C)[C@@H](O)[C@H]1C(=O)N[C@@H](CC)C(=O)N(C)[C@H](C)C(=O)N(C)[C@@H](C(COC)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 6.24 | 1262.8682 |
| 2.12 | 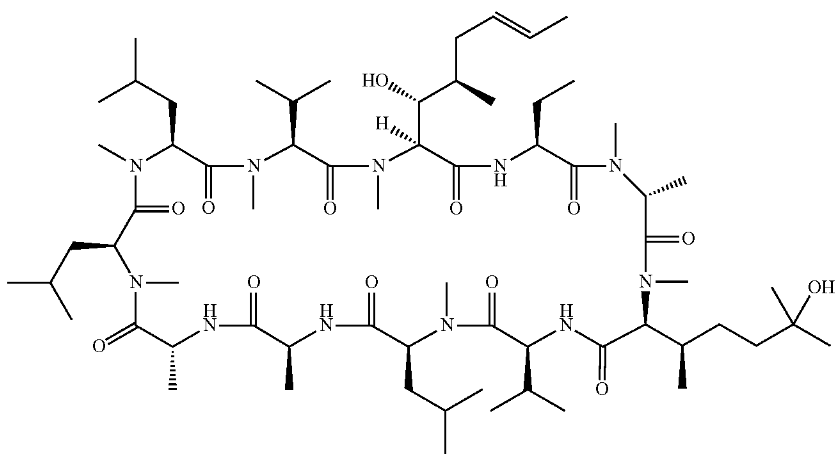 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 6.23 | 1274.9082 |

TABLE 1-continued
UPLC retention time and HRMS
| Structure | Retention time (mins) | HRMS |
|---|---|---|
| 2.12.2 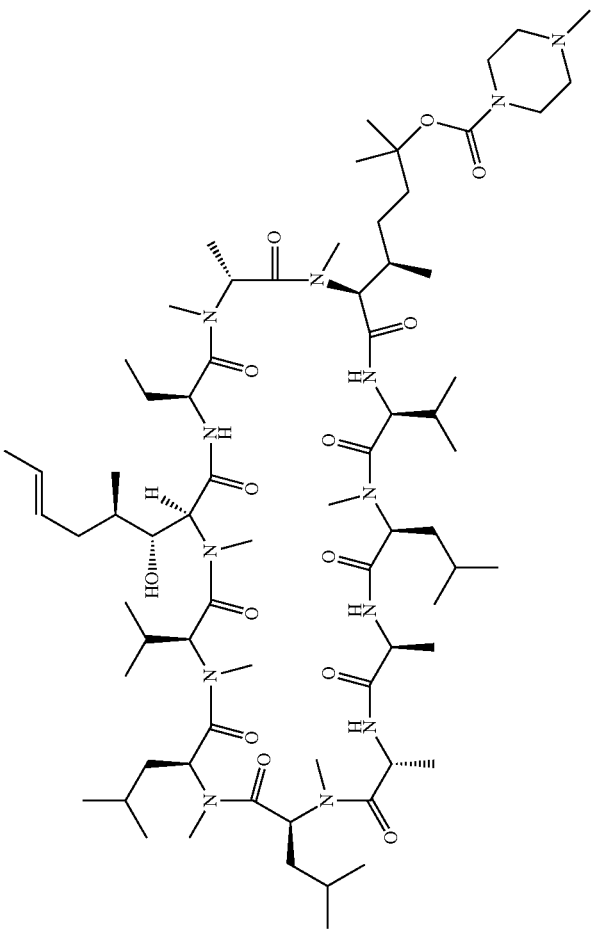 | 5.68 | 1400.9860 |

TABLE 1-continued

UPLC retention time and HRMS

| | Structure | Retention time (mins) | HRMS |
|---|---|---|---|
| 2.13 | 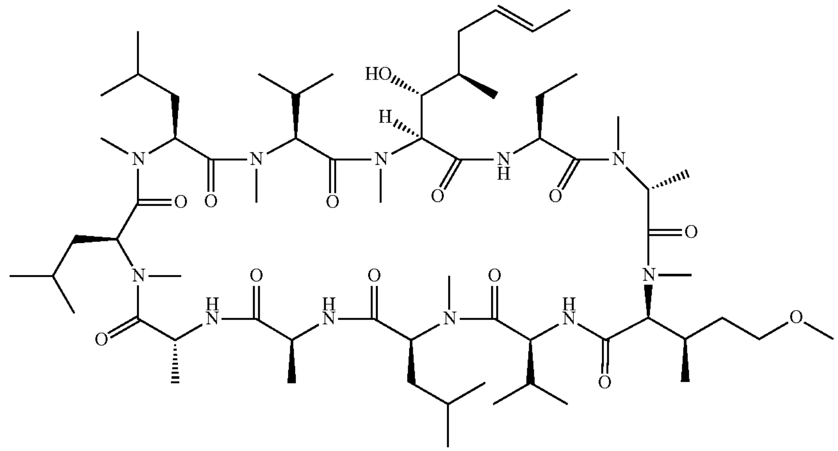 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCOC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 6.32 | 1246.875 |
| 2.14.2 | 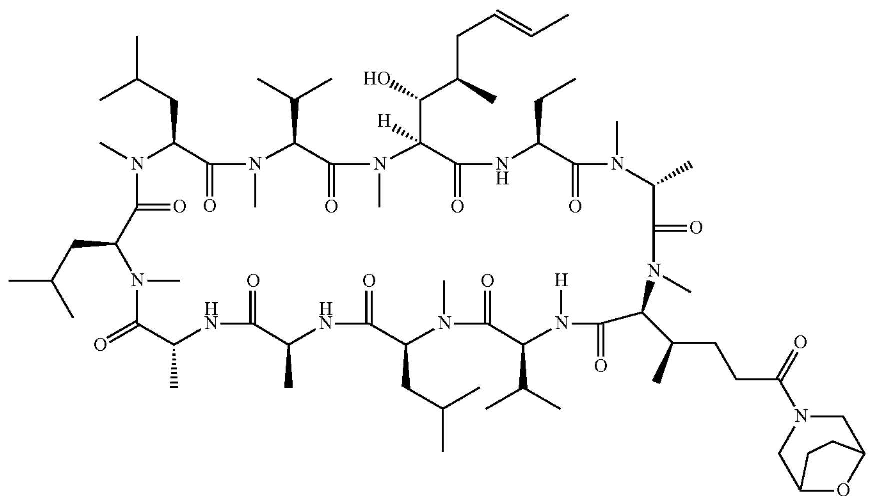 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCC(=O)N2CC3CCC(C2)O3)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.98 | 1355.9243 |

TABLE 1-continued

UPLC retention time and HRMS

| | Structure | Retention time (mins) | HRMS |
|---|---|---|---|
| 2.14.3 | 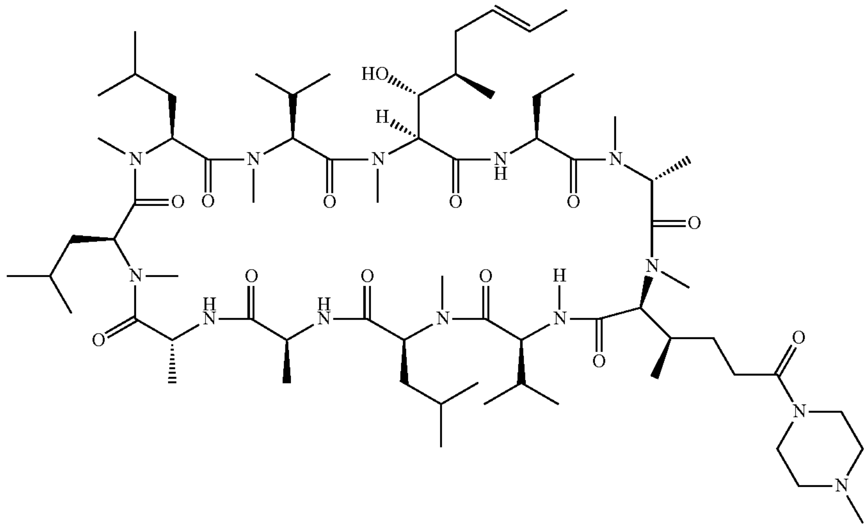 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCC(=O)N2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.13 | 1342.9415 |
| 2.14.4 | 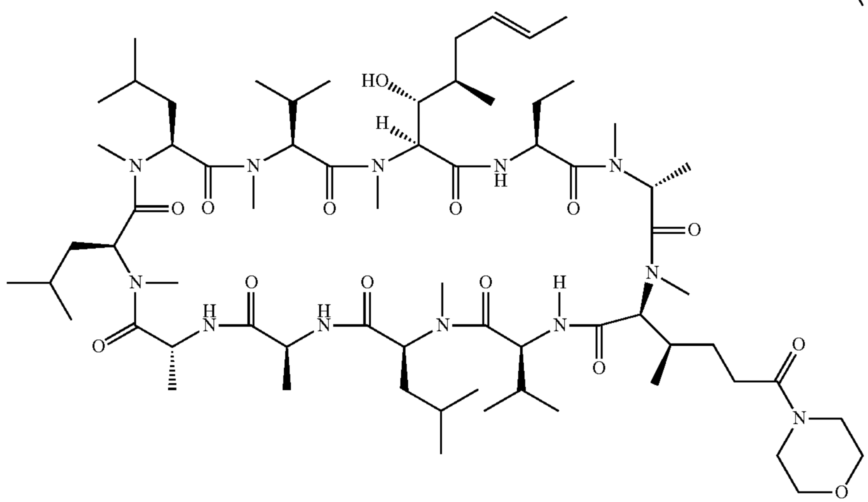 | 5.83 | 1325.9121 |

TABLE 1-continued

UPLC retention time and HRMS

| Structure | Retention time (mins) | HRMS |
|---|---|---|
| 2.16 | 6.30 | 1288.8828 |
| 2.17.1 | 5.00 | 1287.9006 |

TABLE 1-continued
UPLC retention time and HRMS
| | Structure | Retention time (mins) | HRMS |
|---|---|---|---|
| 2.17.2 | 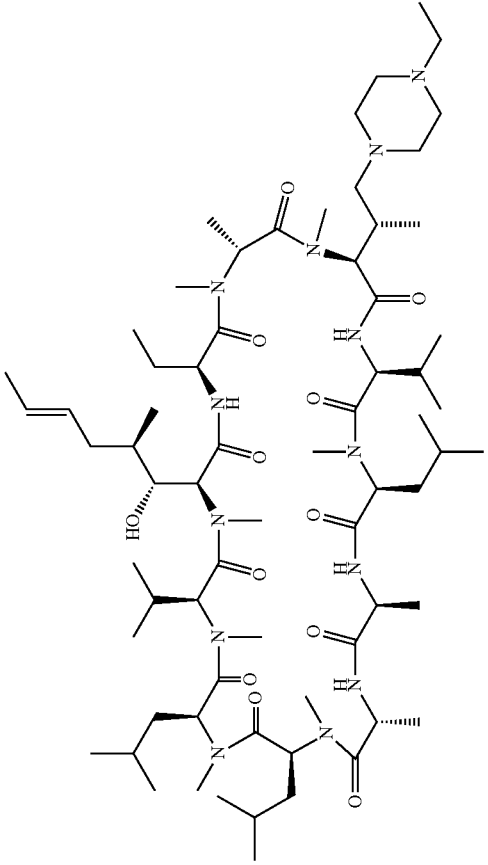 | 4.78 | 1314.9467 |
| 2.17.3 | 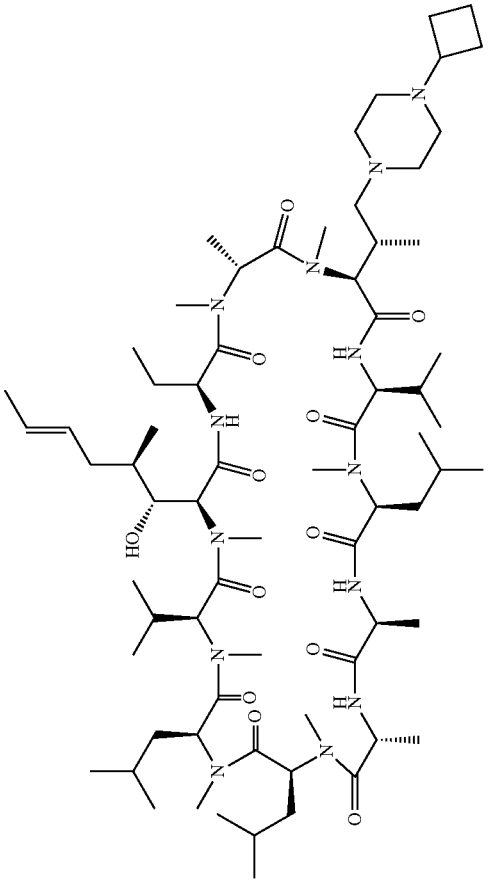 | 5.09 | 1340.9640 |

TABLE 1-continued
UPLC retention time and HRMS
| | Structure | Retention time (mins) | HRMS |
|---|---|---|---|
| 2.17.4 | 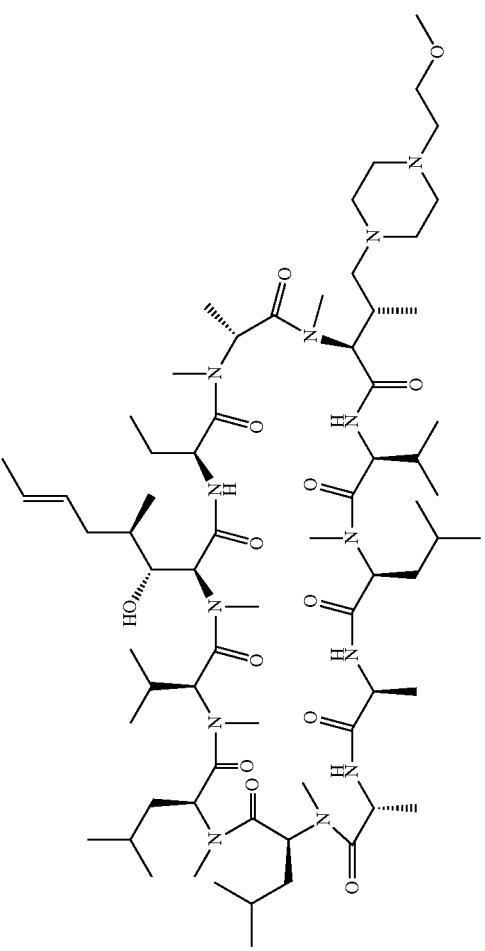 | 4.93 | 1344.9588 |
| 2.17.5 | 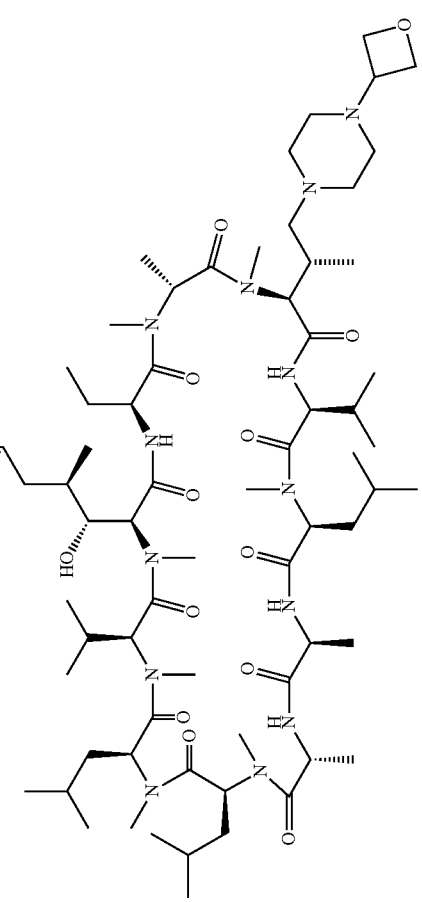 | 4.97 | 1342.9442 |

TABLE 1-continued
UPLC retention time and HRMS
| | Structure | Retention time (mins) | HRMS |
|---|---|---|---|
| 2.17.6 | 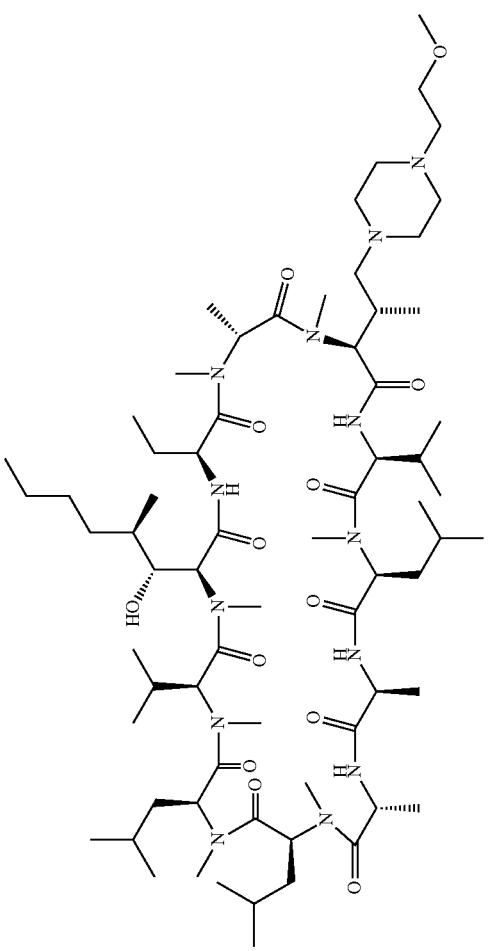 | 5.00 | 1346.9746 |
| 2.17.7 | 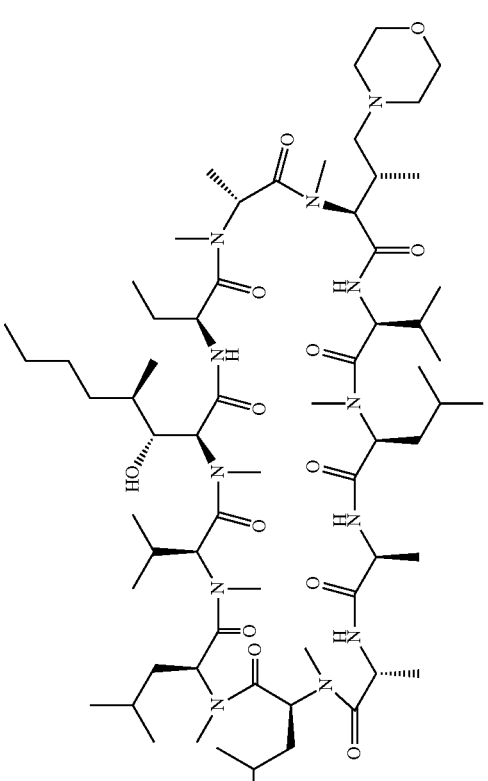 | 5.22 | 1289.9159 |

TABLE 1-continued

UPLC retention time and HRMS

| Structure | Retention time (mins) | HRMS |
|---|---|---|
| 2.17.8 | 5.05 | 1331.9288 |
| 2.17.9 | 5.00 | 1364.8933 |

TABLE 1-continued
UPLC retention time and HRMS
| | Structure | Retention time (mins) | HRMS |
|---|---|---|---|
| 2.17.10 | 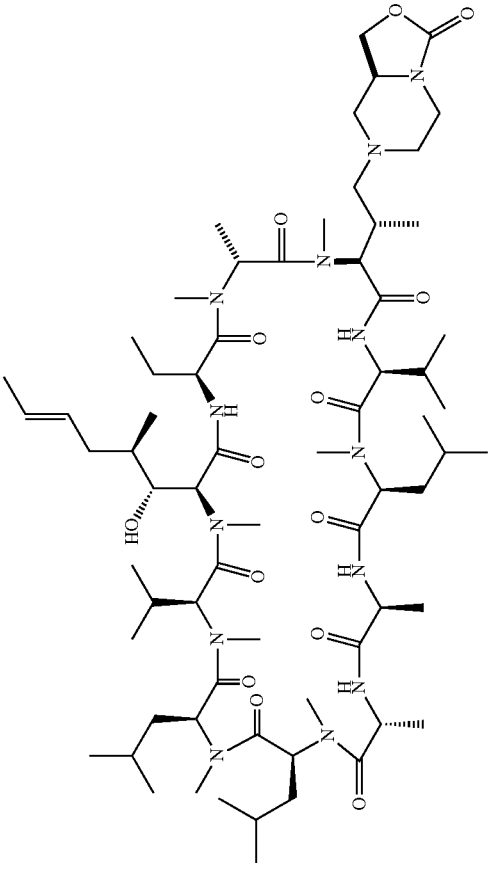 | 4.96 | 1342.9055 |
| 2.17.11 | 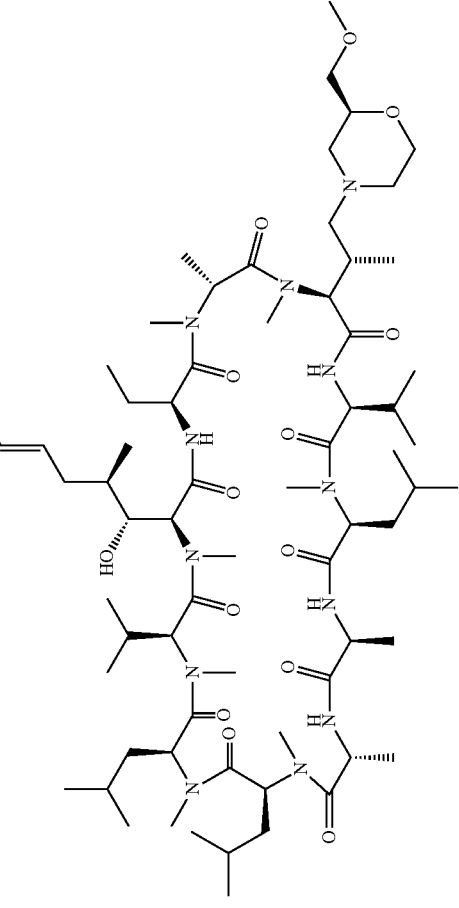 | 5.08 | 1331.9257 |

TABLE 1-continued

UPLC retention time and HRMS

| | Structure | Retention time (mins) | HRMS |
|---|---|---|---|
| 2.17.12 | 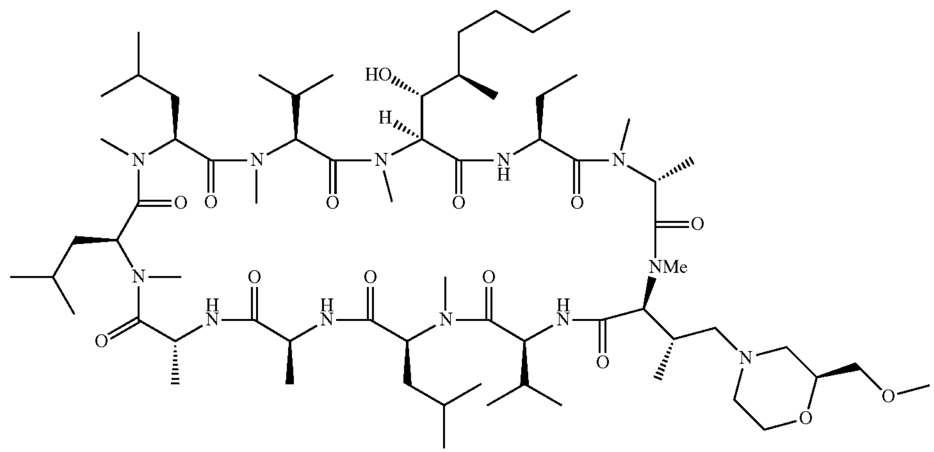 [SMILES: CCCC[C@@H](C)[C@@H](O)[C@H]1C(=O)N[C@@H](CC)C(=O)N(C)[C@H](C)C(=O)N(C)[C@@H]([C@@H](C)CN2CCO[C@H](COC)C2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.30 | 1333.9408 |
| 2.17.13 | 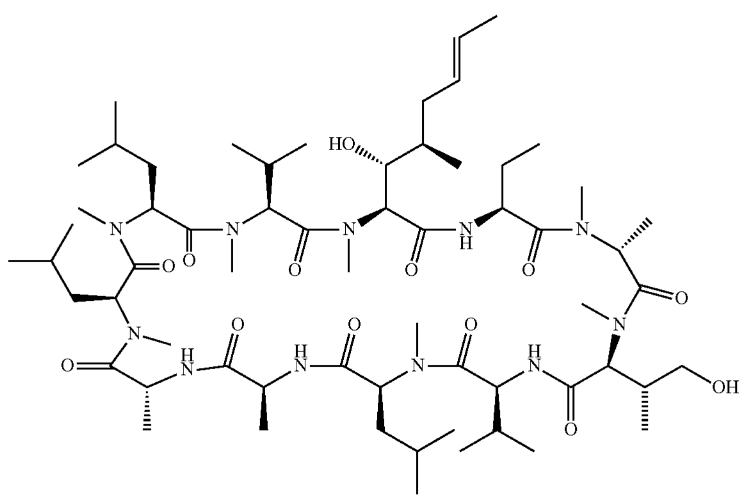 [SMILES: C/C=C/C[C@@H](C)[C@@H](O)[C@H]1C(=O)N[C@@H](CC)C(=O)N(C)[C@H](C)C(=O)N(C)[C@@H]([C@@H](C)CO)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.50 | 1218.8425 |

TABLE 1-continued

UPLC retention time and HRMS

| | Structure | Retention time (mins) | HRMS |
|---|---|---|---|
| 2.17.14 | 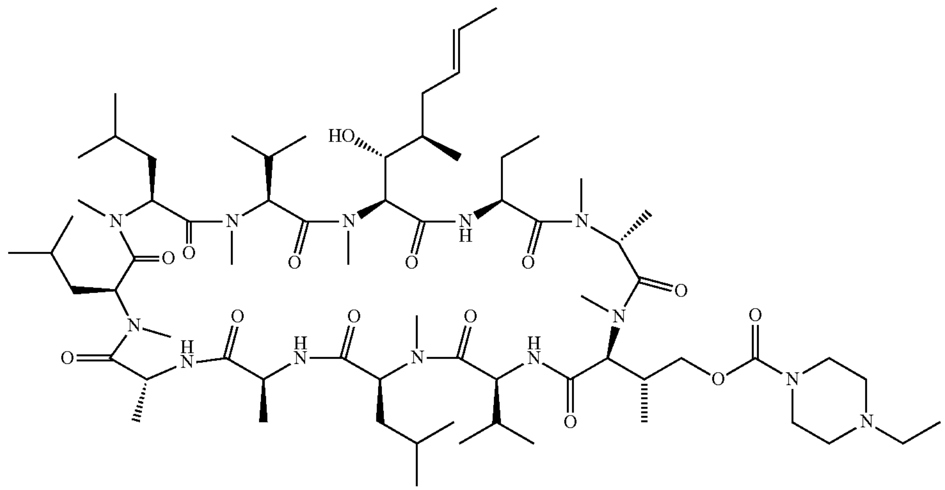 [SMILES: C/C=C/C[C@@H](C)[C@@H](O)[C@H]1C(=O)N[C@@H](CC)C(=O)N(C)[C@H](C)C(=O)N(C)[C@@H]([C@@H](C)COC(=O)N2CCN(CC)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.13 | 1358.9368 |
| 2.18.1 | 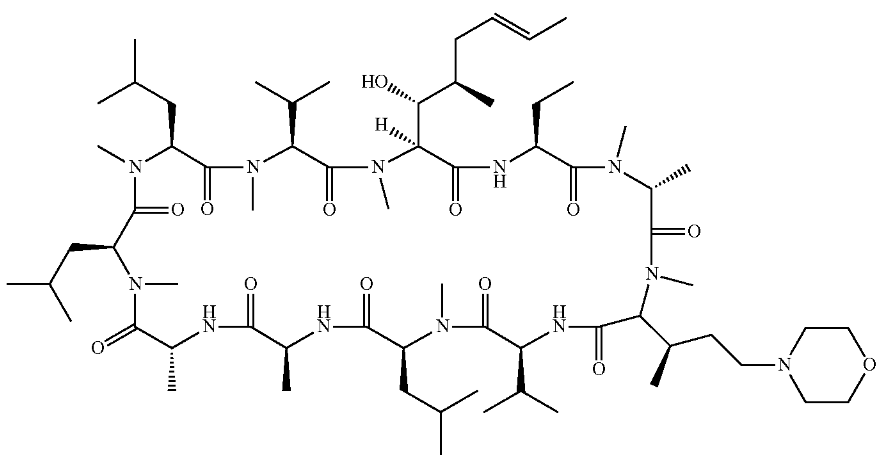 [SMILES: C/C=C/C[C@@H](C)[C@@H](O)[C@H]1C(=O)N[C@@H](CC)C(=O)N(C)[C@H](C)C(=O)N(C)C([C@H](C)CCN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.46 | 1301.9152 |

TABLE 1-continued
UPLC retention time and HRMS
| | Structure | Retention time (mins) | HRMS |
|---|---|---|---|
| 2.18.2 | 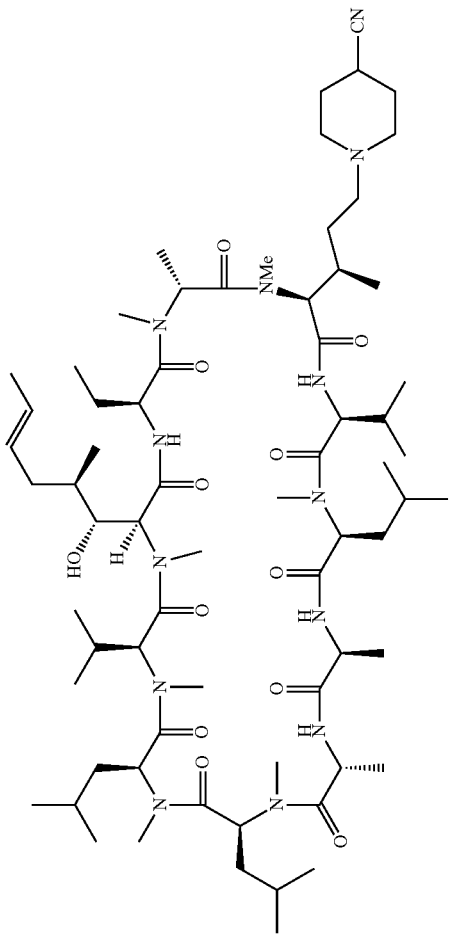 | 5.40 | 1324.93 |
| 2.18.3 | 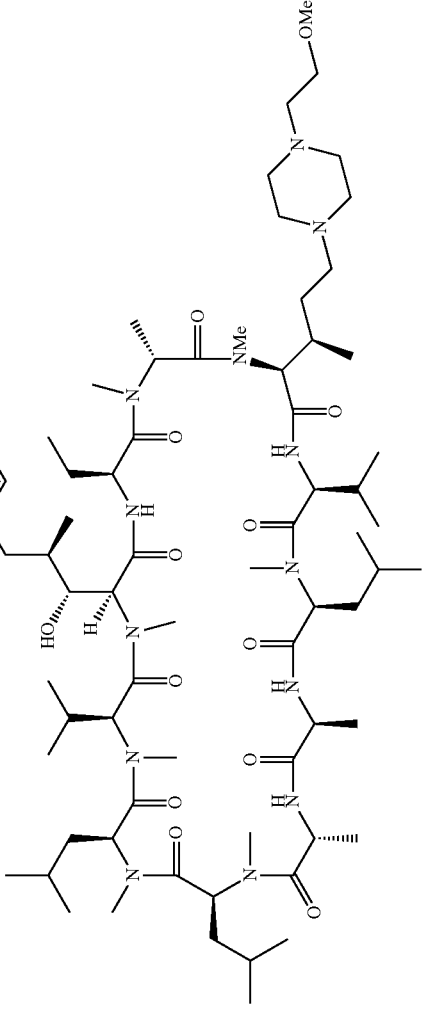 | 4.96 | 1358.9730 |

TABLE 1-continued
UPLC retention time and HRMS
| | Structure | Retention time (mins) | HRMS |
|---|---|---|---|
| 2.18.4 | 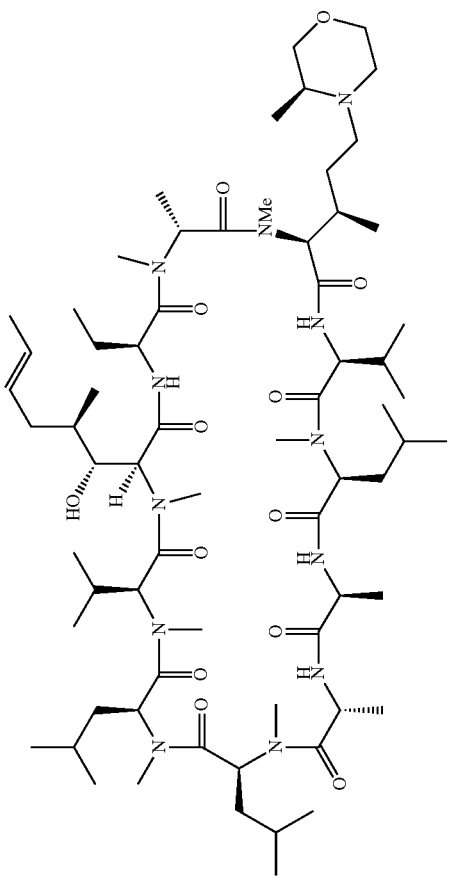 | 5.43 | 1315.9314 |
| 2.18.5 | 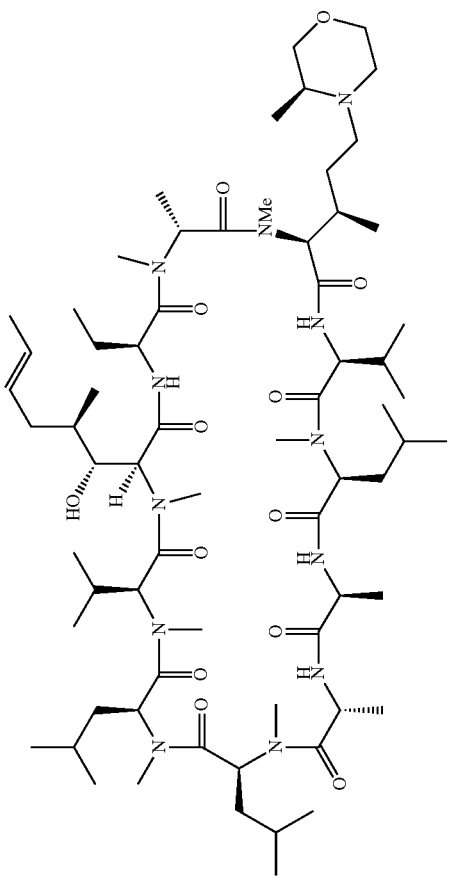 | 5.23 | 1301.9180 |

TABLE 1-continued
UPLC retention time and HRMS
| | Structure | Retention time (mins) | HRMS |
|---|---|---|---|
| 2.18.6 | 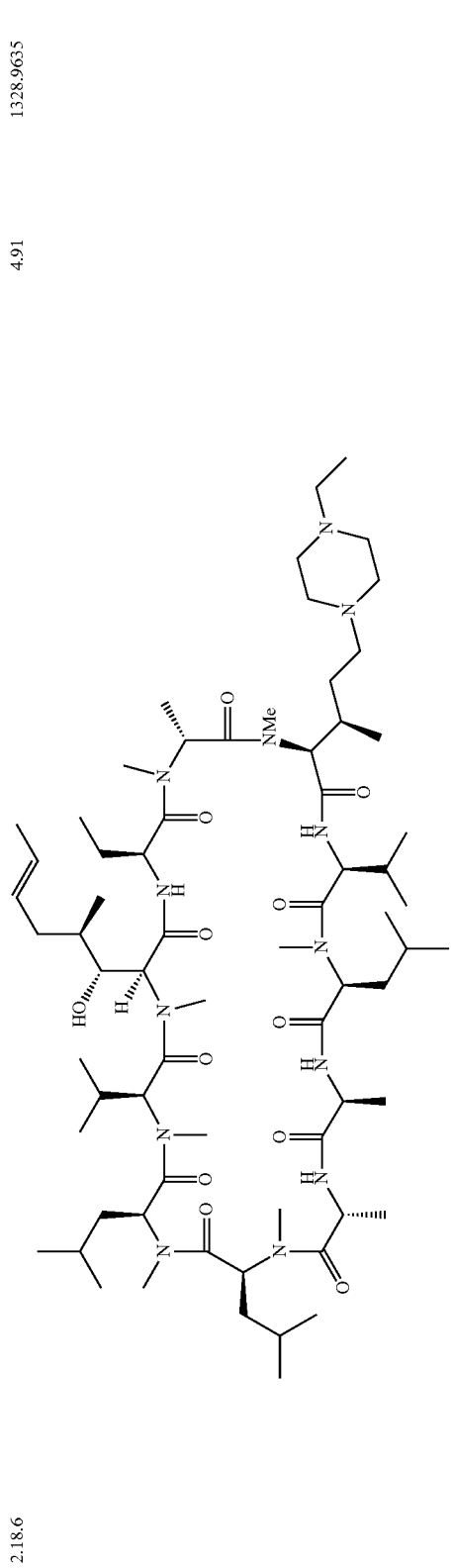 | 4.91 | 1328.9635 |
| 2.18.7 | 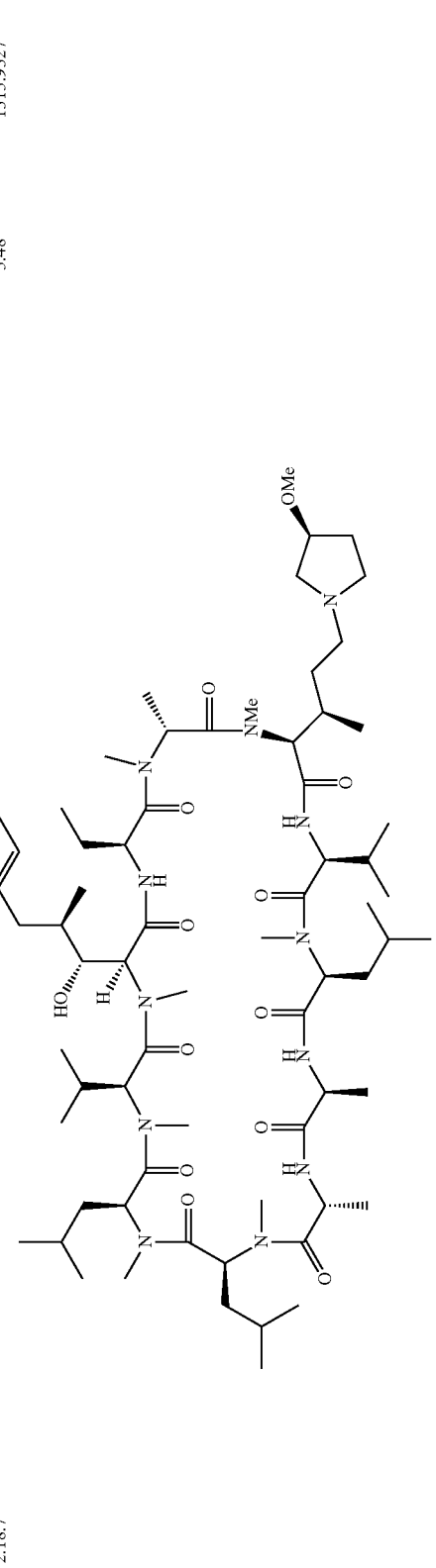 | 5.48 | 1315.9327 |

TABLE 1-continued
UPLC retention time and HRMS
| | Structure | Retention time (mins) | HRMS |
|---|---|---|---|
| 2.18.8 | 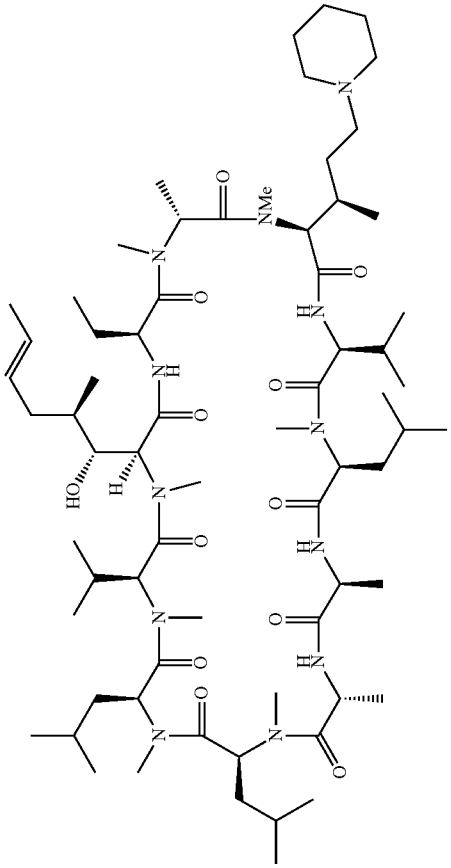 | 5.56 | 1299.9364 |
| 2.18.9 | 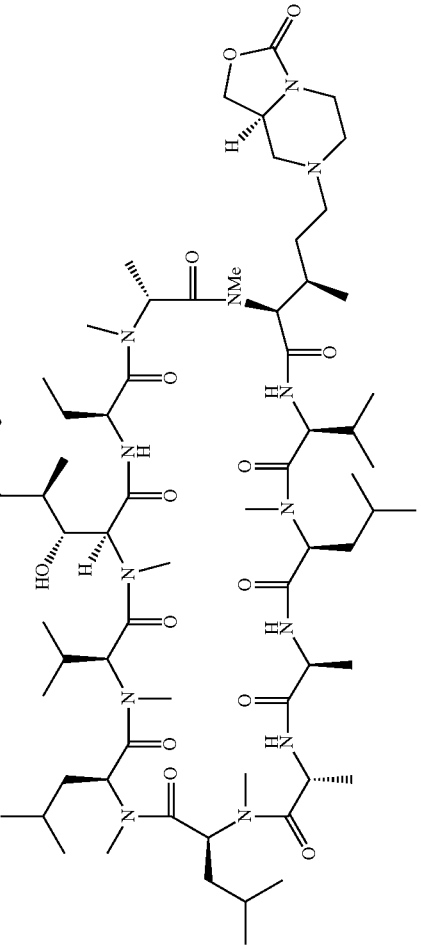 | 5.29 | 1356.9219 |

TABLE 1-continued

UPLC retention time and HRMS

| | Structure | Retention time (mins) | HRMS |
|---|---|---|---|
| 2.18.10 | 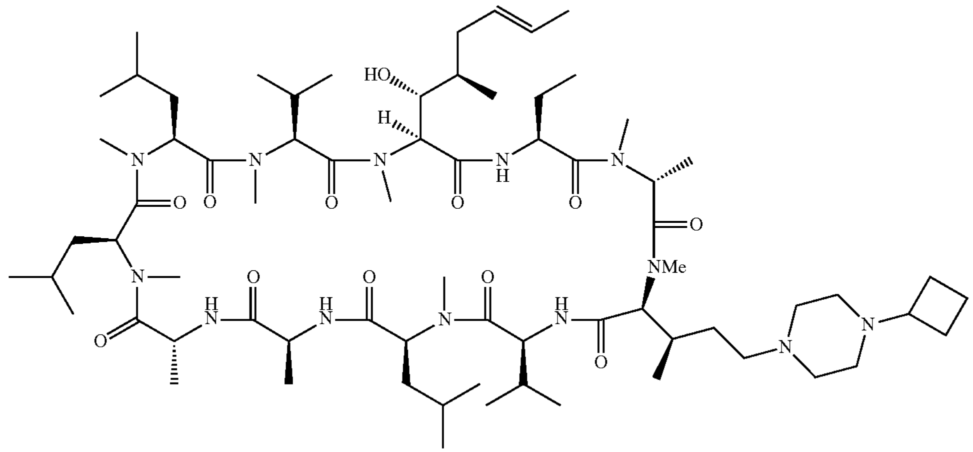 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCN2CCN(C3CCC3)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.06 | 1354.9783 |
| 2.19.1 | 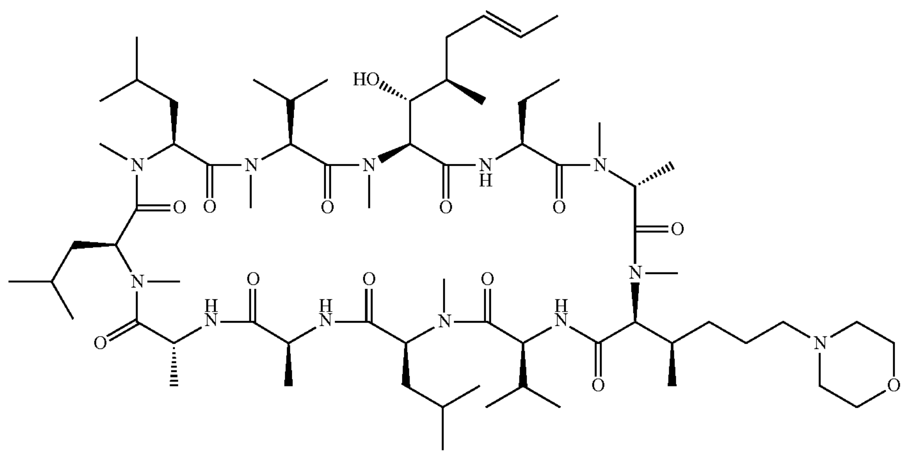 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCCN2CCOCC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.24 | 1315.9336 |

TABLE 1-continued

UPLC retention time and HRMS

| | Structure | Retention time (mins) | HRMS |
|---|---|---|---|
| 2.19.2 | 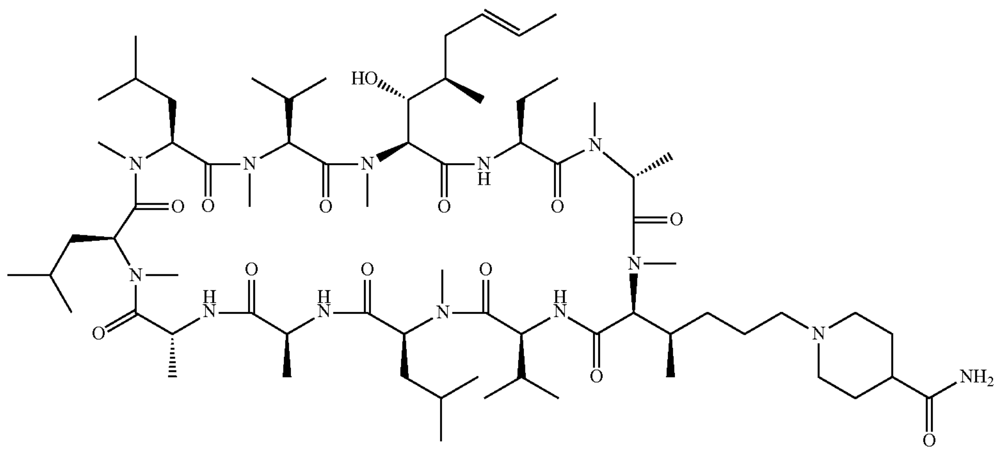 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCCN2CCC(C(N)=O)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.09 | 1356.9602 |
| 2.19.3 | 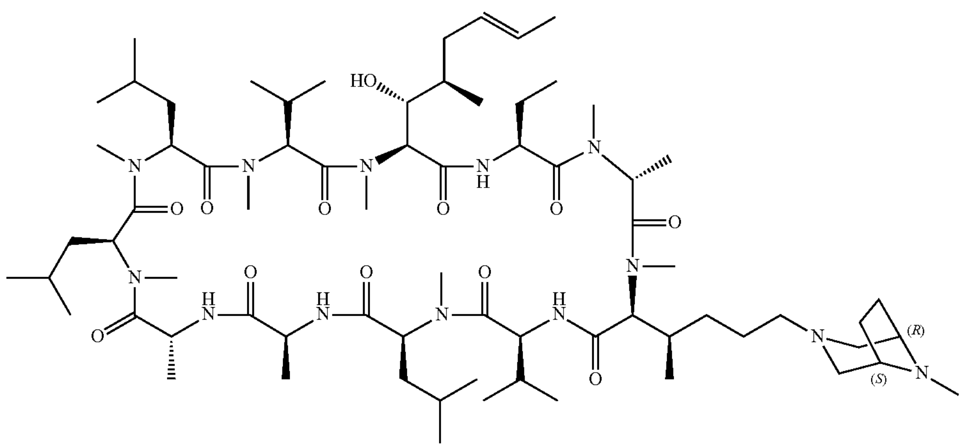 | 4.88 | 1354.9805 |

TABLE 1-continued

UPLC retention time and HRMS

| | Structure | Retention time (mins) | HRMS |
|---|---|---|---|
| 2.19.4 | 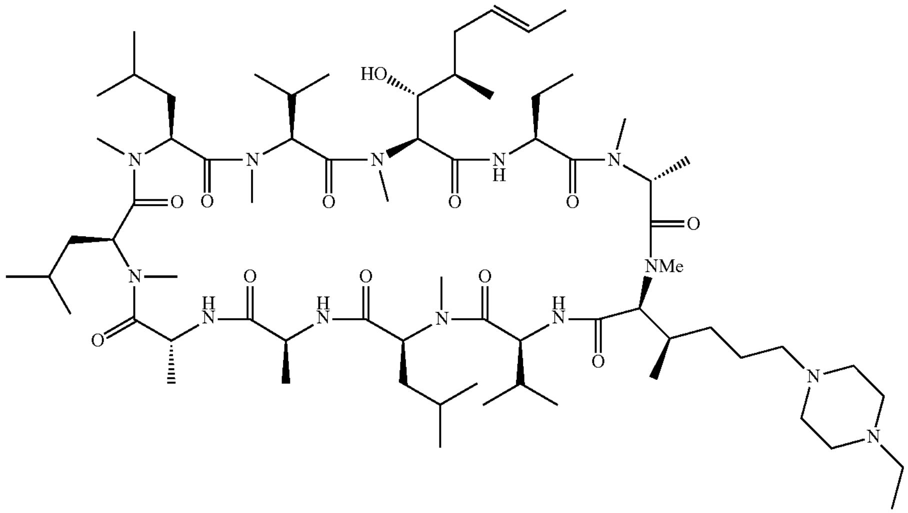 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCCN2CCN(CC)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 4.81 | 1342.9816 |
| 2.19.5 | 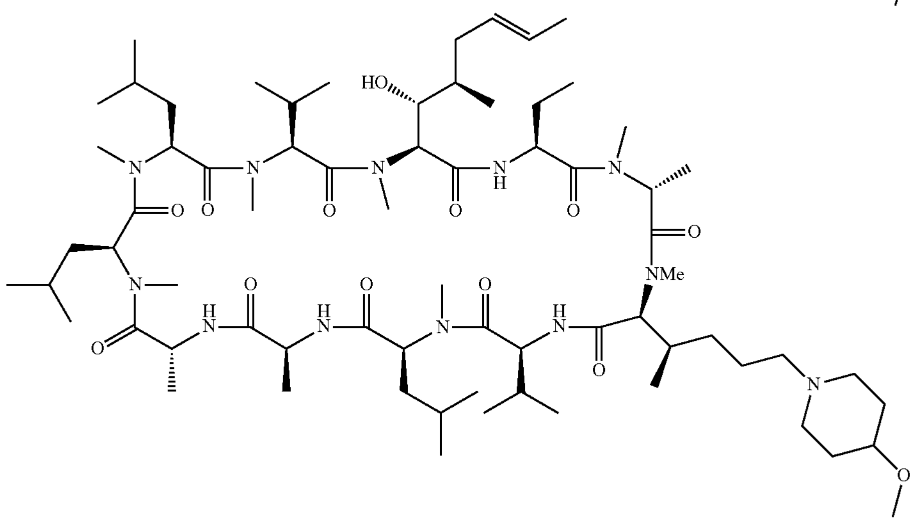 | 5.39 | 1343.9635 |

TABLE 1-continued
UPLC retention time and HRMS
| Structure | Retention time (mins) | HRMS |
|---|---|---|
| 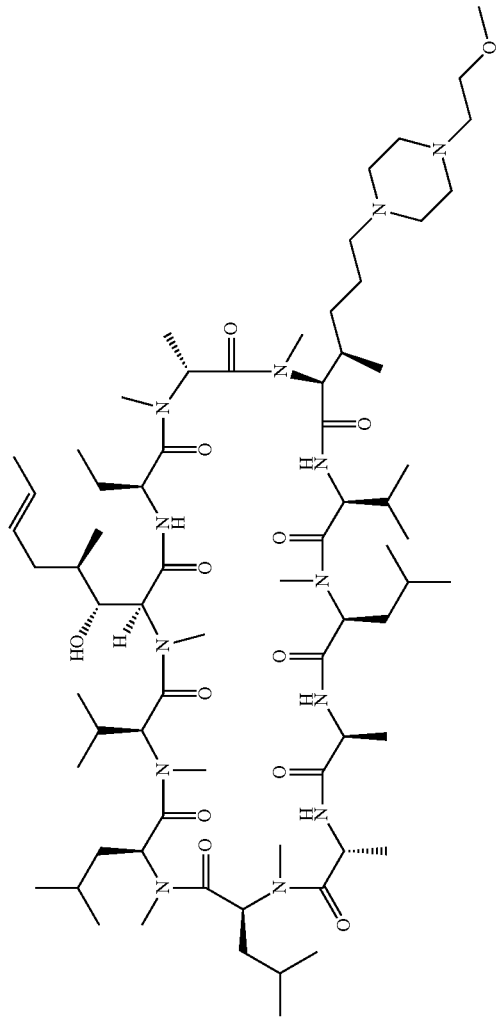 | 4.93 | 1372.9893 |
2.19.6

TABLE 1-continued
UPLC retention time and HRMS
| | Structure | Retention time (mins) | HRMS |
|---|---|---|---|
| 2.19.7 | 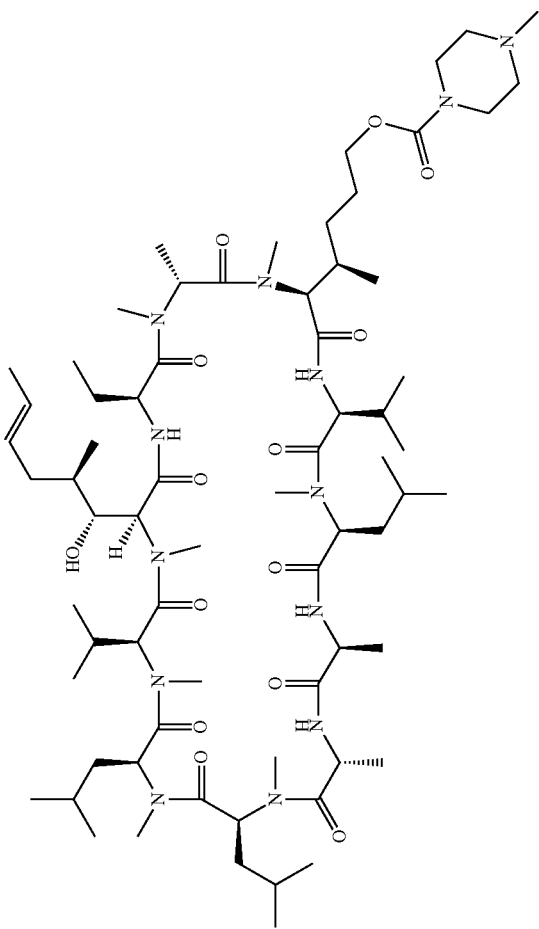 | 5.3 | 1372.9532 |
| 2.19.8 | 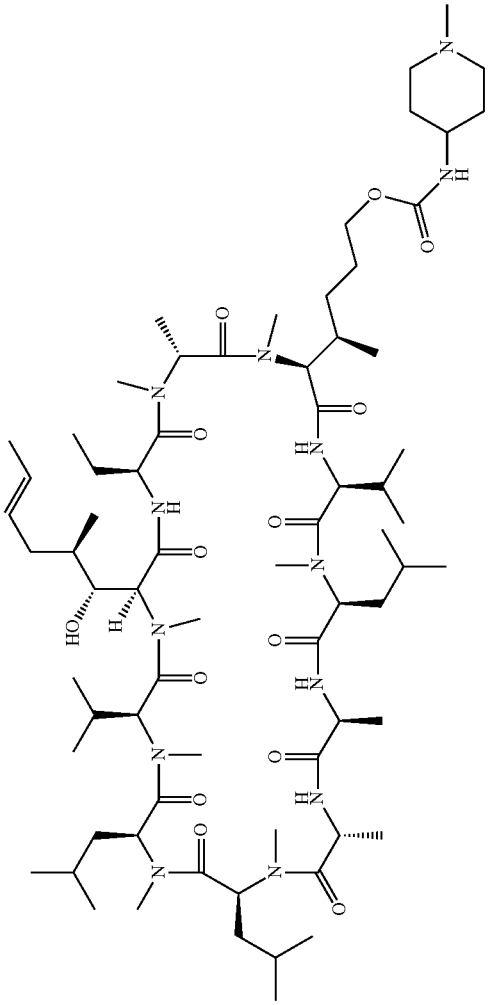 | 5.3 | 1386.9704 |

TABLE 1-continued

UPLC retention time and HRMS

| | Structure | Retention time (mins) | HRMS |
|---|---|---|---|
| 2.19.9 | 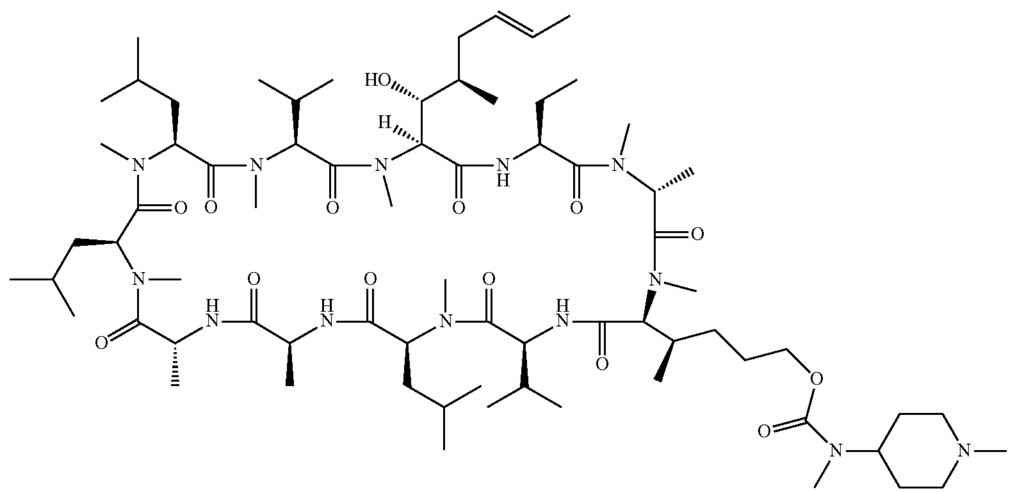 [SMILES: C/C=C/C[C@@H](C)[C@@H](O)[C@H]1C(=O)N[C@@H](CC)C(=O)N(C)[C@H](C)C(=O)N(C)[C@@H]([C@H](C)CCCOC(=O)N(C)C2CCN(C)CC2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.29 | 1400.9860 |
| 2.20.1 | 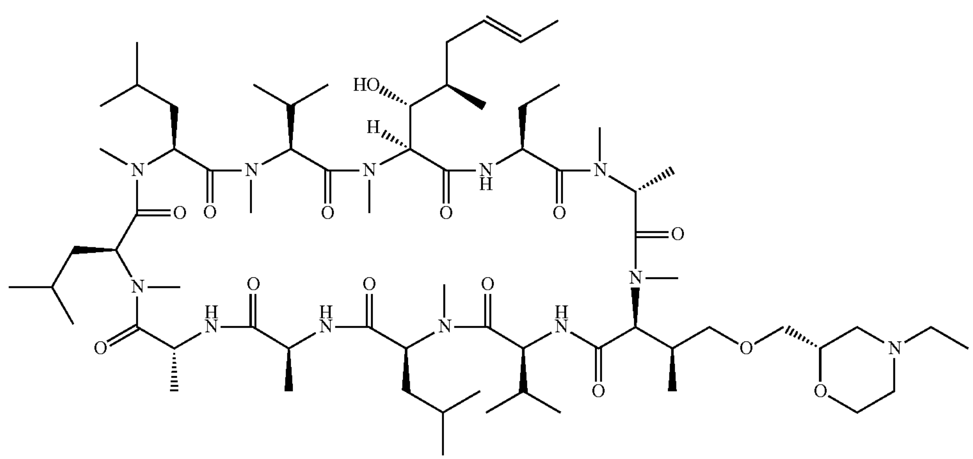 [SMILES: C/C=C/C[C@@H](C)[C@@H](O)[C@H]1C(=O)N[C@@H](CC)C(=O)N(C)[C@H](C)C(=O)N(C)[C@@H]([C@H](C)COC[C@@H]2CN(CC)CCO2)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | 5.34 | 1345.9418 |

TABLE 1-continued
UPLC retention time and HRMS
| | Structure | Retention time (mins) | HRMS |
|---|---|---|---|
| 2.20.2 | 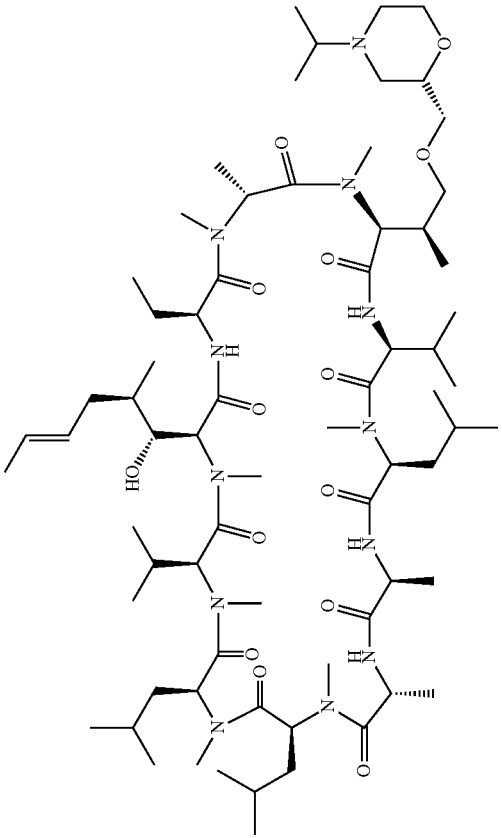 | 5.41 | 1359.9602 |
| 2.21.1 | 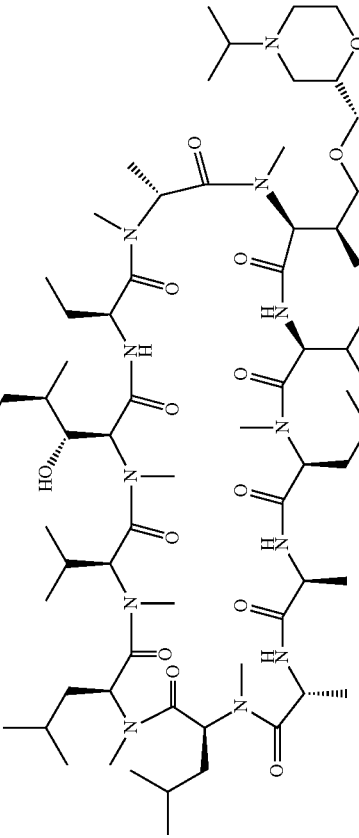 | 5.42 | 1303.8954 |

TABLE 1-continued
UPLC retention time and HRMS
| | Structure | Retention time (mins) | HRMS |
|---|---|---|---|
| 2.21.2 | 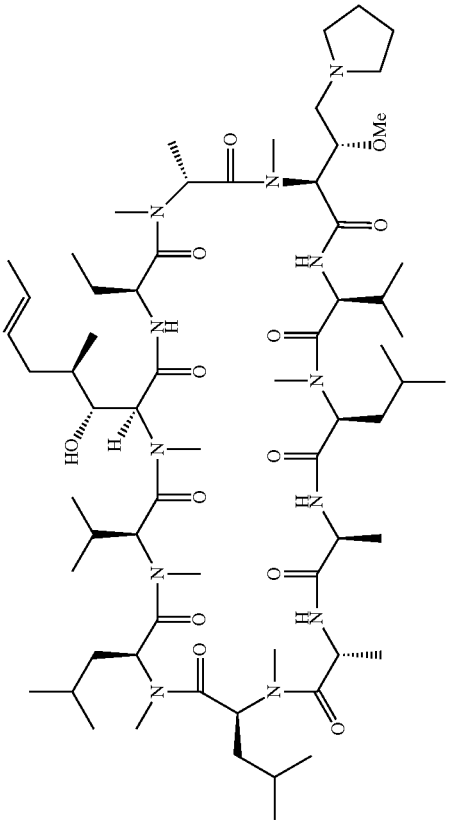 | 5.31 | 1287.8993 |
| 2.21.3 | 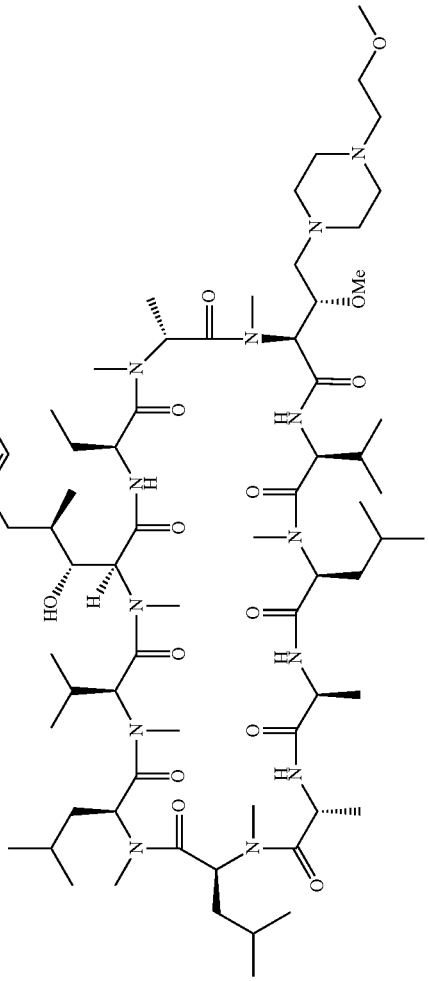 | 5.03 | 1360.9542 |

TABLE 1-continued
UPLC retention time and HRMS
| | Structure | Retention time (mins) | HRMS |
|---|---|---|---|
| 3.1 | 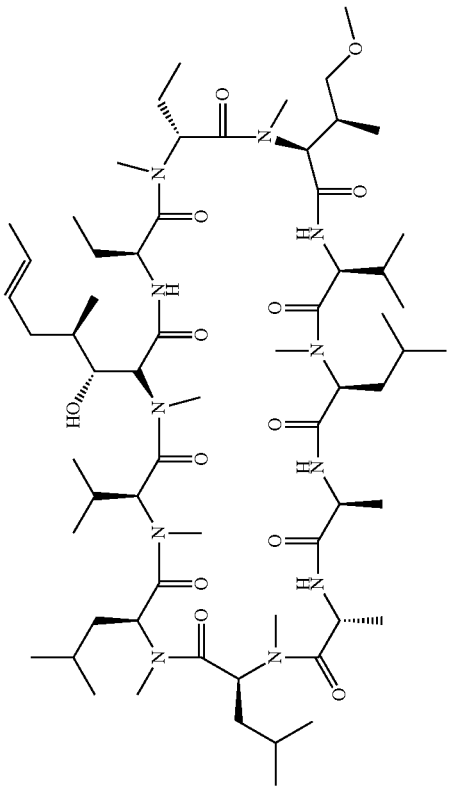 | 6.52 | 1246.8738 |
| 3.2.1 | 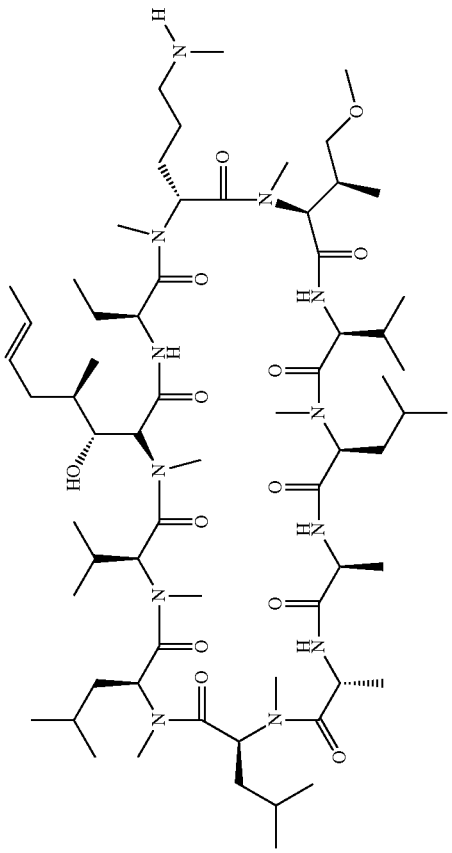 | 5.19 | 1289.9219 |

TABLE 1-continued

UPLC retention time and HRMS

| | Structure | Retention time (mins) | HRMS |
|---|---|---|---|
| 3.2.2 | 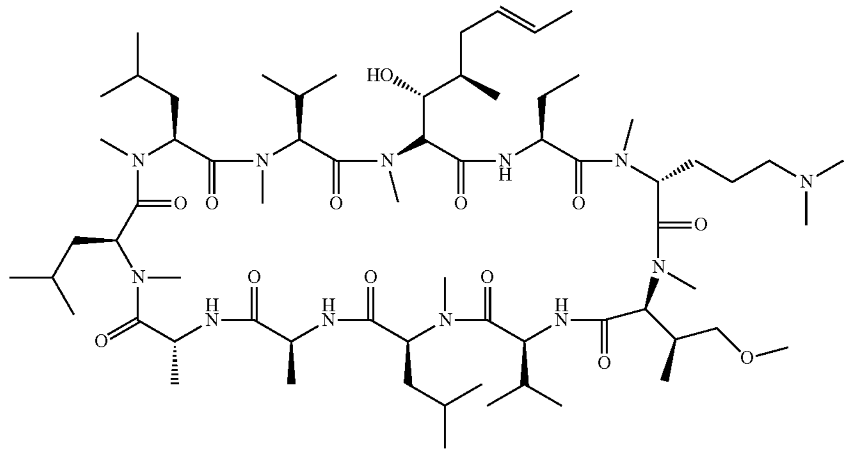 | 5.22 | 1303.9313 |
| 3.2.3 | 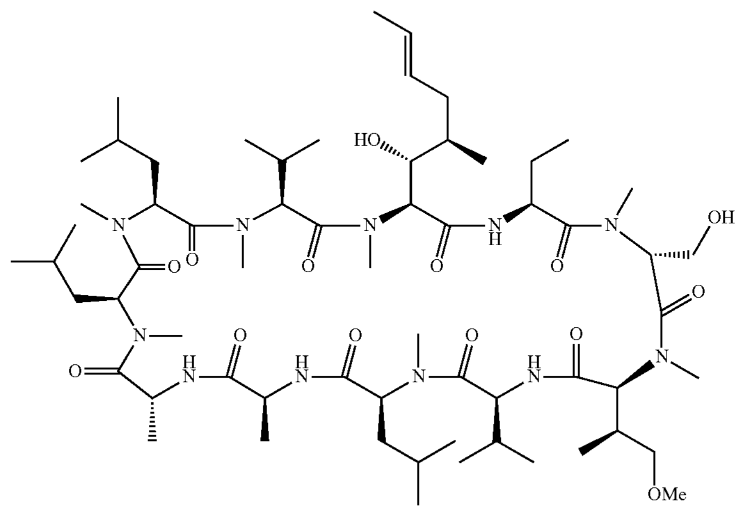 [SMILES: C/C=C/C[C@@H](C)[C@@H](O)[C@H]1C(=O)N[C@@H](CC)C(=O)N(C)[C@H](CO)C(=O)N(C)[C@@H]([C@H](C)COC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | | |

TABLE 1-continued
UPLC retention time and HRMS
| | Structure | Retention time (mins) | HRMS |
|---|---|---|---|
| 3.3 | 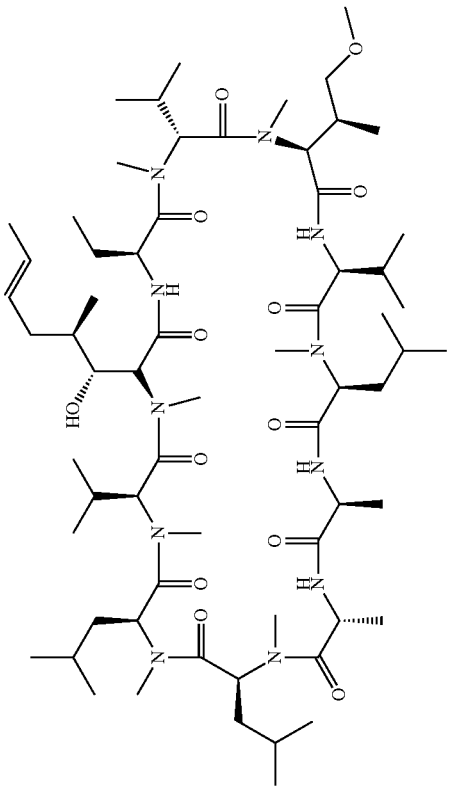 | 6.69 | 1260.8887 |
| 3.4.1 | 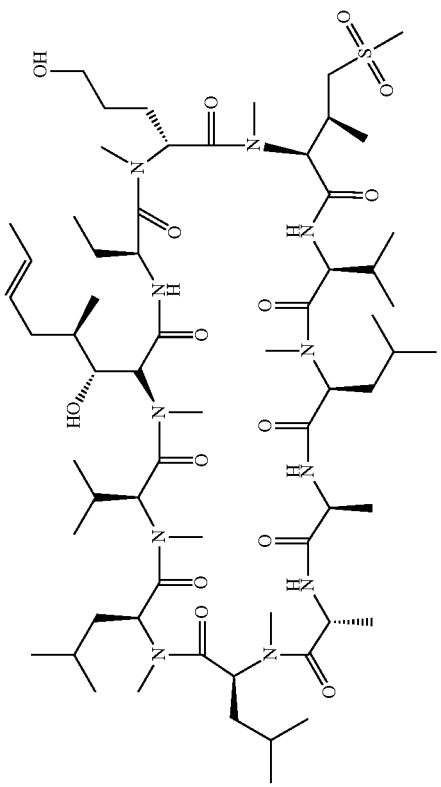 | 5.595 | 1324.8527 |

TABLE 1-continued
UPLC retention time and HRMS
| Structure | Retention time (mins) | HRMS |
|---|---|---|
| 3.4.2 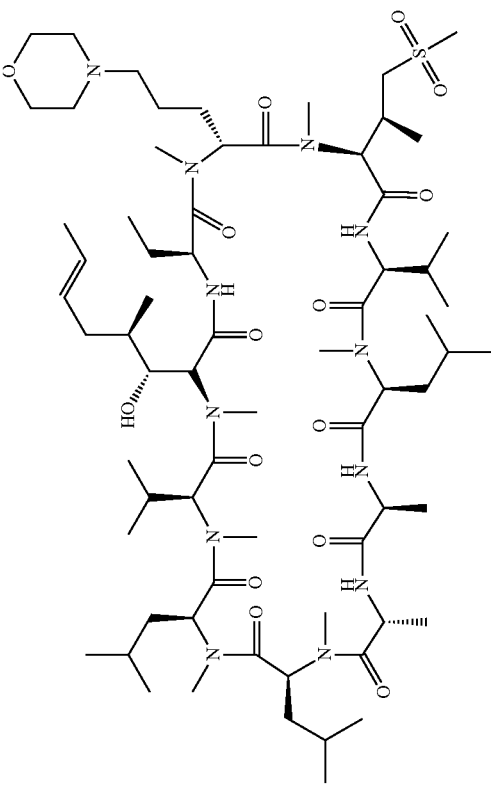 | 5.006 | |

Methods of Use

The compounds according to any one of Formulae I to IVb in free form or in pharmaceutically acceptable salt form, exhibit valuable pharmacological properties, e.g. interference with the interaction of cyclophilins with other proteins, for example interference of the interaction of cyclophilin A with proteins needed for viral replication or of cyclophilin D with the mitochondrial permeability transition (PT) pore; e.g. as indicated in in vitro and in vivo tests as provided in the next sections and are therefore indicated for therapy.

The replication of several viruses, such as, but not limited to, human immunodeficiency virus (HIV), hepatitis B virus (HBV), Human Papilloma virus (HPV) and hepatitis C virus (HCV), have been shown to be dependant upon cyclophilin function. In the case of HIV-1, it has been shown unequivocally that NIM 811 blocks the interaction between $p55^{gag}$ and cyclophilin A, the major cytoplasmic isoform of human cyclophilins, and as a consequence results in the formation of inactive HIV-1 virions.

In HCV patients, coadministration of CsA with interferon alpha2b, significantly reduces viral load when compared to patients given interferon alpha 2b alone. However, the use of CsA in some therapeutic settings may be complicated by calcineurin-mediated immunosuppression. It has been shown that the immunosuppressive activity and the viral replication inhibitory properties are separable activities and suppression of hepatitis C virus replication by cyclosporin A is mediated by blockade of cyclophilins. For example, NIM811, a natural derivative of CsA, inhibits virus replication but does not show immunosuppressive activity and therefore may be used to treat HCV infected patients. The anti-HCV activity of CsA is mediated through the blockage of cyclophilins. Similar to CsA, the anti-HIV activity of NIM811 is correlated with its binding to cyclophilins. In addition, DEBIO-025, a potent pan-cyclophilin binder lacking immunosuppression, significantly decreased mean hepatitis C load in patients treated with 1200 mg twice daily The cyclophilin inhibitor Debio025 shows potent anti-hepatitis C effect in patients coinfected with hepatitis C and human immunodeficiency virus.

Cyclophilin D, encoded by the gene Ppif and first identified from rat heart and liver mitochondria, is consistently demonstrated to be a key mediator of the mitochondrial permeability transition pore (mPTP), which lies within the mitochondrial inner membrane. The mPTP is a voltage-dependent, high-conductance channel of uncertain structure. Under normal conditions, the mPTP are closed or opened transiently and asynchronously. Pore opening is favored by multiple stress factors, such as increased $Ca^{2+}$ concentration and oxidative stress. The primary consequence of synchronous, global mPTP opening is mitochondrial depolarization, followed by equilibration of the electrochemical gradients used to drive ATP production. Therefore, cyclophilin D blockade is desired for conditions and disease settings in which cells and/or tissue is acutely or chronically exposed to stress, including, but not limited to $Ca^{2+}$-overload and/or oxidative stress.

Swelling of isolated mitochondria in response to applied stress serves as a phenotypic readout of mPTP opening. Mitochondrial swelling in response to $Ca^{2+}$-overload or oxidative stress is blocked by loss of cyclophilin D or treatment with cyclophilin binders. In wild-type mitochondria, 100 µM $Ca^{2+}$-induced swelling is blocked by treatment with 1 µM CsA. Likewise, mitochondria isolated from Ppif$^{-/-}$ cells exhibit resistance to 100 µM $Ca^{2+}$-induced swelling. Loss of cyclophilin D reveals a critical role for mitochondrial permeability transition in cell death. Cyclophilin D is a component of mitochondrial permeability transition and mediates neuronal cell death after focal cerebral ischemia.

In intact cells, such as mouse embryonic fibroblasts, cardiomyocytes, hepatocytes, and neurons, loss of cyclophilin D confers resistance to oxidative stress-induced death by $H_2O_2$ treatment. Likewise, opening of the mPTP can be inhibited by cyclophilin D binders, such as cyclosporin A (CsA), NIM811, DEBIO-025, SCY-635, and sanglifehrin A (SfA) and compound according to anyone of Formulae I to IVb, or a pharmaceutically acceptable salt thereof.

The improved survival and stress tolerance of hepatocytes, neurons, and myocytes (both cardiac and skeletal) is particularly well documented with either loss and/or pharmacologic blockade of cyclophilin D. However, the role of cyclophilin D in disease is not limited to the survival of neuron and myocyte cell types. The use of CsA in a variety of conditions and disease settings outside allograft rejection, such as, but not limited to HCV infection, stroke, multiple sclerosis, HBV infection, HPV infection, asthma, cancer, muscular dystrophy, sepsis, ischemia/reperfusion injury, and heart failure follows directly from its potent cyclophilin D binding and lies outside of Cn-binding and immunosuppressive effects.

Cardiovascular Indications

Ischemia/Reperfusion (I/R) provides one example of an event that induces mPTP opening. The standard clinic practice of reperfusing the ischemic heart of patients suffering from myocardial infarction (MI), is estimated to reduce tissue damage by 40%. However, the increased $Ca^{2+}$ concentration and oxidative stress introduced by the reperfusion is estimated to account for the loss of >50% of the cardiac myocytes surviving the initial ischemic event. Introduction of a cardioprotective agent, specifically an mPTP blocker, prior to reperfusion is proposed to mitigate mPTP-dependent necrosis and minimize infarct size.

In animal models of ischemia/reperfusion injury, mPTP blockers such as cyclosporin A, NIM811, and sanglifehrin A (SfA) have been shown to lower damage to the cardiac tissue. CsA reduces infarct size in a rat model of I/R injury. mPTP blockers reduce cardiomyocyte apoptosis in a rabbit model of I/R Injury. Ppif$^{-/-}$ mice offer further insight into the role of CyD in tissue survival. Ppif$^{-/-}$ mice are resistant to myocardial infarction. Recent reports demonstrate an advantage for CyD deficient mice versus wild-type mice in models of I/R, muscular dystrophy, and heart failure. With specific regard to models of cardiac I/R injury, loss of CyD is sufficient for tissue protection; CyD deficient mice are resistant to pharmacological cardioprotection.

Recent human data bolsters the hypothesis that a cyclophilin binder can positively impact clinical outcome in I/R Injury. In human trials (n=53 inclusions), introduction of CsA to the ischemic hearts of patients (n=26) is associated with >40% reduction of protein biomarkers of cardiac myocyte death relative to control patients (n=27). Troponin I (TnI), a myocyte-specific contractile protein, and casein kinase (CK) are monitored in plasma. While only a portion of the 53 patients were monitored by MRI, of those tested, the CsA-treated patients showed smaller infarct size relative to controls.

Necrosis likewise plays a role in chronic heart failure ($Ca^{2+-}$ and mitochondrial-dependent cardiomyocyte necrosis is implicated as a primary mediator of heart failure. Ppif$^{-/-}$ mice are protected from $Ca^{2+}$-overload induced myocyte necrosis and hypertrophy.

Muscular Dystrophy

Genetic and pharmacologic inhibition of mitochondrial dependent necrosis attenuates muscular dystrophy. Scgd$^{-/-}$ Ppif$^{-/-}$ show markedly reduced muscular dystrophy than do Scgd$^{-/-}$ comparators.

HPV Infection

Cyclophilin B (CyPB) activity facilitates infection of human papillomavirus type 16 (HPV16) and HPV18. Data suggest that CyP is required during two distinct steps of HPV16 infection. Identification of cell surface CyPB will facilitate the study of the complex events preceding internalization and adds a putative drug target for prevention of HPV-induced diseases.

HBV Infection

A study by investigators looked at HBV replication and virus particle release in a panel of liver cell lines exposed to alisporivir and NIM811. Stably transfected HepG2215 cells were cultured for 7 days and then treated with 0.25, 1.0, and 5.0 mcg/mL of alisporivir or NIM811. They were analyzed at baseline and at 6, 24, 48, and 72 hours after adding of the drugs. Similar experiments were repeated with Huh-7 cells and PLC/PRF/5 cells. Both cyclophilin inhibitors significantly reduced core-particle-associated HBV DNA levels in cells by 2-fold to 10-fold compared with control cells. The most pronounced reduction in intracellular HBV DNA levels—by 10-fold at 72 hours—was seen after exposure to 5.0 mcg/mL alisporivir. Alisporivir at both 1.0 and 5.0 mcg/mL doses reduced HBV virion production more than NIM811. Both compounds significantly reduced HBsAg secretion from cells by about 50% compared with controls.

HCV Infection

It was first reported by Watashi that CsA and CsA analogs, including NIM811 also inhibit HCV replication. CsA inhibited HCV replicon at both protein and RNA levels in a time- and concentration-dependent manner. The inhibitory activity of 1 μg/ml of CsA was similar to that of 100 U/mL of IFN-α. CsA inhibited HCV replication in cultured hepatocytes that have been infected with HCV-positive serum. Again, the inhibitory activity of 1 μg/mL of CsA was similar to that of 100 U/mL of IFN-α. The effect of CsA on HCV replicon was independent of IFN pathway. Anti-HCV activity of CsA was independent of its immunosuppressive function. This inhibitory activity of CsA itself was also confirmed by a second report. CsA suppressed HCV replicon in a dose-dependent manner, with an apparent IC50 between 0.3 and 1 μg/ml after 48 h of treatment. No cytotoxicity was observed with up to 10 μg/ml of CsA. In contrast, FK506, another immunosuppressive agent and inhibitor of the calcineurin/NFAT pathway, did not have significant effect on HCV replication. The effect of CsA on HCV replicon is independent of IFN pathway.

The use of CsA in some therapeutic settings may be complicated by calcineurin-mediated immunosuppression. Since the discovery of CsA, several analogs have been identified that also potently bind the cylcophilins, but lack the ability of CsA to bind potently to calcineurin (Cn). Compounds with weak activity relative to CsA in the mouse mixed lymphocyte reaction (mMLR) are expected to offer an advantage in those disease settings where immunosuppression may not be beneficial to the patient. CsA derivatives, such as NIM811, DEBIO-025, SCY-635, and compounds according to anyone of Formulae I to IVb exhibit lower mMLR activity and are expected to be advantageous in cases where immune suppression is not desired.

Therefore, compounds of the invention may be useful in the prevention or treatment of an indication selected from HCV infection, stroke, multiple sclerosis, HBV infection, HPV infection, asthma, cancer, muscular dystrophy, sepsis, ischemia/reperfusion injury, and heart failure.

The pharmaceutical composition or combination of the present invention can be in unit dosage of about 1-5000 mg of active ingredient(s) for a subject of about 50-70 kg, or about 1-1000 mg or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Pharmaceutical Activity

The activity of a compound according to the present invention can be assessed by the following in vitro & in vivo methods.

Method 1: Measuring Inhibitor Binding to Cyclophilin Proteins

Binding of inhibitors to expressed cyclophilins was determined using surface plasmon resonance (SPR) experiments. Briefly, avi-tagged cyclophilin proteins with mono-biotinylation were immobilized onto a Biotin CAPture chip (GE Healthcare, cat. #28920234). SPR experiments were carried out on an upgraded Biacore T200 system using a running buffer containing the inhibitor, 10 mM HEPES, pH 7.4, 150 mM NaCl, 0.05% P20, and 3% DMSO. Single-cycle kinetics measurements were used to study the interactions between cyclophilin inhibitors and different cyclophlins. Accordingly, compound at various concentrations was injected to the flow cells with a contact time of 1 min each at a flow rate of 50 μL/min. The final dissociation phase lasts for 10 min following the sample injection. Data was analyzed using Biacore T200 Evaluation Software Version 1.0 and a 1:1 binding model was applied to fit the data to obtain $k_{on}$, $k_{off}$ and $K_D$.

Method 2: Measuring Inhibitory Effects in a HCV Replicon System

Susceptibility to compounds was analyzed in Huh7.5 cells containing genotype 1a or 1b subgenomic HCV replicons co-expressing a luciferase reporter gene. The original replicons, pFK389lucubineo_3_3'_ET and pH/SG-Neo(L+I), were licensed from ReBlicon GmbH (Germany) and Apath LLC (Saint Louis, Mo.), respectively. The firefly reporter gen was replaced by renilla luciferase reporter gene using standard molecular biology techniques as follows.

Generation of genotype 1b subgenomic replicon: The renilla firefly-neomycin phosphotransferase cassette was amplified from pF9 cytomegalovirus (CMV) hRluc-Neo Flexi(R) (Promega) by PCR using Accuprime super mix II (Invitrogen) and a primer set of Ascl hRlucNeo Fwd and NotI hRluc Rev. These two primers have the following sequences and introduce restriction sites for subsequent cloning: AscI hRlucNeo Fwd, 5 GGG CGC GCC ATG GCT TCC AAG GTG TAC G 3(AscI site underlined) (SEQ. ID No. 1), and NotI hRluc Rev, 5CGC GGC CGC TCA GAA GAA CTC GTC AAG 3(NotI site underlined) (SEQ ID No. 2). The amplification product was subcloned into pCR2.1-TOPO (Invitrogen). The resulting plasmid was digested with AscI and NotI, and the excised fragment (hRluc-Neo) was ligated with the Roche Quick Ligation Kit (Roche) into pFK1389lucubineo_3_3'_ET digested with the same enzymes.

Generation of genotype 1a subgenomic replicon: pH/SG-Neo(L+I) was modified by adding the luciferase reporter gene and additional adaptive mutations by replacing the pH/SG-Neo(L+I) NS3-NS5A coding region with the corresponding region of pH77-S creating pH/SG-lucubineo-H775 as described (Borawski J et al. 2009, J Virol 83: 10058-10074). Subsequently, the firefly luciferase-neomycin phosphotransferase cassette was replaced by the renilla firefly-neomycin phosphotransferase cassette. To create a unique cloning site, the NotI restriction site in NS5B was removed using QuickChange II XL Site-Directed Mutagenesis Kit (Agilent). The two site-directed mutagenesis primers have the following sequences and introduce a mutation to knock out the NotI site in NS5B for subsequent cloning: NotI KO Fwd 5CTC AAA CTC ACT CCA ATA GCT GCC GCT GGC CGG CTG GAC 3(G T mutation underlined) (SEQ. ID No. 3) and NotI KO Rev 5CTC CAG CGG GCC AGC GGC AGC TAT TGG AGT GAG TTT GAG 3(C→A mutation underlined) (SEQ. ID No. 4). The resulting vector, pH/SG-lucubineo-H77S-NotIKO was sequenced to confirm the correct sequence on the NS5B gene. The hRluc-Neo gene was amplified from pF9 cytomegalovirus (CMV) hRluc-Neo Flexi(R) (Promega) by PCR using Accuprime super mix II (Invitrogen) and a primer set of AscI hRlucNeo Fwd and NotI hRluc Rev. These two primers have the following sequences and introduce restriction sites for subsequent cloning: AscI hRlucNeo Fwd, 5 GGG CGC GCC ATG GCT TCC AAG GTG TAC G 3(AscI site underlined) (SEQ. ID No. 5), and NotI hRluc Rev, 5CGC GGC CGC TCA GAA GAA CTC GTC AAG 3(NotI site underlined) (SEQ ID No. 6). The amplification product was subcloned into pCR2.1-TOPO (Invitrogen). The resulting plasmid was digested with AscI and NotI, and the excised fragment (hRluc-Neo) was ligated with the Promega Rapid Ligation Ligation Kit (Promega) into pH/SG-lucubineo-H77S-NotIKO digested with the same enzymes. Cell maintenance: Cells were grown in Dulbecco's modified Eagle medium, 2 mM L-glutamine, 0.1 mM essential amino acids, 1× penicillin-streptomycin, 1 mM sodium pyruvate, 10% heat inactivated FBS (Invitrogen), and 500 µg/ml gentamycin (G418). Cells were routinely split 1:4 two times a week.

The assay medium for both, luciferase reporter HCV replicon and cytotoxicity assays contains phenol red-free DMEM and lacks G418. Sixteen half-log dilutions of compounds are stamped into twelve 384-well plates which allows parallel $EC_{50}$ determination in triplicate for genotype 1a and 1b replicon cells, the analysis of cytotoxicity and of protein binding through addition of 40% human serum to genotype 1b replicon cells. Luciferase activity of compound treated cells is measured relative to DMSO treated cells after 72 h incubation using Renilla-Glo™ Luciferase Assay (Promega). Cytotoxicity ($CC_{50}$) is analyzed using Cell Titer-Glo™ (Promega).

Method 3: Measuring Anti-Proliferative or Immunosuppressive Activity

The potential anti-proliferative activity of compounds on T-cells was analyzed based on the amount of bromodesoxyuridine (BrdU) incorporated into DNA of fresh peripheral blood mononuclear cells (PBMC) using the BrdU ELISA kit (Roche). The assay is performed in 96-well plate format with 30,000 PBMCs seeded per well in X-VIVO 15 medium (Lonza). T-cell proliferation was stimulated by addition of 3 µg/ml phytohemagglutinin (PHA) in PBMCs obtained from two donors. 60 hour compound treatment in half logarithmic serial dilutions was chosen to obtain $IC_{50}$ values. Cyclosporin A (CsA) and its non-immunosuppressive analog NIM811, are being included in each assay as controls.

Method 4: Measuring Hepatic Transporter Interactions

In order to determine whether the compounds of the present invention interact with hepatic transporters, experiments were carried out that compared the concentration-dependent inhibition toward the organic anion transporting polypeptide 1B1 (OATP1B1) and the multidrug resistance associated protein 2 (MRP2). These transporters are involved in the distribution and excretion of bilirubin, bioconjugates of bilirubin, and various xenobiotics.

OATP Assay: CHO-vector and CHO-OATP1B1 cells were seeded at a density of 30,000 cells/well of a 96-well plate (Costar 3904). The cells were cultured in DMEM/F12 +10% FBS+2 mM Ala-Gln+1% Pen-Strep for a period of two days, and the media was changed one day post-seeding. Prior to the assay, media was aspirated and were washed −3× with HBSS+10 mM HEPES and the solution was equilibrated for 15 min in HBSS+10 mM HEPES. Solutions containing the inhibitor were prepared in HBSS+10 mM HEPES (up to 1% DMSO). At time=0 the wash solution was aspirated and the substrate (8-fluorescein-cAMP, Concentration: 2.5 µM) or substrate/inhibitor (0-30 µM) solution was added to each well. After 10 min, the substrate or substrate/inhibitor solution was aspirated and the cells were washed 3× with HBSS+10 mM HEPES. The amount of the transported probe substrate was determined by fluorescent photometry after cell lysis, and the IC50 was derived from the concentration-response curve.

MRP2 Assay: Human MRP2 inhibition was tested using a BD Gentest Transporter Vesicle Assay Kit. Inside-out vesicles were prepared from insect Sf9 cells infected with baculovirus expressing hMRP2. The ATP-dependent uptake activity of the MRP2 probe substrate 5(6)-carboxy-2,'7'-dichlorofluorescein (CDCF) was measured by the difference between uptake in the presence of ATP and in the presence of AMP. The percent remaining of ATP dependent uptake activity was calculated as uptake activity in the presence of inhibitor divided by the uptake activity in the absence of inhibitor. The $IC_{50}$ values were calculated as described by the vendor according to the equation $IC_{50}=[(50\%-\text{Low }\%\text{ Inhibition})]/[(\text{High }\%\text{ inhibition}-\text{Low }\%\text{ Inhibition})]$.

Method 5: Measuring Time-Dependent Inhibition of CYP3A4

The CYP3A4 time dependent inhibition potential of various inhibitors was determined by a two step in vitro assay. Several concentrations of test compound were pre-incubated in the presence or absence of NADPH for 0, 5, 15, or 30 minutes, followed by an incubation of CYP3A4 probe substrate (midazolam at 25 µM) with the 20-fold dilution of these pre-incubation mixture for 2 minutes to measure remaining activities. The inactivation rate constant (kobs) was obtained by plotting the activity remaining over pre-incubation time for each concentration of compound. The maximal inactivation rate ($k_{inact}$) and the inactivation potency ($K_I$) were calculated by non linear regression analysis of the inactivation rate constant (kobs) versus compound concentrations [I] curve according to the equation $k_{obs}=[k_{inact} \cdot [I]]/[K_I+[I]]$ Using the test assays described above, compounds of the invention generated the following in accordance to Table 2 and Table 3, provided infra.

TABLE 2

Cyclophilin and replicon data

| Compound number | CypA Kd (nmol)$^{-1}$ | CypB Kd (nmol)$^{-1}$ | CypF Kd (nmol)$^{-1}$ | RPLN-1b IC$_{50}$ (uM) |
|---|---|---|---|---|
| 2.1 | 2.05 | 1.45 | 1.3 | 0.029 |
| 2.2 | 1.7 | 0.8 | 0.8 | 0.048 |
| 2.3 | 12.7 | 5.2 | 5.0 | 0.15 |
| 2.4 | 1.5 | 0.6 | 0.6 | 0.095 |
| 2.5.1 | 4.8 | 3.5 | 2.2 | 0.4 |
| 2.5.2 | 4.3 | 2.9 | 2.2 | 0.10 |
| 2.5.3 | 2.4 | 1.8 | 1.4 | 0.042 |
| 2.5.5 | 3.3 | 1.9 | 1.7 | 0.066 |
| 2.5.6 | 5.0 | 2.7 | 2.5 | 0.035 |
| 2.5.7 | 2.1 | 1.3 | 1.5 | 0.048 |
| 2.5.8 | 1.7 | 1.0 | 1.0 | |
| 2.5.9 | 0.8 | 0.5 | 0.3 | 0.09 |
| 2.5.10 | 1.2 | 1.2 | 0.9 | 0.039 |
| 2.5.11 | 1.6 | 1.2 | 1.0 | 0.050 |
| 2.5.12 | 1.0 | 0.7 | 0.4 | 0.044 |
| 2.5.13 | 0.9 | 0.8 | 0.5 | 0.050 |
| 2.5.14 | 1.0 | 0.7 | 0.5 | 0.032 |
| 2.5.15 | 1.4 | 0.7 | 0.6 | 0.018 |
| 2.5.16 | 1.4 | 0.7 | 0.7 | 0.010 |
| 2.5.17 | 1.9 | 0.9 | 1.0 | 0.044 |
| 2.5.18 | 3.9 | 1.8 | 2.0 | 0.009 |
| 2.5.19 | 2.8 | 1.2 | 1.6 | 0.075 |
| 2.5.20 | 3.7 | 1.2 | 1.6 | 0.109 |
| 2.5.21 | 1.9 | 0.9 | 0.8 | 0.037 |
| 2.5.22 | 1.7 | 0.9 | 0.9 | 0.041 |
| 2.5.23 | 1.6 | 0.7 | 0.8 | 0.047 |
| 2.5.24 | 0.5 | 0.3 | 0.3 | 0.023 |
| 2.5.25 | 1.8 | 1.0 | 1.0 | 0.022 |
| 2.5.26 | 1.3 | 0.8 | 0.8 | 0.029 |
| 2.5.27 | 1.4 | 0.8 | 0.8 | 0.026 |
| 2.5.28 | 1.4 | 0.8 | 0.8 | 0.017 |
| 2.5.29 | 1.5 | 0.7 | 0.6 | 0.056 |
| 2.5.30 | 1.7 | 1.0 | 1.1 | 0.204 |
| 2.5.31 | 2.5 | 1.1 | 1.3 | 0.055 |
| 2.5.32 | 0.7 | 0.5 | 0.4 | 0.15 |
| 2.5.33 | 1.1 | 0.8 | 0.8 | 0.046 |
| 2.5.34 | 1.3 | 0.6 | 0.6 | 0.027 |
| 2.5.35 | | | | 0.047 |
| 2.6.1 | 1.0 | 0.7 | 0.4 | 5.0 |
| 2.6.2 | 1.3 | 0.7 | 0.6 | 0.14 |
| 2.6.3 | 1.5 | 0.8 | 0.5 | 0.49 |
| 2.6.4 | 1.4 | 1.1 | 0.6 | 0.55 |
| 2.6.5 | 5.7 | 2.3 | 5.3 | |
| 2.6.6 | 3.0 | 1.6 | 1.7 | 0.17 |
| 2.7 | 2.5 | 1.2 | 0.9 | 0.064 |
| 2.8.1 | 1.4 | 0.7 | 0.7 | 0.055 |
| 2.8.2 | 1.6 | 0.6 | 0.6 | 0.077 |
| 2.8.3 | 4.4 | 3.3 | 4.1 | 0.060 |
| 2.8.4 | 0.9 | 0.7 | 0.7 | 0.045 |
| 2.8.5 | 0.6 | 0.5 | 0.4 | 0.0989 |
| 2.8.6 | 1.3 | 0.9 | 0.8 | 0.013 |
| 2.8.7 | 0.6 | 0.4 | 0.3 | 0.045 |
| 2.8.8 | 0.5 | 0.5 | 0.3 | 0.035 |
| 2.8.9 | 0.6 | 0.4 | 0.3 | 0.24 |
| 2.8.10 | 2.1 | 1.2 | 1.1 | 0.11 |
| 2.8.11 | 1.3 | 0.6 | 0.5 | 0.058 |
| 2.9 | 0.9 | 0.5 | 0.4 | 0.058 |
| 2.10 | 1.2 | 0.5 | 0.5 | 0.027 |
| 2.11 | 1.9 | 1.3 | 1.2 | 0.058 |
| 2.12 | 2.1 | 1.1 | 1.1 | 0.080 |
| 2.12.2 | 22 | 6.8 | 10 | 0.18 |
| 2.13 | 1.7 | 0.8 | 0.8 | 0.041 |
| 2.14.2 | 2.4 | 0.9 | 1.0 | 0.075 |
| 2.14.3 | 2.0 | 0.9 | 0.9 | 0.19 |
| 2.14.4 | 2.1 | 1.5 | 1.1 | 0.10 |
| 2.16 | 1.0 | 0.5 | 0.4 | 0.025 |
| 2.17.1 | 0.6 | 0.4 | 0.3 | 0.029 |
| 2.17.2 | 0.6 | 0.5 | 0.5 | 0.035 |
| 2.17.3 | 0.5 | 0.4 | 0.3 | 0.031 |
| 2.17.4 | 0.6 | 0.5 | 0.3 | 0.031 |
| 2.17.5 | 0.7 | 0.5 | 0.4 | 0.033 |
| 2.17.6 | 0.9 | 0.6 | 0.5 | 0.020 |
| 2.17.7 | 1.5 | 0.7 | 0.7 | 0.015 |
| 2.17.8 | 1.2 | 0.7 | 0.6 | 0.022 |
| 2.17.9 | 0.9 | 0.6 | 0.5 | 0.023 |
| 2.17.10 | 0.6 | 0.5 | 0.4 | 0.031 |
| 2.17.11 | 1.1 | 0.7 | 0.6 | 0.022 |
| 2.17.12 | 1.7 | 0.7 | 0.8 | 0.075 |
| 2.17.13 | | | | 0.085 |
| 2.17.14 | 0.5 | 0.4 | 0.5 | 0.057 |
| 2.18.1 | 1.5 | 0.8 | 0.9 | 0.022 |
| 2.18.2 | 1.1 | 0.7 | 0.6 | 0.058 |
| 2.18.3 | 0.9 | 0.6 | 0.5 | 0.073 |
| 2.18.4 | 1.2 | 0.7 | 0.7 | 0.044 |
| 2.18.5 | 0.9 | 0.6 | 0.5 | 0.078 |
| 2.18.6 | | | | |
| 2.18.7 | | | | |
| 2.18.8 | 0.9 | 0.7 | 0.5 | 0.045 |
| 2.18.9 | 1.8 | 2.7 | 1.0 | 0.17 |
| 2.18.10 | 1.5 | 1.1 | 0.7 | 0.096 |
| 2.19.1 | 0.9 | 0.5 | 0.5 | 0.038 |
| 2.19.2 | 0.9 | 0.6 | 0.5 | 2.7 |
| 2.19.3 | 0.8 | 0.4 | 0.3 | 0.29 |
| 2.19.4 | 0.6 | 0.4 | 0.4 | 0.060 |
| 2.19.5 | 0.7 | 0.5 | 0.4 | 0.080 |
| 2.19.6 | 0.7 | 0.7 | 0.5 | 0.11 |
| 2.19.7 | 1.1 | 0.7 | 0.7 | 0.011 |
| 2.19.8 | 0.8 | 0.4 | 0.4 | 0.062 |
| 2.19.9 | 0.8 | 0.4 | 0.4 | 0.048 |
| 2.20.1 | 0.7 | 0.7 | 0.5 | 0.057 |
| 2.20.2 | 0.6 | 0.5 | 0.3 | 0.044 |
| 2.21.1 | 2.8 | 1.2 | 1.2 | 0.023 |
| 2.21.2 | 1.3 | 0.7 | 0.6 | 0.068 |
| 2.21.3 | 1.3 | 0.8 | 0.7 | 0.042 |
| 3.1 | 3.4 | 1.6 | 1.9 | 0.040 |
| 3.2.1 | 6.3 | 3.0 | 3.4 | 4.8 |
| 3.2.2 | 5.7 | 3.7 | 3.2 | 0.52 |
| 3.2.3 | 15 | 7 | 7 | 0.33 |
| 3.3 | 13.7 | 7.4 | 8.2 | 0.10 |
| 3.4.1 | 7.0 | 2.8 | 3.8 | 4.5 |
| 3.4.2 | 8.7 | 4.4 | 5.0 | 1.3 |

TABLE 3

PMBC, OATP1B1, MRP2 and TDI data

| | EMV PBMC IC50 (uM) | OATP1B13 IC$_{50}$ (uM) | MRP2 IC50 (uM) | NIM TDI kinact/Ki |
|---|---|---|---|---|
| 2.1 | 10.6 | 5.1 | 14 | Ki > 50 uM |
| 2.2 | 12.6 | 1.9 | 15 | 0.0003 (uL/min/pmol) |
| 2.3 | 5.2 | | | |
| 2.4 | 1.9 | 1.4 | 9 | Ki > 50 uM |
| 2.5.1 | 6.8 | 3.6 | | No TDI |
| 2.5.2 | 6.3 | 8.2 | 18 | Ki > 50 uM |
| 2.5.3 | 5.8 | 1.7 | | |
| 2.5.5 | 2.8 | 4.8 | 13 | |
| 2.5.6 | 3.4 | 2.6 | | |
| 2.5.7 | 19.3 | 2.3 | | |
| 2.5.8 | | | | |
| 2.5.9 | 17.7 | 6.7 | 21 | Ki > 50 uM |
| 2.5.10 | 16.8 | 6.1 | | Ki > 50 uM |
| 2.5.11 | 13.9 | 1.17 | | Ki > 50 uM |
| 2.5.12 | 3.1 | 2.44 | | |
| 2.5.13 | 5.3 | 4.56 | | Ki > 50 uM |
| 2.5.14 | 8.1 | 5.2 | | Ki > 50 uM |

TABLE 3-continued

PMBC, OATP1B1, MRP2 and TDI data

| | EMV PBMC IC50 (uM) | OATP1B13 IC$_{50}$ (uM) | MRP2 IC50 (uM) | NIM TDI kinact/Ki |
|---|---|---|---|---|
| 2.5.15 | 7.6 | | | Ki > 50 uM |
| 2.5.16 | 18.0 | 3.4 | | |
| 2.5.17 | 17.6 | 4.2 | | Ki > 50 uM |
| 2.5.18 | 12.1 | 1.4 | | |
| 2.5.19 | 12.6 | 1.0 | | |
| 2.5.20 | 29.2 | 1.8 | | |
| 2.5.21 | 4.5 | 1.7 | | |
| 2.5.22 | 8.9 | 1.9 | | |
| 2.5.23 | 22.8 | 2.3 | | |
| 2.5.24 | 3.6 | 1.9 | | |
| 2.5.25 | 5.6 | 1.0 | | |
| 2.5.26 | 11.6 | 1.9 | | |
| 2.5.27 | 14.8 | 2.7 | | |
| 2.5.28 | 6.1 | 2.1 | | |
| 2.5.29 | 12.2 | 7.9 | | Ki > 50 uM |
| 2.5.30 | 34.1 | 2.1 | | |
| 2.5.31 | 18.9 | 2.1 | | |
| 2.5.32 | 9.5 | | | |
| 2.5.33 | 10.3 | 2.0 | | |
| 2.5.34 | 19.0 | | | |
| 2.5.35 | | | | |
| 2.6.1 | 22.9 | 6.9 | | |
| 2.6.2 | 17.3 | 3.5 | | |
| 2.6.3 | | 9.4 | | |
| 2.6.4 | 20.6 | 8.0 | | |
| 2.6.5 | 12.1 | | | |
| 2.6.6 | 29.8 | | | |
| 2.7 | 9.1 | 1.8 | | 0.0015 |
| 2.8.1 | 9.7 | 7.6 | 23 | Ki > 50 uM |
| 2.8.2 | 19.0 | 3.0 | 28 | |
| 2.8.3 | 9.0 | 1.9 | | |
| 2.8.4 | 10.7 | 3.6 | | |
| 2.8.5 | 8.1 | 4.4 | | |
| 2.8.6 | | 4.8 | | |
| 2.8.7 | 6.8 | 5.0 | | |
| 2.8.8 | 18.9 | 3.5 | | 0.0007 |
| 2.8.9 | 9.1 | | | |
| 2.8.10 | 14.5 | | | |
| 2.8.11 | 12.4 | | | |
| 2.9 | 13.3 | 8.7 | 30 | Ki > 50 uM |
| 2.10 | 12.9 | 0.9 | | Ki > 50 uM |
| 2.11 | 7.9 | 2.6 | | Ki > 50 uM |
| 2.12 | 7.1 | 2.2 | | Ki > 50 uM |
| 2.12.2 | 11.6 | 4.7 | | |
| 2.13 | 2.6 | 2.3 | 13 | Ki > 50 uM |
| 2.14.2 | 6.7 | 1.9 | | |
| 2.14.3 | 14.1 | 5.4 | | |
| 2.14.4 | 7.1 | 4.8 | | |
| 2.16 | 13.7 | 1.9 | | Ki > 50 uM |
| 2.17.1 | 18.0 | 3.6 | | Ki > 50 uM |
| 2.17.2 | 14.5 | 5.1 | | Ki > 50 uM |
| 2.17.3 | 6.7 | 4.0 | | Ki > 50 uM |
| 2.17.4 | 2.7 | 3.2 | | Ki > 50 uM |
| 2.17.5 | 35.2 | 1.8 | | Ki > 50 uM |
| 2.17.6 | 14.6 | 3.3 | | Ki > 50 uM |
| 2.17.7 | | | | Ki > 50 uM |
| 2.17.8 | 36.4 | | | Ki > 50 uM |
| 2.17.9 | 31.9 | 0.4 | | |
| 2.17.10 | 15.0 | 1.4 | | |
| 2.17.11 | 36.4 | | | |
| 2.17.12 | | | | |
| 2.17.13 | | | | |
| 2.17.14 | 8.1 | 2.2 | | |
| 2.18.1 | 16.2 | 3.9 | | Ki > 50 uM |
| 2.18.2 | 7.3 | 2.4 | | |
| 2.18.3 | 11.1 | 9.1 | | Ki > 50 uM |
| 2.18.4 | 10.6 | 1.7 | | |
| 2.18.5 | 8.1 | 1.4 | | |
| 2.18.6 | | | | |
| 2.18.7 | | | | |
| 2.18.8 | 1.0 | 2.3 | | |
| 2.18.9 | 9.2 | 2.8 | | |
| 2.18.10 | 1.6 | 2.1 | | |
| 2.19.1 | 16.6 | 6.9 | | 0.001 |
| 2.19.2 | 32.3 | | | |
| 2.19.3 | 2.0 | | | |
| 2.19.4 | 8.8 | 2.6 | | |
| 2.19.5 | 8.9 | 4.3 | | |
| 2.19.6 | 1.6 | 2.2 | | |
| 2.19.7 | 15.9 | 2.9 | | |
| 2.19.8 | 8.2 | 7.8 | | Ki > 50 uM |
| 2.19.9 | 3.5 | 3.7 | | |
| 2.20.1 | 5.8 | 1.9 | | 0.0004 |
| 2.20.2 | 6.4 | 4.3 | | |
| 2.21.1 | 15.7 | 0.9 | | |
| 2.21.2 | 12.0 | | | |
| 2.21.3 | 12.5 | | | |
| 3.1 | 20.8 | 2.1 | | |
| 3.2.1 | 34.9 | | | |
| 3.2.2 | 24.5 | | | |
| 3.2.3 | 8.9 | | | |
| 3.3 | 13.2 | 2.0 | | |
| 3.4.1 | 5.8 | 2.7 | | |
| 3.4.2 | 13.8 | | | Ki > 50 uM |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of Formula I:

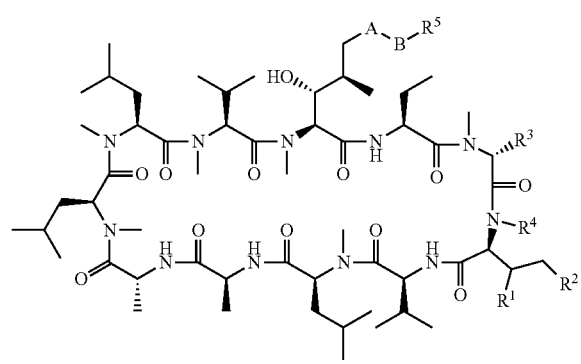

I or a pharmaceutically acceptable salt thereof, wherein

A-B is —CH=CH or $CH_2CH_2$;

$R^1$ is $C_1$-$C_4$alkoxy or $C_1$-$C_4$ alkyl;

$R^2$ is —$OR^{1a}$, or a 4 to 8 membered heterocycle containing 1 to 3 heteroatoms selected from N, S, and O, wherein said heterocycle is optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, and $C_1$-$C_4$ alkyl optionally substituted with $C_1$-$C_4$alkoxy;

$R^{1a}$ is $C_1$-$C_4$alkyl, ($C_1$-$C_4$)alkyl-OH, ($C_1$-$C_4$)alkyl-$C_1$-$C_4$alkoxy, ($C_2$-$C_4$)alkyl-$NR^9R^{10}$, a 4 to 8 membered heterocycle containing 1 to 3 heteroatom selected from N, S, and O, or a ($C_1$-$C_4$)alkyl-4 to 8 membered heterocycle containing 1 to 3 heteroatoms selected from N, S, and O, wherein said heterocycles are optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, and $C_1$-$C_4$ alkyl optionally substituted with $C_1$-$C_4$alkoxy;

$R^3$ is $C_1$-$C_6$alkyl optionally substituted with at least one substituent selected from the group consisting of OH, O($C_1$-$C_4$alkyl), —NR$^7$R$^8$, and S($C_1$-$C_6$ alkyl);

$R^4$ is $C_1$-$C_4$ alkyl;

$R^5$ is H, ($C_1$-$C_6$)alkyl;

$R^7$ is H or $C_1$-$C_4$ alkyl;

$R^8$ is H or $C_1$-$C_4$ alkyl; or $R^7$ and $R^8$ taken together with the nitrogen to which they are attached form a 4 to 8 membered heterocycle containing 1 to 3 heteroatoms selected from N, S, and O, wherein said heterocycle is optionally substituted with at least one substituent selected from the group consisting of halogen and $C_1$-$C_4$ alkyl;

$R^9$ is H, $C_1$-$C_4$alkyl optionally substituted with one or more halogen, one or more hydroxy, $C_1$-$C_4$alkoxy, 5 to 6 membered heteroaryl or 5 to 6 membered heterocycle; and $R^{10}$ is H, $C_1$-$C_4$alkyl optionally substituted with one or more halogen, $C_1$-$C_4$alkoxy or one or more hydroxy.

2. The compound or a pharmaceutically acceptable salt thereof of claim 1 having the following Formula II:

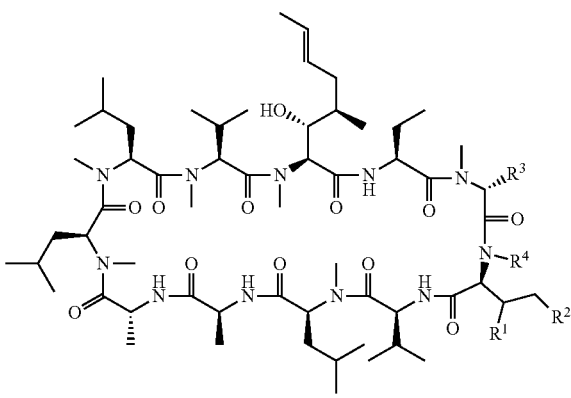

or a pharmaceutically acceptable salt thereof, wherein $R^1$, $R^2$, $R^3$ and $R^4$ are defined in claim 1.

3. The compound or a pharmaceutically acceptable salt thereof according to claim 2, wherein $R^2$ is —OR$^{1a}$.

4. The compound or a pharmaceutically acceptable salt thereof according to claim 2, wherein $R^2$ is a 4 to 8 membered heterocycle containing 1 to 3 heteroatoms selected from N, S, and O, wherein said heterocycle is optionally substituted with at least one substituent selected from the group consisting of halogen, —OH, CN, —O($C_1$-$C_4$)alkyl, oxo (=O), —S(O)$_2$($C_1$-$C_4$)alkyl, —C(O)($C_1$-$C_4$)alkyl, —C(O)$_2$($C_1$-$C_4$)alkyl, $C_1$-$C_4$haloalkyl, $C_3$-$C_7$cycloalkyl, and $C_1$-$C_4$ alkyl optionally substituted with $C_1$-$C_4$alkoxy; and $R^4$ is methyl.

5. The compound or a pharmaceutically acceptable salt thereof according to claim 2, wherein $R^4$ is methyl.

6. The compound or a pharmaceutically acceptable salt thereof according to claim 5, wherein $R^1$ is $C_1$-$C_4$ alkyl.

7. The compound according to claim 3, wherein the compound is represented by formula IIIa:

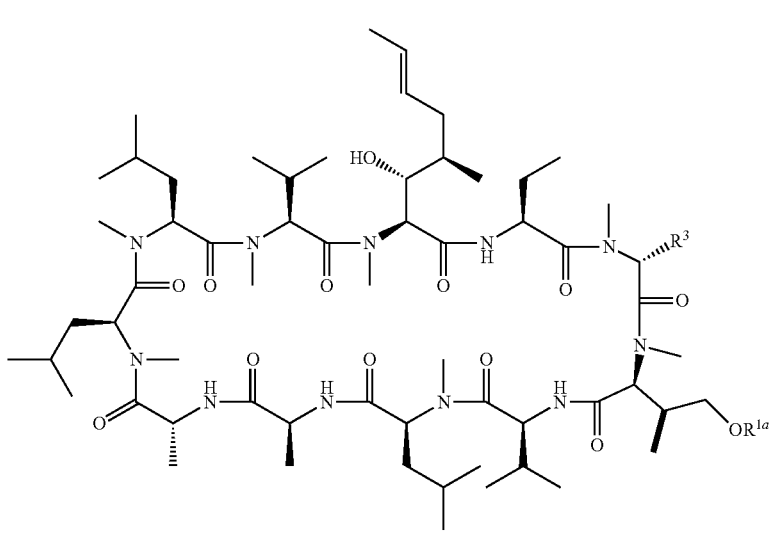

or a pharmaceutically acceptable salt thereof.

8. The compound or a pharmaceutically acceptable salt thereof according to claim 7, wherein $R^{1a}$ is —CH$_3$, —CH$_2$CH$_3$,

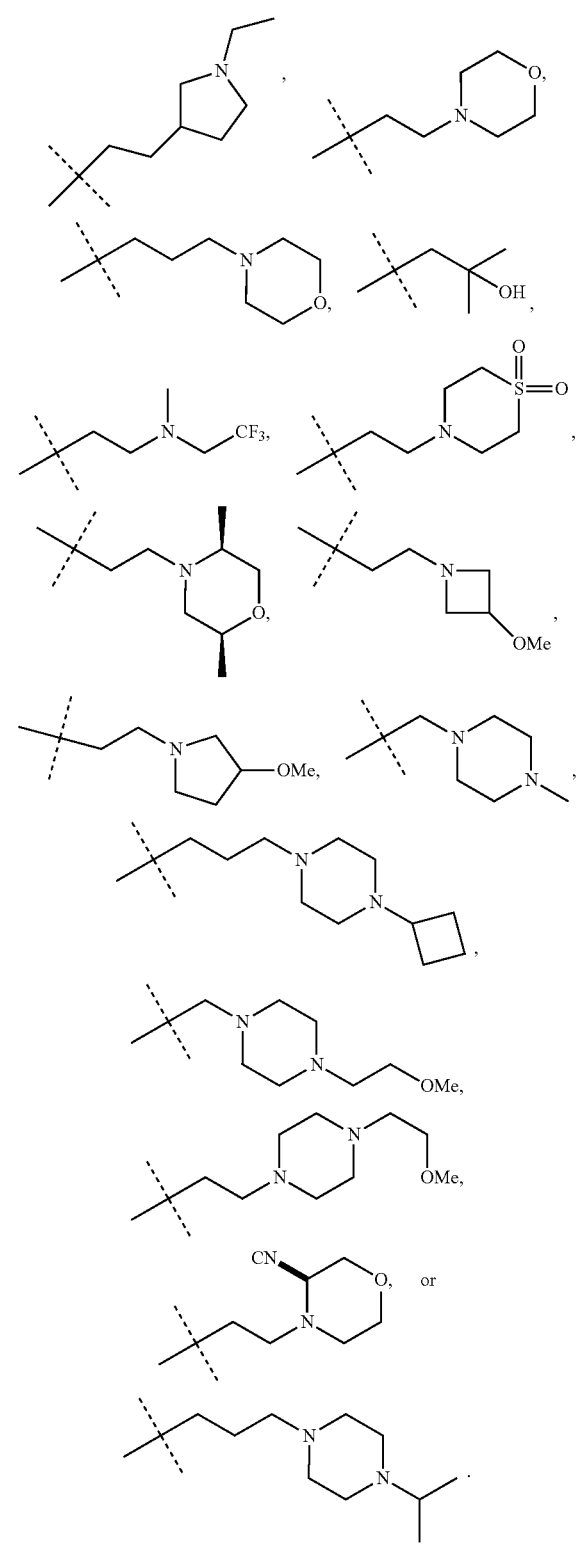

9. The compound or a pharmaceutically acceptable salt thereof according to claim 1, wherein $R^2$ is

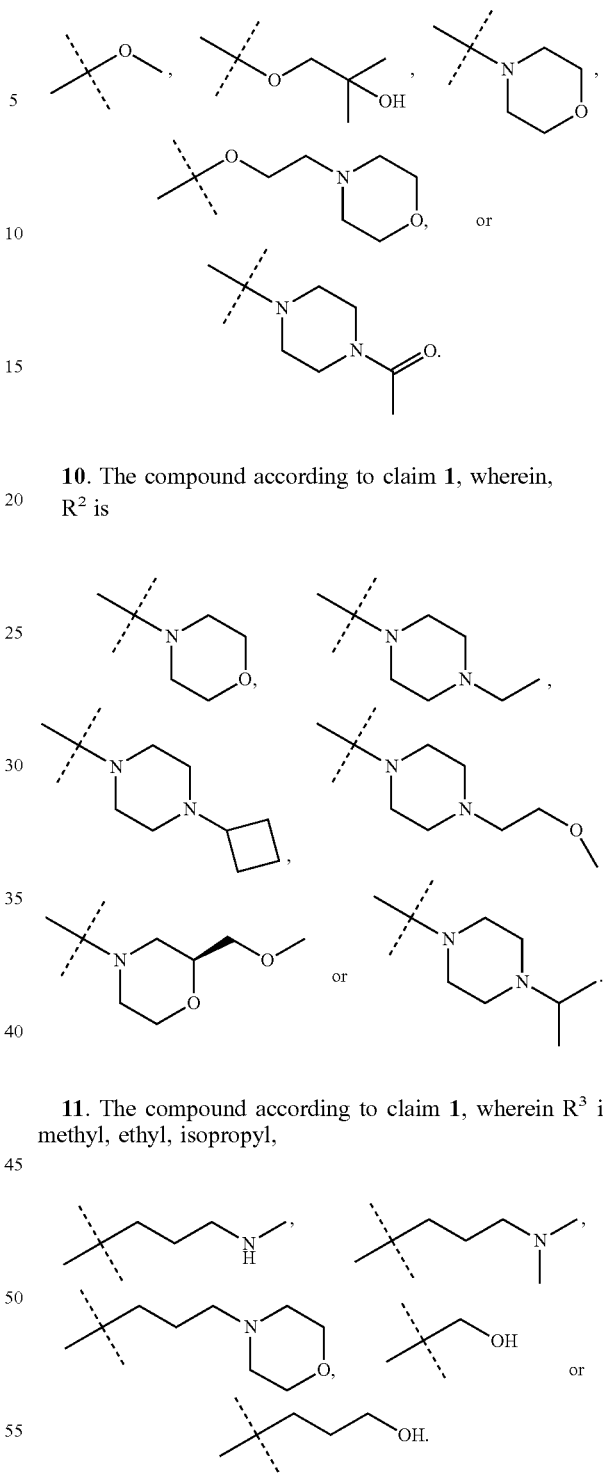

10. The compound according to claim 1, wherein, $R^2$ is

11. The compound according to claim 1, wherein $R^3$ is methyl, ethyl, isopropyl,

12. The compound according to claim 1, wherein A-B is —CH═CH.

13. The compound according to claim 1, wherein A-B is CH$_2$CH$_2$.

14. The compound of claim 1, which is:
1-dihydro-3-[D-Ala]-4-[(2S,3S)-3-methyl-2-(methyl-amino)-4-(2-morpholinoethoxy)butanoyl]-cyclosporin, or a pharmaceutically acceptable salt thereof.

15. The compound of claim 1, which is
1-dihydro-3-[D-Ala]-4[(2S,3S)-2-Amino-3-methyl-4-morpholin-4-yl-butanoyl]-cyclosporin
or a pharmaceutically acceptable salt thereof.

16. The compound of claim 1, which is
3-[D-Ala]-4[(2S,3R)-2-Amino-4-[4-(2-methoxy-ethyl)-piperazin-1-yl]-3-methyl-butanoyl]-cyclosporin or a pharmaceutically acceptable salt thereof.

17. The compound of claim 1, which is
1-dihydro-3-[D-Ala]-4[(2S,3R)-2-Amino-4-(4-cyclobutyl-piperazin-1-yl)-butanoyl]-cyclosporin
or a pharmaceutically acceptable salt thereof.

18. The compound of claim 1, which is
3-[D-Ala]-4-[(2S,3R)-4-(3,3-difluoropyrrolidin-1-yl)-3-methyl-2-(methylamino)butanoyl]-cyclosporin
or a pharmaceutically acceptable salt thereof.

19. The compound of claim 1, which is
3-[D-Ala]-4-[(2S,3S)-3-methyl-2-(methylamino)-4-(2-((S)-3-methylmorpholino)ethoxy)-butanoyl]-cyclosporin
or a pharmaceutically acceptable salt thereof.

20. A pharmaceutical composition, comprising:
the compound according to claim 1 or a pharmaceutically acceptable salt thereof, and a pharmaceutically acceptable carrier.

21. A pharmaceutical combination composition, comprising:
a therapeutically effective amount of the compound according to claim 1 or a pharmaceutically acceptable salt thereof, and
one or more therapeutically active agents selected from Interferons, ribavirin and ribavirin analogs, HCV NS3 protease inhibitors, HCV NS5a inhibitors, nucleoside and non-nucleoside NS5b inhibitors, HCV NS4a antagonists, TLR-7 agonists, HCV IRES inhibitors, pharmacokinetic enhancers, anti-fibrotic agents, or mixtures thereof.

22. A method of treating a disorder or a disease selected from HCV infection, stroke, multiple sclerosis, HBV infection, HPV infection, asthma, muscular dystrophy, sepsis, ischemia/reperfusion injury, and heart failure in a subject, which comprises administering to the subject a therapeutically effective amount of the compound according to claim 1 or a pharmaceutically acceptable salt thereof.

* * * * *

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Synthetic Primer

<400> SEQUENCE: 1
gggcgcgcca tggcttccaa ggtgtacg                                          28

<210> SEQ ID NO 2
<211> LENGTH: 27
<212> TYPE: DNA
```

```
<213> ORGANISM: Artificial Sequence
<220> FEATURE:
<223> OTHER INFORMATION: Synthetic Primer

<400> SEQUENCE: 2
cgcggccgct cagaagaact cgtcaag                                         27

<210> SEQ ID NO 3
<211> LENGTH: 39
<212> TYPE: DNA
<213> ORGANISM: Artificial Sequence
<220> FEATURE:
<223> OTHER INFORMATION: Synthetic Primer

<400> SEQUENCE: 3
ctcaaactca ctccaatagc tgccgctggc cggctggac                            39

<210> SEQ ID NO 4
<211> LENGTH: 39
<212> TYPE: DNA
<213> ORGANISM: Artificial Sequence
<220> FEATURE:
<223> OTHER INFORMATION: Synthetic Primer

<400> SEQUENCE: 4
gtccagcggg ccagcggcag ctattggagt gagtttgag                            39

<210> SEQ ID NO 5
<211> LENGTH: 28
<212> TYPE: DNA
<213> ORGANISM: Artificial Sequence
<220> FEATURE:
<223> OTHER INFORMATION: Synthetic Primer

<400> SEQUENCE: 5
gggcgcgcca tggcttccaa ggtgtacg                                        28

<210> SEQ ID NO 6
<211> LENGTH: 27
<212> TYPE: DNA
<213> ORGANISM: Artificial Sequence
<220> FEATURE:
<223> OTHER INFORMATION: Synthetic Primer

<400> SEQUENCE: 6
cgcggccgct cagaagaact cgtcaag                                         27
```